(12) United States Patent
Chartier-Courtaud et al.

(10) Patent No.: US 12,104,172 B2
(45) Date of Patent: Oct. 1, 2024

(54) PROCESSES FOR GENERATING TIL PRODUCTS ENRICHED FOR TUMOR ANTIGEN-SPECIFIC T-CELLS

(71) Applicant: Iovance Biotherapeutics, Inc., San Carlos, CA (US)

(72) Inventors: Cecile Chartier-Courtaud, Palo Alto, CA (US); Krit Ritthipichai, Tampa, FL (US)

(73) Assignee: Iovance Biotherapeutics, Inc., San Carlos, CA (US)

( * ) Notice: Subject to any disclaimer, the term of this patent is extended or adjusted under 35 U.S.C. 154(b) by 704 days.

(21) Appl. No.: 16/960,310

(22) PCT Filed: Jan. 8, 2019

(86) PCT No.: PCT/US2019/012729
§ 371 (c)(1),
(2) Date: Jul. 6, 2020

(87) PCT Pub. No.: WO2019/136456
PCT Pub. Date: Jul. 11, 2019

(65) Prior Publication Data
US 2022/0204932 A1 Jun. 30, 2022

Related U.S. Application Data

(60) Provisional application No. 62/773,715, filed on Nov. 30, 2018, provisional application No. 62/734,868, filed on Sep. 21, 2018, provisional application No. 62/697,921, filed on Jul. 13, 2018, provisional application No. 62/669,319, filed on May 9, 2018, provisional application No. 62/664,034, filed on Apr. 27, 2018, provisional application No. 62/614,887, filed on Jan. 8, 2018.

(51) Int. Cl.
*A61K 39/00* (2006.01)
*A61K 35/17* (2015.01)
*C12N 5/0783* (2010.01)

(52) U.S. Cl.
CPC ............ *C12N 5/0638* (2013.01); *A61K 35/17* (2013.01); *C12N 2501/2302* (2013.01); *C12N 2501/2315* (2013.01); *C12N 2501/2321* (2013.01); *C12N 2501/515* (2013.01); *C12N 2501/998* (2013.01); *C12N 2502/11* (2013.01)

(58) Field of Classification Search
None
See application file for complete search history.

(56) References Cited

U.S. PATENT DOCUMENTS

| | | |
|---|---|---|
| 4,766,106 A | 8/1988 | Katre et al. |
| 4,897,355 A | 1/1990 | Eppstein et al. |
| 4,902,502 A | 2/1990 | Nitecki et al. |
| 5,089,261 A | 2/1992 | Nitecki et al. |
| 5,126,132 A | 6/1992 | Rosenberg |
| 5,206,344 A | 4/1993 | Katre et al. |
| 5,279,833 A | 1/1994 | Rose |
| 5,443,983 A | 8/1995 | Ochoa et al. |
| 5,593,875 A | 1/1997 | Wurm et al. |
| 5,672,695 A | 9/1997 | Eckstein et al. |
| 5,766,902 A | 6/1998 | Craig et al. |
| 5,849,902 A | 12/1998 | Arrow et al. |
| 5,908,635 A | 6/1999 | Thierry |
| 5,928,893 A | 7/1999 | Kang et al. |
| 6,010,613 A | 1/2000 | Walters et al. |
| 6,025,337 A | 2/2000 | Truong et al. |
| 6,056,938 A | 5/2000 | Unger et al. |
| 6,078,490 A | 6/2000 | Walters |
| 6,110,490 A | 8/2000 | Thierry |
| 6,210,669 B1 | 4/2001 | Aruffo et al. |
| 6,248,878 B1 | 6/2001 | Matulic-Adamic et al. |
| 6,303,121 B1 | 10/2001 | Kwon |
| 6,312,700 B1 | 11/2001 | Weinberg |
| 6,352,694 B1 | 3/2002 | June et al. |
| 6,362,325 B1 | 3/2002 | Kwon |
| 6,410,517 B1 | 6/2002 | Truong et al. |
| 6,475,994 B2 | 11/2002 | Tomalia et al. |
| 6,534,055 B1 | 3/2003 | June et al. |
| 6,534,484 B1 | 3/2003 | Wheeler et al. |
| 6,569,997 B1 | 5/2003 | Kwon |
| 6,627,442 B1 | 9/2003 | Humeau et al. |
| 6,706,289 B2 | 3/2004 | Lewis et al. |
| 6,867,041 B2 | 3/2005 | Berenson et al. |
| 6,887,466 B2 | 5/2005 | June et al. |

(Continued)

FOREIGN PATENT DOCUMENTS

| CN | 106244538 A | 12/2016 |
|---|---|---|
| CN | 106591232 A | 4/2017 |

(Continued)

OTHER PUBLICATIONS

Hall et al. (Journal for Immuno Therapy of Cancer (2016) 4:61) (Year: 2016).*
Amado, I. F., Berges, J., Luther, R. J., Mailhé, M. P., Garcia, S., Bandeira, A., . . . & Freitas, A. A. (2013). IL-2 coordinates IL-2-producing and regulatory T cell interplay. Journal of Experimental Medicine, 210(12), 2707-2720. (Year: 2013).*
Dudley, M. E., Wunderlich, J. R., Shelton, T. E., Even, J., & Rosenberg, S. A. (2003). Generation of tumor-infiltrating lymphocyte cultures for use in adoptive transfer therapy for melanoma patients. Journal of immunotherapy (Hagerstown, Md.: 1997), 26(4), 332. (Year: 2003).*

(Continued)

*Primary Examiner* — Evelyn Y Pyla
(74) *Attorney, Agent, or Firm* — Morgan, Lewis & Bockius LLP

(57) ABSTRACT

The present invention provides improved and/or shortened processes and methods for reprogramming TILs in order to prepare therapeutic populations of TILs with increased therapeutic efficacy. Such reprogrammed TILs find use in therapeutic treatment regimens.

13 Claims, 64 Drawing Sheets
Specification includes a Sequence Listing.

(56) References Cited

U.S. PATENT DOCUMENTS

| | | |
|---|---|---|
| 6,887,673 B2 | 5/2005 | Kunkel et al. |
| 6,905,680 B2 | 6/2005 | June et al. |
| 6,905,681 B1 | 6/2005 | June et al. |
| 6,905,685 B2 | 6/2005 | Kwon |
| 6,974,863 B2 | 12/2005 | Kwon |
| 7,144,575 B2 | 12/2006 | June et al. |
| 7,175,843 B2 | 2/2007 | June et al. |
| 7,189,705 B2 | 3/2007 | Lam et al. |
| 7,214,493 B2 | 5/2007 | Kunkel et al. |
| 7,232,566 B2 | 6/2007 | June et al. |
| 7,288,638 B2 | 10/2007 | Jure-Kunkel et al. |
| 7,479,269 B2 | 1/2009 | June et al. |
| 7,504,101 B2 | 3/2009 | Weinberg |
| 7,550,140 B2 | 6/2009 | Bakker et al. |
| 7,572,631 B2 | 8/2009 | Berenson et al. |
| 7,622,444 B2 | 11/2009 | Weinberg |
| 7,687,070 B2 | 3/2010 | Gebeyehu et al. |
| 7,696,175 B2 | 4/2010 | Epstein et al. |
| 7,834,170 B2 | 11/2010 | Khvorova et al. |
| 7,943,743 B2 | 5/2011 | Korman et al. |
| 7,951,365 B2 | 5/2011 | Winqvist et al. |
| 7,960,515 B2 | 6/2011 | Min et al. |
| 7,961,515 B2 | 6/2011 | Kato et al. |
| 8,007,785 B2 | 8/2011 | Winqvist et al. |
| 8,008,449 B2 | 8/2011 | Korman et al. |
| 8,034,334 B2 | 10/2011 | Dudley et al. |
| 8,090,542 B2 | 1/2012 | Khvorova et al. |
| 8,133,983 B2 | 3/2012 | Bakker et al. |
| 8,206,702 B2 | 6/2012 | Winqvist et al. |
| 8,211,424 B2 | 7/2012 | Winqvist et al. |
| 8,211,425 B2 | 7/2012 | Winqvist et al. |
| 8,236,930 B2 | 8/2012 | Min et al. |
| 8,252,755 B2 | 8/2012 | Yamada et al. |
| 8,287,857 B2 | 11/2012 | Dudley et al. |
| 8,337,850 B2 | 12/2012 | Ahrens et al. |
| 8,383,099 B2 | 2/2013 | Dudley et al. |
| 8,450,460 B2 | 5/2013 | Hill et al. |
| 8,501,706 B2 | 8/2013 | Yamada et al. |
| 8,617,884 B2 | 12/2013 | Berenson et al. |
| 8,809,050 B2 | 8/2014 | Vera et al. |
| 8,815,818 B2 | 8/2014 | Samarsky et al. |
| 8,821,867 B2 | 9/2014 | Ahrens et al. |
| 8,859,229 B2 | 10/2014 | Rabinovich et al. |
| 8,921,519 B2 | 12/2014 | Hill et al. |
| 8,956,860 B2 | 2/2015 | Vera et al. |
| 8,962,804 B2 | 2/2015 | Williams et al. |
| 9,006,399 B2 | 4/2015 | Liu et al. |
| 9,028,824 B2 | 5/2015 | Min et al. |
| 9,074,185 B2 | 7/2015 | Dudley et al. |
| 9,080,171 B2 | 7/2015 | Khvorova et al. |
| 9,163,085 B2 | 10/2015 | Liu et al. |
| 9,340,599 B2 | 5/2016 | Hill et al. |
| 9,359,420 B2 | 6/2016 | Hill et al. |
| 9,468,678 B2 | 10/2016 | Ahrens et al. |
| 9,476,028 B2 | 10/2016 | Karlsson-Parra et al. |
| 9,528,088 B2 | 12/2016 | Berenson et al. |
| 9,687,510 B2 | 6/2017 | Borrello et al. |
| 9,844,569 B2 | 12/2017 | Gros et al. |
| 9,914,783 B1 | 3/2018 | Afar et al. |
| 2004/0224405 A1 | 11/2004 | Leake et al. |
| 2005/0095244 A1 | 5/2005 | Jure-Kunkel et al. |
| 2005/0106717 A1 | 5/2005 | Wilson et al. |
| 2006/0276635 A1 | 12/2006 | McSwiggen et al. |
| 2007/0031844 A1 | 2/2007 | Khvorova et al. |
| 2007/0039072 A1 | 2/2007 | Khvorova et al. |
| 2007/0207974 A1 | 9/2007 | Khvorova et al. |
| 2007/0213520 A1 | 9/2007 | Khvorova et al. |
| 2007/0213521 A1 | 9/2007 | Khvorova et al. |
| 2007/0219362 A1 | 9/2007 | Khvorova et al. |
| 2007/0238868 A1 | 10/2007 | Khvorova et al. |
| 2010/0136030 A1 | 6/2010 | Salah-Eddine et al. |
| 2011/0027218 A1 | 2/2011 | Hill et al. |
| 2011/0039914 A1 | 2/2011 | Pavco et al. |
| 2011/0052530 A1 | 3/2011 | Dudley et al. |
| 2011/0111494 A1 | 5/2011 | Hill et al. |
| 2011/0136228 A1 | 6/2011 | Vera et al. |
| 2011/0263680 A1 | 10/2011 | Khvorova et al. |
| 2012/0052487 A9 | 3/2012 | Khvorova et al. |
| 2012/0244133 A1 | 9/2012 | Rosenberg et al. |
| 2013/0102075 A1 | 4/2013 | Vera et al. |
| 2013/0115617 A1 | 5/2013 | Wilson |
| 2013/0131141 A1 | 5/2013 | Khvorova et al. |
| 2013/0131142 A1 | 5/2013 | Khvorova et al. |
| 2013/0315884 A1 | 11/2013 | Galetto et al. |
| 2014/0030806 A1* | 1/2014 | Dudley ................. A61K 35/26 435/375 |
| 2014/0148362 A1 | 5/2014 | Khvorova et al. |
| 2014/0227237 A1 | 8/2014 | June et al. |
| 2014/0287509 A1 | 9/2014 | Sharei et al. |
| 2014/0328791 A1 | 11/2014 | Bossard et al. |
| 2014/0377284 A1 | 12/2014 | Simons et al. |
| 2014/0377739 A1 | 12/2014 | Welch et al. |
| 2015/0110734 A1 | 4/2015 | Hill et al. |
| 2015/0126709 A1 | 5/2015 | Hill et al. |
| 2015/0126710 A1 | 5/2015 | Hill et al. |
| 2015/0132288 A1 | 5/2015 | Simons et al. |
| 2015/0157636 A1 | 6/2015 | Perrine et al. |
| 2015/0175966 A1 | 6/2015 | Vera et al. |
| 2015/0190506 A1 | 7/2015 | Cheung et al. |
| 2015/0320798 A1 | 11/2015 | Borrello et al. |
| 2016/0010058 A1 | 1/2016 | Gros et al. |
| 2016/0137731 A1 | 5/2016 | Freeman et al. |
| 2016/0193242 A1 | 7/2016 | Khvorova et al. |
| 2016/0194646 A1 | 7/2016 | Khvorova et al. |
| 2016/0201058 A1 | 7/2016 | Khvorova et al. |
| 2016/0201065 A1 | 7/2016 | Khvorova et al. |
| 2016/0208216 A1 | 7/2016 | Vera et al. |
| 2016/0215262 A1 | 7/2016 | Powell |
| 2016/0230188 A1 | 8/2016 | Rabinovich et al. |
| 2016/0304873 A1 | 10/2016 | Wolfson et al. |
| 2016/0319278 A1 | 11/2016 | Khvorova et al. |
| 2017/0043024 A1 | 2/2017 | Khvorova et al. |
| 2017/0044496 A1 | 2/2017 | Sarnaik et al. |
| 2017/0081635 A1 | 3/2017 | Sarnaik et al. |
| 2017/0107490 A1 | 4/2017 | Maeurer |
| 2017/0114321 A1 | 4/2017 | Berenson et al. |
| 2017/0152478 A1 | 6/2017 | Rosenberg et al. |
| 2017/0258838 A1 | 9/2017 | Borrello et al. |
| 2017/0312367 A1 | 11/2017 | Khvorova et al. |
| 2017/0340799 A1 | 11/2017 | Schlinker et al. |
| 2017/0349904 A1 | 12/2017 | Khvorova et al. |
| 2017/0362556 A1 | 12/2017 | Ali |
| 2017/0369882 A1 | 12/2017 | Khvorova et al. |
| 2018/0119144 A1 | 5/2018 | Khvorova et al. |
| 2018/0127715 A1 | 5/2018 | Veerapathran et al. |
| 2018/0148690 A1 | 5/2018 | Gros et al. |
| 2018/0187150 A1 | 7/2018 | De Larichaudy |
| 2018/0201889 A1 | 7/2018 | Sharei et al. |
| 2018/0207201 A1 | 7/2018 | Wardell et al. |
| 2018/0228841 A1 | 8/2018 | Frank et al. |
| 2018/0245089 A1 | 8/2018 | Sharei et al. |
| 2019/0000070 A1 | 1/2019 | De Larichaudy |
| 2019/0062706 A1 | 2/2019 | Almaasbak et al. |
| 2019/0136186 A1 | 5/2019 | Germeroth et al. |

FOREIGN PATENT DOCUMENTS

| | | |
|---|---|---|
| CN | 107384867 A | 11/2017 |
| EP | 0672141 B1 | 5/2003 |
| EP | 1539929 B1 | 4/2013 |
| EP | 2925329 A1 | 10/2015 |
| EP | 3188740 A1 | 7/2017 |
| EP | 3365434 A1 | 8/2018 |
| EP | 3368659 A1 | 9/2018 |
| EP | 3487990 A1 | 5/2019 |
| JP | 2009-507827 A | 2/2009 |
| JP | 2014-514245 A | 6/2014 |
| JP | 2017-525754 A | 9/2017 |
| WO | WO 90/14074 | 11/1990 |
| WO | WO 91/16024 | 10/1991 |
| WO | WO 91/17424 | 11/1991 |
| WO | WO 95/21925 | 2/1994 |
| WO | WO 95/12673 | 5/1995 |
| WO | WO 98/13526 | 4/1998 |

(56) References Cited

FOREIGN PATENT DOCUMENTS

| | | |
|---|---|---|
| WO | WO 2004/031370 A1 | 4/2004 |
| WO | WO 2006/121810 A2 | 11/2006 |
| WO | WO 2008/025516 A2 | 3/2008 |
| WO | WO 2009/007120 A2 | 1/2009 |
| WO | WO 2009/040789 A2 | 4/2009 |
| WO | WO 2010/003766 A1 | 1/2010 |
| WO | WO 2010/010051 A1 | 1/2010 |
| WO | WO 2010/042433 A1 | 4/2010 |
| WO | WO 2010/078966 A1 | 7/2010 |
| WO | WO 2011/072088 A2 | 6/2011 |
| WO | WO 2012/027328 A3 | 3/2012 |
| WO | WO 2012/032433 A1 | 3/2012 |
| WO | WO 2012/065086 A1 | 5/2012 |
| WO | WO 2012/129201 A1 | 9/2012 |
| WO | WO 2012/177788 A1 | 12/2012 |
| WO | WO 2013/028231 A1 | 2/2013 |
| WO | WO 2013/038191 A2 | 3/2013 |
| WO | WO 2013/057500 A1 | 4/2013 |
| WO | WO 2013/059343 A1 | 4/2013 |
| WO | WO 2013/088147 A1 | 6/2013 |
| WO | WO 2013/173835 A1 | 11/2013 |
| WO | WO 2013/188427 A1 | 12/2013 |
| WO | WO 2014/148895 A1 | 9/2014 |
| WO | WO 2014/184744 A1 | 11/2014 |
| WO | WO 2014/210036 A1 | 12/2014 |
| WO | WO 2015/009604 A1 | 1/2015 |
| WO | WO 2015/119923 A1 | 8/2015 |
| WO | WO 2015/157636 A1 | 10/2015 |
| WO | WO 2015/188839 A1 | 12/2015 |
| WO | WO 2015/189357 A1 | 12/2015 |
| WO | WO 2015189356 A1 | 12/2015 |
| WO | WO 2016/041945 A1 | 3/2016 |
| WO | WO 2016/053338 A1 | 4/2016 |
| WO | WO 2016/096903 A1 | 6/2016 |
| WO | WO 2016/113369 A1 | 7/2016 |
| WO | WO 2017/008063 A1 | 1/2017 |
| WO | WO 2017048614 A1 | 3/2017 |
| WO | WO 2017/117418 A1 | 7/2017 |
| WO | WO 2017/123663 A1 | 7/2017 |
| WO | WO 2017/219150 A1 | 12/2017 |
| WO | WO 2018/081473 A1 | 5/2018 |
| WO | WO 2018102761 A1 | 6/2018 |
| WO | WO 2018/129332 A1 | 7/2018 |
| WO | WO 2018170188 A2 | 9/2018 |
| WO | WO 2018/182817 A1 | 10/2018 |
| WO | WO 2018/209115 A1 | 11/2018 |
| WO | WO 2018/226714 A1 | 12/2018 |

OTHER PUBLICATIONS

Klapper, J. A., Thomasian, A. A., Smith, D. M., Gorgas, G. C., Wunderlich, J. R., Smith, F. O., . . . & Dudley, M. E. (2009). Single-pass, closed-system rapid expansion of lymphocyte cultures for adoptive cell therapy. Journal of immunological methods, 345(1-2), 90. (Year: 2009).*

Forget, M. A. . . . & Radvanyi, L. G. (2014). Activation and propagation of tumor infiltrating lymphocytes on clinical-grade designer artificial antigen presenting cells for adoptive immunotherapy of melanoma. Journal of immunotherapy (Hagerstown, Md.: 1 (Year: 2014).*

General Electric Company, 'Xuri Cellbag Bioreactor' [online] [retrieved on Mar. 24, 2023] [first published Aug. 2014] retrieved from 'gels.yilimart.com' [Data File 29-1165-48 AA] (Year: 2014).*

Ahmad, Z. et al., "scFv Antibody: Principles and Clinical Application," Clin. & Dev. Immunol., 2012, 980250, 1-15.

Akkök, C. A et al., "Use of different DMSO concentrations for cryopreservation of autologous peripheral blood stem cell grafts does not have any major impact on levels of leukocyte- and platelet-derived soluble mediators," Cytotherapy, vol. 11,6 (2009): 749-60. doi:10.3109/14653240902980443.

Amaxa Nucleofector® II Manual (available on the World Wide Web at http://icob.sinica.edu.tw/pubweb/bio-chem/Core%20Facilities/Data/R401-core/Nucleofector_Manual_II_Apr06.pdf), 2009.

Andersen, Rikke et al. "Long-Lasting Complete Responses in Patients with Metastatic Melanoma after Adoptive Cell Therapy with Tumor-Infiltrating Lymphocytes and an Attenuated IL2 Regimen." Clinical cancer research : an official journal of the American Association for Cancer Research vol. 22,15 (2016): 3734-45. doi:10.1158/1078-0432.CCR-15-1879.

Arnaud-Barbe, N. et al., "Transcription of RNA templates by T7 RNA polymerase," Nuc. Acids Res., Mar. 1998, 26(15):3550-3554.

Augustyns, K., et al., "Incorporation of hexose nucleoside analogues into oligonucleotides: synthesis, base-pairing properties and enzymatic stability," Nucl. Acids. Res., 1992, 20(18):4711-4716.

Axelsson et al., "Cryopreserved peripheral blood mononuclear cells are suitable for the assessment of immunological markers in type 1 diabetic children", Cryobiology, Aug. 2008, 57, 201-208.

Bajgain, P. et al., "Optimizing the production of suspension cells using the G-Rex "M" series", Molecular Therapy—Methods and Clinical Development, vol. 1, Jan. 1, 2014.

Baruch et al., "Adoptive T cell therapy: An overview of obstacles and opportunities : ACT Obstacles and Opportunities", Cancer, vol. 123, No. S11, May 19, 2017, pp. 2154-2162.

Belopolski, I. et al., "Signatures of a time-reversal symmetric Weyl semimetal with only four Weyl points," Nat Comm, 2017, 8:942, 1-7.

Bergan, R. et al., "Electroporation enhances c-myc antisense oligodeoxynucleotide efficacy," Nucleic Acids Research, 1993, 21(15):3567-3573.

Besser et al., "Minimally Cultured or Selected Autologous Tumor-infiltrating Lymphocytes After a Lympho-depleting Chemotherapy Regimen in Metastatic Melanoma Patients"; J Immunother 32, 415-423 (2009).

Besser, et al., "Adoptive Transfer of Tumor-Infiltrating Lymphocytes in Patients with Metastatic Melanoma: Intent-to-Treat Analysis and Efficacy after Failure to Prior Immunotherapies"; Clin Cancer Res, 19(17):0F1-0F9 (2013).

Besser, Michal J et al. "Clinical responses in a phase II study using adoptive transfer of short-term cultured tumor infiltration lymphocytes in metastatic melanoma patients." Clinical cancer research : an official journal of the American Association for Cancer Research vol. 16,9 (2010): 2646-55. doi:10.1158/1078-0432.CCR-10-0041.

Boczkowski, D. et al., "Induction of Tumor Immunity and Cytotoxic T Lymphocyte Responses Using Dendritic Cells Transfected with Messenger RNA Amplified from Tumor Cells[1]," Cancer Res., Feb. 15, 2000, 60:1028-1034.

Boyerinas, Benjamin et al., "Antibody-dependent cellular cytotoxicity (ADCC) activity of a novel anti-PD-L1 antibody avelumab (MSB0010718C) on human tumor cells," Cancer Immunol. Res. Oct. 2015, 3(10):1148-1157.

Byrne, M. et al., "Novel Hydrophobically Modified Asymmetric RNAi Compounds (sd-rxRNA) Demonstrate Robust Efficacy in the Eye," J. Ocular Pharmacology and Therapeutics, 2013, 00:00, 1-10.

Cepko and Pear, "Transduction of Genes Using Retrovirus Vectors," Cur. Prot. Mol. Biol. 1996, 9.9.1-9.9.16.

Chacon et al., "Co-stimulation through 4-1BB/CD137 Improves the Expansion and Function of CD8+ Melanoma Tumor-Infiltrating Lymphocytes for Adoptive T-Cell Therapy", Plos One, vol. 8, No. 4, Apr. 1, 2013, 25 pages.

Chang C.- H. et al., "Metabolic competition in the tumor microenvironment is a driver of cancer progression", Cell., Sep. 10, 2015, vol. 162, No. 6, pp. 1229-1241.

Chang et al., "Emerging concepts in immunotherapy T-cell metabolism as a therapeutic target", Nat. Immunol., Apr. 2016, 17(4), 364-368.

Chen and Okayarea, "High-Efficiency Transformation of Mammalian Cells by Plasmid DNA," Mol. Cell. Biol., Aug. 1987, 7(8):2745-2752.

Cieri, N. et al., "IL-7 and IL-15 instruct the generation of human memory stem T cells from naive precursors," Jan. 2013, Blood, 121 (4): 573-584.

Cougot, N. et al., "'Cap-tabolism'," Trends in Biochem. Sci., Aug. 2004, 29(8):436-444.

Curti, B. et al., "OX40 is a potent immune stimulating target in late stage cancer patients," Dec. 15, 2013, Cancer Res., 73(24):7189-7198.

(56) References Cited

OTHER PUBLICATIONS

Damsky, W. et al., "Mouse melanoma models and cell lines," Pigment Cell & Melanoma Res., 2010, 23:853-859.
De Marco, A., "Biotechnological applications of recombinant single-domain antibody fragments," Microbial Cell Factories, 2011, 10:44, 1-14.
Donia, M et al., "Characterization and comparison of 'standard' and 'young' tumour-infiltrating lymphocytes for adoptive cell therapy at a Danish translational research institution." Scandinavian journal of immunology vol. 75,2 (2012): 157-67.
Donia, M, et al.. "Simplified protocol for clinical-grade tumor-infiltrating lymphocyte manufacturing with use of the Wave bioreactor", Cytotherapy. Aug. 2014;16(8):1117-20. doi: 10.1016/j.jcyt.2014.02.004; PubMed PMID: 24831841.
Dudley et al., "CD8+ Enriched "Young" Tumor Infiltrating Lymphocytes Can Mediate Regression of Metastatic Melanoma" Clin Cancer Res, 16:6122-6131 (2010).
Dudley et al., "Generation of Tumor-Infiltrating Lymphocyte Cultures for Use in Adoptive Transfer Therapy for Melanoma Patients," J Immunother., 2003: 26(4): 332-342.
Dudley, et al., "Adoptive Cell Therapy for Patients with Metastatic Melanoma: Evaluation of Intensive Myeloablative Chemoradiation Preparative Regimens" , J. Clin. Oncol., Nov. 2008, 26(32), 5233-39.
Dudley, et al., "Cancer Regression and Autoimmunity in Patients After Clonal Repopulation with Antitumor Lymphocytes", Science, Oct. 2002, 298, 850-54.
Dudley, et at.. "Adoptive Cell Transfer Following Non-Myeloablative but Lymphodepleting Chemotherapy for the Treatment of Patients with Refractory Metastatic Melanoma", J. Clin. Oncol. Apr. 2005, 23(10), 2346-57.
Dull, T. et al., "A Third-Generation Lentivirus Vector with a Conditional Packaging System," J. Virology, Nov. 1998, 72, 8463-8471.
Dunn and Studier, "Complete Nucleotide Sequence of Bacteriophage T7 DNA and the Locations of T7 Genetic Elements," J. Mol. Biol., 1983, 166:477-535.
Elango, N. et al., "Optimized transfection of mRNA transcribed from a d(A/T)100 tail-containing vector," Biochem Riophys Res Commun., 2005, 330:958-966.
Eton, O. et al., "A Phase II Study of 'Decrescendo' Interleukin-2 plus Interferon-α-2a in Patients with Progressive Metastatic Melanoma after Chemotherapy," Cancer, Apr. 1, 2000, 88(7):1703-1709.
Fantozzi, A., "Mouse models of breast cancer metastasis," Breast Cancer Res., Jul. 26, 2006, 8:212, 1-11.
Fda, Tissue Guidances, http://www.fda.gov/cber/guidelines.htm, 3 pages.
Fehniger and Caligiuri, "Interleukin 15: biology and relevance to human disease," Blood Jan. 1, 2001, 97(1):14-32.
Felgner, P. et al., "Lipofection: A highly efficient, lipid-mediated DNA-transfection procedure," Proc. Natl. Acad. Sci. USA, Nov. 1987, 84:7413-7417.
Fisher, T. et al., "Targeting of 4-1BB by monoclonal antibody PF-05082566 enhances T-cell function and promotes anti-tumor activity," Cancer Immunolog. & Immunother., 2012, 61:1721-1733.
Fong, M. et al., Ovarian cancer mouse models: a summary of current models and their limitations, J. Ovarian Res., 2009, 2:12, 1-8.
Forget et al., "Activation and propagation of tumor infiltrating lymphocytes on clinical-grade designer artificial antigen presenting cells for adoptive immunotherapy of melanoma", Journal of Immunotherapy, vol. 37 No. 9, Nov. 1, 2014, pp. 448-460.
Forget, Marie-Andrée et al. "The beneficial effects of a gas-permeable flask for expansion of Tumor-Infiltrating lymphocytes as reflected in their mitochondrial function and respiration capacity." Oncoimmunology vol. 5,2 e1057386. Jun. 5, 2015, doi:10.1080/2162402X.2015.1057386.
Forget, M. et al., "A Novel Method to Generate and Expand Clinical-Grade, Genetically Modified, Tumor-Infiltrating Lymphocytes," Frontiers Immunology, Aug. 2, 2017, 8:908, 1-8.

Frank et al., "Remarkably Stable Tumor-Infiltrating Lymphocytes (TIL) for Infusion Phenotype Following Cryopreservation", Nov. 6, 2016, Retrieved from the Internet: http://www.iovance.com/wp-content/uploads/2017/05/LION16701_Frank_POSTER3_final-0005.
Fry and Mackall, Interleukin-7: from bench to clinic, Blood, Jun. 1, 2002, 99(11):3892-3904.
Garaud, Soizic et al. "A simple and rapid protocol to non-enzymatically dissociate fresh human tissues for the analysis of infiltrating lymphocytes." Journal of visualized experiments : JoVE , 94 52392. Dec. 6, 2014, doi: 10.3791/52392.
Gassner, et al., "Fludarabine modulates composition and function of the T Cell pool in patients with chronic lymphocytic leukaemia", Cancer. Immunol. Immunother., 2011, 60, 75-85.
Gattinoni, et al., "Adoptive immunotherapy for cancer: building on success", Nat. Rev. Immunol. May 2006, 6(5), 383-393.
Gattinoni, L. et al., "Wnt signaling arrests effector T cell differentiation and generates CD8+ memory stem cells," Nat. Med., Jul. 2009, 15(7):808-813.
Gattinoni, L. et al., "A human memory T-cell subset with stem cell-like properties," Nat. Med., Apr. 1, 2012, 17(10):1290-1297.
Gattinoni, L. et al., "Paths to stemness: building the ultimate antitumour T cell," Nature Rev. Cancer, Oct. 2012, 12(10):671-684.
Gautam, S. et al., "The transcription factor Myb enhances CD8+ T cell stemness and polyfunctionality to promote curative antitumor immunity," SITC 2017, Nov. 10-12, 2017, 035, 100.
Gieffers, C., et al., "APG350 Induces Superior Clustering of TRAIL Receptors and Shows Therapeutic Antitumor Efficacy Independent of Cross-Linking via Fcγ Receptors," Mol. Cancer Therapeutics, Dec. 2013, 12(12):2735-2747.
Gladstone, D E et al. "Infusion of cryopreserved autologous lymphocytes using a standard peripheral i.v. catheter." Bone marrow transplantation vol. 49,8 (2014): 1119-20. doi:10.1038/bmt.2014.98.
Glassman, A B, and C E Bennett. "Cryopreservation of human lymphocytes: a brief review and evaluation of an automated liquid nitrogen freezer." Transfusion vol. 19,2 (1979): 178-81. doi: 10.1046/j.1537-2995.1979.19279160289.x.
Goff et al., "Tumor Infiltrating Lymphocyte Therapy for Metastatic Melanoma: Analysis of Tumors Resected for TIL", J. Immunother, Oct. 2010, 33(8), 840-847.
Goff SL, et al., "Randomized, Prospective Evaluation Comparing Intensity of Lymphodepletion Before Adoptive Transfer of Tumor-Infiltrating Lymphocytes for Patients With Metastatic Melanoma", J Clin Oncol. Jul. 10, 2016;34(20):2389-97.
Graham and van der Eb, "A New Technique for the Assay of Infectivity of Human Adenovirus 5 DNA," Virology, 1973, 52:456-467.
Greisbeck, M. et al., "Sex Differences in Plasmacytoid Dendritic Cell Levels of IRF5 Drive Higher IFN-a Production in Women," The Journal of Immunology, 2015, 195:5327-5336.
Hackett, P. et al., "A Transposon and Transposase System for Human Application," Mol. Therapy, Apr. 2010, 18(4):674-683.
Hall et al., "Expansion of tumor-infiltrating lymphocytes (TIL) from human pancreatic tumors", Journal for ImmunoTherapy of Cancer, vol. 4, No. 1, pp. 1-12.
Hasan et al., "Artificial Antigen Presenting Cells: An Off the Shelf Approach for Generation of Desirable T-Cell Populations for Broad Application of Adoptive Immunotherapy", Adv Genet Eng, 2015, 4:3.
Heemskerk, Bianca et al., "Adoptive Cell Therapy for Patients with Melanoma, Using Tumor-Infiltrating Lymphocytes Genetically Engineered to Secrete Interleukin-2," Hum. Gene Ther., May 2008, 19(5):496-510.
Henning AL,et al.. Measurement of T-Cell Telomere Length Using Amplified-Signal FISH Staining and Flow Cytometry. Curr Protoc Cytom. Jan. 5, 2017;79:7.47.1-7.47.10. doi: 10.1002/cpcy.11. PubMed PMID 28055115.
Hernandez-Chacon et al., "Costimulation through the CD137/4-1BB Pathway Protects Human Melanoma Tumor-infiltrating Lymphocytes from Activation-induced Cell Death and Enhances Anti-tumor Effector Function", Journal of ImmunoTherapy, vol. 34, No. 3, Apr. 1, 2011, pp. 236-250.

(56) References Cited

OTHER PUBLICATIONS

Herreros-Villanueva, M. et al., "Mouse models of pancreatic cancer," World J. Gastroenterol., Mar. 28, 2012, 18(12):1286-1294.
Hinrichs CS, Rosenberg SA. Exploiting the curative potential of adoptive T-cell therapy for cancer. Immunol Rev. Jan. 2014;257(1):56-71. doi:10.1111/imr.12132. Review. PubMed PMID: 24329789; PubMed Central PMCID: PMC3920180.
Huang et al., "Survival, Persistence, and Progressive Differentiation of Adoptively Transferred Tumor-Reactive T Cells Associated with Tumor Regression"; J. Immunother, 28(3), 258-267 (2005).
Ikarashi, H et al., "Solid-phase anti-CD3 antibody activation and cryopreservation of human tumor-infiltrating lymphocytes derived from epithelial ovarian cancer", Japanese Journal of Cancer Research, vol. 83, No. 12, Dec. 1, 1992.
International Search Report and Written Opinion for International Patent Application No. PCT/US2017/058610 dated Mar. 8, 2018, 13 pages.
International Search Report and Written Opinion for International Patent Application No. PCT/US2018/012633 dated May 25, 2018, 14 pages.
International Search Report and Written Opinion for International Patent Application No. PCT/US2018/040474 dated Nov. 14, 2018, 17 pages.
International Search Report and Written Opinion for International Patent Application No. PCT/US2017/041241 dated Sep. 19, 2017, 13 pages.
Itzhaki, Orit et al. "Establishment and large-scale expansion of minimally cultured "young" tumor infiltrating lymphocytes for adoptive transfer therapy." Journal of immunotherapy (Hagerstown, Md. : 1997) vol. 34,2 (2011): 212-20. doi:10.1097/CJI.0b013e318209c94c.
Iyer, R.K. et al., "Industrializing Autologous Adoptive Immunotherapies: Manufacturing Advances and Challenges", Frontiers in Medicine, vol. 5, May 23, 2018.
Jia HE et al., "Ex vivo expansion of tumor-infiltrating lymphocytes from nasopharyngeal carcinoma patients for adoptive immunotherapy," Chinese Journal of Cancer, vol. 31, No. 6, Jun. 5, 2012.
Jin et al., "Enhanced clinical-scale manufacturing of TCR transduced T-cells using closed culture system modules", Journal of Transactional Medicine, col. 16. No. 1, Jan. 24, 2018.
Jin et al., "Simplified method of the growth of human tumor infiltrating lymphocytes in gas-permiable flasks to numbers needed for patient treatment", J. Immunotherapy, 2012, 35:283-292.
Junker, Niels et al. "Bimodal ex vivo expansion of T cells from patients with head and neck squamous cell carcinoma: a prerequisite for adoptive cell transfer." Cytotherapy vol. 13,7 (2011): 822-34. doi:10.3109/14653249.2011.563291.
Khvorova and Watts, "The chemical evolution of oligonucleotide therapies of clinical utility," Nat. Biotechnol., Mar. 2017, 35(3):238-248.
Kim, S., "Animal Models of Cancer in the Head and Neck Region," Clin. Exp. Otorhinolaryngol., Jun. 2009, 2(2):55-60.
Kiyama and Oishi, "In vitro transcription of a poly(dA). poly(dT)-containing sequence is inhibited by interaction between the template and its transcripts," Nuc. Acids Res., 1996, 24(22):4577-4583.
Klapper, J.A. et al., "Single-pass, closed-system rapid expansion of lymphocyte cultures for adoptive cell therapy", Journal of Immunological Methods, vol. 345, No. 1-2, Jun. 30, 2009.
Klebanoff, C. et al., "Sorting through subsets: Which T cell populations mediate highly effective adoptive immunotherapy?" J Immunother., Nov. 2012, 35(9):651-660.
Lee et al., "Tumor-Infiltrating Lymphocytes in Melanoma", Curr Oncol Rep. Aug. 2012, 14, 468-474.
Lee, D. et al., "4-1BB Signaling Activates the T Cell Factor 1 Effector/β-Catenin Pathway with Delayed Kinetics via ERK Signaling and Delayed PI3K/AKT Activation to Promote the Proliferation of CD8+ T Cells," PLOS One, Jul. 2013, 8(7): e69677, 1-11.
Levine, B. et al., "Gene transfer in humans using a conditionally replicating lentiviral vector," Proc. Nat'l Acad. Sci., Nov. 14, 2006, 103(46):17372-17377.

Li et al. MART-1-specific melanoma tumor-infiltrating lymphocytes maintaining CD28 expression have improved survival and expansion capability following antigenic restimulation in vitro. J Immunol. Jan. 1, 2010;184(1):452-65. doi: 10.4049/jimmunol.0901101. Epub Nov. 30, 2009. PubMed PMID: 19949105.
Ligtenberg, M. et al., "Self-Delivering RNAi Targeting PD-1 Improves Tumor-Specific T Cell Functionality for Adoptive Cell Therapy of Malignant Melanoma," Mol. Therapy, Jun. 2018, 26(6):1482-1493.
Macdonald et al., "Termination and Slippage by Bacteriophage T7 RNA Polymerase," J. Mol. Biol., 1993, 232:1030-1047.
Malek, T., "The Biology of Interleukin-2," Annu. Rev. Immunol., 2008, 26:453-479.
Menger, L. et al., "TALEN-Mediated Inactivation of PD-1 in Tumor-Reactive Lymphocytes Promotes Intratumoral T-cell Persistence and Rejection of Established Tumors," Cancer Res., Apr. 15, 2016, 76(8):2087-2093.
Merhavi-Shoham et al., "Adoptive Cell Therapy for Metastatic Melanoma", Cancer Journal, vol. 23, No. 1, Jan. 1, 2017.
Meuwissen, R. et al., "Mouse models for human lung cancer," Genes & Development, 2005, 19:643-664.
Monnier, P. et al., "In Vivo Applications of Single Chain Fv (Variable Domain) (scFv) Fragments," Antibodies, 2013, 2:193-208.
Mullany, L. et al., "Minireview: Animal Models and Mechanisms of Ovarian Cancer Development," Endocrinology, Apr. 2012, 153(4):1585-1592.
Mullinax et al., "Combination of Ipilimumab and Adoptive Cell Therapy with Tumor-Infiltrating Lymphocytes for Patients with Metastatic Melanoma", Frontiers in Oncology, vol. 8, Mar. 2, 2018.
Muranski, et al., "Increased intensity lymphodepletion and adoptive immunotherapy—how far can we go?", Nat. Clin. Pract. Oncol., Dec. 2006, 3, 668-681.
Nacheva and Berzal-Herranz, "Preventing nondesired RNA-primed RNA extension catalyzed by T7 RNA polymerase," Eur. J. Biochem., Feb. 2003, 270:1485-1465.
Nakano et al., "Efficient Coupled Transcription/Translation from PCR Template by a Hollow-Fiber Membrane Bioreactor," Biotechnol. Bioeng., 1999, 64:194-199.
Nelson, B., "IL-2, Regulatory T Cells, and Tolerance," J. Immunol., 2004, 172:3983-3988.
Nguyen, Linh T et al. "Expansion and characterization of human melanoma tumor-infiltrating lymphocytes (TILs)." PloS one vol. 5,11 e13940. Nov. 10, 2010, doi:10.1371/journal.pone.0013940.
NIH—U.S. National Library of Medicine, "A Phase 1 Study of MEDI0562 in Adult Subjects With Selected Advanced Solid Tumors," ClinicalTrials.gov Identifier: NCT02318394, Dec. 17, 2014, 7 pages.
NIH—U.S. National Library of Medicine, "A Study to Evaluate MEDI0562 in Combination With Immune Therapeutic Agents in Adult Subjects With Advanced Solid Tumors," ClinicalTrials.gov Identifier: NCT02705482, Mar. 10, 2016, 10 pages.
Nishikawa, M. et al., "Nonviral Vectors in the New Millennium: Delivery Barriers in Gene Transfer," Hum Gene Ther., May 20, 2001, 12:861-870.
O'Day, S. et al., "Advantages of Concurrent Biochemistry Modified by Decrescendo Interleukin-2, Granulocyte Colony-Stimulating Factor, and Tamoxifen for Patients With Metastatic Melanoma," J. Clin. Oncol., Sep. 1999, 17(9):2752-2761.
Peng, W. et al., "Transduction of Tumor-Specific T Cells with CXCR2 Chemokine Receptor Improves Migration to Tumor and Antitumor Immune Responses," Clin. Cancer Res., Nov. 15, 2010, 16(22):5458-5468.
Radvanyi, L. et al., "Specific lymphocyte subsets predict response to adoptive cell therapy using expanded autologous tumor-infiltrating lymphocytes in metastatic melanoma patients," Clin Cancer Res., Dec. 15, 2012, 18(24):6758-6770.
Riddell, et al., "Restoration of Viral Immunity in Immunodeficient Humans by the Adoptive Transfer of T Cell Clones", Science, Jul. 1992, 257, 238-41.
Robbins, et al., "Cutting Edge: Persistence of Transferred Lymphocyte Clonotypes Correlates with Cancer Regression in Patients Receiving Cell Transfer Therapy"; J. Immunol 2004; 173, 7125-7130.

(56) References Cited

OTHER PUBLICATIONS

Rohaan et al., "Adoptive transfer of tumor-infiltrating lymphocytes in melanoma: a viable treatment option", Journal for Immunotherapy of Cancer, vol. 6, No. 1, Oct. 3, 2018, pp. 1-16.
Rose, J K et al., "A new cationic liposome reagent mediating nearly quantitative transfection of animal cells," Biotechniques, Apr. 1991, 10(4):520-525.
Rosenberg SA, Dudley ME. Adoptive cell therapy for the treatment of patients with metastatic melanoma. Curr Opin Immunol. Apr. 2009;21(2):233-40.
Rosenberg SA, et al. "Durable Complete Responses in Heavily Pretreated Patients with Metastatic Melanoma Using T Cell Transfer Immunotherapy", Clinical Cancer research, vol. 17, No. 13, Jul. 1, 2011 pp. 4550-4557.
Rosenberg, "IL-2: The First Effective Immunotherapy for Human Cancer," The Journal of Immunology, col. 192, No. 12, Jun. 6, 2014.
Rosenberg, S A et al. "A new approach to the adoptive immunotherapy of cancer with tumor-infiltrating lymphocytes." Science (New York, N.Y.) vol. 233,4770 (1986): 1318-21. doi:10.1126/science.3489291.
Rosenberg, S A et al. "Treatment of patients with metastatic melanoma with autologous tumor-infiltrating lymphocytes and interleukin 2." Journal of the National Cancer Institute vol. 86,15 (1994): 1159-66. doi:10.1093/jnci/86.15.1159.
Rosenberg, S A et al. "Use of tumor-infiltrating lymphocytes and interleukin-2 in the immunotherapy of patients with metastatic melanoma. A preliminary report." The New England journal of medicine vol. 319,25 (1988): 1676-80. doi:10.1056/NEJM198812223192527.
Rufer N, et al., "Telomere length dynamics in human lymphocyte subpopulations measured by flow cytometry", Nat Biotechnol. Aug. 1998; 16(8):743-7. PubMed PMID: 9702772.
Ruby, C. et al., "OX40-Enhanced Tumor Rejection and Effector T Cell Differentiation Decreases with Age," J. Immunother., 2009, 182:1481-1489.
Sadeghi, et al., "Rapid expansion of T cells: Effects of culture and cryopreservation and improtance of short-term cell recovery", Acta Oncologica 2013, 52, 978-986.
Saeboe-Larssen, S. et al., "mRNA-based electrotransfection of human dendritic cells and induction of cytotoxic T lymphocyte responses against the telomerase catalytic subunit (hTERT)," J. Immunol. Meth., 2002, 259:191-203.
Sano, D. et al., "Xenograft models of head and neck cancers," Head Neck Oncol., Aug. 13, 2009, 1:32, 1-6.
Santegoets, S. J., J Transl Med., 2013, 11:37 (https://www.ncbi.nlm.nih.gov/pmc/articles/PMC36267970.
Schenborn and Mierendorf, "A novel transcription property of SP6 and T7 RNA polymerases: dependence on template structure," Nuc. Acids Res., 1985, 13(17):6223-6236.
Schietinger, A. et al. "Tumor-Specific T Cell Dysfunction Is a Dynamic Antigen-Driven Differentiation Program Initiated Early during Tumorigenesis," Immunity, 2016, 45:389-401.
Schiltz, P M et al. "Characterization of tumor-infiltrating lymphocytes derived from human tumors for use as adoptive immunotherapy of cancer." Journal of immunotherapy (Hagerstown, Md. : 1997) vol. 20,5 (1997): 377-86. doi:10.1097/00002371-199709000-00007.
Segal, et al., Clin. Cancer Res. 2016, available at http:/dx.doi.org/10.1158/1078-0432.CCR-16-1272.
Sharei, A. et al. "A vector-free microfluidic platform for intracellular delivery," PNAS, Feb. 5, 2013, 110(6): 2082-2087.
Sharei, A. et al., "Ex Vivo Cytosolic Delivery of Functional Macromolecules to Immune Cells," Plos One, Apr. 13, 2015, 10(4): e0118803, 1-12.
Shen X,et al.. Persistence of tumor infiltrating lymphocytes in adoptive immunotherapy correlates with telomere length. J Immunother. Jan. 2007;30(1):123-9. PubMed PMID:17198091; PubMed Central PMCID: PMC2151201.
Somerville RP, et al.. Clinical scale rapid expansion of lymphocytes for adoptive cell transfer therapy in the WAVER® bioreactor. J Transl Med. Apr. 4, 2012(10):69.
Spiess, P J et al. "In vivo antitumor activity of tumor-infiltrating lymphocytes expanded in recombinant interleukin-2." Journal of the National Cancer Institute vol. 79,5 (1987): 1067-75.
Spolski and Leonard, "Interleukin-21: a double-edged sword with therapeutic potential," Nat. Rev. Drug. Disc., May 2014, 13:379-395.
Steinke and Borish, "Th2 cytokines and asthma Interleukin-4: its role in the pathogenesis of asthma, and targeting it for asthma treatment with interleukin-4 receptor antagonists," Respir. Res., 2001, 2:66-70.
Stepinski, J., Synthesis and properties of mRNAs containing the novel 'anti-reverse' cap analogs 7-methyl(3'-O-methyl)GpppG and 7-methyl(3'-deoxy) GpppG,, RNA, 2001, 7:1468-1495.
Stewart, M. et al., "In vitro and ex vivo strategies for intracellular delivery," Oct. 13, 2016, 538:183-192.
Sunshine, Joel et al., "PD-1/PD-L1 inhibitors," Curr. Opin. Pharmacol., Aug. 2015, 23:32-38.
Swartz, M., "Tumor Microenvironment Complexity: Emerging Roles in Cancer Therapy," et al., Cancer Res., May 15, 2012, 72(10):2473-2480.
Sznol, Mario et al., "Antagonist Antibodies to PD-1 and B7-H1 (PD-L1) in the Treatment of Advanced Human Cancer", Clin. Cancer Res., Mar. 1, 2013, 19(5):1021-1034.
Tran et al., "Minimally Cultured tumor-infiltrating lymphocytes display optimal characteristics for adoptive cell therapy", 2008, J. Immunother., Oct. 2008 31(8), 742-751.
Triana-Alonso, F. et al., "Self-coded 3'-Extension of Run-off Transcripts Produces Aberrant Products during in Vitro Transcription with T7 RNA Polymerase," J. Biol. Chem., Mar. 17, 1995, 270(11):6298-6307.
Tsong, T., "Electroporation of cell membranes," Biophys. J., Aug. 1991, 60:297-306.
Tsoukas et al., "Activation of resting T lymphocytes by anti-CD3 (T3) antibodies in the absence of monocytes", J. Immunol. 1985, 135, 1719.
Van den Bossche, J. et al. "Metabolic Characterization of Polarized M1 and M2 Bone Marrow-derived Macrophages Using Real-time Extracellular Flux Analysis." Journal of visualized experiments : JoVE , 105 53424. Nov. 28, 2015, doi: 10.3791/53424.
Vizcardo, R. et al., "Regeneration of Human Tumor Antigen-Specific T Cells from iPSCs Derived from Mature CD8+ T Cells," Cell Stem Cell, Jan. 3, 2013, 12:31-36.
Wang & Riviere, "Manufacture of tumor- and virus-specific T lymphocytes for adoptive cell therapies", Cancer Gene Therapy, 2015, 22: 85-94.
Wardell et al., "A cryopreserved tumor infiltrating lymphocyte (TIL) product for LN-44", Nov. 8, 2017, retrieved from the Internet: URL: http://www.iovance.com/wp-content/uploads/2017/11/SITC2017_Seth_poster_FINAL_SWDE_PRINT_7Nov2017.pdf.
Weinberg, A. et al., "Anti-OX40 (CD134) Administration to Non-human Primates: Immunostimulatory Effects and Toxicokinetic Study," J. Immunother. Nov./Dec. 2006, 29(6):575-585.
Wigler, M. et al., "DNA-mediated transfer of the adenine phosphoribosyltransferase locus into mammalian cells," Proc. Natl. Acad. Sci., Mar. 1979, 76(3):1373-1376.
Wilson Wolf Manufacturing, G-Rex for T Cell Therapy, G-Rex: The Gold Standard for T Cell Therapy, https://www.wilsonwolf.com/q-rex-t-cell/.
Ye, et al., "Engineered Artificial antigen presenting cells facilitate direct and efficient expansion of tumor infiltrating lymphocytes", J. Translat. Med. 2011, 9(131), 13 pages.
Zhou J, et al.. Telomere length of transferred lymphocytes correlates with in vivo persistence and tumor regression in melanoma patients receiving cell transfer therapy. J Immunol. Nov. 15, 2005;175(10):7046-52. PubMed PMID: 16272366; PubMed Central Pmcid: PMC135131.
Zhou, et al., "Persistence of Multiple Tumor-Specific T-Cell Clones Is Associated with Complete Tumor Regression in a Melanoma Patient Receiving Adoptive Cell Transfer Therapy"; J. Immunother, 28, 53-62 (2005).
Zufferey, R. et al., "Multiply attenuated lentiviral vector achieves efficient gene delivery in vivo," Nat. Biotechnol., Sep. 1997, 15:871-875.

(56) References Cited

OTHER PUBLICATIONS

Zuliani, T. et al., "Value of large scale expansion of tumor infiltrating lymphocytes in a compartmentalised gas-permiable bag: interests for adoptive immunotherapy", Journal of Translational Medicine, vol. 9, No. 1, May 16, 2011.
Chacon, J. A., "Co-Stimulation through 4-1BB/CD137 Improves the Expansion and Function of CD8+ Melanoma Tumor-Infiltrating Lymphocytes for Adoptive T-Cell Therapy," Plos One, Apr. 2013, 8(4):e60031, pp. 1-14.
Duraiswamy, J. et al., "Dual Blockade of PD-1 and CTLA-4 Combined with Tumor Vaccine Effectively Restores T-Cell Rejection Function in Tumors," Cancer Res, Jun. 15, 2013, 73(12):3591-3603.
Forget, M. et al., "Activation and propagation of tumor infiltrating lymphocytes on clinical-grade designer artificial antigen presenting cells for adoptive immunotherapy of melanoma," J Immunother., 2014, 37(9): 448-460.
Hall, M. et al., "Expansion of tumor-infiltrating lymphocytes (TIL) from human pancreatic tumors," Journal for Immuno Therapy of Cancer, 2016, 4:61, pp. 1-12.
He, J. et al., "Ex vivo expansion of tumor-infiltrating lymphocytes from nasopharyngeal carcinoma patients for adoptive immunotherapy," Chin J Cancer, 2012, 31(6): 287-294.
Hernandez-Chacon, J. A., et al., "Co-stimulation through the CD137/4-1BB pathway protects human melanoma tumor-infiltrating lymphocytes from activation-induced cell death and enhances anti-tumor effector function," J Immunother., Apr. 2011, 34(3): 236-250.
Somerville, R. et al., "Clinical scale rapid expansion of lymphocytes for adoptive cell transfer therapy in the WAVE® bioreactor," Journal of Translational Medicine, 2012, 10:69, pp. 1-11.
Yang, Z. et al., "Small interfering RNA (siRNA)-mediated knockdown of Notch1 suppresses tumor growth and enhances the effect of IL-2 immunotherapy in malignant melanoma," JBUON, 2015, 20(6): 1553-1564.
Heemskerk, B. et al., "Adoptive Cell Therapy for Patients with Melanoma, Using-Tumor-Infiltrating Lymphocytes Genetically Engineered to Secrete Interleukin-2," Hum. Gene. Ther., May 2008, 19(5):496-510.
Jin, J. et al., "Simplified Method of the Growth of Human Tumor Infiltrating Lymphocytes (TIL) in Gas-Permeable Flasks to Numbers Needed for Patient Treatment," J. Immunother., Apr. 2012, 35(3):283-292.
U.S. Appl. No. 15/863,634, filed Jan. 5, 2018, now U.S. Pat. No. 10,894,063.
U.S. Appl. No. 15/874,718, filed Jan. 18, 2018, now U.S. Pat. No. 10,166,257.
U.S. Appl. No. 15/892,311, filed Feb. 8, 2018, now U.S. Pat. No. 10,130,659.
U.S. Appl. No. 16/136,147, filed Sep. 19, 2018, now U.S. Pat. No. 10,272,113.
U.S. Appl. No. 16/136,157, filed Sep. 19, 2018, now U.S. Pat. No. 10,420,799.
U.S. Appl. No. 16/201,957, filed Nov. 27, 2018, now U.S. Pat. No. 10,398,734.
U.S. Appl. No. 16/192,707, filed Nov. 15, 2018, now U.S. Pat. No. 10,537,595.
U.S. Appl. No. 16/425,746, filed May 29, 2019, now U.S. Pat. No. 10,639,330.
U.S. Appl. No. 16/203,467, filed Nov. 28, 2018, now U.S. Pat. No. 10,463,697.
U.S. Appl. No. 16/203,478, filed Nov. 28, 2018, now U.S. Pat. No. 10,363,273.
U.S. Appl. No. 16/425,767, filed May 29, 2019, now U.S. Pat. No. 10,695,372.
U.S. Appl. No. 16/425,778, filed May 29, 2019, now U.S. Pat. No. 10,646,517.
U.S. Appl. No. 16/746,416, filed Jan. 17, 2020, now U.S. Pat. No. 10,653,723.
U.S. Appl. No. 16/848,361, filed Apr. 14, 2020, now U.S. Pat. No. 10,905,718.
U.S. Appl. No. 16/848,386, filed Apr. 14, 2020, now U.S. Pat. No. 10,953,046.
U.S. Appl. No. 16/848,454, filed Apr. 14, 2020, now U.S. Pat. No. 10,946,044.
U.S. Appl. No. 16/848,426, filed Apr. 14, 2020, now U.S. Pat. No. 10,953,047.
U.S. Appl. No. 16/848,442, filed Apr. 14, 2020, now U.S. Pat. No. 10,933,094.
U.S. Appl. No. 16/848,474, filed Apr. 14, 2020, now U.S. Pat. No. 10,946,045.
U.S. Appl. No. 16/879,711, filed May 20, 2020, now U.S. Pat. No. 10,925,900.
U.S. Appl. No. 17/110,207, filed Dec. 2, 2020, now U.S. Pat. No. 11,083,752.
U.S. Appl. No. 17/127,768, filed Dec. 18, 2020, now U.S. Pat. No. 11,007,225.
U.S. Appl. No. 17/127,840, filed Dec. 18, 2020, now U.S. Pat. No. 11,052,116.
U.S. Appl. No. 17/127,790, filed Dec. 18, 2020, now U.S. Pat. No. 11,007,226.
U.S. Appl. No. 17/127,795, filed Dec. 18, 2020, now U.S. Pat. No. 11,052,115.
U.S. Appl. No. 17/147,073, filed Jan. 12, 2021, now U.S. Pat. No. 11,013,770.
U.S. Appl. No. 17/147,080, filed Jan. 12, 2021.
U.S. Appl. No. 17/147,090, filed Jan. 12, 2021, now U.S. Pat. No. 11,040,070.
U.S. Appl. No. 17/147,096, filed Jan. 12, 2021.
U.S. Appl. No. 17/326,088, filed May 20, 2021, now U.S. Pat. No. 11,202,803.
U.S. Appl. No. 17/382,831, filed Jul. 22, 2021, now U.S. Pat. No. 11,241,456.
U.S. Appl. No. 17/383,272, filed Jul. 22, 2021, now U.S. Pat. No. 11,202,804.
U.S. Appl. No. 17/383,276, filed Jul. 22, 2021, now U.S. Pat. No. 11,273,180.
U.S. Appl. No. 17/383,280, filed Jul. 22, 2021, now U.S. Pat. No. 11,304,979.
U.S. Appl. No. 17/480,525, filed Sep. 21, 2021, now U.S. Pat. No. 11,273,181.
U.S. Appl. No. 17/480,534, filed Sep. 21, 2021, now U.S. Pat. No. 11,291,687.
U.S. Appl. No. 17/480,587, filed Sep. 21, 2021, now U.S. Pat. No. 11,344,579.
U.S. Appl. No. 17/480,596, filed Sep. 21, 2021, now U.S. Pat. No. 11,337,998.
U.S. Appl. No. 17/856,793, filed Jul. 1, 2022.
U.S. Appl. No. 17/856,800, filed Jul. 1, 2022, now U.S. Pat. No. 11,517,592.
U.S. Appl. No. 17/856,806, filed Jul. 1, 2022.
U.S. Appl. No. 17/817,207, filed Aug. 3, 2022, now allowed.
U.S. Appl. No. 17/817,273, filed Aug. 3, 2022.
U.S. Appl. No. 17/817,276, filed Aug. 3, 2022, now allowed.
U.S. Appl. No. 17/817,217, filed Aug. 3, 2022.
U.S. Appl. No. 17/817,279, filed Aug. 3, 2022, now U.S. Pat. No. 11,541,077.
U.S. Appl. No. 17/817,226, filed Aug. 3, 2022, now allowed.
U.S. Appl. No. 17/817,232, filed Aug. 3, 2022, now allowed.
U.S. Appl. No. 17/817,239, filed Aug. 3, 2022.
U.S. Appl. No. 17/817,281, filed Aug. 3, 2022, now U.S. Pat. No. 11,529,372.
U.S. Appl. No. 17/817,247, filed Aug. 3, 2022.
U.S. Appl. No. 15/751,440, filed Feb. 8, 2018, now U.S. Pat. No. 11,026,974.
U.S. Appl. No. 15/892,331, filed Feb. 8, 2018, now U.S. Pat. No. 10,517,894.
U.S. Appl. No. 17/225,993, filed Apr. 8, 2021, now U.S. Pat. No. 11,058,728.
U.S. Appl. No. 17/233,290, filed Apr. 16, 2021, now U.S. Pat. No. 11,179,419.
U.S. Appl. No. 17/233,295, filed Apr. 16, 2021, now U.S. Pat. No. 11,123,371.

(56) References Cited

OTHER PUBLICATIONS

U.S. Appl. No. 17/233,299, filed Apr. 16, 2021, now U.S. Pat. No. 11,141,438.
U.S. Appl. No. 17/459,988, filed Aug. 27, 2021, now U.S. Pat. No. 11,304,980.
U.S. Appl. No. 17/480,900, filed Sep. 21, 2021, now U.S. Pat. No. 11,311,578.
U.S. Appl. No. 17/480,916, filed Sep. 21, 2021, now U.S. Pat. No. 11,351,197.
U.S. Appl. No. 17/480,919, filed Sep. 21, 2021, now U.S. Pat. No. 11,351,198.
U.S. Appl. No. 17/480,935, filed Sep. 21, 2021, now U.S. Pat. No. 11,344,580.
U.S. Appl. No. 17/480,941, filed Sep. 21, 2021, now U.S. Pat. No. 11,266,694.
U.S. Appl. No. 17/548,502, filed Dec. 11, 2021, now U.S. Pat. No. 11,364,266.
U.S. Appl. No. 17/548,504, filed Dec. 11, 2021, now U.S. Pat. No. 11,369,637.
U.S. Appl. No. 17/547,190, filed Dec. 9, 2021, now U.S. Pat. No. 11,344,581.
U.S. Appl. No. 17/547,192, filed Dec. 9, 2021, now U.S. Pat. No. 11,351,199.
U.S. Appl. No. 17/829,087, filed May 31, 2022.
U.S. Appl. No. 17/819,209, filed Aug. 11, 2022.
U.S. Appl. No. 17/819,214, filed Aug. 11, 2022.
U.S. Appl. No. 17/819,219, filed Aug. 11, 2022.
U.S. Appl. No. 17/819,909, filed Aug. 11, 2022.
U.S. Appl. No. 17/819,910, filed Aug. 11, 2022.
U.S. Appl. No. 15/940,901, filed Mar. 29, 2018, now U.S. Pat. No. 10,918,666.
U.S. Appl. No. 17/041,305, filed Sep. 24, 2020.
U.S. Appl. No. 17/110,179, filed Dec. 2, 2020.
U.S. Appl. No. 17/147,412, filed Jan. 12, 2021.
U.S. Appl. No. 17/148,475, filed Jan. 13, 2021, now U.S. Pat. No. 11,168,303.
U.S. Appl. No. 17/148,508, filed Jan. 13, 2021, now U.S. Pat. No. 11,168,304.
U.S. Appl. No. 17/353,430, filed Jun. 21, 2021, now U.S. Pat. No. 11,254,913.
U.S. Appl. No. 17/823,445, filed Aug. 30, 2022.
U.S. Appl. No. 17/823,448, filed Aug. 30, 2022.
U.S. Appl. No. 17/823,454, filed Aug. 30, 2022.
U.S. Appl. No. 17/823,419, filed Aug. 30, 2022.
U.S. Appl. No. 16/618,039, filed Nov. 27, 2019.
U.S. Appl. No. 16/211,159, filed Dec. 5, 2018.

* cited by examiner

Process Development

| Step | Current Process-1C | New Process-2A | Impact |
|---|---|---|---|
| 1 | 4 Fragments/10 G-Rex 10-21 Days | 40 Fragments/1-G-Rex 100 CS- (x2?) 11 Days | Increases Tumor Sample/Container, Shortens Culture, Reduces Steps, Amenable To Closed System |
| 2 | PreREP Freeze-> Testing-> Thaw- ~Day 27->40e6TIL | Direct To REP- Day 11 - <200e6 | Shorten Process, Reduces Steps, Eliminates Testing |
| 3 | 36 G-Rex 100-~Day 30 >5e6TIL - Split ~Day 36 | 4-5 G-Rex 500CS- TIL- Split Day 16 | Reduces Steps, Closed System, Shorter REP |
| 4 | Harvest Day ~43+ Harvesting By Centrifugation | Harvest Day 22 LOVO-Automated Cell Washer | Reduces Steps, Automated, Closed System |
| 5 | Fresh Product- Hypothermosol-Single Infusion Bag | Cryopreserved Product-CS10 In $LN_2$, Multiple Aliquots | Shipping Flexibility, Patient Scheduling, Easier Release Testing, Global Trials |
| 6 | 43+ Day Process Time | 22 Day Process Time | Turnaround To Patient, Clean Room Throughput, COGs |

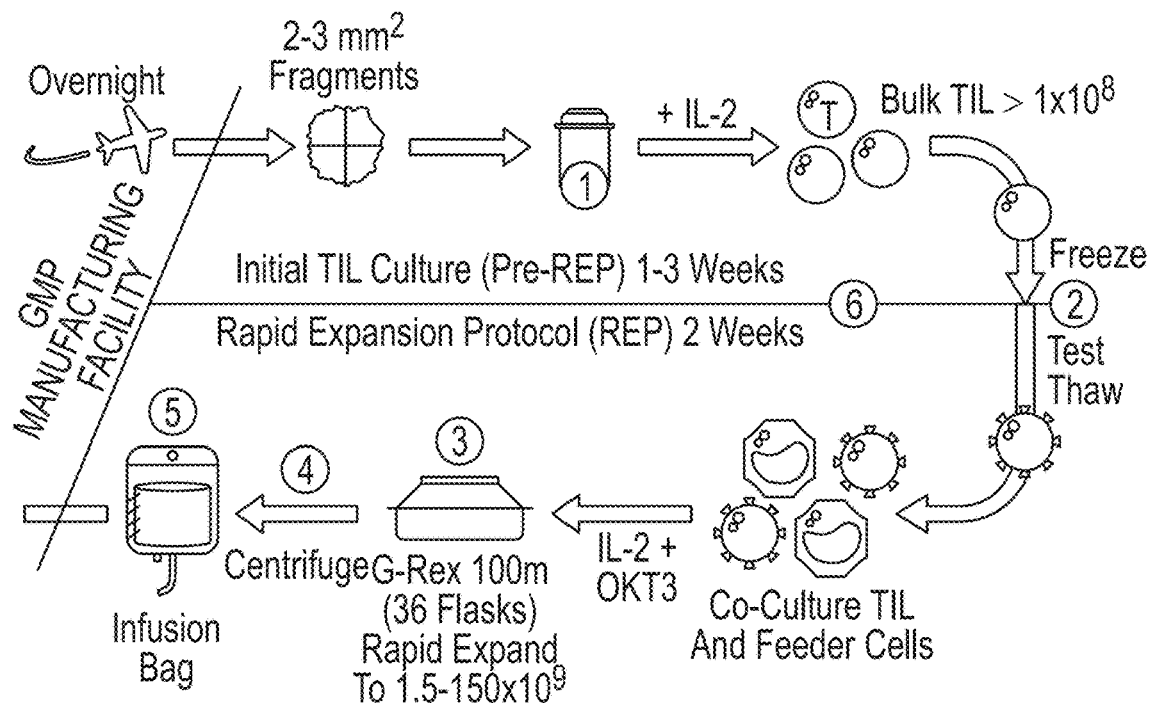

Figure 2

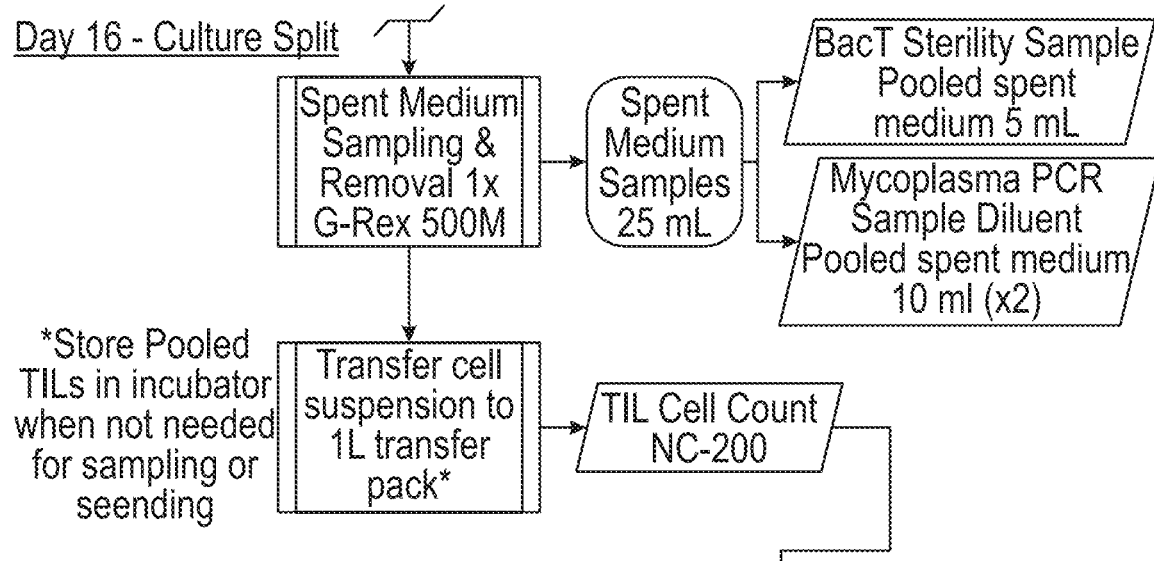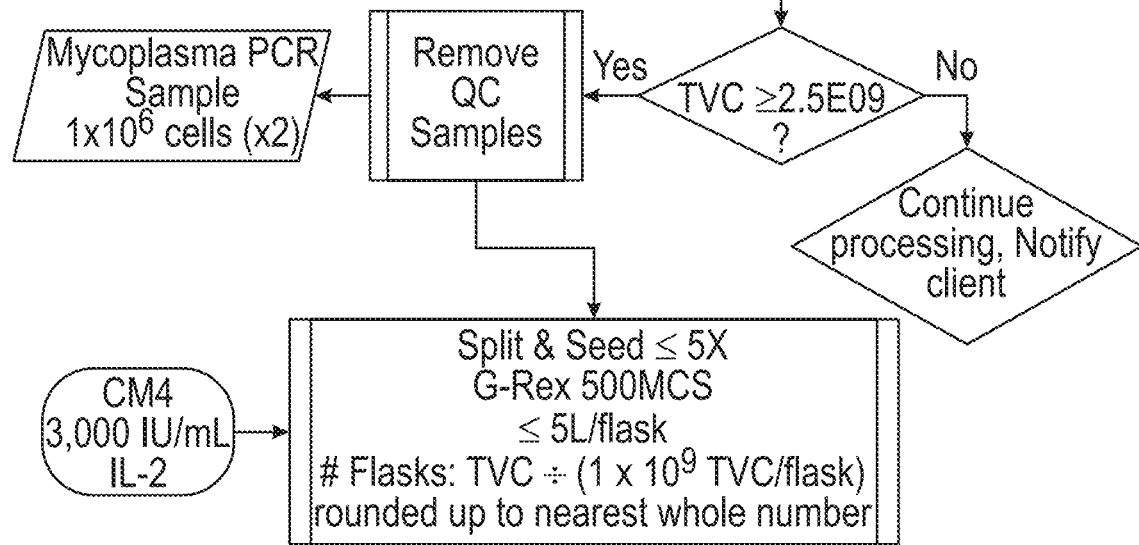
Figure 7B

Process 2A: about 22 days from Steps A - E

1. STEP A

Obtain Patient Tumor Sample

2. STEP B

Fragmentation and First Expansion 3 days to 14 days

3. STEP C

First Expansion to Second Expansion Transition

No Storage and Closed System

4. STEP D

Second Expansion

IL-2, OKT-3, and antigen-presenting feeder cells

Closed System

5. STEP E

Harvest TILS from Step D

Closed System

6. STEP F

Final Formulation and/or Transfer to Infusion Bag (optionally cryopreserve)

Figure 8

| Process 1C: 43-55 Days for Steps A - E | Process 2A: about 22 Days from Steps A - E |
|---|---|
| 1. STEP A<br>Obtain Patient Tumor Sample | 1. STEP A<br>Obtain Patient Tumor Sample |
| 2. STEP B<br>Fragmentation and First Expansion<br>11 days to 21 days | 2. STEP B<br>Fragmentation and First Expansion<br>3 days to 14 days |
| 3. STEP C<br>First Expansion to Second<br>Expansion Transition<br>Optional Storage until Selection | 3. STEP C<br>First Expansion to Second<br>Expansion Transition<br>No Storage and Closed System |
| 4. STEP D<br>Second Expansion<br>IL-2, OKT-3, antigen-presenting<br>feeder cells<br>Optionally repeat one or more times | 4. STEP D<br>Second Expansion<br>IL-2, OKT-3, antigen-presenting<br>feeder cells<br>Closed System |
| 5. STEP E<br>Harvest TILS from Step D | 5. STEP E<br>Harvest TILS from Step D<br>Closed System |
| 6. STEP F<br>Final Formulation and/or Transfer<br>to infusion Bag | 6. STEP F<br>Final Formulation and/or Transfer<br>to infusion Bag<br>(optionally cryopreserve) |

Figure 13

| Process Step | Process 1C Embodiment | Process 2A Embodiment | Advantages |
|---|---|---|---|
| Pre-REP | • 4 fragments per 10 GREX-10 flasks<br>• 11-21 day duration | • 40 fragments per 1 GREX-100M flasks<br>• 11 day duration | • Increase tumor fragments per flask<br>• Shortened culture time<br>• Reduced number of steps<br>• Amenable to closed system |
| Pre-REP to REP Transition | • Pre-REP TIL are frozen until phenotyped for selection then thawed to proceed to the REP (~day30)<br>• REP requires >40x10$^6$ TIL | • Pre-REP TIL directly move to REP on day 11<br>• REP requires 25-200 x10$^6$ TIL | • Shortened pre-REP-to-REP process<br>• Reduced number of steps<br>• Eliminated phenotyping selection<br>• Amenable to closed system |
| REP | • 6 GREX-100M flasks on REP day 0<br>• 5x10$^6$ TIL and 5x10$^8$ PBMC feeders per flask on REP day 0<br>• Split to 18-36 flasks on REP day 17<br>• 14 day duration | • 1 GREX-500M flask on day 11<br>• 25-200x10$^6$ TIL and 5x10$^9$ PBMC feeders on day 11<br>• Split to ≤ 6 GREX-500M flasks on day 16<br>• 11 day duration | • Reduce number of steps<br>• Shorter REP duration<br>• Closed system transfer to TIL between flasks<br>• Closed system media exchanges |
| Harvest | • TIL harvested via centrifugation | • TIL harvested via LOVO automated cell washing system' | • Reduce number of steps<br>• Automated cell washing<br>• Closed system<br>• Reduce loss of product during wash |
| Final Formulation | • Fresh product in Hypothermosol<br>• Single infusion bag<br>• Limited shipping stability | • Cyropreserved product in PlasmaLyte-A + 1% HSA and CS10 stored in LN$_2$<br>• Multiple aliquots<br>• Longer shipping stability | • Shipping flexibility<br>• Flexible patient scheduling<br>• More timely release testing |
| Overall Estimated Process Time | • 43-55 days | • 22 days | • Faster turnaround to patient |

Figure 14

| PROCESS STEP | GEN 1 | GEN 2 | IMPACT |
|---|---|---|---|
| Fragment Culture | ≤21 days, multiple bioreactors, multiple operator interventions | ≤11 days, single closed bioreactor, no intervention | Shortens culture, reduces interventions |
| TIL selection | IL-2 expanded TIL cryopreserved, tested, selection based on phenotype, thaw, rest, co-culture | Bulk TIL direct to co-culture | Reduces steps, eliminates testing, increases clonal diversity |
| Harvest/ Wash | Manual volume reduction and harvest. Manual wash and concentration | Closed semi-automated volume reduction and harvest. Automated wash and concentration | Reduces operator interventions, reduces processing time, maintains functionally closed system |
| Formulation | Fresh hypothermic product (2-8°C) | Cryopreserved product (≤-150°C) | Allows for global trials through increased flexibility in shipping and patient scheduling |
| Manufacturing Time | 38 day process time | 22 day process time | Turnaround to patient, clean room throughput, lower cost of goods |

Figure 16

Weld H to G

Weld H To G

| | KO | KD | KI | TR | TA |
|---|---|---|---|---|---|
| Tumor targeting (trafficking) | | | CXCR1/2<br>CD44<br>CCR4/5 | | CXCR1/2<br>CD44<br>CCR4/5 |
| Effector function/TCR signaling | PD1<br>CISH<br>VHL<br>CBL-B<br>TGFBR<br>PKA<br>LAG3<br>TIM3 | PD1<br>CISH<br>VHL<br>CBL-B<br>TGFBR<br>PKA<br>LAG3<br>TIM3 | CCR5<br>IL2, 12, or 15<br>(PD1 locus) | Pd1<br>CISH (inducible)<br>VHL<br>CBL-B<br>TGFBR<br>PKA<br>LAG3<br>TIM3 | |
| Persistence | PIK3CD<br>SOCS1 | PIK3CD<br>SOCS1 | NOTCH1/2 ICD<br>BCL2L1 | PIK3CD<br>SOCS1 | |
| Tumor targeting (specificity) | | | Neoantigen-spe TCRs | | |

Figure 33

| Chemokine | Chemokine Receptor |
|---|---|
| CCL2 (MCP-1) | CCR4/CCR2 |
| CCL3 (MIP-Iα) | CCR4 |
| CCL4 (MIP-Iβ) | CCR5 |
| CCL5 (RANTES) | CCR5 |
| CXCL1/CXCL8 | CXCR2* |
| CXCL9 (MIG) | CXCR3 |
| CXCLIO (IP-10) | CXCR3 |

Figure 34

| Chemokines overexpressed | Chemokine receptors overexpressed |
|---|---|
| CCL2 (MCP-1)<br>CCL3 (MIP-1α)<br>CCL4 (MIP1-β)<br>CCL5 (RANTES)<br>CXCL1/CXCL8 | • Healthy donor T cells were activated to overexpresss CCR1, CCR2, CCR5, CCR7, CXCR3, CXCR4.<br>• CXCR3+, CCR5+ T cells showed highest recruitment in transwell assays |
| CCL22 | CCR4<br>(Cytotoxic T cells modified to express CCR4 showed increased tumor engraftment and tumor killing) |
| CCL 17 | CCR4<br>(CD30+ CAR T cells modified to express CCR4 showed improved migration and enhanced anti-tumor activity) |
| CXCL1/CXCL8 | CXCR2<br>(PBMC derived T cells modified to express CXCR2 showed improved migration and increase in IFN-γ, production) |

Figure 35

| Target gene | sd-rxRNA sequence | RXi reagent | KD detection method |
|---|---|---|---|
| PDCD1 | Not provided | Provided | Flow cytometry |
| TIM3 (HAVCR1) | Not provided | Provided | Flow cytometry |
| CBLB | Not provided | Provided | qPCR, Flow cytometry, Western blot |
| LAG3 | Not provided | Provided | Flow cytometry |
| CISH | Not provided | Provided | qPCR, Flow cytometry, Western blot |

Figure 39

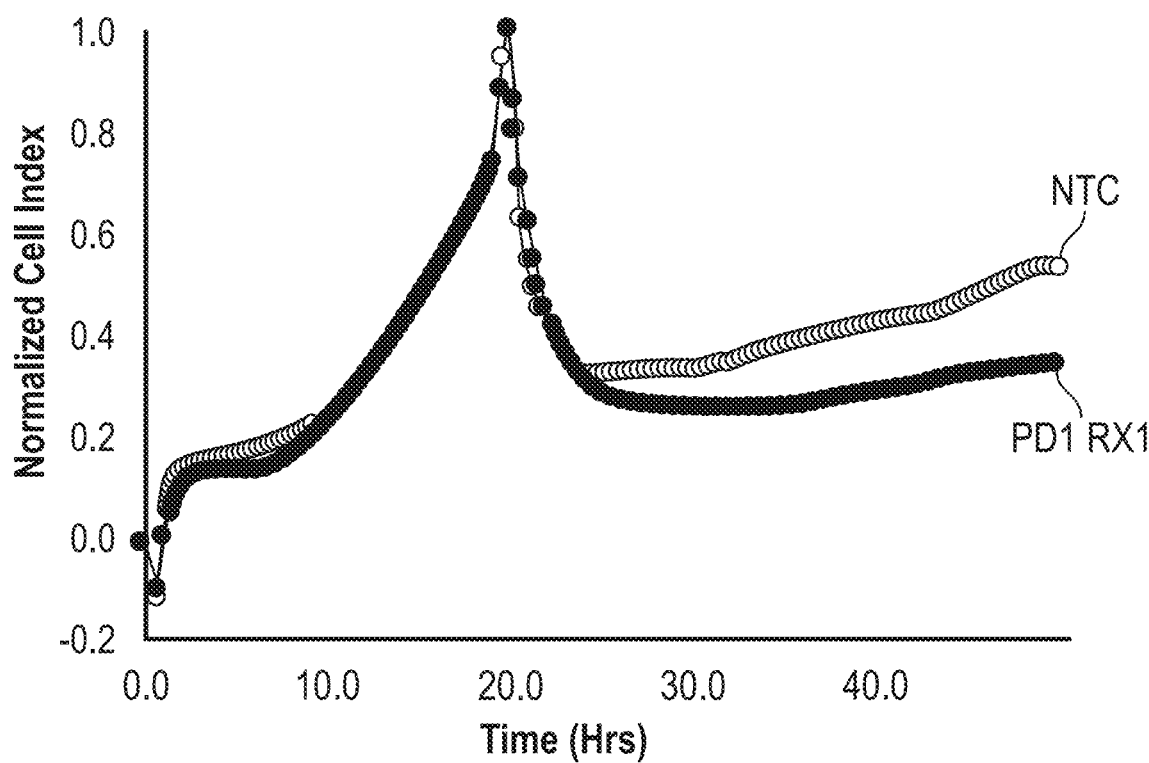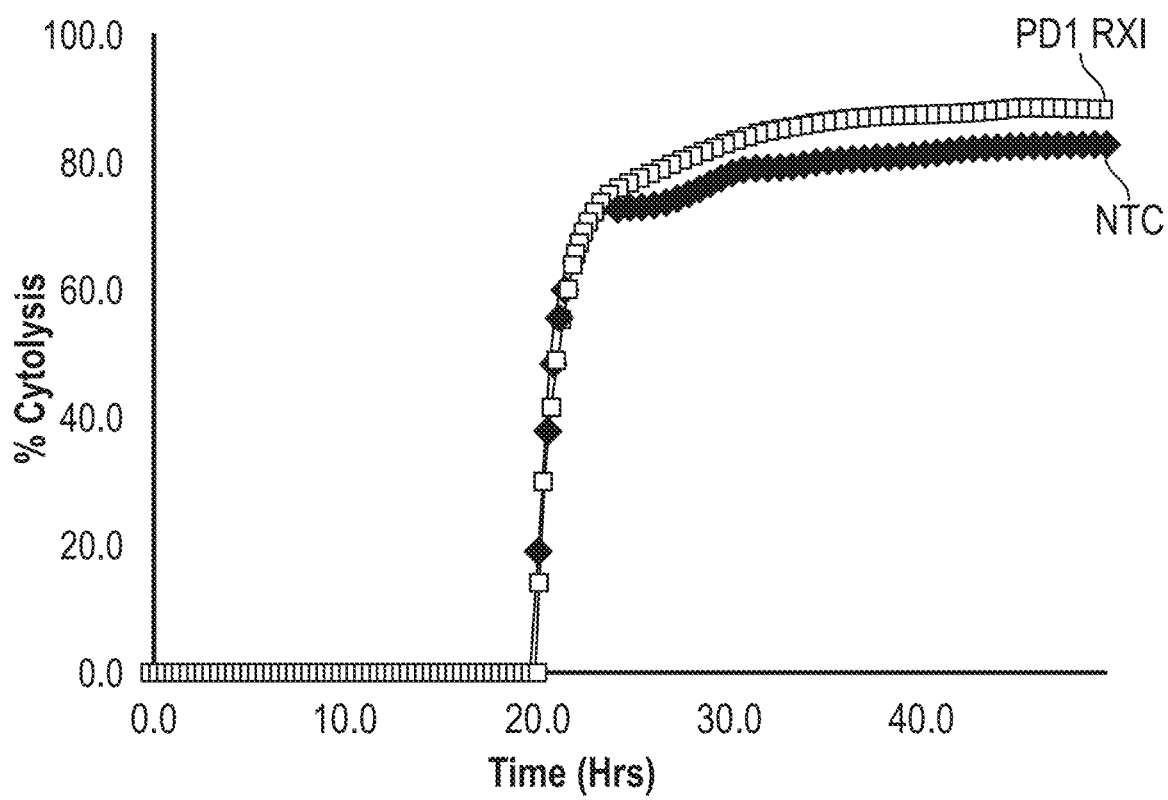
Figure 49A

- Compared the efficacy of 3 SFM with 3 tumors:
  - CTS OpTimizer (Life Tech) +/- SR or PL
  - X-vivo 20 (Lonza) +/- SR or PL
  - Prime T-CDM (Irvine) +/- SR or PL
- Tested the candidate in G-REX 5Ms (1:100 scale)
- n=3

Selection of SFM purveyor → Testing in mini-scale 2A runs

PROCESSES FOR GENERATING TIL PRODUCTS ENRICHED FOR TUMOR ANTIGEN-SPECIFIC T-CELLS

CROSS REFERENCE TO RELATED APPLICATIONS

This application is a 371 National Phase of PCT/US19/12729 filed Jan. 8, 2019, which claims priority to U.S. Provisional Patent Application No. 62/614,887, filed on Jan. 8, 2018, U.S. Provisional Patent Application No. 62/664,034, filed on Apr. 27, 2018, U.S. Provisional Patent Application No. 62/669,319, filed on May 9, 2018, U.S. Provisional Patent Application No. 62/697,921, filed on Jul. 13, 2018, U.S. Provisional Patent Application No. 62/734,868, filed on Sep. 21, 2018, and U.S. Provisional Patent Application No. 62/773,715, filed on Nov. 30, 2018, which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jan. 7, 2019, is named 116983-5034-WO_ST25.txt and is 122 kilobytes in size.

BACKGROUND OF THE INVENTION

Treatment of bulky, refractory cancers using adoptive transfer of tumor infiltrating lymphocytes (TILs) represents a powerful approach to therapy for patients with poor prognoses. Gattinoni, et al., *Nat. Rev. Immunol.* 2006, 6, 383-393. A large number of TILs are required for successful immunotherapy, and a robust and reliable process is needed for commercialization. This has been a challenge to achieve because of technical, logistical, and regulatory issues with cell expansion. IL-2-based TIL expansion followed by a "rapid expansion process" (REP) has become a preferred method for TIL expansion because of its speed and efficiency. Dudley, et al., *Science* 2002, 298, 850-54; Dudley, et al., *J. Clin. Oncol.* 2005, 23, 2346-57; Dudley, et al., *J. Clin. Oncol.* 2008, 26, 5233-39; Riddell, et al., *Science* 1992, 257, 238-41; Dudley, et al., *J. Immunother.* 2003, 26, 332-42. REP can result in a 1,000-fold expansion of TILs over a 14-day period, although it requires a large excess (e.g., 200-fold) of irradiated allogeneic peripheral blood mononuclear cells (PBMCs, also known as mononuclear cells (MNCs)), often from multiple donors, as feeder cells, as well as anti-CD3 antibody (OKT3) and high doses of IL-2. Dudley, et al., *J. Immunother.* 2003, 26, 332-42. TILs that have undergone an REP procedure have produced successful adoptive cell therapy following host immunosuppression in patients with melanoma.

There is an urgent need to provide more potent or efficacious TIL manufacturing processes and therapies based on such processes that are appropriate for commercial scale manufacturing and regulatory approval for use in human patients at multiple clinical centers. The present invention meets this need by providing transient genetic alteration processes for reprogramming TILs in order to prepare therapeutic populations of TILs with increased therapeutic efficacy.

BRIEF SUMMARY OF THE INVENTION

The present invention provides improved and/or shortened methods for expanding TILs and producing therapeutic populations of TILs.

The present invention provides a method for expanding tumor infiltrating lymphocytes (TILs) into a therapeutic population of TILs comprising: (i) obtaining a first population of TILs from a tumor resected from a patient; (ii) performing a first expansion by culturing the first population of TILs in a cell culture medium comprising IL-2, and optionally OKT-3, to produce a second population of TILs; (iii) performing a second expansion by supplementing the cell culture medium of the second population of TILs with additional IL-2, OKT-3, and antigen presenting cells (APCs), to produce a third population of TILs, wherein the third population of TILs is at least 100-fold greater in number than the second population of TILs, and wherein the second expansion is performed for at least 14 days in order to obtain the third population of TILs, wherein the third population of TILs is a therapeutic population of TILs; and (iv) exposing the second and/or third population of TILs to transcription factors (TFs) and/or other molecules capable of transiently altering protein expression, wherein the TFs and/or other molecules capable of transiently altering protein expression provide for altered expression of tumor antigens and/or an alteration in the number of tumor antigen-specific T cells in the therapeutic population of TILs.

In some embodiments, the method further comprises exposing the second and/or third population of TILs to transcription factors (TFs) and/or other molecules capable of transiently altering protein expression, wherein the TFs and/or other molecules capable of transiently altering protein expression provide for altered expression of tumor antigens and/or an alteration in the number of tumor antigen-specific T cells in the therapeutic population of TILs.

The present invention also provides a method for expanding tumor infiltrating lymphocytes (TILs) into a therapeutic population of TILs comprising:
  (a) obtaining a first population of TILs from a tumor resected from a patient by processing a tumor sample obtained from the patient into multiple tumor fragments;
  (b) adding the tumor fragments into a closed system;
  (c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
  (d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;
  (e) exposing the second and/or third population of TILs to transcription factors (TFs) and/or other molecules capable of transiently altering protein expression, wherein the TFs and/or other molecules capable of transiently altering protein expression provide for altered expression of tumor antigens and/or an alteration in the number of tumor antigen-specific T cells in the therapeutic population of TILs;

(f) harvesting the therapeutic population of TILs obtained from step (d), wherein the transition from step (d) to step (e) occurs without opening the system; and (g) transferring the harvested TIL population from step (e) to an infusion bag, wherein the transfer from step (e) to (f) occurs without opening the system.

In some embodiments, the method further comprises performing an additional second expansion before or after step (iv) by supplementing the cell culture medium of the third population of TILs with additional IL-2, additional OKT-3, and additional APCs, wherein the additional second expansion is performed for at least 14 days to obtain a larger therapeutic population of TILs than obtained in step (iii), wherein the larger therapeutic population of TILs exhibits an alteration in the number of tumor antigen-specific T cells.

In some embodiments, the method further comprises the step of cryopreserving the infusion bag comprising the harvested TIL population in step (f) using a cryopreservation process.

In some embodiments, the cryopreservation process is performed using a 1:1 ratio of harvested TIL population to cryopreservation media.

In some embodiments, the antigen-presenting cells are peripheral blood mononuclear cells (PBMCs). In some embodiments, the PBMCs are irradiated and allogeneic. In some embodiments, the PBMCs are added to the cell culture on any of days 9 through 14 in step (d). In some embodiments, the antigen-presenting cells are artificial antigen-presenting cells.

In some embodiments, the harvesting in step (e) is performed using a membrane-based cell processing system.

In some embodiments, the harvesting in step (e) is performed using a LOVO cell processing system.

In some embodiments, the multiple fragments comprise about 4 to about 50 fragments, wherein each fragment has a volume of about 27 mm$^3$.

In some embodiments, the multiple fragments comprise about 30 to about 60 fragments with a total volume of about 1300 mm$^3$ to about 1500 mm$^3$.

In some embodiments, the multiple fragments comprise about 50 fragments with a total volume of about 1350 mm$^3$.

In some embodiments, the multiple fragments comprise about 50 fragments with a total mass of about 1 gram to about 1.5 grams.

In some embodiments, the cell culture medium is provided in a container selected from the group consisting of a G-container and a Xuri cell bag.

In some embodiments, the cell culture medium in step (d) further comprises IL-15 and/or IL-21.

In some embodiments, the the IL-2 concentration is about 10,000 IU/mL to about 5,000 IU/mL.

In some embodiments, the IL-15 concentration is about 500 IU/mL to about 100 IU/mL.

In some embodiments, the IL-21 concentration is about 20 IU/mL to about 0.5 IU/mL.

In some embodiments, the infusion bag in step (f) is a HypoThermosol-containing infusion bag.

In some embodiments, the cryopreservation media comprises dimethylsulfoxide (DMSO). In some embodiments, the cryopreservation media comprises 7% to 10% dimethylsulfoxide (DMSO).

In some embodiments, the first period in step (c) and the second period in step (e) are each individually performed within a period of 10 days, 11 days, or 12 days.

In some embodiments, the first period in step (c) and the second period in step (e) are each individually performed within a period of 11 days.

In some embodiments, steps (a) through (f) are performed within a period of about 10 days to about 22 days.

In some embodiments, steps (a) through (f) are performed within a period of about 20 days to about 22 days.

In some embodiments, steps (a) through (f) are performed within a period of about 15 days to about 20 days.

In some embodiments, steps (a) through (f) are performed within a period of about 10 days to about 20 days.

In some embodiments, steps (a) through (f) are performed within a period of about 10 days to about 15 days.

In some embodiments, steps (a) through (f) are performed in 22 days or less.

In some embodiments, steps (a) through (f) are performed in 20 days or less.

In some embodiments, steps (a) through (f) are performed in 15 days or less.

In some embodiments, steps (a) through (f) are performed in 10 days or less.

In some embodiments, steps (a) through (f) and cryopreservation are performed in 22 days or less.

In some embodiments, the therapeutic population of TILs harvested in step (e) comprises sufficient TILs for a therapeutically effective dosage of the TILs.

In some embodiments, the number of TILs sufficient for a therapeutically effective dosage is from about $2.3 \times 10^{10}$ to about $13.7 \times 10^{10}$.

In some embodiments, steps (b) through (e) are performed in a single container, wherein performing steps (b) through (e) in a single container results in an increase in TIL yield per resected tumor as compared to performing steps (b) through (e) in more than one container.

In some embodiments, the antigen-presenting cells are added to the TILs during the second period in step (d) without opening the system.

In some embodiments, the third population of TILs in step (d) provides for at least a five-fold or more interferon-gamma production when administered to a subject.

In some embodiments, the risk of microbial contamination is reduced as compared to an open system.

In some embodiments, the TILs from step (f) or (g) are infused into a patient.

In some embodiments, the multiple fragments comprise about 4 fragments.

The present invention also provides a method for treating a subject with cancer, the method comprising administering expanded tumor infiltrating lymphocytes (TILs) comprising:

(a) obtaining a first population of TILs from a tumor resected from a subject by processing a tumor sample obtained from the patient into multiple tumor fragments;

(b) adding the tumor fragments into a closed system;

(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;

(e) exposing the second and/or third population of TILs to transcription factors (TFs) and/or other molecules capable of transiently altering protein expression, wherein the TFs and/or other molecules capable of transiently altering protein expression provide for increased expression of tumor antigens and/or an increase in the number of tumor antigen-specific T cells in the therapeutic population of TILs;

(f) harvesting the therapeutic population of TILs obtained from step (d), wherein the transition from step (d) to step (e) occurs without opening the system; and (g) transferring the harvested TIL population from step (e) to an infusion bag, wherein the transfer from step (e) to (f) occurs without opening the system;

(h) optionally cryopreserving the infusion bag comprising the harvested TIL population from step (f) using a cryopreservation process; and (i) administering a therapeutically effective dosage of the third population of TILs from the infusion bag in step (g) to the patient.

In some embodiments, the therapeutic population of TILs harvested in step (f) comprises sufficient TILs for administering a therapeutically effective dosage of the TILs in step (h).

In some embodiments, the number of TILs sufficient for administering a therapeutically effective dosage in step (h) is from about $2.3 \times 10^{10}$ to about $13.7 \times 10^{10}$.

In some embodiments, the antigen presenting cells (APCs) are PBMCs.

In some embodiments, the PBMCs are added to the cell culture on any of days 9 through 14 in step (d).

In some embodiments, prior to administering a therapeutically effective dosage of TIL cells in step (h), a non-myeloablative lymphodepletion regimen has been administered to the patient.

In some embodiments, the non-myeloablative lymphodepletion regimen comprises the steps of administration of cyclophosphamide at a dose of 60 mg/m2/day for two days followed by administration of fludarabine at a dose of 25 mg/m2/day for five days.

In some embodiments, the method further comprises the step of treating the patient with a high-dose IL-2 regimen starting on the day after administration of the TIL cells to the patient in step (h).

In some embodiments, the high-dose IL-2 regimen comprises 600,000 or 720,000 IU/kg administered as a 15-minute bolus intravenous infusion every eight hours until tolerance.

In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), renal cancer, and renal cell carcinoma.

In some embodiments, the cancer is selected from the group consisting of melanoma, HNSCC, cervical cancers, and NSCLC.

In some embodiments, the cancer is melanoma.
In some embodiments, the cancer is HNSCC.
In some embodiments, the cancer is a cervical cancer.
In some embodiments, the cancer is NSCLC.

The present invention also provides methods for expanding tumor infiltrating lymphocytes (TILs) into a therapeutic population of TILs comprising:

(a) adding processed tumor fragments from a tumor resected from a patient into a closed system to obtain a first population of TILs;

(b) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (a) to step (b) occurs without opening the system;

(c) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (b) to step (c) occurs without opening the system;

(d) harvesting the therapeutic population of TILs obtained from step (c), wherein the transition from step (c) to step (d) occurs without opening the system; and (e) transferring the harvested TIL population from step (d) to an infusion bag, wherein the transfer from step (d) to (e) occurs without opening the system.

In some embodiments, the therapeutic population of TILs harvested in step (d) comprises sufficient TILs for a therapeutically effective dosage of the TILs.

In some embodiments, the number of TILs sufficient for a therapeutically effective dosage is from about $2.3 \times 10^{10}$ to about $13.7 \times 10^{10}$.

In some embodiments, the method further comprises the step of cryopreserving the infusion bag comprising the harvested TIL population using a cryopreservation process.

In some embodiments, the cryopreservation process is performed using a 1:1 ratio of harvested TIL population to cryopreservation media.

In some embodiments, the antigen-presenting cells are peripheral blood mononuclear cells (PBMCs).

In some embodiments, the PBMCs are irradiated and allogeneic.

The method according to claim 68, wherein the PBMCs are added to the cell culture on any of days 9 through 14 in step (c).

In some embodiments, the antigen-presenting cells are artificial antigen-presenting cells.

In some embodiments, the harvesting in step (d) is performed using a LOVO cell processing system.

In some embodiments, the multiple fragments comprise about 4 to about 50 fragments, wherein each fragment has a volume of about 27 mm$^3$.

In some embodiments, the multiple fragments comprise about 30 to about 60 fragments with a total volume of about 1300 mm$^3$ to about 1500 mm$^3$.

In some embodiments, the multiple fragments comprise about 50 fragments with a total volume of about 1350 mm$^3$.

In some embodiments, the multiple fragments comprise about 50 fragments with a total mass of about 1 gram to about 1.5 grams.

In some embodiments, the multiple fragments comprise about 4 fragments.

In some embodiments, the second cell culture medium is provided in a container selected from the group consisting of a G-container and a Xuri cell bag.

In some embodiments, the infusion bag in step (e) is a HypoThermosol-containing infusion bag.

In some embodiments, the first period in step (b) and the second period in step (c) are each individually performed within a period of 10 days, 11 days, or 12 days.

In some embodiments, the first period in step (b) and the second period in step (c) are each individually performed within a period of 11 days.

In some embodiments, steps (a) through (e) are performed within a period of about 10 days to about 22 days.

In some embodiments, steps (a) through (e) are performed within a period of about 10 days to about 20 days.

In some embodiments, steps (a) through (e) are performed within a period of about 10 days to about 15 days.

In some embodiments, steps (a) through (e) are performed in 22 days or less.

In some embodiments, steps (a) through (e) and cryopreservation are performed in 22 days or less.

In some embodiments, steps (b) through (e) are performed in a single container, wherein performing steps (b) through (e) in a single container results in an increase in TIL yield per resected tumor as compared to performing steps (b) through (e) in more than one container.

In some embodiments, the antigen-presenting cells are added to the TILs during the second period in step (c) without opening the system.

In some embodiments, the risk of microbial contamination is reduced as compared to an open system.

In some embodiments, the TILs from step (e) are infused into a patient.

In some embodiments, the closed container comprises a single bioreactor.

In some embodiments, the closed container comprises a G-REX-10.

In some embodiments, the closed container comprises a G-REX-100.

In some embodiments, at step (d) the antigen presenting cells (APCs) are added to the cell culture of the second population of TILs at a APC:TIL ratio of 25:1 to 100:1.

In some embodiments, the cell culture has a ratio of $2.5 \times 10^9$ APCs to $100 \times 10^6$ TILs.

In some embodiments, at step (c) the antigen presenting cells (APCs) are added to the cell culture of the second population of TILs at a APC:TIL ratio of 25:1 to 100:1.

In some embodiments, the cell culture has ratio of $2.5 \times 10^9$ APCs to $100 \times 10^6$ TILs.

The present invention also provides a population of expanded TILs for use in the treatment of a subject with cancer, wherein the population of expanded TILs is a third population of TILs obtainable by a method comprising:

(a) obtaining a first population of TILs from a tumor resected from a subject by processing a tumor sample obtained from the patient into multiple tumor fragments;

(b) adding the tumor fragments into a closed system;

(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;

(e) exposing the second and/or third population of TILs to transcription factors (TFs) and/or other molecules capable of transiently altering protein expression, wherein the TFs and/or other molecules capable of transiently altering protein expression provide for increased expression of tumor antigens and/or an increase in the number of tumor antigen-specific T cells in the therapeutic population of TILs;

(f) harvesting the therapeutic population of TILs obtained from step (d), wherein the transition from step (d) to step (e) occurs without opening the system; and (g) transferring the harvested TIL population from step (e) to an infusion bag, wherein the transfer from step (e) to (f) occurs without opening the system; and (h) optionally cryopreserving the infusion bag comprising the harvested TIL population from step (f) using a cryopreservation process.

In some embodiments, the population of TILs is for use to treat a subject with cancer according the methods described above and herein, wherein the method further comprises one or more of the features recited above and herein.

The present invention also provides assay methods for determining TIL viability. The present disclosure provides methods for assaying TILs for viability by expanding tumor infiltrating lymphocytes (TILs) into a larger population of TILs comprising:

(i) obtaining a first population of TILs which has been previously expanded;

(ii) performing a first expansion by culturing the first population of TILs in a cell culture medium comprising IL-2 to produce a second population of TILs; and (iii) performing a second expansion by supplementing the cell culture medium of the second population of TILs with additional IL-2, OKT-3, and antigen presenting cells (APCs), to produce a third population of TILs, wherein the third population of TILs is at least 100-fold greater in number than the second population of TILs, wherein the second expansion is performed for at least 14 days in order to obtain the third population of TILs, and wherein the third population of TILs is further assayed for viability.

In some embodiments, the method further comprises:
(iv) performing an additional second expansion by supplementing the cell culture medium of the third population of TILs with additional IL-2, additional OKT-3, and additional APCs, wherein the additional second expansion is performed for at least 14 days to obtain a larger population of TILs than obtained in step (iii), and wherein the third population is further assayed for viability.

In some embodiments, prior to step (i), the cells are cryopreserved.

In some embodiments, the cells are thawed prior to performing step (i).

In some embodiments, step (iv) is repeated one to four times in order to obtain sufficient TILs for analysis.

In some embodiments, steps (i) through (iii) or (iv) are performed within a period of about 40 days to about 50 days.

In some embodiments, steps (i) through (iii) or (iv) are performed within a period of about 42 days to about 48 days.

In some embodiments, steps (i) through (iii) or (iv) are performed within a period of about 42 days to about 45 days.

In some embodiments, steps (i) through (iii) or (iv) are performed within about 44 days.

In some embodiments, the cells from steps (iii) or (iv) express CD4, CD8, and TCR α β at levels similar to freshly harvested cells.

In some embodiments, the antigen presenting cells are peripheral blood mononuclear cells (PBMCs).

In some embodiments, the PBMCs are added to the cell culture on any of days 9 through 17 in step (iii).

In some embodiments, the APCs are artificial APCs (aAPCs).

In some embodiments, the method further comprises the step of transducing the first population of TILs with an expression vector comprising a nucleic acid encoding a high-affinity T cell receptor.

In some embodiments, the step of transducing occurs before step (i).

In some embodiments, the method further comprises the step of transducing the first population of TILs with an expression vector comprising a nucleic acid encoding a chimeric antigen receptor (CAR) comprising a single chain variable fragment antibody fused with at least one endodomain of a T-cell signaling molecule.

In some embodiments, the step of transducing occurs before step (i).

In some embodiments, the TILs are assayed for viability.

In some embodiments, the TILs are assayed for viability after cryopreservation.

In some embodiments, the TILs are assayed for viability after cryopreservation and after step (iv).

The present invention also provides a method for expanding tumor infiltrating lymphocytes (TILs) into a therapeutic population of TILs comprising exposing TILs to transcription factors (TFs) and/or other molecules capable of transiently altering protein expression in order to generate a therapeutic population of TILs, wherein the TFs and/or other molecules capable of transiently altering protein expression provide for increased expression of tumor antigens and/or an increase in the number of tumor antigen-specific T cells in the therapeutic population of TILs.

In some embodiments, the transient altering of protein expression results in induction of protein expression.

In some embodiments, the transient altering of protein expression results in a reduction of protein expression.

In some embodiments, one or more sd-RNA(s) is employed to reduce the transient protein expression.

The present invention also provides a method for evaluating transcription factors (TFs) and/or other molecules capable of transiently altering protein expression, wherein the method comprises expanding tumor infiltrating lymphocytes (TILs) into a therapeutic population of TILs, exposing TILs to transcription factors (TFs) and/or other molecules capable of transiently altering protein expression in order to generate a therapeutic population of TILs, wherein the TFs and/or other molecules capable of transiently altering protein expression provide for altered expression of tumor antigens and/or an alteration in the number of tumor antigen-specific T cells in the therapeutic population of TILs.

In some embodiments, the transient altering of protein expression targets a gene selected from the group consisting of PD-1, TGFBR2, CBLB (CBL-B), CISH, CCRs (chimeric co-stimulatory receptors), IL-2, IL-12, IL-15, IL-21, NOTCH 1/2 ICD, TIM3, LAG3, TIGIT, TGFβ, CCR2, CCR4, CCR5, CXCR1, CXCR2, CSCR3, CCL2 (MCP-1), CCL3 (MIP-1α), CCL4 (MIP1-β), CCL5 (RANTES), CXCL1/CXCL8, CCL22, CCL17, CXCL1/CXCL8, VHL, CD44, PIK3CD, SOCS1, and cAMP protein kinase A (PKA).

In some embodiments, the present invention provides a method for expanding tumor infiltrating lymphocytes (TILs) into a therapeutic population of TILs comprising:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising a 4-1BB agonist antibody for about 2 to 5 days;
(d) contacting the first population of TILs with at least one sd-RNA, wherein the sd-RNA is added at a concentration of 0.1 µM sd-RNA/10,000 TILs/100 µL media, 0.5 µM sd-RNA/10,000 TILs/100 µL media, 0.75 µM sd-RNA/10,000 TILs/100 µL media, 1 µM sd-RNA/10,000 TILs/100 µL media, 1.25 µM sd-RNA/10,000 TILs/100 µL media, 1.5 µM sd-RNA/10,000 TILs/100 µL media, 2 µM sd-RNA/10,000 TILs/100 µL media, 5 µM sd-RNA/10,000 TILs/100 µL media, or 10 µM sd-RNA/10,000 TILs/100 µL media, and wherein the sd-RNA is for inhibiting the expression of a molecule selected from the group consisting of PD-1, LAG-3, TIM-3, CISH, and CBLB, and combinations thereof;
(e) optionally performing a sterile electroporation step on the first population of TILs, wherein the sterile electroporation step mediates the transfer of the at least one sd-RNA;
(f) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transitions from step (c) to step (f) occur without opening the system;
(g) resting the second population of TILs for about 1 day;
(h) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transitions from step (c) to step (h) occur without opening the system;

(i) harvesting the therapeutic population of TILs obtained from step (h) to provide a harvested TIL population, wherein the transition from step (h) to step (i) occurs without opening the system, wherein the harvested population of TILs is a therapeutic population of TILs;

(j) transferring the harvested TIL population from step (i) to an infusion bag, wherein the transfer from step (i) to (j) occurs without opening the system; and (k) cryopreserving the harvested TIL population using a dimethylsulfoxide-based cryopreservation medium.

In some embodiments, the present invention provides a method for expanding tumor infiltrating lymphocytes (TILs) into a therapeutic population of TILs comprising:

(a) obtaining a first population of TILs from a tumor resected from a patient by processing a tumor sample obtained from the patient into multiple tumor fragments;

(b) adding the tumor fragments into a closed system;

(c) performing a first expansion by culturing the first population of TILs in a cell culture medium comprising IL-2 and optionally comprising a 4-1BB agonist antibody for about 2 to 5 days;

(d) contacting the first population of TILs with at least one sd-RNA, wherein the sd-RNA is added at a concentration of 0.1 μM sd-RNA/10,000 TILs, 0.5 μM sd-RNA/10,000 TILs, 0.75 μM sd-RNA/10,000 TILs, 1 μM sd-RNA/10,000 TILs, 1.25 μM sd-RNA/10,000 TILs, 1.5 μM sd-RNA/10,000 TILs, 2 μM sd-RNA/10,000 TILs, 5 μM sd-RNA/10,000 TILs, or 10 μM sd-RNA/10,000 TILs, and wherein the sd-RNA is for inhibiting the expression of a molecule selected from the group consisting of PD-1, LAG-3, TIM-3, CISH, and CBLB, and combinations thereof;

(e) optionally performing a sterile electroporation step on the first population of TILs, wherein the sterile electroporation step mediates the transfer of the at least one sd-RNA;

(f) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transitions from step (c) to step (f) occur without opening the system;

(g) resting the second population of TILs for about 1 day;

(h) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (g) to step (h) occurs without opening the system;

(i) harvesting the therapeutic population of TILs obtained from step (h) to provide a harvested TIL population, wherein the transition from step (h) to step (i) occurs without opening the system, wherein the harvested population of TILs is a therapeutic population of TILs;

(j) transferring the harvested TIL population from step (i) to an infusion bag, wherein the transfer from step (i) to (j) occurs without opening the system; and (k) cryopreserving the harvested TIL population using a dimethylsulfoxide-based cryopreservation medium.

In some embodiments, the present invention provides a method for expanding tumor infiltrating lymphocytes (TILs) into a therapeutic population of TILs comprising:

(a) obtaining a first population of TILs from a tumor resected from a patient by processing a tumor sample obtained from the patient into multiple tumor fragments;

(b) adding the tumor fragments into a closed system;

(c) performing a first expansion by culturing the first population of TILs in a cell culture medium comprising IL-2 and optionally comprising a 4-1BB agonist antibody for about 2 to 5 days;

(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;

(e) resting the second population of TILs for about 1 day;

(f) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transitions from step (c) to step (f) occur without opening the system;

(g) contacting the second population of TILs during any of steps (d), (e), and/or (f) with at least one sd-RNA, wherein the sd-RNA is added at a concentration of 0.1 μM sd-RNA/10,000 TILs/100 μL media, 0.5 μM sd-RNA/10,000 TILs/100 μL media, 0.75 μM sd-RNA/10,000 TILs/100 μL media, 1 μM sd-RNA/10,000 TILs/100 μL media, 1.25 μM sd-RNA/10,000 TILs/100 μL media, 1.5 μM sd-RNA/10,000 TILs/100 μL media, 2 μM sd-RNA/10,000 TILs/100 μL media, 5 μM sd-RNA/10,000 TILS/100 μL media, or 10 μM sd-RNA/10,000 TILs/100 μL media, and wherein the sd-RNA is for inhibiting the expression of a molecule selected from the group consisting of PD-1, LAG-3, TIM-3, CISH, and CBLB, and combinations thereof;

(h) optionally performing a sterile electroporation step on the second population of TILs, wherein the sterile electroporation step mediates the transfer of the at least one sd-RNA;

(i) harvesting the therapeutic population of TILs obtained from steps (g) or (h) to provide a harvested TIL population, wherein the transitions from step (g) to step (i) occur without opening the system, wherein the harvested population of TILs is a therapeutic population of TILs;

(j) transferring the harvested TIL population from step (i) to an infusion bag, wherein the transfer from step (i) to (j) occurs without opening the system; and (k) cryopreserving the harvested TIL population using a dimethylsulfoxide-based cryopreservation medium.

In some embodiments, the present invention provides a method for expanding tumor infiltrating lymphocytes (TILs) into a therapeutic population of TILs comprising:

(a) obtaining a first population of TILs from a tumor resected from a patient by processing a tumor sample obtained from the patient into multiple tumor fragments;

(b) adding the tumor fragments into a closed system;

(c) performing a first expansion by culturing the first population of TILs in a cell culture medium comprising IL-2 and optionally comprising a 4-1BB agonist antibody for about 2 to 5 days;

(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;

(e) resting the second population of TILs for about 1 day;

(f) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (e) to step (f) occurs without opening the system;

(g) contacting the second population of TILs during any of steps (d), (e), and/or (f) with at least one sd-RNA, wherein the sd-RNA is added at a concentration of 0.1 μM sd-RNA/10,000 TILs, 0.5 μM sd-RNA/10,000 TILs, 0.75 μM sd-RNA/10,000 TILs, 1 μM sd-RNA/10,000 TILs, 1.25 μM sd-RNA/10,000 TILs, 1.5 μM sd-RNA/10,000 TILs, 2 μM sd-RNA/10,000 TILs, 5 μM sd-RNA/10,000 TILs, or 10 μM sd-RNA/10,000 TILs, and wherein the sd-RNA is for inhibiting the expression of a molecule selected from the group consisting of PD-1, LAG-3, TIM-3, CISH, and CBLB, and combinations thereof;

(h) optionally performing a sterile electroporation step on the second population of TILs, wherein the sterile electroporation step mediates the transfer of the at least one sd-RNA;

(i) harvesting the therapeutic population of TILs obtained from steps (g) or (h) to provide a harvested TIL population, wherein the transitions from step (e) to step (h) occur without opening the system, wherein the harvested population of TILs is a therapeutic population of TILs;

(j) transferring the harvested TIL population from step (i) to an infusion bag, wherein the transfer from step (h) to (i) occurs without opening the system; and (k) cryopreserving the harvested TIL population using a dimethylsulfoxide-based cryopreservation medium.

In some embodiments, the sd-RNA is added to the first population of cells twice a day, once a day, every two days, every three days, every four days, every five days, every six days, or every seven days during the first expansion period.

In some embodiments, the sd-RNA is added to the second population of cells twice a day, once a day, every two days, every three days, every four days, every five days, every six days, or every seven days during the first expansion period.

In some embodiments, two sd-RNAs are added for inhibiting the expression of two molecules selected from the group consisting of PD-1, LAG-3, TIM-3, CISH, and CBLB.

In some embodiments, two sd-RNAs are added for inhibiting the expression of two molecules, wherein the two molecules are selected from the groups consisting of:
 i. PD-1 and LAG-3,
 ii. PD-1 and TIM-3,
 iii. PD-1 and CISH,
 iv. PD-1 and CBLB,
 v. LAG-3 and TIM-3,
 vi. LAG-3 and CISH,
 vii. LAG-3 and CBLB,
 viii. TIM-3 and CISH,
 ix. TIM-3 and CBLB, and
 x. CISH and CBLB.

In some embodiments, more than two sd-RNAs are added for inhibiting the expression of more than two molecules selected from the group consisting of PD-1, LAG-3, TIM-3, CISH, and CBLB.

In some embodiments, the expression of at least one molecule selected from the group consisting of PD-1, LAG-3, TIM-3, CISH, and CBLB is reduced by at least 80%, 85%, 90%, or 95% in the TILs contacted with the at least one sd-RNA.

In some embodiments, the expression of at least one molecule selected from the group consisting of PD-1, LAG-3, TIM-3, CISH, and CBLB is reduced by at least 80%, 85%, 90%, or 95% for at least 12 hours, at least 24 hours, or at least 48 hours, in the TILs contacted with the at least one sd-RNA.

BRIEF DESCRIPTION OF THE DRAWINGS

FIG. 2: Shows a comparison between the 1C process and an embodiment of the 2A process for TIL manufacturing.

FIG. 7A-FIG. 7C: Depicts the major steps of an embodiment of process 2A including the cryopreservation steps.

FIG. 8: Exemplary Process 2A chart providing an overview of Steps A through F.

FIG. 13: Comparison table of Steps A through F from exemplary embodiments of process 1C and process 2A.

FIG. 14: Detailed comparison of an embodiment of process 1C and an embodiment of process 2A.

FIG. 16: Table of process improvements from Gen 1 to Gen 2.

FIG. 33: Shows an overview of proposed genetic engineering approaches for transiently altering gene expression in TILs.

FIG. 34: Shows an overview of chemokines and chemokine receptors for which transiently gene expression alteration can be employed to improve TIL trafficking to the tumor site.

FIG. 35: Shows a second overview of chemokines and chemokine receptors for which transiently gene expression alteration can be employed to improve TIL trafficking to the tumor site.

FIG. 39: Chart showing Sd-rxRNA-mediated silencing of PDCD1, TIM3, CBLB, LAG3, and CISH.

FIG. 49A and FIG. 49B: PD1 KD TILs elicited greater killing efficiency. A) Representative figure of killing efficiency. B) Representative figure of n=3, Melanoma TILs, 2 uM sd-rxRNA.

BRIEF DESCRIPTION OF THE SEQUENCE LISTING

Figure 1:
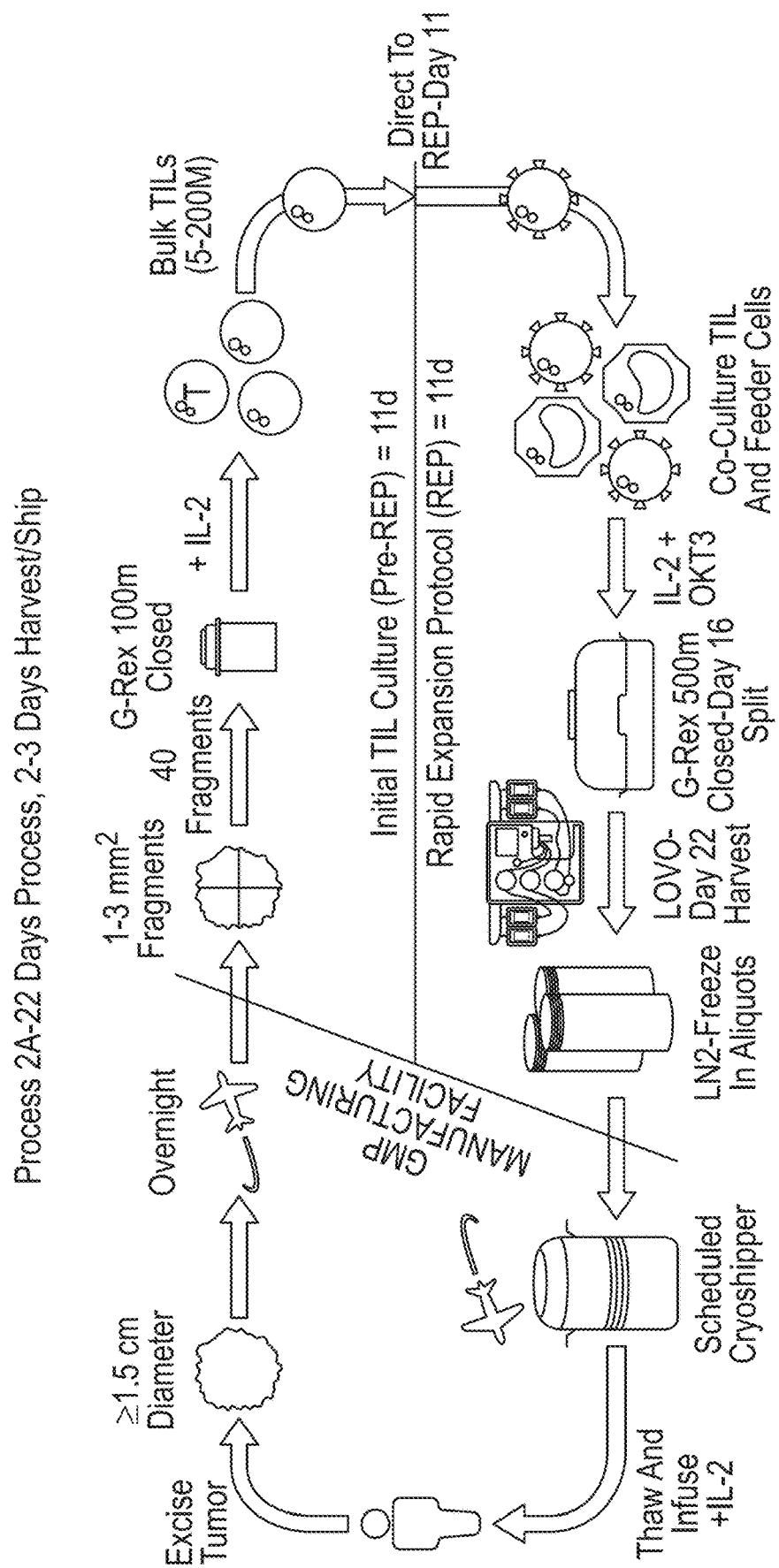
FIG. 1: Shows a diagram of an embodiment of process 2A, a 22-day process for TIL manufacturing.

SEQ ID NO:1 is the amino acid sequence of the heavy chain of muromonab.

SEQ ID NO:2 is the amino acid sequence of the light chain of muromonab.

SEQ ID NO:3 is the amino acid sequence of a recombinant human IL-2 protein.

SEQ ID NO:4 is the amino acid sequence of aldesleukin.

SEQ ID NO:5 is the amino acid sequence of a recombinant human IL-4 protein.

SEQ ID NO:6 is the amino acid sequence of a recombinant human IL-7 protein.

SEQ ID NO:7 is the amino acid sequence of a recombinant human IL-15 protein.

SEQ ID NO:8 is the amino acid sequence of a recombinant human IL-21 protein.

SEQ ID NO:9 is the amino acid sequence of human 4-1BB.

SEQ ID NO:10 is the amino acid sequence of murine 4-1BB.

SEQ ID NO:11 is the heavy chain for the 4-1BB agonist monoclonal antibody utomilumab (PF-05082566).

SEQ ID NO:12 is the light chain for the 4-1BB agonist monoclonal antibody utomilumab (PF-05082566).

SEQ ID NO:13 is the heavy chain variable region (VH) for the 4-1BB agonist monoclonal antibody utomilumab (PF-05082566).

SEQ ID NO:14 is the light chain variable region (VL) for the 4-1BB agonist monoclonal antibody utomilumab (PF-05082566).

SEQ ID NO:15 is the heavy chain CDR1 for the 4-1BB agonist monoclonal antibody utomilumab (PF-05082566).

SEQ ID NO:16 is the heavy chain CDR2 for the 4-1BB agonist monoclonal antibody utomilumab (PF-05082566).

SEQ ID NO:17 is the heavy chain CDR3 for the 4-1BB agonist monoclonal antibody utomilumab (PF-05082566).

SEQ ID NO:18 is the light chain CDR1 for the 4-1BB agonist monoclonal antibody utomilumab (PF-05082566).

SEQ ID NO:19 is the light chain CDR2 for the 4-1BB agonist monoclonal antibody utomilumab (PF-05082566).

SEQ ID NO:20 is the light chain CDR3 for the 4-1BB agonist monoclonal antibody utomilumab (PF-05082566).

SEQ ID NO:21 is the heavy chain for the 4-1BB agonist monoclonal antibody urelumab (BMS-663513).

SEQ ID NO:22 is the light chain for the 4-1BB agonist monoclonal antibody urelumab (BMS-663513).

SEQ ID NO:23 is the heavy chain variable region (VH) for the 4-1BB agonist monoclonal antibody urelumab (BMS-663513).

SEQ ID NO:24 is the light chain variable region (VL) for the 4-1BB agonist monoclonal antibody urelumab (BMS-663513).

SEQ ID NO:25 is the heavy chain CDR1 for the 4-1BB agonist monoclonal antibody urelumab (BMS-663513).

SEQ ID NO:26 is the heavy chain CDR2 for the 4-1BB agonist monoclonal antibody urelumab (BMS-663513).

SEQ ID NO:27 is the heavy chain CDR3 for the 4-1BB agonist monoclonal antibody urelumab (BMS-663513).

SEQ ID NO:28 is the light chain CDR1 for the 4-1BB agonist monoclonal antibody urelumab (BMS-663513).

SEQ ID NO:29 is the light chain CDR2 for the 4-1BB agonist monoclonal antibody urelumab (BMS-663513).

SEQ ID NO:30 is the light chain CDR3 for the 4-1BB agonist monoclonal antibody urelumab (BMS-663513).

SEQ ID NO:31 is an Fc domain for a TNFRSF agonist fusion protein.

SEQ ID NO:32 is a linker for a TNFRSF agonist fusion protein.

SEQ ID NO:33 is a linker for a TNFRSF agonist fusion protein.

SEQ ID NO:34 is a linker for a TNFRSF agonist fusion protein.

SEQ ID NO:35 is a linker for a TNFRSF agonist fusion protein.

SEQ ID NO:36 is a linker for a TNFRSF agonist fusion protein.

SEQ ID NO:37 is a linker for a TNFRSF agonist fusion protein.

SEQ ID NO:38 is a linker for a TNFRSF agonist fusion protein.

SEQ ID NO:39 is a linker for a TNFRSF agonist fusion protein.

SEQ ID NO:40 is a linker for a TNFRSF agonist fusion protein.

SEQ ID NO:41 is a linker for a TNFRSF agonist fusion protein.

SEQ ID NO:42 is an Fc domain for a TNFRSF agonist fusion protein.

SEQ ID NO:43 is a linker for a TNFRSF agonist fusion protein.

SEQ ID NO:44 is a linker for a TNFRSF agonist fusion protein.

SEQ ID NO:45 is a linker for a TNFRSF agonist fusion protein.

SEQ ID NO:46 is a 4-1BB ligand (4-1BBL) amino acid sequence.

SEQ ID NO:47 is a soluble portion of 4-1BBL polypeptide.

SEQ ID NO:48 is a heavy chain variable region (VH) for the 4-1BB agonist antibody 4B4-1-1 version 1.

SEQ ID NO:49 is a light chain variable region (VL) for the 4-1BB agonist antibody 4B4-1-1 version 1.

SEQ ID NO:50 is a heavy chain variable region (VH) for the 4-1BB agonist antibody 4B4-1-1 version 2.

SEQ ID NO:51 is a light chain variable region (VL) for the 4-1BB agonist antibody 4B4-1-1 version 2.

SEQ ID NO:52 is a heavy chain variable region (VH) for the 4-1BB agonist antibody H39E3-2.

SEQ ID NO:53 is a light chain variable region (VL) for the 4-1BB agonist antibody H39E3-2.

SEQ ID NO:54 is the amino acid sequence of human OX40.

SEQ ID NO:55 is the amino acid sequence of murine OX40.

SEQ ID NO:56 is the heavy chain for the OX40 agonist monoclonal antibody tavolixizumab (MEDI-0562).

SEQ ID NO:57 is the light chain for the OX40 agonist monoclonal antibody tavolixizumab (MEDI-0562).

SEQ ID NO:58 is the heavy chain variable region (VH) for the OX40 agonist monoclonal antibody tavolixizumab (MEDI-0562).

SEQ ID NO:59 is the light chain variable region (VL) for the OX40 agonist monoclonal antibody tavolixizumab (MEDI-0562).

SEQ ID NO:60 is the heavy chain CDR1 for the OX40 agonist monoclonal antibody tavolixizumab (MEDI-0562).

SEQ ID NO:61 is the heavy chain CDR2 for the OX40 agonist monoclonal antibody tavolixizumab (MEDI-0562).

SEQ ID NO:62 is the heavy chain CDR3 for the OX40 agonist monoclonal antibody tavolixizumab (MEDI-0562).

SEQ ID NO:63 is the light chain CDR1 for the OX40 agonist monoclonal antibody tavolixizumab (MEDI-0562).

SEQ ID NO:64 is the light chain CDR2 for the OX40 agonist monoclonal antibody tavolixizumab (MEDI-0562).

SEQ ID NO:65 is the light chain CDR3 for the OX40 agonist monoclonal antibody tavolixizumab (MEDI-0562).

SEQ ID NO:66 is the heavy chain for the OX40 agonist monoclonal antibody 11D4.

SEQ ID NO:67 is the light chain for the OX40 agonist monoclonal antibody 11D4.

SEQ ID NO:68 is the heavy chain variable region (VH) for the OX40 agonist monoclonal antibody 11D4.

SEQ ID NO:69 is the light chain variable region (VL) for the OX40 agonist monoclonal antibody 11D4.

SEQ ID NO:70 is the heavy chain CDR1 for the OX40 agonist monoclonal antibody 11D4.

SEQ ID NO:71 is the heavy chain CDR2 for the OX40 agonist monoclonal antibody 11D4.

SEQ ID NO:72 is the heavy chain CDR3 for the OX40 agonist monoclonal antibody 11D4.

SEQ ID NO:73 is the light chain CDR1 for the OX40 agonist monoclonal antibody 11D4.

SEQ ID NO:74 is the light chain CDR2 for the OX40 agonist monoclonal antibody 11D4.

SEQ ID NO:75 is the light chain CDR3 for the OX40 agonist monoclonal antibody 11D4.

SEQ ID NO:76 is the heavy chain for the OX40 agonist monoclonal antibody 18D8.

SEQ ID NO:77 is the light chain for the OX40 agonist monoclonal antibody 18D8.

SEQ ID NO:78 is the heavy chain variable region (VH) for the OX40 agonist monoclonal antibody 18D8.

SEQ ID NO:79 is the light chain variable region (VL) for the OX40 agonist monoclonal antibody 18D8.

SEQ ID NO:80 is the heavy chain CDR1 for the OX40 agonist monoclonal antibody 18D8.

SEQ ID NO:81 is the heavy chain CDR2 for the OX40 agonist monoclonal antibody 18D8.

SEQ ID NO:82 is the heavy chain CDR3 for the OX40 agonist monoclonal antibody 18D8.

SEQ ID NO:83 is the light chain CDR1 for the OX40 agonist monoclonal antibody 18D8.

SEQ ID NO:84 is the light chain CDR2 for the OX40 agonist monoclonal antibody 18D8.

SEQ ID NO:85 is the light chain CDR3 for the OX40 agonist monoclonal antibody 18D8.

SEQ ID NO:86 is the heavy chain variable region (VH) for the OX40 agonist monoclonal antibody Hu119-122.

SEQ ID NO:87 is the light chain variable region (VL) for the OX40 agonist monoclonal antibody Hu119-122.

SEQ ID NO:88 is the heavy chain CDR1 for the OX40 agonist monoclonal antibody Hu119-122.

SEQ ID NO:89 is the heavy chain CDR2 for the OX40 agonist monoclonal antibody Hu119-122.

SEQ ID NO:90 is the heavy chain CDR3 for the OX40 agonist monoclonal antibody Hu119-122.

SEQ ID NO:91 is the light chain CDR1 for the OX40 agonist monoclonal antibody Hu119-122.

SEQ ID NO:92 is the light chain CDR2 for the OX40 agonist monoclonal antibody Hu119-122.

SEQ ID NO:93 is the light chain CDR3 for the OX40 agonist monoclonal antibody Hu119-122.

SEQ ID NO:94 is the heavy chain variable region (VH) for the OX40 agonist monoclonal antibody Hu106-222.

SEQ ID NO:95 is the light chain variable region (VL) for the OX40 agonist monoclonal antibody Hu106-222.

SEQ ID NO:96 is the heavy chain CDR1 for the OX40 agonist monoclonal antibody Hu106-222.

SEQ ID NO:97 is the heavy chain CDR2 for the OX40 agonist monoclonal antibody Hu106-222.

SEQ ID NO:98 is the heavy chain CDR3 for the OX40 agonist monoclonal antibody Hu106-222.

SEQ ID NO:99 is the light chain CDR1 for the OX40 agonist monoclonal antibody Hu106-222.

SEQ ID NO:100 is the light chain CDR2 for the OX40 agonist monoclonal antibody Hu106-222.

SEQ ID NO:101 is the light chain CDR3 for the OX40 agonist monoclonal antibody Hu106-222.

SEQ ID NO:102 is an OX40 ligand (OX40L) amino acid sequence.

SEQ ID NO:103 is a soluble portion of OX40L polypeptide.

SEQ ID NO:104 is an alternative soluble portion of OX40L polypeptide.

SEQ ID NO:105 is the heavy chain variable region (VH) for the OX40 agonist monoclonal antibody 008.

SEQ ID NO:106 is the light chain variable region (VL) for the OX40 agonist monoclonal antibody 008.

SEQ ID NO:107 is the heavy chain variable region (VH) for the OX40 agonist monoclonal antibody 011.

SEQ ID NO:108 is the light chain variable region (VL) for the OX40 agonist monoclonal antibody 011.

SEQ ID NO:109 is the heavy chain variable region (VH) for the OX40 agonist monoclonal antibody 021.

SEQ ID NO:110 is the light chain variable region (VL) for the OX40 agonist monoclonal antibody 021.

SEQ ID NO:111 is the heavy chain variable region (VH) for the OX40 agonist monoclonal antibody 023.

SEQ ID NO:112 is the light chain variable region (VL) for the OX40 agonist monoclonal antibody 023.

SEQ ID NO:113 is the heavy chain variable region (VH) for an OX40 agonist monoclonal antibody.

SEQ ID NO:114 is the light chain variable region (VL) for an OX40 agonist monoclonal antibody.

SEQ ID NO:115 is the heavy chain variable region (VH) for an OX40 agonist monoclonal antibody.

SEQ ID NO:116 is the light chain variable region (VL) for an OX40 agonist monoclonal antibody.

SEQ ID NO:117 is the heavy chain variable region (VH) for a humanized OX40 agonist monoclonal antibody.

SEQ ID NO:118 is the heavy chain variable region (VH) for a humanized OX40 agonist monoclonal antibody.

SEQ ID NO:119 is the light chain variable region (VL) for a humanized OX40 agonist monoclonal antibody.

SEQ ID NO:120 is the light chain variable region (VL) for a humanized OX40 agonist monoclonal antibody.

SEQ ID NO:121 is the heavy chain variable region (VH) for a humanized OX40 agonist monoclonal antibody.

SEQ ID NO:122 is the heavy chain variable region (VH) for a humanized OX40 agonist monoclonal antibody.

SEQ ID NO:123 is the light chain variable region (VL) for a humanized OX40 agonist monoclonal antibody.

SEQ ID NO:124 is the light chain variable region (VL) for a humanized OX40 agonist monoclonal antibody.

SEQ ID NO:125 is the heavy chain variable region (VH) for an OX40 agonist monoclonal antibody.

SEQ ID NO:126 is the light chain variable region (VL) for an OX40 agonist monoclonal antibody.

DETAILED DESCRIPTION OF THE INVENTION

I. Introduction

Adoptive cell therapy utilizing TILs cultured ex vivo by the Rapid Expansion Protocol (REP) has produced successful adoptive cell therapy following host immunosuppression in patients with melanoma. Current infusion acceptance parameters rely on readouts of the composition of TILs (e.g., CD28, CD8, or CD4 positivity) and on the numerical folds of expansion and viability of the REP product.

Current REP protocols give little insight into the health of the TIL that will be infused into the patient. T cells undergo a profound metabolic shift during the course of their maturation from naïve to effector T cells (see Chang, et al., *Nat. Immunol.* 2016, 17, 364, hereby expressly incorporated in its entirety, and in particular for the discussion and markers of anaerobic and aerobic metabolism). For example, naïve T cells rely on mitochondrial respiration to produce ATP, while mature, healthy effector T cells such as TIL are highly glycolytic, relying on aerobic glycolysis to provide the bioenergetics substrates they require for proliferation, migration, activation, and anti-tumor efficacy.

Current TIL manufacturing processes are limited by length, cost, sterility concerns, and other factors described herein such that the potential to commercialize such processes is severely limited, and for these and other reasons, at the present time no commercial process has become available. The present invention provides TIL manufacturing processes employing transient protein expression alteration methodologies and therapies based on such processes that are appropriate for commercial scale manufacturing and regulatory approval for use in human patients at multiple clinical centers. The present invention provides transient genetic alteration processes for reprogramming TILs in order to prepare therapeutic populations of TILs with increased therapeutic efficacy.

II. Definitions

Unless defined otherwise, all technical and scientific terms used herein have the same meaning as is commonly understood by one of skill in the art to which this invention belongs. All patents and publications referred to herein are incorporated by reference in their entireties.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "ex vivo" refers to an event which involves treating or performing a procedure on a cell, tissue and/or organ which has been removed from a subject's body. Aptly, the cell, tissue and/or organ may be returned to the subject's body in a method of surgery or treatment.

The term "rapid expansion" means an increase in the number of antigen-specific TILs of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week. A number of rapid expansion protocols are outlined below.

By "tumor infiltrating lymphocytes" or "TILs" herein is meant a population of cells originally obtained as white blood cells that have left the bloodstream of a subject and migrated into a tumor. TILs include, but are not limited to, $CD8^+$ cytotoxic T cells (lymphocytes), Th1 and Th17 $CD4^+$ T cells, natural killer cells, dendritic cells and M1 macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs and expanded TILs ("REP TILs" or "post-REP TILs"). TIL cell populations can include genetically modified TILs.

By "population of cells" (including TILs) herein is meant a number of cells that share common traits. In general, populations generally range from $1 \times 10^6$ to $1 \times 10^{10}$ in number, with different TIL populations comprising different numbers. For example, initial growth of primary TILs in the presence of IL-2 results in a population of bulk TILs of roughly $1 \times 10^8$ cells. REP expansion is generally done to provide populations of $1.5 \times 10^9$ to $1.5 \times 10^{10}$ cells for infusion.

By "cryopreserved TILs" herein is meant that TILs, either primary, bulk, or expanded (REP TILs), are treated and stored in the range of about −150° C. to −60° C. General methods for cryopreservation are also described elsewhere herein, including in the Examples. For clarity, "cryopreserved TILs" are distinguishable from frozen tissue samples which may be used as a source of primary TILs.

By "thawed cryopreserved TILs" herein is meant a population of TILs that was previously cryopreserved and then treated to return to room temperature or higher, including but not limited to cell culture temperatures or temperatures wherein TILs may be administered to a patient.

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally and alternatively, TILs can be functionally defined by their ability to infiltrate solid tumors upon reintroduction into a patient.

The term "cryopreservation media" or "cryopreservation medium" refers to any medium that can be used for cryopreservation of cells. Such media can include media comprising 7% to 10% DMSO. Exemplary media include CryoStor CS10, Hyperthermasol, as well as combinations thereof. The term "CS10" refers to a cryopreservation medium which is obtained from Stemcell Technologies or from Biolife Solutions. The CS10 medium may be referred to by the trade name "CryoStor® CS10". The CS10 medium is a serum-free, animal component-free medium which comprises DMSO.

The term "central memory T cell" refers to a subset of T cells that in the human are CD45R0+ and constitutively express CCR7 ($CCR7^{hi}$) and CD62L ($CD62^{hi}$). The surface phenotype of central memory T cells also includes TCR, CD3, CD127 (IL-7R), and IL-15R. Transcription factors for central memory T cells include BCL-6, BCL-6B, MBD2, and BMI1. Central memory T cells primarily secret IL-2 and CD40L as effector molecules after TCR triggering. Central memory T cells are predominant in the CD4 compartment in blood, and in the human are proportionally enriched in lymph nodes and tonsils.

The term "effector memory T cell" refers to a subset of human or mammalian T cells that, like central memory T cells, are CD45R0+, but have lost the constitutive expression of CCR7 ($CCR7^{lo}$) and are heterogeneous or low for CD62L expression) ($CD62L^{lo}$). The surface phenotype of central memory T cells also includes TCR, CD3, CD127 (IL-7R), and IL-15R. Transcription factors for central memory T cells include BLIMP1. Effector memory T cells rapidly secret high levels of inflammatory cytokines following antigenic stimulation, including interferon-γ, IL-4, and IL-5. Effector memory T cells are predominant in the CD8 compartment in blood, and in the human are proportionally enriched in the lung, liver, and gut. CD8+ effector memory T cells carry large amounts of perforin.

The term "closed system" refers to a system that is closed to the outside environment. Any closed system appropriate for cell culture methods can be employed with the methods of the present invention. Closed systems include, for example, but are not limited to closed G-containers. Once a tumor segment is added to the closed system, the system is no opened to the outside environment until the TILs are ready to be administered to the patient.

The terms "fragmenting," "fragment," and "fragmented," as used herein to describe processes for disrupting a tumor, includes mechanical fragmentation methods such as crushing, slicing, dividing, and morcellating tumor tissue as well as any other method for disrupting the physical structure of tumor tissue.

The terms "peripheral blood mononuclear cells" and "PBMCs" refers to a peripheral blood cell having a round nucleus, including lymphocytes (T cells, B cells, NK cells) and monocytes. Preferably, the peripheral blood mononuclear cells are irradiated allogeneic peripheral blood mononuclear cells. PBMCs are a type of antigen-presenting cell.

The term "anti-CD3 antibody" refers to an antibody or variant thereof, e.g., a monoclonal antibody and including human, humanized, chimeric or murine antibodies which are directed against the CD3 receptor in the T cell antigen receptor of mature T cells. Anti-CD3 antibodies include OKT-3, also known as muromonab. Anti-CD3 antibodies also include the UHCT1 clone, also known as T3 and CD3ε. Other anti-CD3 antibodies include, for example, otelixizumab, teplizumab, and visilizumab.

The term "OKT-3" (also referred to herein as "OKT3") refers to a monoclonal antibody or biosimilar or variant thereof, including human, humanized, chimeric, or murine antibodies, directed against the CD3 receptor in the T cell antigen receptor of mature T cells, and includes commercially-available forms such as OKT-3 (30 ng/mL, MACS GMP CD3 pure, Miltenyi Biotech, Inc., San Diego, CA, USA) and muromonab or variants, conservative amino acid substitutions, glycoforms, or biosimilars thereof. The amino acid sequences of the heavy and light chains of muromonab are given in Table 1 (SEQ ID NO:1 and SEQ ID NO:2). A hybridoma capable of producing OKT-3 is deposited with the American Type Culture Collection and assigned the ATCC accession number CRL 8001. A hybridoma capable of producing OKT-3 is also deposited with European Collection of Authenticated Cell Cultures (ECACC) and assigned Catalogue No. 86022706.

TABLE 1

Amino acid sequences of muromonab.

| Identifier | Sequence (One-Letter Amino Acid Symbols) | | | | | |
|---|---|---|---|---|---|---|
| SEQ ID NO: 1 | QVQLQQSGAE | LARPGASVKM | SCKASGYTFT | RYTMHWVKQR | PGQGLEWIGY | INPSRGYTNY | 60 |
| Muromonab heavy | NQKFKDKATL | TTDKSSSTAY | MQLSSLTSED | SAVYYCARYY | DDHYCLDYWG | QGTTLTVSSA | 120 |
| chain | KTTAPSVYPL | APVCGGTTGS | SVTLGCLVKG | YFPEPVTLTW | NSGSLSSGVH | TFPAVLQSDL | 180 |
| | YTLSSSVTVT | SSTWPSQSIT | CNVAEPASST | KVDKKIEPRP | KSCDKTHTCP | PCPAPELLGG | 240 |
| | PSVFLFPPKP | KDTLMISRTP | EVTCVVVDVS | HEDPEVKFNW | YVDGVEVHNA | KTKPREEQYN | 300 |
| | STYRVVSVLT | VLHQDWLNGK | EYKCKVSNKA | LPAPIEKTIS | KAKGQPREPQ | VYTLPPSRDE | 360 |
| | LTKNQVSLTC | LVKGFYPSDI | AVEWESNGQP | ENNYKTTPPV | LDSDGSFFLY | SKLTVDKSRW | 420 |
| | QQGNVFSCSV | MHEALHNHYT | QKSLSLSPGK | | | | 450 |
| SEQ ID NO: 2 | QIVLTQSPAI | MSASPGEKVT | MTCSASSSVS | YMNWYQQKSG | TSPKRWIYDT | SKLASGVPAH | 60 |
| Muromonab light | FRGSGSGTSY | SLTISGMEAE | DAATYYCQQW | SSNPFTFGSG | TKLEINRADT | APTVSIFPPS | 120 |
| chain | SEQLTSGGAS | VVCFLNNFYP | KDINVKWKID | GSERQNGVLN | SWTDQDSKDS | TYSMSSTLTL | 180 |
| | TKDEYERHNS | YTCEATHKTS | TSPIVKSFNR | NEC | | | 213 |

The term "IL-2" (also referred to herein as "IL2") refers to the T cell growth factor known as interleukin-2, and includes all forms of IL-2 including human and mammalian forms, conservative amino acid substitutions, glycoforms, biosimilars, and variants thereof. IL-2 is described, e.g., in Nelson, *J. Immunol.* 2004, 172, 3983-88 and Malek, *Annu. Rev. Immunol.* 2008, 26, 453-79, the disclosures of which are incorporated by reference herein. The amino acid sequence of recombinant human IL-2 suitable for use in the invention is given in Table 2 (SEQ ID NO:3). For example, the term IL-2 encompasses human, recombinant forms of IL-2 such as aldesleukin (PROLEUKIN, available commercially from multiple suppliers in 22 million IU per single use vials), as well as the form of recombinant IL-2 commercially supplied by CellGenix, Inc., Portsmouth, NH, USA (CELL-GRO GMP) or ProSpec-Tany TechnoGene Ltd., East Brunswick, NJ, USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The amino acid sequence of aldesleukin suitable for use in the invention is given in Table 2 (SEQ ID NO:4). The term IL-2 also encompasses pegylated forms of IL-2, as described herein, including the pegylated IL2 prodrug NKTR-214, available from Nektar Therapeutics, South San Francisco, CA, USA. NKTR-214 and pegylated IL-2 suitable for use in the invention is described in U.S. Patent Application Publication No. US 2014/0328791 A1 and International Patent Application Publication No. WO 2012/065086 A1, the disclosures of which are incorporated by reference herein. Alternative forms of conjugated IL-2 suitable for use in the invention are described in U.S. Pat. Nos. 4,766,106, 5,206,344, 5,089,261 and 4902,502, the disclosures of which are incorporated by reference herein. Formulations of IL-2 suitable for use in the invention are described in U.S. Pat. No. 6,706,289, the disclosure of which is incorporated by reference herein.

TABLE 2

Amino acid sequences of interleukins.

| Identifier | Sequence (One-Letter Amino Acid Symbols) | |
|---|---|---|
| SEQ ID NO: 3 recombinant human IL-2 (rhIL-2) | MAPTSSSTKK TQLQLEHLLL DLQMILNGIN NYKNPKLTRM LTFKFYMPKK ATELKHLQCL<br>EEELKPLEEV LNLAQSKNFH LRPRDLISNI NVIVLELKGS ETTFMCEYAD ETATIVEFLN<br>RWITFCQSII STLT | 60<br>120<br>134 |
| SEQ ID NO: 4 Aldesleukin | PTSSSTKKTQ LQLEHLLLDL QMILNGINNY KNPKLTRMLT FKFYMPKKAT ELKHLQCLEE<br>ELKPLEEVLN LAQSKNFHLR PRDLISNINV IVLELKGSET TFMCEYADET ATIVEFLNRW<br>ITFSQSIIST LT | 60<br>120<br>132 |
| SEQ ID NO: 5 recombinant human IL-4 (rhIL-4) | MHKCDITLQE IIKTLNSLTE QKTLCTELTV TDIFAASKNT TEKETFCRAA TVLRQFYSHH<br>EKDTRCLGAT AQQFHRHKQL IRFLKRLDRN LWGLAGLNSC PVKEANQSTL ENFLERLKTI<br>MREKYSKCSS | 60<br>120<br>130 |
| SEQ ID NO: 6 recombinant human IL-7 (rhIL-7) | MDCDIEGKDG KQYESVLMVS IDQLLDSMKE IGSNCLNNEF NFFKRHICDA NKEGMFLFRA<br>ARKLRQFLKM NSTGDFDLHL LKVSEGTTIL LNCTGQVKGR KPAALGEAQP TKSLEENKSL<br>KEQKKLNDLC FLKRLLQEIK TCWNKILMGT KEH | 60<br>120<br>153 |
| SEQ ID NO: 7 recombinant human IL-15 (rhIL-15) | MNWVNVISDL KKIEDLIQSM HIDATLYTES DVHPSCKVTA MKCFLLELQV ISLESGDASI<br>HDTVENLIIL ANNSLSSNGN VTESGCKECE ELEEKNIKEF LQSFVHIVQM FINTS | 60<br>115 |
| SEQ ID NO: 8 recombinant human IL-21 (rhIL-21) | MQDRHMIRMR QLIDIVDQLK NYVNDLVPEF LPAPEDVETN CEWSAFSCFQ KAQLKSANTG<br>NNERIINVSI KKLRKPPST NAGRRQKHRL TCPSCDSYEK KPPKEFLERF KSLLQKMIHQ<br>HLSSRTHGSE DS | 60<br>120<br>132 |

The term "IL-4" (also referred to herein as "IL4") refers to the cytokine known as interleukin 4, which is produced by Th2 T cells and by eosinophils, basophils, and mast cells. IL-4 regulates the differentiation of naïve helper T cells (Th0 cells) to Th2 T cells. Steinke and Borish, *Respir. Res.* 2001, 2, 66-70. Upon activation by IL-4, Th2 T cells subsequently produce additional IL-4 in a positive feedback loop. IL-4 also stimulates B cell proliferation and class II MHC expression, and induces class switching to IgE and $IgG_1$ expression from B cells. Recombinant human IL-4 suitable for use in the invention is commercially available from multiple suppliers, including ProSpec-Tany TechnoGene Ltd., East Brunswick, NJ, USA (Cat. No. CYT-211) and ThermoFisher Scientific, Inc., Waltham, MA, USA (human IL-15 recombinant protein, Cat. No. Gibco CTP0043). The amino acid sequence of recombinant human IL-4 suitable for use in the invention is given in Table 2 (SEQ ID NO:5).

The term "IL-7" (also referred to herein as "IL7") refers to a glycosylated tissue-derived cytokine known as interleukin 7, which may be obtained from stromal and epithelial cells, as well as from dendritic cells. Fry and Mackall, *Blood* 2002, 99, 3892-904. IL-7 can stimulate the development of T cells. IL-7 binds to the IL-7 receptor, a heterodimer consisting of IL-7 receptor alpha and common gamma chain receptor, which in a series of signals important for T cell development within the thymus and survival within the periphery. Recombinant human IL-7 suitable for use in the invention is commercially available from multiple suppliers, including ProSpec-Tany TechnoGene Ltd., East Brunswick, NJ, USA (Cat. No. CYT-254) and ThermoFisher Scientific, Inc., Waltham, MA, USA (human IL-15 recombinant protein, Cat. No. Gibco PHC0071). The amino acid sequence of recombinant human IL-7 suitable for use in the invention is given in Table 2 (SEQ ID NO:6).

The term "IL-15" (also referred to herein as "IL15") refers to the T cell growth factor known as interleukin-15, and includes all forms of IL-2 including human and mammalian forms, conservative amino acid substitutions, glycoforms, biosimilars, and variants thereof. IL-15 is described, e.g., in Fehniger and Caligiuri, *Blood* 2001, 97, 14-32, the disclosure of which is incorporated by reference herein. IL-15 shares β and γ signaling receptor subunits with IL-2. Recombinant human IL-15 is a single, non-glycosylated polypeptide chain containing 114 amino acids (and an N-terminal methionine) with a molecular mass of 12.8 kDa. Recombinant human IL-15 is commercially available from multiple suppliers, including ProSpec-Tany TechnoGene Ltd., East Brunswick, NJ, USA (Cat. No. CYT-230-b) and ThermoFisher Scientific, Inc., Waltham, MA, USA (human IL-15 recombinant protein, Cat. No. 34-8159-82). The amino acid sequence of recombinant human IL-15 suitable for use in the invention is given in Table 2 (SEQ ID NO:7).

The term "IL-21" (also referred to herein as "IL21") refers to the pleiotropic cytokine protein known as interleukin-21, and includes all forms of IL-21 including human and mammalian forms, conservative amino acid substitutions, glycoforms, biosimilars, and variants thereof. IL-21 is described, e.g., in Spolski and Leonard, *Nat. Rev. Drug. Disc.* 2014, 13, 379-95, the disclosure of which is incorporated by reference herein. IL-21 is primarily produced by natural killer T cells and activated human CD4⁺ T cells. Recombinant human IL-21 is a single, non-glycosylated polypeptide chain containing 132 amino acids with a molecular mass of 15.4 kDa. Recombinant human IL-21 is commercially available from multiple suppliers, including ProSpec-Tany TechnoGene Ltd., East Brunswick, NJ, USA (Cat. No. CYT-408-b) and ThermoFisher Scientific, Inc., Waltham, MA, USA (human IL-21 recombinant protein, Cat. No. 14-8219-80). The amino acid sequence of recombinant human IL-21 suitable for use in the invention is given in Table 2 (SEQ ID NO:8).

When "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the tumor infiltrating lymphocytes (e.g. secondary TILs or genetically modified cytotoxic lymphocytes) described herein may be administered at a dosage of $10^4$ to $10^{11}$ cells/kg body weight (e.g., $10^5$ to $10^6$, $10^5$ to $10^{10}$, $10^5$ to $10^{11}$, $10^6$ to $10^{10}$, $10^6$ to $10^{11}$, $10^7$ to $10^{11}$, $10^7$ to $10^{10}$, $10^8$ to $10^{11}$, $10^8$ to $10^{10}$, $10^9$ to $10^{11}$, or $10^9$ to $10^{10}$ cells/kg body weight), including all integer values within those ranges. Tumor infiltrating lymphocytes (including in some cases, genetically modified cytotoxic lymphocytes) compositions may also be administered multiple times at these dosages. The tumor infiltrating lymphocytes (including in some cases, genetically) can be administered by using infusion techniques that are commonly known in immunotherapy (see, e.g., Rosenberg et al., *New Eng. J. of Med.* 319: 1676, 1988). The optimal dosage and treatment regime for a particular patient can readily be determined by one skilled in the art of medicine by monitoring the patient for signs of disease and adjusting the treatment accordingly.

The term "hematological malignancy" refers to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

The term "solid tumor" refers to an abnormal mass of tissue that usually does not contain cysts or liquid areas. Solid tumors may be benign or malignant. The term "solid tumor cancer refers to malignant, neoplastic, or cancerous solid tumors. Solid tumor cancers include, but are not limited to, sarcomas, carcinomas, and lymphomas, such as cancers of the lung, breast, prostate, colon, rectum, and bladder. The tissue structure of solid tumors includes interdependent tissue compartments including the parenchyma (cancer cells) and the supporting stromal cells in which the cancer cells are dispersed and which may provide a supporting microenvironment.

The term "liquid tumor" refers to an abnormal mass of cells that is fluid in nature. Liquid tumor cancers include, but are not limited to, leukemias, myelomas, and lymphomas, as well as other hematological malignancies. TILs obtained from liquid tumors may also be referred to herein as marrow infiltrating lymphocytes (MILs).

The term "microenvironment," as used herein, may refer to the solid or hematological tumor microenvironment as a whole or to an individual subset of cells within the microenvironment. The tumor microenvironment, as used herein, refers to a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz, et al., Cancer Res., 2012, 72, 2473. Although tumors express antigens that should be recognized by T cells, tumor clearance by the immune system is rare because of immune suppression by the microenvironment.

In an embodiment, the invention includes a method of treating a cancer with a population of TILs, wherein a patient is pre-treated with non-myeloablative chemotherapy prior to an infusion of TILs according to the invention. In some embodiments, the population of TILs may be provided wherein a patient is pre-treated with nonmyeloablative chemotherapy prior to an infusion of TILs according to the present invention. In an embodiment, the non-myeloablative chemotherapy is cyclophosphamide 60 mg/kg/d for 2 days (days 27 and 26 prior to TIL infusion) and fludarabine 25 mg/m2/d for 5 days (days 27 to 23 prior to TIL infusion). In an embodiment, after non-myeloablative chemotherapy and TIL infusion (at day 0) according to the invention, the patient receives an intravenous infusion of IL-2 intravenously at 720,000 IU/kg every 8 hours to physiologic tolerance.

Experimental findings indicate that lymphodepletion prior to adoptive transfer of tumor-specific T lymphocytes plays a key role in enhancing treatment efficacy by eliminating regulatory T cells and competing elements of the immune system ("cytokine sinks"). Accordingly, some embodiments of the invention utilize a lymphodepletion step (sometimes also referred to as "immunosuppressive conditioning") on the patient prior to the introduction of the rTILs of the invention.

The terms "co-administration," "co-administering," "administered in combination with," "administering in combination with," "simultaneous," and "concurrent," as used herein, encompass administration of two or more active pharmaceutical ingredients (in a preferred embodiment of the present invention, for example, at least one potassium channel agonist in combination with a plurality of TILs) to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, or the manner of administration. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

The term "heterologous" when used with reference to portions of a nucleic acid or protein indicates that the nucleic acid or protein comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source, or coding regions from different sources. Similarly, a heterologous protein indicates that the protein comprises two or more subsequences that are not found in the same relationship to each other in nature (e.g., a fusion protein).

The terms "sequence identity," "percent identity," and "sequence percent identity" (or synonyms thereof, e.g., "99% identical") in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, California) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

As used herein, the term "variant" encompasses but is not limited to antibodies or fusion proteins which comprise an amino acid sequence which differs from the amino acid sequence of a reference antibody by way of one or more substitutions, deletions and/or additions at certain positions within or adjacent to the amino acid sequence of the reference antibody. The variant may comprise one or more conservative substitutions in its amino acid sequence as compared to the amino acid sequence of a reference antibody. Conservative substitutions may involve, e.g., the substitution of similarly charged or uncharged amino acids. The variant retains the ability to specifically bind to the antigen of the reference antibody. The term variant also includes pegylated antibodies or proteins.

By "tumor infiltrating lymphocytes" or "TILs" herein is meant a population of cells originally obtained as white blood cells that have left the bloodstream of a subject and migrated into a tumor. TILs include, but are not limited to, $CD8^+$ cytotoxic T cells (lymphocytes), Th1 and Th17 $CD4^+$ T cells, natural killer cells, dendritic cells and M1 macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs, expanded TILs ("REP TILs") as well as "reREP TILs" as discussed herein. reREP TILs can include for example second expansion TILs or second additional expansion TILs (such as, for example, those described in Step D of FIG. 8, including TILs referred to as reREP TILs).

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally, and alternatively, TILs can be functionally defined by their ability to infiltrate solid tumors upon reintroduction into a patient. TILS may further be characterized by potency—for example, TILS may be considered potent if, for example, interferon (IFN) release is greater than about 50 pg/mL, greater than about 100 pg/mL, greater than about 150 pg/mL, or greater than about 200 pg/mL.

The term "deoxyribonucleotide" encompasses natural and synthetic, unmodified and modified deoxyribonucleotides. Modifications include changes to the sugar moiety, to the base moiety and/or to the linkages between deoxyribonucleotide in the oligonucleotide.

The term "RNA" defines a molecule comprising at least one ribonucleotide residue. The term "ribonucleotide" defines a nucleotide with a hydroxyl group at the 2' position of a b-D-ribofuranose moiety. The term RNA includes double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Nucleotides of the RNA molecules described herein may also comprise non-standard nucleotides, such as non-naturally occurring nucleotides or chemically synthesized nucleotides or deoxynucleotides. These altered RNAs can be referred to as analogs or analogs of naturally-occurring RNA.

The terms "modified nucleotide" refer to a nucleotide that has one or more modifications to the nucleoside, the nucleobase, pentose ring, or phosphate group. For example, modified nucleotides exclude ribonucleotides containing adenosine monophosphate, guanosine monophosphate, uridine monophosphate, and cytidine monophosphate and deoxyribonucleotides containing deoxyadenosine monophosphate, deoxyguanosine monophosphate, deoxythymidine monophosphate, and deoxycytidine monophosphate. Modifications include those naturally-occurring that result from modification by enzymes that modify nucleotides, such as methyltransferases.

Modified nucleotides also include synthetic or non-naturally occurring nucleotides. Synthetic or non-naturally occurring modifications in nucleotides include those with 2' modifications, e.g., 2'-O-methyl, 2'-methoxyethoxy, 2'-fluoro, 2'-allyl, 2'-O-[2-(methylamino)-2-oxoethyl], 4'-thio, 4'-CH2-O-2'-bridge, 4'-(CH2) 2-O-2'-bridge, 2'-LNA, and 2'-O—(N-methylcarbamate) or those comprising base analogs. In connection with 2'-modified nucleotides as described for the present disclosure, by "amino" is meant 2'-NH2 or 2'-O—NH2, which can be modified or unmodified. Such modified groups are described, for example, in U.S. Pat. Nos. 5,672,695 and 6,248,878; incorporated by reference herein.

The terms "microRNA" or "miRNA" refer to a nucleic acid that forms a single-stranded RNA, which single-stranded RNA has the ability to alter the expression (reduce or inhibit expression; modulate expression; directly or indirectly enhance expression) of a gene or target gene when the miRNA is expressed in the same cell as the gene or target gene. In one embodiment, a miRNA refers to a nucleic acid that has substantial or complete identity to a target gene and forms a single-stranded miRNA. In some embodiments miRNA may be in the form of pre-miRNA, wherein the pre-miRNA is double-stranded RNA. The sequence of the miRNA can correspond to the full length target gene, or a subsequence thereof. Typically, the miRNA is at least about 15-50 nucleotides in length (e.g., each sequence of the single-stranded miRNA is 15-50 nucleotides in length, and the double stranded pre-miRNA is about 15-50 base pairs in length). In some embodiments the miRNA is 20-30 base nucleotides. In some embodiments the miRNA is 20-25 nucleotides in length. In some embodiments the miRNA is 20, 21, 22, 23, 24, 25, 26, 27, 28, 29, or 30 nucleotides in length.

The terms "target gene" include genes known or identified as modulating the expression of a gene involved in an immune resistance mechanism, and can be one of several groups of genes, such as suppressor receptors, for example, CTLA4 and PD1; cytokine receptors that inactivate immune cells, for example, TGF-beta receptor, LAG3, and/or TIM3, and combinations thereof. In some embodiments, the target gene includes one or more of PD-1, TGFBR2, CBLB (CBL-B), CISH, CCRs (chimeric co-stimulatory receptors), IL-2, IL-4, IL-7, IL-10, IL-12, IL-15, IL-21, NOTCH 1/2 intracellular domain (ICD), NOTCH ligand mDLL1, TIM3, LAG3, TIGIT, TGFβ, CCR2, CCR4, CCR5, CXCR1, CXCR2, CSCR3, CCL2 (MCP-1), CCL3 (MIP-1α), CCL4 (MIP1-β), CCL5 (RANTES), CXCL1/CXCL8, CCL22, CCL17, CXCL1/CXCL8, VHL, CD44, PIK3CD, SOCS1, and/or cAMP protein kinase A (PKA).

The phrases "small interfering RNA" or siRNA" or "short interfering RNA" or "silencing RNA", define a group of double-stranded RNA molecules, comprising sense and antisense RNA strands, each generally of about 1022 nucleotides in length, optionally including a 3' overhang of 1-3 nucleotides. siRNA is active in the RNA interference (RNAi) pathway, and interferes with expression of specific target genes with complementary nucleotide sequences.

The term sd-RNA refers to "self-deliverable" RNAi agents that are formed as an asymmetric double-stranded RNA-antisense oligonucleotide hybrid. The double stranded RNA includes a guide (sense) strand of about 19-25 nucleotides and a passenger (antisense) strand of about 10-19 nucleotides with a duplex formation that results in a single-stranded phosphorothiolated tail of about 5-9 nucleotides. In some embodiments, the RNA sequences may be modified with stabilizing and hydrophobic modifications such as sterols, for example, cholesterol, vitamin D, naphtyl, isobutyl, benzyl, indol, tryptophane, and phenyl, which confer stability and efficient cellular uptake in the absence of any transfection reagent or formulation. In some embodiments, immune response assays testing for IFN-induced proteins indicate sd-RNAs produce a reduced immunostimulatory profile as compared other RNAi agents. See, for example, Byrne et al., December 2013, J. Ocular Pharmacology and Therapeutics, 29(10): 855-864, incorporated by reference. In some embodiments, the sd-RNAs described herein are commercially available from Advirna LLC, Worcester, MA, USA.

The terms "pharmaceutically acceptable carrier" or "pharmaceutically acceptable excipient" are intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

The terms "about" and "approximately" mean within a statistically meaningful range of a value. Such a range can be within an order of magnitude, preferably within 50%, more preferably within 20%, more preferably still within 10%, and even more preferably within 5% of a given value or range. The allowable variation encompassed by the terms "about" or "approximately" depends on the particular system under study, and can be readily appreciated by one of ordinary skill in the art. Moreover, as used herein, the terms "about" and "approximately" mean that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

The transitional terms "comprising," "consisting essentially of" and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compositions, methods, and kits described herein that embody the present invention can, in alternate embodiments, be more specifically defined by any of the transitional terms "comprising," "consisting essentially of" and "consisting of."

III. Methods of Transiently Altered Protein Expression in TILs

In some embodiments, the expanded TILs of the present invention are further manipulated before, during, or after an expansion step, including during closed, sterile manufacturing processes, each as provided herein, in order to alter protein expression. In some embodiments, the transiently altered protein expression is due to transient gene editing. In some embodiments, the expanded TILs of the present invention are treated with transcription factors (TFs) and/or other molecules capable of transiently altering protein expression in the TILs. In some embodiments, the TFs and/or other molecules that are capable of transiently altering protein expression provide for altered expression of tumor antigens and/or an alteration in the number of tumor antigen-specific T cells in a population of TILs.

In some embodiments, the present invention includes genetic editing through nucleotide insertion, such as through ribonucleic acid (RNA) insertion, including insertion of messenger RNA (mRNA) or small (or short) interfering RNA (siRNA), into a population of TILs for promotion of the expression of one or more proteins or inhibition of the expression of one or more proteins, as well as simultaneous combinations of both promotion of one set of proteins with inhibition of another set of proteins.

In some embodiments, the expanded TILs of the present invention undergo transient alteration of protein expression. In some embodiments, the transient alteration of protein expression occurs in the bulk TIL population prior to first expansion, including for example in the TIL population obtained from for example, Step A as indicated in FIG. 8. In some embodiments, the transient alteration of protein expression occurs during the first expansion, including for example in the TIL population expanded in for example, Step B as indicated in FIG. 8. In some embodiments, the transient alteration of protein expression occurs after the first expansion, including for example in the TIL population in transition between the first and second expansion, the TIL population obtained from for example, Step B and included in Step C as indicated in FIG. 8. In some embodiments, the transient alteration of protein expression occurs in the bulk TIL population prior to second expansion, including for example in the TIL population obtained from for example, Step C and prior to its expansion in Step D as indicated in FIG. 8. In some embodiments, the transient alteration of protein expression occurs during the second expansion, including for example in the TIL population expanded in for example, Step D as indicated in FIG. 8. In some embodiments, the transient alteration of protein expression occurs after the second expansion, including for example in the TIL population obtained from the expansion in for example, Step D as indicated in FIG. 8.

Figure 30:
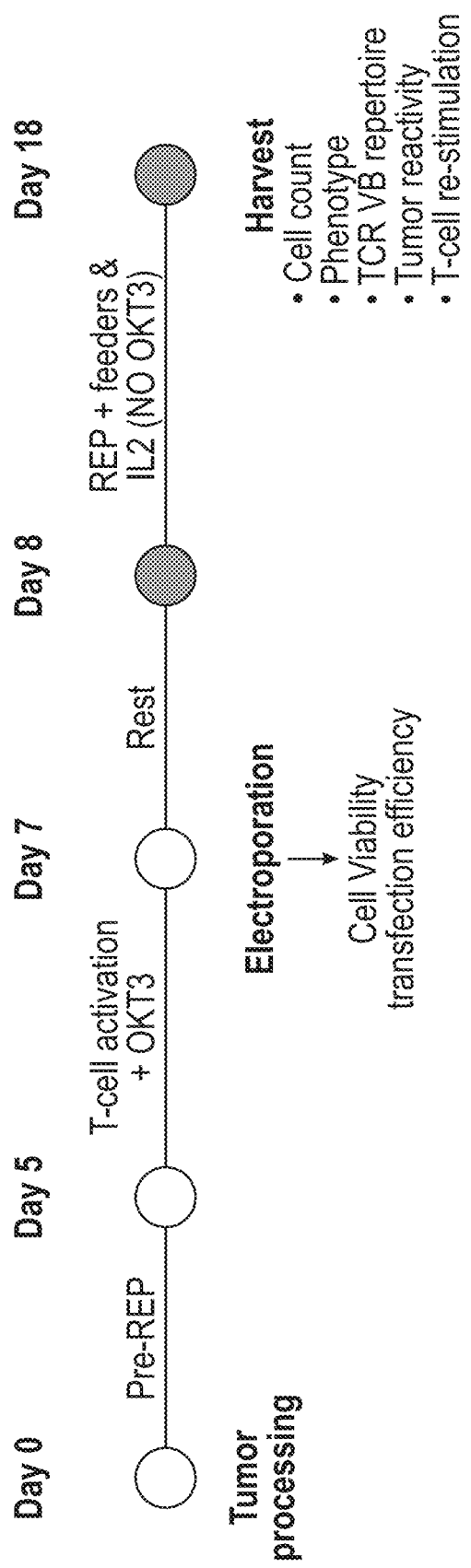
FIG. 30: Shows a schematic of an embodiment of a TIL process for transient gene editing.
Figure 31:
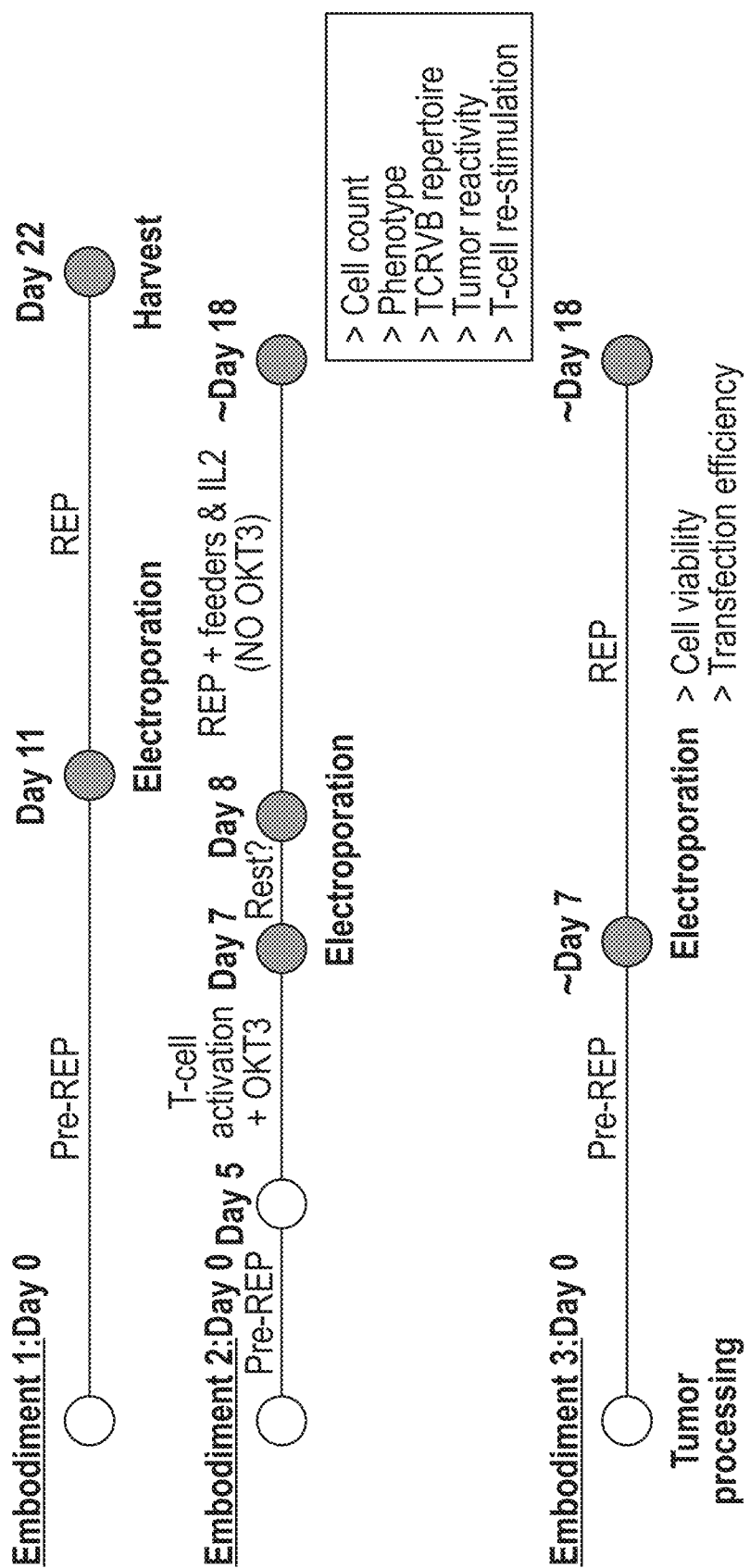
FIG. 31: Shows schematics of embodiments of TIL processes for transient gene editing.

In an embodiment, a method of transiently altering protein expression in a population of TILs includes the step of electroporation. In an embodiment, a method of transiently altering protein expression in a population of TILs is performed according to methods depicted in FIG. 30 and FIG. 31. Electroporation methods are known in the art and are described, e.g., in Tsong, *Biophys. J.* 1991, 60, 297-306, and U.S. Patent Application Publication No. 2014/0227237 A1, the disclosures of each of which are incorporated by reference herein. In an embodiment, a method of transiently altering protein expression in population of TILs includes the step of calcium phosphate transfection. Calcium phosphate transfection methods (calcium phosphate DNA precipitation, cell surface coating, and endocytosis) are known in the art and are described in Graham and van der Eb, *Virology* 1973, 52, 456-467; Wigler, et al., *Proc. Natl. Acad. Sci.* 1979, 76, 1373-1376; and Chen and Okayarea, *Mol. Cell. Biol.* 1987, 7, 2745-2752; and in U.S. Pat. No. 5,593,875, the disclosures of each of which are incorporated by reference herein. In an embodiment, a method of transiently altering protein expression in a population of TILs includes the step of liposomal transfection. Liposomal transfection methods, such as methods that employ a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE) in filtered water, are known in the art and are described in Rose, et al., *Biotechniques* 1991, 10, 520-525 and Felgner, et al., *Proc. Natl. Acad. Sci. USA,* 1987, 84, 7413-7417 and in U.S. Pat. Nos. 5,279,833; 5,908,635; 6,056,938; 6,110,490; 6,534,484; and 7,687,070, the disclosures of each of which are incorporated by reference herein. In an embodiment, a method of transiently altering protein expression in a population of TILs includes the step of transfection using methods described in U.S. Pat. Nos. 5,766,902; 6,025,337; 6,410,517; 6,475,994; and 7,189,705; the disclosures of each of which are incorporated by reference herein.

In some embodiments, transient alteration of protein expression results in an increase in Stem Memory T cells (TSCMs). TSCMs are early progenitors of antigen-experienced central memory T cells. TSCMs generally display the long-term survival, self-renewal, and multipotency abilities that define stem cells, and are generally desirable for the generation of effective TIL products. TSCM have shown enhanced anti-tumor activity compared with other T cell subsets in mouse models of adoptive cell transfer (Gattinoni et al. Nat Med 2009, 2011; Gattinoni, Nature Rev. Cancer, 2012; Cieri et al. Blood 2013). In some embodiments, transient alteration of protein expression results in a TIL population with a composition comprising a high proportion of TSCM. In some embodiments, transient alteration of protein expression results in an at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% increase in TSCM percentage. In some embodiments, transient alteration of protein expression results in an at least a 1-fold, 2-fold, 3-fold, 4-fold, 5-fold, or 10-fold increase in TSCMs in the TIL population. In some embodiments, transient alteration of protein expression results in a TIL population with at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% TSCMs. In some embodiments, transient alteration of protein expression results in a therapeutic TIL population with at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% TSCMs.

In some embodiments, transient alteration of protein expression results in rejuvenation of antigen-experienced T-cells. In some embodiments, rejuvenation includes, for example, increased proliferation, increased T-cell activation, and/or increased antigen recognition.

In some embodiments, transient alteration of protein expression alters the expression in a large fraction of the T-cells in order to preserve the tumor-derived TCR repertoire. In some embodiments, transient alteration of protein expression does not alter the tumor-derived TCR repertoire. In some embodiments, transient alteration of protein expression maintains the tumor-derived TCR repertoire.

In some embodiments, transient alteration of protein results in altered expression of a particular gene. In some embodiments, the transient alteration of protein expression targets a gene including but not limited to PD-1 (also referred to as PDCD1 or CD279), TGFBR2, CCR4/5, CBLB (CBL-B), CISH, CCRs (chimeric co-stimulatory receptors), IL-2, IL-7, IL-10, IL-12, IL-15, IL-21, NOTCH 1/2 ICD, TIM3, LAG3, TIGIT, TGFβ, CCR2, CCR4, CCR5, CXCR1, CXCR2, CSCR3, CCL2 (MCP-1), CCL3 (MIP-1α), CCL4 (MIP1-β), CCL5 (RANTES), CXCL1/CXCL8, CCL22, CCL17, CXCL1/CXCL8, VHL, CD44, PIK3CD, SOCS1, and/or cAMP protein kinase A (PKA). In some embodiments, the transient alteration of protein expression targets a gene selected from the group consisting of PD-1, TGFBR2, CCR4/5, CBLB (CBL-B), CISH, CCRs (chimeric co-stimulatory receptors), IL-2, IL-7, IL-10, IL-12, M-15, IL-21, NOTCH 1/2 ICD, TIM3, LAG3, TIGIT, TGFβ, CCR2, CCR4, CCR5, CXCR1, CXCR2, CSCR3, CCL2 (MCP-1), CCL3 (MIP-1α), CCL4 (MIP1-β), CCL5 (RANTES), CXCL1/CXCL8, CCL22, CCL17, CXCL1/CXCL8, VHL, CD44, PIK3CD, SOCS1, and/or cAMP protein kinase A (PKA). In some embodiments, the transient alteration of protein expression targets PD-1. In some embodiments, the transient alteration of protein expression targets TGFBR2. In some embodiments, the transient alteration of protein expression targets CCR4/5. In some embodiments, the transient alteration of protein expression targets CBLB. In some embodiments, the transient alteration of protein expression targets CISH. In some embodiments, the transient alteration of protein expression targets CCRs (chimeric co-stimulatory receptors). In some embodiments, the transient alteration of protein expression targets IL-2. In some embodiments, the transient alteration of protein expression targets IL-7. In some embodiments, the transient alteration of protein expression targets IL-10. In some embodiments, the transient alteration of protein expression targets IL-12. In some embodiments, the transient alteration of protein expression targets IL-15. In some embodiments, the transient alteration of protein expression targets IL-21. In some embodiments, the transient alteration of protein expression targets NOTCH 1/2 ICD.

In some embodiments, the transient alteration of protein expression targets the NOTCH signaling pathway, such as through the NOTCH 1/2 ICD and/or through other NOTCH ligand, such as mDLL1 (see, for example Kondo, T. et al., NOTCH-mediated conversion of activated T cells into stem cell memory-like T cells for adoptive immunotherapy, Nature Communications, Vol. 8, Article number: 15338 (2017), which is incorporated by reference herein in its entirety).

In some embodiments, the transient alteration of protein expression targets TIM3. In some embodiments, the transient alteration of protein expression targets LAG3. In some embodiments, the transient alteration of protein expression targets TIGIT. In some embodiments, the transient alteration of protein expression targets TGFβ. In some embodiments, the transient alteration of protein expression targets CCR1. In some embodiments, the transient alteration of protein expression targets CCR2. In some embodiments, the transient alteration of protein expression targets CCR4. In some embodiments, the transient alteration of protein expression targets CCR5. In some embodiments, the transient alteration of protein expression targets CXCR1. In some embodiments, the transient alteration of protein expression targets CXCR2. In some embodiments, the transient alteration of protein expression targets CSCR3. In some embodiments, the transient alteration of protein expression targets CCL2 (MCP-1). In some embodiments, the transient alteration of protein expression targets CCL3 (MIP-1α). In some embodiments, the transient alteration of protein expression targets CCL4 (MIP1-β). In some embodiments, the transient alteration of protein expression targets CCL5 (RANTES). In some embodiments, the transient alteration of protein expression targets CXCL1. In some embodiments, the transient alteration of protein expression targets CXCL8. In some embodiments, the transient alteration of protein expression targets CCL22. In some embodiments, the transient alteration of protein expression targets CCL17. In some embodiments, the transient alteration of protein expression targets VHL. In some embodiments, the transient alteration of protein expression targets CD44. In some embodiments, the transient alteration of protein expression targets PIK3CD. In some embodiments, the transient alteration of protein expression targets SOCS1. In some embodiments, the transient alteration of protein expression targets cAMP protein kinase A (PKA).

In some embodiments, the transient alteration of protein expression results in increased and/or overexpression of a chemokine receptor. In some embodiments, the chemokine receptor that is overexpressed by transient protein expression includes a receptor with a ligand that includes but is not limited to CCL2 (MCP-1), CCL3 (MIP-1α), CCL4 (MIP1-β), CCL5 (RANTES), CXCL1, CXCL8, CCL22, and/or CCL17. In some embodiments, the chemokine receptor that is overexpressed by transient protein expression includes a receptor with a ligand that includes but is not limited to IL-2, IL-7, IL-10, IL-15, and IL-21, and also NOTCH 1/2 intracellular domain (ICD). In some embodiments, the transient alteration of protein expression targets the NOTCH signaling pathway, such as through the NOTCH 1/2 ICD and/or through other NOTCH ligand, such as mDLL1 (see, for example Kondo, T. et al., NOTCH-mediated conversion of activated T cells into stem cell memory-like T cells for adoptive immunotherapy, Nature Communications, Vol. 8, Article number: 15338 (2017), which is incorporated by reference herein in its entirety).

In some embodiments, the transient alteration of protein expression results in a decrease and/or reduced expression of PD-1, CTLA-4, TIM-3, LAG-3, TIGIT, TGFβR2, and/or TGFβ (including resulting in, for example, TGFβ pathway blockade). In some embodiments, the transient alteration of protein expression results in a decrease and/or reduced expression of CBLB (CBL-B). In some embodiments, the transient alteration of protein expression results in a decrease and/or reduced expression of CISH.

In some embodiments, the transient alteration of protein expression results in increased and/or overexpression of chemokine receptors in order to, for example, improve TIL trafficking or movement to the tumor site. In some embodiments, the transient alteration of protein expression results in increased and/or overexpression of a CCR (chimeric co-stimulatory receptor). In some embodiments, the transient alteration of protein expression results in increased and/or overexpression of a chemokine receptor selected from the group consisting of CCR1, CCR2, CCR4, CCR5, CXCR1, CXCR2, and/or CSCR3.

In some embodiments, the transient alteration of protein expression results in increased and/or overexpression of an interleukin. In some embodiments, the transient alteration of protein expression results in increased and/or overexpression of an interleukin selected from the group consisting of IL-2, IL-12, IL-15, and/or IL-21.

In some embodiments, the transient alteration of protein expression targets the NOTCH signaling pathway, such as through the NOTCH 1/2 ICD and/or through other NOTCH ligand, such as mDLL1 (see, for example Kondo, T. et al., NOTCH-mediated conversion of activated T cells into stem cell memory-like T cells for adoptive immunotherapy, Nature Communications, Vol. 8, Article number: 15338 (2017), which is incorporated by reference herein in its entirety). In some embodiments, the transient alteration of protein expression results in increased and/or overexpression of NOTCH 1/2 ICD. In some embodiments, the transient alteration of protein expression results in increased and/or overexpression of a NOTCH ligand, such as mDLL1. In some embodiments, the transient alteration of protein expression results in increased and/or overexpression of VHL. In some embodiments, the transient alteration of protein expression results in increased and/or overexpression of CD44. In some embodiments, the transient alteration of protein expression results in increased and/or overexpression of PIK3CD. In some embodiments, the transient alteration of protein expression results in increased and/or overexpression of SOCS1, In some embodiments, the transient alteration of protein expression results in decreased and/or reduced expression of cAMP protein kinase A (PKA).

In some embodiments, the transient alteration of protein expression results in decreased and/or reduced expression of a molecule selected from the group consisting of PD-1, LAG3, TIM3, CTLA-4, TIGIT, CISH, TGFβR2, PKA, CBLB, BAFF (BR3), and combinations thereof. In some embodiments, the transient alteration of protein expression results in decreased and/or reduced expression of two molecules selected from the group consisting of PD-1, LAG3, TIM3, CTLA-4, TIGIT, CISH, TGFβR2, PKA, CBLB, BAFF (BR3), and combinations thereof. In some embodiments, the transient alteration of protein expression results in decreased and/or reduced expression of PD-1 and one molecule selected from the group consisting of LAG3, TIM3, CTLA-4, TIGIT, CISH, TGFβR2, PKA, CBLB, BAFF (BR3), and combinations thereof. In some embodiments, the transient alteration of protein expression results in decreased and/or reduced expression of PD-1, LAG-3, CISH, CBLB, TIM3, and combinations thereof. In some embodiments, the transient alteration of protein expression results in decreased and/or reduced expression of PD-1 and one of LAG3, CISH, CBLB, TIM3, and combinations thereof. In some embodiments, the transient alteration of protein expression results in decreased and/or reduced expression of PD-1 and LAG3. In some embodiments, the transient alteration of protein expression results in decreased and/or reduced expression of PD-1 and CISH. In some embodiments, the transient alteration of protein expression results in decreased and/or reduced expression of PD-1 and CBLB. In some embodiments, the transient alteration of protein expression results in decreased and/or reduced expression of LAG3 and CISH. In some embodiments, the transient alteration of protein expression results in decreased and/or reduced expression of LAG3 and CBLB. In some embodiments, the transient alteration of protein expression results in decreased and/or reduced expression of CISH and CBLB. In some embodiments, the transient alteration of protein expression results in decreased and/or reduced expression of TIM3 and PD-1. In some embodiments, the transient alteration of protein expression results in decreased and/or reduced expression of TIM3 and LAG3. In some embodiments, the transient alteration of protein expression results in decreased and/or reduced expression of TIM3 and CISH. In some embodiments, the transient alteration of protein expression results in decreased and/or reduced expression of TIM3 and CBLB.

In some embodiments, an adhesion molecule selected from the group consisting of CCR2, CCR4, CCR5, CXCR2, CXCR3, CX3CR1, and combinations thereof, is inserted by a gamma retroviral or lentiviral method into the first population of TILs, second population of TILs, or harvested population of TILs (e.g., the expression of the adhesion molecule is increased).

In some embodiments, the transient alteration of protein expression results in decreased and/or reduced expression of a molecule selected from the group consisting of PD-1, LAG3, TIM3, CTLA-4, TIGIT, CISH, TGFβR2, PKA, CBLB, BAFF (BR3), and combinations thereof, and increased and/or enhanced expression of CCR2, CCR4, CCR5, CXCR2, CXCR3, CX3CR1, and combinations thereof. In some embodiments, the transient alteration of protein expression results in decreased and/or reduced expression of a molecule selected from the group consisting of PD-1, LAG3, TIM3, CISH, CBLB, and combinations thereof, and increased and/or enhanced expression of CCR2, CCR4, CCR5, CXCR2, CXCR3, CX3CR1, and combinations thereof.

In some embodiments, there is a reduction in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is a reduction in expression of at least about 65%, about 70%, about 75%, about 80%, about 85%, about 90%, or about 95%. In some embodiments, there is a reduction in expression of at least about 75%, about 80%, about 85%, about 90%, or about 95%. In some embodiments, there is a reduction in expression of at least about 80%, about 85%, about 90%, or about 95%. In some embodiments, there is a reduction in expression of at least about 85%, about 90%, or about 95%. In some embodiments, there is a reduction in expression of at least about 80%. In some embodiments, there is a reduction in expression of at least about 85%. In some embodiments, there is a reduction in expression of at least about 90%. In some embodiments, there is a reduction in expression of at least about 95%. In some embodiments, there is a reduction in expression of at least about 99%.

In some embodiments, there is an increase in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is an increase in expression of at least about 65%, about 70%, about 75%, about 80%, about 85%, about 90%, or about 95%. In some embodiments, there is an increase in expression of at least about 75%, about 80%, about 85%, about 90%, or about 95%. In some embodiments, there is an increase in expression of at least about 80%, about 85%, about 90%, or about 95%. In some embodiments, there is an increase in expression of at least about 85%, about 90%, or about 95%. In some embodiments, there is an increase in expression of at least about 80%. In some embodiments, there is an increase in expression of at least about 85%, In some embodiments, there is an increase in expression of at least about 90%. In some embodiments, there is an increase in expression of at least about 95%. In some embodiments, there is an increase in expression of at least about 99%.

In some embodiments, transient alteration of protein expression is induced by treatment of the TILs with transcription factors (TFs) and/or other molecules capable of transiently altering protein expression in the TILs. In some embodiments, the SQZ vector-free microfluidic platform is employed for intracellular delivery of the transcription factors (TFs) and/or other molecules capable of transiently altering protein expression. Such methods demonstrating the ability to deliver proteins, including transcription factors, to a variety of primary human cells, including T cells (Sharei et al. PNAS 2013, as well as Sharei et al. PLOS ONE 2015 and Greisbeck et al. J. Immunology vol. 195, 2015) have been described, including rapid methods for deforming cells using a microfluidic constriction such that a TF or other molecule enters the cells; see, for example, International Patent Application Publication Nos. WO 2013/059343A1, WO 2017/008063A1, or WO 2017/123663A1, or U.S. Patent Application Publication Nos. US 2014/0287509A1, US 2018/0201889A1, or US 2018/0245089A1, all of which are incorporated by reference herein in their entireties. Such methods as described in International Patent Application Publication Nos. WO 2013/059343A1, WO 2017/008063A1, or WO 2017/123663A1, or U.S. Patent Application Publication Nos. US 2014/0287509A1, US 2018/0201889A1, or US 2018/0245089A1 can be employed with the present invention in order to expose a population of TILs to transcription factors (TFs) and/or other molecules capable of inducing transient protein expression, wherein the TFs and/or other molecules capable of inducing transient protein expression provide for increased expression of tumor antigens and/or an increase in the number of tumor antigen-specific T cells in the population of TILs, thus resulting in reprogramming of the TIL population and an increase in therapeutic efficacy of the reprogrammed TIL population as compared to a non-reprogrammed TIL population. In some embodiments, the reprogramming results in an increased subpopulation of effector T cells and/or central memory T cells relative to the starting or prior population (i.e., prior to reprogramming) population of TILs, as described herein.

In some embodiments, the transcription factor (TF) includes but is not limited to TCF-1, NOTCH 1/2 ICD, and/or MYB. In some embodiments, the transcription factor (TF) is TCF-1. In some embodiments, the transcription factor (TF) is NOTCH 1/2 ICD. In some embodiments, the transcription factor (TF) is MYB. In some embodiments, the transcription factor (TF) is administered with induced pluripotent stem cell culture (iPSC), such as the commercially available KNOCKOUT Serum Replacement (Gibco/ThermoFisher), to induce additional TIL reprogramming. In some embodiments, the transcription factor (TF) is administered with an iPSC cocktail to induce additional TIL reprogramming. In some embodiments, the transcription factor (TF) is administered without an iPSC cocktail. In some embodiments, reprogramming results in an increase in the percentage of TSCMs. In some embodiments, reprogramming results in an increase in the percentage of TSCMs by about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95% TSCMs.

In some embodiments, the method for expanding tumor infiltrating lymphocytes (TILs) into a therapeutic population of TILs comprising:

(i) obtaining a first population of TILs from a tumor resected from a patient;

(ii) performing a first expansion by culturing the first population of TILs in a cell culture medium comprising IL-2, and optionally OKT-3, to produce a second population of TILs;

(iii) performing a second expansion by supplementing the cell culture medium of the second population of TILs with additional IL-2, OKT-3, and antigen presenting cells (APCs), to produce a third population of TILs, wherein the third population of TILs is at least 100-fold greater in number than the second population of TILs, and wherein the second expansion is performed for at least 14 days in order to obtain the third population of TILs, wherein the third population of TILs is a therapeutic population of TILs; and (iv) exposing the second and/or third population of TILs to transcription factors (TFs) and/or other molecules capable of transiently altering protein expression, wherein the TFs and/or other molecules capable of transiently altering protein expression provide for altered expression of tumor antigens and/or an alteration in the number of tumor antigen-specific T cells in the therapeutic population of TILs.

In an embodiment, a method for expanding tumor infiltrating lymphocytes (TILs) into a therapeutic population of TILs comprises:

(a) obtaining a first population of TILs from a tumor resected from a patient by processing a tumor sample obtained from the patient into multiple tumor fragments;

(b) adding the tumor fragments into a closed system;

(c) performing a first expansion by culturing the first population of TILs in a cell culture medium comprising IL-2 and optionally comprising a 4-1BB agonist antibody for about 2 to 5 days;

(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;

(e) performing a sterile electroporation step on the second population of TILs, wherein the sterile electroporation step mediates the transfer of at least one short interfering RNA or one messenger RNA;

(f) resting the second population of TILs for about 1 day;

(g) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (f) to step (g) occurs without opening the system;

(h) harvesting the therapeutic population of TILs obtained from step (g) to provide a harvested TIL population, wherein the transition from step (g) to step (h) occurs without opening the system, wherein the harvested population of TILs is a therapeutic population of TILs;

(i) transferring the harvested TIL population from step (e) to an infusion bag, wherein the transfer from step (e) to (f) occurs without opening the system; and (j) cryopreserving the harvested TIL population using a dimethylsulfoxide-based cryopreservation medium, wherein the sterile electroporation step comprises the delivery of a short interfering RNA for inhibiting the expression of a molecule selected from the group consisting of PD-1, LAG-3, TIM-3, CTLA-4, TIGIT, CISH, TGFβR2, PKA, CBLB, BAFF (BR3), and combinations thereof.

According to one embodiment, a method for expanding tumor infiltrating lymphocytes (TILs) into a therapeutic population of TILs comprises:

(a) obtaining a first population of TILs from a tumor resected from a patient by processing a tumor sample obtained from the patient into multiple tumor fragments;

(b) adding the tumor fragments into a closed system;

(c) performing a first expansion by culturing the first population of TILs in a cell culture medium comprising IL-2 and optionally comprising a 4-1BB agonist antibody for about 2 to 5 days;

(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;

(e) performing a SQZ microfluidic membrane disruption step on the second population of TILs, wherein the SQZ microfluidic membrane disruption step mediates the transfer of at least one short interfering RNA or one messenger RNA;

(f) resting the second population of TILs for about 1 day;

(g) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (f) to step (g) occurs without opening the system;

(h) harvesting the therapeutic population of TILs obtained from step (g) to provide a harvested TIL population, wherein the transition from step (g) to step (h) occurs without opening the system, wherein the harvested population of TILs is a therapeutic population of TILs;

(i) transferring the harvested TIL population from step (e) to an infusion bag, wherein the transfer from step (e) to (f) occurs without opening the system; and (j) cryopreserving the harvested TIL population using a dimethylsulfoxide-based cryopreservation medium, wherein the SQZ microfluidic membrane disruption step comprises the delivery of a short interfering RNA for inhibiting the expression of a molecule selected from the group consisting of PD-1, LAG-3, TIM-3, CTLA-4, TIGIT, CISH, TGFβR2, PKA, CBLB, BAFF (BR3), and combinations thereof.

In some embodiments, a method of transient altering protein expression, as described above, may be combined with a method of genetically modifying a population of TILs includes the step of stable incorporation of genes for production of one or more proteins. In an embodiment, a method of genetically modifying a population of TILs includes the step of retroviral transduction. In an embodiment, a method of genetically modifying a population of TILs includes the step of lentiviral transduction. Lentiviral transduction systems are known in the art and are described, e.g., in Levine, et al., *Proc. Nat'l Acad. Sci.* 2006, 103, 17372-77; Zufferey, et al., *Nat. Biotechnol.* 1997, 15, 871-75; Dull, et al. *J. Virology* 1998, 72, 8463-71, and U.S. Pat. No. 6,627,442, the disclosures of each of which are incorporated by reference herein. In an embodiment, a method of genetically modifying a population of TILs includes the step of gamma-retroviral transduction. Gamma-retroviral transduction systems are known in the art and are described, e.g., Cepko and Pear, *Cur. Prot. Mol. Biol.* 1996, 9.9.1-9.9.16, the disclosure of which is incorporated by reference herein. In an embodiment, a method of genetically modifying a population of TILs includes the step of transposon-mediated gene transfer. Transposon-mediated gene transfer systems are known in the art and include systems wherein the transposase is provided as DNA expression vector or as an expressible RNA or a protein such that long-term expression of the transposase does not occur in the transgenic cells, for example, a transposase provided as an mRNA (e.g., an mRNA comprising a cap and poly-A tail). Suitable transposon-mediated gene transfer systems, including the salmonid-type Tel-like transposase (SB or Sleeping Beauty transposase), such as SB10, SB11, and SB100x, and engineered enzymes with increased enzymatic activity, are described in, e.g., Hackett, et al., *Mol. Therapy* 2010, 18, 674-83 and U.S. Pat. No. 6,489,458, the disclosures of each of which are incorporated by reference herein.

In an embodiment, a method for expanding tumor infiltrating lymphocytes (TILs) into a therapeutic population of TILs comprises:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising a 4-1BB agonist antibody for about 2 to 5 days;
(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
(e) performing a sterile electroporation step or a SQZ microfluidic membrane disruption step on the second population of TILs, wherein the sterile electroporation step or SQZ microfluidic membrane disruption step mediates the transfer of at least one short interfering RNA or one messenger RNA;
(f) resting the second population of TILs for about 1 day;
(g) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (f) to step (g) occurs without opening the system;
(h) harvesting the therapeutic population of TILs obtained from step (g) to provide a harvested TIL population, wherein the transition from step (g) to step (h) occurs without opening the system, wherein the harvested population of TILs is a therapeutic population of TILs;
(i) transferring the harvested TIL population from step (e) to an infusion bag, wherein the transfer from step (e) to (f) occurs without opening the system; and
(j) cryopreserving the harvested TIL population using a dimethylsulfoxide-based cryopreservation medium, wherein the electroporation step he delivery of a short interfering RNA for inhibiting the expression of a molecule selected from the group consisting of PD-1, LAG-3, TIM-3, CTLA-4, TIGIT, CISH, TGFβR2, PKA, CBLB, BAFF (BR3), and combinations thereof, and further wherein an adhesion molecule selected from the group consisting of CCR2, CCR4, CCR5, CXCR2, CXCR3, CX3CR1, and combinations thereof is inserted by a gammaretroviral or lentiviral method into the first population of TILs, second population of TILs, or harvested population of TILs.

In some embodiments, transient alteration of protein expression is a reduction in expression induced by self-delivering RNA interference (sd-RNA), which is a chemically-synthesized asymmetric siRNA duplex with a high percentage of 2'-OH substitutions (typically fluorine or —OCH$_3$) which comprises a 20-nucleotide antisense (guide) strand and a 13 to 15 base sense (passenger) strand conjugated to cholesterol at its 3' end using a tetraethylenglycol (TEG) linker. Methods of using sd-RNA have been described in Khvorova and Watts, *Nat. Biotechnol.* 2017, 35, 238-248; Byrne, et al., *J. Ocul. Pharmacol. Ther.* 2013, 29, 855-864; and Ligtenberg, et al., *Mol. Therapy*, 2018, in press, the disclosures of which are incorporated by reference herein. In an embodiment, delivery of sd-RNA to a TIL population is accomplished without use of electroporation, SQZ, or other methods, instead using a 1 to 3 day period in which a TIL population is exposed to sd-RNA at a concentration of 1 µM/10,000 TILs in medium. In an embodiment, delivery of sd-RNA to a TIL population is accomplished using a 1 to 3 day period in which a TIL population is exposed to sd-RNA at a concentration of 10 µM/10,000 TILs in medium. In an embodiment, delivery of sd-RNA to a TIL population is accomplished using a 1 to 3 day period in which a TIL population is exposed to sd-RNA at a concentration of 50 µM/10,000 TILs in medium. In an embodiment, delivery of sd-RNA to a TIL population is accomplished using a 1 to 3 day period in which a TIL population is exposed to sd-RNA at a concentration of between 0.1 µM/10,000 TILs and 50 µM/10,000 TILs in medium. In an embodiment, delivery of sd-RNA to a TIL population is accomplished using a 1 to 3 day period in which a TIL population is exposed to sd-RNA at a concentration of between 0.1 µM/10,000 TILs and 50 µM/10,000 TILs in medium, wherein the exposure to sd-RNA is performed two, three, four, or five times by addition of fresh sd-RNA to the media. Other suitable processes are described, for example, in U.S. Patent Application Publication No. US 2011/0039914 A1, US 2013/0131141 A1, and US 2013/0131142

A1, and U.S. Pat. No. 9,080,171, the disclosures of which are incorporated by reference herein.

Figure 32:
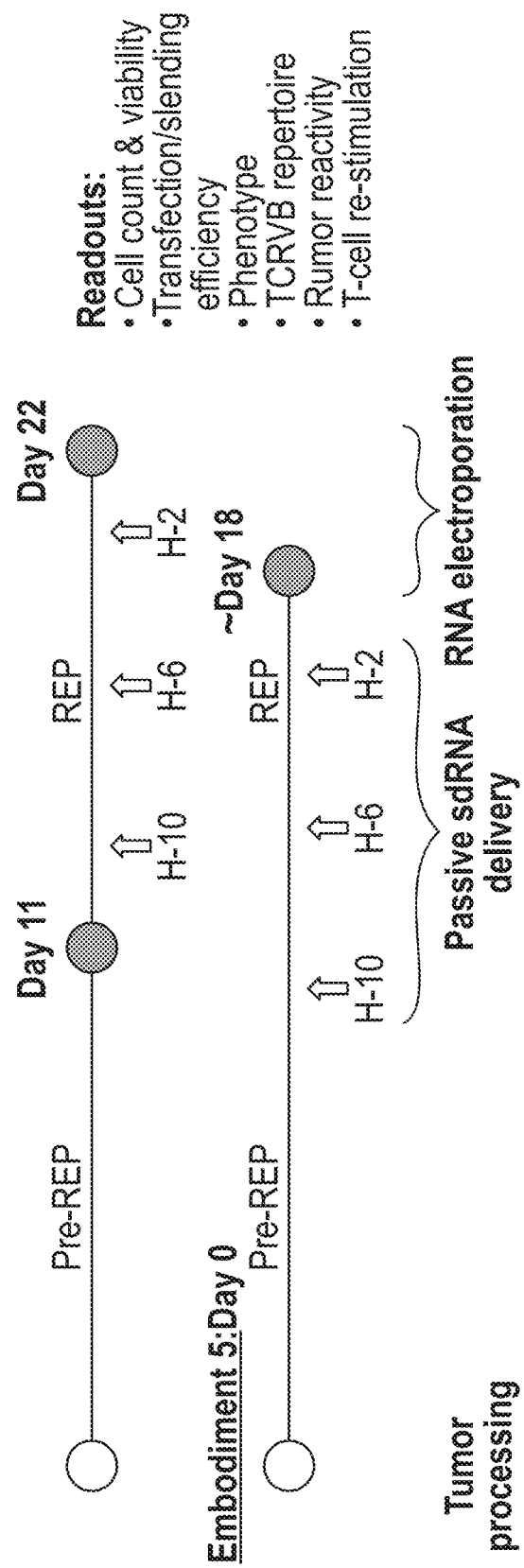
FIG. 32: Shows a schematic regarding incorporating an RNA transfer step into the TIL process for transient gene reprogramming purposes.

In some embodiments, sd-RNA is inserted into a population of TILs during manufacturing using a process according to FIG. 32. In some embodiments, the sd-RNA encodes RNA that interferes with NOTCH 1/2 ICD, NOTCH ligand mDLL1, PD-1, CTLA-4 TIM-3, LAG-3, TIGIT, TGFβ, TGFBR2, cAMP protein kinase A (PKA), BAFF BR3, CISH, and/or CBLB. In some embodiments, the reduction in expression is determined based on a percentage of gene silencing, for example, as assessed by flow cytometry and/or qPCR. In some embodiments, there is a reduction in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is a reduction in expression of at least about 65%, about 70%, about 75%, about 80%, about 85%, about 90%, or about 95%. In some embodiments, there is a reduction in expression of at least about 75%, about 80%, about 85%, about 90%, or about 95%. In some embodiments, there is a reduction in expression of at least about 80%, about 85%, about 90%, or about 95%. In some embodiments, there is a reduction in expression of at least about 85%, about 90%, or about 95%. In some embodiments, there is a reduction in expression of at least about 80%. In some embodiments, there is a reduction in expression of at least about 85%, In some embodiments, there is a reduction in expression of at least about 90%. In some embodiments, there is a reduction in expression of at least about 95%. In some embodiments, there is a reduction in expression of at least about 99%.

In an embodiment, a method for expanding tumor infiltrating lymphocytes (TILs) into a therapeutic population of TILs comprises:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising a 4-1BB agonist antibody for about 2 to 5 days;
(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
(e) performing a second expansion by supplementing the cell culture medium of the second population of TILs with additional IL-2, one or more self-delivering RNA (sd-RNA), optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (f) to step (g) occurs without opening the system;
(h) harvesting the therapeutic population of TILs obtained from step (g) to provide a harvested TIL population, wherein the transition from step (g) to step (h) occurs without opening the system, wherein the harvested population of TILs is a therapeutic population of TILs;
(i) transferring the harvested TIL population from step (e) to an infusion bag, wherein the transfer from step (e) to (f) occurs without opening the system; and
(j) cryopreserving the harvested TIL population using a dimethylsulfoxide-based cryopreservation medium, wherein the one or more sd-RNA transiently inhibits the expression of a molecule selected from the group consisting of PD-1, LAG-3, TIM-3, CTLA-4, TIGIT, CISH, TGFβR2, PKA, CBLB, BAFF (BR3), and combinations thereof.

In an embodiment, a method for expanding tumor infiltrating lymphocytes (TILs) into a therapeutic population of TILs comprises:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising a 4-1BB agonist antibody for about 2 to 5 days;
(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
(e) performing a second expansion by supplementing the cell culture medium of the second population of TILs with additional IL-2, one or more self-delivering RNA (sd-RNA), optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (f) to step (g) occurs without opening the system;
(h) harvesting the therapeutic population of TILs obtained from step (g) to provide a harvested TIL population, wherein the transition from step (g) to step (h) occurs without opening the system, wherein the harvested population of TILs is a therapeutic population of TILs;
(i) transferring the harvested TIL population from step (e) to an infusion bag, wherein the transfer from step (e) to (f) occurs without opening the system; and
(j) cryopreserving the harvested TIL population using a dimethylsulfoxide-based cryopreservation medium, wherein the one or more sd-RNA transiently inhibits the expression of a molecule selected from the group consisting of PD-1, LAG-3, TIM-3, CTLA-4, TIGIT, CISH, TGFβR2, PKA, CBLB, BAFF (BR3), and combinations thereof, and further wherein an adhesion molecule selected from the group consisting of CCR2, CCR4, CCR5, CXCR2, CXCR3, CX3CR1, and combinations thereof is inserted by a gammaretroviral or lentiviral method into the first population of TILs, second population of TILs, or harvested population of TILs.

A. sd-RNA Methods

The self-deliverable RNAi technology based on the chemical modification of siRNAs can be employed with the methods of the present invention to successfully deliver the sd-RNAs to the TILs as described herein. The combination of backbone modifications with asymmetric siRNA structure and a hydrophobic ligand (see, for example, Ligtenberg, et al., *Mol. Therapy,* 2018 and US Patent Publication No. 20160304873, as well as FIGS. 36 and 37 herein) allow sd-RNAs to penetrate cultured mammalian cells without additional formulations and methods by simple addition to the culture media, capitalizing on the nuclease stability of sd-RNAs. This stability allows the support of constant levels of RNAi-mediated reduction of target gene activity simply by maintaining the active concentration of sd-RNA in the media. While not being bound by theory, the backbone stabilization of sd-RNA provides for extended reduction in gene expression effects which can last for months in non-dividing cells.

Figure 36:
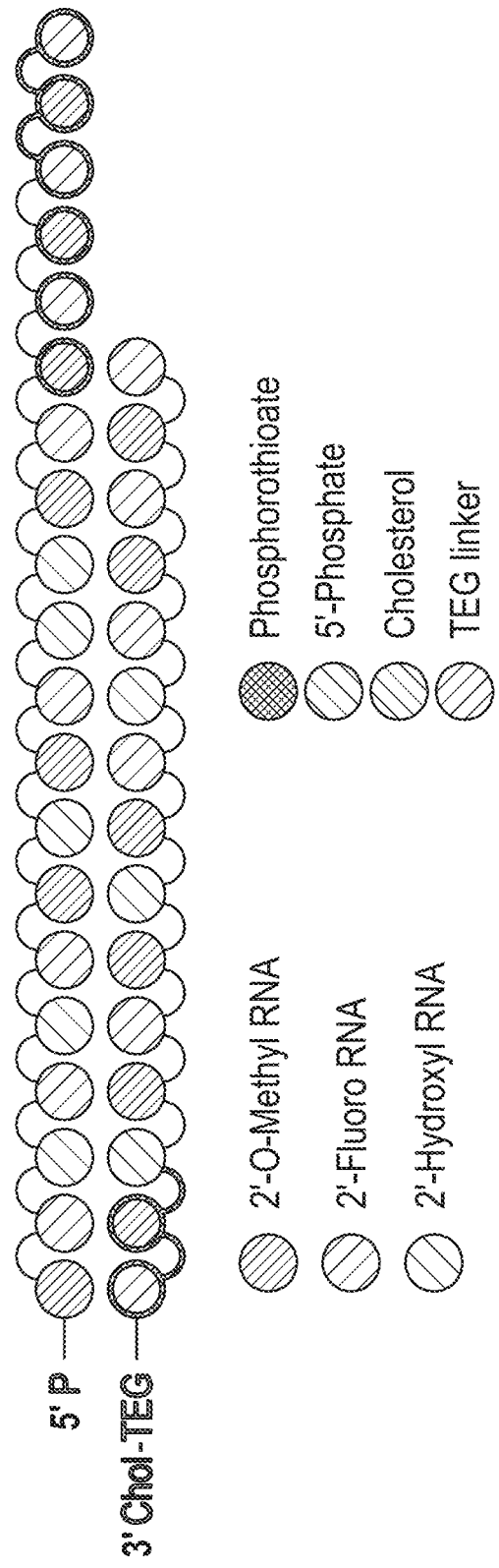
FIG. 36: Shows a schematic structural representation of an exemplary self-delivering ribonucleic acid (sd-RNA) embodiment. See, Ligtenberg, et al., *Mol. Therapy*, 2018.
Figure 37:
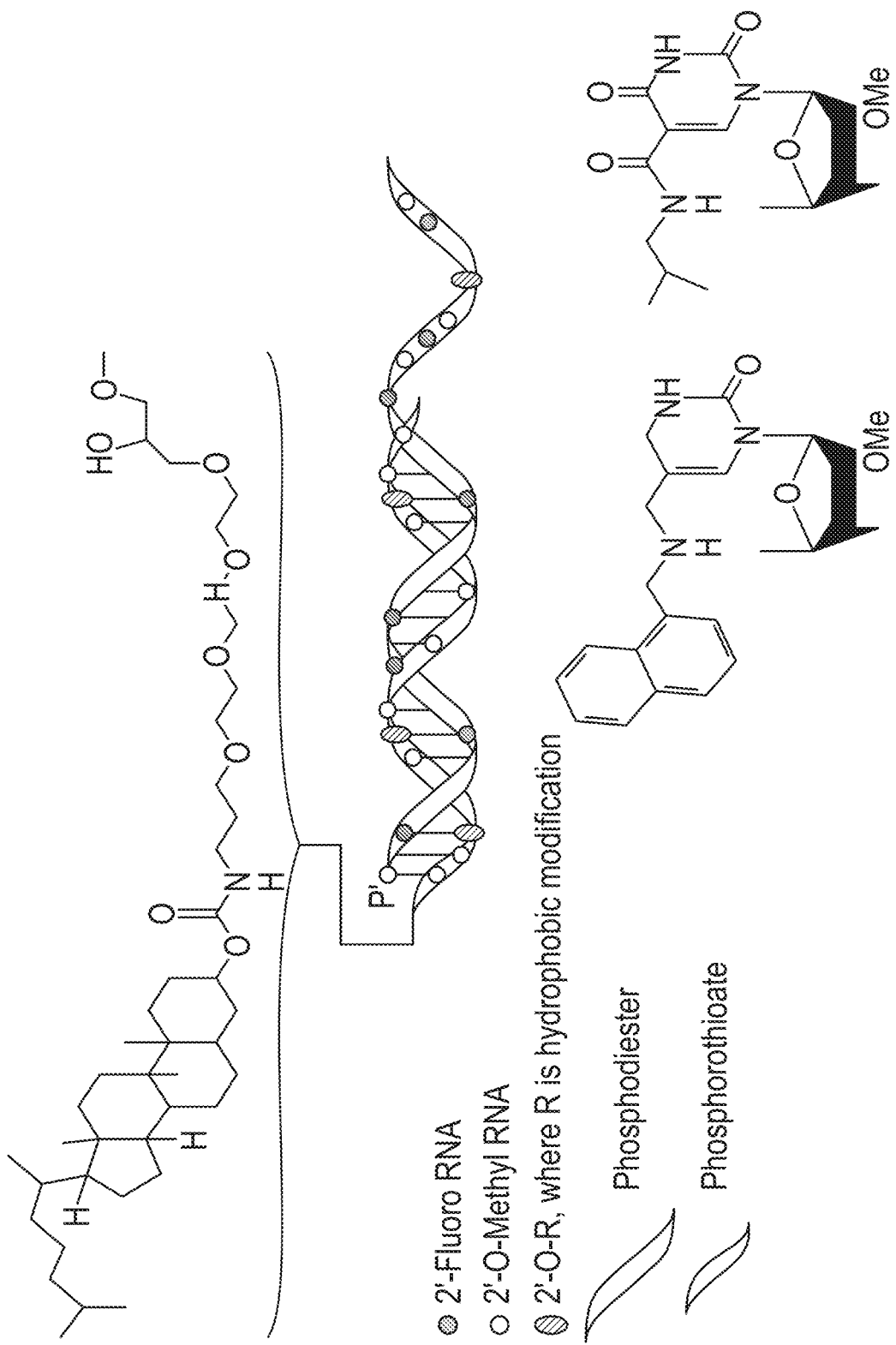
FIG. 37: Shows a schematic structural representation of an exemplary sd-RNA embodiment. See, US Patent Publication No. 2016/0304873.

In an embodiment, an sd-RNA used herein to target genes disclosed herein has the structure shown in FIG. 36 or FIG. 37.

In some embodiments, over 95% transfection efficiency of TILs and a reduction in expression of the target by various specific sd-RNA occurs. In some embodiments, sd-RNAs containing several unmodified ribose residues were replaced with fully modified sequences to increase potency and/or the longevity of RNAi effect. In some embodiments, a reduction in expression effect is maintained for 12 hours, 24 hours, 36 hours, 48 hours, 5 days, 6 days, 7 days, or 8 days or more. In some embodiments, the reduction in expression effect decreases at 10 days or more post sd-RNA treatment of the TILs. In some embodiments, more than 70% reduction in expression of the target expression is maintained. In some embodiments, more than 70% reduction in expression of the target expression is maintained TILs. In some embodiments, a reduction in expression in the PD-1/PD-L1 pathway allows for the TILs to exhibit a more potent in vivo effect, which is in some embodiments, due to the avoidance of the suppressive effects of the PD-1/PD-L1 pathway. In some embodiments, a reduction in expression of PD-1 by sd-RNA results in an increase TIL proliferation.

1. sd-RNA Selection and Features a. sd-RNA Oligonucleotide Structure

Small interfering RNA (siRNA), sometimes known as short interfering RNA or silencing RNA, is a double stranded RNA molecule, generally 19-25 base pairs in length. siRNA is used in RNA interference (RNAi), where it interferes with expression of specific genes with complementary nucleotide sequences.

Double stranded DNA (dsRNA) can be generally used to define any molecule comprising a pair of complementary strands of RNA, generally a sense (passenger) and antisense (guide) strands, and may include single-stranded overhang regions. The term dsRNA, contrasted with siRNA, generally refers to a precursor molecule that includes the sequence of an siRNA molecule which is released from the larger dsRNA molecule by the action of cleavage enzyme systems, including Dicer.

sd-RNA (self-deliverable RNA) are a new class of covalently modified RNAi compounds that do not require a delivery vehicle to enter cells and have improved pharmacology compared to traditional siRNAs. "Self-deliverable RNA" or "sd-RNA" is a hydrophobically modified RNA interfering-antisense hybrid, demonstrated to be highly efficacious in vitro in primary cells and in vivo upon local administration. Robust uptake and/or silencing without toxicity has been demonstrated. sd-RNAs are generally asymmetric chemically modified nucleic acid molecules with minimal double stranded regions. sd-RNA molecules typically contain single stranded regions and double stranded regions, and can contain a variety of chemical modifications within both the single stranded and double stranded regions of the molecule. Additionally, the sd-RNA molecules can be attached to a hydrophobic conjugate such as a conventional and advanced sterol-type molecule, as described herein. sd-RNAs (and/or RNAs capable of being employed in similar manners to sd-RNAs) and associated methods for making such sd-RNAs have also been described extensively in, for example, U.S. Patent Publication No. US 2016/0304873, International Patent Application Publication No. WO2010/033246, International Patent Application Publication No. WO2017/070151, International Patent Application Publication No. WO2009/102427, International Patent Application Publication No. WO201/119887, International Patent Application Publication No. WO2010/033247, International Patent Application Publication No. WO2009045457, International Patent Application Publication No. WO2011/119852, International Patent Application Publication No. WO2011/119871, US Patent Publication No. US 2011/0263680, International Patent Application Publication No. WO2010/033248, International Patent Application Publication No. WO2010/078536, International Patent Application Publication No. WO2010/090762, U.S. Patent Publication No. US 20110039914, International Publication No. WO2011/109698, International Patent Application Publication No. WO2010/090762, U.S. Pat. No. 8,815,818, International Patent Application Publication No. WO2016/094845, International Patent Application Publication No. WO2017/193053, U.S. Patent Publication No. US 2006/0276635, International Patent Application Publication No. WO2001/009312, U.S. Patent Publication No. US 2017/0043024, U.S. Patent Publication No. US 2017/0312367, U.S. Patent Publication No. US 2016/0319278, U.S. Patent Publication No. US 2017/0369882, U.S. Pat. No. 8,501,706, U.S. Patent Publication No. US 2004/0224405, U.S. Pat. No. 8,252,755, U.S. Patent Publication No. US 2007/0031844, U.S. Patent Publication No. US 2007/0039072, U.S. Patent Publication No. US 2007/0207974, U.S. Patent Publication No. US 2007/0213520, U.S. Patent Publication No. US 2007/0213521, U.S. Patent Publication No. US 2007/0219362, U.S. Patent Publication No. US 2007/0238868, U.S. Patent Publication No. US 2014/0148362, U.S. Patent Publication No. US 2016/0193242, U.S. Patent Publication No. US 2016/01946461, U.S. Patent Publication No. US 2016/0201058, U.S. Patent Publication No. US 2016/0201065, U.S. Patent Publication No. US 2017/0349904, U.S. Patent Publication No. US 2018/0119144, U.S. Pat. Nos. 7,834,170, 8,090,542, and U.S. Patent Publication No. US 2012/0052487, all of which are incorporated by reference herein in their entireties for all purposes; also sd-RNAs are commercially available from Advirna LLC, Worcester, MA, USA. To optimize sd-RNA structure, chemistry, targeting position, sequence preferences, and the like, a proprietary algorithm has been developed and utilized for sd-RNA potency prediction (see, for example, US 20160304873). Based on these analyses, functional sd-RNA sequences have been generally defined as having over 70% reduction in expression at 1 µM concentration, with a probability over 40%.

b. sd-RNA Oligonucleotide Structure

In some embodiments, one or more sd-RNAs for use in the present invention can be generated from a linear double-stranded DNA template. In some embodiments, the linear double-stranded DNA template for generating the one or more sd-RNAs is one as described in U.S. Pat. No. 8,859,229, as well as described below.

In some embodiments, a linear double-stranded DNA template obtained by polymerase chain reaction (PCR) and suitable for in vitro transcription of an mRNA comprises from 5' to 3': an RNA polymerase promoter on the coding strand of the double-stranded DNA, a 5' untranslated region less than 3,000 nucleotides in length and effective for translation of the mRNA into a detectable polypeptide after transfection into a eukaryotic cell, an open reading frame that encodes the polypeptide, wherein the polypeptide is heterologous to the cell to be transfected and wherein the polypeptide is selected from the group consisting of a ligand or a receptor of an immune cell, a polypeptide that stimulates or inhibits a function of the immune system, and a polypeptide that inhibits the function of an oncogenic polypeptide, 3' untranslated region effective for translation of the mRNA into a detectable polypeptide after transfection into a eukaryotic cell, and a poly(A) stretch of 50-5,000 nucleotides on the coding strand of the double-stranded DNA, wherein the promoter is heterologous to the open reading frame, and wherein the DNA template is not contained within a DNA vector and terminates with the 3' end of the poly(A) stretch. In some embodiments, the RNA polymerase promoter comprises a consensus binding sequence for an RNA polymerase selected from the group consisting of T7, T3 or SP6 RNA polymerase. In some embodiments, the open reading frame encodes a fusion polypeptide. In some embodiments, the open reading frame encodes a polypeptide selected from the group consisting of PD-1, TGFBR2, CBLB (CBL-B), CISH, CCRs (chimeric co-stimulatory receptors), IL-2, IL-12, IL-15, IL-21, NOTCH 1/2 ICD, TIM3, LAG3, TIGIT, TGFβ, CCR2, CCR4, CCR5, CXCR1, CXCR2, CSCR3, CCL2 (MCP-1), CCL3 (MIP-1α), CCL4 (MIP1-β), CCL5 (RANTES), CXCL1/CXCL8, CCL22, CCL17, CXCL1/CXCL8, VHL, CD44, PIK3CD, SOCS1, cAMP protein kinase A (PKA), and combinations thereof. In some embodiments, the open reading frame encodes a polypeptide selected from the group consisting of PD-1, LAG-3, TIM-3, CTLA-4, TIGIT, CISH, TGFβR2, PKA, CBLB, BAFF (BR3), and combinations thereof. In some embodiments, the linear double-stranded further comprises an internal ribosome entry site. In some embodiments, the poly(A) stretch is 300-400 nucleotides in length.

In some embodiments, the linear double-stranded DNA template of claim 1, wherein from 5' to 3' the template consists of an RNA polymerase promoter on the coding strand of the double-stranded DNA, a 5' untranslated region less than 3,000 nucleotides in length and effective for translation of the mRNA into a detectable polypeptide after transfection into a eukaryotic cell, an open reading frame that encodes the polypeptide, wherein the polypeptide is heterologous to the cell to be transfected and wherein the polypeptide is selected from the group consisting of a ligand or a receptor of an immune cell, a polypeptide that stimulates or inhibits a function of the immune system, and a polypeptide that inhibits the function of an oncogenic polypeptide, a 3' untranslated region effective for translation of the mRNA into a detectable polypeptide after transfection into a eukaryotic cell, and a poly(A) stretch of 50-5,000 nucleotides on the coding strand of the double-stranded DNA, wherein the promoter is heterologous to the open reading frame, and wherein the DNA template is not contained within a DNA vector and terminates with the 3' end of the poly(A) stretch. In some embodiments, the 3' untranslated region is at least 100 nucleotides in length.

In some embodiments, the present invention provides a method of generating the linear double-stranded DNA template described above, wherein the method comprises generating forward and reverse primers, wherein the forward primer comprises a plurality of nucleotides that are substantially complementary to the non-coding strand of a target double-stranded DNA of interest, and a plurality of nucleotides that function as a binding site for an RNA polymerase, wherein the reverse primer comprises a plurality of nucleotides that are substantially complementary to the coding strand of a target double-stranded DNA of interest, and a plurality of deoxythymidine nucleotides, and performing polymerase chain reaction amplification of the target DNA using the forward and reverse primers to form the linear double-stranded DNA template. In some embodiments, the present invention provides a method of generating the linear double-stranded DNA template described above, wherein the method comprises generating forward and reverse primers, wherein the forward primer comprises a plurality of nucleotides that are substantially complementary to a region of nucleotides directly upstream of a target double-stranded DNA of interest, wherein the reverse primer comprises a plurality of nucleotides that are substantially complementary to a region of nucleotides directly downstream of a target double-stranded DNA of interest, and performing polymerase chain reaction amplification of the target DNA using the forward and reverse primers to form the linear double-stranded DNA template. In some embodiments, the primers comprise nucleotide sequences that are substantially complementary to stretches of nucleotides in the 5' and 3' untranslated regions of a double-stranded DNA of interest. In some embodiments, the primers comprise nucleotide sequences that are substantially complementary to stretches of nucleotides within the open reading frame of a double-stranded DNA of interest. In some embodiments, the primers comprise nucleotide sequences that are substantially complementary to stretches of nucleotides within the open reading frame of a double-stranded DNA of interest, wherein the primers further comprise stretches of nucleotides that comprise 5' and 3' untranslated regions, wherein the stretch of nucleotides in the forward primer that comprise the 5' untranslated region is between the nucleotides that comprise the RNA polymerase promoter and the nucleotides that are substantially complementary to the non-coding strand of a target double-stranded DNA of interest, and wherein the stretch of nucleotides in the reverse primer that comprise the 3' untranslated region is between the plurality of deoxythymidine nucleotides and the nucleotides that are substantially complementary to the coding strand of a target double-stranded DNA of interest. In some embodiments, the forward primer and open reading frame comprise a consensus Kozak sequence.

In some embodiments, the invention provides a method of generating one or more RNAs for transfection of cells comprising performing in vitro transcription from the linear double-stranded DNA template. In some embodiments, the method further comprises using a poly(A) polymerase to extend the poly(A) tail of the RNA with one or more adenine nucleotides or analogs thereof. In some embodiments, the method further comprises adding nucleotides during transcription that function as a 5' cap for the transcribed RNA. In some embodiments, the RNA targets a polypeptide selected from the group consisting of PD-1, TGFBR2, CBLB (CBL-B), CISH, CCRs (chimeric co-stimulatory receptors), IL-2, IL-12, IL-15, IL-21, NOTCH 1/2 ICD, TIM3, LAG3, TIGIT, TGFβ, CCR2, CCR4, CCR5, CXCR1, CXCR2, CSCR3, CCL2 (MCP-1), CCL3 (MIP-1α), CCL4

(MIP1-β), CCL5 (RANTES), CXCL1/CXCL8, CCL22, CCL17, CXCL1/CXCL8, VHL, CD44, PIK3CD, SOCS1, cAMP protein kinase A (PKA), and combinations thereof. In some embodiments, the RNA targets a polypeptide selected from the group consisting of PD-1, LAG-3, TIM-3, CTLA-4, TIGIT, CISH, TGFβR2, PKA, CBLB, BAFF (BR3), and combinations thereof.

In some embodiments, the invention employs the use of one or more isolated RNAs comprising one or more open reading frames, produced from the linear double-stranded DNA template. In some embodiments, the invention provides a method for expressing one or more RNAs in a cell comprising contacting cells with one or more RNAs produced from the linear double-stranded DNA template. In some embodiments, the RNAs are present in unequal molar amounts to provide separate expression levels of the RNAs in the cells. In some embodiments, the one or more RNAs target a polypeptide selected from the group consisting of PD-1, TGFBR2, CBLB (CBL-B), CISH, CCRs (chimeric co-stimulatory receptors), IL-2, IL-12, IL-15, IL-21, NOTCH 1/2 ICD, TIM3, LAG3, TIGIT, TGFβ, CCR2, CCR4, CCR5, CXCR1, CXCR2, CSCR3, CCL2 (MCP-1), CCL3 (MIP-1α), CCL4 (MIP1-β), CCL5 (RANTES), CXCL1/CXCL8, CCL22, CCL17, CXCL1/CXCL8, VHL, CD44, PIK3CD, SOCS1, cAMP protein kinase A (PKA), and combinations thereof. In some embodiments, the one or more RNAs target a polypeptide selected from the group consisting of PD-1, LAG-3, TIM-3, CTLA-4, TIGIT, CISH, TGFβR2, PKA, CBLB, BAFF (BR3), and combinations thereof.

(i) Untranslated Regions

Chemical structures with the ability to promote stability and/or translation efficiency may also be used. The RNA preferably has 5' and 3' UTRs. The examples below demonstrate that inclusion of 44 base pairs of 5' UTR into the PCR template enabled greater translation efficiency of transcribed CFP RNA when compared to PCR templates containing only 6 base pairs of 5' UTR. The examples also demonstrate that the addition of 113 base pairs of 3, UTR enables greater translation efficiency of transcribed GFP RNA when compared to PCR templates containing only 11 base pairs of 3, UTR. In general, the length of the 3' UTR exceeds 100 nucleotides, and therefore 3' UTR longer than 100 nucleotides is preferred. In one embodiment the 3' UTR sequence is between 100 and 5000 nucleotides. The length of the 5' UTR is not as critical as the length of the 3' UTR and can be shorter. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

(ii) RNA Polymerase Promoter

To enable synthesis of RNA from a DNA template without the need for gene cloning, a promoter of transcription should be attached to the DNA template upstream of the sequence to be transcribed. Bacteriophage RNA polymerase promoter sequences can be attached to the St UTR by different genetic engineering methods, such as DNA ligation, or can be added to the forward primer (5') of the sequence that is substantially complementary to the target DNA. When a sequence that functions as a promoter for an RNA polymerase is added to 5' end of the forward primer, the RNA polymerase promoter becomes incorporated into the PCR product upstream of the open reading frame that is to be transcribed. In one preferred embodiment, the promoter is a T7 polymerase promoter, as described above. Other useful promoters include, but are not limited to, T3 and SP6 RNA polymerase promoters. Consensus nucleotide sequences for T7, T3 and SP6 promoters are known in the art.

(iii) Poly(A) Tail and 5' Cap

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, *Nuc. Acids Res.*, 13:6223-36 (1985); Nacheva and Berzal-Herranz, *Eur. J. Biochem.*, 270:1485-65 (2003). This could lead to runoff transcript bending followed by template exchange with the second DNA strand or transcription of RNA itself (Triana-Alonso et al., *J. Biol. Chem.*, 270:6298-307 (1995); Dunn and Studier, *J. Mol. Biol.*, 166:477-535 (1983); Arnaud-Barbe et al., *Nuc. Acids Res.*, 26:3550-54 (1998); Macdonald et al., 1993), and then to the aberrant transcription in a reverse direction and accumulation of double stranded RNA, which can inhibit gene expression. DNA linearization itself is not sufficient for correct transcription (Triana-Alonso et al., J. Biol. Chem., 270:6298-307 (1995); Dunn and Studier, *J. Mol. Biol.*, 166:477-535 (1983); Arnaud-Barbe et al., 1998 *Nuc. Acids Res.*, 26:3550-54 (1998); Macdonald et al., *J. Mol. Biol.*, 232:1030-47 (1993); Nakano et al., *Biotechnol. Bioeng.*, 64:194-99 (1999), plasmid DNA linearized downstream of a poly(A/T) stretch of 64-100 nucleotides results in good templates (Saeboe-Larssen et al., *J. Immunol. Meth.*, 259:191-203 (2002); Boczkowski et al., *Cancer Res.*, 60:1028-34 (2000); Elango et al., *Biochem Riophys Res*

Figure 38:
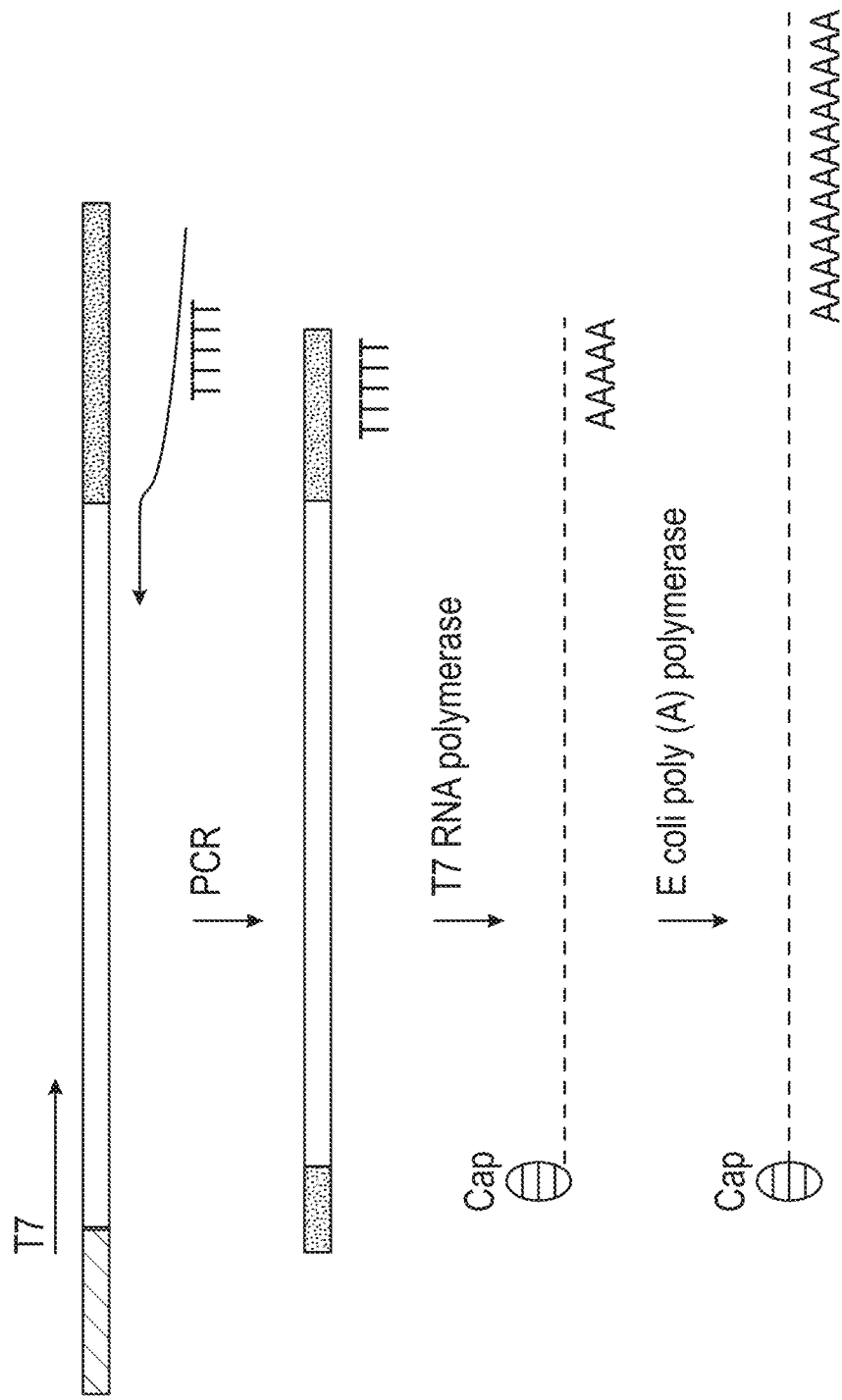
FIG. 38: Shows an exemplary scheme for mRNA synthesis using a DNA template obtained by PCR with use of specially designed primers. The forward primer contains a bacteriophage promoter suitable for in vitro transcription and the reverse primer contains a polyT stretch. The PCR product is an expression cassette suitable for in vitro transcription. Polyadenylates on the 3' end of the nascent mRNA can prevent aberrant RNA runoff synthesis and creation of double strand RNA product. After completion of transcription polyA tail can be additionally extended with poly(A) polymerase. (See, U.S. Pat. No. 8,859,229.)

Commun., 330:958-966 2005). An endogenous termination signal for T7 RNA polymerase encodes an RNA that can fold into a stem-loop structure followed by a track of uridine residues (Dunn and Studier, *J. Mol. Biol.*, 166:477-535 (1983); Arnaud-Barbe et al., 1998 *Nuc. Acids Res.*, 26:3550-54 (1998)). Even without a hairpin, a track of synthesized uridines can attenuate transcription (Kiyama and Oishi, *Nuc. Acids Res.*, 24:4577-4583 (1996). It was hypothesized that the linearization of plasmid DNA downstream of the poly (A/T) stretch probably formed a type of "dynamic" terminator preventing potential aberrant transcription: a 3' extension of the RNA transcript over a poly(A/T) stretch and transcription in the reverse direction will create a growing termination-like signal—an extended poly(U) stretch and a poly(A/U) hairpin. Accordingly, reversed PCR primers were designed with a 3' anchoring sequence downstream of the GFP gene and a 5' 100 base stretch of poly(T) (FIG. 38).

The conventional method of integration of polyA/T stretches into a DNA template is molecular cloning. However, polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines. The examples below demonstrate that a 100 base pair stretch of poly(A) is sufficient to enable efficient translation of an RNA transcript.

Poly(A) tails of RNAs can be further extended following in vitro transcription with the use of a poly(A) polymerase, such as E. coli polyA polymerase (E-PAP). The examples below demonstrate that increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA. Suitable ATP analogs include, but are not limited to, cordiocipin and 8-azaadenosine.

5' caps can also provide stability to RNA molecules. In a preferred embodiment, RNAs produced by the methods disclosed herein include a 5' cap. The 5' cap may, for example, be $m^7G(5')ppp(5')G$, $m^7G(5')ppp(5')A$, $G(5')ppp(5')G$ or $G(5')ppp(5')A$ cap analogs, which are all commercially available. The 5' cap can also be an anti-reverse-cap-analog (ARCA) (see, Stepinski, et al., *RNA*, 7:1468-95 (2001)) or any other suitable analog. The 5' cap is provided using techniques known in the art and described herein (Cougot, et al., *Trends in Biochem. Sci.*, 29:436-444 (2001); Stepinski, et al., *RNA*, 7:1468-95 (2001); Elango, et al., *Biochim. Biophys. Res. Commun.*, 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In some embodiments, the sd-RNA sequences used in the invention exhibit a 70% reduction in expression of the target gene. In some embodiments, the sd-RNA sequences used in the invention exhibit a 75% reduction in expression of the target gene. In some embodiments, the sd-RNA sequences used in the invention exhibit an 80% reduction in expression of the target gene. In some embodiments, the sd-RNA sequences used in the invention exhibit an 85% reduction in expression of the target gene. In some embodiments, the sd-RNA sequences used in the invention exhibit a 90% reduction in expression of the target gene. In some embodiments, the sd-RNA sequences used in the invention exhibit a 95% reduction in expression of the target gene. In some embodiments, the sd-RNA sequences used in the invention exhibit a 99% reduction in expression of the target gene. In some embodiments, the sd-RNA sequences used in the invention exhibit a reduction in expression of the target gene when delivered at a concentration of about 0.25 µM to about 10 µM, in some embodiments, about 0.25 µM to about 4 µM. In some embodiments, the sd-RNA sequences used in the invention exhibit a reduction in expression of the target gene when delivered at a concentration of about 0.25 µM. In some embodiments, the sd-RNA sequences used in the invention exhibit a reduction in expression of the target gene when delivered at a concentration of about 0.5 µM. In some embodiments, the sd-RNA sequences used in the invention exhibit a reduction in expression of the target gene when delivered at a concentration of about 0.75 µM. In some embodiments, the sd-RNA sequences used in the invention exhibit a reduction in expression of the target gene when delivered at a concentration of about 1.0 µM. In some embodiments, the sd-RNA sequences used in the invention exhibit a reduction in expression of the target gene when delivered at a concentration of about 1.25 µM. In some embodiments, the sd-RNA sequences used in the invention exhibit a reduction in expression of the target gene when delivered at a concentration of about 1.5 µM. In some embodiments, the sd-RNA sequences used in the invention exhibit a reduction in expression of the target gene when delivered at a concentration of about 1.75 µM. In some embodiments, the sd-RNA sequences used in the invention exhibit a reduction in expression of the target gene when delivered at a concentration of about 2.0 µM. In some embodiments, the sd-RNA sequences used in the invention exhibit a reduction in expression of the target gene when delivered at a concentration of about 2.25 µM. In some embodiments, the sd-RNA sequences used in the invention exhibit a reduction in expression of the target gene when delivered at a concentration of about 2.5 µM. In some embodiments, the sd-RNA sequences used in the invention exhibit a reduction in expression of the target gene when delivered at a concentration of about 2.75 µM. In some embodiments, the sd-RNA sequences used in the invention exhibit a reduction in expression of the target gene when delivered at a concentration of about 3.0 µM. In some embodiments, the sd-RNA sequences used in the invention exhibit a reduction in expression of the target gene when delivered at a concentration of about 3.25 µM. In some embodiments, the sd-RNA sequences used in the invention exhibit a reduction in expression of the target gene when delivered at a concentration of about 3.5 µM. In some embodiments, the sd-RNA sequences used in the invention exhibit a reduction in expression of the target gene when delivered at a concentration of about 3.75 µM. In some embodiments, the sd-RNA sequences used in the invention exhibit a reduction in expression of the target gene when delivered at a concentration of about 4.0 µM. In some embodiments, the sd-RNA sequences used in the invention exhibit a reduction in expression of the target gene when delivered at a concentration of about 5.0 µM. In some embodiments, the sd-RNA sequences used in the invention exhibit a reduction in expression of the target gene when delivered at a concentration of about 6.0 µM. In some embodiments, the sd-RNA sequences used in the invention exhibit a reduction in expression of the target gene when delivered at a concentration of about 7.0 µM. In some embodiments, the sd-RNA sequences used in the invention exhibit a reduction in expression of the target gene when delivered at a concentration of about 8.0 µM. In some embodiments, the sd-RNA sequences used in the invention exhibit a reduction in expression of the target gene when delivered at a concentration of about 9.0 µM. In some embodiments, the sd-RNA sequences used in the invention exhibit a reduction in expression of the target gene when delivered at a concentration of about 10.0 µM. In some embodiments, the sd-RNA sequences used in the invention exhibit a reduction in expression of the target gene when delivered at a concentration of about 0.25 µM to about 10 µM/10,000 TILs, or about 0.25 µM to about 4 µM/10,000 TILs. In some embodiments, the sd-RNA sequences used in the invention exhibit a reduction in expression of the target gene when delivered at a concentration of about 0.25 µM/10,000 TILs. In some embodiments, the sd-RNA sequences used in the invention exhibit a reduction in expression of the target gene when delivered at a concentration of about 0.5 µM/10,000 TILs. In some embodiments, the sd-RNA sequences used in the invention exhibit a reduction in expression of the target gene when delivered at a concentration of about 0.75 µM/10,000 TILs. In some embodiments, the sd-RNA sequences used in the invention exhibit a reduction in expression of the target gene when delivered at a concentration of about 1.0 µM/10,000 TILs. In some embodiments, the sd-RNA sequences used in the invention exhibit a reduction in expression of the target gene when delivered at a concentration of about 1.25 µM/10,000 TILs. In some embodiments, the sd-RNA sequences used in the invention exhibit a reduction in expression of the target gene when delivered at a concentration of about 1.5 µM/10,000 TILs. In some embodiments, the sd-RNA sequences used in the invention exhibit a reduction in expression of the target gene when delivered at a concentration of about 1.75 µM/10,000 TILs. In some embodiments, the sd-RNA sequences used in the invention exhibit a reduction in expression of the target gene when delivered at a concentration of about 2.0 µM/10,000 TILs. In some embodiments, the sd-RNA sequences used in the invention exhibit a reduction in expression of the target gene when delivered at a concentration of about 2.25 µM/10,000 TILs. In some embodiments, the sd-RNA sequences used in the invention exhibit a reduction in expression of the target gene when delivered at a concentration of about 2.5 µM/10,000 TILs. In some embodiments, the sd-RNA sequences used in the invention exhibit a reduction in expression of the target gene when delivered at a concentration of about 2.75 µM/10,000 TILs. In some embodiments, the sd-RNA sequences used in the invention exhibit a reduction in expression of the target gene when delivered at a concentration of about 3.0 µM/10,000 TILs. In some embodiments, the sd-RNA sequences used in the invention exhibit a reduction in expression of the target gene when delivered at a concentration of about 3.25 µM/10,000 TILs. In some embodiments, the sd-RNA sequences used in the invention exhibit a reduction in expression of the target gene when delivered at a concentration of about 3.5 µM/10,000 TILs. In some embodiments, the sd-RNA sequences used in the invention exhibit a reduction in expression of the target gene when delivered at a concentration of about 3.75 µM/10,000 TILs. In some embodiments, the sd-RNA sequences used in the invention exhibit a reduction in expression of the target gene when delivered at a concentration of about 4.0 µM/10,000 TILs. In some embodiments, the sd-RNA sequences used in the invention exhibit a reduction in expression of the target gene when delivered at a concentration of about 5.0 µM/10,000 TILs. In some embodiments, the sd-RNA sequences used in the invention exhibit a reduction in expression of the target gene when delivered at a concentration of about 6.0 µM/10,000 TILs. In some embodiments, the sd-RNA sequences used in the invention exhibit a reduction in expression of the target gene when delivered at a concentration of about 7.0 µM/10,000 TILs. In some embodiments, the sd-RNA sequences used in the invention exhibit a reduction in expression of the target gene when delivered at a concentration of about 8.0 µM/10,000 TILs. In some embodiments, the sd-RNA sequences used in the invention exhibit a reduction in expression of the target gene when delivered at a concentration of about 9.0 µM/10,000 TILs. In some embodiments, the sd-RNA sequences used in the invention exhibit a reduction in expression of the target gene when delivered at a concentration of about 10.0 µM/10,000 TILs. In some embodiments, the sd-RNA sequences used in the invention exhibit a reduction in expression of the target gene when delivered at a concentration of about 0.25 µM/10,000 TILs/100 µL media. In some embodiments, the sd-RNA sequences used in the invention exhibit a reduction in expression of the target gene when delivered at a concentration of about 0.5 µM/10,000 TILs/100 µL media. In some embodiments, the sd-RNA sequences used in the invention exhibit a reduction in expression of the target gene when delivered at a concentration of about 0.75 µM/10,000 TILs/100 µL media. In some embodiments, the sd-RNA sequences used in the invention exhibit a reduction in expression of the target gene when delivered at a concentration of about 1.0 µM/10,000 TILs/100 µL media. In some embodiments, the sd-RNA sequences used in the invention exhibit a reduction in expression of the target gene when delivered at a concentration of about 1.25 µM/10,000 TILs/100 µL media. In some embodiments, the sd-RNA sequences used in the invention exhibit a reduction in expression of the target gene when delivered at a concentration of about 1.5 µM/10,000 TILs/100 µL media. In some embodiments, the sd-RNA sequences used in the invention exhibit a reduction in expression of the target gene when delivered at a concentration of about 1.75 µM/10,000 TILs/100 µL media. In some embodiments, the sd-RNA sequences used in the invention exhibit a reduction in expression of the target gene when delivered at a concentration of about 2.0 µM/10,000 TILs/100 µL media. In some embodiments, the sd-RNA sequences used in the invention exhibit a reduction in expression of the target gene when delivered at a concentration of about 2.25 µM/10,000 TILs/100 µL media. In some embodiments, the sd-RNA sequences used in the invention exhibit a reduction in expression of the target gene when delivered at a concentration of about 2.5 µM/10,000 TILs/100 µL media. In some embodiments, the sd-RNA sequences used in the invention exhibit a reduction in expression of the target gene when delivered at a concentration of about 2.75 μM/10,000 TILs/100 μL media. In some embodiments, the sd-RNA sequences used in the invention exhibit a reduction in expression of the target gene when delivered at a concentration of about 3.0 μM/10,000 TILs/100 μL media. In some embodiments, the sd-RNA sequences used in the invention exhibit a reduction in expression of the target gene when delivered at a concentration of about 3.25 μM/10,000 TILs/100 μL media. In some embodiments, the sd-RNA sequences used in the invention exhibit a reduction in expression of the target gene when delivered at a concentration of about 3.5 μM/10,000 TILs/100 μL media. In some embodiments, the sd-RNA sequences used in the invention exhibit a reduction in expression of the target gene when delivered at a concentration of about 3.75 μM/10,000 TILs/100 μL media. In some embodiments, the sd-RNA sequences used in the invention exhibit a reduction in expression of the target gene when delivered at a concentration of about 4.0 μM/10,000 TILs/100 μL media. In some embodiments, the sd-RNA sequences used in the invention exhibit a reduction in expression of the target gene when delivered at a concentration of about 5.0 μM/10,000 TILs/100 μL media. In some embodiments, the sd-RNA sequences used in the invention exhibit a reduction in expression of the target gene when delivered at a concentration of about 6.0 μM/10,000 TILs/100 μL media. In some embodiments, the sd-RNA sequences used in the invention exhibit a reduction in expression of the target gene when delivered at a concentration of about 7.0 μM/10,000 TILs/100 μL media. In some embodiments, the sd-RNA sequences used in the invention exhibit a reduction in expression of the target gene when delivered at a concentration of about 8.0 μM/10,000 TILs/100 μL media. In some embodiments, the sd-RNA sequences used in the invention exhibit a reduction in expression of the target gene when delivered at a concentration of about 9.0 μM/10,000 TILs/100 μL media. In some embodiments, the sd-RNA sequences used in the invention exhibit a reduction in expression of the target gene when delivered at a concentration of about 10.0 μM/10,000 TILs/100 μL media.

c. sd-RNA Modifications

In some embodiments, the oligonucleotide agents comprise one or more modification to increase stability and/or effectiveness of the therapeutic agent, and to effect efficient delivery of the oligonucleotide to the cells or tissue to be treated. Such modifications can include a 2'-O-methyl modification, a 2'-O-Fluro modification, a diphosphorothioate modification, 2' F modified nucleotide, a 2'-O-methyl modified and/or a 2'deoxy nucleotide. In some embodiments, the oligonucleotide is modified to include one or more hydrophobic modifications including for example, sterol, cholesterol, vitamin D, naphtyl, isobutyl, benzyl, indol, tryptophane, and/or phenyl. In an additional particular embodiment, chemically modified nucleotides are combination of phosphorothioates, 2'-O-methyl, 2'deoxy, hydrophobic modifications and phosphorothioates. In some embodiments, the sugars can be modified and modified sugars can include but are not limited to D-ribose, 2'-O-alkyl (including 2'-O-methyl and 2'-0-ethyl), i.e., 2'-alkoxy, 2'-amino, 2'-S-alkyl, 2'-halo (including 2'-fluoro), T-methoxyethoxy, 2'-allyloxy ($-OCH_2CH=CH_2$), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., *Nucl. Acids. Res.*, 18:4711 (1992)).

In some embodiments, the double-stranded oligonucleotide of the invention is double-stranded over its entire length, i.e., with no overhanging single-stranded sequence at either end of the molecule, i.e., is blunt-ended. In some embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). In some embodiments, when a single nucleic acid molecule is used a portion of the molecule at either end can remain single-stranded.

In some embodiments, a double-stranded oligonucleotide of the invention contains mismatches and/or loops or bulges, but is double-stranded over at least about 70% of the length of the oligonucleotide. In some embodiments, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In some embodiments, a double-stranded oligonucleotide of the invention is double-stranded over at least about 96%-98% of the length of the oligonucleotide. In some embodiments, the double-stranded oligonucleotide of the invention contains at least or up to 1, 2, 3, 4, 5, 6, 7, 8, 9, 10, 11, 12, 13, 14, or 15 mismatches.

In some embodiments, the oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2$—$CH_2$—$CH_3$), glycol (-0-$CH_2$—$CH_2$—O—) phosphate ($PO_3^{2"}$), hydrogen phosphonate, or phosphoramidite). "Blocking groups" can also include "end blocking groups" or "exonuclease blocking groups" which protect the 5' and 3' termini of the oligonucleotide, including modified nucleotides and non-nucleotide exonuclease resistant structures.

In some embodiments, at least a portion of the contiguous polynucleotides within the sd-RNA are linked by a substitute linkage, e.g., a phosphorothioate linkage.

In some embodiments, chemical modification can lead to at least a 1.5, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500 enhancements in cellular uptake. In some embodiments, at least one of the C or U residues includes a hydrophobic modification. In some embodiments, a plurality of Cs and Us contain a hydrophobic modification. In some embodiments, at least 10%, 15%, 20%, 30%, 40%, 50%, 55%, 60% 65%, 70%, 75%, 80%, 85%, 90% or at least 95% of the Cs and Us can contain a hydrophobic modification. In some embodiments, all of the Cs and Us contain a hydrophobic modification.

In some embodiments, the sd-RNA or sd-rxRNAs exhibit enhanced endosomal release of sd-rxRNA molecules through the incorporation of protonatable amines. In some embodiments, protonatable amines are incorporated in the sense strand (in the part of the molecule which is discarded after RISC loading). In some embodiments, the sd-RNA compounds of the invention comprise an asymmetric compound comprising a duplex region (required for efficient RISC entry of 10-15 bases long) and single stranded region of 4-12 nucleotides long; with a 13 nucleotide duplex. In some embodiments, a 6 nucleotide single stranded region is employed. In some embodiments, the single stranded region of the sd-RNA comprises 2-12 phosphorothioate internucleotide linkages (referred to as phosphorothioate modifications). In some embodiments, 6-8 phosphorothioate internucleotide linkages are employed. In some embodiments, the sd-RNA compounds of the invention also include a unique chemical modification pattern, which provides stability and is compatible with RISC entry.

The guide strand, for example, may also be modified by any chemical modification which confirms stability without interfering with RISC entry. In some embodiments, the chemical modification pattern in the guide strand includes the majority of C and U nucleotides being 2' F modified and the 5' end being phosphorylated.

In some embodiments, at least 30% of the nucleotides in the sd-RNA or sd-rxRNA are modified. In some embodiments, at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the sd-RNA or sd-rxRNA are modified. In some embodiments, 100% of the nucleotides in the sd-RNA or sd-rxRNA are modified.

In some embodiments, the sd-RNA molecules have minimal double stranded regions. In some embodiments the region of the molecule that is double stranded ranges from 8-15 nucleotides long. In some embodiments, the region of the molecule that is double stranded is 8, 9, 10, 11, 12, 13, 14 or 15 nucleotides long. In some embodiments the double stranded region is 13 nucleotides long. There can be 100% complementarity between the guide and passenger strands, or there may be one or more mismatches between the guide and passenger strands. In some embodiments, on one end of the double stranded molecule, the molecule is either blunt-ended or has a one-nucleotide overhang. The single stranded region of the molecule is in some embodiments between 4-12 nucleotides long. In some embodiments, the single stranded region can be 4, 5, 6, 7, 8, 9, 10, 11 or 12 nucleotides long. In some embodiments, the single stranded region can also be less than 4 or greater than 12 nucleotides long. In certain embodiments, the single stranded region is 6 or 7 nucleotides long.

In some embodiments, the sd-RNA molecules have increased stability. In some instances, a chemically modified sd-RNA or sd-rxRNA molecule has a half-life in media that is longer than 1, 2, 3, 4, 5, 6, 7, 8, 9, 10, 11, 12, 13, 14, 15, 16, 17, 18, 19, 20, 21, 22, 23, 24 or more than 24 hours, including any intermediate values. In some embodiments, the sd-rxRNA has a half-life in media that is longer than 12 hours.

In some embodiments, the sd-RNA is optimized for increased potency and/or reduced toxicity. In some embodiments, nucleotide length of the guide and/or passenger strand, and/or the number of phosphorothioate modifications in the guide and/or passenger strand, can in some aspects influence potency of the RNA molecule, while replacing 2'-fluoro (2'F) modifications with 2'-0-methyl (2'OMe) modifications can in some aspects influence toxicity of the molecule. In some embodiments, reduction in 2'F content of a molecule is predicted to reduce toxicity of the molecule. In some embodiments, the number of phosphorothioate modifications in an RNA molecule can influence the uptake of the molecule into a cell, for example the efficiency of passive uptake of the molecule into a cell. In some embodiments, the sd-RNA has no 2'F modification and yet are characterized by equal efficacy in cellular uptake and tissue penetration.

In some embodiments, a guide strand is approximately 18-19 nucleotides in length and has approximately 2-14 phosphate modifications. For example, a guide strand can contain 2, 3, 4, 5, 6, 7, 8, 9, 10, 11, 12, 13, 14 or more than 14 nucleotides that are phosphate-modified. The guide strand may contain one or more modifications that confer increased stability without interfering with RISC entry. The phosphate modified nucleotides, such as phosphorothioate modified nucleotides, can be at the 3' end, 5' end or spread throughout the guide strand. In some embodiments, the 3' terminal 10 nucleotides of the guide strand contains 1, 2, 3, 4, 5, 6, 7, 8, 9 or 10 phosphorothioate modified nucleotides. The guide strand can also contain 2'F and/or 2'OMe modifications, which can be located throughout the molecule. In some embodiments, the nucleotide in position one of the guide strand (the nucleotide in the most 5' position of the guide strand) is 2'OMe modified and/or phosphorylated. C and U nucleotides within the guide strand can be 2'F modified. For example, C and U nucleotides in positions 2-10 of a 19 nt guide strand (or corresponding positions in a guide strand of a different length) can be 2'F modified. C and U nucleotides within the guide strand can also be 2'OMe modified. For example, C and U nucleotides in positions 11-18 of a 19 nt guide strand (or corresponding positions in a guide strand of a different length) can be 2'OMe modified. In some embodiments, the nucleotide at the most 3' end of the guide strand is unmodified. In certain embodiments, the majority of Cs and Us within the guide strand are 2'F modified and the 5' end of the guide strand is phosphorylated. In other embodiments, position 1 and the Cs or Us in positions 11-18 are 2'OMe modified and the 5' end of the guide strand is phosphorylated. In other embodiments, position 1 and the Cs or Us in positions 11-18 are 2'OMe modified, the 5' end of the guide strand is phosphorylated, and the Cs or Us in position 2-10 are 2'F modified.

d. Delivery of sd-RNA

The self-deliverable RNAi technology provides a method of directly transfecting cells with the RNAi agent, without the need for additional formulations or techniques. The ability to transfect hard-to-transfect cell lines, high in vivo activity, and simplicity of use, are characteristics of the compositions and methods that present significant functional advantages over traditional siRNA-based techniques, and as such, the sd-RNA methods are employed in several embodiments related to the methods of reduction in expression of the target gene in the TILs of the present invention. The sd-RNAi methods allows direct delivery of chemically synthesized compounds to a wide range of primary cells and tissues, both ex-vivo and in vivo. The sd-RNAs described in some embodiments of the invention herein are commercially available from Advirna LLC, Worcester, MA, USA.

The general structure of sd-RNA molecules is shown in FIG. 36. sd-RNA are formed as hydrophobically-modified siRNA-antisense oligonucleotide hybrid structures, and are disclosed, for example in Byrne et al., December 2013, J. Ocular Pharmacology and Therapeutics, 29(10): 855-864, incorporated by reference herein in its entirety.

In some embodiments, the sd-RNA oligonucleotides can be delivered to the TILs described herein using sterile electroporation.

In some embodiments, the oligonucleotides can be delivered to the cells in combination with a transmembrane delivery system. In some embodiments, this transmembrane delivery system comprises lipids, viral vectors, and the like. In some embodiments, the oligonucleotide agent is a self-delivery RNAi agent, that does not require any delivery agents.

In embodiments, the oligonucleotides, such as RNAs or sd-RNAs described herein, can be introduced into target cells using different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, MA), Neon™ Transfection System (commercially available from ThermoFisher Scientific, Waltham, MA), and/or the Gene Pulser II (BioRad, Denver, CO), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001), incorporated by reference herein in its entirety. See, also, U.S. Pat. No. 8,859,229, U.S. Patent Application No. 2016/0230188, as well as the Amaxa Nucleofector® II Manual (available on the World Wide Web at http://icob-.sinica.edu.tw/pubweb/bio-chem/Core%20Facilities/Data/R401-core/Nucleofector_Manual_II_Apr06.pdf).

In some embodiments, electroporation can be performed using an Amaxa NUCLEOFECTOR™-II in accordance with manufacturer recommendations. In some embodiments, TILs can be transfected using NUCLEOFECTOR™-II solution V and the set of recommended regimes for electroporation. In some embodiments, TILs can be transfected using solutions V, T and R and different regimes of electroporation. In some embodiments, TILs can be transfected using T cell NUCLEOFECTOR™-II solution and different regimes of electroporation. Alternative methods of nucleic acids delivery can also be employed to transfect the oligonucleotides described herein used: cationic liposome mediated transfection was performed using LIPOFECTIN or LIPOFECTAMIN (Invitrogen). Electroporation was also performed with the ECM 830 (BTX) (Harvard Instruments, Boston, MA), the Gene Pulser II (BioRad, Denver, CO), Multiporator (Eppendorf, Hamburg Germany), and/or the Neon™ Transfection System (commercially available from ThermoFisher Scientific, Waltham, MA). In some embodiments, a pmaxGFP plasmid DNA (Amaxa Biosystems) can be employed as the DNA control. In some embodiments, the efficiency of transfection (ET) can be determined approximately 3, 6, 9, 12, 15, and/or 18 hours after transfection by fluorescence activated cell sorting (FACS). In some experiments transfectants can be further analyzed every 12 hours to 24 hours until GFP could no longer be detected for GFP controls. In some embodiments, cell viability can be determined by trypan blue dye exclusion.

Oligonucleotides and oligonucleotide compositions are contacted with (e.g., brought into contact with, also referred to herein as administered or delivered to) and taken up by TILs described herein, including through passive uptake by TILs. The sd-RNA can be added to the TILs as described herein during the first expansion, for example Step B, after the first expansion, for example, during Step C, before or during the second expansion, for example before or during Step D, after Step D and before harvest in Step E, during or after harvest in Step F, before or during final formulation and/or transfer to infusion Bag in Step F, as well as before any optional cryopreservation step in Step F. Moreover, sd-RNA can be added after thawing from any cryopreservation step in Step F. In an embodiment, one or more sd-RNAs targeting genes as described herein, including PD-1, LAG-3, TIM-3, CISH, and CBLB, may be added to cell culture media comprising TILs and other agents at concentrations selected from the group consisting of 100 nM to 20 mM, 200 nM to 10 mM, 500 nm to 1 mM, 1 µM to 100 µM, and 1 µM to 100 µM. In an embodiment, one or more sd-RNAs targeting genes as described herein, including PD-1, LAG-3, TIM-3, CISH, and CBLB, may be added to cell culture media comprising TILs and other agents at amounts selected from the group consisting of 0.1 µM sd-RNA/10,000 TILs/100 µL media, 0.5 µM sd-RNA/10,000 TILs/100 µL media, 0.75 µM sd-RNA/10,000 TILs/100 µL media, 1 µM sd-RNA/10,000 TILs/100 µL media, 1.25 µM sd-RNA/10,000 TILs/100 µL media, 1.5 µM sd-RNA/10,000 TILs/100 µL media, 2 µM sd-RNA/10,000 TILs/100 µL media, 5 µM sd-RNA/10,000 TILs/100 µL media, or 10 µM sd-RNA/10,000 TILs/100 µL media. In an embodiment, one or more sd-RNAs targeting genes as described herein, including PD-1, LAG-3, TIM-3, CISH, and CBLB, may be added to TIL cultures during the pre-REP or REP stages twice a day, once a day, every two days, every three days, every four days, every five days, every six days, or every seven days. In an embodiment, one or more sd-RNAs targeting genes as described herein, including PD-1, LAG-3, TIM-3, CISH, and CBLB, may be added to cell culture media comprising TILs and other agents at amounts selected from the group consisting of 0.1 µM sd-RNA/10,000 TILs, 0.5 µM sd-RNA/10,000 TILs, 0.75 µM sd-RNA/10,000 TILs, 1 µM sd-RNA/10,000 TILs, 1.25 µM sd-RNA/10,000 TILs, 1.5 µM sd-RNA/10,000 TILs, 2 µM sd-RNA/10,000 TILs, 5 µM sd-RNA/10,000 TILs, or 10 µM sd-RNA/10,000 TILs. In an embodiment, one or more sd-RNAs targeting genes as described herein, including PD-1, LAG-3, TIM-3, CISH, and CBLB, may be added to TIL cultures during the first, second, and or additional expansion stages twice a day, once a day, every two days, every three days, every four days, every five days, every six days, or every seven days.

Oligonucleotide compositions of the invention, including sd-RNA, can be contacted with TILs as described herein during the expansion process, for example by dissolving sd-RNA at high concentrations in cell culture media and allowing sufficient time for passive uptake to occur. In some embodiments, the high concentrations include 0.1 µM sd-RNA/10,000 TILs, 0.5 µM sd-RNA/10,000 TILs, 0.75 µM sd-RNA/10,000 TILs, 1 µM sd-RNA/10,000 TILs, 1.25 µM sd-RNA/10,000 TILs, 1.5 µM sd-RNA/10,000 TILs, 2 µM sd-RNA/10,000 TILs, 5 µM sd-RNA/10,000 TILs, or 10 µM sd-RNA/10,000 TILs. In some embodiments, the high concentrations include 2 µM sd-RNA/10,000 TILs, 5 µM sd-RNA/10,000 TILs, or 10 µM sd-RNA/10,000 TILs. In some embodiments, the high concentrations include 5 µM sd-RNA/10,000 TILs or up to 10 µM sd-RNA/10,000 TILs.

In some embodiments, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see, e.g., WO 90/14074; WO 91/16024; WO 91/17424; U.S. Pat. No. 4,897,355; Bergan et a 1993. Nucleic Acids Research. 21:3567).

e. sd-RNA Combinations

In some embodiments, more than one sd-RNA is used to reduce expression of a target gene. In some embodiments, one or more of PD-1, TIM-3, CBLB, LAG3 and/or CISH targeting sd-RNAs are used together. In some embodiments, a PD-1 sd-RNA is used with one or more of TIM-3, CBLB, LAG3 and/or CISH in order to reduce expression of more than one gene target. In some embodiments, a LAG3 sd-RNA is used in combination with a CISH targeting sd-RNA to reduce gene expression of both targets. In some embodiments, the sd-RNAs targeting one or more of PD-1, TIM-3, CBLB, LAG3 and/or CISH herein are commercially available from Advirna LLC, Worcester, MA, USA. In some embodiments, the sd-RNAs targeting one or more of PD-1, TIM-3, CBLB, LAG3 and/or CISH have the structure shown in FIG. 36 or FIG. 37.

In some embodiments, the sd-RNA targets a gene selected from the group consisting of PD-1, LAG3, TIM3, CTLA-4, TIGIT, CISH, TGFβR2, PKA, CBLB, BAFF (BR3), and combinations thereof. In some embodiments, the sd-RNA targets a gene selected from the group consisting of PD-1, LAG3, TIM3, CTLA-4, TIGIT, CISH, TGFβR2, PKA, CBLB, BAFF (BR3), and combinations thereof. In some embodiments, one sd-RNA targets PD-1 and another sd-RNA targets a gene selected from the group consisting of LAG3, TIM3, CTLA-4, TIGIT, CISH, TGFβR2, PKA, CBLB, BAFF (BR3), and combinations thereof. In some embodiments, the sd-RNA targets a gene selected from PD-1, LAG-3, CISH, CBLB, TIM3, and combinations thereof. In some embodiments, the sd-RNA targets a gene selected from PD-1 and one of LAG3, CISH, CBLB, TIM3, and combinations thereof. In some embodiments, one sd-RNA targets PD-1 and one sd-RNA targets LAG3. In some embodiments, one sd-RNA targets PD-1 and one sd-RNA targets CISH. In some embodiments, one sd-RNA targets PD-1 and one sd-RNA targets CBLB. In some embodiments, one sd-RNA targets LAG3 and one sd-RNA targets CISH. In some embodiments, one sd-RNA targets LAG3 and one sd-RNA targets CBLB. In some embodiments, one sd-RNA targets CISH and one sd-RNA targets CBLB. In some embodiments, one sd-RNA targets TIM3 and one sd-RNA targets PD-1. In some embodiments, one sd-RNA targets TIM3 and one sd-RNA targets LAG3. In some embodiments, one sd-RNA targets TIM3 and one sd-RNA targets CISH. In some embodiments, one sd-RNA targets TIM3 and one sd-RNA targets CBLB.

f. Overexpression of Co-Stimulatory Receptors or Adhesion Molecules

According to additional embodiments, altering the protein expression of TILs during the TIL expansion method can also allow for expression of one or more immune checkpoint genes to be enhanced in at least a portion of the therapeutic population of TILs. For example, altering the protein expression may cause the expression of a stimulatory receptor to be enhanced, which means that it is overexpressed as compared to the expression of a stimulatory receptor that has not been genetically modified. Non-limiting examples of immune checkpoint genes that may exhibit enhanced expression by transiently altering the protein expression in TILs of the present invention include certain chemokine receptors and interleukins, such as CCR2, CCR4, CCR5, CXCR2, CXCR3, CX3CR1, IL-2, IL-4, IL-7, IL-10, IL-15, IL-21, the NOTCH 1/2 intracellular domain (ICD), and/or the NOTCH ligand mDLL1.

(i) CCRs & CCLs

For adoptive T cell immunotherapy to be effective, T cells need to be trafficked properly into tumors by chemokines. A match between chemokines secreted by tumor cells, chemokines present in the periphery, and chemokine receptors expressed by T cells is important for successful trafficking of T cells into a tumor bed.

According to particular embodiments, altering the protein expression methods of the present invention may be used to increase the expression of certain chemokine receptors in the TILs, such as one or more of CCR2, CCR4, CCR5, CXCR2, CXCR3, and/or CX3CR1. Over-expression of CCRs may help promote effector function and proliferation of TILs following adoptive transfer. In some embodiments, altering the protein expression methods of the present invention may be used to increase the expression of CCL2 (MCP-1), CCL3 (MIP-1α), CCL4 (MIP1-β), CCL5 (RANTES), CXCL1, CXCL8, CCL22, and/or CCL17 in the TILs.

Figure 20:
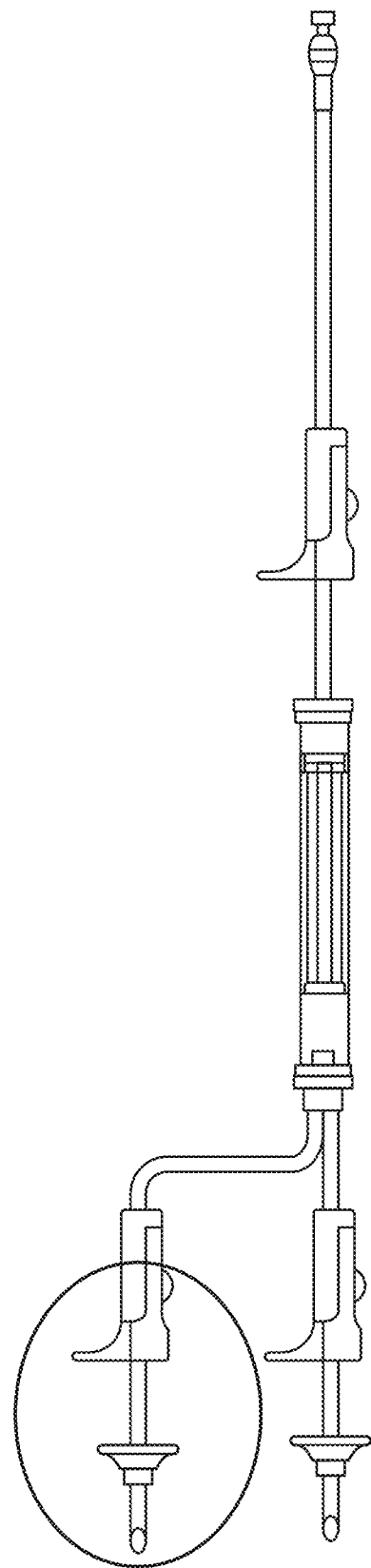
FIG. 20: Shows a schematic of the sterile weld (see, Process Note 5.11 in Example 16) the red media removal line from the GRex100MCS to the "Supernatant" transfer pack.
Figure 21:
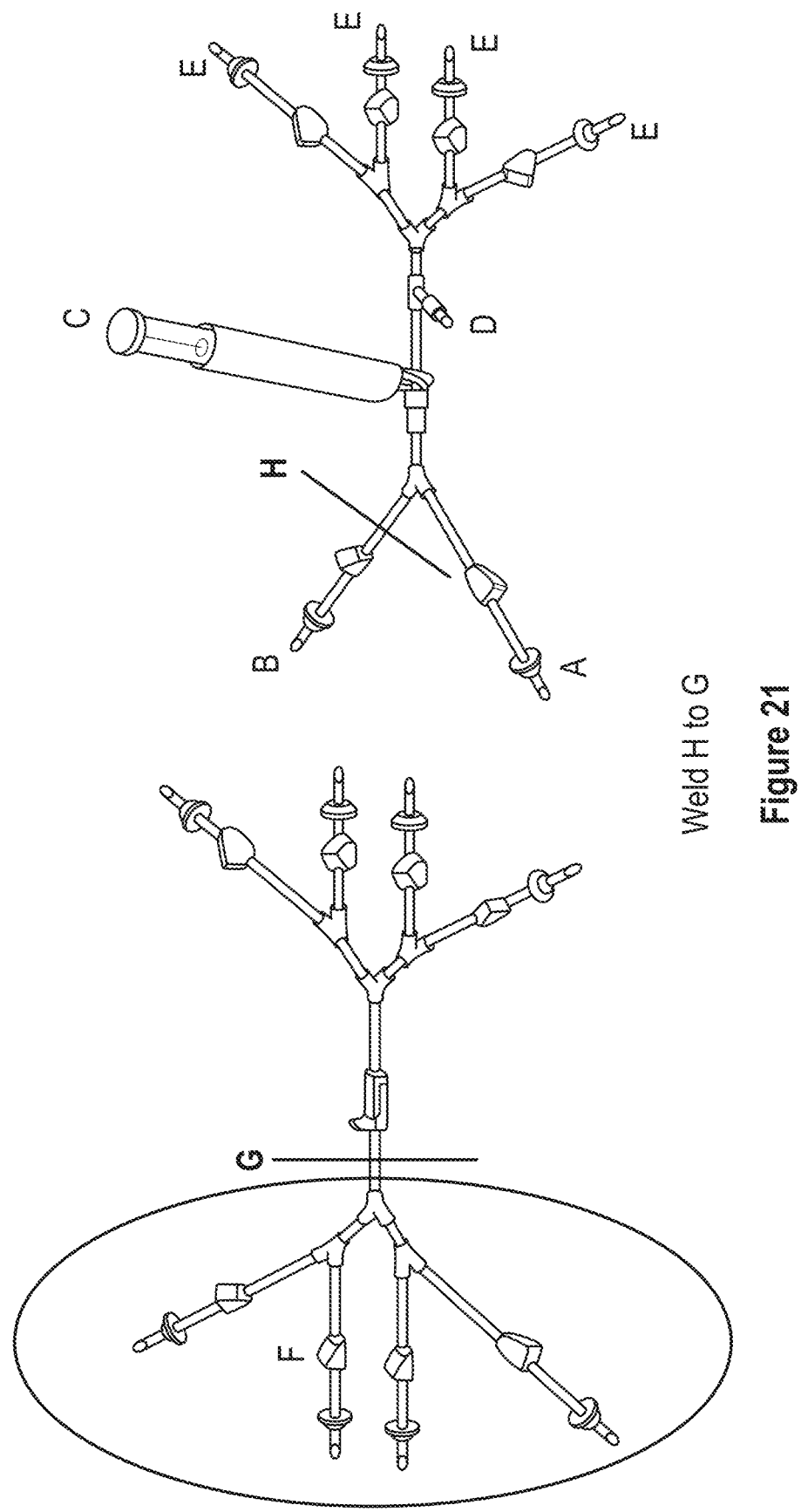
FIG. 21: Shows a schematic of the weld (see, Process Note 5.11 in Example 16) 4S-4M60 to a CC2 Cell Connect, replacing a single spike of the Cell Connect apparatus (B) with the 4-spike end of the 4S-4M60 manifold at (G).
Figure 22:
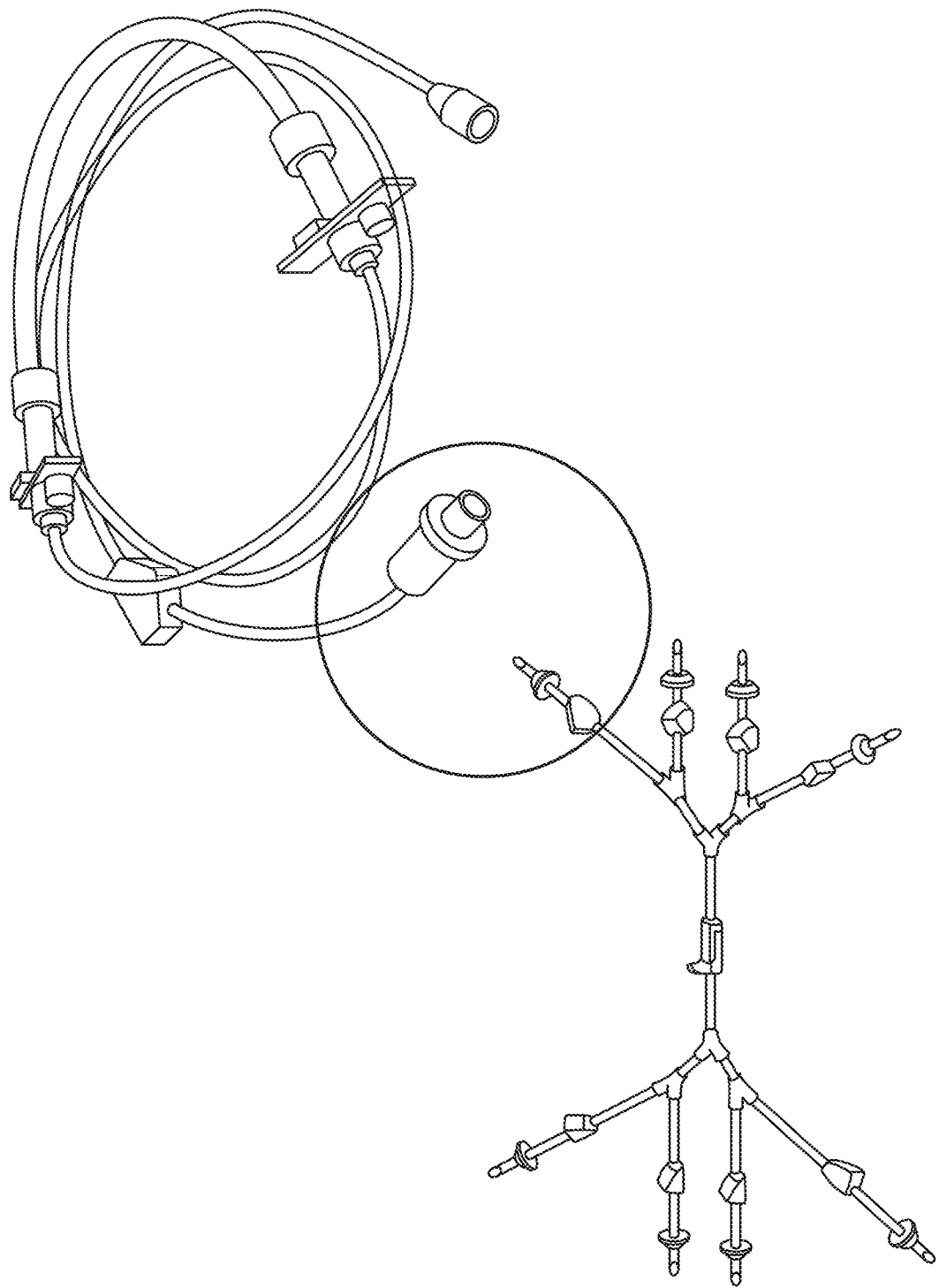
FIG. 22: Shows a schematic of the weld (see, Process Note 5.11 in Example 16) repeater fluid transfer set to one of the male luer ends of 45-4M60.
Figure 23:
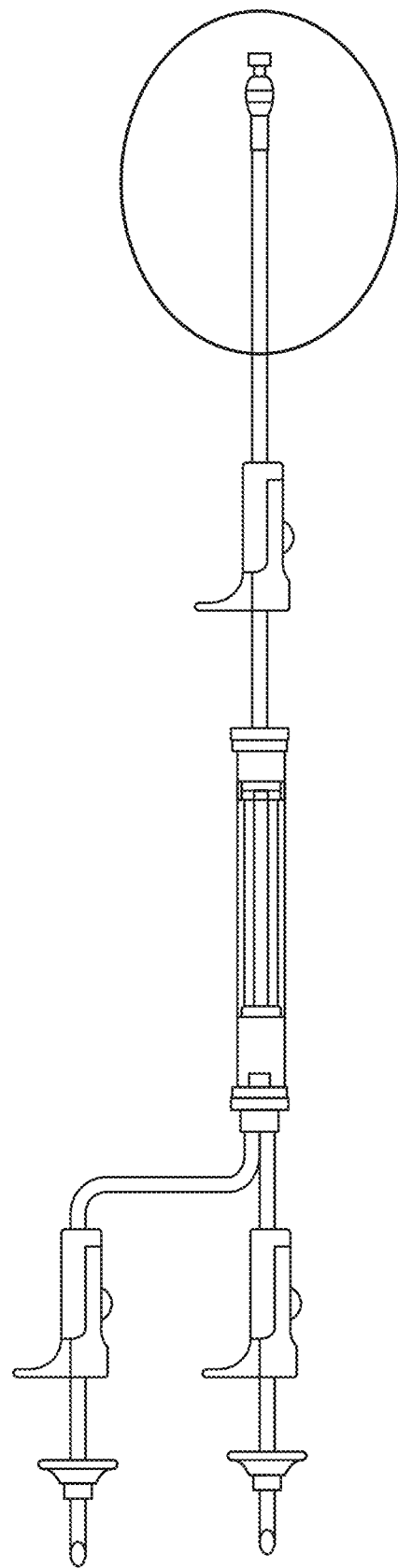
FIG. 23: Shows a schematic of the sterile weld (see, Process Note 5.11 in Example 16) the long terminal end of the gravity blood filter to the LOVO source bag.
Figure 24:
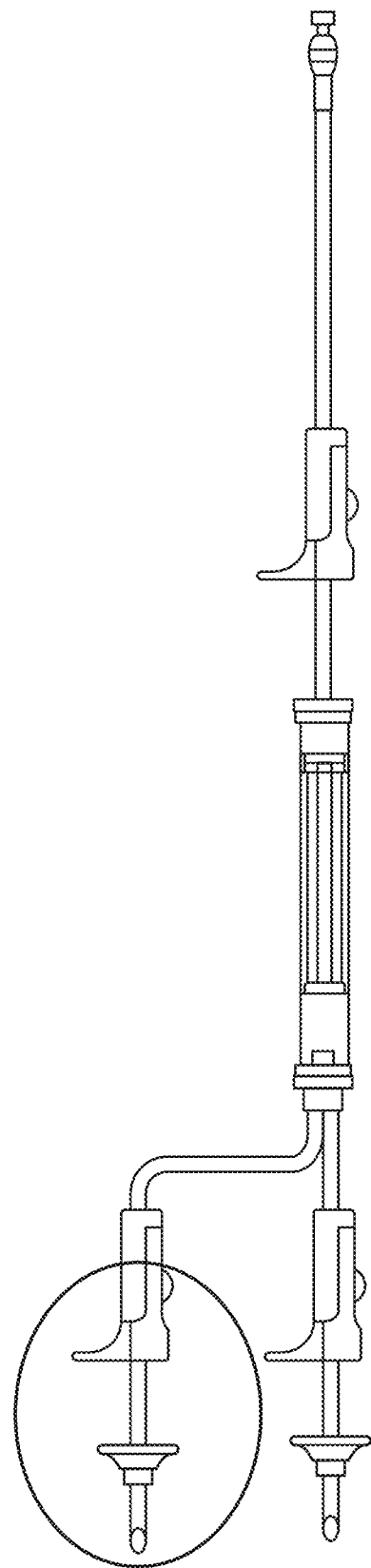
FIG. 24: Shows a schematic of the sterile weld (see, Process Note 5.11 in Example 16) one of the two source lines of the filter to "pooled TIL suspension" collection bag.
Figure 25:
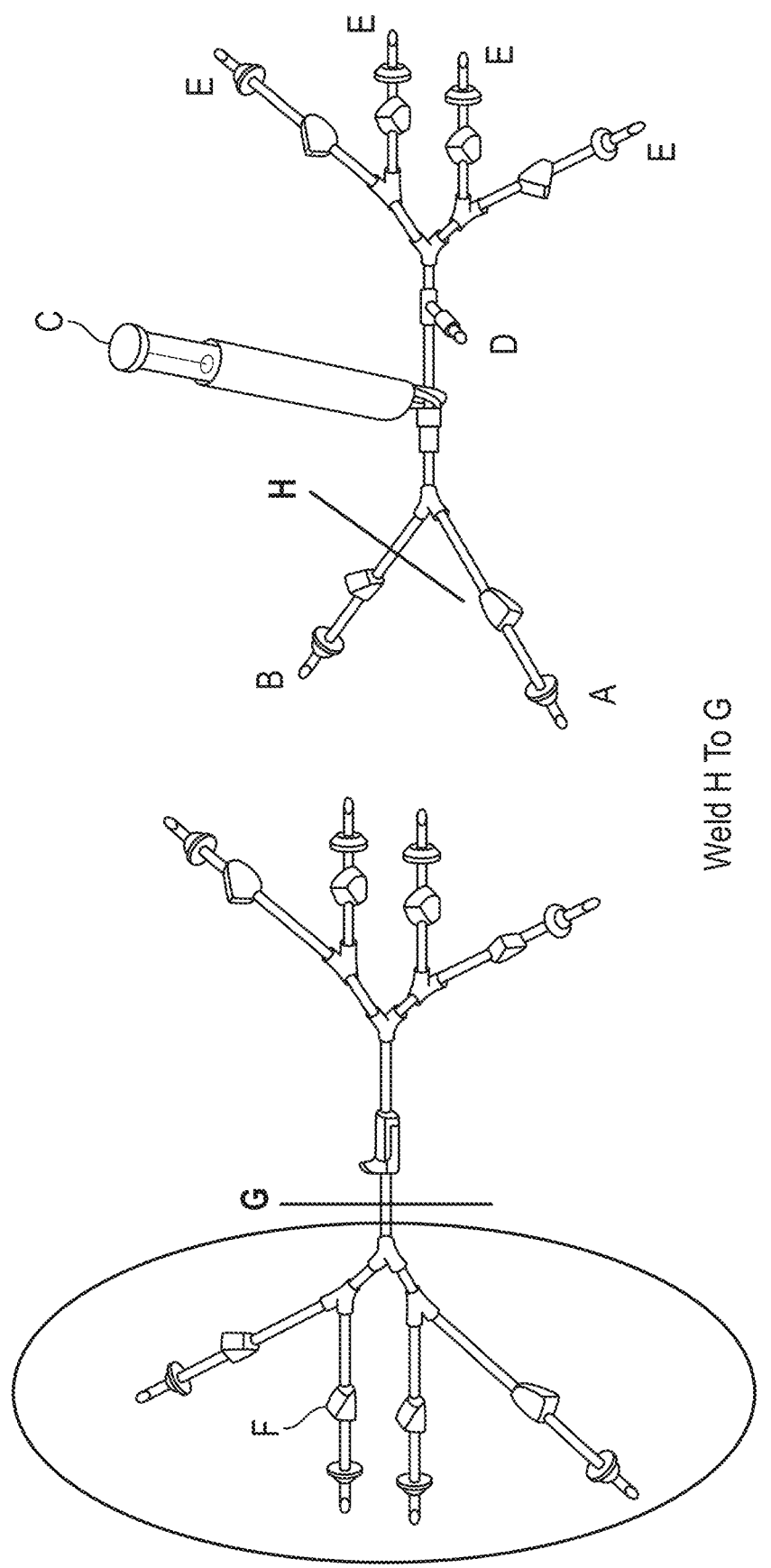
FIG. 25: Shows a schematic of the sterile weld (see, Process Note 5.11 in Example 16) a 4S-4M60 to a CC2 Cell Connect replacing a single spike of the Cell Connect apparatus (B) with the 4-spike end of the 4S-4M60 manifold at (G).

According to particular embodiments, expression of one or more of CCR2, CCR4, CCR5, CXCR2, CXCR3 and/or CX3CR1 in TILs is enhanced in accordance with compositions and methods of the present invention. For example, a method for expanding tumor infiltrating lymphocytes (TILs) into a therapeutic population of TILs may be carried out in accordance with any embodiment of the methods described herein (e.g., process 2A or the methods shown in FIGS. 20 and 21), wherein the method comprises gene-editing at least a portion of the TILs by enhancing the expression of one or more of CCR2, CCR4, CCR5, CXCR2, CXCR3 and/or CX3CR1. As described in more detail below, the gene-editing process may comprise the use of a programmable nuclease that mediates the generation of a double-strand or single-strand break at a chemokine receptor gene. For example, a CRISPR method, a TALE method, or a zinc finger method may be used to enhance the expression of certain chemokine receptors in the TILs.

In an embodiment, CCR4 and/or CCR5 adhesion molecules are inserted into a TIL population using a gamma-retroviral or lentiviral method as described herein. In an embodiment, CXCR2 adhesion molecule are inserted into a TIL population using a gamma-retroviral or lentiviral method as described in Forget, et al., *Frontiers Immunology* 2017, 8, 908 or Peng, et al., *Clin. Cancer Res.* 2010, 16, 5458, the disclosures of which are incorporated by reference herein.

In some embodiments, the present invention provides a method for expanding tumor infiltrating lymphocytes (TILs) into a therapeutic population of TILs comprising:
(i) obtaining a first population of TILs from a tumor resected from a patient;
(ii) performing a first expansion by culturing the first population of TILs in a cell culture medium comprising IL-2, and optionally OKT-3, to produce a second population of TILs;
(iii) performing a second expansion by supplementing the cell culture medium of the second population of TILs with additional IL-2, OKT-3, and antigen presenting cells (APCs), to produce a third population of TILs, wherein the third population of TILs is at least 100-fold greater in number than the second population of TILs, and wherein the second expansion is performed for at least 14 days in order to obtain the third population of TILs, wherein the third population of TILs is a therapeutic population of TILs; and
(iv) exposing the second and/or third population of TILs to transcription factors (TFs) and/or other molecules capable of transiently altering protein expression, wherein the TFs and/or other molecules capable of transiently altering protein expression provide for altered expression of tumor antigens and/or an alteration in the number of tumor antigen-specific T cells in the therapeutic population of TILs, wherein is the altered expression is an increase in the expression of one or more of CCR2, CCR4, CCR5, CXCR2, CXCR3, CX3CR1, CCL2 (MCP-1), CCL3 (MIP-1α), CCL4 (MIP1-β), CCL5 (RANTES), CXCL1, CXCL8, and/or CCL22.

(ii) Interleukins & Others

According to additional embodiments, gene-editing methods of the present invention may be used to increase the expression of certain interleukins, such as one or more of IL-2, IL-4, IL-7, IL-10, IL-15, and IL-21, and also the NOTCH 1/2 intracellular domain (ICD). Certain interleukins have been demonstrated to augment effector functions of T cells and mediate tumor control.

According to particular embodiments, expression of one or more of IL-2, IL-4, IL-7, IL-10, IL-15, and IL-21, and also the NOTCH 1/2 intracellular domain (ICD) in TILs is enhanced in accordance with compositions and methods of the present invention. some embodiments, the present invention provides a method for expanding tumor infiltrating lymphocytes (TILs) into a therapeutic population of TILs comprising:

(i) obtaining a first population of TILs from a tumor resected from a patient;
(ii) performing a first expansion by culturing the first population of TILs in a cell culture medium comprising IL-2, and optionally OKT-3, to produce a second population of TILs;
(iii) performing a second expansion by supplementing the cell culture medium of the second population of TILs with additional IL-2, OKT-3, and antigen presenting cells (APCs), to produce a third population of TILs, wherein the third population of TILs is at least 100-fold greater in number than the second population of TILs, and wherein the second expansion is performed for at least 14 days in order to obtain the third population of TILs, wherein the third population of TILs is a therapeutic population of TILs; and
(iv) exposing the second and/or third population of TILs to transcription factors (TFs) and/or other molecules capable of transiently altering protein expression, wherein the TFs and/or other molecules capable of transiently altering protein expression provide for altered expression of tumor antigens and/or an alteration in the number of tumor antigen-specific T cells in the therapeutic population of TILs, wherein is the altered expression is an increase in the expression of one or more of IL-2, IL-4, IL-7, IL-10, IL-15, and IL-21, and also the NOTCH 1/2 intracellular domain (ICD).

IV. TIL Manufacturing Processes

Figure 3:
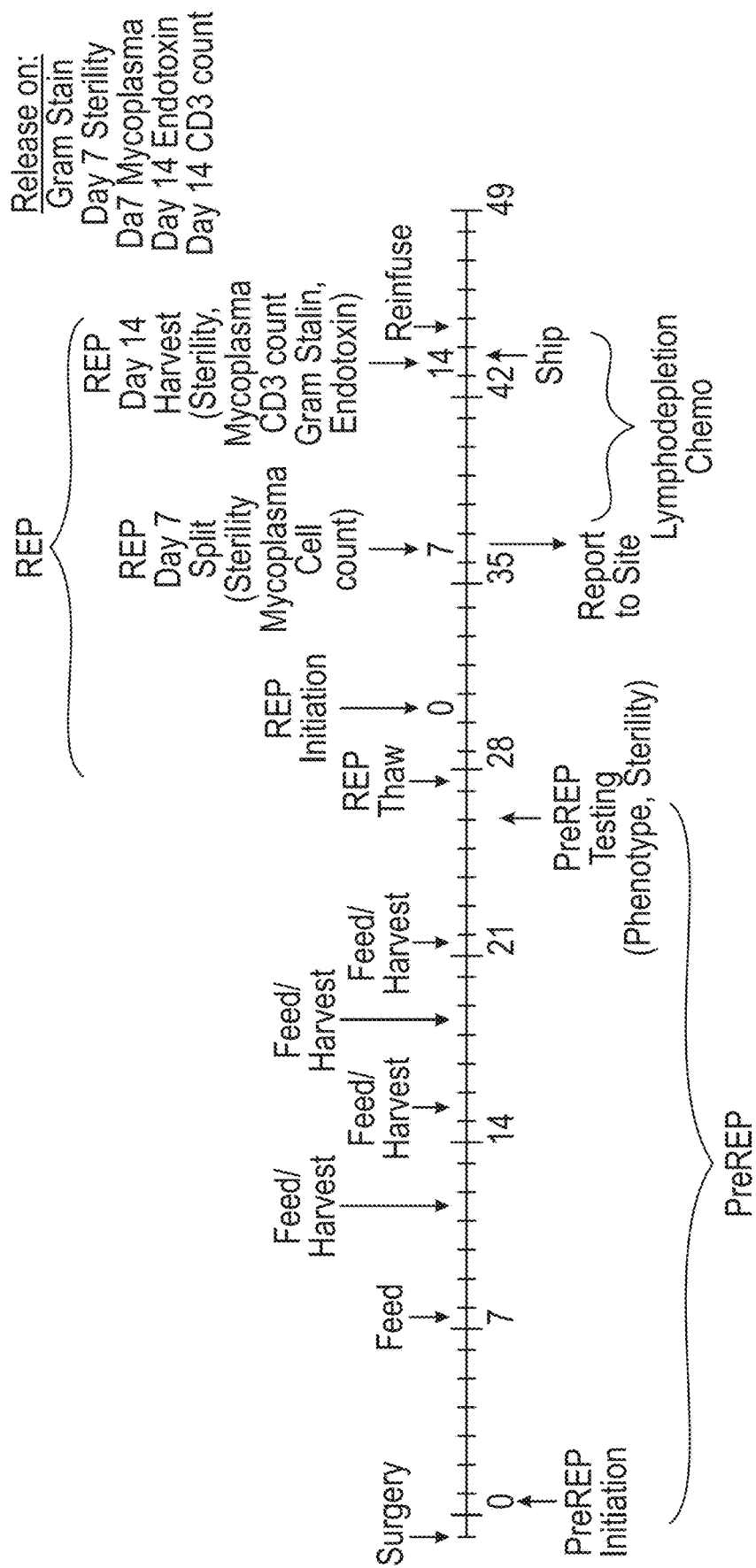
FIG. 3: Shows the 1C process timeline.
Figure 4:
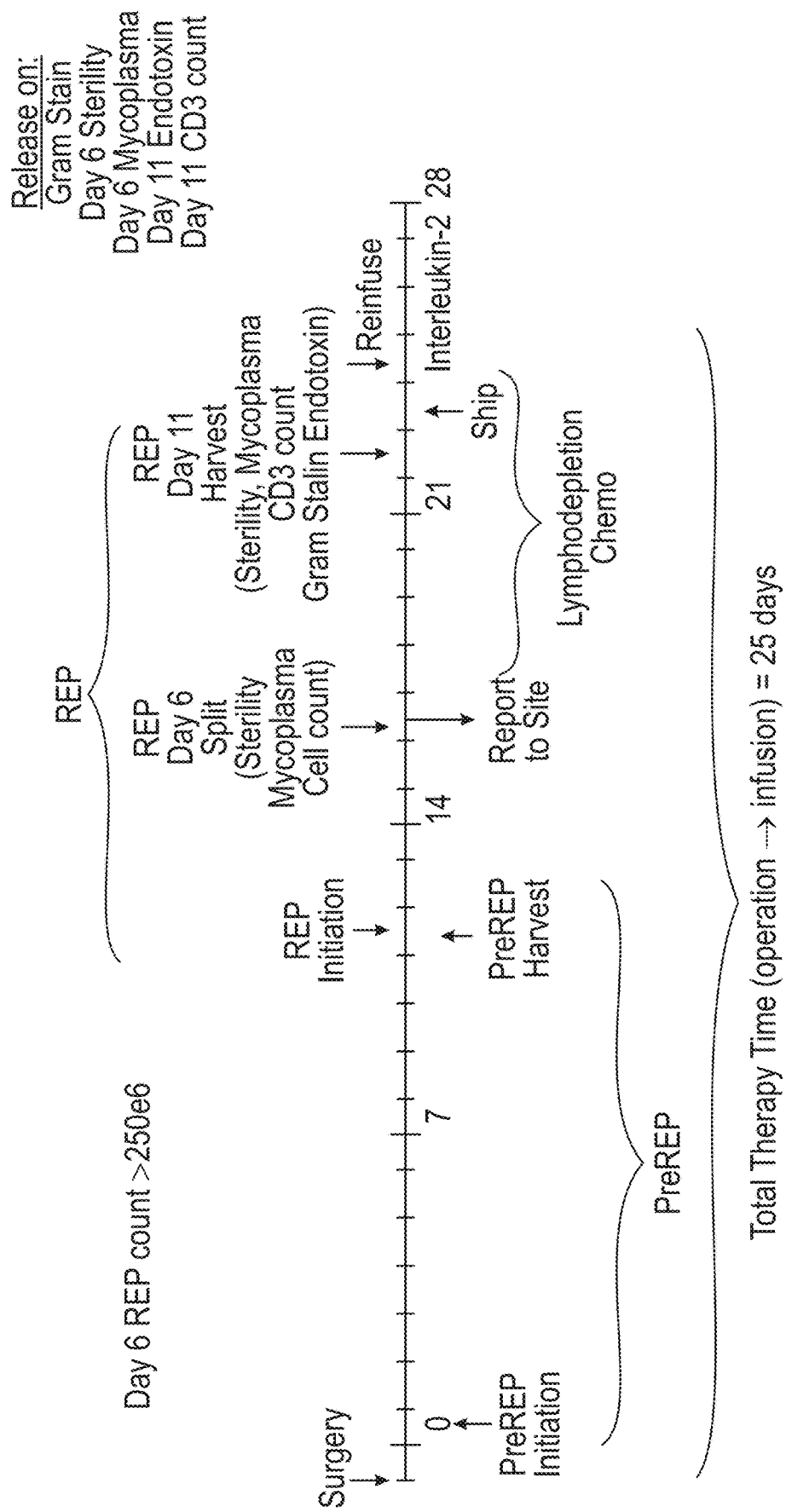
FIG. 4: Shows the process of an embodiment of TIL therapy using process 2A for TIL manufacturing, including administration and co-therapy steps, for higher cell counts.
Figure 5:
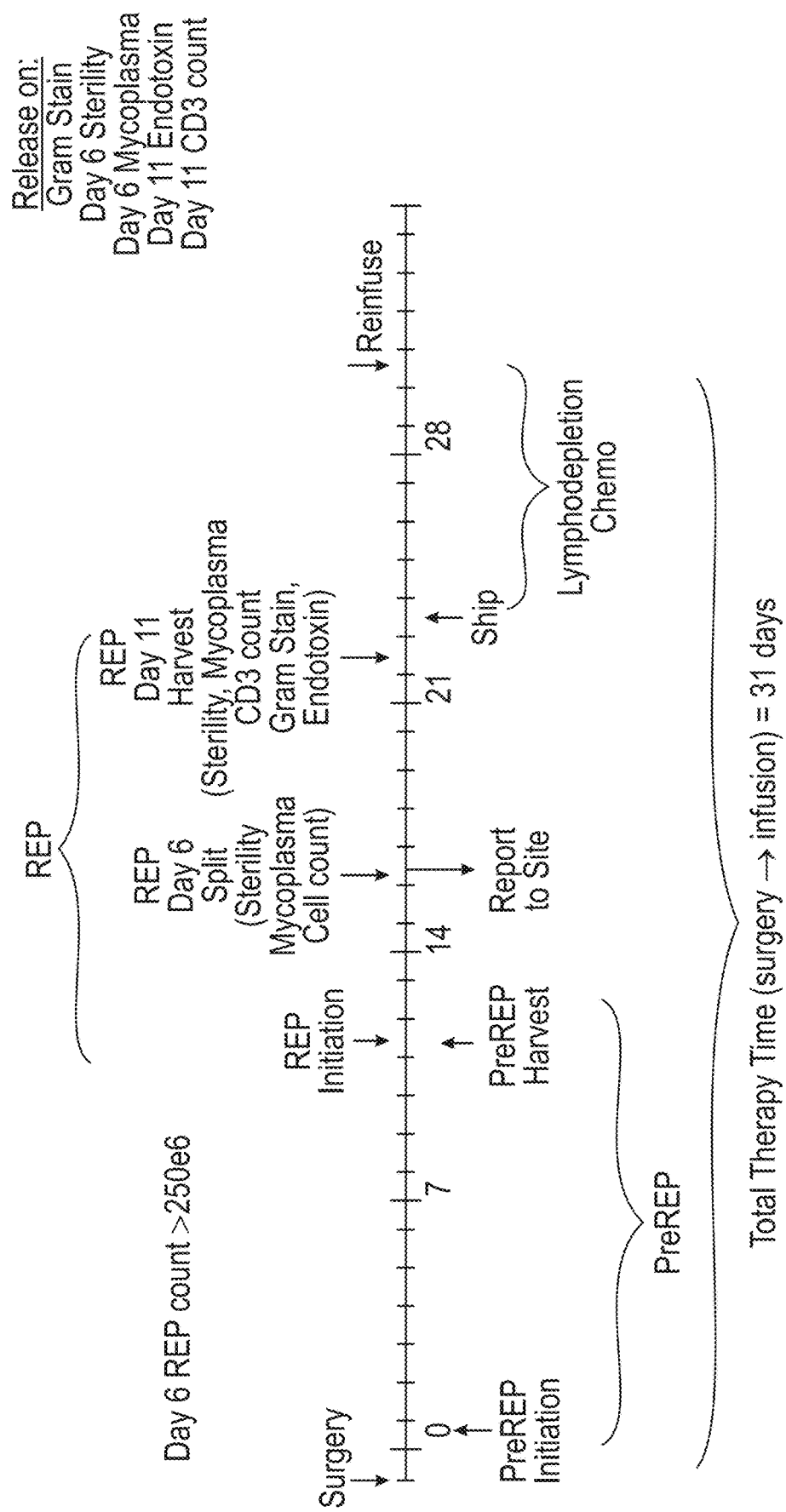
FIG. 5: Shows the process of an embodiment of TIL therapy using process 2A for TIL manufacturing, including administration and co-therapy steps, for lower cell counts.
Figure 6:
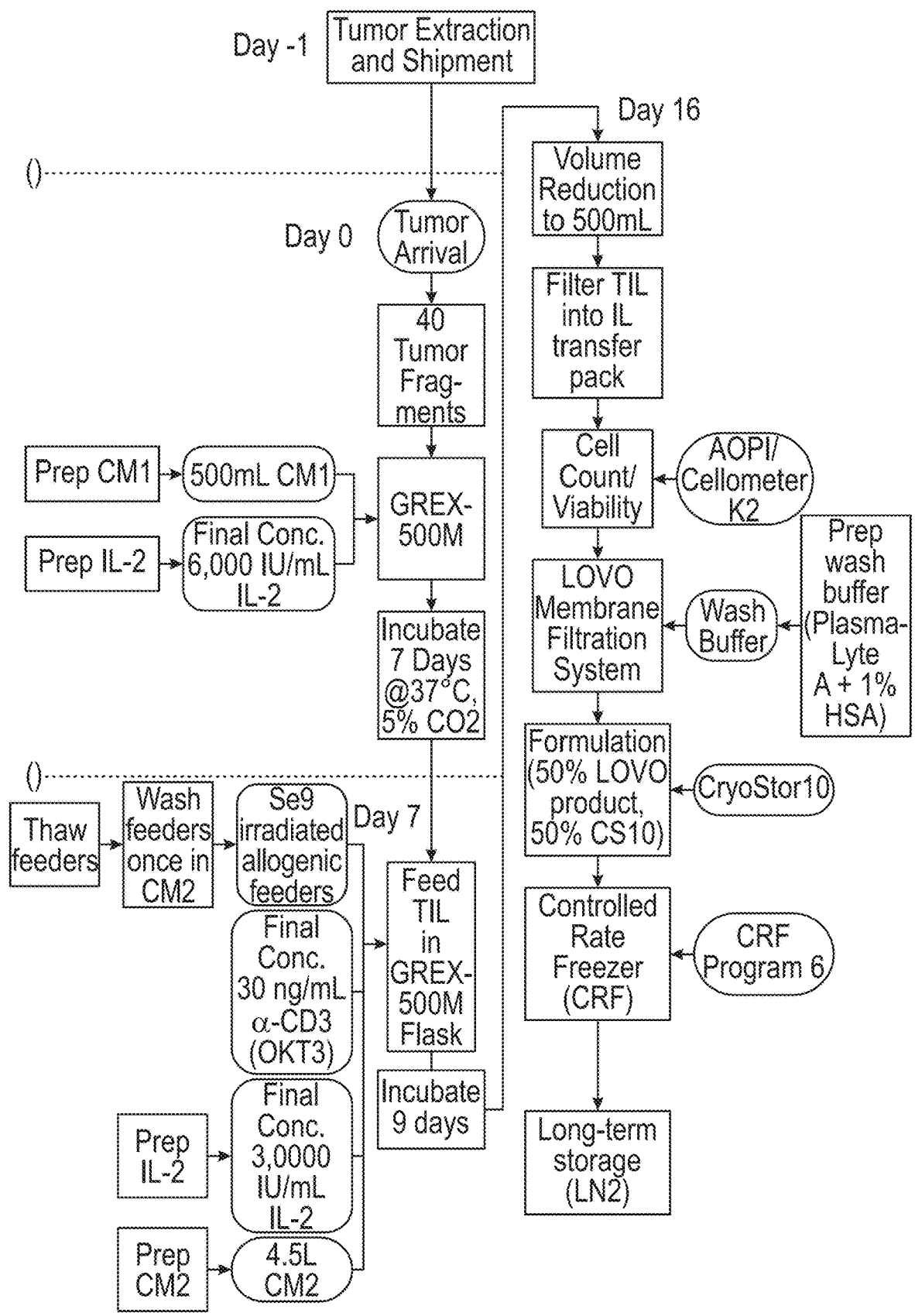
FIG. 6: Shows a detailed schematic for an embodiment of the 2A process.
Figure 7A:
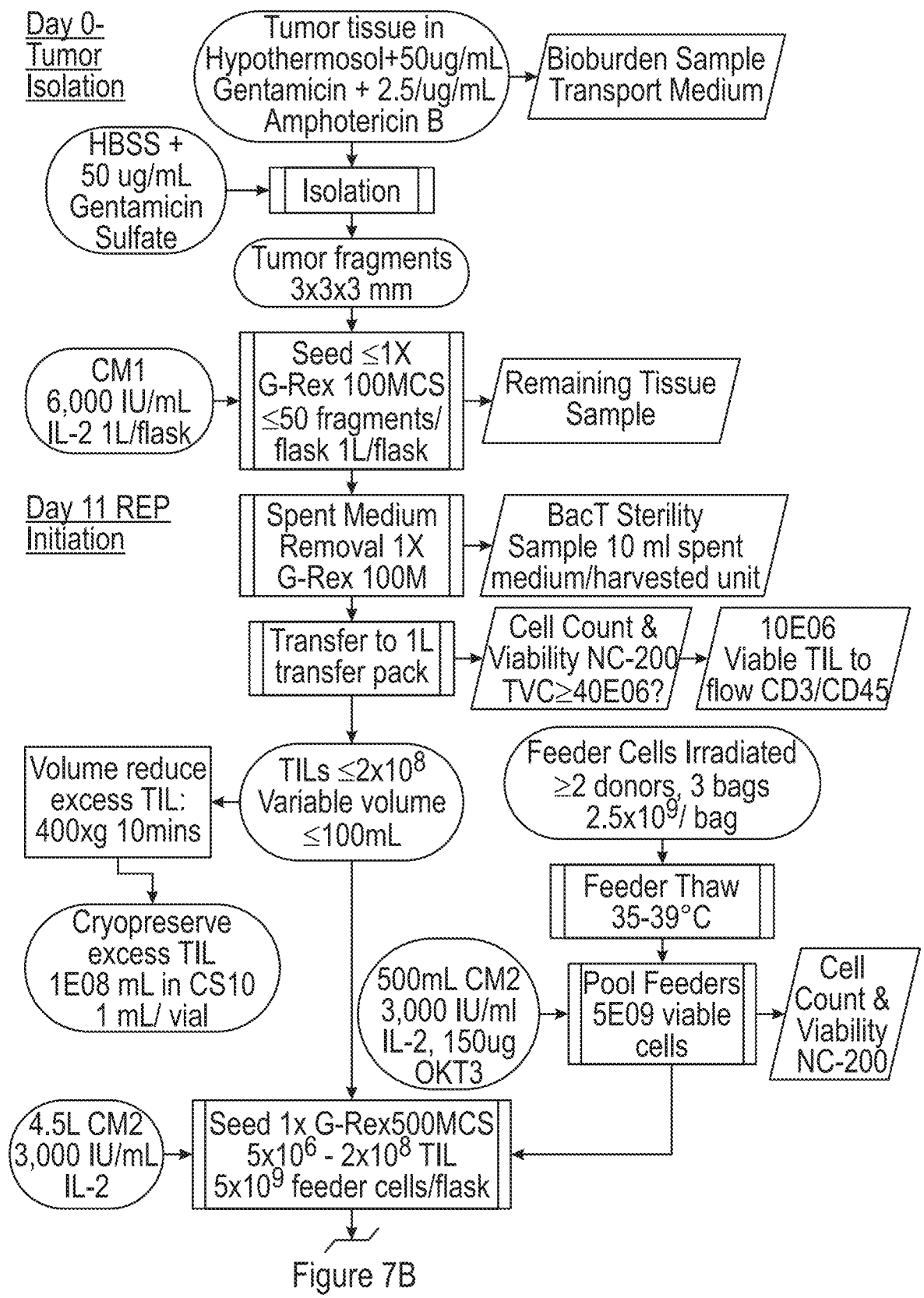
Figure 7C:
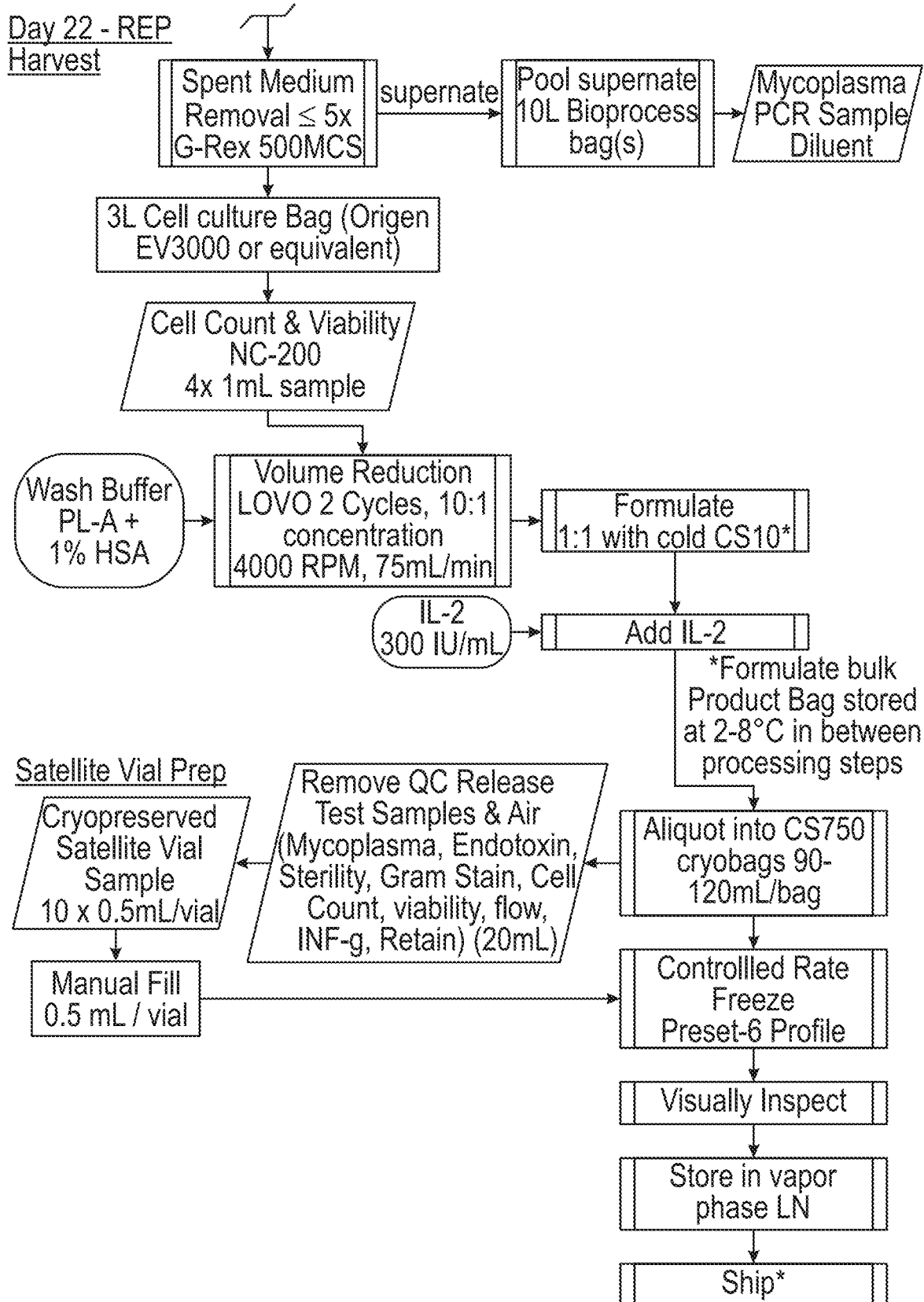
Figure 9:
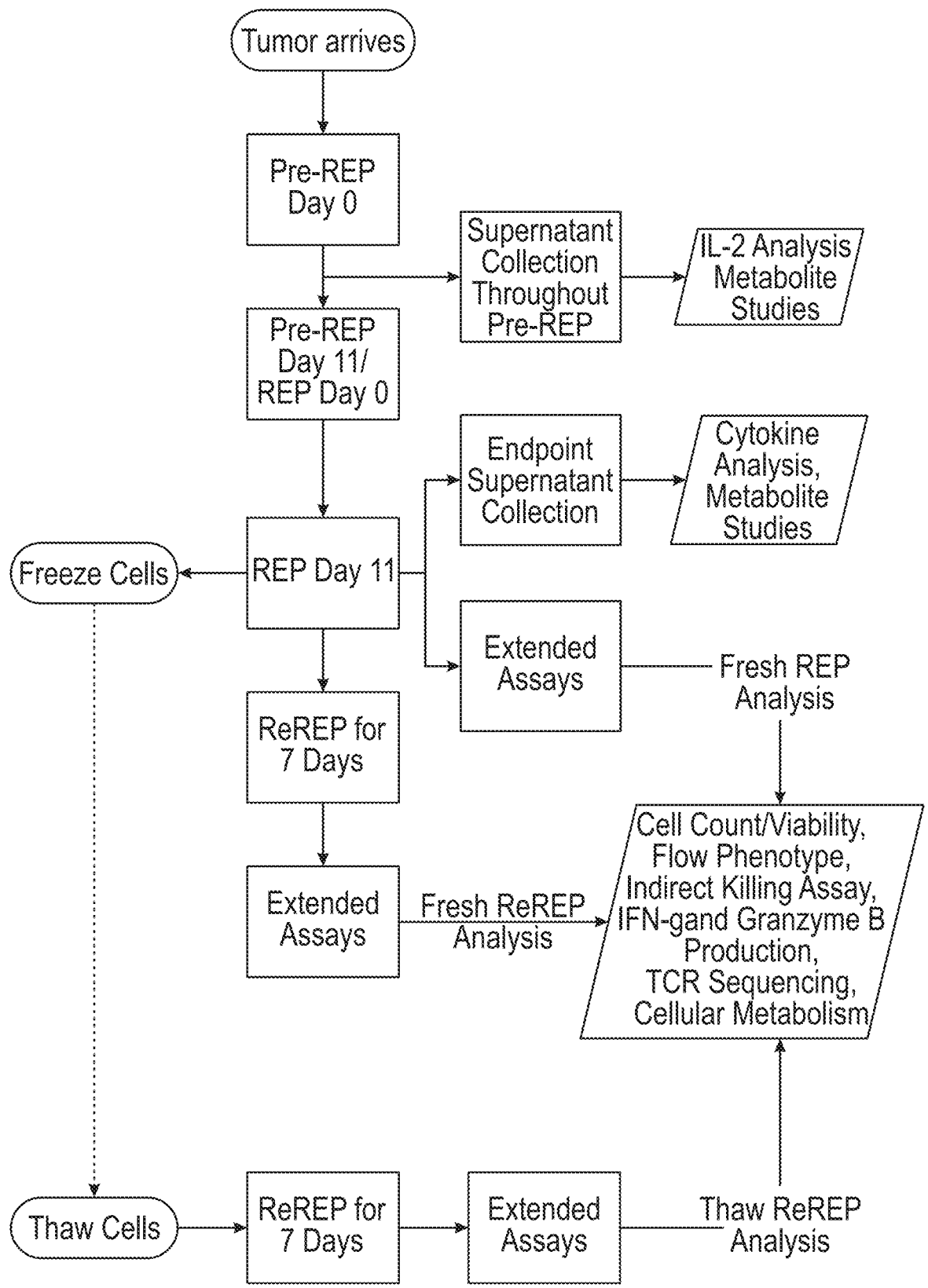
FIG. 9: Process Flow Chart on Process 2A Data Collection Plan
Figure 10:
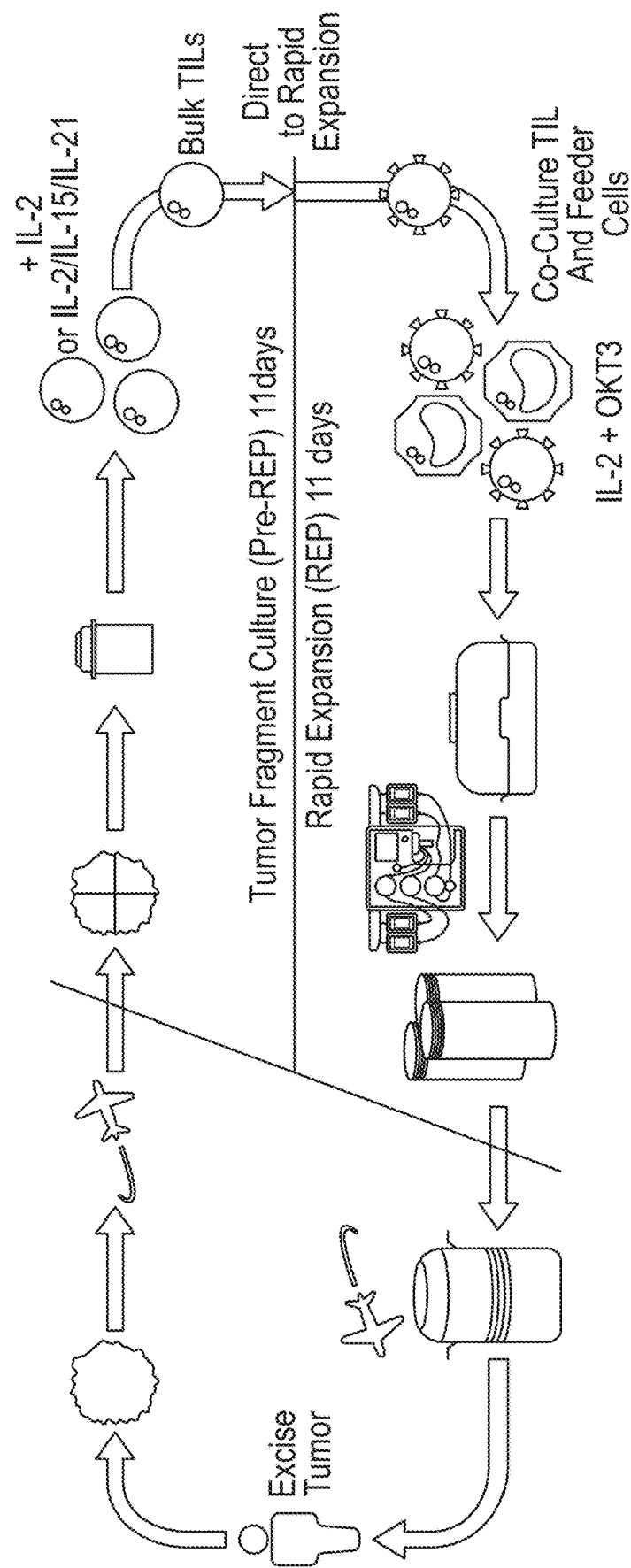
FIG. 10: Scheme of on exemplary embodiment of the Rapid Expansion Protocol (REP). Upon arrival the tumor is fragmented, placed into G-Rex flasks with IL-2 for TIL expansion (pre-REP expansion), for 11 days. For the triple cocktail studies, IL-2/IL-15/IL-21 is added at the initiation of the pre-REP. For the Rapid Expansion Protocol (REP), TIL are cultured with feeders and OKT3 for REP expansion for an additional 11 days.
Figure 11:
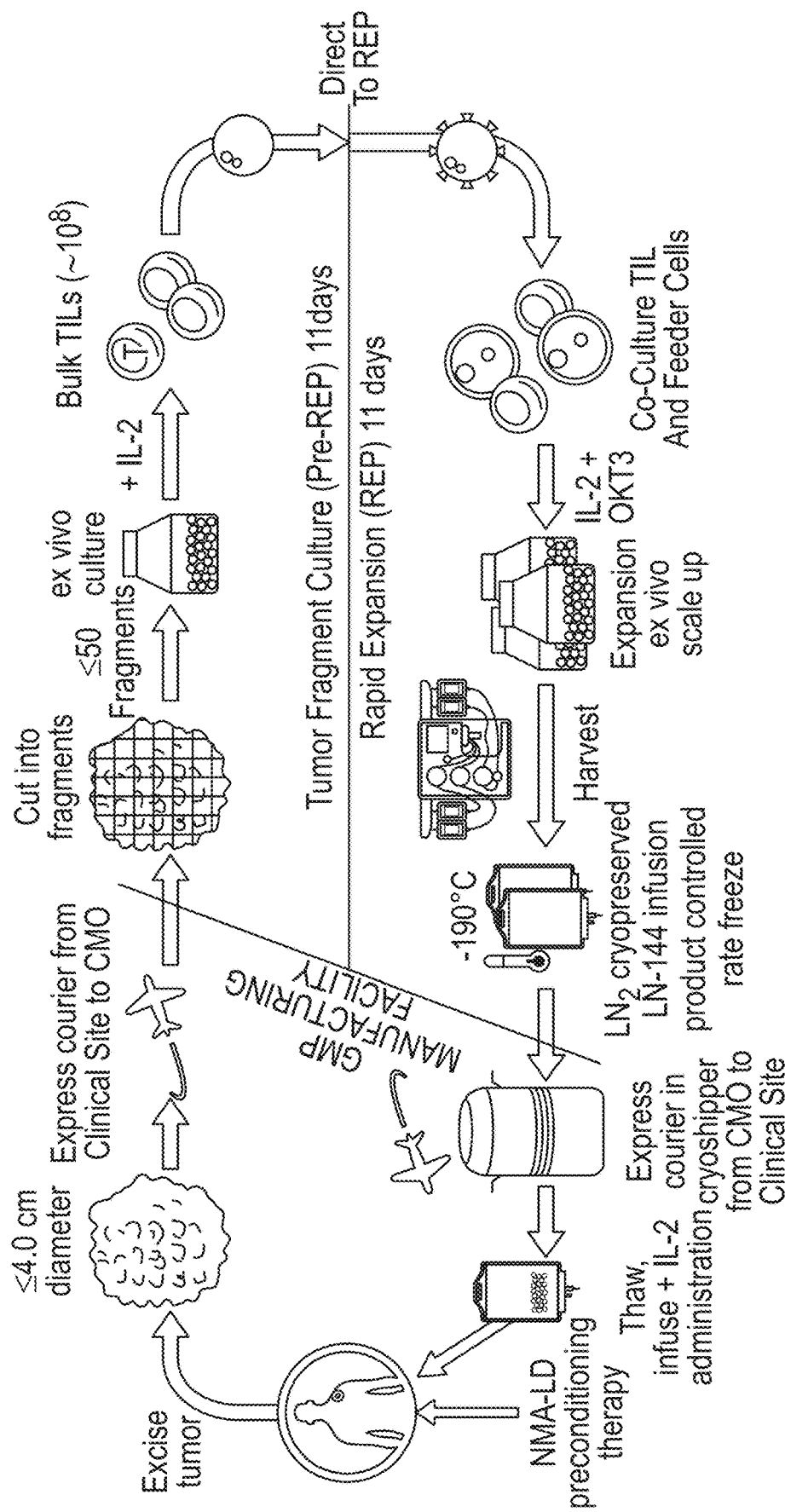
FIG. 11: Cryopreserved TIL exemplary manufacturing process (~22 days).
Figure 12:
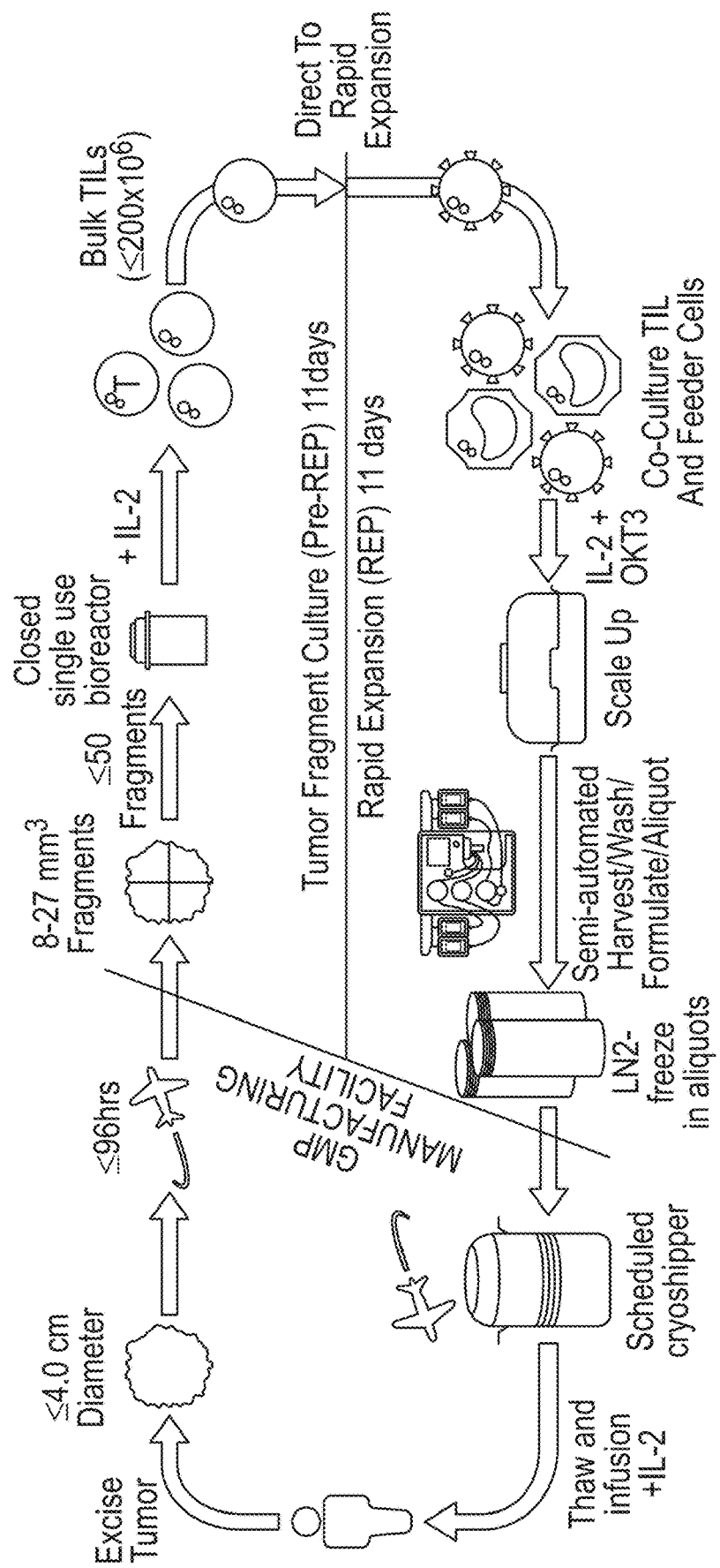
FIG. 12: Shows a diagram of an embodiment of process 2A, a 22-day process for TIL manufacturing.
Figure 15:
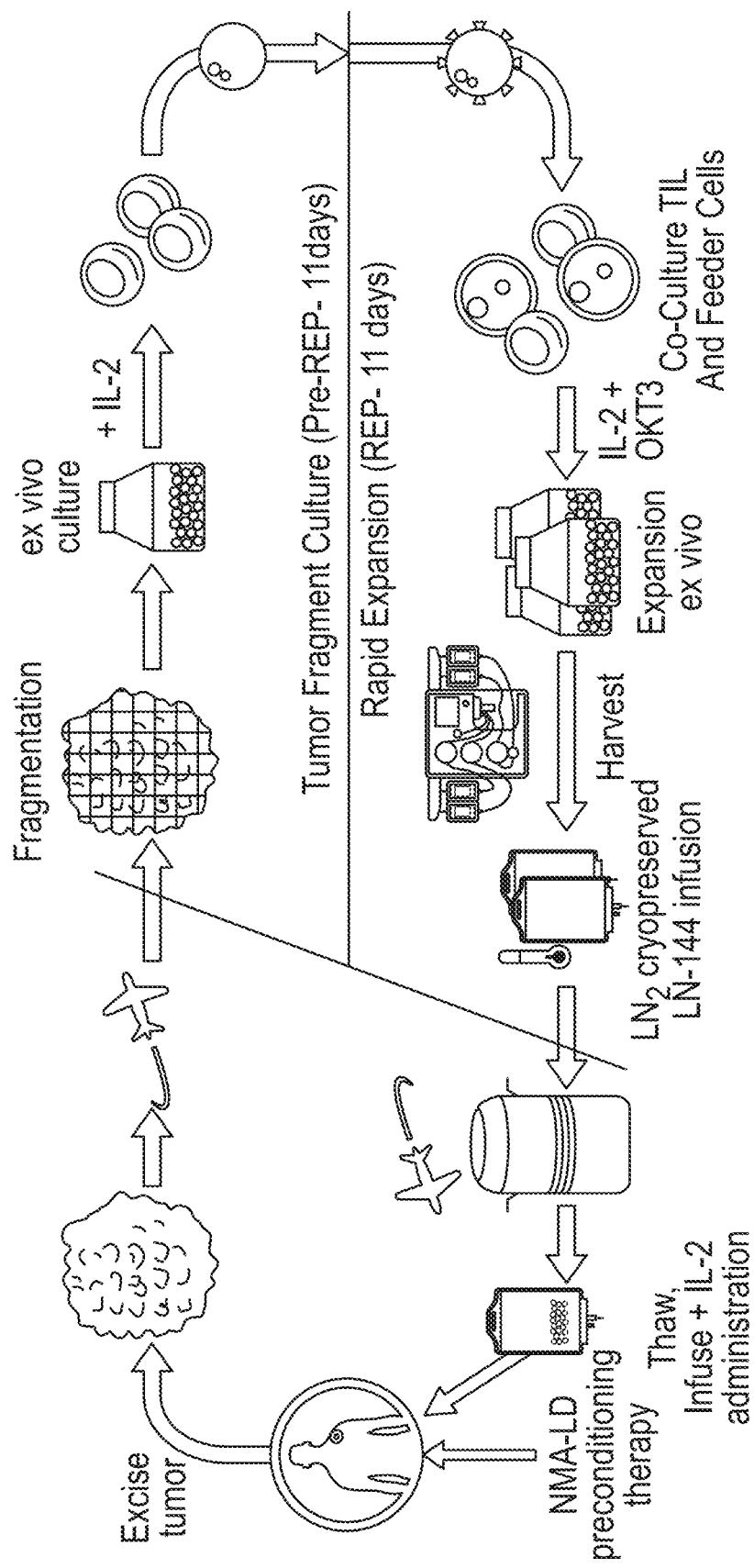
FIG. 15: Depiction of an embodiment of a cryopreserved TIL manufacturing process (22 days).
Figure 17:
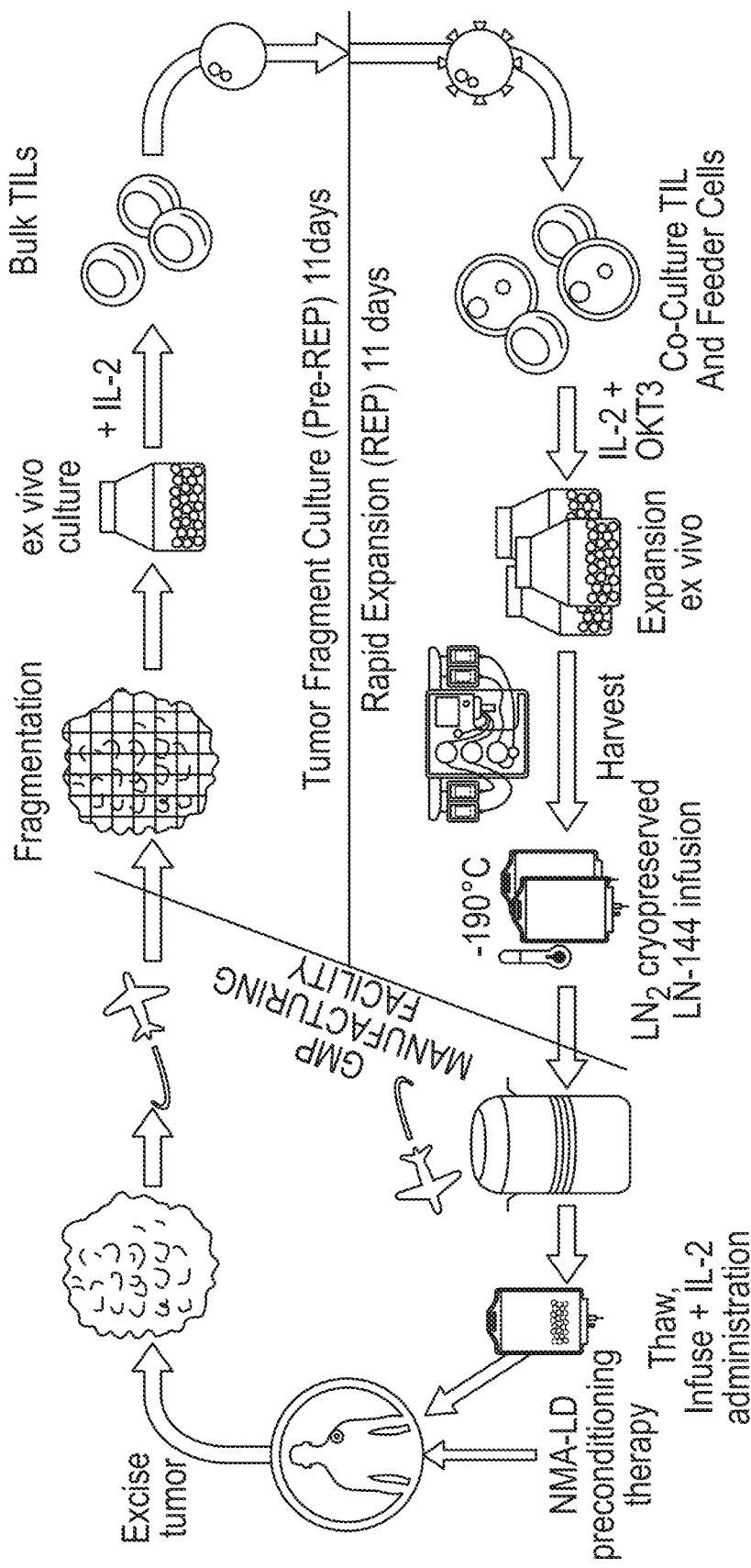
FIG. 17: Scheme of Gen 2 cryopreserved LN-144 manufacturing process.
Figure 18:
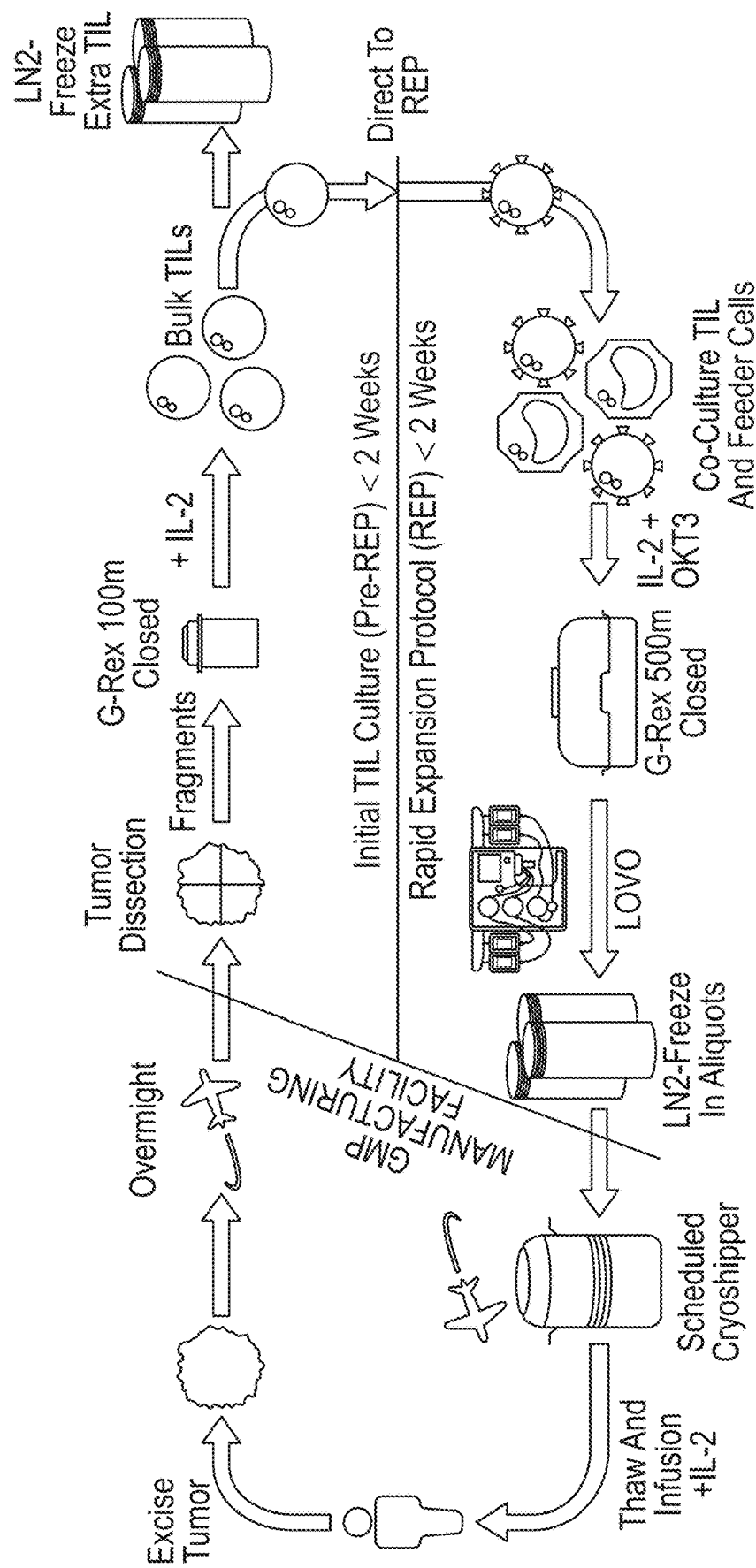
FIG. 18: Shows a diagram of an embodiment of process 2A, a 22-day process for TIL manufacturing.
Figure 19:
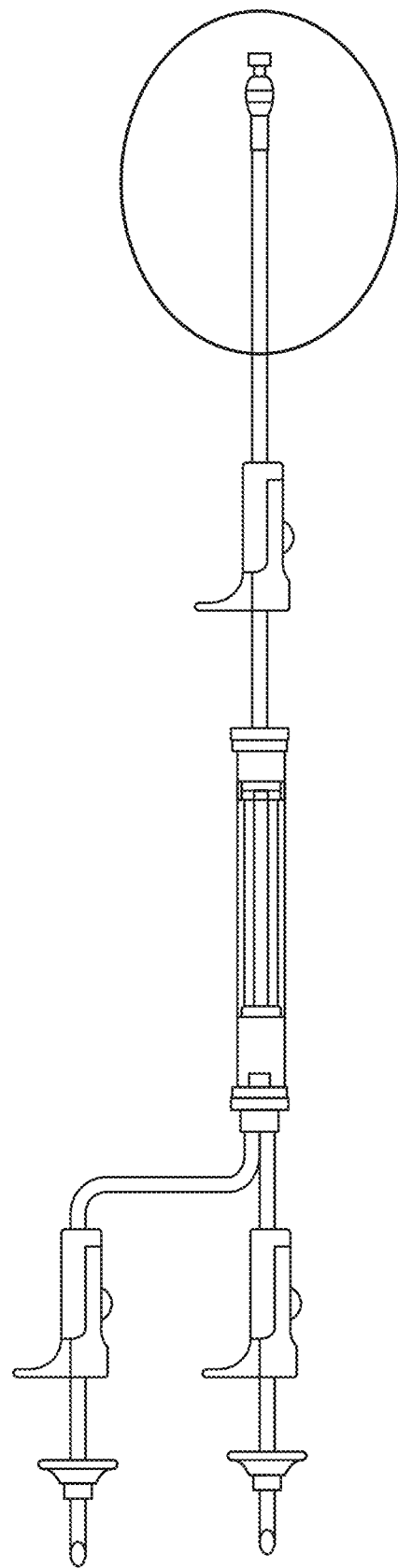
FIG. 19: Shows a schematic of the sterile weld (see, Process Note 5.11 in Example 16) the TIL Suspension transfer pack to the bottom (single line) of a Gravity Blood Filter.

An exemplary TIL process known as process 2A containing some of these features is depicted in FIG. 1, and some of the advantages of this embodiment of the present invention over process 1C are described in FIG. 2, as does FIGS. 13 and 14. Process 1C is shown for comparison in FIG. 3. Two alternative timelines for TIL therapy based on process 2A are shown in FIG. 4 (higher cell counts) and FIG. 5 (lower cell counts). An embodiment of process 2A is shown in FIG. 6 as well as FIG. 8. FIGS. 13 and 14 further provides an exemplary 2A process compared to an exemplary 1C process.

As discussed herein, the present invention can include a step relating to the restimulation of cryopreserved TILs to increase their metabolic activity and thus relative health prior to transplant into a patient, and methods of testing the metabolic health. As generally outlined herein, TILs are generally taken from a patient sample and manipulated to expand their number prior to transplant into a patient. In some embodiments, the TILs may be optionally genetically manipulated as discussed below.

In some embodiments, the TILs may be cryopreserved. Once thawed, they may also be restimulated to increase their metabolism prior to infusion into a patient.

In some embodiments, the first expansion (including processes referred to as the preREP as well as processes shown in FIG. 8 as Step A) is shortened to 3 to 14 days and the second expansion (including processes referred to as the REP as well as processes shown in FIG. 8 as Step B) is shorted to 7 to 14 days, as discussed in detail below as well as in the examples and figures. In some embodiments, the first expansion (for example, an expansion described as Step B in FIG. 8) is shortened to 11 days and the second expansion (for example, an expansion as described in Step D in FIG. 8) is shortened to 11 days, as discussed in the Examples and shown in FIGS. 4, 5 6, and 7. In some embodiments, the combination of the first expansion and second expansion (for example, expansions described as Step B and Step D in FIG. 8) is shortened to 22 days, as discussed in detail below and in the examples and figures.

The "Step" Designations A, B, C, etc., below are in reference to FIG. 8 and in reference to certain embodiments described herein. The ordering of the Steps below and in FIG. 8 is exemplary and any combination or order of steps, as well as additional steps, repetition of steps, and/or omission of steps is contemplated by the present application and the methods disclosed herein.

A. Step A: Obtain Patient Tumor Sample

In general, TILs are initially obtained from a patient tumor sample ("primary TILs") and then expanded into a larger population for further manipulation as described herein, optionally cryopreserved, restimulated as outlined herein and optionally evaluated for phenotype and metabolic parameters as an indication of TIL health.

A patient tumor sample may be obtained using methods known in the art, generally via surgical resection, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. The solid tumor may be of any cancer type, including, but not limited to, breast, pancreatic, prostate, colorectal, lung, brain, renal, stomach, and skin (including but not limited to squamous cell carcinoma, basal cell carcinoma, and melanoma). In some embodiments, useful TILs are obtained from malignant melanoma tumors, as these have been reported to have particularly high levels of TILs.

The term "solid tumor" refers to an abnormal mass of tissue that usually does not contain cysts or liquid areas. Solid tumors may be benign or malignant. The term "solid tumor cancer" refers to malignant, neoplastic, or cancerous solid tumors. Solid tumor cancers include, but are not limited to, sarcomas, carcinomas, and lymphomas, such as cancers of the lung, breast, triple negative breast cancer, prostate, colon, rectum, and bladder. In some embodiments, the cancer is selected from cervical cancer, head and neck cancer (including, for example, head and neck squamous cell carcinoma (HNSCC)) glioblastoma, ovarian cancer, sarcoma, pancreatic cancer, bladder cancer, breast cancer, triple negative breast cancer, and non-small cell lung carcinoma. The tissue structure of solid tumors includes interdependent tissue compartments including the parenchyma (cancer cells) and the supporting stromal cells in which the cancer cells are dispersed and which may provide a supporting microenvironment.

The term "hematological malignancy" refers to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

Once obtained, the tumor sample is generally fragmented using sharp dissection into small pieces of between 1 to about 8 mm$^3$, with from about 2-3 mm$^3$ being particularly useful. The TILs are cultured from these fragments using enzymatic tumor digests. Such tumor digests may be produced by incubation in enzymatic media (e.g., Roswell Park Memorial Institute (RPMI) 1640 buffer, 2 mM glutamate, 10 mcg/mL gentamicine, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

In general, the harvested cell suspension is called a "primary cell population" or a "freshly harvested" cell population.

In some embodiments, fragmentation includes physical fragmentation, including for example, dissection as well as digestion. In some embodiments, the fragmentation is physical fragmentation. In some embodiments, the fragmentation is dissection. In some embodiments, the fragmentation is by digestion. In some embodiments, TILs can be initially cultured from enzymatic tumor digests and tumor fragments obtained from patients. In an embodiment, TILs can be initially cultured from enzymatic tumor digests and tumor fragments obtained from patients.

In some embodiments, where the tumor is a solid tumor, the tumor undergoes physical fragmentation after the tumor sample is obtained in, for example, Step A (as provided in FIG. 8). In some embodiments, the fragmentation occurs before cryopreservation. In some embodiments, the fragmentation occurs after cryopreservation. In some embodiments, the fragmentation occurs after obtaining the tumor and in the absence of any cryopreservation. In some embodiments, the tumor is fragmented and 10, 20, 30, 40 or more fragments or pieces are placed in each container for the first expansion. In some embodiments, the tumor is fragmented and 30 or 40 fragments or pieces are placed in each container for the first expansion. In some embodiments, the tumor is fragmented and 40 fragments or pieces are placed in each container for the first expansion. In some embodiments, the multiple fragments comprise about 4 to about 50 fragments, wherein each fragment has a volume of about 27 mm$^3$. In some embodiments, the multiple fragments comprise about 30 to about 60 fragments with a total volume of about 1300 mm$^3$ to about 1500 mm$^3$. In some embodiments, the multiple fragments comprise about 50 fragments with a total volume of about 1350 mm$^3$. In some embodiments, the multiple fragments comprise about 50 fragments with a total mass of about 1 gram to about 1.5 grams. In some embodiments, the multiple fragments comprise about 4 fragments.

In some embodiments, the TILs are obtained from tumor fragments. In some embodiments, the tumor fragment is obtained by sharp dissection. In some embodiments, the tumor fragment is between about 1 mm$^3$ and 10 mm$^3$. In some embodiments, the tumor fragment is between about 1 mm$^3$ and 8 mm$^3$. In some embodiments, the tumor fragment is about 1 mm$^3$. In some embodiments, the tumor fragment is about 2 mm$^3$. In some embodiments, the tumor fragment is about 3 mm$^3$. In some embodiments, the tumor fragment is about 4 mm$^3$. In some embodiments, the tumor fragment is about 5 mm$^3$. In some embodiments, the tumor fragment is about 6 mm$^3$. In some embodiments, the tumor fragment is about 7 mm$^3$. In some embodiments, the tumor fragment is about 8 mm$^3$. In some embodiments, the tumor fragment is about 9 mm$^3$. In some embodiments, the tumor fragment is about 10 mm$^3$. In some embodiments, the tumors are 1-4 mm×1-4 mm×1-4 mm. In some embodiments, the tumors are 1 mm×1 mm×1 mm. In some embodiments, the tumors are 2 mm×2 mm×2 mm. In some embodiments, the tumors are 3 mm×3 mm×3 mm. In some embodiments, the tumors are 4 mm×4 mm×4 mm.

In some embodiments, the tumors are resected in order to minimize the amount of hemorrhagic, necrotic, and/or fatty tissues on each piece. In some embodiments, the tumors are resected in order to minimize the amount of hemorrhagic tissue on each piece. In some embodiments, the tumors are resected in order to minimize the amount of necrotic tissue on each piece. In some embodiments, the tumors are resected in order to minimize the amount of fatty tissue on each piece.

In some embodiments, the tumor fragmentation is performed in order to maintain the tumor internal structure. In some embodiments, the tumor fragmentation is performed without preforming a sawing motion with a scapel. In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

In some embodiments, the harvested cell suspension prior to the first expansion step is called a "primary cell population" or a "freshly harvested" cell population.

In some embodiments, cells can be optionally frozen after sample harvest and stored frozen prior to entry into the expansion described in Step B, which is described in further detail below, as well as exemplified in FIG. 8.

B. Step B: First Expansion

In some embodiments, the present methods provide for obtaining young TILs, which are capable of increased replication cycles upon administration to a subject/patient and as such may provide additional therapeutic benefits over older TILs (i.e., TILs which have further undergone more rounds of replication prior to administration to a subject/patient). Features of young TILs have been described in the literature, for example Donia, at al., *Scandinavian Journal of Immunology*, 75:157-167 (2012); Dudley et al., *Clin Cancer Res*, 16:6122-6131 (2010); Huang et al., *J Immunother*, 28(3):258-267 (2005); Besser et al., *Clin Cancer Res*, 19(17):OF1-OF9 (2013); Besser et al., *J Immunother* 32:415-423 (2009); Robbins, et al., *J Immunol* 2004; 173: 7125-7130; Shen et al., J Immunother, 30:123-129 (2007); Zhou, et al., *J Immunother*, 28:53-62 (2005); and Tran, et al., J Immunother, 31:742-751 (2008), all of which are incorporated herein by reference in their entireties.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained by the present method exhibit an increase in the T-cell repertoire diversity as compared to freshly harvested TILs and/or TILs prepared using other methods than those provide herein including for example, methods other than those embodied in FIG. 8. In some embodiments, the TILs obtained by the present method exhibit an increase in the T-cell repertoire diversity as compared to freshly harvested TILs and/or TILs prepared using methods referred to as process 1C, as exemplified in FIG. 13. In some embodiments, the TILs obtained in the first expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

After dissection or digestion of tumor fragments, for example such as described in Step A of FIG. 8, the resulting cells are cultured in serum containing IL-2 under conditions that favor the growth of TILs over tumor and other cells. In some embodiments, the tumor digests are incubated in 2 mL wells in media comprising inactivated human AB serum with 6000 IU/mL of IL-2. This primary cell population is cultured for a period of days, generally from 3 to 14 days, resulting in a bulk TIL population, generally about $1\times10^8$ bulk TIL cells. In some embodiments, this primary cell population is cultured for a period of 7 to 14 days, resulting in a bulk TIL population, generally about $1\times10^8$ bulk TIL cells. In some embodiments, this primary cell population is cultured for a period of 10 to 14 days, resulting in a bulk TIL population, generally about $1\times10^8$ bulk TIL cells. In some embodiments, this primary cell population is cultured for a period of about 11 days, resulting in a bulk TIL population, generally about $1\times10^8$ bulk TIL cells.

In a preferred embodiment, expansion of TILs may be performed using an initial bulk TIL expansion step (for example such as those described in Step B of FIG. 8, which can include processes referred to as pre-REP) as described below and herein, followed by a second expansion (Step D, including processes referred to as rapid expansion protocol (REP) steps) as described below under Step D and herein, followed by optional cryopreservation, and followed by a second Step D (including processes referred to as restimulation REP steps) as described below and herein. The TILs obtained from this process may be optionally characterized for phenotypic characteristics and metabolic parameters as described herein.

In embodiments where TIL cultures are initiated in 24-well plates, for example, using Costar 24-well cell culture cluster, flat bottom (Corning Incorporated, Corning, NY, each well can be seeded with $1\times10^6$ tumor digest cells or one tumor fragment in 2 mL of complete medium (CM) with IL-2 (6000 IU/mL; Chiron Corp., Emeryville, CA). In some embodiments, the tumor fragment is between about 1 mm$^3$ and 10 mm$^3$.

In some embodiments, the first expansion culture medium is referred to as "CM", an abbreviation for culture media. In some embodiments, CM for Step B consists of RPMI 1640 with GlutaMAX, supplemented with 10% human AB serum, 25 mM Hepes, and 10 mg/mL gentamicin. In embodiments where cultures are initiated in gas-permeable flasks with a 40 mL capacity and a 10 cm$^2$ gas-permeable silicon bottom (for example, G-Rex10; Wilson Wolf Manufacturing, New Brighton, MN) (FIG. 1), each flask was loaded with 10-40× $10^6$ viable tumor digest cells or 5-30 tumor fragments in 10-40 mL of CM with IL-2. Both the G-Rex10 and 24-well plates were incubated in a humidified incubator at 37° C. in 5% $CO_2$ and 5 days after culture initiation, half the media was removed and replaced with fresh CM and IL-2 and after day 5, half the media was changed every 2-3 days.

After preparation of the tumor fragments, the resulting cells (i.e., fragments) are cultured in serum containing IL-2 under conditions that favor the growth of TILs over tumor and other cells. In some embodiments, the tumor digests are incubated in 2 mL wells in media comprising inactivated human AB serum (or, in some cases, as outlined herein, in the presence of aAPC cell population) with 6000 IU/mL of IL-2. This primary cell population is cultured for a period of days, generally from 10 to 14 days, resulting in a bulk TIL population, generally about $1\times10^8$ bulk TIL cells. In some embodimes, the growth media during the first expansion comprises IL-2 or a variant thereof. In some embodiments, the IL is recombinant human IL-2 (rhIL-2). In some embodiments the IL-2 stock solution has a specific activity of 20-30×$10^6$ IU/mg for a 1 mg vial. In some embodiments the IL-2 stock solution has a specific activity of 20×10$^6$ IU/mg for a 1 mg vial. In some embodiments the IL-2 stock solution has a specific activity of 25×10$^6$ IU/mg for a 1 mg vial. In some embodiments the IL-2 stock solution has a specific activity of 30×10$^6$ IU/mg for a 1 mg vial. In some embodiments, the IL-2 stock solution has a final concentration of 4-8×10$^6$ IU/mg of IL-2. In some embodiments, the IL-2 stock solution has a final concentration of 5-7×10$^6$ IU/mg of IL-2. In some embodiments, the IL-2 stock solution has a final concentration of 6×10$^6$ IU/mg of IL-2. In some embodiments, the IL-2 stock solution is prepare as described in Example 4. In some embodiments, the first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, the first expansion culture media comprises about 9,000 IU/mL of IL-2 to about 5,000 IU/mL of IL-2. In some embodiments, the first expansion culture media comprises about 8,000 IU/mL of IL-2 to about 6,000 IU/mL of IL-2. In some embodiments, the first expansion culture media comprises about 7,000 IU/mL of IL-2 to about 6,000 IU/mL of IL-2. In some embodiments, the first expansion culture media comprises about 6,000 IU/mL of IL-2. In an embodiment, the cell culture medium further comprises IL-2. In some embodiments, the cell culture medium comprises about 3000 IU/mL of IL-2. In an embodiment, the cell culture medium further comprises IL-2. In a preferred embodiment, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or about 8000 IU/mL of IL-2.

In some embodiments, first expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the first expansion culture media comprises about 500 IU/mL of IL-15 to about 100 IU/mL of IL-15. In some embodiments, the first expansion culture media comprises about 400 IU/mL of IL-15 to about 100 IU/mL of IL-15. In some embodiments, the first expansion culture media comprises about 300 IU/mL of IL-15 to about 100 IU/mL of IL-15. In some embodiments, the first expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, first expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the first expansion culture media comprises about 20 IU/mL of IL-21 to about 0.5 IU/mL of IL-21. In some embodiments, the first expansion culture media comprises about 15 IU/mL of IL-21 to about 0.5 IU/mL of IL-21. In some embodiments, the first expansion culture media comprises about 12 IU/mL of IL-21 to about 0.5 IU/mL of IL-21. In some embodiments, the first expansion culture media comprises about 10 IU/mL of IL-21 to about 0.5 IU/mL of IL-21. In some embodiments, the first expansion culture media comprises about 5 IU/mL of IL-21 to about 1 IU/mL of IL-21. In some embodiments, the first expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In an embodiment, the cell culture medium comprises OKT-3 antibody. In some embodiments, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 µg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In some embodiments, the cell culture medium does not comprise OKT-3 antibody.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 µg/mL and 100 µg/mL. In some embodiments, the TNFRSF agonist is added at a concentration sufficient to achieve a concentration in the cell culture medium of between 20 µg/mL and 40 µg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, the first expansion culture medium is referred to as "CM", an abbreviation for culture media. In some embodiments, it is referred to as CM1 (culture medium 1). In some embodiments, CM consists of RPMI 1640 with GlutaMAX, supplemented with 10% human AB serum, 25 mM Hepes, and 10 mg/mL gentamicin. In embodiments where cultures are initiated in gas-permeable flasks with a 40 mL capacity and a 10 cm$^2$ gas-permeable silicon bottom (for example, G-Rex10; Wilson Wolf Manufacturing, New Brighton, MN) (FIG. 1), each flask was loaded with 10-40×10$^6$ viable tumor digest cells or 5-30 tumor fragments in 10-40 mL of CM with IL-2. Both the G-Rex10 and 24-well plates were incubated in a humidified incubator at 37° C. in 5% $CO_2$ and 5 days after culture initiation, half the media was removed and replaced with fresh CM and IL-2 and after day 5, half the media was changed every 2-3 days. In some embodiments, the CM is the CM1 described in the Examples, see, Example 5. In some embodiments, the first expansion occurs in an initial cell culture medium or a first cell culture medium. In some embodiments, the initial cell culture medium or the first cell culture medium comprises IL-2.

In some embodiments, the first expansion (including processes such as for example those described in Step B of FIG. 8, which can include those sometimes referred to as the pre-REP) process is shortened to 3-14 days, as discussed in the examples and figures. In some embodiments, the first expansion (including processes such as for example those described in Step B of FIG. 8, which can include those sometimes referred to as the pre-REP) is shortened to 7 to 14 days, as discussed in the Examples and shown in FIGS. 4 and 5, as well as including for example, an expansion as described in Step B of FIG. 8. In some embodiments, the first expansion of Step B is shortened to 10-14 days, as discussed in the Examples and shown in FIGS. 4 and 5. In some embodiments, the first expansion is shortened to 11 days, as discussed in the Examples and shown in FIGS. 4 and 5, as well as including for example, an expansion as described in Step B of FIG. 8.

In some embodiments, the first TIL expansion can proceed for 1 day, 2 days, 3 days, 4 days, 5 days, 6 days, 7 days, 8 days, 9 days, 10 days, 11 days, 12 days, 13 days, or 14 days. In some embodiments, the first TIL expansion can proceed for 1 day to 14 days. In some embodiments, the first TIL expansion can proceed for 2 days to 14 days. In some embodiments, the first TIL expansion can proceed for 3 days to 14 days. In some embodiments, the first TIL expansion can proceed for 4 days to 14 days. In some embodiments, the first TIL expansion can proceed for 5 days to 14 days. In some embodiments, the first TIL expansion can proceed for 6 days to 14 days. In some embodiments, the first TIL expansion can proceed for 7 days to 14 days. In some embodiments, the first TIL expansion can proceed for 8 days to 14 days. In some embodiments, the first TIL expansion can proceed for 9 days to 14 days. In some embodiments, the first TIL expansion can proceed for 10 days to 14 days. In some embodiments, the first TIL expansion can proceed for 11 days to 14 days. In some embodiments, the first TIL expansion can proceed for 12 days to 14 days. In some embodiments, the first TIL expansion can proceed for 13 days to 14 days. In some embodiments, the first TIL expansion can proceed for 14 days. In some embodiments, the first TIL expansion can proceed for 1 day to 11 days. In some embodiments, the first TIL expansion can proceed for 2 days to 11 days. In some embodiments, the first TIL expansion can proceed for 3 days to 11 days. In some embodiments, the first TIL expansion can proceed for 4 days to 11 days. In some embodiments, the first TIL expansion can proceed for 5 days to 11 days. In some embodiments, the first TIL expansion can proceed for 6 days to 11 days. In some embodiments, the first TIL expansion can proceed for 7 days to 11 days. In some embodiments, the first TIL expansion can proceed for 8 days to 11 days. In some embodiments, the first TIL expansion can proceed for 9 days to 11 days. In some embodiments, the first TIL expansion can proceed for 10 days to 11 days. In some embodiments, the first TIL expansion can proceed for 11 days.

In some embodiments, a combination of IL-2, IL-7, IL-15, and/or IL-21 are employed as a combination during the first expansion. In some embodiments, IL-2, IL-7, IL-15, and/or IL-21 as well as any combinations thereof can be included during the first expansion, including for example during a Step B processes according to FIG. 8, as well as described herein. In some embodiments, a combination of IL-2, IL-15, and IL-21 are employed as a combination during the first expansion. In some embodiments, IL-2, IL-15, and IL-21 as well as any combinations thereof can be included during Step B processes according to FIG. 8 and as described herein.

In some embodiments, the first expansion (including processes referred to as the pre-REP; for example, Step B according to FIG. 8) process is shortened to 3 to 14 days, as discussed in the examples and figures. In some embodiments, the first expansion of Step B is shortened to 7 to 14 days, as discussed in the Examples and shown in FIGS. 4 and 5. In some embodiments, the first expansion of Step B is shortened to 10 to 14 days, as discussed in the Examples and shown in FIGS. 4, 5, 6, and 7. In some embodiments, the first expansion is shortened to 11 days, as discussed in the Examples and shown in FIGS. 4, 5, 6, and 7.

In some embodiments, the first expansion, for example, Step B according to FIG. 8, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

In some embodiments, one or more sd-RNAs targeting genes as described herein, including PD-1, LAG-3, TIM-3, CISH, and CBLB, may be added to cell culture media during the first expansion, for Example, Step B according to FIG. 8, comprising TILs and other agents at amounts selected from the group consisting of 0.1 µM sd-RNA/10,000 TILs/100 µL media, 0.5 µM sd-RNA/10,000 TILs/100 µL media, 0.75 µM sd-RNA/10,000 TILs/100 µL media, 1 µM sd-RNA/10,000 TILs/100 µL media, 1.25 µM sd-RNA/10,000 TILs/100 µL media, 1.5 µM sd-RNA/10,000 TILs/100 µL media, 2 µM sd-RNA/10,000 TILs/100 µL media, 5 µM sd-RNA/10,000 TILs/100 µL media, or 10 µM sd-RNA/10,000 TILs/100 µL media. In some embodiments, one or more sd-RNAs targeting genes as described herein, including PD-1, LAG-3, TIM-3, CISH, and CBLB, may be added to TIL cultures during the first expansion, for Example, Step B according to FIG. 8, twice a day, once a day, every two days, every three days, every four days, every five days, every six days, or every seven days. In an embodiment, one or more sd-RNAs targeting genes as described herein, including PD-1, LAG-3, TIM-3, CISH, and CBLB, may be added to cell culture media comprising TILs and other agents during the first expansion, for Example, Step B according to FIG. 8, at amounts selected from the group consisting of 0.1 µM sd-RNA/10,000 TILs, 0.5 µM sd-RNA/10,000 TILs, 0.75 µM sd-RNA/10,000 TILs, 1 µM sd-RNA/10,000 TILs, 1.25 µM sd-RNA/10,000 TILs, 1.5 µM sd-RNA/10,000 TILs, 2 µM sd-RNA/10,000 TILs, 5 µM sd-RNA/10,000 TILs, or 10 µM sd-RNA/10,000 TILs. In an embodiment, one or more sd-RNAs targeting genes as described herein, including PD-1, LAG-3, TIM-3, CISH, and CBLB, may be added to TIL cultures during the during the first expansion, for Example, Step B according to FIG. 8, twice a day, once a day, every two days, every three days, every four days, every five days, every six days, or every seven days.

C. Step C: First Expansion to Second Expansion Transition

In some cases, the bulk TIL population obtained from the first expansion, including for example the TIL population obtained from for example, Step B as indicated in FIG. 8, can be cryopreserved immediately, using the protocols discussed herein below. Alternatively, the TIL population obtained from the first expansion, referred to as the second TIL population, can be subjected to a second expansion (which can include expansions sometimes referred to as REP) and then cryopreserved as discussed below. Similarly, in the case where genetically modified TILs will be used in therapy, the first TIL population (sometimes referred to as the bulk TIL population) or the second TIL population (which can in some embodiments include populations referred to as the REP TIL populations) can be subjected to genetic modifications for suitable treatments prior to expansion or after the first expansion and prior to the second expansion.

In some embodiments, the TILs obtained from the first expansion (for example, from Step B as indicated in FIG. 8) are stored until phenotyped for selection. In some embodiments, the TILs obtained from the first expansion (for example, from Step B as indicated in FIG. 8) are not stored and proceed directly to the second expansion. In some embodiments, the TILs obtained from the first expansion are not cryopreserved after the first expansion and prior to the second expansion. In some embodiments, the transition from the first expansion to the second expansion occurs at about 3 days, 4, days, 5 days, 6 days, 7 days, 8 days, 9 days, 10 days, 11 days, 12 days, 13 days, or 14 days from when fragmentation occurs. In some embodiments, the transition from the first expansion to the second expansion occurs at about 3 days to 14 days from when fragmentation occurs. In some embodiments, the transition from the first expansion to the second expansion occurs at about 4 days to 14 days from when fragmentation occurs. In some embodiments, the transition from the first expansion to the second expansion occurs at about 4 days to 10 days from when fragmentation occurs. In some embodiments, the transition from the first expansion to the second expansion occurs at about 7 days to 14 days from when fragmentation occurs. In some embodiments, the transition from the first expansion to the second expansion occurs at about 14 days from when fragmentation occurs.

In some embodiments, the transition from the first expansion to the second expansion occurs at 1 day, 2 days, 3 days, 4 days, 5 days, 6 days, 7 days, 8 days, 9 days, 10 days, 11 days, 12 days, 13 days, or 14 days from when fragmentation occurs. In some embodiments, the transition from the first expansion to the second expansion occurs 1 day to 14 days from when fragmentation occurs. In some embodiments, the first TIL expansion can proceed for 2 days to 14 days. In some embodiments, the transition from the first expansion to the second expansion occurs 3 days to 14 days from when fragmentation occurs. In some embodiments, the transition from the first expansion to the second expansion occurs 4 days to 14 days from when fragmentation occurs. In some embodiments, the transition from the first expansion to the second expansion occurs 5 days to 14 days from when fragmentation occurs. In some embodiments, the transition from the first expansion to the second expansion occurs 6 days to 14 days from when fragmentation occurs. In some embodiments, the transition from the first expansion to the second expansion occurs 7 days to 14 days from when fragmentation occurs. In some embodiments, the transition from the first expansion to the second expansion occurs 8 days to 14 days from when fragmentation occurs. In some embodiments, the transition from the first expansion to the second expansion occurs 9 days to 14 days from when fragmentation occurs. In some embodiments, the transition from the first expansion to the second expansion occurs 10 days to 14 days from when fragmentation occurs. In some embodiments, the transition from the first expansion to the second expansion occurs 11 days to 14 days from when fragmentation occurs. In some embodiments, the transition from the first expansion to the second expansion occurs 12 days to 14 days from when fragmentation occurs. In some embodiments, the transition from the first expansion to the second expansion occurs 13 days to 14 days from when fragmentation occurs. In some embodiments, the transition from the first expansion to the second expansion occurs 14 days from when fragmentation occurs. In some embodiments, the transition from the first expansion to the second expansion occurs 1 day to 11 days from when fragmentation occurs. In some embodiments, the transition from the first expansion to the second expansion occurs 2 days to 11 days from when fragmentation occurs. In some embodiments, the transition from the first expansion to the second expansion occurs 3 days to 11 days from when fragmentation occurs. In some embodiments, the transition from the first expansion to the second expansion occurs 4 days to 11 days from when fragmentation occurs. In some embodiments, the transition from the first expansion to the second expansion occurs 5 days to 11 days from when fragmentation occurs. In some embodiments, the transition from the first expansion to the second expansion occurs 6 days to 11 days from when fragmentation occurs. In some embodiments, the transition from the first expansion to the second expansion occurs 7 days to 11 days from when fragmentation occurs. In some embodiments, the transition from the first expansion to the second expansion occurs 8 days to 11 days from when fragmentation occurs. In some embodiments, the transition from the first expansion to the second expansion occurs 9 days to 11 days from when fragmentation occurs. In some embodiments, the transition from the first expansion to the second expansion occurs 10 days to 11 days from when fragmentation occurs. In some embodiments, the transition from the first expansion to the second expansion occurs 11 days from when fragmentation occurs.

In some embodiments, the TILs are not stored after the first expansion and prior to the second expansion, and the TILs proceed directly to the second expansion (for example, in some embodiments, there is no storage during the transition from Step B to Step D as shown in FIG. 8). In some embodiments, the transition occurs in closed system, as described herein. In some embodiments, the TILs from the first expansion, the second population of TILs, proceeds directly into the second expansion with no transition period.

In some embodiments, the transition from the first expansion to the second expansion, for example, Step C according to FIG. 8, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

In some embodiments, one or more sd-RNAs targeting genes as described herein, including PD-1, LAG-3, TIM-3, CISH, and CBLB, may be added to cell culture media during the transition from the first expansion to the second expansion, for Example, Step C according to FIG. 8, comprising TILs and other agents at amounts selected from the group consisting of 0.1 µM sd-RNA/10,000 TILs/100 µL media, 0.5 µM sd-RNA/10,000 TILs/100 µL media, 0.75 µM sd-RNA/10,000 TILs/100 µL media, 1 µM sd-RNA/10,000 TILs/100 µL media, 1.25 µM sd-RNA/10,000 TILs/100 µL media, 1.5 µM sd-RNA/10,000 TILs/100 µL media, 2 µM sd-RNA/10,000 TILs/100 µL media, 5 µM sd-RNA/10,000 TILs/100 µL media, or 10 µM sd-RNA/10,000 TILs/100 µL media. In some embodiment, one or more sd-RNAs targeting genes as described herein, including PD-1, LAG-3, TIM-3, CISH, and CBLB, may be added to TIL cultures during the transition from the first expansion to the second expansion, for Example, Step C according to FIG. 8, twice a day, once a day, every two days, every three days, every four days, every five days, every six days, or every seven days. In an embodiment, one or more sd-RNAs targeting genes as described herein, including PD-1, LAG-3, TIM-3, CISH, and CBLB, may be added to cell culture media comprising TILs and other agents during the transition from the first expansion to the second expansion, for Example, Step C according to FIG. 8 at amounts selected from the group consisting of 0.1 µM sd-RNA/10,000 TILs, 0.5 µM sd-RNA/10,000 TILs, 0.75 µM sd-RNA/10,000 TILs, 1 µM sd-RNA/10,000 TILs, 1.25 µM sd-RNA/10,000 TILs, 1.5 µM sd-RNA/10,000 TILs, 2 µM sd-RNA/10,000 TILs, 5 µM sd-RNA/10,000 TILs, or 10 µM sd-RNA/10,000 TILs. In an embodiment, one or more sd-RNAs targeting genes as described herein, including PD-1, LAG-3, TIM-3, CISH, and CBLB, may be added to TIL cultures during the during the transition from the first expansion to the second expansion, for Example, Step C according to FIG. 8, twice a day, once a day, every two days, every three days, every four days, every five days, every six days, or every seven days.

1. Cytokines

The expansion methods described herein generally use culture media with high doses of a cytokine, in particular IL-2, as is known in the art.

Alternatively, using combinations of cytokines for the rapid expansion and or second expansion of TILS is additionally possible, with combinations of two or more of IL-2, IL-15 and IL-21 as is generally outlined in International Publication No. WO 2015/189356 and W International Publication No. WO 2015/189357, hereby expressly incorporated by reference in their entirety. Thus, possible combinations include IL-2 and IL-15, IL-2 and IL-21, IL-15 and IL-21 and IL-2, IL-15 and IL-21, with the latter finding particular use in many embodiments. The use of combinations of cytokines specifically favors the generation of lymphocytes, and in particular T-cells as described therein.

D. Step D: Second Expansion

In some embodiments, the TIL cell population is expanded in number after harvest and initial bulk processing for example, after Step A and Step B, and the transition referred to as Step C, as indicated in FIG. 8). This further expansion is referred to herein as the second expansion, which can include expansion processes generally referred to in the art as a rapid expansion process (REP; as well as processes as indicated in Step D of FIG. 8). The second expansion is generally accomplished using a culture media comprising a number of components, including feeder cells, a cytokine source, and an anti-CD3 antibody, in a gas-permeable container.

In some embodiments, the second expansion or second TIL expansion (which can include expansions sometimes referred to as REP; as well as processes as indicated in Step D of FIG. 8) of TIL can be performed using any TIL flasks or containers known by those of skill in the art. In some embodiments, the second TIL expansion can proceed for 7 days, 8 days, 9 days, 10 days, 11 days, 12 days, 13 days, or 14 days. In some embodiments, the second TIL expansion can proceed for about 7 days to about 14 days. In some embodiments, the second TIL expansion can proceed for about 8 days to about 14 days. In some embodiments, the second TIL expansion can proceed for about 9 days to about 14 days. In some embodiments, the second TIL expansion can proceed for about 10 days to about 14 days. In some embodiments, the second TIL expansion can proceed for about 11 days to about 14 days. In some embodiments, the second TIL expansion can proceed for about 12 days to about 14 days. In some embodiments, the second TIL expansion can proceed for about 13 days to about 14 days. In some embodiments, the second TIL expansion can proceed for about 14 days.

In an embodiment, the second expansion can be performed in a gas permeable container using the methods of the present disclosure (including for example, expansions referred to as REP; as well as processes as indicated in Step D of FIG. 8). For example, TILs can be rapidly expanded using non-specific T-cell receptor stimulation in the presence of interleukin-2 (IL-2) or interleukin-15 (IL-15). The non-specific T-cell receptor stimulus can include, for example, an anti-CD3 antibody, such as about 30 ng/ml of OKT3, a mouse monoclonal anti-CD3 antibody (commercially available from Ortho-McNeil, Raritan, NJ or Miltenyi Biotech, Auburn, CA) or UHCT-1 (commercially available from BioLegend, San Diego, CA, USA). TILs can be expanded to induce further stimulation of the TILs in vitro by including one or more antigens during the second expansion, including antigenic portions thereof, such as epitope(s), of the cancer, which can be optionally expressed from a vector, such as a human leukocyte antigen A2 (HLA-A2) binding peptide, e.g., 0.3 µM MART-1:26-35 (27 L) or gpl 00:209-217 (210M), optionally in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+ allogeneic lymphocytes and IL-2. In some embodiments, the re-stimulation occurs as part of the second expansion. In some embodiments, the second expansion occurs in the presence of irradiated, autologous lymphocytes or with irradiated HLA-A2+ allogeneic lymphocytes and IL-2.

In an embodiment, the cell culture medium further comprises IL-2. In some embodiments, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises OKT-3 antibody. In some embodiments, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 µg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In some embodiments, the cell culture medium does not comprise OKT-3 antibody.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 µg/mL and 100 µg/mL. In some embodiments, the TNFRSF agonist is added at a concentration sufficient to achieve a concentration in the cell culture medium of between 20 µg/mL and 40 µg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, a combination of IL-2, IL-7, IL-15, and/or IL-21 are employed as a combination during the second expansion. In some embodiments, IL-2, IL-7, IL-15, and/or IL-21 as well as any combinations thereof can be included during the second expansion, including for example during a Step D processes according to FIG. 8, as well as described herein. In some embodiments, a combination of IL-2, IL-15, and IL-21 are employed as a combination during the second expansion. In some embodiments, IL-2, IL-15, and IL-21 as well as any combinations thereof can be included during Step D processes according to FIG. 8 and as described herein.

In some embodiments, the second expansion can be conducted in a supplemented cell culture medium comprising IL-2, OKT-3, antigen-presenting feeder cells, and optionally a TNFRSF agonist. In some embodiments, the second expansion occurs in a supplemented cell culture medium. In some embodiments, the supplemented cell culture medium comprises IL-2, OKT-3, and antigen-presenting feeder cells. In some embodiments, the second cell culture medium comprises IL-2, OKT-3, and antigen-presenting cells (APCs; also referred to as antigen-presenting feeder cells). In some embodiments, the second expansion occurs in a cell culture medium comprising IL-2, OKT-3, and antigen-presenting feeder cells (i.e., antigen presenting cells).

In some embodiments, the second expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the second expansion culture media comprises about 500 IU/mL of IL-15 to about 100 IU/mL of IL-15. In some embodiments, the second expansion culture media comprises about 400 IU/mL of IL-15 to about 100 IU/mL of IL-15. In some embodiments, the second expansion culture media comprises about 300 IU/mL of IL-15 to about 100 IU/mL of IL-15. In some embodiments, the second expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, the second expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the second expansion culture media comprises about 20 IU/mL of IL-21 to about 0.5 IU/mL of IL-21. In some embodiments, the second expansion culture media comprises about 15 IU/mL of IL-21 to about 0.5 IU/mL of IL-21. In some embodiments, the second expansion culture media comprises about 12 IU/mL of IL-21 to about 0.5 IU/mL of IL-21. In some embodiments, the second expansion culture media comprises about 10 IU/mL of IL-21 to about 0.5 IU/mL of IL-21. In some embodiments, the second expansion culture media comprises about 5 IU/mL of IL-21 to about 1 IU/mL of IL-21. In some embodiments, the second expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In some embodiments the antigen-presenting feeder cells (APCs) are PBMCs. In an embodiment, the ratio of TILs to PBMCs and/or antigen-presenting cells in the rapid expansion and/or the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to PBMCs in the rapid expansion and/or the second expansion is between 1 to 50 and 1 to 300. In an embodiment, the ratio of TILs to PBMCs in the rapid expansion and/or the second expansion is between 1 to 100 and 1 to 200.

In an embodiment, REP and/or the second expansion is performed in flasks with the bulk TILs being mixed with a 100- or 200-fold excess of inactivated feeder cells, 30 mg/mL OKT3 anti-CD3 antibody and 3000 IU/mL IL-2 in 150 ml media. Media replacement is done (generally ⅔ media replacement via respiration with fresh media) until the cells are transferred to an alternative growth chamber. Alternative growth chambers include G-REX flasks and gas permeable containers as more fully discussed below.

In some embodiments, the second expansion (which can include processes referred to as the REP process) is shortened to 7-14 days, as discussed in the examples and figures. In some embodiments, the second expansion is shortened to 11 days.

In an embodiment, REP and/or the second expansion may be performed using T-175 flasks and gas permeable bags as previously described (Tran, et al., *J. Immunother.* 2008, 31, 742-51; Dudley, et al., *J. Immunother.* 2003, 26, 332-42) or gas permeable cultureware (G-Rex flasks). In some embodiments, the second expansion (including expansions referred to as rapid expansions) is performed in T-175 flasks, and about 1×10⁶ TILs suspended in 150 mL of media may be added to each T-175 flask. The TILs may be cultured in a 1 to 1 mixture of CM and AIM-V medium, supplemented with 3000 IU per mL of IL-2 and 30 ng per ml of anti-CD3. The T-175 flasks may be incubated at 37° C. in 5% $CO_2$. Half the media may be exchanged on day 5 using 50/50 medium with 3000 IU per mL of IL-2. In some embodiments, on day 7 cells from two T-175 flasks may be combined in a 3 L bag and 300 mL of AIM V with 5% human AB serum and 3000 IU per mL of IL-2 was added to the 300 ml of TIL suspension. The number of cells in each bag was counted every day or two and fresh media was added to keep the cell count between 0.5 and 2.0×10⁶ cells/mL.

In an embodiment, the second expansion (which can include expansions referred to as REP, as well as those referred to in Step D of FIG. 8) may be performed in 500 mL capacity gas permeable flasks with 100 cm gas-permeable silicon bottoms (G-Rex 100, commercially available from Wilson Wolf Manufacturing Corporation, New Brighton, MN, USA), 5×10⁶ or 10×10⁶ TIL may be cultured with PBMCs in 400 mL of 50/50 medium, supplemented with 5% human AB serum, 3000 IU per mL of IL-2 and 30 ng per ml of anti-CD3 (OKT3). The G-Rex 100 flasks may be incubated at 37° C. in 5% $CO_2$. On day 5, 250 mL of supernatant may be removed and placed into centrifuge bottles and centrifuged at 1500 rpm (491×g) for 10 minutes. The TIL pellets may be re-suspended with 150 mL of fresh medium with 5% human AB serum, 3000 IU per mL of IL-2, and added back to the original G-Rex 100 flasks. When TIL are expanded serially in G-Rex 100 flasks, on day 7 the TIL in each G-Rex 100 may be suspended in the 300 mL of media present in each flask and the cell suspension may be divided into 3 100 mL aliquots that may be used to seed 3 G-Rex 100 flasks. Then 150 mL of AIM-V with 5% human AB serum and 3000 IU per mL of IL-2 may be added to each flask. The G-Rex 100 flasks may be incubated at 37° C. in 5% $CO_2$ and after 4 days 150 mL of AIM-V with 3000 IU per mL of IL-2 may be added to each G-REX 100 flask. The cells may be harvested on day 14 of culture.

In an embodiment, the second expansion (including expansions referred to as REP) is performed in flasks with the bulk TILs being mixed with a 100- or 200-fold excess of inactivated feeder cells, 30 mg/mL OKT3 anti-CD3 antibody and 3000 IU/mL IL-2 in 150 mL media. In some embodiments, media replacement is done until the cells are transferred to an alternative growth chamber. In some embodiments, ⅔ of the media is replaced by respiration with fresh media. In some embodiments, alternative growth chambers include G-REX flasks and gas permeable containers as more fully discussed below.

In an embodiment, the second expansion (including expansions referred to as REP) is performed and further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

Optionally, a cell viability assay can be performed after the second expansion (including expansions referred to as the REP expansion), using standard assays known in the art. For example, a trypan blue exclusion assay can be done on a sample of the bulk TILs, which selectively labels dead cells and allows a viability assessment. In some embodiments, TIL samples can be counted and viability determined using a Cellometer K2 automated cell counter (Nexcelom Bioscience, Lawrence, MA). In some embodiments, viability is determined according to the Cellometer K2 Image Cytometer Automatic Cell Counter protocol described, for example, in Example 15.

In some embodiments, the second expansion (including expansions referred to as REP) of TIL can be performed using T-175 flasks and gas-permeable bags as previously described (Tran K Q, Zhou J, Durflinger K H, et al., 2008, *J Immunother.*, 31:742-751, and Dudley M E, Wunderlich J R, Shelton T E, et al. 2003, *J Immunother.*, 26:332-342) or gas-permeable G-Rex flasks. In some embodiments, the second expansion is performed using flasks. In some embodiments, the second expansion is performed using gas-permeable G-Rex flasks. In some embodiments, the second expansion is performed in T-175 flasks, and about 1×10⁶ TIL are suspended in about 150 mL of media and this is added to each T-175 flask. The TIL are cultured with irradiated (50 Gy) allogeneic PBMC as "feeder" cells at a ratio of 1 to 100 and the cells were cultured in a 1 to 1 mixture of CM and AIM-V medium (50/50 medium), supplemented with 3000 IU/mL of IL-2 and 30 ng/mL of anti-CD3. The T-175 flasks are incubated at 37° C. in 5% $CO_2$. In some embodiments, half the media is changed on day 5 using 50/50 medium with 3000 IU/mL of IL-2. In some embodiments, on day 7, cells from 2 T-175 flasks are combined in a 3 L bag and 300 mL of AIM-V with 5% human AB serum and 3000 IU/mL of IL-2 is added to the 300 mL of TIL suspension. The number of cells in each bag can be counted every day or two and fresh media can be added to keep the cell count between about 0.5 and about 2.0×10⁶ cells/mL.

In some embodiments, the second expansion (including expansions referred to as REP) are performed in 500 mL capacity flasks with 100 cm² gas-permeable silicon bottoms (G-Rex 100, Wilson Wolf) (FIG. 1), about 5×10⁶ or 10×10⁶ TIL are cultured with irradiated allogeneic PBMC at a ratio of 1 to 100 in 400 mL of 50/50 medium, supplemented with 3000 IU/mL of IL-2 and 30 ng/mL of anti-CD3. The G-Rex 100 flasks are incubated at 37° C. in 5% $CO_2$. In some embodiments, on day 5, 250 mL of supernatant is removed and placed into centrifuge bottles and centrifuged at 1500 rpm (491 g) for 10 minutes. The TIL pellets can then be resuspended with 150 mL of fresh 50/50 medium with 3000 IU/mL of IL-2 and added back to the original G-Rex 100 flasks. In embodiments where TILs are expanded serially in G-Rex 100 flasks, on day 7 the TIL in each G-Rex 100 are suspended in the 300 mL of media present in each flask and the cell suspension was divided into three 100 mL aliquots that are used to seed 3 G-Rex 100 flasks. Then 150 mL of AIM-V with 5% human AB serum and 3000 IU/mL of IL-2 is added to each flask. The G-Rex 100 flasks are incubated at 37° C. in 5% $CO_2$ and after 4 days 150 mL of AIM-V with 3000 IU/mL of IL-2 is added to each G-Rex 100 flask. The cells are harvested on day 14 of culture.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained in the second expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

In some embodiments, the second expansion culture medium (e.g., sometimes referred to as CM2 or the second cell culture medium), comprises IL-2, OKT-3, as well as the antigen-presenting feeder cells (APCs), as discussed in more detail below.

In some embodiments, the second expansion, for example, Step D according to FIG. 8, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

In some embodiments, one or more sd-RNAs targeting genes as described herein, including PD-1, LAG-3, TIM-3, CISH, and CBLB, may be added to cell culture media during the second expansion, for Example, Step D according to FIG. 8, comprising TILs and other agents at amounts selected from the group consisting of 0.1 µM sd-RNA/10,000 TILs/100 µL media, 0.5 µM sd-RNA/10,000 TILs/100 µL media, 0.75 µM sd-RNA/10,000 TILs/100 µL media, 1 µM sd-RNA/10,000 TILs/100 µL media, 1.25 µM sd-RNA/10,000 TILs/100 µL media, 1.5 µM sd-RNA/10,000 TILs/100 µL media, 2 µM sd-RNA/10,000 TILs/100 µL media, 5 µM sd-RNA/10,000 TILs/100 µL media, or 10 µM sd-RNA/10,000 TILs/100 µL media. In some embodiment, one or more sd-RNAs targeting genes as described herein, including PD-1, LAG-3, TIM-3, CISH, and CBLB, may be added to TIL cultures during the second expansion, for Example, Step D according to FIG. 8, twice a day, once a day, every two days, every three days, every four days, every five days, every six days, or every seven days. In an embodiment, one or more sd-RNAs targeting genes as described herein, including PD-1, LAG-3, TIM-3, CISH, and CBLB, may be added to cell culture media comprising TILs and other agents during the second expansion, for Example, Step D according to FIG. 8, at amounts selected from the group consisting of 0.1 µM sd-RNA/10,000 TILs, 0.5 µM sd-RNA/10,000 TILs, 0.75 µM sd-RNA/10,000 TILs, 1 µM sd-RNA/10,000 TILs, 1.25 µM sd-RNA/10,000 TILs, 1.5 µM sd-RNA/10,000 TILs, 2 µM sd-RNA/10,000 TILs, 5 µM sd-RNA/10,000 TILs, or 10 µM sd-RNA/10,000 TILs. In an embodiment, one or more sd-RNAs targeting genes as described herein, including PD-1, LAG-3, TIM-3, CISH, and CBLB, may be added to TIL cultures during the during the second expansion, for Example, Step D according to FIG. 8, twice a day, once a day, every two days, every three days, every four days, every five days, every six days, or every seven days.

1. Feeder Cells and Antigen Presenting Cells

In an embodiment, the second expansion procedures described herein (for example including expansion such as those described in Step D from FIG. 8, as well as those referred to as REP) require an excess of feeder cells during REP TIL expansion and/or during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation.

In general, the allogenic PBMCs are inactivated, either via irradiation or heat treatment, and used in the REP procedures, as described in the examples, which provides an exemplary protocol for evaluating the replication incompetence of irradiate allogeneic PBMCs.

In some embodiments, PBMCs are considered replication incompetent and accepted for use in the TIL expansion procedures described herein if the total number of viable cells on day 14 is less than the initial viable cell number put into culture on day 0 of the REP and/or day 0 of the second expansion (i.e., the start day of the second expansion).

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30 ng/ml OKT3 antibody and 3000 IU/ml IL-2.

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 5-60 ng/ml OKT3 antibody and 1000-6000 IU/ml IL-2. In some embodiments, the PBMCs are cultured in the presence of 10-50 ng/ml OKT3 antibody and 2000-5000 IU/ml IL-2. In some embodiments, the PBMCs are cultured in the presence of 20-40 ng/ml OKT3 antibody and 2000-4000 IU/ml IL-2. In some embodiments, the PBMCs are cultured in the presence of 25-35 ng/ml OKT3 antibody and 2500-3500 IU/ml IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the second expansion procedures described herein require a ratio of about $2.5 \times 10^9$ feeder cells to about $100 \times 10^6$ TILs. In another embodiment, the second expansion procedures described herein require a ratio of about $2.5 \times 10^9$ feeder cells to about $50 \times 10^6$ TILs. In yet another embodiment, the second expansion procedures described herein require about $2.5 \times 10^9$ feeder cells to about $25 \times 10^6$ TILs.

In an embodiment, the second expansion procedures described herein require an excess of feeder cells during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation. In an embodiment, artificial antigen-presenting (aAPC) cells are used in place of PBMCs.

In general, the allogenic PBMCs are inactivated, either via irradiation or heat treatment, and used in the TIL expansion procedures described herein, including the exemplary procedures described in FIGS. 4, 5, 6, and 7.

In an embodiment, artificial antigen presenting cells are used in the second expansion as a replacement for, or in combination with, PBMCs.

2. Cytokines

The expansion methods described herein generally use culture media with high doses of a cytokine, in particular IL-2, as is known in the art.

Alternatively, using combinations of cytokines for the rapid expansion and or second expansion of TILS is additionally possible, with combinations of two or more of IL-2, IL-15 and IL-21 as is generally outlined in International Publication No. WO 2015/189356 and W International Publication No. WO 2015/189357, hereby expressly incorporated by reference in their entirety. Thus, possible combinations include IL-2 and IL-15, IL-2 and IL-21, IL-15 and IL-21 and IL-2, IL-15 and IL-21, with the latter finding particular use in many embodiments. The use of combinations of cytokines specifically favors the generation of lymphocytes, and in particular T-cells as described therein.

E. Step E: Harvest TILS

After the second expansion step, cells can be harvested. In some embodiments the TILs are harvested after one, two, three, four or more expansion steps, for example as provided in FIG. 8. In some embodiments the TILs are harvested after two expansion steps, for example as provided in FIG. 8.

TILs can be harvested in any appropriate and sterile manner, including for example by centrifugation. Methods for TIL harvesting are well known in the art and any such know methods can be employed with the present process. In some embodiments, TILS are harvest using an automated system.

Cell harvesters and/or cell processing systems are commercially available from a variety of sources, including, for example, Fresenius Kabi, Tomtec Life Science, Perkin Elmer, and Inotech Biosystems International, Inc. Any cell based harvester can be employed with the present methods. In some embodiments, the cell harvester and/or cell processing systems is a membrane-based cell harvester. In some embodiments, cell harvesting is via a cell processing system, such as the LOVO system (manufactured by Fresenius Kabi). The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some embodiments, the cell harvester and/or cell processing system can perform cell separation, washing, fluid-exchange, concentration, and/or other cell processing steps in a closed, sterile system.

In some embodiments, the harvest, for example, Step E according to FIG. 8, is performed from a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

In some embodiments, Step E according to FIG. 8, is performed according to the processes described in Example 16. In some embodiments, the closed system is accessed via syringes under sterile conditions in order to maintain the sterility and closed nature of the system. In some embodiments, a closed system as described in Example 16 is employed.

In some embodiments, TILs are harvested according to the methods described in Example 16. In some embodiments, TILs between days 1 and 11 are harvested using the methods as described in Section 8.5 (referred to as the Day 11 TIL harvest in Example 16). In some embodiments, TILs between days 12 and 22 are harvested using the methods as described in Section 8.12 (referred to as the Day 22 TIL harvest in Example 16).

F. Step F: Final Formulation/Transfer to Infusion Bag

After Steps A through E as provided in an exemplary order in FIG. 8 and as outlined in detailed above and herein are complete, cells are transferred to a container for use in administration to a patient. In some embodiments, once a therapeutically sufficient number of TILs are obtained using the expansion methods described above, they are transferred to a container for use in administration to a patient.

In an embodiment, TILs expanded using APCs of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic.

1. Pharmaceutical Compositions, Dosages, and Dosing Regimens

In an embodiment, TILs expanded using the methods of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic administration.

Any suitable dose of TILs can be administered. In some embodiments, from about $2.3 \times 10^{10}$ to about $13.7 \times 10^{10}$ TILs are administered, with an average of around $7.8 \times 10^{10}$ TILs, particularly if the cancer is melanoma. In an embodiment, about $1.2 \times 10^{10}$ to about $4.3 \times 10^{10}$ of TILs are administered. In some embodiments, about $3 \times 10^{10}$ to about $12 \times 10^{10}$ TILs are administered. In some embodiments, about $4 \times 10^{10}$ to about $10 \times 10^{10}$ TILs are administered. In some embodiments, about $5 \times 10^{10}$ to about $8 \times 10^{10}$ TILs are administered. In some embodiments, about $6 \times 10^{10}$ to about $8 \times 10^{10}$ TILs are administered. In some embodiments, about $7 \times 10^{10}$ to about $8 \times 10^{10}$ TILs are administered. In some embodiments, the therapeutically effective dosage is about $2.3 \times 10^{10}$ to about $13.7 \times 10^{10}$. In some embodiments, the therapeutically effective dosage is about $7.8 \times 10^{10}$ TILs, particularly of the cancer is melanoma. In some embodiments, the therapeutically effective dosage is about $1.2 \times 10^{10}$ to about $4.3 \times 10^{10}$ of TILs. In some embodiments, the therapeutically effective dosage is about $3 \times 10^{10}$ to about $12 \times 10^{10}$ TILs. In some embodiments, the therapeutically effective dosage is about $4 \times 10^{10}$ to about $10 \times 10^{10}$ TILs. In some embodiments, the therapeutically effective dosage is about $5 \times 10^{10}$ to about $8 \times 10^{10}$ TILs. In some embodiments, the therapeutically effective dosage is about $6 \times 10^{10}$ to about $8 \times 10^{10}$ TILs. In some embodiments, the therapeutically effective dosage is about $7 \times 10^{10}$ to about $8 \times 10^{10}$ TILs.

In some embodiments, the number of the TILs provided in the pharmaceutical compositions of the invention is about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, and $9 \times 10^{13}$. In an embodiment, the number of the TILs provided in the pharmaceutical compositions of the invention is in the range of $1 \times 10^6$ to $5 \times 10^6$, $5 \times 10^6$ to $1 \times 10^7$, $1 \times 10^7$ to $5 \times 10^7$, $5 \times 10^7$ to $1 \times 10^8$, $1 \times 10^8$ to $5 \times 10^8$, $5 \times 10^8$ to $1 \times 10^9$, $1 \times 10^9$ to $5 \times 10^9$, $5 \times 10^9$ to $1 \times 10^{10}$, $1 \times 10^{10}$ to $5 \times 10^{10}$, $5 \times 10^{10}$ to $1 \times 10^{11}$, $5 \times 10^{11}$ to $1 \times 10^{12}$, $1 \times 10^{12}$ to $5 \times 10^{12}$, and $5 \times 10^{12}$ to $1 \times 10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the TILs provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, and $9 \times 10^{13}$. In some embodiments, an effective dosage of TILs is in the range of $1 \times 10^6$ to $5 \times 10^6$, $5 \times 10^6$ to $1 \times 10^7$, $1 \times 10^7$ to $5 \times 10^7$, $5 \times 10^7$ to $1 \times 10^8$, $1 \times 10^8$ to $5 \times 10^8$, $5 \times 10^8$ to $1 \times 10^9$, $1 \times 10^9$ to $5 \times 10^9$, $5 \times 10^9$ to $1 \times 10^{10}$, $1 \times 10^{10}$ to $5 \times 10^{10}$, $5 \times 10^{10}$ to $1 \times 10^{11}$, $5 \times 10^{11}$ to $1 \times 10^{12}$, $1 \times 10^{12}$ to $5 \times 10^{12}$, and $5 \times 10^{12}$ to $1 \times 10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

G. Optional Cell Medium Components

1. Anti-CD3 Antibodies

In some embodiments, the culture media used in expansion methods described herein (including those referred to as REP, see for example, Figure A) also includes an anti-CD3 antibody. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

As will be appreciated by those in the art, there are a number of suitable anti-human CD3 antibodies that find use in the invention, including anti-human CD3 polyclonal and monoclonal antibodies from various mammals, including, but not limited to, murine, human, primate, rat, and canine antibodies. In particular embodiments, the OKT3 anti-CD3 antibody is used (commercially available from Ortho-McNeil, Raritan, NJ or Miltenyi Biotech, Auburn, CA).

2. 4-1BB (CD137) Agonists

In an embodiment, the TNFRSF agonist is a 4-1BB (CD137) agonist. The 4-1BB agonist may be any 4-1BB binding molecule known in the art. The 4-1BB binding molecule may be a monoclonal antibody or fusion protein capable of binding to human or mammalian 4-1BB. The 4-1BB agonists or 4-1BB binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The 4-1BB agonist or 4-1BB binding molecule may have both a heavy and a light chain. As used herein, the term binding molecule also includes antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to 4-1BB. In an embodiment, the 4-1BB agonist is an antigen binding protein that is a fully human antibody. In an embodiment, the 4-1BB agonist is an antigen binding protein that is a humanized antibody. In some embodiments, 4-1BB agonists for use in the presently disclosed methods and compositions include anti-4-1BB antibodies, human anti-4-1BB antibodies, mouse anti-4-1BB antibodies, mammalian anti-4-1BB antibodies, monoclonal anti-4-1BB antibodies, polyclonal anti-4-1BB antibodies, chimeric anti-4-1BB antibodies, anti-4-1BB adnectins, anti-4-1BB domain antibodies, single chain anti-4-1BB fragments, heavy chain anti-4-1BB fragments, light chain anti-4-1BB fragments, anti-4-1BB fusion proteins, and fragments, derivatives, conjugates, variants, or biosimilars thereof. Agonistic anti-4-1BB antibodies are known to induce strong immune responses. Lee, et al., *PLOS One* 2013, 8, e69677. In a preferred embodiment, the 4-1BB agonist is an agonistic, anti-4-1BB humanized or fully human monoclonal antibody (i.e., an antibody derived from a single cell line). In an embodiment, the 4-1BB agonist is EU-101 (Eutilex Co. Ltd.), utomilumab, or urelumab, or a fragment, derivative, conjugate, variant, or biosimilar thereof. In a preferred embodiment, the 4-1BB agonist is utomilumab or urelumab, or a fragment, derivative, conjugate, variant, or biosimilar thereof.

In a preferred embodiment, the 4-1BB agonist or 4-1BB binding molecule may also be a fusion protein. In a preferred embodiment, a multimeric 4-1BB agonist, such as a trimeric or hexameric 4-1BB agonist (with three or six ligand binding domains), may induce superior receptor (4-1BBL) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic 4-1BB antibodies and fusion proteins are known to induce strong immune responses. In a preferred embodiment, the 4-1BB agonist is a monoclonal antibody or fusion protein that binds specifically to 4-1BB antigen in a manner sufficient to reduce toxicity. In some embodiments, the 4-1BB agonist is an agonistic 4-1BB monoclonal antibody or fusion protein that abrogates antibody-dependent cellular toxicity (ADCC), for example NK cell cytotoxicity. In some embodiments, the 4-1BB agonist is an agonistic 4-1BB monoclonal antibody or fusion protein that abrogates antibody-dependent cell phagocytosis (ADCP). In some embodiments, the 4-1BB agonist is an agonistic 4-1BB monoclonal antibody or fusion protein that abrogates complement-dependent cytotoxicity (CDC). In some embodiments, the 4-1BB agonist is an agonistic 4-1BB monoclonal antibody or fusion protein which abrogates Fc region functionality.

In some embodiments, the 4-1BB agonists are characterized by binding to human 4-1BB (SEQ ID NO:9) with high affinity and agonistic activity. In an embodiment, the 4-1BB agonist is a binding molecule that binds to human 4-1BB (SEQ ID NO:9). In an embodiment, the 4-1BB agonist is a binding molecule that binds to murine 4-1BB (SEQ ID NO:10). The amino acid sequences of 4-1BB antigen to which a 4-1BB agonist or binding molecule binds are summarized in Table 3.

slower, binds to human or murine 4-1BB with a $k_{dissoc}$ of about $2.1 \times 10^{-5}$ 1/s or slower, binds to human or murine 4-1BB with a $k_{dissoc}$ of about $2.2 \times 10^{-5}$ 1/s or slower, binds to human or murine 4-1BB with a $k_{dissoc}$ of about $2.3 \times 10^{-5}$ 1/s or slower, binds to human or murine 4-1BB with a $k_{dissoc}$ of about $2.4 \times 10^{-5}$ 1/s or slower, binds to human or murine 4-1BB with a $k_{dissoc}$ of about $2.5 \times 10^{-5}$ 1/s or slower, binds to human or murine 4-1BB with a $k_{dissoc}$ of about $2.6 \times 10^{-5}$ 1/s or slower or binds to human or murine 4-1BB with a $k_{dissoc}$ of about $2.7 \times 10^{-5}$ 1/s or slower, binds to human or murine 4-1BB with a $k_{dissoc}$ of about $2.8 \times 10^{-5}$ 1/s or slower, binds to human or murine 4-1BB with a $k_{dissoc}$ of about $2.9 \times 10^{-5}$ 1/s or slower, or binds to human or murine 4-1BB with a $k_{dissoc}$ of about $3 \times 10^{-5}$ 1/s or slower.

In some embodiments, the compositions, processes and methods described include a 4-1BB agonist that binds to human or murine 4-1BB with an $IC_{50}$ of about 10 nM or lower, binds to human or murine 4-1BB with an $IC_{50}$ of about 9 nM or lower, binds to human or murine 4-1BB with an $IC_{50}$ of about 8 nM or lower, binds to human or murine

TABLE 3

Amino acid sequences of 4-1BB antigens.

| Identifier | Sequence (One-Letter Amino Acid Symbols) | | | | | |
|---|---|---|---|---|---|---|
| SEQ ID NO: 9 human 4-1BB, Tumor necrosis factor receptor superfamily, member 9 (*Homo sapiens*) | MGNSCYNIVA TCDICRQCKG CFGTFNDQKR PGHSPQIISF CSCRFPEEEE | TLLLVLNFER VFRTRKECSS GICRPWTNCS FLALTSTALL GGCEL | TRSLQDPCSN TSNAECDCTP LDGKSVLVNG FLLFFLTLRF | CPAGTFCDNN GFHCLGAGCS TKERDVVCGP SVVKRGRKKL | RNQICSPCPP MCEQDCKQGQ SPADLSPGAS LYIFKQPFMR | NSFSSAGGQR ELTKKGCKDC SVTPPAPARE PVQTTQEEDG | 60 120 180 240 255 |
| SEQ ID NO: 10 murine 4-1BB, Tumor necrosis factor receptor superfamily, member 9 (*Mus musculus*) | MGNNCYNVVV CNICRVCAGY LGTFNDQNGT GHSLQVLTLF CRCPQEEEGG | IVLLLVGCEK FRFKKFCSST GVCRPWTNCS LALTSALLLA GGGYEL | VGAVQNSCDN HNAECECIEG LDGRSVLKTG LIFITLLFSV | CQPGTFCRKY FHCLGPQCTR TTEKDVVCGP LKWIRKKFPH | NPVCKSCPPS CEKDCRPGQE PVVSFSPSTT IFKQPFKKTT | TFSSIGGQPN LTKQGCKTCS ISVTPEGGPG GAAQEEDACS | 60 120 180 240 256 |

In some embodiments, the compositions, processes and methods described include a 4-1BB agonist that binds human or murine 4-1BB with a $K_D$ of about 100 pM or lower, binds human or murine 4-1BB with a $K_D$ of about 90 pM or lower, binds human or murine 4-1BB with a $K_D$ of about 80 pM or lower, binds human or murine 4-1BB with a $K_D$ of about 70 pM or lower, binds human or murine 4-1BB with a $K_D$ of about 60 pM or lower, binds human or murine 4-1BB with a $K_D$ of about 50 pM or lower, binds human or murine 4-1BB with a $K_D$ of about 40 pM or lower, or binds human or murine 4-1BB with a $K_D$ of about 30 pM or lower.

In some embodiments, the compositions, processes and methods described include a 4-1BB agonist that binds to human or murine 4-1BB with a $k_{assoc}$ of about $7.5 \times 10^5$ 1/M·s or faster, binds to human or murine 4-1BB with a $k_{assoc}$ of about $7.5 \times 10^5$ 1/M·s or faster, binds to human or murine 4-1BB with a $k_{assoc}$ of about $8 \times 10^5$ 1/M·s or faster, binds to human or murine 4-1BB with a $k_{assoc}$ of about $8.5 \times 10^5$ 1/M·s or faster, binds to human or murine 4-1BB with a $k_{assoc}$ of about $9 \times 10^5$ 1/M·s or faster, binds to human or murine 4-1BB with a $k_{assoc}$ of about $9.5 \times 10^5$ 1/M·s or faster, or binds to human or murine 4-1BB with a $k_{assoc}$ of about $1 \times 10^6$ 1/M·s or faster.

In some embodiments, the compositions, processes and methods described include a 4-1BB agonist that binds to human or murine 4-1BB with a $k_{dissoc}$ of about $2 \times 10^{-5}$ 1/s or 4-1BB with an $IC_{50}$ of about 7 nM or lower, binds to human or murine 4-1BB with an $IC_{50}$ of about 6 nM or lower, binds to human or murine 4-1BB with an $IC_{50}$ of about 5 nM or lower, binds to human or murine 4-1BB with an $IC_{50}$ of about 4 nM or lower, binds to human or murine 4-1BB with an $IC_{50}$ of about 3 nM or lower, binds to human or murine 4-1BB with an $IC_{50}$ of about 2 nM or lower, or binds to human or murine 4-1BB with an $IC_{50}$ of about 1 nM or lower.

In a preferred embodiment, the 4-1BB agonist is utomilumab, also known as PF-05082566 or MOR-7480, or a fragment, derivative, variant, or biosimilar thereof. Utomilumab is available from Pfizer, Inc. Utomilumab is an immunoglobulin G2-lambda, anti-[*Homo sapiens* TNFRSF9 (tumor necrosis factor receptor (TNFR) superfamily member 9, 4-1BB, T cell antigen ILA, CD137)], *Homo sapiens* (fully human) monoclonal antibody. The amino acid sequences of utomilumab are set forth in Table 4. Utomilumab comprises glycosylation sites at Asn59 and Asn292; heavy chain intrachain disulfide bridges at positions 22-96 ($V_H$-$V_L$), 143-199 ($C_H$1-$C_L$), 256-316 ($C_H$2) and 362-420 ($C_H$3); light chain intrachain disulfide bridges at positions 22'-87' ($V_H$-$V_L$) and 136'-195' ($C_H$1-$C_L$); interchain heavy chain-heavy chain disulfide bridges at IgG2A isoform positions 218-218, 219-219, 222-222, and 225-225, at IgG2A/B isoform positions 218-130, 219-219, 222-222, and 225-225, and at IgG2B isoform positions 219-130 (2), 222-222, and 225-225; and interchain heavy chain-light chain disulfide bridges at IgG2A isoform positions 130-213' (2), IgG2A/B isoform positions 218-213' and 130-213', and at IgG2B isoform positions 218-213' (2). The preparation and properties of utomilumab and its variants and fragments are described in U.S. Pat. Nos. 8,821,867; 8,337,850; and 9,468,678, and International Patent Application Publication No. WO 2012/032433 A1, the disclosures of each of which are incorporated by reference herein. Preclinical characteristics of utomilumab are described in Fisher, et al., *Cancer Immunolog. & Immunother.* 2012, 61, 1721-33. Current clinical trials of utomilumab in a variety of hematological and solid tumor indications include U.S. National Institutes of Health clinicaltrials.gov identifiers NCT02444793, NCT01307267, NCT02315066, and NCT02554812.

In an embodiment, a 4-1BB agonist comprises a heavy chain given by SEQ ID NO:11 and a light chain given by SEQ ID NO:12. In an embodiment, a 4-1BB agonist comprises heavy and light chains having the sequences shown in SEQ ID NO:11 and SEQ ID NO:12, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:11 and SEQ ID NO:12, respectively. In an embodiment, a 4-1BB agonist comprises heavy and light chains that are each at least 98% identical to the sequences shown in SEQ ID NO:11 and SEQ ID NO:12, respectively. In an embodiment, a 4-1BB agonist comprises heavy and light chains that are each at least 97% identical to the sequences shown in SEQ ID NO:11 and SEQ ID NO:12, respectively. In an embodiment, a 4-1BB agonist comprises heavy and light chains that are each at least 96% identical to the sequences shown in SEQ ID NO:11 and SEQ ID NO:12, respectively. In an embodiment, a 4-1BB agonist comprises heavy and light chains that are each at least 95% identical to the sequences shown in SEQ ID NO:11 and SEQ ID NO:12, respectively.

In an embodiment, the 4-1BB agonist comprises the heavy and light chain CDRs or variable regions (VRs) of utomilumab. In an embodiment, the 4-1BB agonist heavy chain variable region ($V_H$) comprises the sequence shown in SEQ ID NO:13, and the 4-1BB agonist light chain variable region ($V_L$) comprises the sequence shown in SEQ ID NO:14, and conservative amino acid substitutions thereof. In an embodiment, a 4-1BB agonist comprises $V_H$ and $V_L$ regions that are each at least 99% identical to the sequences shown in SEQ ID NO:13 and SEQ ID NO:14, respectively. In an embodiment, a 4-1BB agonist comprises $V_H$ and $V_L$ regions that are each at least 98% identical to the sequences shown in SEQ ID NO:13 and SEQ ID NO:14, respectively. In an embodiment, a 4-1BB agonist comprises $V_H$ and $V_L$ regions that are each at least 97% identical to the sequences shown in SEQ ID NO:13 and SEQ ID NO:14, respectively. In an embodiment, a 4-1BB agonist comprises $V_H$ and $V_L$ regions that are each at least 96% identical to the sequences shown in SEQ ID NO:13 and SEQ ID NO:14, respectively. In an embodiment, a 4-1BB agonist comprises $V_H$ and $V_L$ regions that are each at least 95% identical to the sequences shown in SEQ ID NO:13 and SEQ ID NO:14, respectively. In an embodiment, a 4-1BB agonist comprises an scFv antibody comprising $V_H$ and $V_L$ regions that are each at least 99% identical to the sequences shown in SEQ ID NO:13 and SEQ ID NO:14.

In an embodiment, a 4-1BB agonist comprises heavy chain CDR1, CDR2 and CDR3 domains having the sequences set forth in SEQ ID NO:15, SEQ ID NO:16, and SEQ ID NO:17, respectively, and conservative amino acid substitutions thereof, and light chain CDR1, CDR2 and CDR3 domains having the sequences set forth in SEQ ID NO:18, SEQ ID NO:19, and SEQ ID NO:20, respectively, and conservative amino acid substitutions thereof.

In an embodiment, the 4-1BB agonist is a 4-1BB agonist biosimilar monoclonal antibody approved by drug regulatory authorities with reference to utomilumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is utomilumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is utomilumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab.

TABLE 4

Amino acid sequences for 4-1BB agonist antibodies related to utomilumab.

| Identifier | Sequence (One-Letter Amino Acid Symbols) | | | | | |
|---|---|---|---|---|---|---|
| SEQ ID NO: 11 heavy chain for utomilumab | EVQLVQSGAE | VKKPGESLRI | SCKGSGYSFS | TYWISWVRQM | PGKGLEWMGK | IYPGDSYTNY 60 |
| | SPSFQGQVTI | SADKSISTAY | LQWSSLKASD | TAMYYCARGY | GIFDYWGQGT | LVTVSSASTK 120 |
| | GPSVFPLAPC | SRSTSESTAA | LGCLVKDYFP | EPVTVSWNSG | ALTSGVHTFP | AVLQSSGLYS 180 |
| | LSSVVTVPSS | NFGTQTYTCN | VDHKPSNTKV | DKTVERKCCV | ECPPCPAPPV | AGPSVFLFPP 240 |
| | KPKDTLMISR | TPEVTCVVVD | VSHEDPEVQF | NWYVDGVEVH | NAKTKPREEQ | FNSTFRVVSV 300 |
| | LTVVHQDWLN | GKEYKCKVSN | KGLPAPIEKT | ISKTKGQPRE | PQVYTLPPSR | EEMTKNQVSL 360 |
| | TCLVKGFYPS | DIAVEWESNG | QPENNYKTTP | PMLDSDGSFF | LYSKLTVDKS | RWQQGNVFSC 420 |
| | SVMHEALHNH | YTQKSLSLSP | G | | | 441 |

TABLE 4-continued

Amino acid sequences for 4-1BB agonist antibodies related to utomilumab.

| Identifier | Sequence (One-Letter Amino Acid Symbols) | |
|---|---|---|
| SEQ ID NO: 12<br>light chain for<br>utomilumab | SYELTQPPSV SVSPGQTASI TCSGDNIGDQ YAHWYQQKPG QSPVLVIYQD KNRPSGIPER<br>FSGSNSGNTA TLTISGTQAM DEADYYCATY TGFGSLAVFG GGTKLTVLGQ PKAAPSVTLF<br>PPSSEELQAN KATLVCLISD FYPGAVTVAW KADSSPVKAG VETTTPSKQS NNKYAASSYL<br>SLTPEQWKSH RSYSCQVTHE GSTVEKTVAP TECS | 60<br>120<br>180<br>214 |
| SEQ ID NO: 13<br>heavy chain<br>variable region<br>for utomilumab | EVQLVQSGAE VKKPGESLRI SCKGSGYSFS TYWISWVRQM PGKGLEWMG KIYPGDSYTN<br>YSPSFQGQVT ISADKSISTA YLQWSSLKAS DTAMYYCARG YGIFDYWGQ GTLVTVSS | 60<br>118 |
| SEQ ID NO: 14<br>light chain<br>variable region<br>for utomilumab | SYELTQPPSV SVSPGQTASI TCSGDNIGDQ YAHWYQQKPG QSPVLVIYQD KNRPSGIPER<br>FSGSNSGNTA TLTISGTQAM DEADYYCATY TGFGSLAVFG GGTKLTVL | 60<br>108 |
| SEQ ID NO: 15<br>heavy chain CDR1<br>for utomilumab | STYWIS | 6 |
| SEQ ID NO: 16<br>heavy chain CDR2<br>for utomilumab | KIYPGDSYTN YSPSFQG | 17 |
| SEQ ID NO: 17<br>heavy chain CDR3<br>for utomilumab | RGYGIFDY | 8 |
| SEQ ID NO: 18<br>light chain CDR1<br>for utomilumab | SGDNIGDQYA H | 11 |
| SEQ ID NO: 19<br>light chain CDR2<br>for utomilumab | QDKNRPS | 7 |
| SEQ ID NO: 20<br>light chain CDR3<br>for utomilumab | ATYTGFGSLA V | 11 |

In a preferred embodiment, the 4-1BB agonist is the monoclonal antibody urelumab, also known as BMS-663513 and 20H4.9.h4a, or a fragment, derivative, variant, or biosimilar thereof. Urelumab is available from Bristol-Myers Squibb, Inc., and Creative Biolabs, Inc. Urelumab is an immunoglobulin G4-kappa, anti-[*Homo sapiens* TNFRSF9 (tumor necrosis factor receptor superfamily member 9, 4-1BB, T cell antigen ILA, CD137)], *Homo sapiens* (fully human) monoclonal antibody. The amino acid sequences of urelumab are set forth in Table 5. Urelumab comprises N-glycosylation sites at positions 298 (and 298"); heavy chain intrachain disulfide bridges at positions 22-95 ($V_H$-$V_L$), 148-204 ($C_H1$-$C_L$), 262-322 ($C_H2$) and 368-426 ($C_H3$) (and at positions 22"-95", 148"-204", 262"-322", and 368"-426"); light chain intrachain disulfide bridges at positions 23'-88' ($V_H$-$V_L$) and 136'-196' ($C_H1$-$C_L$) (and at positions 23'''-88''' and 136'''-196'''); interchain heavy chain-heavy chain disulfide bridges at positions 227-227" and 230-230"; and interchain heavy chain-light chain disulfide bridges at 135-216' and 135"-216'''. The preparation and properties of urelumab and its variants and fragments are described in U.S. Pat. Nos. 7,288,638 and 8,962,804, the disclosures of which are incorporated by reference herein. The preclinical and clinical characteristics of urelumab are described in Segal, et al., *Clin. Cancer Res.* 2016, available at http://dx.doi.org/10.1158/1078-0432.CCR-16-1272. Current clinical trials of urelumab in a variety of hematological and solid tumor indications include U.S. National Institutes of Health clinicaltrials.gov identifiers NCT01775631, NCT02110082, NCT02253992, and NCT01471210.

In an embodiment, a 4-1BB agonist comprises a heavy chain given by SEQ ID NO:21 and a light chain given by SEQ ID NO:22. In an embodiment, a 4-1BB agonist comprises heavy and light chains having the sequences shown in SEQ ID NO:21 and SEQ ID NO:22, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:21 and SEQ ID NO:22, respectively. In an embodiment, a 4-1BB agonist comprises heavy and light chains that are each at least 98% identical to the sequences shown in SEQ ID NO:21 and SEQ ID NO:22, respectively. In an embodiment, a 4-1BB agonist comprises heavy and light chains that are each at least 97% identical to the sequences shown in SEQ ID NO:21 and SEQ ID NO:22, respectively. In an embodiment, a 4-1BB agonist comprises heavy and light chains that are each at least 96% identical to the sequences shown in SEQ ID NO:21 and SEQ ID NO:22, respectively. In an embodiment, a 4-1BB agonist comprises heavy and light chains that are each at least 95% identical to the sequences shown in SEQ ID NO:21 and SEQ ID NO:22, respectively.

In an embodiment, the 4-1BB agonist comprises the heavy and light chain CDRs or variable regions (VRs) of urelumab. In an embodiment, the 4-1BB agonist heavy chain variable region (V$_H$) comprises the sequence shown in SEQ ID NO:23, and the 4-1BB agonist light chain variable region (V$_L$) comprises the sequence shown in SEQ ID NO:24, and conservative amino acid substitutions thereof. In an embodiment, a 4-1BB agonist comprises V$_H$ and V$_L$ regions that are each at least 99% identical to the sequences shown in SEQ ID NO:23 and SEQ ID NO:24, respectively. In an embodiment, a 4-1BB agonist comprises V$_H$ and V$_L$ regions that are each at least 98% identical to the sequences shown in SEQ ID NO:23 and SEQ ID NO:24, respectively. In an embodiment, a 4-1BB agonist comprises V$_H$ and V$_L$ regions that are each at least 97% identical to the sequences shown in SEQ ID NO:23 and SEQ ID NO:24, respectively. In an embodiment, a 4-1BB agonist comprises V$_H$ and V$_L$ regions that are each at least 96% identical to the sequences shown in SEQ ID NO:23 and SEQ ID NO:24, respectively. In an embodiment, a 4-1BB agonist comprises V$_H$ and V$_L$ regions that are each at least 95% identical to the sequences shown in SEQ ID NO:23 and SEQ ID NO:24, respectively. In an embodiment, a 4-1BB agonist comprises an scFv antibody comprising V$_H$ and V$_L$ regions that are each at least 99% identical to the sequences shown in SEQ ID NO:23 and SEQ ID NO:24.

In an embodiment, a 4-1BB agonist comprises heavy chain CDR1, CDR2 and CDR3 domains having the sequences set forth in SEQ ID NO:25, SEQ ID NO:26, and SEQ ID NO:27, respectively, and conservative amino acid substitutions thereof, and light chain CDR1, CDR2 and CDR3 domains having the sequences set forth in SEQ ID NO:28, SEQ ID NO:29, and SEQ ID NO:30, respectively, and conservative amino acid substitutions thereof.

In an embodiment, the 4-1BB agonist is a 4-1BB agonist biosimilar monoclonal antibody approved by drug regulatory authorities with reference to urelumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is urelumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is urelumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab.

TABLE 5

Amino acid sequences for 4-1BB agonist antibodies related to urelumab.

| Identifier | Sequence (One-Letter Amino Acid Symbols) | |
| --- | --- | --- |
| SEQ ID NO: 21 heavy chain for urelumab | QVQLQQWGAG LLKPSETLSL TCAVYGGSFS GYYWSIRQS PEKGLEWIGE INHGGYVTYN<br>PSLESRVTIS VDTSKNQFSL KLSSVTAADT AVYYCARDYG PGNYDWYFDL WGRGTLVTVS<br>SASTKGPSVF PLAPCSRSTS ESTAALGCLV KDYFPEPVTV SWNSGALTSG VETFPAVLQS<br>SGLYSLSSVV TVPSSSLGTK TYTCNVDHKP SNTKVDKRVE SKYGPPCPPC PAPEFLGGPS<br>VFLFPPKPKD TLMISRTPEV TCVVVDVSQE DPEVQFNWYV DGVEVHNAKT KPREEQFNST<br>YRVVSVLTVL HQDWLNGKEY KCKVSNKGLP SSIEKTISKA KGQPREPQVY TLPPSQEEMT<br>KNQVSLTCLV KGFYPSDIAV EWESNGQPEN NYKTTPPVLD SDGSFFLYSR LTVDKSRWQE<br>GNVFSCSVMH EALHNHYTQK SLSLSLGK | 60<br>120<br>180<br>240<br>300<br>360<br>420<br>448 |
| SEQ ID NO: 22 light chain for urelumab | EIVLTQSPAT LSLSPGERAT LSCRASQSVS SYLAWYQQKP GQAPRLLIYD ASNRATGIPA<br>RFSGSGSGTD FTLTISSLEP EDFAVYYCQQ RSNWPPALTF CGGTKVEIKR TVAAPSVFIF<br>PPSDEQLKSG TASVVCLLNN FYPREAKVQW KVDNALQSGN SQESVTEQDS KDSTYSLSST<br>LTLSKADYEK HKVYACEVTH QGLSSPVTKS FNRGEC | 60<br>120<br>180<br>216 |
| SEQ ID NO: 23 variable heavy chain for urelumab | MKHLWFFLLL VAAPRWVLSQ VQLQQWGAGL LKPSETLSLT CAVYGGSFSG YYWSWIRQSP<br>EKGLEWIGEI NHGGYVTYNP SLESRVTISV DTSKNQFSLK LSSVTAADTA VYYCARDYGP | 60<br>120 |
| SEQ ID NO: 24 variable light chain for urelumab | MEAPAQLLFL LLLWLPDTTG EIVLTQSPAT LSLSPGERAT LSCRASQSVS SYLAWYQQKP<br>GQAPRLLIYD ASNRATGIPA RFSGSGSGTD FTLTISSLEP EDFAVYYCQQ | 60<br>110 |
| SEQ ID NO: 25 heavy chain CDR1 for urelumab | GYYWS | 5 |
| SEQ ID NO: 26 heavy chain CDR2 for urelumab | EINHGGVVTY NPSLES | 16 |

TABLE 5-continued

Amino acid sequences for 4-1BB agonist antibodies related to urelumab.

| Identifier | Sequence (One-Letter Amino Acid Symbols) | |
|---|---|---|
| SEQ ID NO: 27<br>heavy chain CDR3<br>for urelumab | DYGPGNYDWY FDL | 13 |
| SEQ ID NO: 28<br>light chain CDR1<br>for urelumab | RASQSVSSYL A | 11 |
| SEQ ID NO: 29<br>light chain CDR2<br>for urelumab | DASNRAT | 7 |
| SEQ ID NO: 30<br>light chain CDR3<br>for urelumab | QQRSDWPPAL T | 11 |

In an embodiment, the 4-1BB agonist is selected from the group consisting of 1D8, 3Elor, 4B4 (BioLegend 309809), H4-1BB-M127 (BD Pharmingen 552532), BBK2 (Thermo Fisher MS621PABX), 145501 (Leinco Technologies B591), the antibody produced by cell line deposited as ATCC No. HB-11248 and disclosed in U.S. Pat. No. 6,974,863, 5F4 (BioLegend 31 1503), C65-485 (BD Pharmingen 559446), antibodies disclosed in U.S. Patent Application Publication No. US 2005/0095244, antibodies disclosed in U.S. Pat. No. 7,288,638 (such as 20H4.9-IgG1 (BMS-663031)), antibodies disclosed in U.S. Pat. No. 6,887,673 (such as 4E9 or BMS-554271), antibodies disclosed in U.S. Pat. No. 7,214,493, antibodies disclosed in U.S. Pat. No. 6,303,121, antibodies disclosed in U.S. Pat. No. 6,569,997, antibodies disclosed in U.S. Pat. No. 6,905,685 (such as 4E9 or BMS-554271), antibodies disclosed in U.S. Pat. No. 6,362,325 (such as 1D8 or BMS-469492; 3H3 or BMS-469497; or 3El), antibodies disclosed in U.S. Pat. No. 6,974,863 (such as 53A2); antibodies disclosed in U.S. Pat. No. 6,210,669 (such as 1D8, 3B8, or 3El), antibodies described in U.S. Pat. No. 5,928,893, antibodies disclosed in U.S. Pat. No. 6,303,121, antibodies disclosed in U.S. Pat. No. 6,569,997, antibodies disclosed in International Patent Application Publication Nos. WO 2012/177788, WO 2015/119923, and WO 2010/042433, and fragments, derivatives, conjugates, variants, or biosimilars thereof, wherein the disclosure of each of the foregoing patents or patent application publications is incorporated by reference here.

In an embodiment, the 4-1BB agonist is a 4-1BB agonistic fusion protein described in International Patent Application Publication Nos. WO 2008/025516 A1, WO 2009/007120 A1, WO 2010/003766 A1, WO 2010/010051 A1, and WO 2010/078966 A1; U.S. Patent Application Publication Nos. US 2011/0027218 A1, US 2015/0126709 A1, US 2011/0111494 A1, US 2015/0110734 A1, and US 2015/0126710 A1; and U.S. Pat. Nos. 9,359,420, 9,340,599, 8,921,519, and 8,450,460, the disclosures of which are incorporated by reference herein.

Figure 56:
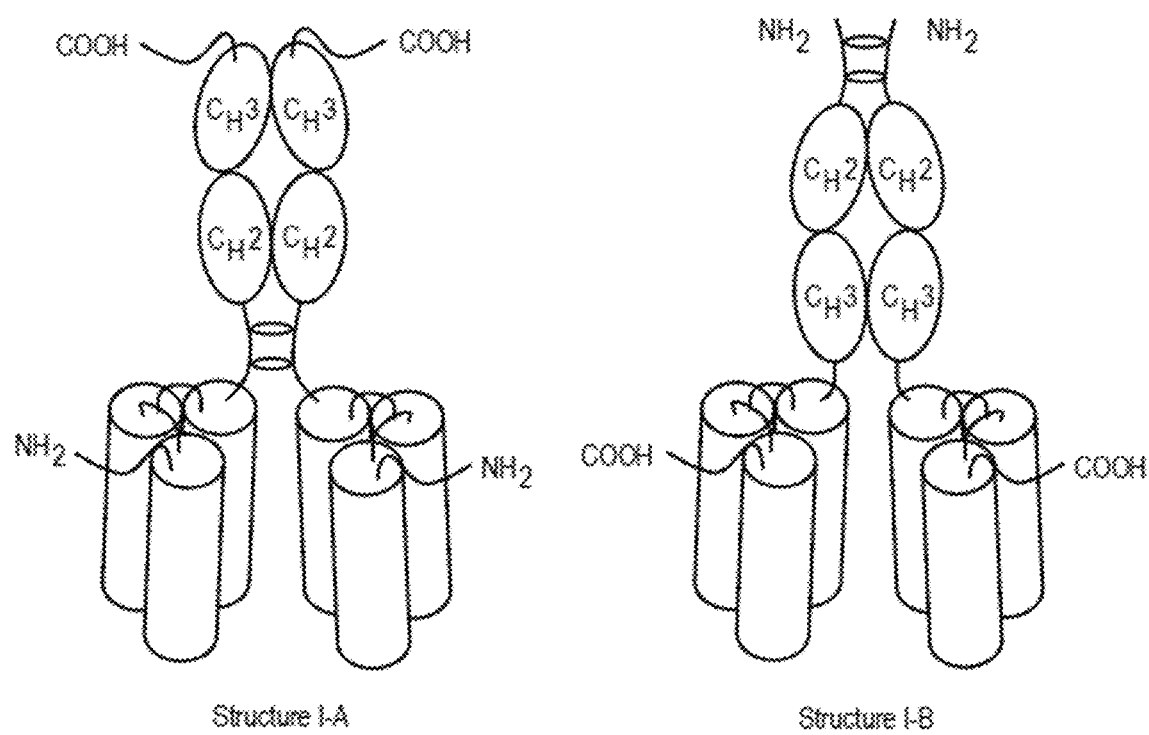
FIG. 56: Schematic of fusion proteins having Structure I-A (C-terminal Fc-antibody fragment fusion protein) and Structure I-B (N-terminal Fc-antibody fragment fusion protein).

In an embodiment, the 4-1BB agonist is a 4-1BB agonistic fusion protein as depicted in Structure I-A (C-terminal Fc-antibody fragment fusion protein) or Structure I-B (N-terminal Fc-antibody fragment fusion protein) of FIG. 56, or a fragment, derivative, conjugate, variant, or biosimilar thereof.

In structures I-A and I-B, the cylinders refer to individual polypeptide binding domains. Structures I-A and I-B comprise three linearly-linked TNFRSF binding domains derived from e.g., 4-1BBL or an antibody that binds 4-1BB, which fold to form a trivalent protein, which is then linked to a second triavelent protein through IgG1-Fc (including CH3 and CH2 domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a VH and a VL chain connected by a linker that may comprise hydrophilic residues and Gly and Ser sequences for flexibility, as well as Glu and Lys for solubility. Any scFv domain design may be used, such as those described in de Marco, *Microbial Cell Factories*, 2011, 10, 44; Ahmad, et al., *Clin. & Dev. Immunol.* 2012, 980250; Monnier, et al., *Antibodies*, 2013, 2, 193-208; or in references incorporated elsewhere herein. Fusion protein structures of this form are described in U.S. Pat. Nos. 9,359,420, 9,340,599, 8,921,519, and 8,450,460, the disclosures of which are incorporated by reference herein.

Amino acid sequences for the other polypeptide domains of structure I-A are given in Table 6. The Fc domain preferably comprises a complete constant domain (amino acids 17-230 of SEQ ID NO:31) the complete hinge domain (amino acids 1-16 of SEQ ID NO:31) or a portion of the hinge domain (e.g., amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides.

TABLE 6

Amino acid sequences for TNFRSF fusion proteins, including 4-1BB fusion proteins, with C-terminal Fc-antibody fragment fusion protein design (structure I-A).

| Identifier | Sequence (One-Letter Amino Acid Symbols) | |
|---|---|---|
| SEQ ID NO: 31 Fc domain | KSCDKTHTCP PCPAPELLGG PSVFLFPPKP KDTLMISRTP EVTCVVVDVS HEDPEVKFNW | 60 |
| | YVDGVEVHNA KTKPREEQYN STYRVVSVLT VLHQDWLNGK EYKCKVSNKA LPAPIEKTIS | 120 |
| | KAKGQPREPQ VYTLPPSREE MTKNQVSLTC LVKGFYPSDI AVEWESNGQP ENNYKTTPPV | 180 |
| | LDSDGSFFLY SKLTVDKSRW QQGNVFSCSV MHEALHNHYT QKSLSLSPGK | 230 |
| SEQ ID NO: 32 linker | GGPGSSKSCD KTHTCPPCPA PE | 22 |
| SEQ ID NO: 33 linker | GGSGSSKSCD KTHTCPPCPA PE | 22 |
| SEQ ID NO: 34 linker | GGPGSSSSSS SKSCDKTHTC PPCPAPE | 27 |
| SEQ ID NO: 35 linker | GGSGSSSSSS SKSCDKTHTC PPCPAPE | 27 |
| SEQ ID NO: 36 linker | GGPGSSSSSS SSSKSCDKTH TCPPCPAPE | 29 |
| SEQ ID NO: 37 linker | GGSGSSSSSS SSSKSCDKTH TCPPCPAPE | 29 |
| SEQ ID NO: 38 linker | GGPGSSGSGS SDKTHTCPPC PAPE | 24 |
| SEQ ID NO: 39 linker | GGPGSSGSGS DKTHTCPPCP APE | 23 |
| SEQ ID NO: 40 linker | GGPSSSGSDK THTCPPCPAP E | 21 |
| SEQ ID NO: 41 linker | GGSSSSSSSS GSDKTHTCPP CPAPE | 25 |

Amino acid sequences for the other polypeptide domains of structure I-B are given in Table 7. If an Fc antibody fragment is fused to the N-terminus of an TNRFSF fusion protein as in structure I-B, the sequence of the Fc module is preferably that shown in SEQ ID NO:42, and the linker sequences are preferably selected from those embodiments set forth in SED ID NO:43 to SEQ ID NO:45.

TABLE 7

Amino acid sequences for TNFRSF fusion proteins, including 4-1BB fusion proteins, with N-terminal Fc-antibody fragment fusion protein design (structure I-B).

| Identifier | Sequence (One-Letter Amino Acid Symbols) | |
|---|---|---|
| SEQ ID NO: 42 Fc domain | METDTLLLWV LLLWVPAGNG DKTHTCPPCP APELLGGPSV FLFPPKPKDT LMISRTPEVT | 60 |
| | CVVVDVSHED PEVKFNWYVD GVEVHNAKTK PREEQYNSTY RVVSVLTVLH QDWLNGKEYK | 120 |
| | CKVSNKALPA PIEKTISKAK GQPREPQVYT LPPSREEMTK NQVSLTCLVK GFYPSDIAVE | 180 |
| | WESNGQPENN YKTTPPVLDS DGSFFLYSKL TVDKSRWQQG NVFSCSVMHE ALHNHYTQKS | 240 |
| | LSLSPG | 246 |
| SEQ ID NO: 43 linker | SGSGSGSGSG S | 11 |
| SEQ ID NO: 44 linker | SSSSSSGSGS GS | 12 |
| SEQ ID NO: 45 linker | SSSSSSGSGS GSGSGS | 16 |

In an embodiment, a 4-1BB agonist fusion protein according to structures I-A or I-B comprises one or more 4-1BB binding domains selected from the group consisting of a variable heavy chain and variable light chain of utomilumab, a variable heavy chain and variable light chain of urelumab, a variable heavy chain and variable light chain of utomilumab, a variable heavy chain and variable light chain selected from the variable heavy chains and variable light chains described in Table 8, any combination of a variable heavy chain and variable light chain of the foregoing, and fragments, derivatives, conjugates, variants, and biosimilars thereof.

In an embodiment, a 4-1BB agonist fusion protein according to structures I-A or I-B comprises one or more 4-1BB binding domains comprising a 4-1BBL sequence. In an embodiment, a 4-1BB agonist fusion protein according to structures I-A or I-B comprises one or more 4-1BB binding domains comprising a sequence according to SEQ ID NO:46. In an embodiment, a 4-1BB agonist fusion protein according to structures I-A or I-B comprises one or more 4-1BB binding domains comprising a soluble 4-1BBL sequence. In an embodiment, a 4-1BB agonist fusion protein according to structures I-A or I-B comprises one or more 4-1BB binding domains comprising a sequence according to SEQ ID NO:47.

In an embodiment, a 4-1BB agonist fusion protein according to structures I-A or I-B comprises one or more 4-1BB binding domains that is a scFv domain comprising $V_H$ and $V_L$ regions that are each at least 95% identical to the sequences shown in SEQ ID NO:13 and SEQ ID NO:14, respectively, wherein the $V_H$ and $V_L$ domains are connected by a linker. In an embodiment, a 4-1BB agonist fusion protein according to structures I-A or I-B comprises one or more 4-1BB binding domains that is a scFv domain comprising $V_H$ and $V_L$ regions that are each at least 95% identical to the sequences shown in SEQ ID NO:23 and SEQ ID NO:24, respectively, wherein the $V_H$ and $V_L$ domains are connected by a linker. In an embodiment, a 4-1BB agonist fusion protein according to structures I-A or I-B comprises one or more 4-1BB binding domains that is a scFv domain comprising $V_H$ and $V_L$ regions that are each at least 95% identical to the VH and VL sequences given in Table 8, wherein the $V_H$ and $V_L$ domains are connected by a linker.

TABLE 8

Additional polypeptide domains useful as 4-1BB binding domains in fusion proteins or as scFv 4-1BB agonist antibodies.

| Identifier | Sequence (One-Letter Amino Acid Symbols) | |
|---|---|---|
| SEQ ID NO: 46<br>4-1BBL | MEYASDASLD PEAPWPPAPR ARACRVLPWA LVAGLLLLLL LAAACAVFLA CPWAVSGARA<br>SPGSAASPRL REGPELSPDD PAGLLDLRQG MFAQLVAQNV LLIDGPLSWY SDPGLAGVSL<br>TGGLSYKEDT KELVVAKAGV YYVFFQLELR RVVAGEGSGS VSLALHLQPL RSAAGAAALA<br>LTVDLPPASS EARNSAFGFQ GRLLHLSAGQ RLGVHLHTEA RARHAWQLTQ GATVLGLFRV<br>TPEIPAGLPS PRSE | 60<br>120<br>180<br>240<br>254 |
| SEQ ID NO: 47<br>4-1BBL soluble<br>domain | LRQGMFAQLV AQNVLLIDGP LSWYSDPGLA GVSLTGGLSY KEDTKELVVA KAGVYYVFFQ<br>LELRRVVAGE GSGSVSLALH LQPLRSAAGA AALALTVDLP PASSEARNSA FGFQGRLLHL<br>SAGQRLGVEL HTEARARHAW QLTQGATVLG LFRVTPEIPA GLPSPRSE | 60<br>120<br>168 |
| SEQ ID NO: 48<br>variable heavy<br>chain for 4B4-1-<br>1 version 1 | QVQLQQPGAE LVKPGASVKL SCKASGYTFS SYWMHWVKQR PGQVLEWIGE INPGNGHTNY<br>NEKFKSKATL TVDKSSSTAY MQLSSLTSED SAVYYCARSF TTARGFAYWG QGTLVTVS | 60<br>118 |
| SEQ ID NO: 49<br>variable light<br>chain for 4B4-1-<br>1 version 1 | DIVMTQSPAT QSVTPGDRVS LSCRASQTIS DYLHWYQQKS HESPRLLIKY ASQSISGIPS<br>RFSGSGSGSD FTLSINSVEP EDVGVYYCQD GHSFPPTFGG GTKLEIK | 60<br>107 |
| SEQ ID NO: 50<br>variable heavy<br>chain for 4B4-1-<br>1 version 2 | QVQLQQPGAE LVKPGASVKL SCKASGYTFS SYWMHWVKQR PGQVLEWIGE INPGNGHTNY<br>NEKFKSKATL TVDKSSSTAY MQLSSLTSED SAVYYCARSF TTARGFAYWG QGTLVTVSA | 60<br>119 |
| SEQ ID NO: 51<br>variable light<br>chain for 4B4-1-<br>1 version 2 | DIVMTQSPAT QSVTPGDRVS LSCRASQTIS DYLHWYQQKS HESPRLLIKY ASQSISGIPS<br>RFSGSGSGSD FTLSINSVEP EDVGVYYCQD GHSFPPTFGG GTKLEIKR | 60<br>108 |
| SEQ ID NO: 52<br>variable heavy<br>chain for H39E3-<br>2 | MDWTWRILFL VAAATGAHSE VQLVESGGGL VQPGGSLRLS CAASGFTFSD YWMSWVRQAP<br>GKGLEWVADI KNDGSYTNYA PSLTNRFTIS RDNAKNSLYL QMNSLRAEDT AVYYCARELT | 60<br>120 |
| SEQ ID NO: 53<br>variable light<br>chain for H39E3-<br>2 | MEAPAQLLFL LLLWLPDTTG DIVMTQSPDS LAVSLGERAT INCKSSQSLL SSGNQKNYL<br>WYQQKPGQPP KLLIYYASTR QSGVPDRFSG SGSGTDFTLT ISSLQAEDVA | 60<br>110 |

In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, and wherein the additional domain is a Fab or Fc fragment domain. In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, wherein the additional domain is a Fab or Fc fragment domain, wherein each of the soluble 4-1BB domains lacks a stalk region (which contributes to trimerisation and provides a certain distance to the cell membrane, but is not part of the 4-1BB binding domain) and the first and the second peptide linkers independently have a length of 3-8 amino acids.

In an embodiment, the 4-1BB agonist is a 4-1BB agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein each TNF superfamily cytokine domain is a 4-1BB binding domain.

In an embodiment, the 4-1BB agonist is a 4-1BB agonistic scFv antibody comprising any of the foregoing $V_H$ domains linked to any of the foregoing $V_L$ domains.

In an embodiment, the 4-1BB agonist is BPS Bioscience 4-1BB agonist antibody catalog no. 79097-2, commercially available from BPS Bioscience, San Diego, CA, USA. In an embodiment, the 4-1BB agonist is Creative Biolabs 4-1BB agonist antibody catalog no. MOM-18179, commercially available from Creative Biolabs, Shirley, NY, USA.

3. OX40 (CD134) Agonists

In an embodiment, the TNFRSF agonist is an OX40 (CD134) agonist. The OX40 agonist may be any OX40 binding molecule known in the art. The OX40 binding molecule may be a monoclonal antibody or fusion protein capable of binding to human or mammalian OX40. The OX40 agonists or OX40 binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The OX40 agonist or OX40 binding molecule may have both a heavy and a light chain. As used herein, the term binding molecule also includes antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to OX40. In an embodiment, the OX40 agonist is an antigen binding protein that is a fully human antibody. In an embodiment, the OX40 agonist is an antigen binding protein that is a humanized antibody. In some embodiments, OX40 agonists for use in the presently disclosed methods and compositions include anti-OX40 antibodies, human anti-OX40 antibodies, mouse anti-OX40 antibodies, mammalian anti-OX40 antibodies, monoclonal anti-OX40 antibodies, polyclonal anti-OX40 antibodies, chimeric anti-OX40 antibodies, anti-OX40 adnectins, anti-OX40 domain antibodies, single chain anti-OX40 fragments, heavy chain anti-OX40 fragments, light chain anti-OX40 fragments, anti-OX40 fusion proteins, and fragments, derivatives, conjugates, variants, or biosimilars thereof. In a preferred embodiment, the OX40 agonist is an agonistic, anti-OX40 humanized or fully human monoclonal antibody (i.e., an antibody derived from a single cell line).

In a preferred embodiment, the OX40 agonist or OX40 binding molecule may also be a fusion protein. OX40 fusion proteins comprising an Fc domain fused to OX40L are described, for example, in Sadun, et al., *J. Immunother.* 2009, 182, 1481-89. In a preferred embodiment, a multimeric OX40 agonist, such as a trimeric or hexameric OX40 agonist (with three or six ligand binding domains), may induce superior receptor (OX40L) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic OX40 antibodies and fusion proteins are known to induce strong immune responses. Curti, et al., *Cancer Res.* 2013, 73, 7189-98. In a preferred embodiment, the OX40 agonist is a monoclonal antibody or fusion protein that binds specifically to OX40 antigen in a manner sufficient to reduce toxicity. In some embodiments, the OX40 agonist is an agonistic OX40 monoclonal antibody or fusion protein that abrogates antibody-dependent cellular toxicity (ADCC), for example NK cell cytotoxicity. In some embodiments, the OX40 agonist is an agonistic OX40 monoclonal antibody or fusion protein that abrogates antibody-dependent cell phagocytosis (ADCP). In some embodiments, the OX40 agonist is an agonistic OX40 monoclonal antibody or fusion protein that abrogates complement-dependent cytotoxicity (CDC). In some embodiments, the OX40 agonist is an agonistic OX40 monoclonal antibody or fusion protein which abrogates Fc region functionality.

In some embodiments, the OX40 agonists are characterized by binding to human OX40 (SEQ ID NO:54) with high affinity and agonistic activity. In an embodiment, the OX40 agonist is a binding molecule that binds to human OX40 (SEQ ID NO:54). In an embodiment, the OX40 agonist is a binding molecule that binds to murine OX40 (SEQ ID NO:55). The amino acid sequences of OX40 antigen to which an OX40 agonist or binding molecule binds are summarized in Table 9.

TABLE 9

Amino acid sequences of OX40 antigens.

| Identifier | Sequence (One-Letter Amino Acid Symbols) | | | | | |
|---|---|---|---|---|---|---|
| SEQ ID NO: 54 | MCVGARRLGR | GPCAALLLLG | LGLSTVTGLH | CVGDTYPSND | RCCHECRPGN | GMVSRCSRSQ 60 |
| human OX40 | NTVCRPCGPG | FYNDVVSSKP | CKPCTWCNLR | SGSERKQLCT | ATQDTVCRCR | AGTQPLDSYK 120 |
| (Homo sapiens) | PGVDCAPCPP | GHFSPGDNQA | CKPWTNCTLA | GKHTLQPASN | SSDAICEDRD | PPATQPQETQ 180 |
|  | GPPARPITVQ | PTEAWPRTSQ | GPSTRPVEVP | GGRAVAAILG | LGLVLGLLGP | LAILLALYLL 240 |
|  | RRDQRLPPDA | HKPPGGGSFR | TPIQEEQADA | HSTLAKI |  | 277 |
|  |  |  |  |  |  |  |
| SEQ ID NO: 55 | MYVWVQQPTA | LLLLGLTLGV | TARRLNCVKH | TYPSGHKCCR | ECQPGHGMVS | RCDHTRDTLC 60 |
| murine OX40 | HPCETGFYNE | AVNYDTCKQC | TQCNHRSGSE | LKQNCTPTQD | TVCRCRPGTQ | PRQDSGYKLG 120 |
| (Mus musculus) | VDCVPCPPGH | FSPGNNQACK | PWTNCTLSGK | QTRHPASDSL | DAVCEDRSLL | ATLLWETQRP 180 |
|  | TFRPTTVQST | TVWPRTSELP | SPPTLVTPEG | PAFAVLLGLG | LGLLAPLTVL | LALYLLRKAW 240 |
|  | RLPNTPKPCW | GNSFRTPIQE | EHTDAHFTLA | KI |  | 272 |

In some embodiments, the compositions, processes and methods described include a OX40 agonist that binds human or murine OX40 with a $K_D$ of about 100 pM or lower, binds human or murine OX40 with a $K_D$ of about 90 pM or lower, binds human or murine OX40 with a $K_D$ of about 80 pM or lower, binds human or murine OX40 with a $K_D$ of about 70 pM or lower, binds human or murine OX40 with a $K_D$ of about 60 pM or lower, binds human or murine OX40 with a $K_D$ of about 50 pM or lower, binds human or murine OX40 with a $K_D$ of about 40 pM or lower, or binds human or murine OX40 with a $K_D$ of about 30 pM or lower.

In some embodiments, the compositions, processes and methods described include a OX40 agonist that binds to human or murine OX40 with a $k_{assoc}$ of about $7.5 \times 10^5$ 1/M·s or faster, binds to human or murine OX40 with a $k_{assoc}$ of about $7.5 \times 10^5$ 1/M·s or faster, binds to human or murine OX40 with a $k_{assoc}$ of about $8 \times 10^5$ 1/M·s or faster, binds to human or murine OX40 with a $k_{assoc}$ of about $8.5 \times 10^5$ 1/M·s or faster, binds to human or murine OX40 with a $k_{assoc}$ of about $9 \times 10^5$ 1/M·s or faster, binds to human or murine OX40 with a $k_{assoc}$ of about $9.5 \times 10^5$ 1/M·s or faster, or binds to human or murine OX40 with a $k_{assoc}$ of about $1 \times 10^6$ 1/M·s or faster.

In some embodiments, the compositions, processes and methods described include a OX40 agonist that binds to human or murine OX40 with a $k_{dissoc}$ of about $2 \times 10^{-5}$ 1/s or slower, binds to human or murine OX40 with a $k_{dissoc}$ of about $2.1 \times 10^{-5}$ 1/s or slower, binds to human or murine OX40 with a $k_{dissoc}$ of about $2.2 \times 10^{-5}$ 1/s or slower, binds to human or murine OX40 with a $k_{dissoc}$ of about $2.3 \times 10^{-5}$ 1/s or slower, binds to human or murine OX40 with a $k_{dissoc}$ of about $2.4 \times 10^{-5}$ 1/s or slower, binds to human or murine OX40 with a $k_{dissoc}$ of about $2.5 \times 10^{-5}$ 1/s or slower, binds to human or murine OX40 with a $k_{dissoc}$ of about $2.6 \times 10^{-5}$ 1/s or slower or binds to human or murine OX40 with a $k_{dissoc}$ of about $2.7 \times 10^{-5}$ 1/s or slower, binds to human or murine OX40 with a $k_{dissoc}$ of about $2.8 \times 10^{-5}$ 1/s or slower, binds to human or murine OX40 with a $k_{dissoc}$ of about $2.9 \times 10^{-5}$ 1/s or slower, or binds to human or murine OX40 with a $k_{dissoc}$ of about $3 \times 10^{-5}$ 1/s or slower.

In some embodiments, the compositions, processes and methods described include OX40 agonist that binds to human or murine OX40 with an $IC_{50}$ of about 10 nM or lower, binds to human or murine OX40 with an $IC_{50}$ of about 9 nM or lower, binds to human or murine OX40 with an $IC_{50}$ of about 8 nM or lower, binds to human or murine OX40 with an $IC_{50}$ of about 7 nM or lower, binds to human or murine OX40 with an $IC_{50}$ of about 6 nM or lower, binds to human or murine OX40 with an $IC_{50}$ of about 5 nM or lower, binds to human or murine OX40 with an $IC_{50}$ of about 4 nM or lower, binds to human or murine OX40 with an $IC_{50}$ of about 3 nM or lower, binds to human or murine OX40 with an $IC_{50}$ of about 2 nM or lower, or binds to human or murine OX40 with an $IC_{50}$ of about 1 nM or lower.

In some embodiments, the OX40 agonist is tavolixizumab, also known as MEDI0562 or MEDI-0562. Tavolixizumab is available from the MedImmune subsidiary of AstraZeneca, Inc. Tavolixizumab is immunoglobulin G1-kappa, anti-[*Homo sapiens* TNFRSF4 (tumor necrosis factor receptor (TNFR) superfamily member 4, OX40, CD134)], humanized and chimeric monoclonal antibody. The amino acid sequences of tavolixizumab are set forth in Table 10. Tavolixizumab comprises N-glycosylation sites at positions 301 and 301", with fucosylated complex bi-antennary CHO-type glycans; heavy chain intrachain disulfide bridges at positions 22-95 ($V_H$-$V_L$), 148-204 ($C_H$1-$C_L$), 265-325 ($C_H$2) and 371-429 ($C_H$3) (and at positions 22"-95", 148"-204", 265"-325", and 371"-429"); light chain intrachain disulfide bridges at positions 23'-88' ($V_H$-$V_L$) and 134'-194' ($C_H$1-$C_L$) (and at positions 23'"-88'" and 134'"-194'"); interchain heavy chain-heavy chain disulfide bridges at positions 230-230" and 233-233"; and interchain heavy chain-light chain disulfide bridges at 224-214' and 224"-214'". Current clinical trials of tavolixizumab in a variety of solid tumor indications include U.S. National Institutes of Health clinicaltrials.gov identifiers NCT02318394 and NCT02705482.

In an embodiment, a OX40 agonist comprises a heavy chain given by SEQ ID NO:56 and a light chain given by SEQ ID NO:57. In an embodiment, a OX40 agonist comprises heavy and light chains having the sequences shown in SEQ ID NO:56 and SEQ ID NO:57, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:56 and SEQ ID NO:57, respectively. In an embodiment, a OX40 agonist comprises heavy and light chains that are each at least 98% identical to the sequences shown in SEQ ID NO:56 and SEQ ID NO:57, respectively. In an embodiment, a OX40 agonist comprises heavy and light chains that are each at least 97% identical to the sequences shown in SEQ ID NO:56 and SEQ ID NO:57, respectively. In an embodiment, a OX40 agonist comprises heavy and light chains that are each at least 96% identical to the sequences shown in SEQ ID NO:56 and SEQ ID NO:57, respectively. In an embodiment, a OX40 agonist comprises heavy and light chains that are each at least 95% identical to the sequences shown in SEQ ID NO:56 and SEQ ID NO:57, respectively.

In an embodiment, the OX40 agonist comprises the heavy and light chain CDRs or variable regions (VRs) of tavolixizumab. In an embodiment, the OX40 agonist heavy chain variable region ($V_H$) comprises the sequence shown in SEQ ID NO:58, and the OX40 agonist light chain variable region ($V_L$) comprises the sequence shown in SEQ ID NO:59, and conservative amino acid substitutions thereof. In an embodiment, a OX40 agonist comprises $V_H$ and $V_L$ regions that are each at least 99% identical to the sequences shown in SEQ ID NO:58 and SEQ ID NO:59, respectively. In an embodiment, a OX40 agonist comprises $V_H$ and $V_L$ regions that are each at least 98% identical to the sequences shown in SEQ ID NO:58 and SEQ ID NO:59, respectively. In an embodiment, a OX40 agonist comprises $V_H$ and $V_L$ regions that are each at least 97% identical to the sequences shown in SEQ ID NO:58 and SEQ ID NO:59, respectively. In an embodiment, a OX40 agonist comprises $V_H$ and $V_L$ regions that are each at least 96% identical to the sequences shown in SEQ ID NO:58 and SEQ ID NO:59, respectively. In an embodiment, a OX40 agonist comprises $V_H$ and $V_L$ regions that are each at least 95% identical to the sequences shown in SEQ ID NO:58 and SEQ ID NO:59, respectively. In an embodiment, an OX40 agonist comprises an scFv antibody comprising $V_H$ and $V_L$ regions that are each at least 99% identical to the sequences shown in SEQ ID NO:58 and SEQ ID NO:59.

In an embodiment, a OX40 agonist comprises heavy chain CDR1, CDR2 and CDR3 domains having the sequences set forth in SEQ ID NO:60, SEQ ID NO:61, and SEQ ID NO:62, respectively, and conservative amino acid substitutions thereof, and light chain CDR1, CDR2 and CDR3 domains having the sequences set forth in SEQ ID NO:63, SEQ ID NO:64, and SEQ ID NO:65, respectively, and conservative amino acid substitutions thereof.

In an embodiment, the OX40 agonist is a OX40 agonist biosimilar monoclonal antibody approved by drug regulatory authorities with reference to tavolixizumab. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is tavolixizumab. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is tavolixizumab. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab.

TABLE 10

Amino acid sequences for OX40 agonist antibodies related to tavolixizumab.

| Identifier | Sequence (One-Letter Amino Acid Symbols) | |
|---|---|---|
| SEQ ID NO: 56 heavy chain for tavolixizumab | QVQLQESGPG LVKPSQTLSL TCAVYGGSFS SGYWNWIRKH PGKGLEYIGY ISYNGITYHN<br>PSLKSRITIN RDTSKNQYSL QLNSVTPEDT AVYYCARYKY DYDGGHAMDY WGQGTLVTVS<br>SASTKGPSVF PLAPSSKSTS GGTAALGCLV KDYFPEPVTV SWNSGALTSG VHTFPAVLQS<br>SGLYSLSSVV TVPSSSLGTQ TYICNVNHKP SNTKVDKRVE PKSCDKTHTC PPCPAPELLG<br>GPSVFLFPPK PKDTLMISRT PEVTCVVVDV SHEDPEVKFN WYVDGVEVHN AKTKPREEQY<br>NSTYRVVSVL TVLHQDWLNG KEYKCKVSNK ALPAPIEKTI SKAKGQPREP QVYTLPPSRE<br>EMTKNQVSLT CLVNGFYPSD IAVEWESNGQ PENNYKTTPP VLDSDGSFFL YSKLTVDKSR<br>WQQGNVFSCS VMHEALHNHY TQKSLSLSPG K | 60<br>120<br>180<br>240<br>300<br>360<br>420<br>451 |
| SEQ ID NO: 57 light chain for tavolixizumab | DIQMTQSPSS LSASVGDRVT ITCRASQDIS NYLNWYQQKP GKAPKLLIYY TSKLHSGVPS<br>RFSGSGSGTD YTLTISSLQP EDFATYYCQQ GSALPWTFGQ GTKVEIKRTV AAPSVFIFPP<br>SDEQLKSGTA SVVCLLNNFY PREAKVQWKV DNALQSGNSQ ESVTEQDSKD STYSLSSTLT<br>LSKADYEKHK VYACEVTHQG LSSPVTKSFN RGEC | 60<br>120<br>180<br>214 |
| SEQ ID NO: 58 heavy chain variable region for tavolixizumab | QVQLQESGPG LVKPSQTLSL TCAVYGGSFS SGYWNWIRKH PGKGLEYIGY ISYNGITYHN<br>PSLKSRITIN RDTSKNQYSL QLNSVTPEDT AVYYCARYKY DYDGGHAMDY WGQGTLVT | 60<br>118 |
| SEQ ID NO: 59 light chain variable region for tavolixizumab | DIQMTQSPSS LSASVGDRVT ITCRASQDIS NYLNWYQQKP GKAPKLLIYY TSKLHSGVPS<br>RFSGSGSGTD YTLTISSLQP EDFATYYCQQ GSALPWTFGQ GTKVEIKR | 60<br>108 |
| SEQ ID NO: 60 heavy chain CDR1 for tavolixizumab | GSFSSGYWN | 9 |

TABLE 10-continued

Amino acid sequences for OX40 agonist antibodies related to tavolixizumab.

| Identifier | Sequence (One-Letter Amino Acid Symbols) | |
|---|---|---|
| SEQ ID NO: 61 heavy chain CDR2 for tavolixizumab | YIGYISYNGI TYH | 13 |
| SEQ ID NO: 62 heavy chain CDR3 for tavolixizumab | RYKYDYDGGH AMDY | 14 |
| SEQ ID NO: 63 light chain CDR1 for tavolixizumab | QDISNYLN | 8 |
| SEQ ID NO: 64 light chain CDR2 for tavolixizumab | LLIYYTSKLH S | 11 |
| SEQ ID NO: 65 light chain CDR3 for tavolixizumab | QQGSALPW | 8 |

In some embodiments, the OX40 agonist is 11D4, which is a fully human antibody available from Pfizer, Inc. The preparation and properties of 11D4 are described in U.S. Pat. Nos. 7,960,515; 8,236,930; and 9,028,824, the disclosures of which are incorporated by reference herein. The amino acid sequences of 11D4 are set forth in Table 11.

In an embodiment, a OX40 agonist comprises a heavy chain given by SEQ ID NO:66 and a light chain given by SEQ ID NO:67. In an embodiment, a OX40 agonist comprises heavy and light chains having the sequences shown in SEQ ID NO:66 and SEQ ID NO:67, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:66 and SEQ ID NO:67, respectively. In an embodiment, a OX40 agonist comprises heavy and light chains that are each at least 98% identical to the sequences shown in SEQ ID NO:66 and SEQ ID NO:67, respectively. In an embodiment, a OX40 agonist comprises heavy and light chains that are each at least 97% identical to the sequences shown in SEQ ID NO:66 and SEQ ID NO:67, respectively. In an embodiment, a OX40 agonist comprises heavy and light chains that are each at least 96% identical to the sequences shown in SEQ ID NO:66 and SEQ ID NO:67, respectively. In an embodiment, a OX40 agonist comprises heavy and light chains that are each at least 95% identical to the sequences shown in SEQ ID NO:66 and SEQ ID NO:67, respectively.

In an embodiment, the OX40 agonist comprises the heavy and light chain CDRs or variable regions (VRs) of 11D4. In an embodiment, the OX40 agonist heavy chain variable region ($V_H$) comprises the sequence shown in SEQ ID NO:68, and the OX40 agonist light chain variable region ($V_L$) comprises the sequence shown in SEQ ID NO:69, and conservative amino acid substitutions thereof. In an embodiment, a OX40 agonist comprises $V_H$ and $V_L$ regions that are each at least 99% identical to the sequences shown in SEQ ID NO:68 and SEQ ID NO:69, respectively. In an embodiment, a OX40 agonist comprises $V_H$ and $V_L$ regions that are each at least 98% identical to the sequences shown in SEQ ID NO:68 and SEQ ID NO:69, respectively. In an embodiment, a OX40 agonist comprises $V_H$ and $V_L$ regions that are each at least 97% identical to the sequences shown in SEQ ID NO:68 and SEQ ID NO:69, respectively. In an embodiment, a OX40 agonist comprises $V_H$ and $V_L$ regions that are each at least 96% identical to the sequences shown in SEQ ID NO:68 and SEQ ID NO:69, respectively. In an embodiment, a OX40 agonist comprises $V_H$ and $V_L$ regions that are each at least 95% identical to the sequences shown in SEQ ID NO:68 and SEQ ID NO:69, respectively.

In an embodiment, a OX40 agonist comprises heavy chain CDR1, CDR2 and CDR3 domains having the sequences set forth in SEQ ID NO:70, SEQ ID NO:71, and SEQ ID NO:72, respectively, and conservative amino acid substitutions thereof, and light chain CDR1, CDR2 and CDR3 domains having the sequences set forth in SEQ ID NO:73, SEQ ID NO:74, and SEQ ID NO:75, respectively, and conservative amino acid substitutions thereof.

In an embodiment, the OX40 agonist is a OX40 agonist biosimilar monoclonal antibody approved by drug regulatory authorities with reference to 11D4. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 11D4. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 11D4. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4.

TABLE 11

Amino acid sequences for OX40 agonist antibodies related to 11D4.

| Identifier | Sequence (One-Letter Amino Acid Symbols) | |
|---|---|---|
| SEQ ID NO: 66 heavy chain for 11D4 | EVQLVESGGG LVQPGGSLRL SCAASGFTFS SYSMNWVRQA PGKGLEWVSY ISSSSSTIDY<br>ADSVKGRFTI SRDNAKNSLY LQMNSLRDED TAVYYCARES GWYLFDYWGQ GTLVTVSSAS<br>TKGPSVFPLA PCSRSTSEST AALGCLVKDY FPEPVTVSWN SGALTSGVHT FPAVLQSSGL<br>YSLSSVVTVP SSNFGTQTYT CNVDHKPSNT KVDKTVERKC CVECPPCPAP PVAGPSVFLF<br>PPKPKDTLMI SRTPEVTCVV VDVSHEDPEV QFNWYVDGVE VHNAKTKPRE EQFNSTFRVV<br>SVLTVVHQDW LNGKEYKCKV SNKGLPAPIE KTISKTKGQP REPQVYTLPP SREEMTKNQV<br>SLTCLVKGFY PSDIAVEWES NGQPENNYKT TPPMLDSDGS FFLYSKLTVD KSRWQQGNVF<br>SCSVMHEALH NHYTQKSLSL SPGK | 60<br>120<br>180<br>240<br>300<br>360<br>420<br>444 |
| SEQ ID NO: 67 light chain for 11D4 | DIQMTQSPSS LSASVGDRVT ITCRASQGIS SWLAWYQQKP EKAPKSLIYA ASSLQSGVPS<br>RFSGSGSGTD FTLTISSLQP EDFATYYCQQ YNSYPPTFGG GTKVEIKRTV AAPSVFIFPP<br>SDEQLKSGTA SVVCLLNNFY PREAKVQWKV DNALQSGNSQ ESVTEQDSKD STYSLSSTLT<br>LSKADYEKHK VYACEVTHQG LSSPVTKSFN RGEC | 60<br>120<br>180<br>214 |
| SEQ ID NO: 68 heavy chain variable region for 11D4 | EVQLVESGGG LVQPGGSLRL SCAASGFTFS SYSMNWVRQA PGKGLEWVSY ISSSSSTIDY<br>ADSVKGRFTI SRDNAKNSLY LQMNSLRDED TAVYYCARES GWYLFDYWGQ GTLVTVSS | 60<br>118 |
| SEQ ID NO: 69 light chain variable region for 11D4 | DIQMTQSPSS LSASVGDRVT ITCRASQGIS SWLAWYQQKP EKAPKSLIYA ASSLQSGVPS<br>RFSGSGSGTD FTLTISSLQP EDFATYYCQQ YNSYPPTFGG GTKVEIK | 60<br>107 |
| SEQ ID NO: 70 heavy chain CDR1 for 11D4 | SYSMN | 5 |
| SEQ ID NO: 71 heavy chain CDR2 for 11D4 | YISSSSSTID YADSVKG | 17 |
| SEQ ID NO: 72 heavy chain CDR3 for 11D4 | ESGWYLFDY | 9 |
| SEQ ID NO: 73 light chain CDR1 for 11D4 | RASQGISSWL A | 11 |
| SEQ ID NO: 74 light chain CDR2 for 11D4 | AASSLQS | 7 |
| SEQ ID NO: 75 light chain CDR3 for 11D4 | QQYNSYPPT | 9 |

In some embodiments, the OX40 agonist is 18D8, which is a fully human antibody available from Pfizer, Inc. The preparation and properties of 18D8 are described in U.S. Pat. Nos. 7,960,515; 8,236,930; and 9,028,824, the disclosures of which are incorporated by reference herein. The amino acid sequences of 18D8 are set forth in Table 12.

In an embodiment, a OX40 agonist comprises a heavy chain given by SEQ ID NO:76 and a light chain given by SEQ ID NO:77. In an embodiment, a OX40 agonist comprises heavy and light chains having the sequences shown in SEQ ID NO:76 and SEQ ID NO:77, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:76 and SEQ ID NO:77, respectively. In an embodiment, a OX40 agonist comprises heavy and light chains that are each at least 98% identical to the sequences shown in SEQ ID NO:76 and SEQ ID NO:77, respectively. In an embodiment, a OX40 agonist comprises heavy and light chains that are each at least 97% identical to the sequences shown in SEQ ID NO:76 and SEQ ID NO:77, respectively. In an embodiment, a OX40 agonist comprises heavy and light chains that are each at least 96% identical to the sequences shown in SEQ ID NO:76 and SEQ ID NO:77, respectively. In an embodiment, a OX40 agonist comprises heavy and light chains that are each at least 95% identical to the sequences shown in SEQ ID NO:76 and SEQ ID NO:77, respectively.

In an embodiment, the OX40 agonist comprises the heavy and light chain CDRs or variable regions (VRs) of 18D8. In an embodiment, the OX40 agonist heavy chain variable region ($V_H$) comprises the sequence shown in SEQ ID NO:78, and the OX40 agonist light chain variable region ($V_L$) comprises the sequence shown in SEQ ID NO:79, and conservative amino acid substitutions thereof. In an embodiment, a OX40 agonist comprises $V_H$ and $V_L$ regions that are each at least 99% identical to the sequences shown in SEQ ID NO:78 and SEQ ID NO:79, respectively. In an embodiment, a OX40 agonist comprises $V_H$ and $V_L$ regions that are each at least 98% identical to the sequences shown in SEQ ID NO:78 and SEQ ID NO:79, respectively. In an embodiment, a OX40 agonist comprises $V_H$ and $V_L$ regions that are each at least 97% identical to the sequences shown in SEQ ID NO:78 and SEQ ID NO:79, respectively. In an embodiment, a OX40 agonist comprises $V_H$ and $V_L$ regions that are each at least 96% identical to the sequences shown in SEQ ID NO:78 and SEQ ID NO:79, respectively. In an embodiment, a OX40 agonist comprises $V_H$ and $V_L$ regions that are each at least 95% identical to the sequences shown in SEQ ID NO:78 and SEQ ID NO:79, respectively.

In an embodiment, a OX40 agonist comprises heavy chain CDR1, CDR2 and CDR3 domains having the sequences set forth in SEQ ID NO:80, SEQ ID NO:81, and SEQ ID NO:82, respectively, and conservative amino acid substitutions thereof, and light chain CDR1, CDR2 and CDR3 domains having the sequences set forth in SEQ ID NO:83, SEQ ID NO:84, and SEQ ID NO:85, respectively, and conservative amino acid substitutions thereof.

In an embodiment, the OX40 agonist is a OX40 agonist biosimilar monoclonal antibody approved by drug regulatory authorities with reference to 18D8. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 18D8. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 18D8. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8.

TABLE 12

Amino acid sequences for OX40 agonist antibodies related to 18D8.

| Identifier | Sequence (One-Letter Amino Acid Symbols) | | | | | |
|---|---|---|---|---|---|---|
| SEQ ID NO: 76 heavy chain for 18D8 | EVQLVESGGG | LVQPGRSLRL | SCAASGFTFD | DYAMHWVRQA | PGKGLEWVSG | ISWNSGSIGY | 60 |
| | ADSVKGRFTI | SRDNAKNSLY | LQMNSLRAED | TALYYCAKDQ | STADYYFYYG | MDVWGQGTTV | 120 |
| | TVSSASTKGP | SVFPLAPCSR | STSESTAALG | CLVKDYFPEP | VTVSWNSGAL | TSGVHTFPAV | 180 |
| | LQSSGLYSLS | SVVTVPSSNF | GTQTYTCNVD | HKPSNTKVDK | TVERKCCVEC | PPCPAPPVAG | 240 |
| | PSVFLFPPKP | KDTLMISRTP | EVTCVVVDVS | HEDPEVQFNW | YVDGVEVHNA | KTKPREEQFN | 300 |
| | STERVVSVLT | VVHQDWLNGK | EYKCKVSNKG | LPAPIEKTIS | KTKGQPREPQ | VYTLPPSREE | 360 |
| | MTKNQVSLTC | LVKGFYPSDI | AVEWESNGQP | ENNYKTTPPM | LDSDGSFFLY | SKLTVDKSRW | 420 |
| | QQGNVFSCSV | MHEALHNHYT | QKSLSLSPGK | | | | 450 |
| SEQ ID NO: 77 light chain for 18D8 | EIVVTQSPAT | LSLSPGERAT | LSCRASQSVS | SYLAWYQQKP | GQAPRLLIYD | ASNRATGIPA | 60 |
| | RFSGSGSGTD | FTLTISSLEP | EDFAVYYCQQ | RSNWPFTGQG | TKVEIKRTVA | APSVFIFPPS | 120 |
| | DEQLKSGTAS | VVCLLNNFYP | REAKVQWKVD | NALQSGNSQE | SVTEQDSKDS | TYSLSSTLTL | 180 |
| | SKADYEKHKV | YACEVTHQGL | SSPVTKSFNR | GEC | | | 213 |

TABLE 12-continued

Amino acid sequences for OX40 agonist antibodies related to 18D8.

| Identifier | Sequence (One-Letter Amino Acid Symbols) | |
|---|---|---|
| SEQ ID NO: 78<br>heavy chain<br>variable region<br>for 18D8 | EVQLVESGGG LVQPGRSLRL SCAASGFTFD DYAMHWVRQA PKGGLEWVSG ISWNSGSIGY<br>ADSVKGRFTI SRDNAKNSLY LQMNSLRAED TALYYCAKDQ STADYYFYYG MDVWGQGTTV<br>TVSS | 60<br>120<br>124 |
| SEQ ID NO: 79<br>light chain<br>variable region<br>for 18D8 | EIVVTQSPAT LSLSPGERAT LSCRASQSVS SYLAWYQQKP GQAPRLLIYD ASNRATGIPA<br>RFSGSGSGTD FTLTISSLEP EDFAVYYCQQ RSNWPTFGQG TKVEIK | 60<br>106 |
| SEQ ID NO: 80<br>heavy chain CDR1<br>for 18D8 | DYAMH | 5 |
| SEQ ID NO: 81<br>heavy chain CDR2<br>for 18D8 | GISWNSGSIG YADSVKG | 17 |
| SEQ ID NO: 82<br>heavy chain CDR3<br>for 18D8 | DQSTADYYFY YGMDV | 15 |
| SEQ ID NO: 83<br>light chain CDR1<br>for 18D8 | RASQSVSSYL A | 11 |
| SEQ ID NO: 84<br>light chain CDR2<br>for 18D8 | DASNRAT | 7 |
| SEQ ID NO: 85<br>light chain CDR3<br>for 18D8 | QQRSNWPT | 8 |

In some embodiments, the OX40 agonist is Hu119-122, which is a humanized antibody available from GlaxoSmithKline plc. The preparation and properties of Hu119-122 are described in U.S. Pat. Nos. 9,006,399 and 9,163,085, and in International Patent Publication No. WO 2012/027328, the disclosures of which are incorporated by reference herein. The amino acid sequences of Hu119-122 are set forth in Table 13.

In an embodiment, the OX40 agonist comprises the heavy and light chain CDRs or variable regions (VRs) of Hu119-122. In an embodiment, the OX40 agonist heavy chain variable region ($V_H$) comprises the sequence shown in SEQ ID NO:86, and the OX40 agonist light chain variable region ($V_L$) comprises the sequence shown in SEQ ID NO:87, and conservative amino acid substitutions thereof. In an embodiment, a OX40 agonist comprises $V_H$ and $V_L$ regions that are each at least 99% identical to the sequences shown in SEQ ID NO:86 and SEQ ID NO:87, respectively. In an embodiment, a OX40 agonist comprises $V_H$ and $V_L$ regions that are each at least 98% identical to the sequences shown in SEQ ID NO:86 and SEQ ID NO:87, respectively. In an embodiment, a OX40 agonist comprises $V_H$ and $V_L$ regions that are each at least 97% identical to the sequences shown in SEQ ID NO:86 and SEQ ID NO:87, respectively. In an embodiment, a OX40 agonist comprises $V_H$ and $V_L$ regions that are each at least 96% identical to the sequences shown in SEQ ID NO:86 and SEQ ID NO:87, respectively. In an embodiment, a OX40 agonist comprises $V_H$ and $V_L$ regions that are each at least 95% identical to the sequences shown in SEQ ID NO:86 and SEQ ID NO:87, respectively.

In an embodiment, a OX40 agonist comprises heavy chain CDR1, CDR2 and CDR3 domains having the sequences set forth in SEQ ID NO:88, SEQ ID NO:89, and SEQ ID NO:90, respectively, and conservative amino acid substitutions thereof, and light chain CDR1, CDR2 and CDR3 domains having the sequences set forth in SEQ ID NO:91, SEQ ID NO:92, and SEQ ID NO:93, respectively, and conservative amino acid substitutions thereof.

In an embodiment, the OX40 agonist is a OX40 agonist biosimilar monoclonal antibody approved by drug regulatory authorities with reference to Hu119-122. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu119-122. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu119-122. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122.

TABLE 13

Amino acid sequences for OX40 agonist antibodies related to Hu119-122.

| Identifier | Sequence (One-Letter Amino Acid Symbols) | |
|---|---|---|
| SEQ ID NO: 86 heavy chain variable region for Hu119-122 | EVQLVESGGG LVQPGGSLRL SCAASEYEFP SHDMSWVRQA PGKGLELVAA INSDGGSTYY PDTMERRFTI SRDNAKNSLY LQMNSLRAED TAVYYCARHY DDYYAWFAYW GQGTMVTVSS | 60 120 |
| SEQ ID NO: 87 light chain variable region for Hu119-122 | EIVLTQSPAT LSLSPGERAT LSCRASKSVS TSGYSYMHWY QQKPGQAPRL LIYLASNLES GVPARFSGSG SGTDFTLTIS SLEPEDFAVY YCQHSRELPL TFGGGTKVEI K | 60 111 |
| SEQ ID NO: 88 heavy chain CDR1 for Hu119-122 | SHDMS | 5 |
| SEQ ID NO: 89 heavy chain CDR2 for Hu119-122 | AINSDGGSTY YPDTMER | 17 |
| SEQ ID NO: 90 heavy chain CDR3 for Hu119-122 | HYDDYYAWFA Y | 11 |
| SEQ ID NO: 91 light chain CDR1 for Hu119-122 | RASKSVSTSG YSYMH | 15 |
| SEQ ID NO: 92 light chain CDR2 for Hu119-122 | LASNLES | 7 |
| SEQ ID NO: 93 light chain CDR3 for Hu119-122 | QHSRELPLT | 9 |

In some embodiments, the OX40 agonist is Hu106-222, which is a humanized antibody available from GlaxoSmithKline plc. The preparation and properties of Hu106-222 are described in U.S. Pat. Nos. 9,006,399 and 9,163,085, and in International Patent Publication No. WO 2012/027328, the disclosures of which are incorporated by reference herein. The amino acid sequences of Hu106-222 are set forth in Table 14.

In an embodiment, the OX40 agonist comprises the heavy and light chain CDRs or variable regions (VRs) of Hu106-222. In an embodiment, the OX40 agonist heavy chain variable region ($V_H$) comprises the sequence shown in SEQ ID NO:94, and the OX40 agonist light chain variable region ($V_L$) comprises the sequence shown in SEQ ID NO:95, and conservative amino acid substitutions thereof. In an embodiment, a OX40 agonist comprises $V_H$ and $V_L$ regions that are each at least 99% identical to the sequences shown in SEQ ID NO:94 and SEQ ID NO:95, respectively. In an embodiment, a OX40 agonist comprises $V_H$ and $V_L$ regions that are each at least 98% identical to the sequences shown in SEQ ID NO:94 and SEQ ID NO:95, respectively. In an embodiment, a OX40 agonist comprises $V_H$ and $V_L$ regions that are each at least 97% identical to the sequences shown in SEQ ID NO:94 and SEQ ID NO:95, respectively. In an embodiment, a OX40 agonist comprises $V_H$ and $V_L$ regions that are each at least 96% identical to the sequences shown in SEQ ID NO:94 and SEQ ID NO:95, respectively. In an embodiment, a OX40 agonist comprises $V_H$ and $V_L$ regions that are each at least 95% identical to the sequences shown in SEQ ID NO:94 and SEQ ID NO:95, respectively.

In an embodiment, a OX40 agonist comprises heavy chain CDR1, CDR2 and CDR3 domains having the sequences set forth in SEQ ID NO:96, SEQ ID NO:97, and SEQ ID NO:98, respectively, and conservative amino acid substitutions thereof, and light chain CDR1, CDR2 and CDR3 domains having the sequences set forth in SEQ ID NO:99, SEQ ID NO:100, and SEQ ID NO:101, respectively, and conservative amino acid substitutions thereof.

In an embodiment, the OX40 agonist is a OX40 agonist biosimilar monoclonal antibody approved by drug regulatory authorities with reference to Hu106-222. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu106-222. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu106-222. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222.

TABLE 14

Amino acid sequences for OX40 agonist antibodies related to Hu106-222.

| Identifier | Sequence (One-Letter Amino Acid Symbols) | |
|---|---|---|
| SEQ ID NO: 94 heavy chain variable region for Hu106-222 | QVQLVQSGSE LKKPGASVKV SCKASGYTFT DYSMHWVRQA PGQGLKWMGW INTETGEPTY ADDFKGREVF SLDTSVSTAY LQISSLKAED TAVYYCANPY YDYVSYYAMD YWGQGTTVTV SS | 60 120 122 |
| SEQ ID NO: 95 light chain variable region for Hu106-222 | DIQMTQSPSS LSASVGDRVT ITCKASQDVS TAVAWYQQKP GKAPKLLIYS ASYLYTGVPS RFSGSGSGTD FTFTISSLQP EDIATYYCQQ HYSTPRTFGQ GTKLEIK | 60 107 |
| SEQ ID NO: 96 heavy chain CDR1 for Hu106-222 | DYSMH | 5 |
| SEQ ID NO: 97 heavy chain CDR2 for Hu106-222 | WINTETGEPT YADDFKG | 17 |
| SEQ ID NO: 98 heavy chain CDR3 for Hu106-222 | PYYDYVSYYA MDY | 13 |
| SEQ ID NO: 99 light chain CDR1 for Hu106-222 | KASQDVSTAV A | 11 |
| SEQ ID NO: 100 light chain CDR2 for Hu106-222 | SASYLYT | 7 |
| SEQ ID NO: 101 light chain CDR3 for Hu106-222 | QQHYSTPRT | 9 |

In some embodiments, the OX40 agonist antibody is MEDI6469 (also referred to as 9B12). MEDI6469 is a murine monoclonal antibody. Weinberg, et al., *J. Immunother.* 2006, 29, 575-585. In some embodiments the OX40 agonist is an antibody produced by the 9B12 hybridoma, deposited with Biovest Inc. (Malvern, MA, USA), as described in Weinberg, et al., *J. Immunother.* 2006, 29, 575-585, the disclosure of which is hereby incorporated by reference in its entirety. In some embodiments, the antibody comprises the CDR sequences of MEDI6469. In some embodiments, the antibody comprises a heavy chain variable region sequence and/or a light chain variable region sequence of MEDI6469.

In an embodiment, the OX40 agonist is L106 BD (Pharmingen Product #340420). In some embodiments, the OX40 agonist comprises the CDRs of antibody L106 (BD Pharmingen Product #340420). In some embodiments, the OX40 agonist comprises a heavy chain variable region sequence and/or a light chain variable region sequence of antibody L106 (BD Pharmingen Product #340420). In an embodiment, the OX40 agonist is ACT35 (Santa Cruz Biotechnology, Catalog #20073). In some embodiments, the OX40 agonist comprises the CDRs of antibody ACT35 (Santa Cruz Biotechnology, Catalog #20073). In some embodiments, the OX40 agonist comprises a heavy chain variable region sequence and/or a light chain variable region sequence of antibody ACT35 (Santa Cruz Biotechnology, Catalog #20073). In an embodiment, the OX40 agonist is the murine monoclonal antibody anti-mCD134/mOX40 (clone OX86), commercially available from InVivoMAb, BioXcell Inc, West Lebanon, NH.

In an embodiment, the OX40 agonist is selected from the OX40 agonists described in International Patent Application Publication Nos. WO 95/12673, WO 95/21925, WO 2006/121810, WO 2012/027328, WO 2013/028231, WO 2013/038191, and WO 2014/148895; European Patent Application EP 0672141; U.S. Patent Application Publication Nos. US 2010/136030, US 2014/377284, US 2015/190506, and US 2015/132288 (including clones 20E5 and 12H3); and U.S. Pat. Nos. 7,504,101, 7,550,140, 7,622,444, 7,696,175, 7,960,515, 7,961,515, 8,133,983, 9,006,399, and 9,163,085, the disclosure of each of which is incorporated herein by reference in its entirety.

In an embodiment, the OX40 agonist is an OX40 agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof. The properties of structures I-A and I-B are described above and in U.S. Pat. Nos. 9,359,420, 9,340,599, 8,921,519, and 8,450,460, the disclosures of which are incorporated by reference herein. Amino acid sequences for the polypeptide domains of structure I-A are given in Table 6. The Fc domain preferably comprises a complete constant domain (amino acids 17-230 of SEQ ID NO:31) the complete hinge domain (amino acids 1-16 of SEQ ID NO:31) or a portion of the hinge domain (e.g., amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides. Likewise, amino acid sequences for the polypeptide domains of structure I-B are given in Table 7. If an Fc antibody fragment is fused to the N-terminus of an TNRFSF fusion protein as in structure I-B, the sequence of the Fc module is preferably that shown in SEQ ID NO:42, and the linker sequences are preferably selected from those embodiments set forth in SED ID NO:43 to SEQ ID NO:45.

In an embodiment, an OX40 agonist fusion protein according to structures I-A or I-B comprises one or more OX40 binding domains selected from the group consisting of a variable heavy chain and variable light chain of tavolixizumab, a variable heavy chain and variable light chain of 11D4, a variable heavy chain and variable light chain of 18D8, a variable heavy chain and variable light chain of Hu119-122, a variable heavy chain and variable light chain of Hu106-222, a variable heavy chain and variable light chain selected from the variable heavy chains and variable light chains described in Table 15, any combination of a variable heavy chain and variable light chain of the foregoing, and fragments, derivatives, conjugates, variants, and biosimilars thereof.

In an embodiment, an OX40 agonist fusion protein according to structures I-A or I-B comprises one or more OX40 binding domains comprising an OX40L sequence. In an embodiment, an OX40 agonist fusion protein according to structures I-A or I-B comprises one or more OX40 binding domains comprising a sequence according to SEQ ID NO:102. In an embodiment, an OX40 agonist fusion protein according to structures I-A or I-B comprises one or more OX40 binding domains comprising a soluble OX40L sequence. In an embodiment, a OX40 agonist fusion protein according to structures I-A or I-B comprises one or more OX40 binding domains comprising a sequence according to SEQ ID NO:103. In an embodiment, a OX40 agonist fusion protein according to structures I-A or I-B comprises one or more OX40 binding domains comprising a sequence according to SEQ ID NO:104.

In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:58 and SEQ ID NO:59, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:68 and SEQ ID NO:69, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:78 and SEQ ID NO:79, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:86 and SEQ ID NO:87, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:94 and SEQ ID NO:95, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the $V_H$ and $V_L$ sequences given in Table 15, wherein the $V_H$ and $V_L$ domains are connected by a linker.

TABLE 15

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 102 OX40L | MERVQPLEEN VGNAARPRFE RNKLLLVASV IQGLGLLLCF TYICLHFSAL QVSHRYPRIQ | 60 |
| | SIKVQFTEYK KEKGFILTSQ KEDEIMKVQN NSVIINCDGF YLISLKGYFS QEVNISLHYQ | 120 |
| | KDEEPLFQLK KVRSVNSLMV ASLTYKDKVY LNVTTDNTSL DDFHVEGGEL ILIHQNPGEF | 180 |
| | CVL | 183 |
| SEQ ID NO: 103 OX40L soluble domain | SHRYPRIQSI KVQFTEYKKE KGFILTSQKE DEIMKVQNNS VIINCDGFYL ISLKGYFSQE | 60 |
| | VNISLHYQKD EEPLFQLKKV RSVNSLMVAS LTYKDKVYLN VTTDNTSLDD FHVNGGELIL | 120 |
| | IHQNPGEFCV L | 131 |
| SEQ ID NO: 104 OX40L soluble domain (alternative) | YPRIQSIKVQ FTEYKKEKGF ILTSQKEDEI MKVQNNSVII NCDGFYLISL KGYFSQEVNI | 60 |
| | SLHYQKDEEP LFQLKKVRSV NSLMVASLTY KDKVYLNVTT DNTSLDDFHV NGGELILIHQ | 120 |
| | NPGEFCVL | 128 |
| SEQ ID NO: 105 variable heavy chain for 008 | EVQLVESGGG LVQPGGSLRL SCAASGFTFS NYTMNWVRQA PGKGLEWVSA ISGSGGSTYY | 60 |
| | ADSVKGRFTI SRDNSKNTLY LQMNSLRAED TAVYYCAKDR YSQVHYALDY WGQGTLVTVS | 120 |
| SEQ ID NO: 106 variable light chain for 008 | DIVMTQSPDS LPVTPGEPAS ISCRSSQSLL HSNGYNYLDW YLQKAGQSPQ LLIYLGSNRA | 60 |
| | SGVPDRFSGS GSGTDFTLKI SRVEAEDVGV YYCQQYYNHP TTFGQGTK | 108 |
| SEQ ID NO: 107 variable heavy chain for 011 | EVQLVESGGG VVQPGRSLRL SCAASGFTFS DYTMNWVRQA PGKGLEWVSS ISGGSTYLAD | 60 |
| | SRKGRFTISR DNSKNTLYLQ MNNLRAEDTA VYYCARDRYF RQQNAFDYWG QGTLVTVSSA | 120 |
| SEQ ID NO: 108 variable light chain for 011 | DIVMTQSPDS LPVTPGEPAS ISCRSSQSLL HSNGYNYLDW YLQKAGQSPQ LLIYLGSNRA | 60 |
| | SGVPDRFSGS GSGTDFTLKI SRVEAEDVGV YYCQQYYNHP TTFGQGTK | 108 |
| SEQ ID NO: 109 variable heavy chain for 021 | EVQLVESGGG LVQPRGSLRL SCAASGFTFS SYAMNWVRQA PGKGLEWVAV ISYDGSNKYY | 60 |
| | ADSVKGRFTI SRDNSKNTLY LQMNSLRAED TAVYYCAKDR YITLPNALDY WGQGTLVTVS | 120 |
| SEQ ID NO: 110 variable light chain for 021 | DIQMTQSPVS LPVTPGEPAS ISCRSSQSLL HSNGYNYLDW YLQKPGQSPQ LLIYLGSNRA | 60 |
| | SGVPDRFSGS GSGTDFTLKI SRVEAEDVGV YYCQQYKSNP PTFGQGTK | 108 |
| SEQ ID NO: 111 variable heavy chain for 023 | EVQLVESGGG LVHPGGSLRL SCAGSGFTFS SYAMHWVRQA PGKGLEWVSA IGTGGGTYLA | 60 |
| | DSVMGRFTIS RDNSKNTLYL QMNSLRAEDT AVYYCARYDN VMGLYWFDYW GQGTLVTVSS | 120 |
| SEQ ID NO: 112 variable light chain for 023 | EIVLTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ RSNWPPAFGG GTKVEIKR | 108 |
| SEQ ID NO: 113 heavy chain variable region | EVQLQQSGPE LVKPGASVKM SCKASGYTFT SYVMHWVKQK PGQGLEWIGY INPYNDGTKY | 60 |
| | NEKFKGKATL TSDKSSSTAY MELSSLTSED SAVYYCANYY GSSLSMDYWG QGTSVTVSS | 119 |
| SEQ ID NO: 114 light chain variable region | DIQMTQTTSS LSASLGDRVT ISCRASQDIS NYLNWYQQKP DGTVKLLIYY TSRLHSGVPS | 60 |
| | RFSGSGSGTD YSLTISNLEQ EDIATYFCQQ GNTLPWTFGG GTKLEIKR | 108 |
| SEQ ID NO: 115 heavy chain variable region | EVQLQQSGPE LVKPGASVKI SCKTSGYTFK DYTMHWVKQS HGKSLEWIGG IYPNNGGSTY | 60 |
| | NQNFKDKATL TVDKSSSTAY MEFRSLTSED SAVYYCARMG YHGPHLDFDV WGAGTTVTVS | 120 |
| | P | 121 |
| SEQ ID NO: 116 light chain variable region | DIVMTQSHKF MSTSLGDRVS ITCKASQDVG AAVAWYQQKP GQSPKLLIYW ASTRHTGVPD | 60 |
| | RFTGGGSGTD FTLTISNVQS EDLTDYFCQQ YINYPLTFGG GTKLEIKR | 108 |
| SEQ ID NO: 117 heavy chain variable region of humanized antibody | QIQLVQSGPE LKKPGETVKI SCKASGYTFT DYSMHWVKQA PGKGLKWMGW INTETGEPTY | 60 |
| | ADDFKGRFAF SLETSASTAY LQINNLKNED TATYFCANPY YDYVSYYAMD YWGHGTSVTV | 120 |
| | SS | 122 |
| SEQ ID NO: 118 heavy chain variable region of humanized antibody | QVQLVQSGSE LKKPGASVKV SCKASGYTFT DYSMHWVRQA PGQGLKWMGW INTETGEPTY | 60 |
| | ADDFKGREVF SLDTSVSTAY LQISSLKAED TAVYYCANPY YDYVSYYAMD YWGQGTTVTV | 120 |
| | SS | 122 |

TABLE 15-continued

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 119 light chain variable region of humanized antibody | DIVMTQSHKF MSTSVRDRVS ITCKASQDVS TAVAWYQQKP GQSPKLLIYS ASYLYTGVPD<br>RFTGSGSGTD FTFTISSVQA EDLAVYYCQQ HYSTPRTFGG GTKLEIK | 60<br>107 |
| SEQ ID NO: 120 light chain variable region of humanized antibody | DIVMTQSHKF MSTSVRDRVS ITCKASQDVS TAVAWYQQKP GQSPKLLIYS ASYLYTGVPD<br>RFTGSGSGTD FTFTISSVQA EDLAVYYCQQ HYSTPRTFGG GTKLEIK | 60<br>107 |
| SEQ ID NO: 121 heavy chain variable region of humanized antibody | EVQLVESGGG LVQPGESLKL SCESNEYEFP SHDMSWVRKT PEKRLELVAA INSDGGSTYY<br>PDTMERRFII SRDNTKKTLY LQMSSLRSED TALYYCARHY DDYYAWFAYW GQGTLVTVSA | 60<br>120 |
| SEQ ID NO: 122 heavy chain variable region of humanized antibody | EVQLVESGGG LVQPGGSLRL SCAASEYEFP SHDMSWVRQA PGKGLELVAA INSDGGSTYY<br>PDTMERRFTI SRDNAKNSLY LQMNSLRAED TAVYYCARHY DDYYAWFAYW GQGTMVTVSS | 60<br>120 |
| SEQ ID NO: 123 light chain variable region of humanized antibody | DIVLTQSPAS LAVSLGQRAT ISCRASKSVS TSGYSYMHWY QQKPGQPPKL LIYLASNLES<br>GVPARFSGSG SGTDFTLNIH PVEEEDAATY YCQHSRELPL TFGAGTKLEL K | 60<br>111 |
| SEQ ID NO: 124 light chain variable region of humanized antibody | EIVLTQSPAT LSLSPGERAT LSCRASKSVS TSGYSYMHWY QQKPGQAPRL LIYLASNLES<br>GVPARFSGSG SGTDFTLTIS SLEPEDFAVY YCQHSRELPL TFGGGTKVEI K | 60<br>111 |
| SEQ ID NO: 125 heavy chain variable region | MYLGLNYVFI VFLLNGVQSE VKLEESGGGL VQPGGSMKLS CAASGFTFSD AWMDWVRQSP<br>EKGLEWVAEI RSKANNHATY YAESVNGRFT ISRDDSKSSV YLQMPSLRAE DTGILYCTWG<br>EVFYFDYWGQ GTTLTVSS | 60<br>120<br>138 |
| SEQ ID NO: 126 light chain variable region | MRPSIQFLGL LLFWLHGAQC DIQMTQSPSS LSASLGGKVT ITCKSSQDIN KYIAWYQHKP<br>GKGPRLLIHY TSTLQPGIPS RFSGSGSGRD YSFSISPLEP EDIATYYCLQ YDNLLTFGAG<br>TKLELK | 60<br>120<br>126 |

In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, and wherein the additional domain is a Fab or Fc fragment domain. In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, wherein the additional domain is a Fab or Fc fragment domain wherein each of the soluble OX40 binding domains lacks a stalk region (which contributes to trimerisation and provides a certain distance to the cell membrane, but is not part of the OX40 binding domain) and the first and the second peptide linkers independently have a length of 3-8 amino acids.

In an embodiment, the OX40 agonist is an OX40 agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein the TNF superfamily cytokine domain is an OX40 binding domain.

In some embodiments, the OX40 agonist is MEDI6383. MEDI6383 is an OX40 agonistic fusion protein and can be prepared as described in U.S. Pat. No. 6,312,700, the disclosure of which is incorporated by reference herein.

In an embodiment, the OX40 agonist is an OX40 agonistic scFv antibody comprising any of the foregoing $V_H$ domains linked to any of the foregoing $V_L$ domains.

In an embodiment, the OX40 agonist is Creative Biolabs OX40 agonist monoclonal antibody MOM-18455, commercially available from Creative Biolabs, Inc., Shirley, NY, USA.

In an embodiment, the OX40 agonist is OX40 agonistic antibody clone Ber-ACT35 commercially available from BioLegend, Inc., San Diego, CA, USA.

H. Optional Cell Viability Analyses

Optionally, a cell viability assay can be performed after the Step B first expansion, using standard assays known in the art. Optionally, a cell viability assay can be performed after the first expansion (sometimes referred to as the initial bulk expansion), using standard assays known in the art. For example, a trypan blue exclusion assay can be done on a sample of the bulk TILs, which selectively labels dead cells and allows a viability assessment. Other assays for use in testing viability can include but are not limited to the Alamar blue assay; and the MTT assay.

1. Cell Counts, Viability, Flow Cytometry

In some embodiments, cell counts and/or viability are measured. The expression of markers such as but not limited CD3, CD4, CD8, and CD56, as well as any other disclosed or described herein, can be measured by flow cytometry with antibodies, for example but not limited to those commercially available from BD Bio-sciences (BD Biosciences, San Jose, CA) using a FACSCanto™ flow cytometer (BD Biosciences). The cells can be counted manually using a disposable c-chip hemocytometer (VWR, Batavia, IL) and viability can be assessed using any method known in the art, including but not limited to trypan blue staining.

In some cases, the bulk TIL population can be cryopreserved immediately, using the protocols discussed below. Alternatively, the bulk TIL population can be subjected to REP and then cryopreserved as discussed below. Similarly, in the case where genetically modified TILs will be used in therapy, the bulk or REP TIL populations can be subjected to genetic modifications for suitable treatments.

2. Cell Cultures

In an embodiment, a method for expanding TILs may include using about 5,000 mL to about 25,000 mL of cell medium, about 5,000 mL to about 10,000 mL of cell medium, or about 5,800 mL to about 8,700 mL of cell medium. In an embodiment, expanding the number of TILs uses no more than one type of cell culture medium. Any suitable cell culture medium may be used, e.g., AIM-V cell medium (L-glutamine, 50 µM streptomycin sulfate, and 10 µM gentamicin sulfate) cell culture medium (Invitrogen, Carlsbad CA). In this regard, the inventive methods advantageously reduce the amount of medium and the number of types of medium required to expand the number of TIL. In an embodiment, expanding the number of TIL may comprise adding fresh cell culture media to the cells (also referred to as feeding the cells) no more frequently than every third or fourth day. Expanding the number of cells in a gas permeable container simplifies the procedures necessary to expand the number of cells by reducing the feeding frequency necessary to expand the cells.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium therein; obtaining TILs from the tumor tissue sample; expanding the number of TILs in a second gas permeable container containing cell medium therein using aAPCs for a duration of about 14 to about 42 days, e.g., about 28 days.

In an embodiment, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L.

In an embodiment, TILs can be expanded in G-Rex flasks (commercially available from Wilson Wolf Manufacturing). Such embodiments allow for cell populations to expand from about $5 \times 10^5$ cells/cm$^2$ to between $10 \times 10^6$ and $30 \times 10^6$ cells/cm$^2$. In an embodiment this expansion is conducted without adding fresh cell culture media to the cells (also referred to as feeding the cells). In an embodiment, this is without feeding so long as medium resides at a height of about 10 cm in the G-Rex flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. U.S. 2013/0115617 A1, International Publication No. WO 2013/188427 A1, U.S. Patent Application Publication No. US 2011/0136228 A1, U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Pat. No. 8,956,860 B2, International Publication No. WO 2013/173835 A1, U.S. Patent Application Publication No. US 2015/0175966 A1, the disclosures of which are incorporated herein by reference. Such processes are also described in Jin et al., *J. Immunotherapy*, 2012, 35:283-292.

I. Optional Genetic Engineering of TILs

In some embodiments, the TILs are optionally genetically engineered to include additional functionalities, including, but not limited to, a high-affinity T cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19).

J. Optional Cryopreservation of TILs

As discussed above, and exemplified in Steps A through E as provided in FIG. 8, cryopreservation can occur at numerous points throughout the TIL expansion process. In some embodiments, the expanded population of TILs after the second expansion (as provided for example, according to Step D of FIG. 8) can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986. In some embodiments, the TILs are cryopreserved in 5% DMSO. In some embodiments, the TILs are cryopreserved in cell culture media plus 5% DMSO. In some embodiments, the TILs are cryopreserved according to the methods provided in Examples 8 and 9.

When appropriate, the cells are removed from the freezer and thawed in a 37° C. water bath until approximately 4/5 of the solution is thawed. The cells are generally resuspended in complete media and optionally washed one or more times. In some embodiments, the thawed TILs can be counted and assessed for viability as is known in the art.

K. Methods for Phenotypic Characterization of Expanded TILs

Granzyme B Production: Granzyme B is another measure of the ability of TIL to kill target cells. Media supernatants restimulated as described above using antibodies to CD3, CD28, and CD137/4-1BB were also evaluated for their levels of Granzyme B using the Human Granzyme B DuoSet ELISA Kit (R & D Systems, Minneapolis, MN) according to the manufacturer's instructions. In some embodiments, the second expansion TILs or second additional expansion TILs (such as, for example, those described in Step D of FIG. 8, including TILs referred to as reREP TILs) have increased Granzyme B production.

In some embodiments, telomere length can be used as a measure of cell viability and/or cellular function. In some embodiments, the telomeres are surprisingly the same length in the TILs produced by the present invention as compared to TILs prepared using other methods than those provide herein including for example, methods other than those embodied in FIG. 8. Telomere length measurement: Diverse methods have been used to measure the length of telomeres in genomic DNA and cytological preparations. The telomere restriction fragment (TRF) analysis is the gold standard to measure telomere length (de Lange et al., 1990). However, the major limitation of TRF is the requirement of a large amount of DNA (1.5 ˆg). Two widely used techniques for the measurement of telomere lengths namely, fluorescence in situ hybridization (FISH; Agilent Technologies, Santa Clara, CA) and quantitative PCR can be employed with the present invention.

In some embodiments, TIL health is measured by IFN-gamma (IFN-γ) secretion. In some embodiments, IFN-γ secretion is indicative of active TILs. In some embodiments, a potency assay for IFN-γ production is employed. IFN-γ production is another measure of cytotoxic potential. IFN-γ production can be measured by determining the levels of the cytokine IFN-γ in the media of TIL stimulated with antibodies to CD3, CD28, and CD137/4-1BB. IFN-γ levels in media from these stimulated TIL can be determined using by measuring IFN-γ release.

In some embodiments, the cytotoxic potential of TIL to lyse target cells was assessed using a co-culture assay of TIL with the bioluminescent cell line, P815 (Clone G6), according to a bioluminescent redirected lysis assay (potency assay) for TIL assay which measures TIL cytotoxicity in a highly sensitive dose dependent manner.

In some embodiments, the present methods provide an assay for assessing TIL viability, using the methods as described above. In some embodiments, the TILs are expanded as discussed above, including for example as provided in FIG. 8. In some embodiments, the TILs are cryopreserved prior to being assessed for viability. In some embodiments, the viability assessment includes thawing the TILs prior to performing a first expansion, a second expansion, and an additional second expansion. In some embodiments, the present methods provide an assay for assessing cell proliferation, cell toxicity, cell death, and/or other terms related to viability of the TIL population. Viability can be measured by any of the TIL metabolic assays described above as well as any methods know for assessing cell viability that are known in the art. In some embodiments, the present methods provide as assay for assessment of cell proliferation, cell toxicity, cell death, and/or other terms related to viability of the TILs expanded using the methods described herein, including those exemplified in FIG. 8.

The present invention also provides assay methods for determining TIL viability. In some embodiments, the TILs have equal viability as compared to freshly harvested TILs and/or TILs prepared using other methods than those provide herein including for example, methods other than those embodied in FIG. 8. In some embodiments, the TILs have increased viability as compared to freshly harvested TILs and/or TILs prepared using other methods than those provide herein including for example, methods other than those embodied in FIG. 8. The present disclosure provides methods for assaying TILs for viability by expanding tumor infiltrating lymphocytes (TILs) into a larger population of TILs comprising:

(i) obtaining a first population of TILs which has been previously expanded;

(ii) performing a first expansion by culturing the first population of TILs in a cell culture medium comprising IL-2, and optionally OKT-3, to produce a second population of TILs; and (iii) performing a second expansion by supplementing the cell culture medium of the second population of TILs with additional IL-2, OKT-3, and antigen presenting cells (APCs), to produce a third population of TILs, wherein the third population of TILs is at least 100-fold greater in number than the second population of TILs, and wherein the second expansion is performed for at least 14 days in order to obtain the third population of TILs, and wherein the third population of TILs is further assayed for viability.

In some embodiments, the method further comprises:

(iv) performing an additional second expansion by supplementing the cell culture medium of the third population of TILs with additional IL-2, additional OKT-3, and additional APCs, wherein the additional second expansion is performed for at least 14 days to obtain a larger population of TILs than obtained in step (iii), and wherein the third population is further assayed for viability.

In some embodiments, prior to step (i), the cells are cryopreserved.

In some embodiments, the cells are thawed prior to performing step (i).

In some embodiments, step (iv) is repeated one to four times in order to obtain sufficient TILs for analysis.

In some embodiments, steps (i) through (iii) or (iv) are performed within a period of about 40 days to about 50 days.

In some embodiments, steps (i) through (iii) or (iv) are performed within a period of about 42 days to about 48 days.

In some embodiments, steps (i) through (iii) or (iv) are performed within a period of about 42 days to about 45 days.

In some embodiments, steps (i) through (iii) or (iv) are performed within about 44 days.

In some embodiments, the cells from steps (iii) or (iv) express CD4, CD8, and TCR α β at levels similar to freshly harvested cells.

In some embodiments, the antigen presenting cells are peripheral blood mononuclear cells (PBMCs).

In some embodiments, the PBMCs are added to the cell culture on any of days 9 through 17 in step (iii).

In some embodiments, the APCs are artificial APCs (aAPCs).

In some embodiments, the method further comprises the step of transducing the first population of TILs with an expression vector comprising a nucleic acid encoding a high-affinity T cell receptor.

In some embodiments, the step of transducing occurs before step (i).

In some embodiments, the method further comprises the step of transducing the first population of TILs with an expression vector comprising a nucleic acid encoding a chimeric antigen receptor (CAR) comprising a single chain variable fragment antibody fused with at least one endodomain of a T-cell signaling molecule.

In some embodiments, the step of transducing occurs before step (i).

In some embodiments, the TILs are assayed for viability.

In some embodiments, the TILs are assayed for viability after cryopreservation.

In some embodiments, the TILs are assayed for viability after cryopreservation and after step (iv).

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity (sometimes referred to as polyclonality). In some embodiments, the increase in T-cell repertoire diversity is as compared to freshly harvested TILs and/or TILs prepared using other methods than those provide herein including for example, methods other than those embodied in FIG. 8. In some embodiments, the TILs obtained by the present method exhibit an increase in the T-cell repertoire diversity. In some embodiments, the TILs obtained in the first expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

According to the present disclosure, a method for assaying TILs for viability and/or further use in administration to a subject. In some embodiments, the method for assay tumor infiltrating lymphocytes (TILs) comprises:

(i) obtaining a first population of TILs;
(ii) performing a first expansion by culturing the first population of TILs in a cell culture medium comprising IL-2, and optionally OKT-3, to produce a second population of TILs; and
(iii) performing a second expansion by supplementing the cell culture medium of the second population of TILs with additional IL-2, OKT-3, and antigen presenting cells (APCs), to produce a third population of TILs, wherein the third population of TILs is at least 50-fold greater in number than the second population of TILs;
(iv) harvesting, washing, and cryopreserving the third population of TILs;
(v) storing the cryopreserved TILs at a cryogenic temperature;
(vi) thawing the third population of TILs to provide a thawed third population of TILs; and
(vii) performing an additional second expansion of a portion of the thawed third population of TILs by supplementing the cell culture medium of the third population with IL-2, OKT-3, and APCs for an additional expansion period (sometimes referred to as a reREP period) of at least 3 days, wherein the third expansion is performed to obtain a fourth population of TILs, wherein the number of TILs in the fourth population of TILs is compared to the number of TILs in the third population of TILs to obtain a ratio;
(viii) determining based on the ratio in step (vii) whether the thawed population of TILs is suitable for administration to a patient;
(ix) administering a therapeutically effective dosage of the thawed third population of TILs to the patient when the ratio of the number of TILs in the fourth population of TILs to the number of TILs in the third population of TILs is determined to be greater than 5:1 in step (viii).

In some embodiments, the additional expansion period (sometimes referred to as a reREP period) is performed until the ratio of the number of TILs in the fourth population of TILs to the number of TILs in the third population of TILs is greater than 50:1.

In some embodiments, the number of TILs sufficient for a therapeutically effective dosage is from about $2.3 \times 10^{10}$ to about $13.7 \times 10^{10}$.

In some embodiments, steps (i) through (vii) are performed within a period of about 40 days to about 50 days. In some embodiments, steps (i) through (vii) are performed within a period of about 42 days to about 48 days. In some embodiments, steps (i) through (vii) are performed within a period of about 42 days to about 45 days. In some embodiments, steps (i) through (vii) are performed within about 44 days.

In some embodiments, the cells from steps (iii) or (vii) express CD4, CD8, and TCR α β at levels similar to freshly harvested cells. In some embodiments the cells are TILs.

In some embodiments, the antigen presenting cells are peripheral blood mononuclear cells (PBMCs). In some embodiments, the PBMCs are added to the cell culture on any of days 9 through 17 in step (iii).

In some embodiments, the APCs are artificial APCs (aAPCs).

In some embodiments, the step of transducing the first population of TILs with an expression vector comprising a nucleic acid encoding a high-affinity T cell receptor.

In some embodiments, the step of transducing occurs before step (i).

In some embodiments, the step of transducing the first population of TILs with an expression vector comprising a nucleic acid encoding a chimeric antigen receptor (CAR)

comprising a single chain variable fragment antibody fused with at least one endodomain of a T-cell signaling molecule.

In some embodiments, the step of transducing occurs before step (i).

In some embodiments, the TILs are assayed for viability after step (vii).

The present disclosure also provides further methods for assaying TILs. In some embodiments, the disclosure provides a method for assaying TILs comprising:
(i) obtaining a portion of a first population of cryopreserved TILs;
(ii) thawing the portion of the first population of cryopreserved TILs;
(iii) performing a first expansion by culturing the portion of the first population of TILs in a cell culture medium comprising IL-2, OKT-3, and antigen presenting cells (APCs) for an additional expansion period (sometimes referred to as a reREP period) of at least 3 days, to produce a second population of TILs, wherein the portion from the first population of TILs is compared to the second population of TILs to obtain a ratio of the number of TILs, wherein the ratio of the number of TILs in the second population of TILs to the number of TILs in the portion of the first population of TILs is greater than 5:1;
(iv) determining based on the ratio in step (iii) whether the first population of TILs is suitable for use in therapeutic administration to a patient;
(v) determining the first population of TILs is suitable for use in therapeutic administration when the ratio of the number of TILs in the second population of TILs to the number of TILs in the first population of TILs is determined to be greater than 5:1 in step (iv).

In some embodiments, the ratio of the number of TILs in the second population of TILs to the number of TILs in the portion of the first population of TILs is greater than 50:1.

In some embodiments, the method further comprises performing expansion of the entire first population of cryopreserved TILs from step (i) according to the methods as described in any of the embodiments provided herein.

In some embodiments, the method further comprises administering the entire first population of cryopreserved TILs from step (i) to the patient.

L. Closed Systems for TIL Manufacturing

The present invention provides for the use of closed systems during the TIL culturing process. Such closed systems allow for preventing and/or reducing microbial contamination, allow for the use of fewer flasks, and allow for cost reductions. In some embodiments, the closed system uses two containers.

Such closed systems are well-known in the art and can be found, for example, at http://www.fda.gov/cber/guidelines.htm and https://www.fda.gov/BiologicsBloodVaccines/GuidanceComplianceRegulatoryInformation/Guidances/Blood/ucm076779.htm.

In some embodiments, the closed systems include luer lock and heat sealed systems as described in for example, Example 16. In some embodiments, the closed system is accessed via syringes under sterile conditions in order to maintain the sterility and closed nature of the system. In some embodiments, a closed system as described in Example 16 is employed. In some embodiments, the TILs are formulated into a final product formulation container according to the method described in Example 16, section 8.14 "Final Formulation and Fill".

As provided on the FDA website, closed systems with sterile methods are known and well described. See, https://www.fda.gov/BiologicsBloodVaccines/GuidanceComplianceRegulatoryInformation/Guidances/Blood/ucm076779.htm, as referenced above and provided in pertinent part below.

Introduction

Sterile connecting devices (STCDs) produce sterile welds between two pieces of compatible tubing. This procedure permits sterile connection of a variety of containers and tube diameters. This guidance describes recommended practices and procedures for use of these devices. This guidance does not address the data or information that a manufacturer of a sterile connecting device must submit to FDA in order to obtain approval or clearance for marketing. It is also important to note that the use of an approved or cleared sterile connecting device for purposes not authorized in the labeling may cause the device to be considered adulterated and misbranded under the Federal Food, Drug and Cosmetic Act.

In some embodiments, the closed system uses one container from the time the tumor fragments are obtained until the TILs are ready for administration to the patient or cryopreserving. In some embodiments when two containers are used, the first container is a closed G-container and the population of TILs is centrifuged and transferred to an infusion bag without opening the first closed G-container. In some embodiments, when two containers are used, the infusion bag is a HypoThermosol-containing infusion bag. A closed system or closed TIL cell culture system is characterized in that once the tumor sample and/or tumor fragments have been added, the system is tightly sealed from the outside to form a closed environment free from the invasion of bacteria, fungi, and/or any other microbial contamination.

In some embodiments, the reduction in microbial contamination is between about 5% and about 100%. In some embodiments, the reduction in microbial contamination is between about 5% and about 95%. In some embodiments, the reduction in microbial contamination is between about 5% and about 90%. In some embodiments, the reduction in microbial contamination is between about 10% and about 90%. In some embodiments, the reduction in microbial contamination is between about 15% and about 85%. In some embodiments, the reduction in microbial contamination is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, about 99%, or about 100%.

The closed system allows for TIL growth in the absence and/or with a significant reduction in microbial contamination.

Moreover, pH, carbon dioxide partial pressure and oxygen partial pressure of the TIL cell culture environment each vary as the cells are cultured. Consequently, even though a medium appropriate for cell culture is circulated, the closed environment still needs to be constantly maintained as an optimal environment for TIL proliferation. To this end, it is desirable that the physical factors of pH, carbon dioxide partial pressure and oxygen partial pressure within the culture liquid of the closed environment be monitored by means of a sensor, the signal whereof is used to control a gas exchanger installed at the inlet of the culture environment, and the that gas partial pressure of the closed environment be adjusted in real time according to changes in the culture liquid so as to optimize the cell culture environment. In some embodiments, the present invention provides a closed cell culture system which incorporates at the inlet to the closed environment a gas exchanger equipped with a monitoring device which measures the pH, carbon dioxide partial pressure and oxygen partial pressure of the closed environment, and optimizes the cell culture environment by automatically adjusting gas concentrations based on signals from the monitoring device.

In some embodiments, the pressure within the closed environment is continuously or intermittently controlled. That is, the pressure in the closed environment can be varied by means of a pressure maintenance device for example, thus ensuring that the space is suitable for growth of TILs in a positive pressure state, or promoting exudation of fluid in a negative pressure state and thus promoting cell proliferation. By applying negative pressure intermittently, moreover, it is possible to uniformly and efficiently replace the circulating liquid in the closed environment by means of a temporary shrinkage in the volume of the closed environment.

In some embodiments, optimal culture components for proliferation of the TILs can be substituted or added, and including factors such as IL-2 and/or OKT3, as well as combination, can be added.

C. Cell Cultures

In an embodiment, a method for expanding TILs, including those discuss above as well as exemplified in FIG. 8, may include using about 5,000 mL to about 25,000 mL of cell medium, about 5,000 mL to about 10,000 mL of cell medium, or about 5,800 mL to about 8,700 mL of cell medium. In some embodiments, the media is a serum free medium, as described for example in Example 21. In some embodiments, the media in the first expansion is serum free. In some embodiments, the media in the second expansion is serum free. In some embodiments, the media in the first expansion and the second are both serum free. In an embodiment, expanding the number of TILs uses no more than one type of cell culture medium. Any suitable cell culture medium may be used, e.g., AIM-V cell medium (L-glutamine, 50 μM streptomycin sulfate, and 10 μM gentamicin sulfate) cell culture medium (Invitrogen, Carlsbad CA). In this regard, the inventive methods advantageously reduce the amount of medium and the number of types of medium required to expand the number of TIL. In an embodiment, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium therein; obtaining TILs from the tumor tissue sample; expanding the number of TILs in a second gas permeable container containing cell medium for a duration of about 7 to 14 days, e.g., about 11 days. In some embodiments pre-REP is about 7 to 14 days, e.g., about 11 days. In some embodiments, REP is about 7 to 14 days, e.g., about 11 days.

In an embodiment, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L.

In an embodiment, TILs can be expanded in G-Rex flasks (commercially available from Wilson Wolf Manufacturing). Such embodiments allow for cell populations to expand from about $5 \times 10^5$ cells/cm$^2$ to between $10 \times 10^6$ and $30 \times 10^6$ cells/cm$^2$. In an embodiment this is without feeding. In an embodiment, this is without feeding so long as medium resides at a height of about 10 cm in the G-Rex flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. us 2013/0115617 A1, International Publication No. WO 2013/188427 A1, U.S. Patent Application Publication No. US 2011/0136228 A1, U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Pat. No. 8,956,860 B2, International Publication No. WO 2013/173835 A1, U.S. Patent Application Publication No. US 2015/0175966 A1, the disclosures of which are incorporated herein by reference. Such processes are also described in Jin et al., *J. Immunotherapy*, 2012, 35:283-292.

D. Optional Genetic Engineering of TILs

In some embodiments, the TILs are optionally genetically engineered to include additional functionalities, including, but not limited to, a high-affinity T cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19).

E. Optional Cryopreservation of TILs

Either the bulk TIL population or the expanded population of TILs can be optionally cryopreserved. In some embodiments, cryopreservation occurs on the therapeutic TIL population. In some embodiments, cryopreservation occurs on the TILs harvested after the second expansion. In some embodiments, cryopreservation occurs on the TILs in exemplary Step F of FIG. 8. In some embodiments, the TILs are cryopreserved in the infusion bag. In some embodiments, the TILs are cryopreserved prior to placement in an infusion bag. In some embodiments, the TILs are cryopreserved and not placed in an infusion bag. In some embodiments, cryopreservation is performed using a cryopreservation medium. In some embodiments, the cryopreservation media contains dimethylsulfoxide (DMSO). This is generally accomplished by putting the TIL population into a freezing solution, e.g. 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See, Sadeghi, et al., *Acta Oncologica* 2013, 52, 978-986.

When appropriate, the cells are removed from the freezer and thawed in a 37° C. water bath until approximately 4/5 of the solution is thawed. The cells are generally resuspended in complete media and optionally washed one or more times. In some embodiments, the thawed TILs can be counted and assessed for viability as is known in the art.

In a preferred embodiment, a population of TILs is cryopreserved using CS10 cryopreservation media (CryoStor 10, BioLife Solutions). In a preferred embodiment, a population of TILs is cryopreserved using a cryopreservation media containing dimethylsulfoxide (DMSO). In a preferred embodiment, a population of TILs is cryopreserved using a 1:1 (vol:vol) ratio of CS10 and cell culture media. In a preferred embodiment, a population of TILs is cryopreserved using about a 1:1 (vol:vol) ratio of CS10 and cell culture media, further comprising additional IL-2.

As discussed above in Steps A through E, cryopreservation can occur at numerous points throughout the TIL expansion process.

As discussed above, and exemplified in Steps A through E as provided in FIG. 8, cryopreservation can occur at numerous points throughout the TIL expansion process. In some embodiments, the expanded population of TILs after the second expansion (as provided for example, according to Step D of Figure A) can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986. In some embodiments, the TILs are cryopreserved in 5% DMSO. In some embodiments, the TILs are cryopreserved in cell culture media plus 5% DMSO. In some embodiments, the TILs are cryopreserved according to the methods provided in Example 16.

In some embodiments, the bulk TIL population after the first expansion according to Step B or the expanded population of TILs after the one or more second expansions according to Step D can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986.

When appropriate, the cells are removed from the freezer and thawed in a 37° C. water bath until approximately 4/5 of the solution is thawed. The cells are generally resuspended in complete media and optionally washed one or more times. In some embodiments, the thawed TILs can be counted and assessed for viability as is known in the art.

In some cases, the Step B TIL population can be cryopreserved immediately, using the protocols discussed below. Alternatively, the bulk TIL population can be subjected to Step C and Step D and then cryopreserved after Step D. Similarly, in the case where genetically modified TILs will be used in therapy, the Step B or Step D TIL populations can be subjected to genetic modifications for suitable treatments.

V. Methods of Treating Patients

Methods of treatment begin with the initial TIL collection and culture of TILs. Such methods have been both described in the art by, for example, Jin et al., *J Immunotherapy*, 2012, 35(3):283-292, incorporated by reference herein in its entirety. Embodiments of methods of treatment are described throughout the sections below, including the Examples.

The expanded TILs produced according the methods described herein, including for example as described in Steps A through F above or according to Steps A through F above (also as shown, for example, in FIG. 8) find particular use in the treatment of patients with cancer (for example, as described in Goff, et al., *J Clinical Oncology*, 2016, 34(20): 2389-239, as well as the supplemental content; incorporated by reference herein in its entirety). In some embodiments, TIL were grown from resected deposits of metastatic melanoma as previously described (see, Dudley, et al., *J Immunother.*, 2003, 26:332-342; incorporated by reference herein in its entirety). Fresh tumor can be dissected under sterile conditions. A representative sample can be collected for formal pathologic analysis. Single fragments of 2 mm$^3$ to 3 mm$^3$ may be used. In some embodiments, 5, 10, 15, 20, 25 or 30 samples per patient are obtained. In some embodiments, 20, 25, or 30 samples per patient are obtained. In some embodiments, 20, 22, 24, 26, or 28 samples per patient are obtained. In some embodiments, 24 samples per patient are obtained. Samples can be placed in individual wells of a 24-well plate, maintained in growth media with high-dose IL-2 (6,000 IU/mL), and monitored for destruction of tumor and/or proliferation of TIL. Any tumor with viable cells remaining after processing can be enzymatically digested into a single cell suspension and cryopreserved, as described herein.

In some embodiments, successfully grown TIL can be sampled for phenotype analysis (CD3, CD4, CD8, and CD56) and tested against autologous tumor when available. TIL can be considered reactive if overnight coculture yielded interferon-gamma (IFN-γ) levels >200 pg/mL and twice background. (Goff, et al., *J Immunother.*, 2010, 33:840-847; incorporated by reference herein in its entirety). In some embodiments, cultures with evidence of autologous reactivity or sufficient growth patterns can be selected for a second expansion (for example, a second expansion as provided in according to Step D of FIG. 8), including second expansions that are sometimes referred to as rapid expansion (REP). In some embodiments, expanded TILs with high autologous reactivity (for example, high proliferation during a second expansion), are selected for an additional second expansion. In some embodiments, TILs with high autologous reactivity (for example, high proliferation during second expansion as provided in Step D of FIG. 8), are selected for an additional second expansion according to Step D of FIG. 8.

In some embodiments, the patient is not moved directly to ACT (adoptive cell transfer), for example, in some embodiments, after tumor harvesting and/or a first expansion, the cells are not utilized immediately. In such embodiments, TILs can be cryopreserved and thawed 2 days before administration to a patient. In such embodiments, TILs can be cryopreserved and thawed 1 day before administration to a patient. In some embodiments, the TILs can be cryopreserved and thawed immediately before the administration to a patient.

Cell phenotypes of cryopreserved samples of infusion bag TIL can be analyzed by flow cytometry (e.g., FlowJo) for surface markers CD3, CD4, CD8, CCR7, and CD45RA (BD BioSciences), as well as by any of the methods described herein. Serum cytokines were measured by using standard enzyme-linked immunosorbent assay techniques. A rise in serum IFN-g was defined as >100 pg/mL and greater than 4 3 baseline levels.

In some embodiments, the TILs produced by the methods provided herein, for example those exemplified in FIG. 8, provide for a surprising improvement in clinical efficacy of the TILs. In some embodiments, the TILs produced by the methods provided herein, for example those exemplified in FIG. 8, exhibit increased clinical efficacy as compared to TILs produced by methods other than those described herein, including for example, methods other than those exemplified in FIG. 8. In some embodiments, the methods other than those described herein include methods referred to as process 1C and/or Generation 1 (Gen 1). In some embodiments, the increased efficacy is measured by DCR, ORR, and/or other clinical responses. In some embodiments, the TILS produced by the methods provided herein, for example those exemplified in FIG. 8, exhibit a similar time to response and safety profile compared to TILs produced by methods other than those described herein, including for example, methods other than those exemplified in FIG. 8, for example the Gen 1 process.

In some embodiments, IFN-gamma (IFN-γ) is indicative of treatment efficacy and/or increased clinical efficacy. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood, serum, or TILs ex vivo of a subject treated with TILs prepared by the methods of the present invention, including those as described for example in FIG. 8. In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more as compared to an untreated patient and/or as compared to a patient treated with TILs prepared using other methods than those provide herein including for example, methods other than those embodied in FIG. 8. In some embodiments, IFN-γ secretion is increased one-fold as compared to an untreated patient and/or as compared to a patient treated with TILs prepared using other methods than those provide herein including for example, methods other than those embodied in FIG. 8. In some embodiments, IFN-γ secretion is increased two-fold as compared to an untreated patient and/or as compared to a patient treated with TILs prepared using other methods than those provide herein including for example, methods other than those embodied in FIG. 8. In some embodiments, IFN-γ secretion is increased three-fold as compared to an untreated patient and/or as compared to a patient treated with TILs prepared using other methods than those provide herein including for example, methods other than those embodied in FIG. 8. In some embodiments, IFN-γ secretion is increased four-fold as compared to an untreated patient and/or as compared to a patient treated with TILs prepared using other methods than those provide herein including for example, methods other than those embodied in FIG. 8. In some embodiments, IFN-γ secretion is increased five-fold as compared to an untreated patient and/or as compared to a patient treated with TILs prepared using other methods than those provide herein including for example, methods other than those embodied in FIG. 8. In some embodiments, IFN-γ is measured using a Quantikine ELISA kit. In some embodiments, IFN-γ is measured in TILs ex vivo of a subject treated with TILs prepared by the methods of the present invention, including those as described for example in FIG. 8. In some embodiments, IFN-γ is measured in blood of a subject treated with TILs prepared by the methods of the present invention, including those as described for example in FIG. 8. In some embodiments, IFN-γ is measured in TILs serum of a subject treated with TILs prepared by the methods of the present invention, including those as described for example in FIG. 8.

In some embodiments, the TILs prepared by the methods of the present invention, including those as described for example in FIG. 8, exhibit increased polyclonality as compared to TILs produced by other methods, including those not exemplified in FIG. 8, such as for example, methods referred to as process 1C methods. In some embodiments, significantly improved polyclonality and/or increased polyclonality is indicative of treatment efficacy and/or increased clinical efficacy. In some embodiments, polyclonality refers to the T-cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including for example, methods other than those embodied in FIG. 8. In some embodiments, polyclonality is increased one-fold as compared to an untreated patient and/or as compared to a patient treated with TILs prepared using other methods than those provide herein including for example, methods other than those embodied in FIG. 8. In some embodiments, polyclonality is increased two-fold as compared to an untreated patient and/or as compared to a patient treated with TILs prepared using other methods than those provide herein including for example, methods other than those embodied in FIG. 8. In some embodiments, polyclonality is increased ten-fold as compared to an untreated patient and/or as compared to a patient treated with TILs prepared using other methods than those provide herein including for example, methods other than those embodied in FIG. 8. In some embodiments, polyclonality is increased 100-fold as compared to an untreated patient and/or as compared to a patient treated with TILs prepared using other methods than those provide herein including for example, methods other than those embodied in FIG. 8. In some embodiments, polyclonality is increased 500-fold as compared to an untreated patient and/or as compared to a patient treated with TILs prepared using other methods than those provide herein including for example, methods other than those embodied in FIG. 8. In some embodiments, polyclonality is increased 1000-fold as compared to an untreated patient and/or as compared to a patient treated with TILs prepared using other methods than those provide herein including for example, methods other than those embodied in FIG. 8.

Measures of efficacy can include the disease control rate (DCR) as well as overall response rate (ORR), as known in the art as well as described herein.

1. Methods of Treating Cancers and Other Diseases

The compositions and methods described herein can be used in a method for treating diseases. In an embodiment, they are for use in treating hyperproliferative disorders. They may also be used in treating other disorders as described herein and in the following paragraphs.

In some embodiments, the hyperproliferative disorder is cancer. In some embodiments, the hyperproliferative disorder is a solid tumor cancer. In some embodiments, the solid tumor cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), renal cancer, and renal cell carcinoma. In some embodiments, the hyperproliferative disorder is a hematological malignancy. In some embodiments, the solid tumor cancer is selected from the group consisting of chronic lymphocytic leukemia, acute lymphoblastic leukemia, diffuse large B cell lymphoma, non-Hodgkin's lymphoma, Hodgkin's lymphoma, follicular lymphoma, and mantle cell lymphoma.

In an embodiment, the invention includes a method of treating a cancer with a population of TILs, wherein a patient is pre-treated with non-myeloablative chemotherapy prior to an infusion of TILs according to the present disclosure. In an embodiment, the non-myeloablative chemotherapy is cyclophosphamide 60 mg/kg/d for 2 days (days 27 and 26 prior to TIL infusion) and fludarabine 25 mg/m$^2$/d for 5 days (days 27 to 23 prior to TIL infusion). In an embodiment, after non-myeloablative chemotherapy and TIL infusion (at day 0) according to the present disclosure, the patient receives an intravenous infusion of IL-2 intravenously at 720,000 IU/kg every 8 hours to physiologic tolerance.

Efficacy of the compounds and combinations of compounds described herein in treating, preventing and/or managing the indicated diseases or disorders can be tested using various models known in the art, which provide guidance for treatment of human disease. For example, models for determining efficacy of treatments for ovarian cancer are described, e.g., in Mullany, et al., *Endocrinology* 2012, 153, 1585-92; and Fong, et al., *J. Ovarian Res.* 2009, 2, 12. Models for determining efficacy of treatments for pancreatic cancer are described in Herreros-Villanueva, et al., *World J. Gastroenterol.* 2012, 18, 1286-1294. Models for determining efficacy of treatments for breast cancer are described, e.g., in Fantozzi, *Breast Cancer Res.* 2006, 8, 212. Models for determining efficacy of treatments for melanoma are described, e.g., in Damsky, et al., *Pigment Cell & Melanoma Res.* 2010, 23, 853-859. Models for determining efficacy of treatments for lung cancer are described, e.g., in Meuwissen, et al., *Genes & Development,* 2005, 19, 643-664. Models for determining efficacy of treatments for lung cancer are described, e.g., in Kim, *Clin. Exp. Otorhinolaryngol.* 2009, 2, 55-60; and Sano, *Head Neck Oncol.* 2009, 1, 32.

In some embodiments, IFN-gamma (IFN-γ) is indicative of treatment efficacy for hyperproliferative disorder treatment. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood of a subject treated with TILs prepared by the methods of the present invention, including those as described for example in FIG. 8. In some embodiments, the TILs obtained by the present method provide for increased IFN-γ in the blood of subjects treated with the TILs of the present method as compared to subjects treated with TILs prepared using methods referred to as process 1C, as exemplified in FIG. 13. In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more as compared to an untreated patient and/or as compared to a patient treated with TILs prepared using other methods than those provide herein including for example, methods other than those embodied in FIG. 8. In some embodiments, IFN-γ secretion is increased one-fold as compared to an untreated patient and/or as compared to a patient treated with TILs prepared using other methods than those provide herein including for example, methods other than those embodied in FIG. 8. In some embodiments, IFN-γ secretion is increased two-fold as compared to an untreated patient and/or as compared to a patient treated with TILs prepared using other methods than those provide herein including for example, methods other than those embodied in FIG. 8. In some embodiments, IFN-γ secretion is increased three-fold as compared to an untreated patient and/or as compared to a patient treated with TILs prepared using other methods than those provide herein including for example, methods other than those embodied in FIG. 8. In some embodiments, IFN-γ secretion is increased four-fold as compared to an untreated patient and/or as compared to a patient treated with TILs prepared using other methods than those provide herein including for example, methods other than those embodied in FIG. 8. In some embodiments, IFN-γ secretion is increased five-fold as compared to an untreated patient and/or as compared to a patient treated with TILs prepared using other methods than those provide herein including for example, methods other than those embodied in FIG. 8. In some embodiments, IFN-γ is measured using a Quantikine ELISA kit. In some embodiments, IFN-γ is measured using a Quantikine ELISA kit. In some embodiments, IFN-γ is measured in TILs ex vivo from a patient treated with the TILs produced by the methods of the present invention. In some embodiments, IFN-γ is measured in blood in a patient treated with the TILs produced by the methods of the present invention. In some embodiments, IFN-γ is measured in serum in a patient treated with the TILs produced by the methods of the present invention.

In some embodiments, the TILs prepared by the methods of the present invention, including those as described for example in FIG. 8, exhibit increased polyclonality as compared to TILs produced by other methods, including those not exemplified in FIG. 8, such as for example, methods referred to as process 1C methods. In some embodiments, significantly improved polyclonality and/or increased polyclonality is indicative of treatment efficacy and/or increased clinical efficacy for cancer treatment. In some embodiments, polyclonality refers to the T-cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including for example, methods other than those embodied in FIG. 8. In some embodiments, polyclonality is increased one-fold as compared to an untreated patient and/or as compared to a patient treated with TILs prepared using other methods than those provide herein including for example, methods other than those embodied in FIG. 8. In some embodiments, polyclonality is increased two-fold as compared to an untreated patient and/or as compared to a patient treated with TILs prepared using other methods than those provide herein including for example, methods other than those embodied in FIG. 8. In some embodiments, polyclonality is increased ten-fold as compared to an untreated patient and/or as compared to a patient treated with TILs prepared using other methods than those provide herein including for example, methods other than those embodied in FIG. 8. In some embodiments, polyclonality is increased 100-fold as compared to an untreated patient and/or as compared to a patient treated with TILs prepared using other methods than those provide herein including for example, methods other than those embodied in FIG. 8. In some embodiments, polyclonality is increased 500-fold as compared to an untreated patient and/or as compared to a patient treated with TILs prepared using other methods than those provide herein including for example, methods other than those embodied in FIG. 8. In some embodiments, polyclonality is increased 1000-fold as compared to an untreated patient and/or as compared to a patient treated with TILs prepared using other methods than those provide herein including for example, methods other than those embodied in FIG. 8.

2. Methods of Co-Administration

In some embodiments, the TILs produced as described herein, including for example TILs derived from a method described in Steps A through F of FIG. 8, can be administered in combination with one or more immune checkpoint regulators, such as the antibodies described below. For example, antibodies that target PD-1 and which can be co-administered with the TILs of the present invention include, e.g., but are not limited to nivolumab (BMS-936558, Bristol-Myers Squibb; Opdivo®), pembrolizumab (lambrolizumab, MK03475 or MK-3475, Merck; Keytruda®), humanized anti-PD-1 antibody JS001 (Shang-Hai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)—BioXcell cat #BP0146. Other suitable antibodies suitable for use in co-administration methods with TILs produced according to Steps A through F as described herein are anti-PD-1 antibodies disclosed in U.S. Pat. No. 8,008,449, herein incorporated by reference. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immune response, are suitable for use in co-administration methods with TILs produced according to Steps A through F as described herein. For example, antibodies that target PD-L1 and are in clinical trials, include BMS-936559 (Bristol-Myers Squibb) and MPDL3280A (Genentech). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, are suitable for use in co-administration methods with TILs produced according to Steps A through F as described herein. In some embodiments, the subject administered the combination of TILs produced according to Steps A through F is co administered with a and anti-PD-1 antibody when the patient has a cancer type that is refractory to administration of the anti-PD-1 antibody alone. In some embodiments, the patient is administered TILs in combination with and anti-PD-1 when the patient has refractory melanoma. In some embodiments, the patient is administered TILs in combination with and anti-PD-1 when the patient has non-small-cell lung carcinoma (NSCLC).

3. Optional Lymphodepletion Preconditioning of Patients

In an embodiment, the invention includes a method of treating a cancer with a population of TILs, wherein a patient is pre-treated with non-myeloablative chemotherapy prior to an infusion of TILs according to the present disclosure. In an embodiment, the invention includes a population of TILs for use in the treatment of cancer in a patient which has been pre-treated with non-myeloablative chemotherapy. In an embodiment, the population of TILs is for administration by infusion. In an embodiment, the non-myeloablative chemotherapy is cyclophosphamide 60 mg/kg/d for 2 days (days 27 and 26 prior to TIL infusion) and fludarabine 25 mg/m$^2$/d for 5 days (days 27 to 23 prior to TIL infusion). In an embodiment, after non-myeloablative chemotherapy and TIL infusion (at day 0) according to the present disclosure, the patient receives an intravenous infusion of IL-2 (aldesleukin, commercially available as PROLEUKIN) intravenously at 720,000 IU/kg every 8 hours to physiologic tolerance. In certain embodiments, the population of TILs is for use in treating cancer in combination with IL-2, wherein the IL-2 is administered after the population of TILs.

Experimental findings indicate that lymphodepletion prior to adoptive transfer of tumor-specific T lymphocytes plays a key role in enhancing treatment efficacy by eliminating regulatory T cells and competing elements of the immune system (cytokine sinks'). Accordingly, some embodiments of the invention utilize a lymphodepletion step (sometimes also referred to as "immunosuppressive conditioning") on the patient prior to the introduction of the TILs of the invention.

In general, lymphodepletion is achieved using administration of fludarabine or cyclophosphamide (the active form being referred to as mafosfamide) and combinations thereof. Such methods are described in Gassner, et al., *Cancer Immunol. Immunother.* 2011, 60, 75-85, Muranski, et al., *Nat. Clin. Pract. Oncol.*, 2006, 3, 668-681, Dudley, et al., *J. Clin. Oncol.* 2008, 26, 5233-5239, and Dudley, et al., *J. Clin. Oncol.* 2005, 23, 2346-2357, all of which are incorporated by reference herein in their entireties.

In some embodiments, the fludarabine is administered at a concentration of 0.5 µg/mL-10 µg/mL fludarabine. In some embodiments, the fludarabine is administered at a concentration of 1 µg/mL fludarabine. In some embodiments, the fludarabine treatment is administered for 1 day, 2 days, 3 days, 4 days, 5 days, 6 days, or 7 days or more. In some embodiments, the fludarabine is administered at a dosage of 10 mg/kg/day, 15 mg/kg/day, 20 mg/kg/day, 25 mg/kg/day, 30 mg/kg/day, 35 mg/kg/day, 40 mg/kg/day, or 45 mg/kg/day. In some embodiments, the fludarabine treatment is administered for 2-7 days at 35 mg/kg/day. In some embodiments, the fludarabine treatment is administered for 4-5 days at 35 mg/kg/day. In some embodiments, the fludarabine treatment is administered for 4-5 days at 25 mg/kg/day.

In some embodiments, the mafosfamide, the active form of cyclophosphamide, is obtained at a concentration of 0.5 µg/mL-10 µg/mL by administration of cyclophosphamide. In some embodiments, mafosfamide, the active form of cyclophosphamide, is obtained at a concentration of 1 µg/mL by administration of cyclophosphamide. In some embodiments, the cyclophosphamide treatment is administered for 1 day, 2 days, 3 days, 4 days, 5 days, 6 days, or 7 days or more. In some embodiments, the cyclophosphamide is administered at a dosage of 100 mg/m$^2$/day, 150 mg/m$^2$/day, 175 mg/m$^2$/day 200 mg/m$^2$/day, 225 mg/m$^2$/day, 250 mg/m$^2$/day, 275 mg/m$^2$/day, or 300 mg/m$^2$/day. In some embodiments, the cyclophosphamide is administered intravenously (i.e., i.v.) In some embodiments, the cyclophosphamide treatment is administered for 2-7 days at 35 mg/kg/day. In some embodiments, the cyclophosphamide treatment is administered for 4-5 days at 250 mg/m$^2$/day i.v. In some embodiments, the cyclophosphamide treatment is administered for 4 days at 250 mg/m$^2$/day i.v.

In some embodiments, lymphodepletion is performed by administering the fludarabine and the cyclophosphamide together to a patient. In some embodiments, fludarabine is administered at 25 mg/m$^2$/day i.v. and cyclophosphamide is administered at 250 mg/m$^2$/day i.v. over 4 days.

In an embodiment, the lymphodepletion is performed by administration of cyclophosphamide at a dose of 60 mg/m$^2$/day for two days followed by administration of fludarabine at a dose of 25 mg/m$^2$/day for five days.

4. IL-2 Regimens

In an embodiment, the IL-2 regimen comprises a high-dose IL-2 regimen, wherein the high-dose IL-2 regimen comprises aldesleukin, or a biosimilar or variant thereof, administered intravenously starting on the day after administering a therapeutically effective portion of the therapeutic population of TILs, wherein the aldesleukin or a biosimilar or variant thereof is administered at a dose of 0.037 mg/kg or 0.044 mg/kg IU/kg (patient body mass) using 15-minute bolus intravenous infusions every eight hours until tolerance, for a maximum of 14 doses. Following 9 days of rest, this schedule may be repeated for another 14 doses, for a maximum of 28 doses in total.

In an embodiment, the IL-2 regimen comprises a decrescendo IL-2 regimen. Decrescendo IL-2 regimens have been described in O'Day, et al., *J. Clin. Oncol.* 1999, 17, 2752-61 and Eton, et al., *Cancer* 2000, 88, 1703-9, the disclosures of which are incorporated herein by reference. In an embodiment, a decrescendo IL-2 regimen comprises 18×10$^6$ IU/m$^2$ administered intravenously over 6 hours, followed by 18×10$^6$ IU/m$^2$ administered intravenously over 12 hours, followed by 18×10$^6$ IU/m$^2$ administered intravenously over 24 hrs, followed by 4.5×10$^6$ IU/m$^2$ administered intravenously over 72 hours. This treatment cycle may be repeated every 28 days for a maximum of four cycles. In an embodiment, a decrescendo IL-2 regimen comprises 18,000,000 IU/m$^2$ on day 1, 9,000,000 IU/m$^2$ on day 2, and 4,500,000 IU/m$^2$ on days 3 and 4.

In an embodiment, the IL-2 regimen comprises administration of pegylated IL-2 every 1, 2, 4, 6, 7, 14 or 21 days at a dose of 0.10 mg/day to 50 mg/day.

5. Adoptive Cell Transfer

Adoptive cell transfer (ACT) is a very effective form of immunotherapy and involves the transfer of immune cells with antitumor activity into cancer patients. ACT is a treatment approach that involves the identification, in vitro, of lymphocytes with antitumor activity, the in vitro expansion of these cells to large numbers and their infusion into the cancer-bearing host. Lymphocytes used for adoptive transfer can be derived from the stroma of resected tumors (tumor infiltrating lymphocytes or TILs). TILs for ACT can be prepared as described herein. In some embodiments, the TILs are prepared, for example, according to a method as described in FIG. 8. They can also be derived or from blood if they are genetically engineered to express antitumor T-cell receptors (TCRs) or chimeric antigen receptors (CARs), enriched with mixed lymphocyte tumor cell cultures (MLTCs), or cloned using autologous antigen presenting cells and tumor derived peptides. ACT in which the lymphocytes originate from the cancer-bearing host to be infused is termed autologous ACT. U.S. Publication No. 2011/0052530 relates to a method for performing adoptive cell therapy to promote cancer regression, primarily for treatment of patients suffering from metastatic melanoma, which is incorporated by reference in its entirety for these methods. In some embodiments, TILs can be administered as described herein. In some embodiments, TILs can be administered in a single dose. Such administration may be by injection, e.g., intravenous injection. In some embodiments, TILs and/or cytotoxic lymphocytes may be administered in multiple doses. Dosing may be once, twice, three times, four times, five times, six times, or more than six times per year. Dosing may be once a month, once every two weeks, once a week, or once every other day. Administration of TILs and/or cytotoxic lymphocytes may continue as long as necessary.

6. Exemplary Treatment Embodiments

In some embodiments, the present disclosure provides a method of treating a cancer with a population of tumor infiltrating lymphocytes (TILs) comprising the steps of (a) obtaining a first population of TILs from a tumor resected from a patient; (b) performing an initial expansion of the first population of TILs in a first cell culture medium to obtain a second population of TILs, wherein the second population of TILs is at least 5-fold greater in number than the first population of TILs, and wherein the first cell culture medium comprises IL-2; (c) performing a rapid expansion of the second population of TILs using a population of myeloid artificial antigen presenting cells (myeloid aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3; (d) administering a therapeutically effective portion of the third population of TILs to a patient with the cancer. In some embodiments, the present disclosure a population of tumor infiltrating lymphocytes (TILs) for use in treating cancer, wherein the population of TILs are obtainable by a method comprising the steps of (b) performing an initial expansion of a first population of TILs obtained from a tumor resected from a patient in a first cell culture medium to obtain a second population of TILs, wherein the second population of TILs is at least 5-fold greater in number than the first population of TILs, and wherein the first cell culture medium comprises IL-2; (c) performing a rapid expansion of the second population of TILs using a population of myeloid artificial antigen presenting cells (myeloid aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3; (d) administering a therapeutically effective portion of the third population of TILs to a patient with the cancer. In some embodiments, the method comprises a first step (a) of obtaining the first population of TILs from a tumor resected from a patient. In some embodiments, the IL-2 is present at an initial concentration of about 3000 IU/mL and OKT-3 antibody is present at an initial concentration of about 30 ng/mL in the second cell culture medium. In some embodiments, first expansion is performed over a period not greater than 14 days. In some embodiments, the first expansion is performed using a gas permeable container. In some embodiments, the second expansion is performed using a gas permeable container. In some embodiments, the ratio of the second population of TILs to the population of aAPCs in the rapid expansion is between 1 to 80 and 1 to 400. In some embodiments, the ratio of the second population of TILs to the population of aAPCs in the rapid expansion is about 1 to 300. In some embodiments, the cancer for treatment is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HN-SCC)), renal cancer, and renal cell carcinoma. In some embodiments, the cancer for treatment is selected from the group consisting of melanoma, ovarian cancer, and cervical cancer. In some embodiments, the cancer for treatment is melanoma. In some embodiments, the cancer for treatment is ovarian cancer. In some embodiments, the cancer for treatment is cervical cancer. In some embodiments, the method of treating cancer further comprises the step of treating the patient with a non-myeloablative lymphodepletion regimen prior to administering the third population of TILs to the patient. In some embodiments, the non-myeloablative lymphodepletion regimen comprises the steps of administration of cyclophosphamide at a dose of 60 mg/m2/day for two days followed by administration of fludarabine at a dose of 25 mg/m2/day for five days. In some embodiments, the high dose IL-2 regimen comprises 600,000 or 720,000 IU/kg of aldesleukin, or a biosimilar or variant thereof, administered as a 15-minute bolus intravenous infusion every eight hours until tolerance. In some embodiments, the TILs used for treatment have been contacted with one or more sd-RNAs targeting genes as described herein, including PD-1, LAG-3, TIM-3, CISH, and CBLB, which can be added to cell culture media during the first and/or second expansion, for Example, Steps B, C, and/or D according to FIG. 8, wherein the TILs and other agents can be added at amounts selected from the group consisting of 0.1 µM sd-RNA/10,000 TILs/100 µL media, 0.5 µM sd-RNA/10,000 TILs/100 µL media, 0.75 µM sd-RNA/10,000 TILs/100 µL media, 1 µM sd-RNA/10,000 TILs/100 µL media, 1.25 µM sd-RNA/10,000 TILs/100 µL media, 1.5 µM sd-RNA/10,000 TILs/100 µL media, 2 µM sd-RNA/10,000 TILs/100 µL media, 5 µM sd-RNA/10,000 TILs/100 µL media, or 10 µM sd-RNA/10,000 TILs/100 µL media. In some embodiments, the TILs used for treatment have been contacted with one or more sd-RNAs targeting genes as described herein, including PD-1, LAG-3, TIM-3, CISH, and CBLB, which can be added to TIL cultures during the first and/or second expansion, for Example, Steps B, C, and/or D according to FIG. 8, twice a day, once a day, every two days, every three days, every four days, every five days, every six days, or every seven days. In an embodiment, the TILs used for treatment have been contacted with one or more sd-RNAs targeting genes as described herein, including PD-1, LAG-3, TIM-3, CISH, and CBLB, wherein the TILs and other agents can be added during the first and/or second expansion, for Example, Steps B, C, and/or D according to FIG. 8, at amounts selected from the group consisting of 0.1 µM sd-RNA/10,000 TILs, 0.5 µM sd-RNA/10,000 TILs, 0.75 µM sd-RNA/10,000 TILs, 1 µM sd-RNA/10,000 TILs, 1.25 µM sd-RNA/10,000 TILs, 1.5 µM sd-RNA/10,000 TILs, 2 µM sd-RNA/10,000 TILs, 5 µM sd-RNA/10,000 TILs, or 10 µM sd-RNA/10,000 TILs. In an embodiment, the TILs used for treatment have been contacted with one or more sd-RNAs targeting genes as described herein, including PD-1, LAG-3, TIM-3, CISH, and CBLB, wherein the TILs and other agents can be added to TIL cultures during the during the first and/or second expansion, for Example, Steps B, C, and/or D according to FIG. 8, twice a day, once a day, every two days, every three days, every four days, every five days, every six days, or every seven days.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1: Closed System Assays

As discussed herein, protocols and assays were developed for generating TIL from patient tumors in a closed system.

This Example describes a novel abbreviated procedure for generating clinically relevant numbers of TILs from patients' resected tumor tissue in G-REX devices and cryopreservation of the final cell product. Additional aspects of this procedure are described in Examples 2 to 8.

Procedure

Advanced preparation: Day 0 (Performed up to 36 hours in advance), Prepared TIL Isolation Wash Buffer (TIWB) by supplementing 500 mL Hanks Balanced Salt Solution with 50 µg/mL Gentamicin. For 10 mg/mL Gentamicin stock solution transferred 2.5 mL to HBSS. For 50 mg/mL stock solution transferred 0.5 mL to HBSS.

Prepared CM1 media with GlutaMax™ per LAB-005 "Preparation of media for PreREP and REP" for CM2 instructions". Store at 4° C. up to 24 hours. Allowed to warm at 37° C. for at least 1 hour prior to use.

Removed IL-2 aliquot(s) from −20° C. freezer and placed aliquot(s) in 2-8° C. refrigerator. Removed tumor specimen and stored at 4° C. until ready for processing.

Shipped unused tumor either in HypoThermasol or as frozen fragments in CryoStor CS10 (both commercially available from BioLife Solutions, Inc.).

Tumor Processing for TIL

Aseptically transferred the following materials to the BSC, as needed, and labeled according to Table 16 below.

TABLE 16

Materials for tumor isolation.

| Item | Minimum Quantity | In-Process Label |
| --- | --- | --- |
| Tumor | 1 | N/A |
| Petri dish, 150 mm | 1 | Dissection |
| Petri dish, 100 mm | 4 | Wash 1, 2, 3, 4 |
| Petri dish, 100 mm | 1 | Unfavorable Tissue |
| 6 well plate | 2 | Lid Label-"Tumor Fragments" Plate Bottom-"Favorable Tissue" |
| Ruler | 2 | N/A |
| Wash Buffer | 1 | N/A |
| Forceps | 1 | N/A |
| Long forceps | 1 | N/A |
| Scalpel | As needed | N/A |

Transferred 5 mL Gentamicin to the HBSS bottle. Labeled as TIWB. Swirled to mix. Pipetted 50 mL TIWB to each dish. Using long forceps, removed the tumor(s) from the Specimen bottle and transferred to the Wash 1 dish. Incubated the tumor at ambient temperature in the wash dish for 3 minutes. Transferred the tumor to the wash dish and incubated the tumor at ambient temperature in the was dish for 3 minutes. Repeat wash in new wash dish.

Measured and recorded the length of the tumor. Performed an initial dissection of the tumor pieces into 10 intermediate pieces and conserve the tumor structure of each intermediate piece. Working with one intermediate tumor piece at a time, carefully sliced the tumor into up to 3×3×3 mm fragments. Repeated for the remaining intermediate tumor pieces.

If fewer than 4 tumor fragments were available, used other fragments as available to achieve the 40 fragment goal. When less than 40 fragments, 10-40 were placed in a singled G-Rex 100M flask Seeding G-Rex 100M Flask Aseptically transferred the following materials to the BSC, as needed, and labeled according to the Table 4 below.

TABLE 17

Additional Materials for Seeding Flasks.

| Item | Minimum Quantity | In-Process Label |
| --- | --- | --- |
| G-Rex 100M flask | As Needed | Lot# |
| Warm CM1 | As Needed | Lot# |
| IL-2 Aliquots | As Needed | Lot# |

Supplemented each liter of CM1 with 1 mL of IL-2 stock solution ($6 \times 10^6$ IU/mL).

Placed 1000 mL of pre-warmed CM1 containing 6,000 IU/mL of IL-2 in each G-REX 100M bioreactor needed as determined by Table 5 below. Using a transfer pipette, transferred the appropriate number of tumor fragments to each G-Rex 100M flask, distributing fragments per Table 5. When one or more tumor fragments transferred to the G-Rex 100M flask float, obtained one additional tumor fragment as available and transferred it to the G-Rex 100M flask. Recorded the total number of fragments added to each flask. Placed each G-REX 100M bioreactor in 37° C., 5% CO2 incubator.

When >41 fragments were obtained, placed 1000 mL of pre-warmed complete CM1 in a second G-REX 100M bioreactor.

TABLE 18

Number of G-REX bioreactors needed.

| Number of Fragments | G-REX | Number of G-REX | CM1 needed |
| --- | --- | --- | --- |
| 1-40 | G-REX 100M | 1 | 1000 mL |
| 41-80 distribute between flasks | G-REX 100M | 2 | 2000 mL |
| >80 | Freeze fragments in CS10 after 15 minute pre-incubation | | |

Advanced Preparation: Day 11 (Prepared up to 24 hours in advance)

Prepared 6 L of CM2 with GlutaMax. Used reference laboratory procedures for "Preparation of media for PreREP and REP" for CM2 instructions". Warmed at 37° C., 1 hour prior to use. Thawed IL-2 aliquots: Removed IL-2 aliquots from freezer and placed at 4° C.

Harvest TIL (Day 11)

Removed G-REX-100M flasks from incubator and placed in BSC2. Did not disturb the cells on the bottom of the flask. Using GatherRex or peristaltic pump aspirated ~900 mL of cell culture supernatant from flask(s). Resuspended TIL by gently swirling flask. Observed that all cells have been liberated from the membrane. Transferred the residual cell suspension to an appropriately sized blood transfer pack (300-1000 mL). Was careful to not allow the fragments to be transferred to the blood transfer pack. Spiked the transfer pack with a 4" plasma transfer set. Mixed cell suspension and using a 3 mL syringe, removed 1 mL TIL suspension for cell counts. Placed the transfer pack into the incubator until ready to use.

Media Preparation

Allowed media to warm at 37° C. for >1 hr. Added 3 mL of $6 \times 10^6$ IU/mL stock rhIL-2 to 6 L CM2 to reach a final concentration of 3,000 IU/mL rhIL-2 ("complete CM2"). Sterile welded a 4" plasma transfer set with female luer to a 1 L Transfer pack. Transferred 500 mL complete CM2 to a 1 L transfer pack. Using a 1.0 mL syringe with needle drew up 150 μL of 1 mg/mL anti-CD3 (clone OKT3) and transferred to 500 mL "complete CM2". Stored at 37° C. until use.

Flask Preparation

Transferred 4.5 L "complete CM2" to a G-REX-500M flask and placed flask into 37° C. incubator until ready.

Thaw Irradiated Feeders

Utilized $5.0 \times 10^9$ allogenic irradiated feeders from two or more donors for use. Removed feeders from LN2 freezer. Thawed feeders in 37° C. incubator or bead bath. Removed feeders from bath when almost completely thawed but still cold. Added each feeder bag directly to the open G-Rex 500M to assure sufficient number of irradiated cells ($5 \times 10^9$ cells, +/−20%). Removed 1 L transfer pack with 500 mL "complete CM2"+OKT3 and transferred to BSC. Drew the entire contents of the feeder bags into the syringe, recorded the volume, and dispensed $5.0 \times 10^9$ allogenic irradiated feeders into the transfer pack.

When +/−10% of the target cell number ($5.0 \times 10^9$) was reached with >70% viability, proceeded. When less than 90% of the target cell number ($5.0 \times 10^9$) was reached with >70% viability thawed another bag and repeated above. When greater than 110% of the target cell number was achieved, calculated the proper volume required for desired cell dose and proceeded.

Co-Culture TIL and Feeders in G-REX 500M Flask

Removed the G-REX 500M flask containing prepared media from the incubator. Attached feeder transfer pack to G-REX-500M and allowed contents of the bag to drain into the 500M. Calculated volume of TIL suspension to add to achieve $200 \times 10^6$ total viable cells.

(TVC/mL)/$200 \times 10^6$=mL

When TIL were between $5\text{-}200 \times 10^6$ total viable cells, added all TIL (total volume) to the G-REX-500M. When TIL count was greater than $200 \times 10^6$ total viable cells, added calculated volume necessary for $200 \times 10^6$ TIL to be distributed to an individual G-REX-500M. Remaining TIL were spun down and frozen in at least two cryovials at up to $10^8$/mL in CS10, labeled with TIL identification and date frozen.

Placed the G-REX-500M in a 37° C., 5% CO2 incubator for 5 days.

Advanced Preparation: Day 16-18

Warmed one 10 L bag of AIM V for cultures initiated with less than $50\times10^6$ TIL warmed two bags for those initiated with greater than $50\times10^6$ TIL at 37° C. at least 1 hr or until ready to use.

Performed TIL Cell Count: Day 16-18

Removed G-REX-500M flask from incubator and were careful not to disturb the cell culture on the bottom of the flask. Removed 4 L of cell culture media from the G-REX-500M flask and placed into a sterile container. Swirled the G-REX-500M until all TIL had been resuspended from the membrane. Transferred cell suspension to a 2 L transfer pack. Retained the 500M flask for later use. Calculated the total number of flasks required for subculture according to the following formula. Rounded fractions up.

Total viable cells/$1.0\times10^9$=flask #

Prepare CM4

Prepared a 10 L bag of AIM-V for every two 500M flasks needed. Warmed additional media as necessary. For every 10 L of AIM-V needed, added 100 mL of GlutaMAX to make CM4. Supplemented CM4 media with rhIL-2 for a final concentration of 3,000 IU/mL rhIL-2. Split the cell culture. Filled each G-REX-500M to 5 L. Evenly distributed the TIL volume amongst the calculated number of G-REX-500Ms. Placed flasks in a 37° C., 5% CO2 incubator until harvest on Day 22 of REP.

Advanced Preparation: Day 22-24

Prepared 2 L of 1% HSA wash buffer by adding 40 mL of 25% HSA to each of two 1 L bags of PlasmaLyte A 7.4. Pool into a LOVO ancillary bag. Supplemented 200 mL CS10 with IL-2 @ 600 IU/mL. Pre-cooled four 750 mL aluminum freezer canisters at 4° C.

Harvest TIL: Day 22-24

Removed the G-REX-500M flasks from the 37° C. incubator and were careful to not disturb the cell culture on the bottom of the flask. Aspirated and discarded 4.5 L of cell culture supernatant from each flask. Swirled the G-REX-500M flask to completely resuspend the TIL. Harvested TIL into the bioprocess bag. Mixed bag well and using a 3 mL syringe take 2×2 mL samples for cell counting. Weighed the bag and found the difference between the initial and final weight. Used the following calculation to determine the volume of cell suspension.

Net weight of cell suspension(mL)/1.03=volume (mL)

Filter TIL and prepare LOVO Source bag. Once all cells were transferred to the LOVO source bag, closed all clamps and sealed the LOVO source bag tubing to remove filter and weighed. Calculated volume.

Formulate TIL 1:1 in cold CS10 supplemented with 600 IU/mL rhIL-2.

Calculated required number of cryobags needed.

(volume of cell product×2)/100=number of required bags(round down)

Calculated the volume to dispense into each bag.

(volume of cell product×2)/number of required bags=volume to add to each bag

Aseptically transferred the following materials in Table 6 to the BSC.

TABLE 19

Materials for TIL cryopreservation.

| Item | Minimum Quantity | In-Process Label |
|---|---|---|
| Cell product | 1 | Lot# |
| Aluminum freezer cassette (750 ml) | 1 | n/a |
| Cold CS10 + IL-2 @600 IU/mL | As Needed | Lot# |
| Cell Connect CC1 device | 1 | n/a |
| 750 mL cryobags | calculated | Label aliquots 1-largest# |
| 100 mL syringe | #cryobags + 1 | n/a |
| 3 way stopcock | 1 | n/a |
| Cryovials | 5 | TIL Cryo-product satellite vials |

TIL formulation

Attached the LOVO final product, CS10 bag luer lock and the appropriate number of cryobags. The amount of CS10 volume needed was equivalent to the volume of the LOVO final product bag. Mixed LOVO final product bag by inversion.

Transferred 100 mL of formulated product into each cryobag. Removed all air bubbles from cryobag and sealed. Transferred sealed bags to 4° C. while and placed into pre-cooled aluminum freezer canisters.

Cryopreservation of TIL using Control Rate Freezer (CRF).

Followed standard procedure for the controlled rate freezer. After using the CRF, stored cryobags in liquid nitrogen ($LN_2$).

Example 2: Lymphodepletion

Cell counts can be taken at day 7 and prior to lymphodepletion. The final cell product included up to approximately $150\times10^9$ viable cells formulated in a minimum of 50% HypoThermosol™ in Plasma-Lyte A™ (volume/volume) and up to 0.5% HSA (compatible for human infusion) containing 300 IU/mL IL2. The final product was available for administration in one of two volumes for infusion:

1) 250 mL (in a 300-mL capacity infusion bag) when the total TIL harvested are $\leq75\times10^9$

OR 2) 500 mL (in a 600-mL capacity infusion bag) when the total TIL harvested are $<150\times10^9$ The total number of cells that could be generated for the final TIL infusion product for each patient due to patient-to-patient variation in T-cell expansion rates during the REP step cannot be predicted. A lower limit of cells on day 3, 4, 5, 6, 7 of the 3 to 14-day REP is set based on the minimum number of cells needed in order to make a decision to lymphodeplete the patient using the cyclophosphamide plus fludarabine chemotherapy regimen. Once we have begun lymphodepletion based on this minimal attained cell number, we are committed to treating the patient with the available number of TIL we generate in the REP by any of days 3 to 14, and in many cases day 7. The upper limit of the range for infusion ($150\times10^9$ viable cells) is based on the known published upper limit safely infused where a clinical response has been attained. Radvanyi, et al., *Clin Cancer Res* 2012, 18, 6758-6770.

Example 3: Process 2A—Day 0

This example describes the detailed day 0 protocol for the 2A process described in Examples 3 to 6.

Preparation.

Confirmed Tumor Wash Medium, CM1, and IL-2 are within expiration date. Placed CM1 (cell media 1) in incubator.

Method.

Prepared TIL media CM1 containing 6000 IU/mL IL-2: 1 L CM1 and 1 ml IL-2 (6,000,000 IU/mL). Placed 25 ml of CM1+IL2 into 50 ml conical to be used for fragments when adding to G-REX and placed in 37° C. incubator to pre-warm.

Pumped 975 ml of pre-warmed CM1 containing 6,000 IU/ml of IL-2 in each G-REX 100MCS bioreactor. Placed G-REX 100MCS in incubator until needed.

Tissue Dissection

Recorded the start time of tumor processing. Pipetted 3-5 mL of Tumor Wash Medium into each well of one six well plates for excess tumor pieces. Pipetted 50 mL of Tumor Wash Medium to wash dishes 1-3 and holding dish. Placed two 150 mm dissection dishes into biosafety cabinet. Placed 3 sterile 50 mL conical tubes into the BSC. Added 5-20 mL of tumor wash medium to each conical. The forceps and scalpels were dipped into the tumor wash media as needed during the tumor washing and dissection process.

Removed the tumor(s) from the Specimen bottle and transferred to the Wash 1 dish. Incubated the tumor at ambient in the Wash 1 dish for ≥3 minutes. Transferred the tumor to the Wash 2 dish. Incubated the tumor at ambient in the Wash 2 dish for ≥3 minutes. Transferred the tumor to the Wash 3 dish. Incubated the tumor at ambient in the Wash 3 dish for ≥3 minutes. Transferred the tumor to the Dissection dish, measured and recorded the length of the tumor.

Performed an initial dissection of the tumor pieces in the Dissection dish into intermediate pieces taking care to conserve the tumor structure of each intermediate piece. Transferred any intermediate tumor pieces not being actively dissected into fragments to the tissue holding dish to ensure the tissue remained hydrated during the entire dissection procedure.

Worked with one intermediate tumor piece at a time, carefully sliced the tumor into approximately 3×3×3 mm fragments in the Dissection Dish. Continued dissecting fragments from the intermediate tumor piece until all tissue in the intermediate piece had been evaluated. Selected favorable fragments and using a transfer pipette transferred up to 4 favorable fragments into the wash medium drops in one circle in the Tumor Fragments dish. Using a transfer pipette scalpel or forceps, transferred, as much as possible of the unfavorable tissue and waste product to the Unfavorable Tissue. All remaining tissue was place into one of the wells of the six-well plate. (Unfavorable tissue was indicated by yellow adipose tissue or necrotic tissue.) Continued processing for the remaining intermediate tumor pieces, working one intermediate piece at a time until the entire tumor had been processed.

Transferred up to 50 of the best tumor fragments to the 50 mL conical tube labeled tumor fragments containing the CM1. Removed floaters from 50 mL conical. Recorded number of fragments and floaters. Swirled conical with tumor fragments and poured the contents on the 50 ml conical into the G-Rex 100MCS flask. If one or more tumor fragments transferred to the G-Rex 100M flask float, obtained one additional tumor fragment when available from the Favorable Tissue Dish and transfer it to the G-Rex 100M flask.

Recorded incubator # (s) and total number of fragments added to each flask. Placed the G-REX 100M bioreactor in 37° C., 5% $CO_2$ incubator.

Example 4: Process 2A—Day 11

This example describes the detailed day 11 protocol for the 2A process described in Examples 3 to 6.

Prior Preparation.

Day before Processing:

CM2 could be prepared the day before processing occurred. Place at 4° C.

Day of processing.

Prepared the feeder cell harness. Prepared 5 mL of cryopreservation media per CTF-FORM-318 and place at 4° C. until needed.

Prepare G-Rex 500MCS Flask. Using 10 mL syringe aseptically transferred 0.5 mL of IL-2 (stock is 6×10$^6$ IU/mL) for each liter of CM2 (cell media 2) into the bioprocess bag through an unused sterile female luer connector. Ensured all the IL-2 had been mixed with the media. Pumped 4.5 Liters of the CM2 media into the G-Rex 500MCS. Placed G-Rex 500MCS in the incubator.

Prepare Irradiated Feeder Cells

Recorded the dry weight of a 1 L transfer pack (TP). Pumped 500 mL CM2 by weight into the TP. Thawed feeder cells in the 37° C. (+/−1° C.) water bath. Mixed final feeder formulation well. Using a 5 mL syringe and needless port, rinsed port with some cell solution to ensure accurate sampling and remove 1 ml of cells, placed into tube labeled for counting. Performed a single cell counts on the feeder cell sample and record data and attach counting raw data to batch record. If cell count was <5×10$^9$, thawed more cells, count, and added to feeder cells. Re-weighed feeder bag and calculated volume. Calculated volume of cells to remove.

Addition of Feeder to G-REX

Mixed cells well and removed the volume calculated above to achieve 5.0×10$^9$ cells. Discarded unneeded cells. Using a 1 mL syringe and 18G needle draw up 0.150 mL of OKT3, removed needle and transferred to the feeder TP through the female luer. Sterile welded the feeder bag to the red line on the G-Rex 500MCS. Unclamped the line and allowed the feeder cells to flow into the flask by gravity. Returned the G-Rex 500MCS to the incubator and recorded time.

Prepare TIL: Record Time Initiation of TIL Harvest

Carefully removed G-Rex 100MCS from incubator. Using the GatheRex transferred ~900 mL of the culture supernatant to the 1 L transfer pack. Swirled the flask until all the cells had been detached from the membrane. Checked the membrane to make sure all cells are detached. Tilted flask away from collection tubing and allowed tumor fragments to settle along edge. Slowly tipped flask toward collection tubing so fragments remain on opposite side of flask. Using the GatheRex transferred the residual cell suspension into the 300 mL transferred pack avoiding tumor fragments. Rechecked that all cells had been removed from the membrane. If necessary, back washed by releasing clamps on GatheRex and allowed some media to flow into the G-Rex 100MCS flask by gravity. Vigorously tapped flask to release cells and pumped into 300 ml TP. After collection was complete, closed the red line and heat seal.

Recorded mass (including dry mass) of the 300 ml TP containing the cell suspension and calculated the volume of cell suspension. Mixed cells well. Aseptically attached a 5 mL syringe draw 1 mL, placed in cryo vial. Repeated with second syringe. These were used for cell counting, viability. Placed in incubator and recorded time place in incubator. Performed a single cell count on each sample and recorded.

If necessary adjusted total viable TIL density to ≤2×10⁸ viable cells. Calculated volume to remove or note adjustment not necessary.

Transferred excess cells to an appropriately sized conical tube and placed in the incubator with cap loosened for later cryopreservation.

Removed the G-Rex 500MCS from the incubator and pumped cells into flask. Returned the G-Rex 500MCS to the incubator and record the time placed in the G-Rex incubator.

Cryopreservation of Excess

Calculated amount of freezing media to add to cells:

TABLE 20

| Target cell concentration was $1 \times 10^8$/ml | |
|---|---|
| A. Total cells removed (from step 15) | mL |
| B. Target cell concentration | $1 \times 10^8$ cells/mL |
| Volume of freezing media to add (A/B) | mL |

Spun down TIL at 400×g for 5 min at 20° C. with full brake and full acceleration. Aseptically aspirated supernatant. Resuspended cells in remaining fluid, and while resuspending, slowly added prepared freezing media. Aliquoted and placed into −80° C.

Example 5: Process 2A—Day 16

This example describes the detailed day 16 protocol for the 2A process described in Examples 3 to 6.

Harvest and Count TIL.

Warmed one 10 L bag of CM4 for cultures initiated with less than 50×10⁶ TIL in a 37° C. incubator at least 30 minutes or until ready to use. Removed the G-Rex 500MCS flask from the incubator and using the GatheRex transferred ~4 L of culture supernatant to the 10 L Labtainer. Harvested according to appropriate GatheRex harvesting instructions.

After removal of the supernatant, swirled the flask until all the cells had been detached from the membrane. Tilted the flask to ensure hose was at the edge of the flask. Using the GatheRex transferred the residual cell suspension into the 2 L TP maintaining the tilted edge until all cells were collected. Inspected membrane for adherent cells. Vigorously tapped flask to release cells. Added cells to 2 L TP. Heated seal the 2 L transfer pack. Recorded mass of transfer pack with cell suspension and calculated the volume of cell suspension. Determined cell suspension volume, including dry mass.

Mixed the cells gently and draw up 11 ml and aliquoted as shown in Table 21.

TABLE 21

| Testing parameters. | | |
|---|---|---|
| Test | Sample volume | Vessel |
| Cell Count and viability | 2-2 mL samples | Cryovials |
| Mycoplasma | 1 mL | Cryovial stored at 4° C. until testing completed. |
| Sterility | 1 mL | Inoculated 0.5 mL into one each anaerobic and aerobic culture bottles |
| Flow | 2-2 mL | Unused cell count (Cryopreserved for future batch testing) |
| Remainder of cells | | Discarded |

Calculated new volume and recorded Volume in 2 L transfer pack based on volume of cell suspension and volume removed for QC (11 mL).

Inoculated and ordered sterility testing. Stored the mycoplasma sample at 4° C. in the pending rack for mycoplasma testing. Set aside until TIL was seeded.

Cell Count:

Performed single cell counts and recorded data and attach counting raw data to batch record. Documented Dilution. Documented the Cellometer counting program. Verified the correct dilution was entered into the Cellometer. Calculated the total number of flasks required for subculture.

IL-2 Addition to CM

Placed 10 L bag of Aim V with Glutamax. Withdrew 5 mL of IL-2 into the syringe (final concentration is 3000 IU/ml) and dispensed IL-2 into the bag. Repeated for remaining bags of Aim V.

Prepare G-REX500MCS Flasks

Determined amount of CM4 to add to flasks. Recorded volume of cells added per flask and volume of CM4 5000 mL-A. Placed flasks in a 37° C., 5% $CO_2$.

Seeded Flasks with TIL

Placed the cell product bag on analytical balance and recorded time TIL added to G-REX flask. Mixed cells well. Repeated cell transfer for all flasks. Placed flasks in a 37° C., 5% $CO_2$ and recorded time TIL added to G-REX flask. Ordered testing for settle plates to the microbiology lab, as well as testing for aerobic and anaerobic sterility.

Cryopreservation of Flow or Excess Cells:

Calculated amount of freezing media required: Target cell concentration was 1×108/ml; record total cells removed. Target cell concentration was 1×10⁸ cells/mL. Calculated total volume of freezing media to add.

Prepared cryo preservation media and placed at 40° C. until needed. Spun down TIL at 400×g for 5 min at 20° C. with full brake and full acceleration. Aspirated supernatant. Gently tapped bottom of tube to resuspend cells in remaining fluid, and while gently tapping the tube slowly added prepared freezing media. Aliquoted into appropriate sized labelled cryo tubes. Placed in a −80° C. freezer. Within 72 hours transferred to permanent storage location and documented and recorded date and time placed in −80° C. freezer.

Example 6: Process 2A—Day 22

This example describes the detailed day 22 protocol for the 2A process described in Examples 3 to 6.

Advanced Preparation

Placed three 1 L bags of PlasmaLyte A in the BSC. Prepared pool and labeled the PlasmaLyte A bags with 1% HSA. Load 120 mL of 25% has for transfer. Transferred HSA to 3 L PlasmaLyte bag. Mix well. Removed 5 mL of PlasmaLyte with 1% HSA from the needleless port on the 3 liter bag. Labeled as LOVO Wash buffer and date.

IL-2 Preparation

Dispensed Plasmalyte/1% HSA from 5 mL syringe into a labeled 50 ml sterile conical tube. Added 0.05 mL IL-2 stock to the tube containing PlasmaLyte and labeled IL-2 6×10⁴. Store at 2-8° C.

Preparation of Cells

Removed the G-REX 500M flasks from the 37° C. Using the GatheRex pump, volume reduced the first flask. Swirled the G-REX 500M flask until the TIL were completely resuspended while avoiding splashing or foaming. Made sure all cells have been dislodged from the membrane. Tilted the G-Rex flask such that the cell suspension was pooled in the side of the flask where the collection straw was located.

Started GatherRex to collect the cell suspension and ensured all cells had been removed from the flask. If cells remained in the flask, added 100 mL of supernatant back to the flask, swirled, and collected into the cell suspension bag. Repeated for additional flasks. Heated seal and labeled as LOVO Source Bag. Recorded the dry weight.

Allow TIL to drain from the cell suspension bag through the filter and into the LOVO source bag. Once all cells were transferred to the LOVO source bag, closed all clamps, heated seal just above the mark and detached. Mixed bag well and using a two 3 mL syringe take 2 independent 2 mL samples from the syringe sample port for cell counting and viability. Weighed the bag and determined the difference between the initial and final weight. Recorded data and place in incubator, including dry mass.

Cell Count.

Performed a single cell count on each sample and recorded data and attach counting raw data to batch record. Documented the Cellometer counting program. Verified the correct dilution was entered into the Cellometer. Determined total number of nucleated cells. Determined number of TNC to remove to retain=$1.5 \times 10^{11}$ cells for LOVO processing. Place removed cell into appropriate size container for disposal.

LOVO Harvest

The 10 L Labtainer with Baxter extension set in Prior Preparation was the replacement filtrate bag welded to the LOVO kit. Followed LOVO displays. To start the procedure, selected the "TIL G-Rex Harvest" protocol from the drop-down menu and follow instructions.

When Final Product Volume (Retentate Volume) screen displayed, using the Total nucleated cells (TNC) value from Table 15, determined the final product target volume in the table below (Table 16). Entered the Final Product Volume (mL) associated with that Cell Range during LOVO Procedure setup.

TABLE 22

Determination of Final Product Target Volume.

| Cell Range | Final Product (Retentate) Volume to Target (mL) |
| --- | --- |
| 0 < Total (Viable + Dead) Cells ≤ 7.1E10 | 150 |
| 7.1E10 < Total (Viable + Dead) Cells ≤ 1.1E11 | 200 |
| 1.1E11 < Total (Viable + Dead) Cells ≤ 1.5E11 | 250 |

TABLE 23

Product target volume.

| Total nucleated cells (TNC) ×10$^6$ | Final Product (Retentate) Target Volume (mL) |
| --- | --- |

To target the specified volume from Table 16 touched the Final Product Volume (mL) entry field. A numeric keypad displayed. Entered the desired Final Product Volume in unit of mL.

Made a note of the volumes displayed for Filtrate and Solution 1 (read PlasmaLyte). Made a note of the volumes displayed for Filtrate and Solution 1 (read PlasmaLyte).

Pre-coated the IP bag. Mixed the Source bag. During the LOVO procedure, the system automatically paused to allow the operator to interact with different bags. Different screens displayed during different pauses. Followed the corresponding instructions for each screen.

Source Rinse Pause

After draining the Source bag, the LOVO added wash buffer to the Source bag to rinse the bag. After the configured volume of wash buffer had been added to the Source bag, the LOVO paused automatically and displayed the Source Rinse Paused Screen.

The LOVO processed the rinse fluid from the Source bag, then continued with the automated procedure.

Mix IP Bag Pause

To prepare cells for another pass through the spinner, the IP bag was diluted with wash buffer. After adding the wash buffer to the IP bag, the LOVO paused automatically and displayed the "Mix IP bag" Pause Screen.

When the "Mix IP bag" Pause Screen displayed, the operator inverted the IP bag several times to thoroughly mix the cell suspension. Follow instructions to resume the LOVO processing fluid from the IP bag.

Massage IP Corners Pause

During the final wash cycle of the LOVO procedure, cells were pumped from the IP bag, through the spinner, and to the Retentate (Final Product) bag. When the IP bag was empty, 10 mL of wash buffers was added to the bottom port of the IP bag to rinse the bag. After adding the rinse fluid, the LOVO paused automatically and displayed the "Massage IP corners" Pause Screen.

When the "Massage IP corners" Pause Screen displayed, the operator massaged the corners of the bag to bring any residual cells into suspension. Resumed the LOVO to pump out the rinse fluid from the IP bag.

At the end of the LOVO procedure, the Remove Products Screen displayed.

Recorded the data from the results, as formatted in Table 17.

TABLE 24

LOVO results summary table.

| Elapsed Processing Time (parentheses #) | Elapsed Source Processing Time (parentheses #) | Pause Time | Source Volume (mL) | Retentate Volume (mL) | Filtrate Volume (mL) | Solution 1 Volume (mL) |
| --- | --- | --- | --- | --- | --- | --- |
| A. | B. | C. | D. | E. | F. | G. |

Shutdown LOVO Shutdown Procedure

Recorded final formulated product volume. Calculated amount of IL-2 required from final product table.

A. Calculated amount of IL-2 needed for final product.
(300 IU/ml of IL-2 final product):
Final product volume (ml) [Volume of Formulated Cell Product from Final Formulated Product Volume Table] × 300 IU/ml = IU of IL-2 required
ml × 300 IU = IU of IL-2 required
B. IU IL-2 required ÷ working stock dilution
(Concentration of 6 × 10$^4$ IU/mL) prepared in IL-2
preparation step = volume (ml) of IL-2 to add to final product.
IU of IL-2 required from above] ÷ 60,000 IU/ml = ml IL-2 working stock Determined the number of Cryobags and Retain Volume Marked on the Target volume and retain table below the number of cryopreservation bags and volume of retention sample for product.

Targeted volume/bag calculation: (Final formulated volume–volume adjustment due to not getting 100% recovery=10 mL)/# bags.

Prepared cells with 1:1 (vol:vol) CS10 (CryoStor 10, BioLife Solutions) and IL-2.

Prepared cells with IL-2 and connected apparatus. Placed cells and apparatus in transport bag and place at 2-8° C. for ≤15 min.

Addition of CS10

Drew up the amount of cold CS10 determined in the "Final Formulated Product Volume" table. Slowly and with gentle mixing, added CS10 (1:1, vol:vol) to cells.

Addition of Formulated Cell Product into Cryobags

Replaced syringe with appropriate size syringe for volume of cells to be placed in each cryo bag. Mixed cell product. Opened the clamp leading to the cell product bag and drew up appropriate volume.

Record Final Product Volume

Using needless port and appropriate size syringe, drew up amount of retain determined previously. Place retained in 50 mL conical tube labelled "Retain". Using the syringe attached to the harness removed all air from bag drawing up cells to about 1" past bag into tubing. Placed at 2-8° C. Mixed cells in cell product bag and repeat steps 3-8 for remaining CS750 bags using a new syringe on the stopcock and new syringe to obtain cell retain. Retained should be set aside for processing once product was in CRF.

Controlled-Rate Freezer (CRF) Procedure (see also Example 16)

The freezer was held at 4° C. until ready to add samples. Added samples to CRF.

Waited until CRF returns to 4° C. Once temperature was reached, follow CRF program to cryoperserve. Performed a visual inspection of the cryobags for the following (Note: did not inspect for over or underfill): container integrity, port integrity, seal integrity, presence of cell clumps, and presence of particles.

Placed the cryobags into preconditioned cassettes and transferred to the CRF. Evenly distributed the cassettes in the rack in the CRF. Applied ribbon thermocouple to the center cassette, or place dummy bag in center position.

Closed the door to the CRF. Once the chamber temperature reached 4° C.+/−1.5° C. Recorded the time and the chamber temperature that the product is transferred to the CRF.

Processing of Quality Control Sample

Aseptically transferred the following materials, as needed, and labeled according to QC and Retention Table 25. 1-Cell Count tube, 1-Endotoxin tube, 1-Mycoplasma tube, 1-Gram stain tube, 1 tube restimulation tube, and 1-flow tube to QC for immediate testing. The remaining duplicate tubes were placed in the controlled rate freezer.

TABLE 25

Testing and storage instructions.

| Test | Vessel |
|---|---|
| Cell Count and viability | Cryovials. |
| Mycoplasma | Cryovial stored at 4° C. until testing completed. |
| Sterility | Inoculate 0.5 mL into an anaerobic and 0.5 mL into an aerobic culture bottle. |
| Gram Stain | Cryovial stored at 4° C. until testing completed. |
| Endotoxin | Cryovial stored at 4° C. until testing completed. |
| Flow | Cryovial stored at 4° C. until testing completed. |
| Post Formulation | Cryopreserve for future testing: Consist of 5 satellite vial, 1-Cell Count tube, 1-Endotoxin |

TABLE 25-continued

Testing and storage instructions.

| Test | Vessel |
|---|---|
| Retention | tube, 1-Mycoplasma tube, 1-Gram stain tube, and 1-flow tube to QC for immediate testing. |
| Restimulation | Sample is delivered at room temperature and assay must be started within 30 minutes of cell count results. |

Cell Count

Performed a single cell count on each sample and recorded data and attached counting raw data to batch record. Document the Cellometer counting program. Verified the correct dilution was entered into the Cellometer.

Cryopreservation of Post Formulation Retention Cells: Placed vial in CRF. Moved to storage location after completion of freeze and recorded date and time placed in CFR. Recorded date and time moved to $LN_2$.

Microbiology testing: Ordered testing for aerobic and anaerobic sterility.

Post-Cryopreservation of Cell Product Bags

Stopped the freezer after the completion of the run. Removed cryobags from cassette. Transferred cassettes to vapor phase LN2.

Example 7: Use of IL-2, IL-15, and IL-21 Cytokine Cocktail

This example describes the use of IL-2, IL-15, and IL-21 cytokines, which serve as additional T cell growth factors, in combination with the TIL process of Examples 1 to 10.

Using the process of Examples 1 to 10, TILs were grown from colorectal, melanoma, cervical, triple negative breast, lung and renal tumors in presence of IL-2 in one arm of the experiment and, in place of IL-2, a combination of IL-2, IL-15, and IL-21 in another arm at the initiation of culture. At the completion of the pre-REP, cultures were assessed for expansion, phenotype, function (CD107a+ and IFN-γ) and TCR Vβ repertoire. IL-15 and IL-21 are described elsewhere herein and in Gruijl, et al., IL-21 promotes the expansion of CD27+CD28+ tumor infiltrating lymphocytes with high cytotoxic potential and low collateral expansion of regulatory T cells, Santegoets, S. J., J Transl Med., 2013, 11:37 (https://www.ncbi.nlm.nih.gov/pmc/articles/PMC3626797/).

The results showed that enhanced TIL expansion (>20%), in both $CD4^+$ and $CD8^+$ cells in the IL-2, IL-15, and IL-21 treated conditions were observed in multiple histologies relative to the IL-2 only conditions. There was a skewing towards a predominantly $CD8^+$ population with a skewed TCR Vβ repertoire in the TILs obtained from the IL-2, IL-15, and IL-21 treated cultures relative to the IL-2 only cultures. IFN-γ and CD107a were elevated in the IL-2, IL-15, and IL-21 treated TILs, in comparison to TILs treated only IL-2.

Example 8: Phase 2, Multicenter, Three-Cohort Study in Melanoma

Figure 26:
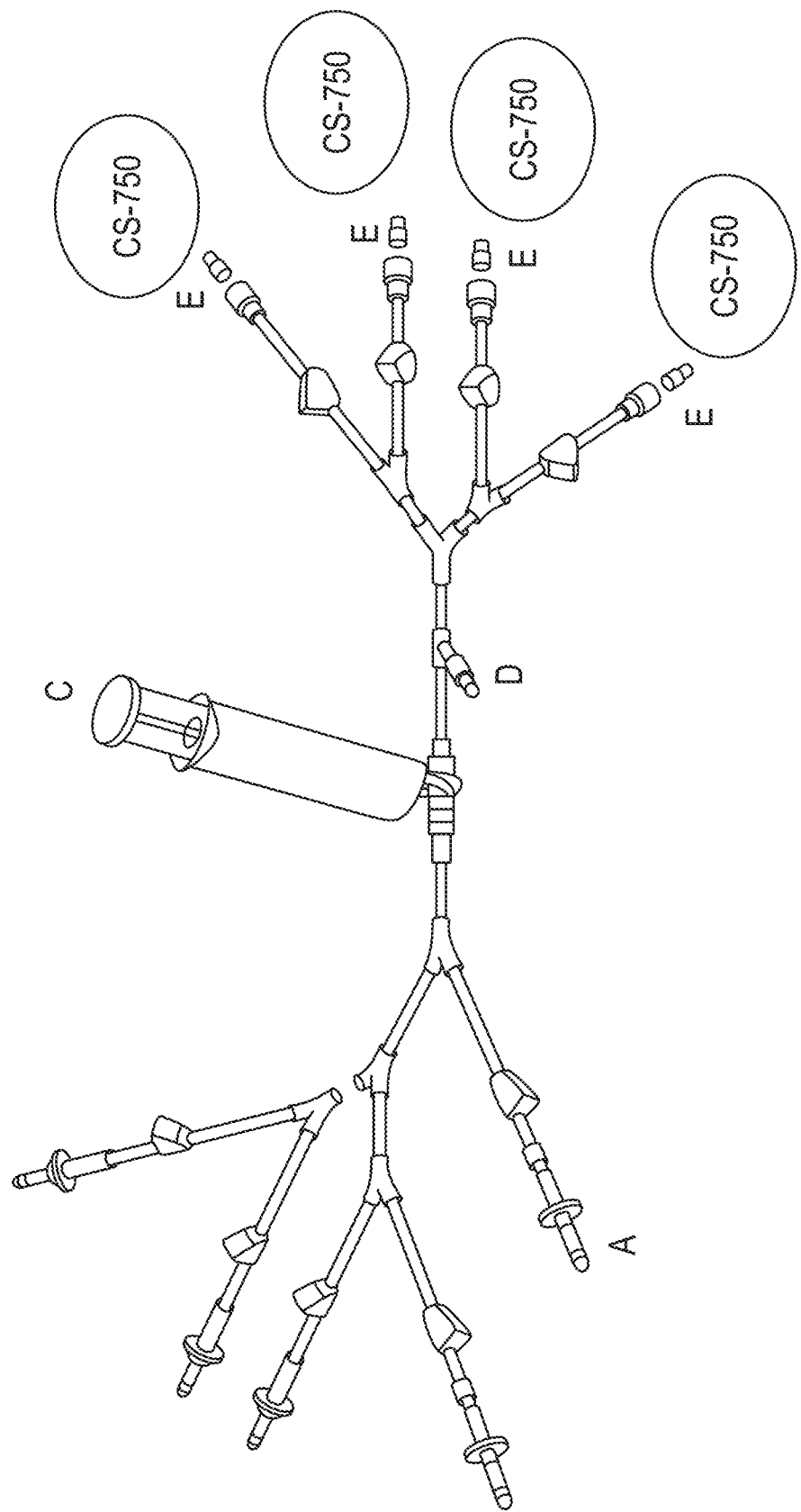
FIG. 26: Shows a schematic of the sterile weld (see, Process Note 5.11 in Example 16) the CS750 Cryobags to the harness prepared in Step 8.14.8, replacing one of the four male luer ends (E) with each bag.
Figure 27:
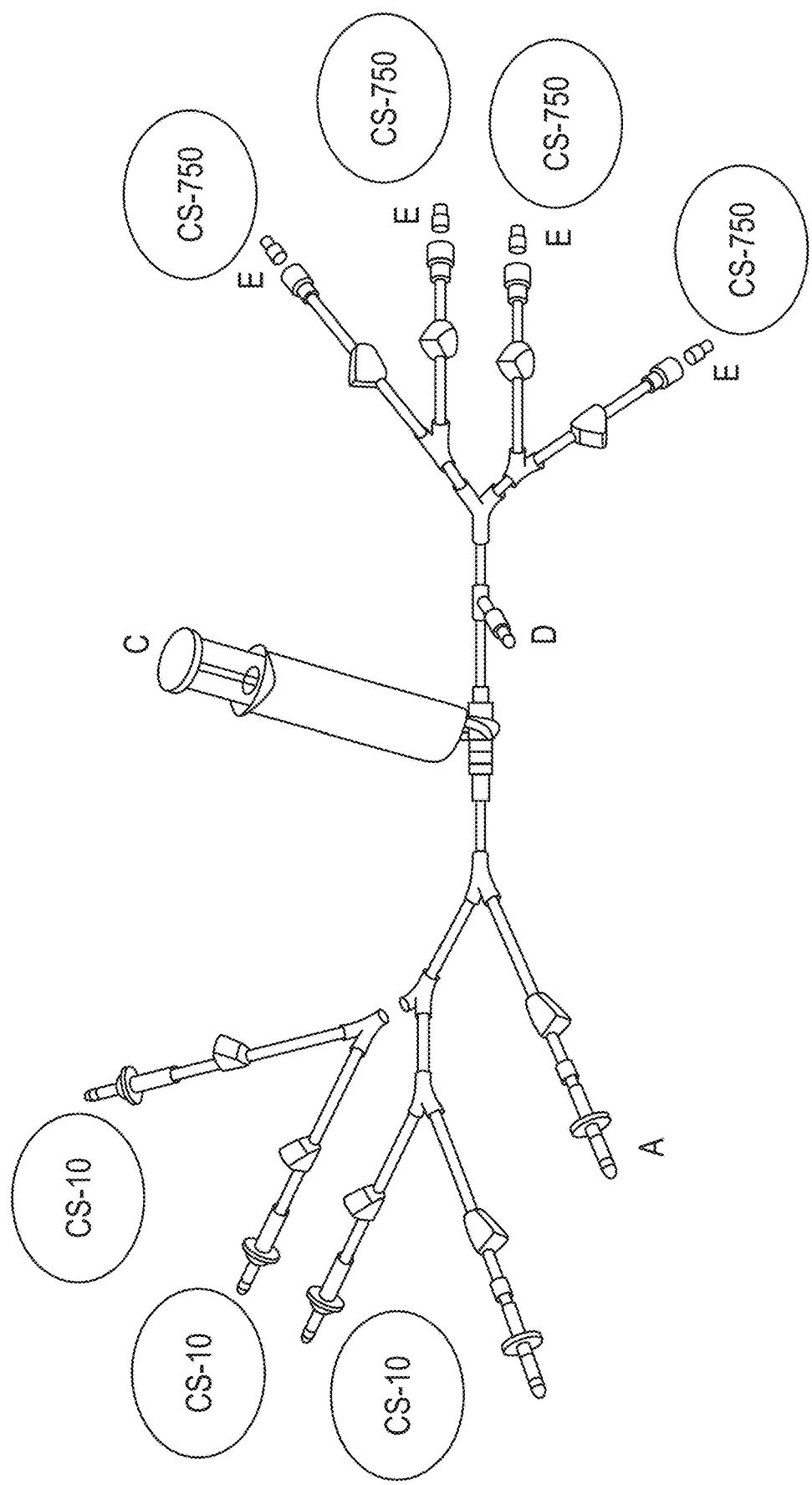
FIG. 27: Shows a schematic of the weld (see, Process Note 5.11 in Example 16) CS-10 bags to spikes of the 45-4M60.
Figure 28:
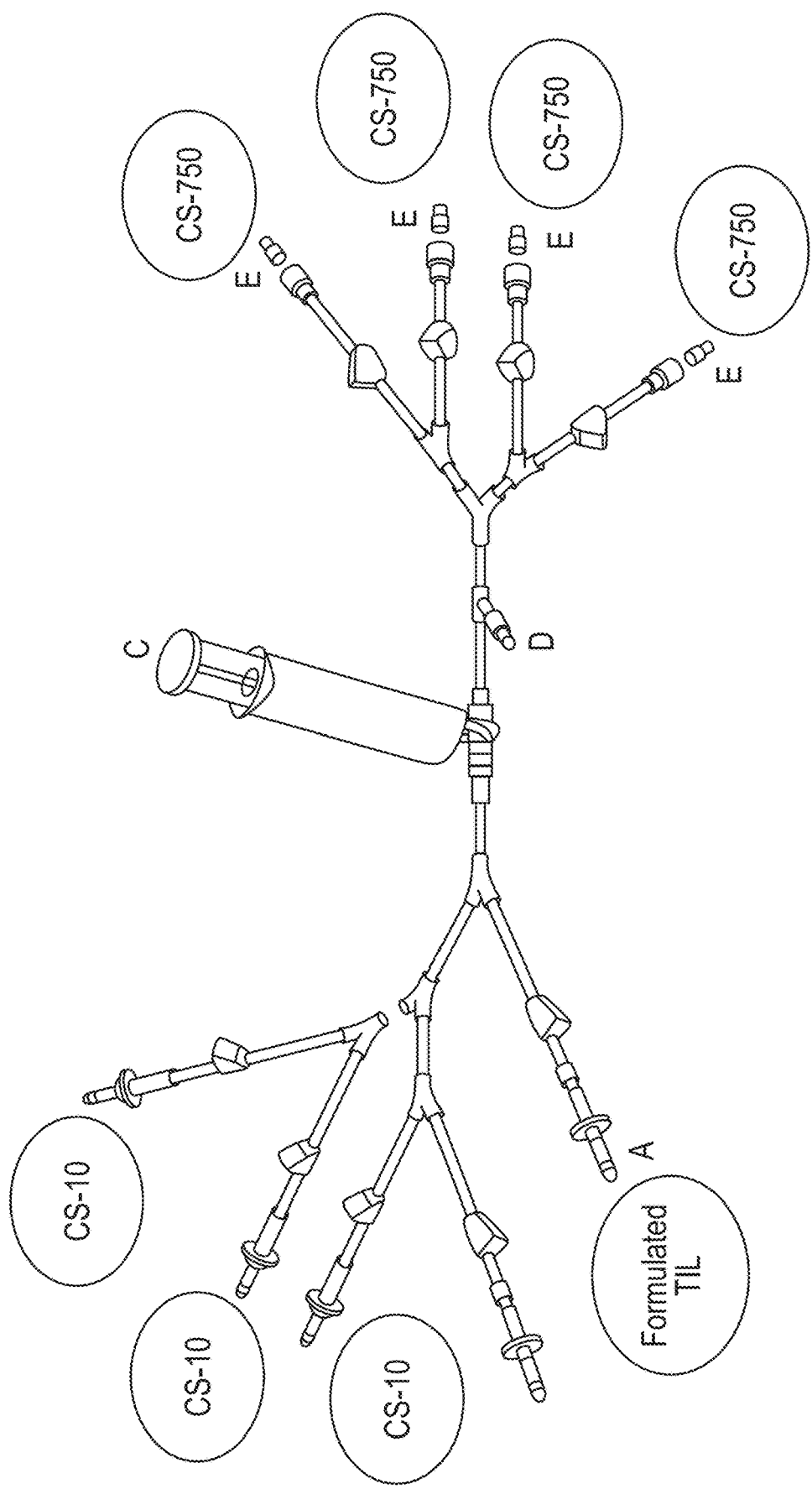
FIG. 28: Shows a schematic of the weld (see, Process Note 5.11 in Example 16) the "Formulated TIL" bag to the remaining spike (A) on the apparatus prepared in Step 8.14.10.
Figure 29:
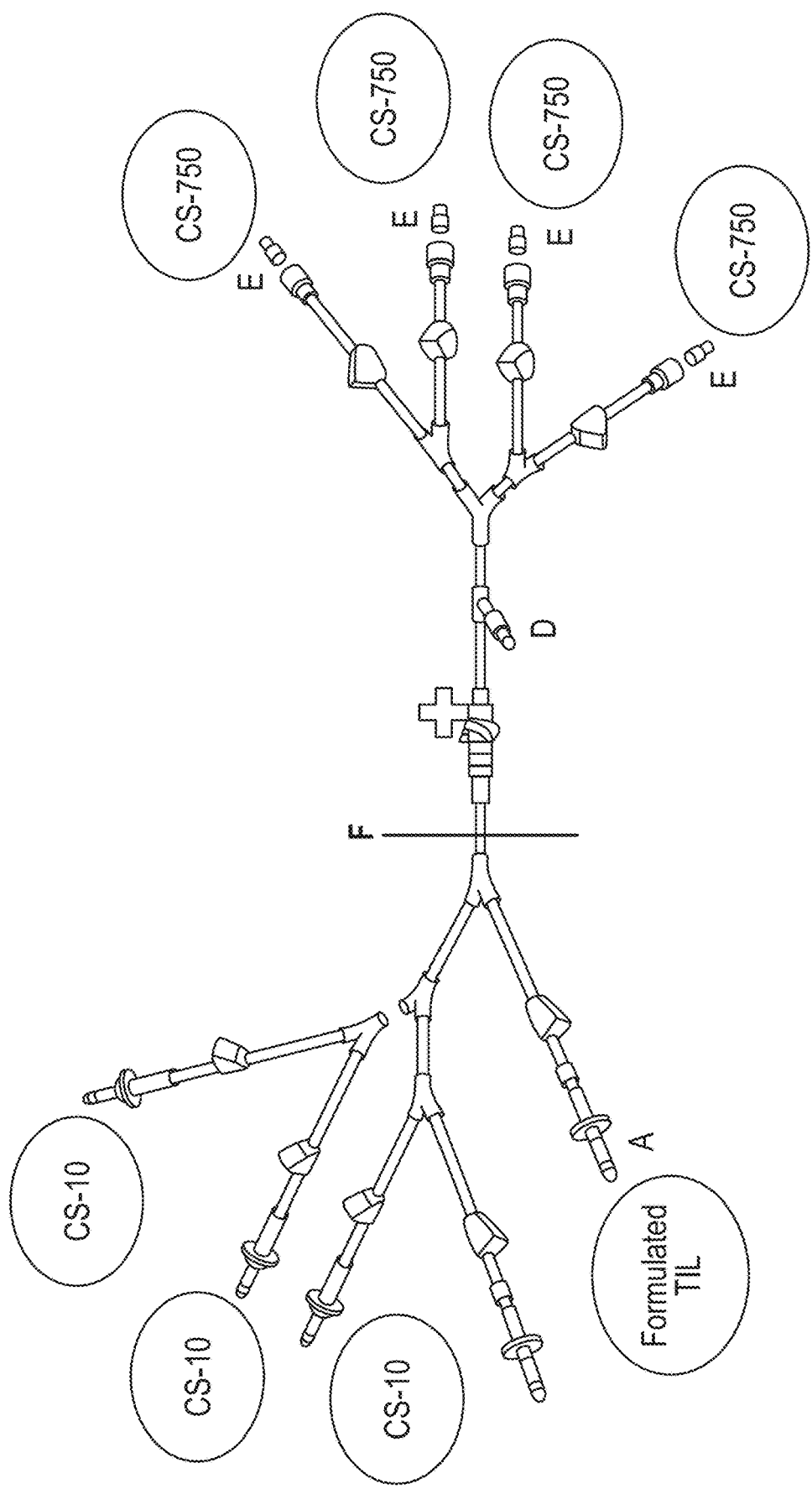
FIG. 29: Shows a diagram of the heat seal (see, Process Note 5.12 in Example 16) at F, removing the empty retentate bag and the CS-10 bags.

This Phase 2, multicenter, three-cohort study is designed to assess the safety and efficacy of a TIL therapy manufactured according to process 1C (as described herein) in patient with metastatic melanoma. Cohorts one and two will enroll up to 30 patients each and cohort three is a re-treatment cohort for a second TIL infusion in up to ten patients. The first two cohorts are evaluating two different manufacturing processes: processes 1C and an embodiment of process 2A (described in Examples 1 to 10, respectively. Patients in cohort one receive fresh, non-cryopreserved TIL and cohort two patients receive product manufactured through the process described in Examples 1 to 10, yielding a cryopreserved product. The study design is shown in FIG. 26. The study is a Phase 2, multicenter, three cohort study to assess the safety and efficacy of autologous TILs for treatment of subpopulations of patients with metastatic melanoma. Key inclusion criteria include: measurable metastatic melanoma and ≥1 lesion resectable for TIL generation; at least one prior line of systemic therapy; age ≥18; and ECOG performance status of 0-1. Treatment cohorts include non-cryopreserved TIL product (prepared using process 1C), cryopreserved TIL product (prepared using an embodiment of process 2A), and retreatment with TIL product for patients without response or who progress after initial response. The primary endpoint is safety and the secondary endpoint is efficacy, defined as objective response rate (ORR), complete remission rate (CRR), progression free survival (PFS), duration of response (DOR), and overall survival (OS).

Example 9: Qualifying Individual Lots of Gamma-Irradiated Peripheral Mononuclear Cells This Example describes a novel abbreviated procedure for qualifying individual lots of gamma-irradiated peripheral mononuclear cells (PBMCs, also known as MNC) for use as allogeneic feeder cells in the exemplary methods described herein.

Each irradiated MNC feeder lot was prepared from an individual donor. Each lot or donor was screened individually for its ability to expand TIL in the REP in the presence of purified anti-CD3 (clone OKT3) antibody and interleukin-2 (IL-2). In addition, each lot of feeder cells was tested without the addition of TIL to verify that the received dose of gamma radiation was sufficient to render them replication incompetent.

Background

Gamma-irradiated, growth-arrested MNC feeder cells were required for REP of TIL. Membrane receptors on the feeder MNCs bind to anti-CD3 (clone OKT3) antibody and crosslink to TIL in the REP flask, stimulating the TIL to expand. Feeder lots were prepared from the leukapheresis of whole blood taken from individual donors. The leukapheresis product was subjected to centrifugation over Ficoll-Hypaque, washed, irradiated, and cryopreserved under GMP conditions.

It is important that patients who received TIL therapy not be infused with viable feeder cells as this can result in Graft-Versus-Host Disease (GVHD). Feeder cells are therefore growth-arrested by dosing the cells with gamma-irradiation, resulting in double strand DNA breaks and the loss of cell viability of the MNC cells upon reculture.

Evaluation Criteria and Experimental Set-Up

Feeder lots were evaluated on two criteria: 1) their ability to expand TIL in co-culture >100-fold and 2) their replication incompetency.

Feeder lots were tested in mini-REP format utilizing two primary pre-REP TIL lines grown in upright T25 tissue culture flasks. Feeder lots were tested against two distinct TIL lines, as each TIL line is unique in its ability to proliferate in response to activation in a REP. As a control, a lot of irradiated MNC feeder cells which has historically been shown to meet the criteria above was run alongside the test lots.

To ensure that all lots tested in a single experiment receive equivalent testing, sufficient stocks of the same pre-REP TIL lines were available to test all conditions and all feeder lots.

For each lot of feeder cells tested, there was a total of six T25 flasks: Pre-REP TIL line #1 (2 flasks); Pre-REP TIL line #2 (2 flasks); and Feeder control (2 flasks). Flasks containing TIL lines #1 and #2 evaluated the ability of the feeder lot to expand TIL. The feeder control flasks evaluated the replication incompetence of the feeder lot.

Experimental Protocol

Day −2/3, Thaw of TIL Lines

Prepared CM2 medium. Warmed CM2 in 37° C. water bath. Prepared 40 ml of CM2 supplemented with 3000 IU/ml IL-2. Keep warm until use. Placed 20 ml of pre-warmed CM2 without IL-2 into each of two 50 ml conical tubes labeled with names of the TIL lines used. Removed the two designated pre-REP TIL lines from LN2 storage and transferred the vials to the tissue culture room. Thawed vials by placing them inside a sealed zipper storage bag in a 37° C. water bath until a small amount of ice remains.

Using a sterile transfer pipet, immediately transferred the contents of vial into the 20 ml of CM2 in the prepared, labeled 50 ml conical tube. QS to 40 ml using CM2 without IL-2 to wash cells. Centrifuged at 400×CF for 5 minutes. Aspirated the supernatant and resuspend in 5 ml warm CM2 supplemented with 3000 IU/ml IL-2.

Removed small aliquot (20 μl) in duplicate for cell counting using an automated cell counter. Record the counts. While counting, placed the 50 ml conical tube with TIL cells into a humidified 37° C., 5% $CO_2$ incubator, with the cap loosened to allow for gas exchange. Determined cell concentration and diluted TIL to $1\times10^6$ cells/ml in CM2 supplemented with IL-2 at 3000 IU/ml.

Cultured in 2 ml/well of a 24-well tissue culture plate in as many wells as needed in a humidified 37° C. incubator until Day 0 of the mini-REP. Cultured the different TIL lines in separate 24-well tissue culture plates to avoid confusion and potential cross-contamination.

Day 0, Initiate Mini-REP

Prepared enough CM2 medium for the number of feeder lots to be tested. (e.g., for testing 4 feeder lots at one time, prepared 800 ml of CM2 medium). Aliquoted a portion of the CM2 prepared above and supplemented it with 3000 IU/ml IL-2 for the culturing of the cells. (e.g., for testing 4 feeder lots at one time, prepare 500 ml of CM2 medium with 3000 IU/ml IL-2).

Working with each TIL line separately to prevent cross-contamination, removed the 24-well plate with TIL culture from the incubator and transferred to the BSC.

Using a sterile transfer pipet or 100-1000 μl Pipettor and tip, removed about 1 ml of medium from each well of TIL to be used and place in an unused well of the 24-well tissue culture plate.

Using a fresh sterile transfer pipet or 100-1000 μl Pipettor and tip, mixed remaining medium with TIL in wells to resuspend the cells and then transferred the cell suspension to a 50 ml conical tube labeled with the TIL name and recorded the volume.

Washed the wells with the reserved media and transferred that volume to the same 50 ml conical tube. Spun the cells at 400×CF to collect the cell pellet. Aspirated off the media supernatant and resuspend the cell pellet in 2-5 ml of CM2 medium containing 3000 IU/ml IL-2, volume to be used based on the number of wells harvested and the size of the pellet—volume should be sufficient to ensure a concentration of $>1.3\times10^6$ cells/ml.

Using a serological pipet, mixed the cell suspension thoroughly and recorded the volume. Removed 200 µl for a cell count using an automated cell counter. While counting, placed the 50 ml conical tube with TIL cells into a humidified, 5% $CO_2$, 37° C. incubator, with the cap loosened to allow gas exchange. Recorded the counts.

Removed the 50 ml conical tube containing the TIL cells from the incubator and resuspended them cells at a concentration of $1.3 \times 10^6$ cells/ml in warm CM2 supplemented with 3000 IU/ml IL-2. Returned the 50 ml conical tube to the incubator with a loosened cap.

Repeated steps above for the second TIL line.

Just prior to plating the TIL into the T25 flasks for the experiment, TIL were diluted 1:10 for a final concentration of $1.3 \times 10^5$ cells/ml as per below.

Prepare MACS GMP CD3 Pure (OKT3) Working Solution

Took out stock solution of OKT3 (1 mg/ml) from 4° C. refrigerator and placed in BSC. A final concentration of 30 ng/ml OKT3 was used in the media of the mini-REP.

600 ng of OKT3 were needed for 20 ml in each T25 flask of the experiment; this was the equivalent of 60 µl of a 10 µg/ml solution for each 20 ml, or 360 µl for all 6 flasks tested for each feeder lot.

For each feeder lot tested, made 400 µl of a 1:100 dilution of 1 mg/ml OKT3 for a working concentration of 10 µg/ml (e.g., for testing 4 feeder lots at one time, make 1600 µl of a 1:100 dilution of 1 mg/ml OKT3: 16 µl of 1 mg/ml OKT3+1.584 ml of CM2 medium with 3000 IU/ml IL-2.)

Prepare T25 Flasks

Labeled each flask and filled flask with the CM2 medium prior to preparing the feeder cells. Placed flasks into 37° C. humidified 5% $CO_2$ incubator to keep media warm while waiting to add the remaining components. Once feeder cells were prepared, the components will be added to the CM2 in each flask.

TABLE 26

Solutions

| Component | Volume in co-culture flasks | Volume in control (feeder only) flasks |
|---|---|---|
| MC2 + 300 IU/ml IL-2 | 18 ml | 19 ml |
| MNC: $1.3 \times 10^7$/ml in CM2 + 3000 IU IL-2 (final concentration $1.3 \times 10^7$/flask) | 1 ml | 1 ml |
| OKT3: 10 µg/ml in CM2 + 3000 IU IL-2 | 60 µl | 60 µl |
| TIL: $1.3 \times 10^5$/ml in CM2 with 3000 IU of IL-2 (final concentration $1.3 \times 10^5$/flask) | 1 ml | 0 |

Prepare Feeder Cells

A minimum of $78 \times 10^6$ feeder cells were needed per lot tested for this protocol. Each 1 ml vial frozen by SDBB had $100 \times 10^6$ viable cells upon freezing. Assuming a 50% recovery upon thaw from LN2 storage, it was recommended to thaw at least two 1 ml vials of feeder cells per lot giving an estimated $100 \times 10^6$ viable cells for each REP. Alternately, if supplied in 1.8 ml vials, only one vial provided enough feeder cells.

Before thawing feeder cells, pre-warmed approximately 50 ml of CM2 without IL-2 for each feeder lot to be tested. Removed the designated feeder lot vials from LN2 storage, placed in zipper storage bag, and place on ice. Thawed vials inside closed zipper storage bag by immersing in a 37° C. water bath. Removed vials from zipper bag, spray or wipe with 70% EtOH and transferred vials to BSC.

Using a transfer pipet immediately transferred the contents of feeder vials into 30 ml of warm CM2 in a 50 ml conical tube. Washed vial with a small volume of CM2 to remove any residual cells in the vial. Centrifuged at 400×CF for 5 minutes. Aspirated the supernatant and resuspended in 4 ml warm CM2 plus 3000 IU/ml IL-2. Removed 200 µl for cell counting using the Automated Cell Counter. Recorded the counts.

Resuspended cells at $1.3 \times 10^7$ cells/ml in warm CM2 plus 3000 IU/ml IL-2. Diluted TIL cells from $1.3 \times 10^6$ cells/ml to $1.3 \times 10^5$ cells/ml.

Setup Co-Culture

Diluted TIL cells from $1.3 \times 10^6$ cells/ml to $1.3 \times 10^5$ cells/ml. Added 4.5 ml of CM2 medium to a 15 ml conical tube. Removed TIL cells from incubator and resuspended well using a 10 ml serological pipet. Removed 0.5 ml of cells from the $1.3 \times 10^6$ cells/ml TIL suspension and added to the 4.5 ml of medium in the 15 ml conical tube. Returned TIL stock vial to incubator. Mixed well. Repeated for the second TIL line.

Transferred flasks with pre-warmed media for a single feeder lot from the incubator to the BSC. Mixed feeder cells by pipetting up and down several times with a 1 ml pipet tip and transferred 1 ml ($1.3 \times 10^7$ cells) to each flask for that feeder lot. Added 60 µl of OKT3 working stock (10 µg/ml) to each flask. Returned the two control flasks to the incubator.

Transferred 1 ml ($1.3 \times 10^5$) of each TIL lot to the correspondingly labeled T25 flask. Returned flasks to the incubator and incubate upright. Did not disturb until Day 5.

Repeated for all feeder lots tested.

Day 5, Media Change

Prepared CM2 with 3000 IU/ml IL-2. 10 ml is needed for each flask. With a 10 ml pipette, transferred 10 ml warm CM2 with 3000 IU/ml IL-2 to each flask. Returned flasks to the incubator and incubated upright until Day 7. Repeated for all feeder lots tested.

Day 7, Harvest

Removed flasks from the incubator and transfer to the BSC, care as taken not to disturb the cell layer on the bottom of the flask. Without disturbing the cells growing on the bottom of the flasks, removed 10 ml of medium from each test flask and 15 ml of medium from each of the control flasks.

Using a 10 ml serological pipet, resuspended the cells in the remaining medium and mix well to break up any clumps of cells. After thoroughly mixing cell suspension by pipetting, removed 200 µl for cell counting. Counted the TIL using the appropriate standard operating procedure in conjunction with the automatic cell counter equipment. Recorded counts in Day 7.

Repeated for all feeder lots tested.

Feeder control flasks were evaluated for replication incompetence and flasks containing TIL were evaluated for fold expansion from Day 0 according to Table TT below.

Day 7, Continuation of Feeder Control Flasks to Day 14

After completing the Day 7 counts of the feeder control flasks, added 15 ml of fresh CM2 medium containing 3000 IU/ml IL-2 to each of the control flasks. Returned the control flasks to the incubator and incubated in an upright position until Day 14.

Day 14, Extended Non-Proliferation of Feeder Control Flasks

Removed flasks from the incubator and transfer to the BSC, care was taken not to disturb the cell layer on the bottom of the flask. Without disturbing the cells growing on the bottom of the flasks, removed approximately 17 ml of medium from each control flasks. Using a 5 ml serological pipet, resuspended the cells in the remaining medium and mixed well to break up any clumps of cells. Recorded the volumes for each flask.

After thoroughly mixing cell suspension by pipetting, removed 200 µl for cell counting. Counted the TIL using the appropriate standard operating procedure in conjunction with the automatic cell counter equipment. Recorded counts.

Repeated for all feeder lots tested.

Results and Acceptance Criteria

Results

The dose of gamma irradiation was sufficient to render the feeder cells replication incompetent. All lots were expected to meet the evaluation criteria and also demonstrated a reduction in the total viable number of feeder cells remaining on Day 7 of the REP culture compared to Day 0.

All feeder lots were expected to meet the evaluation criteria of 100-fold expansion of TIL growth by Day 7 of the REP culture.

Day 14 counts of Feeder Control flasks were expected to continue the non-proliferative trend seen on Day 7.

Acceptance Criteria

The following acceptance criteria were met for each replicate TIL line tested for each lot of feeder cells Acceptance was two-fold, as follows (outlined in Table 27 below).

TABLE 27

Acceptance Criteria

| Test | Acceptance criteria |
|---|---|
| Irradiation of MNC/Replication Incompetence | No growth observed at 7 and 14 days |
| TIL expansion | At least a 100-fold expansion of each TIL (minimum of $1.3 \times 10^7$ viable cells) |

Evaluated whether the dose of radiation was sufficient to render the MNC feeder cells replication incompetent when cultured in the presence of 30 ng/ml OKT3 antibody and 3000 IU/ml IL-2. Replication incompetence was evaluated by total viable cell count (TVC) as determined by automated cell counting on Day 7 and Day 14 of the REP.

Acceptance criteria was "No Growth," meaning the total viable cell number has not increased on Day 7 and Day 14 from the initial viable cell number put into culture on Day 0 of the REP.

Evaluated the ability of the feeder cells to support TIL expansion. TIL growth was measured in terms of fold expansion of viable cells from the onset of culture on Day 0 of the REP to Day 7 of the REP. On Day 7, TIL cultures achieved a minimum of 100-fold expansion, (i.e., greater than 100 times the number of total viable TIL cells put into culture on REP Day 0), as evaluated by automated cell counting.

Contingency Testing of MNC Feeder Lots that do not meet Acceptance Criteria

In the event that an MNC feeder lot did not meet the either of the acceptance criteria outlined above, the following steps will be taken to retest the lot to rule out simple experimenter error as its cause.

If there are two or more remaining satellite testing vials of the lot, then the lot was retested. If there were one or no remaining satellite testing vials of the lot, then the lot was failed according to the acceptance criteria listed above.

In order to be qualified, the lot in question and the control lot had to achieve the acceptance criteria above. Upon meeting these criteria, the lot was then released for use.

Example 10: Qualifying Individual Lots of Gamma-Irradiated Peripheral Blood Mononuclear Cells This Example describes a novel abbreviated procedure for qualifying individual lots of gamma-irradiated peripheral blood mononuclear cells (PBMC) for use as allogeneic feeder cells in the exemplary methods described herein. This example provides a protocol for the evaluation of irradiated PBMC cell lots for use in the production of clinical lots of TIL. Each irradiated PBMC lot was prepared from an individual donor. Over the course of more than 100 qualification protocols, it was been shown that, in all cases, irradiated PBMC lots from SDBB (San Diego Blood Bank) expand TIL >100-fold on Day 7 of a REP. This modified qualification protocol was intended to apply to irradiated donor PBMC lots from SDBB which were then further tested to verify that the received dose of gamma radiation was sufficient to render them replication incompetent. Once demonstrated that they maintained replication incompetence over the course of 14 days, donor PBMC lots were considered "qualified" for usage to produce clinical lots of TIL.

Background

Gamma-irradiated, growth-arrested PBMC were required for current standard REP of TIL. Membrane receptors on the PBMCs bind to anti-CD3 (clone OKT3) antibody and cross-link to TIL in culture, stimulating the TIL to expand. PBMC lots were prepared from the leukapheresis of whole blood taken from individual donors. The leukapheresis product was subjected to centrifugation over Ficoll-Hypaque, washed, irradiated, and cryopreserved under GMP conditions.

It is important that patients who received TIL therapy not be infused with viable PBMCs as this could result in Graft-Versus-Host Disease (GVHD). Donor PBMCs are therefore growth-arrested by dosing the cells with gamma-irradiation, resulting in double strand DNA breaks and the loss of cell viability of the PBMCs upon reculture.

Evaluation Criteria

Evaluation criterion for irradiated PBMC lots was their replication incompetency.

Experimental Set-Up

Feeder lots were tested in mini-REP format as if they were to be co-cultured with TIL, using upright T25 tissue culture flasks. Control lot: One lot of irradiated PBMCs, which had historically been shown to meet the criterion above, was run alongside the experimental lots as a control. For each lot of irradiated donor PBMC tested, duplicate flasks were run.

Experimental Protocol

Day 0

Prepared ~90 ml of CM2 medium for each lot of donor PBMC to be tested. Kept CM2 warm in 37° C. water bath. Thawed an aliquot of $6 \times 10^6$ IU/ml IL-2. Returned the CM2 medium to the BSC, wiping with 70% EtOH prior to placing in hood. For each lot of PBMC tested, removed about 60 ml of CM2 to a separate sterile bottle. Added IL-2 from the thawed $6 \times 10^6$ IU/ml stock solution to this medium for a final concentration of 3000 IU/ml. Labeled this bottle as "CM2/IL2" (or similar) to distinguish it from the unsupplemented CM2.

Prepare OKT3

Took out the stock solution of anti-CD3 (OKT3) from the 4° C. refrigerator and placed in the BSC. A final concentration of 30 ng/ml OKT3 was used in the media of the mini-REP. Prepared a 10 µg/ml working solution of anti-CD3 (OKT3) from the 1 mg/ml stock solution. Placed in refrigerator until needed.

For each PBMC lot tested, prepare 150 µl of a 1:100 dilution of the anti-CD3 (OKT3) stock. For example, for testing 4 PBMC lots at one time, prepare 600 µl of 10 µg/ml anti-CD3 (OKT3) by adding 6 µl of the 1 mg/ml stock solution to 594 µl of CM2 supplemented with 3000 IU/ml IL-2.

Prepare Flasks

Added 19 ml per flask of CM2/IL-2 to the labeled T25 flasks and placed flasks into 37° C., humidified, 5% $CO_2$ incubator while preparing cells.

Prepare Irradiate PBMC

Retrieved vials of PBMC lots to be tested from LN2 storage. These were placed at −80° C. or kept on dry ice prior to thawing. Placed 30 ml of CM2 (without IL-2 supplement) into 50 ml conical tubes for each lot to be thawed. Labeled each tube with the different lot numbers of the PBMC to be thawed. Capped tubes tightly and place in 37° C. water bath prior to use. As needed, returned 50 ml conical tubes to the BSC, wiping with 70% EtOH prior to placing in the hood.

Removed a vial PBMC from cold storage and place in a floating tube rack in a 37° C. water bath to thaw. Allowed thaw to proceed until a small amount of ice remains in the vial. Using a sterile transfer pipet, immediately transferred the contents of the vial into the 30 ml of CM2 in the 50 ml conical tube. Removed about 1 ml of medium from the tube to rinse the vial; returned rinse to the 50 ml conical tube. Capped tightly and swirl gently to wash cells.

Centrifuged at 400×g for 5 min at room temperature. Aspirated the supernatant and resuspend the cell pellet in 1 ml of warm CM2/IL-2 using a 1000 µl pipet tip. Alternately, prior to adding medium, resuspended cell pellet by dragging capped tube along an empty tube rack. After resuspending the cell pellet, brought volume to 4 ml using CM2/IL-2 medium. Recorded volume.

Removed a small aliquot (e.g., 100 µl) for cell counting using an automated cell counter. Performed counts in duplicate according to the particular automated cell counter SOP. It most likely was necessary to perform a dilution of the PBMC prior to performing the cell counts. A recommended starting dilution was 1:10, but this varied depending on the type of cell counter used. Recorded the counts.

Adjusted concentration of PBMC to $1.3 \times 10^7$ cells/ml using CM2/IL-2 medium. Mixed well by gentle swirling or by gently aspirating up-and-down using a serological pipet.

Set Up Culture Flasks

Returned two labeled T25 flasks to the BSC from the tissue culture incubator. Returned the 10 µg/ml vial of anti-CD3/OKT3 to the BSC. Added 1 ml of the $1.3 \times 10^7$ PBMC cell suspension to each flask. Added 60 µl of the 10 µg/ml anti-CD3/OKT3 to each flask. Returned capped flasks to the tissue culture incubators for 14 days of growth without disturbance. Placed anti-CD3/OKT3 vial back into the refrigerator until needed for the next lot. Repeated for each lot of PBMC to be evaluated.

Day 14, Measurement of Non-Proliferation of PBMC

Returned the duplicate T25 flasks to the BSC. For each flask, using a fresh 10 ml serological pipet, removed ~17 ml from each of the flasks, then carefully pulled up the remaining media to measure the volume remaining in the flasks. Recorded volume.

Mixed sample well by pipetting up and down using the same serological pipet.

Removed a 200 µl sample from each flask for counting. Counted cells using an automated cell counter. Repeated steps 7.4.26-7.4.31 for each lot of PBMC being evaluated.

Results and Acceptance Criterion

Results

The dose of gamma irradiation was expected to be sufficient to render the feeder cells replication incompetent. All lots were expected to meet the evaluation criterion, demonstrating a reduction in the total viable number of feeder cells remaining on Day 14 of the REP culture compared to Day 0.

Acceptance Criterion

The following acceptance criterion were met for each irradiated donor PBMC lot tested: "No growth"—meant that the total number of viable cells on Day 14 was less than the initial viable cell number put into culture on Day 0 of the REP.

Contingency Testing of PBMC lots which do not meet Acceptance Criterion.

In the event than an irradiated donor PBMC lot did not meet the acceptance criterion above, the following steps were taken to retest the lot to rule out simple experimenter error as the cause of its failure. If there were two or more remaining satellite vials of the lot, then the lot was retested. If there are one or no remaining satellite vials of the lot, then the lot was failed according to the acceptance criterion above.

To be qualified, a PBMC lot going through contingency testing had both the control lot and both replicates of the lot in question achieve the acceptance criterion. Upon meeting this criterion, the lot was then released for use.

Example 11: Preparation if IL-2 Stock Solution

This Example describes the process of dissolving purified, lyophilized recombinant human interleukin-2 into stock samples suitable for use in further tissue culture protocols, including all of those described in the present application and Examples, including those that involve using rhIL-2.

Procedure

Prepared 0.2% Acetic Acid solution (HAc). Transferred 29 mL sterile water to a 50 mL conical tube. Added 1 mL 1N acetic acid to the 50 mL conical tube. Mixed well by inverting tube 2-3 times. Sterilized the HAc solution by filtration using a Steriflip filter Prepare 1% HSA in PBS. Added 4 mL of 25% HSA stock solution to 96 mL PBS in a 150 mL sterile filter unit. Filtered solution. Stored at 4° C. For each vial of rhIL-2 prepared, fill out forms.

Prepared rhIL-2 stock solution ($6 \times 10^6$ IU/mL final concentration). Each lot of rhIL-2 was different and required information found in the manufacturer's Certificate of Analysis (COA), such as: 1) Mass of rhIL-2 per vial (mg), 2) Specific activity of rhIL-2 (IU/mg) and 3) Recommended 0.2% HAc reconstitution volume (mL).

Calculated the volume of 1% HSA required for rhIL-2 lot by using the equation below:

$$\left( \frac{\text{Vial Mass (mg)} \times \text{Biological Activity}\left(\frac{IU}{mg}\right)}{6 \times 10^6 \frac{IU}{mL}} \right) - HAc\ vol\ (mL) = 1\%\ HSA\ vol\ (mL)$$

For example, according to CellGenix's rhIL-2 lot 10200121 COA, the specific activity for the 1 mg vial is $25 \times 10^6$ IU/mg. It recommends reconstituting the rhIL-2 in 2 mL 0.2% HAc.

$$\left( \frac{1 \text{ mg} \times 25 \times 10^6 \frac{IU}{mg}}{6 \times 10^6 \frac{IU}{mL}} \right) - 2 \text{ mL} = 2.167 \text{ mL } HSA$$

Wiped rubber stopper of IL-2 vial with alcohol wipe. Using a 16 G needle attached to a 3 mL syringe, injected recommended volume of 0.2% HAc into vial. Took care to not dislodge the stopper as the needle is withdrawn. Inverted vial 3 times and swirled until all powder is dissolved. Carefully removed the stopper and set aside on an alcohol wipe. Added the calculated volume of 1% HSA to the vial.

Storage of rhIL-2 solution. For short-term storage (<72 hrs), stored vial at 4° C. For long-term storage (>72 hrs), aliquoted vial into smaller volumes and stored in cryovials at −20° C. until ready to use. Avoided freeze/thaw cycles. Expired 6 months after date of preparation. Rh-IL-2 labels included vendor and catalog number, lot number, expiration date, operator initials, concentration and volume of aliquot.

Example 12: Preparation of Media for Pre-Rep and Rep Processes

This Example describes the procedure for the preparation of tissue culture media for use in protocols involving the culture of tumor infiltrating lymphocytes (TIL) derived from various tumor types including, but not limited to, metastatic melanoma, head and neck squamous cell carcinoma (HN-SCC), ovarian carcinoma, triple-negative breast carcinoma, and lung adenocarcinoma. This media can be used for preparation of any of the TILs described in the present application and Examples.

Preparation of CM1

Removed the following reagents from cold storage and warmed them in a 37° C. water bath: (RPMI1640, Human AB serum, 200 mM L-glutamine). Prepared CM1 medium according to Table 28 below by adding each of the ingredients into the top section of a 0.2 um filter unit appropriate to the volume to be filtered. Store at 4° C.

TABLE 28

Preparation of CM1

| Ingredient | Final concentration | Final Volume 500 ml | Final Volume 1L |
|---|---|---|---|
| RPMI1640 | NA | 450 ml | 900 ml |
| Human AB serum, heat-inactivated 10% | 50 ml | 100 ml | |
| 200 mM L-glutamine | 2 mM | 5 ml | 10 ml |
| 55 mM BME | 55 µM | 0.5 ml | 1 ml |
| 50 mg/ml gentamicin sulfate | 50 µg/ml | 0.5 ml | 1 ml |

On the day of use, prewarmed required amount of CM1 in 37° C. water bath and add 6000 IU/ml IL-2.

Additional supplementation—as needed according to Table 29.

TABLE 29

Additional supplementation of CM1, as needed.

| Supplement | Stock concentration | Dilution | Final concentration |
|---|---|---|---|
| GlutaMAX ™ | 200 mM | 1:100 | 2 mM |
| Penicillin/ streptomycin | 10,000 U/ml penicillin 10,000 µg/ml streptomycin | 1:100 | 100 U/ml penicillin 100 µg/ml streptomycin |
| Amphotericin B | 250 µg/ml | 1:100 | 2.5 µg/ml |

Preparation of CM2

Removed prepared CM1 from refrigerator or prepare fresh CM1 as per Section 7.3 above. Removed AIM-V® from refrigerator and prepared the amount of CM2 needed by mixing prepared CM1 with an equal volume of AIM-V® in a sterile media bottle. Added 3000 IU/ml IL-2 to CM2 medium on the day of usage. Made sufficient amount of CM2 with 3000 IU/ml IL-2 on the day of usage. Labeled the CM2 media bottle with its name, the initials of the preparer, the date it was filtered/prepared, the two-week expiration date and store at 4° C. until needed for tissue culture.

Preparation of CM3

Prepared CM3 on the day it was required for use. CM3 was the same as AIM-V® medium, supplemented with 3000 IU/ml IL-2 on the day of use. Prepared an amount of CM3 sufficient to experimental needs by adding IL-2 stock solution directly to the bottle or bag of AIM-V. Mixed well by gentle shaking. Label bottle with "3000 IU/ml IL-2" immediately after adding to the AIM-V. If there was excess CM3, stored it in bottles at 4° C. labeled with the media name, the initials of the preparer, the date the media was prepared, and its expiration date (7 days after preparation). Discarded media supplemented with IL-2 after 7 days storage at 4° C.

Preparation of CM4

CM4 was the same as CM3, with the additional supplement of 2 mM GlutaMAX™ (final concentration). For every 1 L of CM3, added 10 ml of 200 mM GlutaMAX™. Prepared an amount of CM4 sufficient to experimental needs by adding IL-2 stock solution and GlutaMAX™ stock solution directly to the bottle or bag of AIM-V. Mixed well by gentle shaking. Labeled bottle with "3000 IL/nil IL-2 and GlutaMAX" immediately after adding to the AIM-V. If there was excess CM4, stored it in bottles at 4° C. labeled with the media name, "GlutaMAX", and its expiration date (7 days after preparation). Discarded media supplemented with IL-2 after 7-days storage at 4° C.

Example 13: Evaluation of Serum-Free Media for Use in the 2A Process

This example provides data showing the evaluation of the efficacy of serum-free media as a replacement for the standard CM1, CM2, and CM4 media that is currently used in the 2A process. This study tested efficacy of available serum-free media (SFM) and serum free alternatives as a replacement in three phases;

Phase-1: Compared the efficacy of TIL expansion (n=3) using standard vs CTS Optimizer or Prime T CDM or Xvivo-20 serum free media with or without serum replacement or platelet lysate.

Phase-2: Tested the candidate serum free media condition in mini-scale 2A process using G-Rex 5M (n=3).

Background Information

Though the current media combination used in Pre and Post REP culture has proven to be effective, REP failures may be occurred with the AIM-V. If an effective serum-free alternative were identified, it would be make the process more straight-forward and simple to be performed in CMOs by reducing the number of media types used from 3 to 1. Additionally, SFM reduces the chance of adventitious disease by eliminating the use of human serum. This example provides data that showed supports the use of serum free media in the 2A processes.

TABLE 30

ABBREVIATIONS

| | |
|---|---|
| μl | microliter |
| CM1, 2, 4 | Complete Media 1, 2, 4 |
| CTS OpTimizer SFM | Cell Therapy System OpTimizer Serum Free Media |
| g | Grams |
| Hr | Hour |
| IFU | Instructions for Use |
| IL-2 | Interleukin-2 Cytokine |
| Min | Minute |
| mL | Milliliter |
| ° C. | degrees Celsius |
| PreREP | Pre-Rapid Expansion Protocol |
| REP | Rapid Expansion Protocol |
| RT | Room Temperature |
| SR | Serum Replacement |
| TIL | Tumor Infiltrating Lymphocytes |

Experiment Design

The Pre-REPs and REPs were initiated as mentioned in LAB-008. The overview of this 3 phases of experiment is shown in FIG. 55.

Figure 55:
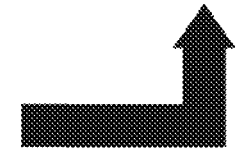
FIG. 55: Overview of 3 phases of experiment described in Example 13.

As provide in FIG. 55, the project was intimated to test the serum free media and supplements in two steps.

Step 1. Selection of serum-free media purveyor. preREP and postREP were set up to mimic 2A process in G-Rex 24 well plate. PreREP were initiated by culturing each fragment/well of G-Rex 24 well plate in triplicates or quatraplicates per conditions. REP were initiated on Day 11 by culturing 4×10e5 TIL/well of G-Rex 24 well, split on Day 16, harvest on Day 22. CTS OpTimizer, X-Vivo 20, and Prime T-CDM were used as potential serum-free media alternatives for use in the PreREP and REP. CTS Immune SR Serum replacement (Life Technologies) or Platelet lysate serum (SDBB) were added at 3% to SFM. Each conditions were planned to test with at least 3 tumors in both preREP and postREP to mimic 2A process.

Step 2. Identified candidates were further tested on mini-scale 2A processes per protocol (TP-17-007). Briefly, pre-REP were initiated by culturing 2 fragments/G-Rex 5M flask in triplicates per condition. REP were initiated on Day 11 using 2×10e6/G-Rex 5M flask, split on Day 16, harvest on Day 22.

Note: Some tumors were processed and setup to measure multiple parameters in one experiment Observations Observed equivalent or statistically better results in cell growth when comparing a serum-free media to the standard used in the 2A process Observed similar phenotype, IFN-y production, and metabolite analysis from the TIL grown in serum-free media when compared to the TIL grown in the standard media used in the 2A process.

Results

Testing the Efficacy of Serum Free Media on Pre and Post REP TIL Expansion.

CTS Optimizer+SR (Serum Replacement) showed enhanced preREP TIL expansion and comparable REP TIL expansion. CTS OpTimizer, X-Vivo 20, and Prime T-CDM were added with or without 3% CTS Immune CTS SR, were tested against standard condition. In M1079 and L4026, CTS OpTimizer+CSR condition showed significantly enhanced preREP TIL expansion (p<0.05) when compared with standard conditions (CM1, CM2, CM4). Conversely, CTS Optimizer without CSR did not help preREP TIL expansion (Appendix-1,2,3). CTS Optimizer+CSR showed comparable TIL expansion in PostREP in the two tumour of 3 tested (FIG. 2B). A large amount of variation occurred in pre and post REP with the X-Vivo 20 and Prime T-CDM conditions, while CTS Optimizer was relatively consistent between quatraplicates. In addition, SFM added platelet lysate did not enhance preREP and postREP TIL expansion when compared to standards. This findings suggesting that serum replacement is certainly needed to provide a comparable growth to our standard, CTS optimizer+CSR may be a candidate.

Testing candidate condition in the G-Rex 5M mini.

Phenotypic analysis of Post REP TIL. See, Table 31 below.

TABLE 31

CD8 skewing with CTS OpTimizer

| | Average % CD8+ | |
|---|---|---|
| | Standard | CTS |
| M1078 | 11 | 34 |
| M1079 | 29.3 | 43.85 |
| M1080 | 33.67 | 54.37 |
| L4020 | 0.02 | 0.17 |
| EP11020 | 28.67 | 25.07 |
| L4030 | 0.13 | 0.09 |
| L4026 | 9.45 | 34.06 |
| M1092 | 5.75 | 52.47 |
| T6030 | 66 | 52.6 |

Interferon-Gamma Comparability

Interferon-gamma ELISA (Quantikine). Production of IFN-y was measured using Quantikine ELISA kit by R&D systems. CTS+SR produced comparable amounts of IFN-y when compared to our standard condition.

Example 14: T-Cell Growth Factor Cocktail IL-2/IL-15/IL-21 Enhances Expansion and Effector Function of Tumor-Infiltrating T Cells Adoptive T cell therapy with autologous tumor infiltrating lymphocytes (TIL) has demonstrated clinical efficacy in patients with metastatic melanoma and cervical carcinoma. In some studies, better clinical outcomes have positively correlated with the total number of cells infused and/or percentage of CD8+ T cells. Most current production regimens solely utilize IL-2 to promote TIL growth. Enhanced lymphocyte expansion has been reported using IL-15 and IL-21-containing regimens. This study describes the positive effects of adding IL-15 and IL-21 to the second generation IL-2-TIL protocol recently implemented in the clinic.

Materials and Methods

The process of generating TIL includes a pre-Rapid Expansion Protocol (pre-REP), in which tumor fragments of 1-3 $mm^3$ size are placed in media containing IL-2. During the pre-REP, TIL emigrate out of the tumor fragments and expand in response to IL-2 stimulation.

To further stimulate TIL growth, TIL are expanded through a secondary culture period termed the Rapid Expansion Protocol (REP) that includes irradiated PBMC feeders, IL-2 and anti-CD3. In this study, a shortened pre-REP and REP expansion protocol was developed to expand TIL while maintaining the phenotypic and functional attributes of the final TIL product.

This shortened TIL production protocol was used to assess the impact of IL-2 alone versus a combination of IL2/IL-15/IL-21. These two culture regimens were compared for the production of TIL grown from colorectal, melanoma, cervical, triple negative breast, lung and renal tumors. At the completion of the pre-REP, cultured TIL were assessed for expansion, phenotype, function (CD107a+ and IFNγ) and TCR Vβ repertoire.

pre-REP cultures were initiated using the standard IL-2 (600 IU/ml) protocol, or with IL-15 (180 IU/ml) and IL-21 (IU/ml) in addition to IL-2. Cells were assessed for expansion at the completion of the pre-REP. A culture was classified as having an increase expansion over the IL-2 if the overall growth was enhanced by at least 20%. The melanoma and lung phenotypic and functional studies are presented herein. See, Table 32 below.

TABLE 32

Enhancement in expansion during the pre-REP with IL-2/IL-15/IL-21 in multiple indications

| Tumor Histology | # of IL-2 versus IL-2/IL-15/IL-21 studies | # of studies demonstrating > 20% enhancement of growth using IL-2/IL-15/IL-21 (compared to IL-2) |
|---|---|---|
| Melanoma | 5 | 1/5 (20%) |
| Lung | 8 | 3/8 (38%) |
| Colorectal | 11 | 7/11 (63%) |
| Cervical | 1 | 1/1 (100%) |
| Pancreatic | 2 | 2/2 (100%) |
| Glioblastoma | 1 | 1/1 (100%) |
| Triple Negative Breast | 1 | 1/2 (50%) |

These data demonstrate an increased TIL product yield when TIL were cultured with IL-2/IL15/IL-21 as compared to IL-2 alone, in addition to phenotypic and functional differences in lung.

The effect of the triple cocktail on TIL expansion was indication-specific and benefited most the low yield tumors.

The CD8+/CD4+ T cell ratio was increased by the treatment in NSCLC TIL product.

T cell activity appeared enhanced by the addition of IL-15 and IL-21 to IL-2, as assessed by CD107a expression levels in both melanoma and NSCLC.

The data provided here shows that TIL expansion using a shorter, more robust process, such as the 2A process described herein in the application and other examples, can be adapted to encompassing the IL-2/IL-15/IL-21 cytokine cocktail, thereby providing a means to further promote TIL expansion in particularly in specific indications.

Ongoing experiments are further evaluating the effects of IL-2/IL-15/IL-21 on TIL function.

Additional experiments will evaluate the effect of the triple cocktail during the REP (first expansion).

These observations are especially relevant to the optimization and standardization of TIL culture regimens necessary for large-scare manufacture of TIL with the broad applicability and availability required of a main-stream anti-cancer therapy.

Example 15: Evaluating a Range of Allogeneic Feeder Cell: TIL Ratios from 100:1 to 25:1

This study tested the proliferation of TIL at 25:1 and 50:1 against the control of 100:1 allogeneic feeder cells to TIL currently utilized in Process 1C.

Studies published by the Surgery Branch at the National Cancer Institute have shown the threshold for optimal activation of TIL in the G-Rex 100 flask at $5 \times 10^6$ allogeneic feeder cells per cm² at the initiation of the REP[1]. This has been verified through mathematical modeling, and, with the same model, predicted that with a feeder layer optimized for cell:cell contact per unit area the proportion of allogeneic feeder cells relative to TIL may be decreased to 25:1 with minimal effect on TIL activation and expansion.

This study established an optimal density of feeder cells per unit area at REP onset, and validated the effective range of allogeneic feeder ratios at REP initiation needed to decrease and normalize the amount of feeder cells used per clinical lot. The study also validated the initiation of the REP with less than $200 \times 10^6$ TIL co-cultured with a fixed number of feeder cells.

A. Volume of a T-cell (10 μm diameter): $V=(4/3)\pi r^3 = 523.6$ μm³
B. Column of G-Rex 100 (M) with a 40 μm (4 cells) height: $V=(4/3)\pi r^3 = 4 \times 10^{12}$ μm³
C. Number cell required to fill column B: $4 \times 10^{12}$ μm³/523.6 μm³ = $7.6 \times 10^8$ μm³ * 0.64 = $4.86 \times 10^8$
D. Number cells that can be optimally activated in 4D space: $4.86 \times 10^8 / 24 = 20.25 \times 10^6$
E. Number of feeders and TIL extrapolated to G-Rex 500: TIL: $100 \times 10^6$ and Feeder: $2.5 \times 10^9$ Equation 1. Approximation of the number of mononuclear cells required to provide an icosahedral geometry for activation of TIL in a cylinder with a 100 cm² base. The calculation derives the experimental result of $\sim 5 \times 10^8$ for threshold activation of T-cells which closely mirrors NCI experimental data.[1] (C) The multiplier (0.64) is the random packing density for equivalent spheres as calculated by Jaeger and Nagel in 1992[2]. (D) The divisor 24 is the number of equivalent spheres that could contact a similar object in 4 dimensional space "the Newton number."[3].

REFERENCES

[1] Jin, Jianjian, et. al., Simplified Method of the Growth of Human Tumor Infiltrating Lymphocytes (TIL) in Gas-Permeable Flasks to Numbers Needed for Patient Treatment. J Immunother. 2012 April; 35(3): 283-292.
[2] Jaeger H M, Nagel S R. Physics of the granular state. Science. 1992 Mar. 20; 255(5051):1523-31.
[3] O. R. Musin (2003). "The problem of the twenty-five spheres". Russ. Math. Surv. 58 (4): 794-795.

Example 16: Production of a Cryopreserved TIL Cell Therapy Using a Closed System This examples describes the cGMP manufacture of Iovance Biotherapeutics, Inc. TIL Cell Therapy Process in G-Rex Flasks according to current Good Tissue Practices and current Good Manufacturing Practices. This material will be manufactured under US FDA Good Manufacturing Practices Regulations (21 CFR Part 210, 211, 1270, and 1271), and applicable ICH Q7 standards for Phase I through Commercial Material.

The process summary is provided in Table 33 below.

TABLE 33

Process summary

| Estimated Day (post-seed) | Activity | Target Criteria | Anticipated Vessels | Estimated Total Volume (mL) |
|---|---|---|---|---|
| 0 | Tumor Dissection | ≤50 desirable tumor fragments per G-Rex100MCS | G-Rex100MCS 1 flask | ≤1000 |
| 11 | REP Seed | 5 – 200 × 10$^6$ viable cells per G-Rex500MCS | G-Rex500MCS 1 flasks | ≤5000 |
| 16 | REP Split | 1 × 10$^9$ viable cells per G-Rex500MCS | G-Rex500MCS ≤ 5 flasks | ≤25000 |
| 22 | Harvest | Total available cells | 3-4 CS-750 bags | ≤530 |

Throughout this Example, assume 1.0 mL/L=1.0 g/kg, unless otherwise specified. Once opened, the following expiries apply at 2° C.-8° C.: Human Serum, type AB (HI) Gemini, 1 month; 2-mercaptoethanol, 1 month. Gentamicin Sulfate, 50 mg/ml stock may be kept at room temperature for 1 month. Bags containing 10 L of AIM-V media may be warmed at room temperature once only for up to 24 hours prior to use. During the Day 22 harvest two Gatherex™ may be used to harvest the TIL from the G-Rex500MCS flasks.

Day 0 CM1 Media Preparation

Prepared RPMI 1640 Media. In the BSC, using an appropriately sized pipette, removed 100.0 mL from 1000 mL RPMI 1640 Media and placed into an appropriately sized container labeled "Waste".

In the BSC added reagents to RPMI 1640 Media bottle. Added the following reagents to the RPMI 1640 Media bottle as shown in in table. Recorded volumes added. Amount Added per bottle: Heat Inactivated Human AB Serum (100.0 mL); GlutaMax (10.0 mL); Gentamicin sulfate, 50 mg/mL (1.0 mL); 2-mercaptoethanol (1.0 mL)

Capped RPMI 1640 Media bottle and swirled bottle to ensure reagents were mixed thoroughly. Filtered RPMI 1640 Media from Step 8.1.6 through 1 L 0.22-micron filter unit. Labeled filtered media. Aseptically capped the filtered media and labeled with the following information.

Thawed one 1.1 mL IL-2 aliquot (6×10$^6$ IU/mL) (BR71424) until all ice had melted. Recorded IL-2: Lot # and Expiry. Transferred IL-2 stock solution to media. In the BSC, transferred 1.0 mL of IL-2 stock solution to the CM1 Day 0 Media Bottle prepared in Step 8.1.8. Added CM1 Day 0 Media 1 bottle and IL-2 (6×10$^6$ IU/mL) 1.0 mL. Capped and swirled the bottle to mix media containing IL-2. Relabeled as "Complete CM1 Day 0 Media".

Removed 20.0 mL of media using an appropriately sized pipette and dispensed into a 50 mL conical tube. In BSC, transferred 25.0 mL of "Complete CM1 Day 0 Media" (prepared in Step 8.1.13) to a 50 mL conical tube. Labeled the tube as "Tissue Pieces". Aseptically passed G-Rex100MCS (W3013130) into the BSC. In the BSC, closed all clamps on the G-Rex100MCS, leaving vent filter clamp open. Connected the red line of G-Rex100MCS flask to the larger diameter end of the repeater pump fluid transfer set (W3009497) via luer connection. Staged Baxa pump next to BSC. Removed pump tubing section of repeater pump fluid transfer set from BSC and installed in repeater pump. Within the BSC, removed the syringe from Pumpmatic Liquid-Dispensing System (PLDS) (W3012720) and discarded.

Connected PLDS pipette to the smaller diameter end of repeater pump fluid transfer set via luer connection and placed pipette tip in "Complete CM1 Day 0 Media" for aspiration. Opened all clamps between media and G-Rex100MCS. Pumped Complete CM1 media into G-Rex100MCS flask. Set the pump speed to "High" and "9" and pumped all Complete CM1 Day 0 Media into G-Rex100MCS flask. Once all media was transferred, cleared the line and stopped pump.

Disconnected pump from flask. Ensured all clamps were closed on the flask, except vent filter. Removed the repeater pump fluid transfer set from the red media line, and placed a red cap (W3012845) on the red media line. Removed G-Rex100MCS flask from BSC, heated seal off the red cap from the red line near the terminal luer. Labeled G-Rex100MCS flask with QA provided in-process "Day 0" label. Attached sample "Day 0" label below. Incubator parameters: 37.0±2.0° C.; CO2 Percentage: 5.0±1.5% $CO_2$.

Placed the 50 mL conical tube" in incubator for ≥30 minutes of warming.

Day 0 Tumor Wash Media Preparation

Added Gentamicin to HBSS. In the BSC, added 5.0 mL Gentamicin (W3009832 or W3012735) to 1×500 mL HBSS Media (W3013128) bottle. Recorded volumes. Added per bottle: HBSS (500.0 mL); Gentamicin sulfate, 50 mg/ml (5.0 mL). Mixed reagents thoroughly. Filtered HBSS containing gentamicin prepared in Step 8.2.1 through a 1 L 0.22-micron filter unit (W1218810). Aseptically capped the filtered media and labeled with the following information.

Day 0 Tumor Processing

Obtained tumor specimen and transferred into suite at 2° C.-8° C. immediately for processing and recorded tumor information. Labeled three 50 ml conical tubes: the first as "Forceps," the second as "Scalpel," and the third as "Fresh Tumor Wash Media". Labeled 5×100 mm petri dishes as "Wash 1," "Wash 2," "Wash 3," "Holding," and "Unfavorable." Labeled one 6 well plate as "Favorable Intermediate Fragments."

Using an appropriately sized pipette, transferred 5.0 mL of "Tumor Wash Media" into each well of one 6-well plate for favorable intermediate tumor fragments (30.0 mL total). Using an appropriately sized pipette, transferred 50.0 mL of "Tumor Wash Media" prepared in Step 8.2.4 into each 100 mm petri dish for "Wash 1," "Wash 2," "Wash 3," and "Holding" (200.0 mL total). Using an appropriately sized pipette, transfer 20.0 mL of "Tumor Wash Media" prepared in Step 8.2.4 into each 50 mL conical (60.0 mL total). Aseptically removed lids from two 6-well plates. The lids were utilized for selected tumor pieces. Aseptically passed the tumor into the BSC. Recorded processing start time.

Tumor Wash 1: Using forceps, removed the tumor from the specimen bottle and transferred to the "Wash 1". Using forceps, gently washed tumor and record time. Transferred 20.0 mL (or available volume) of solution from the tumor specimen bottle into a 50 mL conical per sample plan. Labeled and stored bioburden sample collected at 2-8° C. until submitted for testing.

Tumor Wash 2: Using a new set of forceps, removed the tumor from the "Wash 1" dish and transferred to the "Wash 2" dish. Using forceps, washed tumor specimen by gently agitating for ≥3 minutes and allowed it to sit. Recorded time.

Using a transfer pipette, placed 4 individual drops of Tumor Wash Media from the conical into each of the 6 circles on the upturned lids of the 6-well plates (2 lids). Placed an extra drop on two circles for a total of 50 drops.

Tumor Wash 3: Using forceps, removed the tumor from the "Wash 2" dish and transferred to the "Wash 3" dish. Using forceps, washed tumor specimen by gently agitating and allowed it to sit for ≥3 minutes. Recorded time.

Placed a ruler under 150 mm dish lid. Using forceps, aseptically transferred tumor specimen to the 150 mm dissection dish lid. Arranged all pieces of tumor specimen end to end and recorded the approximate overall length and number of fragments. Assessed the tumor for necrotic/fatty tissue. Assessed whether >30% of entire tumor area observed to be necrotic and/or fatty tissue; if yes, ensure tumor was of appropriate size if so proceeded. Assessed whether <30% of entire tumor area were observed to be necrotic or fatty tissue; if yes, proceeded.

Clean-Up Dissection. If tumor was large and >30% of tissue exterior was observed to be necrotic/fatty, performed "clean up dissection" by removing necrotic/fatty tissue while preserving tumor inner structure using a combination of scalpel and/or forceps. To maintain tumor internal structure, used only vertical cutting pressure. Did not cut in a sawing motion with scalpel.

Using a combination of scalpel and/or forceps, cut the tumor specimen into even, appropriately sized fragments (up to 6 intermediate fragments). To maintain tumor internal structure, use only vertical cutting pressure. Did not cut in a sawing motion with scalpel. Ensured to keep non-dissected intermediate fragments completely submerged in "Tumor Wash Media". Transferred each intermediate fragment to the "holding" dish Manipulated one intermediate fragment at a time, dissected the tumor intermediate fragment in the dissection dish into pieces approximately 3×3×3 mm in size, minimizing the amount of hemorrhagic, necrotic, and/or fatty tissues on each piece. To maintain tumor internal structure, used only vertical cutting pressure. Did not cut in a sawing motion with scalpel.

Selected up to eight (8) tumor pieces without hemorrhagic, necrotic, and/or fatty tissue. Used the ruler for reference. Continued dissection until 8 favorable pieces have been obtained, or the entire intermediate fragment has been dissected. Transferred each selected piece to one of the drops of "Tumor Wash Media".

After selecting up to eight (8) pieces from the intermediate fragment, placed remnants of intermediate fragment into a new single well of "Favorable Intermediate Fragments" 6-well plate.

If desirable tissue remains, selected additional Favorable Tumor Pieces from the "favorable intermediate fragments" 6-well plate to fill the drops for a maximum of 50 pieces. Recorded the total number of dissected pieces created.

Removed the "Tissue Pieces" 50 mL conical tube from the incubator. Ensured conical tube was warmed for ≥30 min. Passed "Tissue Pieces" 50 mL conical into the BSC, ensuring not to compromise the sterility of open processing surfaces.

Using a transfer pipette, scalpel, forceps or combination, transferred the selected 50 best tumor fragments from favorable dish lids to the "Tissue Pieces" 50 mL conical tube. If a tumor piece was dropped during transfer and desirable tissue remains, additional pieces from the favorable tumor intermediate fragment wells were added. Recorded numbers of pieces.

Removed G-Rex100MCS containing media from incubator. Aseptically passed G-Rex100MCS flask into the BSC. When transferring the flask, did not hold from the lid or the bottom of the vessel. Transferred the vessel by handling the sides. In the BSC, lifted G-Rex100MCS flask cap, ensuring that sterility of internal tubing was maintained. Swirled conical tube with tumor pieces to suspend and quickly poured the contents into the G-Rex100MCS flask. Ensured that the tumor pieces were evenly distributed across the membrane of the flask. Gently tilted the flask back and forth if necessary to evenly distribute the tumor pieces. Recorded number of tumor fragments on bottom membrane of vessel and number of observed to be floating in vessel. NOTE: If the number of fragments seeded were NOT equivalent to number of collected, contacted Area Management, and document in Section 10.0.

Incubated G-Rex100MCS at the following parameters: Incubated G-Rex flask: Temperature LED Display: 37.0±2.0° C.; CO2 Percentage: 5.0±1.5% CO2. Performed calculations to determine the proper time to remove G-Rex100MCS incubator on Day 11. Calculations: Time of incubation; lower limit=time of incubation+252 hours; upper limit=time of incubation+276 hours.

Day 11—Media Preparation

Monitored Incubator. Incubator parameters: Temperature LED Display: 37.0±2.0° C.; CO2 Percentage: 5.0±1.5% CO2. Warmed 3×1000 mL RPMI 1640 Media (W3013112) bottles and 3×1000 mL AIM-V (W3009501) bottles in an incubator for ≥30 minutes. Recorded time. Media: RPMI 1640 and AIM-V. Placed an additional 1×1000 ml bottle of AIM-V Media (W3009501) at room temperature for further use.

Removed the RPMI 1640 Media when time was reached. Record end incubation time in Step 8.4.4. Ensure media was warmed for ≥30 min. In the BSC, removed 100.0 mL from each of the three pre-warmed 1000 mL RPMI 1640 Media bottles and placed into an appropriately sized container labeled "Waste". In the BSC added the following reagents to each of the three RPMI 1640 Media bottles and recorded volumes added to each bottle. GemCell Human serum, Heat Inactivated Type AB (100.0 mL), GlutaMax (10.0 mL), Gentamicin sulfate, 50 mg/ml (1.0 mL), 2-mercaptoethanol (1.0 mL).

Caped bottles and swirled to ensure reagents were mixed thoroughly. Filtered each bottle of media through a separate 1 L 0.22-micron filter unit. Aseptically capped the filtered media and labeled each bottle with CM1 Day 11 Media. Thawed 3×1.1 mL aliquots of IL-2 ($6\times10^6$ IU/mL) (BR71424) until all ice had melted Recorded IL 2 lot # and Expiry.

Removed the three bottles of AIM-V Media from the incubator. Recorded end incubation time. Ensured media had been warmed for ≥30 minutes. Using a micropipette, added 3.0 mL of thawed IL-2 into one 1 L bottle of pre-warmed AIM-V media. Rinse micropipette tip with media after dispensing IL-2. Use a new sterile micropipette tip for each aliquot. Recorded the total volume added. Labeled bottle as "AIM-V Containing IL-2". Aseptically transferred a 10 L Labtainer Bag and a repeater pump transfer set into the BSC. Closed all lines on a 10 L Labtainer bag. Attached the larger diameter tubing end of a repeater pump transfer set to the middle female port of the 10 L Labtainer Bag via luer lock connection.

Staged the Baxa pump next to the BSC. Fed the transfer set tubing through the Baxa pump. Set the Baxa Pump to "High" and "9". Removed syringe from Pumpmatic Liquid-Dispensing System (PLDS) and discarded. Ensured to not compromise the sterility of the PLDS pipette.

Connected PLDS pipette to smaller diameter end of repeater pump fluid transfer set via luer connection and placed pipette tip in AIM-V media containing IL-2 bottle (prepared in Step 8.4.13) for aspiration. Opened all clamps between media bottle and 10 L Labtainer.

Using the PLDS, transfer pre-warmed AIM-V media containing IL-2 prepared, as well as two additional AIM-V bottles into the 10 L Labtainer bag. Added the three bottles of filtered CM1 Day 11 Media. After addition of final bottle, cleared the line to the bag. NOTE: Stopped the pump between addition of each bottle of media. Removed PLDS from the transfer set and placed a red cap on the luer of the line in the BSC. Gently massaged the bag to mix. Labeled the media bag with the following information. Expiration date was 24 hours from the preparation date.

Attached a 60 mL syringe to the available female port of the "Complete CM2 Day 11 Media" bag. Removed 20.0 mL of media and place in a 50 mL conical tube. Placed a red cap on the female port of the "Complete CM2 Day 11 Media" Bag. Labeled and stored Media Retain Sample at 2-8° C. until submitted for testing. Heat sealed off the red cap on the transfer set line, close to red cap. Kept the transfer set on the bag.

In the BSC, added 4.5 mL of AIM-V Media that had been labelled with "For Cell Count Dilutions" and lot number to four 15 mL conical tubes. Labeled the tubes with the lot number and tube number (1-4). Labeled 4 cryovials "Feeder" and vial number (1-4). Transferred any remaining 2-mercaptoethanol, GlutaMax, and human serum from the BSC to 2-8° C.

Outside of the BSC, weld a 1 L Transfer Pack to the transfer set attached to the "Complete CM2 Day 11 Media" bag prepared. Labeled transfer pack as "Feeder Cell CM2 Media" and lot number. Made a mark on the tubing of the 1 L Transfer Pack tubing a few inches away from the bag. Placed the empty Transfer Pack onto the scale so that the tubing was on the scale to the point of the mark. Tared the scale and left the empty Transfer Pack on the scale.

Set the Baxa pump to "Medium" and "4." Pumped 500.0±5.0 mL of "Complete CM2 Day 11" media prepared in Step 8.4.22 into Cell CM2 Media" transfer pack. Measured by weight and recorded the volume of Complete CM2 media added to the Transfer Pack.

Once filled, heated seal the line. Separated CM2 Day 11 media bag with transfer set from feeder cell media transfer pack, kept weld toward 1 L transfer pack. Placed "Complete CM2 Day 11 Media" prepared in incubator until use.

Day 11—TIL Harvest

Incubator parameters: Temperature LED Display: 37.0±2.0° C.; CO2 Percentage: 5.0±1.5% CO2. Performed check to ensure incubation parameters are met before removing G-Rex100MCS from incubator. Lower limits the same as described above.

Recorded Time of Removal from incubator. Carefully removed G-Rex100MCS from incubator and ensured all clamps were closed except large filter line. Recorded processing start time.

Labeled a 300 mL Transfer pack as "TIL Suspension". Sterile welded the TIL Suspension transfer (single line) of a Gravity Blood Filter. Placed the 300 mL Transfer Pack on a scale and record dry weight. Labeled 1 L Transfer Pack as "Supernatant".

Sterile welded the red media removal line from the G-Rex100MCS to the "Supernatant" transfer pack. Sterile welded the clear cell removal line from the G-Rex100MCS to one of the two spike lines on the top of the blood filter connected to the "TIL Suspension" transfer pack. Placed G-Rex100MCS on the left side of the GatheRex and the "Supernatant" and "TIL Suspension" transfer packs to the right side.

Install the red media removal line from the G Rex100MCS to the top clamp (marked with a red line) and tubing guides on the GatheRex. Installed the clear harvest line from the G-Rex100MCS to the bottom clamp (marked with a blue line) and tubing guides on the GatheRex. Attached the gas line from the GatheRex to the sterile filter of the G-Rex100MCS flask. Before removing the supernatant from the G-Rex100MCS flask, ensured all clamps on the cell removal lines were closed. Transferred ~900 mL of culture supernatant from the G-Rex100MCS to the 1 L Transfer Pack. Visually inspected G-Rex100MCS flask to ensure flask is level and media has been reduced to the end of the aspirating dip tube.

After removal of the supernatant, closed all clamps to the red line.

Vigorously tapped flask and swirled media to release cells. Performed an inspection of the flask to ensure all cells have detached. NOTE: Contacted area management if cells did not detach. Tilted flask away from collection tubing and allowed tumor pieces to settle along edge. Slowly tipped flask toward collection tubing so pieces remained on the opposite side of the flask. If the cell collection straw is not at the junction of the wall and bottom membrane, rapping the flask while tilted at a 450 angle is usually sufficient to properly position the straw.

Released all clamps leading to the TIL Suspension transfer pack. Using the GatheRex, transferred the cell suspension through the blood filter into the 300 mL transfer pack. Maintained the tilted edge until all cells and media are collected. Inspected membrane for adherent cells. Rinsed the bottom of the G-Rex100MCS. Cover ~¼ of gas exchange membrane with rinse media. Ensured all clamps are closed. Heat sealed (per Process Note 5.12) the TIL suspension transfer pack as close to the weld as possible so that the overall tubing length remains approximately the same. Heat sealed the "Supernatant" transfer pack. Maintained enough line to weld. Recorded weight of TIL Suspension transfer pack and calculated the volume of cell suspension.

Welded a 4" plasma transfer set to "supernatant" transfer pack, retaining the luer connection on the 4" plasma transfer set, and transferred into the BSC. Welded a 4" plasma transfer set to 300 mL "TIL Suspension" transfer pack, retained the luer connection on the 4" plasma transfer set, and transferred into the BSC.

Drew up approximately 20.0 mL of supernatant from the 1 L "Supernatant" transfer pack and dispense into a sterile 50 mL conical tube labeled "Bac-T." Removed a 1.0 mL sample from the 50 mL conical labeled BacT using an appropriately sized syringe and inoculated the anaerobic bottle.

Labeled 4 cryovials with vial number (1-4). Using separate 3 mL syringes, pulled 4×1.0 mL cell count samples from TIL Suspension Transfer Pack using the luer connection, and placed in respective cryovials. Placed a red cap (W3012845) on the line. Placed TIL Transfer Pack in incubator until needed. Perform cell counts and calculations. Perform initial cell counts undiluted. If no dilution needed, "Sample [μL]"=200, "Dilution [μL]"=0.

Record cell counts and TIL numbers. If Total Viable TIL Cells is <5×10$^6$ cells, proceeded to "Day 11 G-Rex Fill and Seed". If Total Viable TIL Cells is >5×10$^6$, proceed to "Calculation for flow cytometry".

Calculation for Flow Cytometry.

If the Total Viable TIL Cell count was ≥4.0×10$^7$, calculated the volume to obtain 1.0×10$^7$ cells for the flow cytometry sample. Total viable cells required for flow cytometry: 1.0×10$^7$ cells. Volume of cells required for flow cytometry: Viable cell concentration divided by 1.0×10$^7$ cells.

If Applicable: Recalculated Total Viable Cells and Volume flow. Calculated the remaining Total Viable Cells and remaining volume after the removal of cytometry sample below.

TIL Cryopreservation of Sample

If Applicable: Calculated Volume for Cryopreservation. Calculated the volume of cells required to obtain $1\times10^7$ cells for cryopreservation.

TABLE 534

Cryopreservation calculation

| Total Viable TIL required for cryopreservation | Viable Cell Concentration | Volume of Cells required for cryopreservation $C = A \div B$ |
|---|---|---|
| A. $1 \times 10^7$ cells | B. cells/mL | C. mL |

If Applicable: Removed sample for Cryopreservation. Removed the calculated volume from the TIL Suspension transfer pack. Placed in appropriately sized conical tube and label as "Cryopreservation Sample $1\times10^7$ cells," dated, and lot number. Placed a red cap (W3012845) on the TIL Suspension transfer pack.

Centrifuged the "Cryopreservation Sample $1\times10^7$ cells" according to the following parameters: Speed: 350×g, Time: 10:00 minutes, Temperature: Ambient, Brake: Full (9); Acceleration: Full (9).

Added CS-10. In BSC, aseptically aspirate supernatant. Gently tapped bottom of tube to resuspend cells in remaining fluid. Added CS-10. Slowly added 0.5 mL of CS10. Recorded volume added. Cryopreservation Sample Vials Filled at ~0.5 mL.

Day 11—Feeder Cells

Obtained 3 bags of feeder cells with at least two different lot numbers from LN2 freezer. Kept cells on dry ice until ready to thaw. Recorded feeder cell information. Confirmed that at least two different lots of feeder cells were obtained. Placed the Feeder Cell bags into individual zip top bags, based on Lot number, and thawed 37.0±2.0° C. water bath or cytotherm for ~3-5 minutes or until ice has just disappeared.

Feeder cell harness preparation. Welded 4S-4M60 to a CC2 Cell Connect (W3012820), replacing a single spike of the Cell Connect apparatus with the 4-spike end of the 4S-4M60 manifold. Welded as needed.

Attached media transfer pack Weld the "Feeder Cell CM2 Media" transfer pack to a CC2 Luer. The bag will be attached to the side of the harness with the needless injection port. Transferred the assembly containing the Complete CM2 Day 11 Media into the BSC.

Pool thawed feeder cells. Within the BSC, pulled 10 mL of air into a 100 mL syringe. Used this to replace the 60 mL syringe on the CC2. Wiped each port on the feeder cell bags with an alcohol pad prior to removing the cover. Spike the three feeder bags using three of the spikes of the CC2. Maintained constant pressure while turning the spike in one direction. Ensure to not puncture the side of the port. Opened the stopcock so that the line from the feeder cell bags is open and the line to the needless injection port is closed. Drew up the contents of the feeder cell bags into the syringe. All three bags drained at once. Once feeder cell bags had been drained, while maintaining pressure on the syringe, clamped off the line to the feeder cell bags. Did not detach syringe below. the syringe from the harness. Recorded the total volume of feeder cells in the syringe.

Added feeder cells to transfer pack. Turned the stopcock so the line to the feeder cell bag was closed and the line to the media Transfer Pack was open. Ensured the line to media transfer pack is unclamped. Dispensed the feeder cells from the syringe into the "Feeder Cell CM2 Media" transfer pack. Clamped off the line to the transfer pack containing the feeder cells and leave the syringe attached to the harness. Massaged bag to mix the pooled feeder cells in the transfer pack. Labeled bag as "Feeder Cell Suspension".

Calculated the total volume of feeder cell suspension. Removed cell count samples. Using a separate 3 mL syringe for each sample, pulled 4×1.0 mL cell count samples from Feeder Cell Suspension Transfer Pack using the needless injection port. Aliquoted each sample into labeled cryovials.

Performed cell counts and calculations utilizing NC-200 and Process Note 5.14. Diluted cell count samples by adding 0.5 mL of cell suspension into 4.5 mL of AIM-V media labelled with the lot number and "For Cell Count Dilutions". This will give a 1:10 dilution.

Recorded Cell Count and Sample volumes. If Total Viable Cells are $<5\times10^9$, proceed. If Total Viable Cells are $\geq 5\times10^9$, proceeded as above for higher cells counts. Obtained additional Feeder Cells as needed and added to transfer pack as discussed above. Calculated the volume of Feeder Cell Suspension that was required to obtain $5\times10^9$ viable feeder cells. Calculated the volume of excess feeder cells to remove. Round down to nearest whole number.

Removed excess feeder cells. In a new 100 mL syringe, pulled up 10 mL of air and attached the syringe to the harness. Opened the line to the "Feeder Cell Suspension" transfer pack. Using the syringe drew up the volume of feeder cells calculated plus an additional 10.0 mL from the Transfer Pack into a 100 mL syringe. Closed the line to the Feeder Cell Suspension transfer pack once the volume of feeder cells is removed. Did not remove final syringe. Once a syringe has been filled, replaced it with a new syringe. Multiple syringes could be used to remove total volume. With each new syringe, pulled in 10 mL of air. Recorded the total volume (including the additional 10 mL) of feeder cells removed.

Added OKT3. In the BSC, using a 1.0 mL syringe and 16 G needle, drew up 0.15 mL of OKT3. Aseptically removed the needle from the syringe and attach the syringe to the needless injection port. Injected the OKT3. Opened the stopcock to the "Feeder Cell Suspension" transfer pack and added 10 mL of feeder cells removed previously to flush OKT3 through the line. Turned the syringe upside down and push air through to clear the line to the Feeder Cell Suspension transfer pack. Left the remaining feeder cell suspension in the syringe. Closed all clamps and remove the harness from the BSC. Heat sealed the Feeder Cell Suspension transfer pack, leaving enough tubing to weld.

Day 11 G-Rex Fill and Seed

Set up G-Rex500MCS. Removed a G-Rex500MCS from packaging and inspected the flask for any cracks or kinks in the tubing. Ensured all luer connections and closures were tight. Closed all clamps on the G-Rex500MCS lines except for the vent filter line. Using a marker drew a line at the 4.5 L gradation. Removed the "Complete CM2 Day 11 Media", from the incubator.

Prepared to pump media. Welded the red line of the G-Rex500MCS to the repeater pump transfer set attached to the complete CM2 Day 11 Media. Hung the "Complete CM2 Day 11 Media" bag on an IV pole. Fed the pump tubing through the Baxa pump. Pumped media into G-Rex500MCS. Set the Baxa pump to "High" and "9". Pumped 4.5 L of media into the G-Rex500MCS, filling to the line marked on the flask at the 4.5 L gradation. Heat sealed the red line of the G-Rex500MCS near the weld. Labeled the flask with the "Day 11" label. Welded the Feeder Cell: Suspension transfer pack to the flask. Sterile welded the red line of the G-Rex500MCS to the "Feeder Cell Suspension" transfer pack.

Added Feeder Cells to G-Rex500MCS. Opened all clamps between Feeder Cell Suspension and G-Rex500MCS and added Feeder Cell Suspension to flask by gravity feed. Heat sealed the red line near the weld. Welded the TIL Suspension transfer pack to the flask. Sterile weld the red line of the G-Rex500MCS to the "TIL Suspension" transfer pack.

Added TIL to G-Rex500MCS. Opened all clamps between TIL Suspension and G-Rex500MCS and added TIL Suspension to flask by gravity feed. Heat sealed the red line near the weld to remove the TIL suspension bag.

Incubated G-Rex500MCS. Checked that all clamps on the G-Rex500MCS were closed except the large filter line and place in the incubator. Incubator parameters: Temperature LED Display: 37.0±2.0° C., CO2 Percentage: 5.0±1.5% CO2.

Calculated incubation window. Performed calculations to determine the proper time to remove G-Rex500MCS from incubator on Day 16. Lower limit: Time of incubation+108 hours. Upper limit: Time of incubation+132 hours.

Day 11 Excess TIL Cryopreservation

Froze Excess TIL Vials. Recorded and verified the total number of vials placed into the Control Rate Freezer (CRF). Upon completion of freeze, transfer vials from CRF to the appropriate storage container.

Day 16 Media Preparation

Pre-warmed AIM-V Media. Removed three CTS AIM V 10 L media bags from 2-8° C. at least 12 hours prior to use and place at room temperature protected from light. Labeled each bag. Record warming start time and date. Ensured all bags have been warmed for a duration between 12 and 24 hours.

Attached the larger diameter end of a fluid pump transfer set to one of the female ports of a 10 L Labtainer bag using the Luer connectors. Setup 10 L Labtainer for Supernatant Label as "Supernatant". Setup 10 L Labtainer for Supernatant. Ensure all clamps were closed prior to removing from the BSC.

Thawed 5×1.1 mL aliquots of IL-2 ($6\times10^6$ IU/mL) (BR71424) per bag of CTS AIM V media until all ice had melted. Aliquoted 100.0 mL of Glutamax into an appropriately sized receiver. Recorded the volume added to each receiver and labeled each receiver as "GlutaMax."

Added IL-2 to GlutaMax. Using a micropipette, added 5.0 mL of IL-2 to each GlutaMax receiver. Ensured to rinse the tip per process note 5.18 and used a new pipette tip for each mL added. Recorded volume added to each Glutamax receiver and labeled each receiver as "GlutaMax+IL-2" and receiver number.

Prepared CTS AIM V media bag for formulation. Ensured CTS AIM V 10 L media bag (W3012717) was warmed at room temperature and protected from light for 12-24 hours prior to use. Recorded end incubation time. In the BSC, closed clamp on a 4" plasma transfer set, then connected to the bag using the spike ports. Maintained constant pressure while turning the spike in one direction. Ensured to not puncture the side of the port. Connected the larger diameter end of a repeater pump fluid transfer set to the 4" plasma transfer set via luer.

Stage Baxa pump next to BSC. Removed pump tubing section of repeater pump fluid transfer set from BSC and installed in repeater pump.

Prepared to formulate media. In BSC, removed syringe from Pumpmatic Liquid-Dispensing System (PLDS) and discarded. Ensured to not compromise the sterility of the PLDS pipette. Connected PLDS pipette to smaller diameter end of repeater pump fluid transfer set via luer connection and placed pipette tip in "GlutaMax+IL-2" prepared above for aspiration. Open all clamps between receiver and 10 L bag.

Pumped GlutaMax+IL-2 into bag. Set the pump speed to "Medium" and "3" and pump all "GlutaMax+IL-2" into 10 L CTS AIM V media bag. Once no solution remains, clear line and stop pump. Recorded the volume of GlutaMax containing IL-2 added to each Aim V bag below.

Removed PLDS. Ensured all clamps were closed, and removed the PLDS pipette from the repeater pump fluid transfer set. Removed repeater pump fluid transfer set and red cap the 4" plasma transfer set.

Labeled each bag of "Complete CM4 Day 16 media" prepared.

Removed Media Retain per Sample Plan. Using a 30 mL syringe, removed 20.0 mL of "Complete CM4 Day 16 media" by attaching syringe to the 4" plasma transfer set and dispensed sample into a 50 mL conical tube. Ensure 4" plasma transfer set was either clamped or red capped after removal of syringe.

Attached new repeater pump fluid transfer set. Attached the larger diameter end of a new fluid pump transfer set onto the 4" plasma transfer set that was connected to the "Complete CM4 Day 16 media" bag. Labeled with sample plan inventory label and stored media retain sample at 2-8° C. until submitted for testing.

Monitored Incubator. If applicable, monitor for additional bags prepared. Incubator parameters: Temperature LED Display: 37.0±2.0° C., CO2 Percentage: 5.0±1.5% CO2.

Warmed Complete CM4 Day 16 Media. Warmed the first bag of Complete CM4 Day 16 Media in incubator for ≥30 minutes until ready for use. If applicable, warmed additional bags.

Prepared Dilutions. In the BSC, added 4.5 mL of AIM-V Media that had been labelled with "For Cell Count Dilutions" to each 4×15 mL conical tube. Labeled the conical tubes. Labeled 4 cryovials.

Day 16 REP Spilt

Monitored Incubator. Incubator parameters: Temperature LED Display: 37.0±2.0° C., CO2 Percentage: 5.0±1.5% CO2

Removed G-Rex500MCS from Incubator. Performed check below to ensure incubation parameters are met before removing G-Rex500MCS from incubator: upper limit, lower limit, time of removal. Removed G-Rex500MCS from the incubator.

Heat sealed a 1 L transfer pack (W3006645), leaving ~12" of line. Labeled 1 L transfer pack as TIL Suspension. Place 1 L transfer pack, including the entire line, on a scale and record dry weight.

GatheRex Setup. Sterile welded the red media removal line from the G-Rex500MCS to the repeater pump transfer set on the 10 L labtainer bag "Supernatant" prepared above. Sterile welded the clear cell removal line from the G-Rex500MCS to the TIL Suspension transfer pack prepared above. Placed G-Rex500MCS flask on the left side of the GatheRex. Placed the supernatant labtainer bag and TIL suspension transfer pack to the right side. Installed the red media removal line from the G-Rex500MCS to the top clamp (marked with a red line) and tubing guides on the GatheRex. Installed the clear harvest line from the G-Rex500MCS to the bottom clamp (marked with a blue line) and tubing guides on the GatheRex. Attached the gas line from the GatheRex to the sterile filter of the G-Rex500

MCS. NOTE: Before removing the supernatant from the G-Rex500MCS, ensured all clamps on the cell removal lines were closed.

Volume Reduction of G-Rex500MCS. Transferred ~4.5 L of culture supernatant from the G-Rex500MCS to the 10 L Labtainer per SOP-01777. Visually inspect G-Rex500MCS to ensure flask as level and media had been reduced to the end of the aspirating dip tube.

Prepared flask for TIL Harvest. After removal of the supernatant, closed all clamps to the red line.

Initiation of TIL Harvest. Recorded the start time of the TIL harvest. Vigorously tap flask and swirl media to release cells. Performed an inspection of the flask to ensure all cells have detached. Tilted the flask to ensure hose is at the edge of the flask. If the cell collection straw is not at the junction of the wall and bottom membrane, rapping the flask while tilted at a 450 angle is usually sufficient to properly position the straw.

TIL Harvest. Released all clamps leading to the TIL suspension transfer pack. Using the GatheRex transferred the cell suspension into the TIL Suspension transfer pack. NOTE: Be sure to maintain the tilted edge until all cells and media are collected. Inspected membrane for adherent cells.

Rinsed flask membrane. Rinsed the bottom of the G-Rex500MCS. Cover ~¼ of gas exchange membrane with rinse media. Closed clamps on G-Rex500MCS. Ensured all clamps were closed on the G-Rex500MCS.

Heat sealed. Heat sealed the Transfer Pack containing the TIL as close to the weld as possible so that the overall tubing length remained approximately the same. Heat sealed the 10 L Labtainer containing the supernatant and passed into the BSC for sample collection.

Recorded weight of Transfer Pack with cell suspension and calculate the volume suspension. Prepared transfer pack for sample removal. Welded a 4" Plasma Transfer Set, to the TIL Suspension transfer pack from above, leaving the female luer end attached as close to the bag as possible.

Removed testing samples from cell supernatant. In the BSC, remove 10.0 mL of supernatant from 10 L labtainer using female luer port and appropriately sized syringe. Placed into a 15 mL conical tube and label as "BacT" and Retain the tube for BacT sample. Using a separate syringe, removed 10.0 mL of supernatant and placed into a 15 mL conical tube. Retained the tube for mycoplasma sample for testing. Labeled tube as "Mycoplasma diluent". Closed supernatant bag. Placed a red cap on the luer port to close the bag, and pass out of BSC.

Removed Cell Count Samples. In the BSC, using separate 3 mL syringes for each sample, removed 4×1.0 mL cell count samples from "TIL Suspension" transfer pack using the luer connection. Placed samples in cryovials prepared above.

Removed Mycoplasma Samples. Using a 3 mL syringe, removed 1.0 mL from TIL Suspension transfer pack and place into 15 mL conical labeled "Mycoplasma diluent" prepared above. Labeled and stored Mycoplasma sample at 2-8° C. until submitted for testing.

Prepared Transfer Pack for Seeding. In the BSC, attached the large diameter tubing end of a Repeater Pump Fluid Transfer Set to the Luer adapter on the transfer pack containing the TIL. Clamped the line close to the transfer pack using a hemostat. Placed a red cap onto the end of the transfer set.

Placed TIL in Incubator. Removed cell suspension from the BSC and place in incubator until needed. Recorded time.

Performed Cell Counts. Performed cell counts and calculations utilizing NC-200. Diluted cell count samples initially by adding 0.5 mL of cell suspension into 4.5 mL of AIM-V media prepared above. This gave a 1:10 dilution.

Calculated flasks for subculture. Calculated the total number of flasks to seed. NOTE: Rounded the number of G-Rex500MCS flasks to see up to the neared whole number.

TABLE 35

Flask calculation

| Total Viable Cell Count A | Target Cells Required per Flask B | Number of G-Rex500MCS Flasks to Seed C = A ÷ B |
|---|---|---|
| cells | $1.0 \times 10^9$ cells/flask | flasks |

The maximum number of G-Rex500MCS flasks to seed was five. If the calculated number of flasks to seed exceeded five, only five were seeded USING THE ENTIRE VOLUME OF CELL SUSPENSION AVAILABLE.

Determined number of additional media bags needed. Calculated the number of media bags required in addition to the bag prepared above. Round the number of media bags required up to the next whole number.

TABLE 36

Media bag calculation

| Number of G-Rex500MCS Flasks to Seed A | Number of Media Bag Required B = A ÷ 2* | Number of Bags Prepared in above C | Number of Additional Bags to Prepare D = B − C |
|---|---|---|---|
| | 1 | | |

Prepared additional media as needed. Prepared one 10 L bag of "CM4 Day 16 Media" for every two G-Rex-500M flask needed calculated above. Proceeded and seeded the first GREX-500M flask(s) while additional media is prepared and warmed.

Prepared additional media bags as needed. Prepared and warmed the calculated number of additional media bags determined above.

Filled G-Rex500MCS. Opened a G-Rex500MCS on the benchtop and inspected for cracks in the vessel or kinks in the tubing. Ensured all luer connections and closures were tight. Made a mark at the 4500 mL line on the outside of the flask with a marker. Closed all clamps on the G-Rex500MCS except the large filter line. Sterile welded the red media line of a G-Rex500MCS to the fluid transfer set on the media bag prepared above.

Prepared to pump media. Hung "CM4 Day 16 Media" on an IV pole. Fed the pump tubing through the Baxa pump.

Pumped media into G-Rex500MCS. Set the Baxa pump on "High" and "9" and pump 4500 mL of media into the flask. Pumped 4.5 L of "CM4 Day 16 Media" into the G-Rex500MCS, filling to the line marked on the flask as above. Once 4.5 L of media had been transferred, stopped the pump.

Heat Sealed. Heat sealed the red media line of G-Rex500MCS, near the weld created, removing the media bag.

Repeated Fill. Repeat filling and sealing steps for each flask calculated in above as media is warmed and prepared for use. Multiple flasks may be filled at the same time using gravity fill or multiple pumps. Fill only two flasks per bag of media.

Recorded and labelled flask(s) filled. Labeled each flask alphabetically and with "Day 16" labels.

As needed incubated flask. Held flask in incubator while waiting to seed with TIL. Recorded the total number of flasks filled.

Calculated volume of cell suspension to add. Calculated the target volume of TIL suspension to add to the new G-Rex500MCS flasks.

TABLE 637

Cell suspension volume

| Total Volume of TIL suspension A | Number of flask(s) filled | Target Volume of cell suspension to transfer to each flask C = A ÷ B |
|---|---|---|
| mL | | mL |

If number of flasks exceeds five only five will be seeded, USING THE ENTIRE VOLUME OF CELL SUSPENSION.

Prepared Flasks for Seeding. Removed G-Rex500MCS from Step 8.10.70 from the incubator.

Prepared for pumping. Closed all clamps on G-Rex500MCS except large filter line. Fed the pump tubing through the Baxa pump.

Removed TIL from incubator. Removed "TIL Suspension" transfer pack from the incubator and record incubation end time.

Prepared cell suspension for seeding. Sterile welded "TIL Suspension" transfer pack from above to pump inlet line.

Placed TIL suspension bag on a scale. Primed the line from the TIL suspension bag to the weld using the Baxa pump set to "Low" and "2". Tared the scale.

Seeded flask with TIL Suspension. Set Baxa pump to "Medium" and "5". Pump the volume of TIL suspension calculated above into flask. Record the volume of TIL Suspension added to each flask.

Heat sealed. Heat sealed the "TIL Suspension" transfer pack, leaving enough tubing to weld on the next flask.

Filled remaining flasks. Between each flask seeded, ensured to mix "TIL Suspension" transfer pack and repeat filling and sealing steps to seed all remaining flaks.

Monitored Incubator. If flasks must be split among two incubators, ensure to monitor both. Incubator parameters: Temperature LED Display: 37.0±2.0° C., CO2 Percentage: 5.0±1.5% CO2. Recorded the time each flask is placed in the incubator.

Calculated incubation window. Performed calculations below to determine the time range to remove G-Rex500MCS from incubator on Day 22. Lower limit: time+132 hours; upper limit: time+156 hours.

Day 22 Wash Buffer Preparation

Prepared 10 L Labtainer Bag. In BSC, attach a 4" plasma transfer set to a 10 L Labtainer Bag via luer connection. Prepared 10 L Labtainer Bag Label as "Supernatant", lot number, and initial/date. Closed all clamps before transferring out of the BSC. NOTE: Prepared one 10 L Labtainer Bag for every two G-Rex500MCS flasks to be harvested.

Welded fluid transfer set. Outside the BSC, closed all clamps on 45-4M60. Welded repeater fluid transfer set to one of the male luer ends of 45-4M60.

Passed Plasmalyte-A and Human Albumin 25% into the BSC. Passed the 4S-4M60 and repeater fluid transfer set assembly into the BSC.

TABLE 38

| Components | |
|---|---|
| Component Description | Amount Needed |
| Plasmalyte-A | 3000.0 mL |
| Human Albumin 25% | 120.0 mL |
| 4S-4M60 with Repeater | 1 Apparatus |
| Fluid Transfer Set | Step 8.11.7 |

TABLE 39

| Plasmalyte-A | |
|---|---|
| Latex: | Not Made with Natural Rubber Latex |
| Container Type: | VIAFLEX |
| PVC: | Contains PVC |
| DEHP: | Contains DEHP |
| Volume: | 500 ML |
| Total Calories: | 21 Kcal/L |
| Sodium: | 140 mEq/L |
| Potassium: | 5 mEq/L |
| Magnesium: | 3 mEq/L |
| Acetate: | 27 mEq/L |
| Chloride: | 98 mEq/L |
| Gluconate: | 23 mEq/L |
| Osmolarity (mOsmol/L): | 294 |
| Specific Gravity: | 1.01 |
| pH: | 7.4 |
| Fill Range Volume (mL): | 530-565 |
| Shelf Life from manufacture: | 15 months |
| Contains Preservative: | No |
| Storage Recommendations: | Store at room temperature (25° C./77° F.); brief exposure up to 40° C./104° F. does not adversely affect the product. |
| Packaging: | Single Pack |
| Rx Only: | Yes |

**As commercially available from http://ecatalog.baxter.com/ecatalog/loadproduct.html?cid=20016&lid=10001&hid=20001&pid=821874.

Pumped Plasmalyte into 3000 mL bag. Spiked three bags of Plasmalyte-A to the 4S-4M60 Connector set. NOTE: Wipe the port cover with an alcohol swab (W3009488) prior to removing. NOTE: Maintain constant pressure while turning the spike in one direction. Ensure to not puncture the side of the port. Connected an Origen 3000 mL collection bag via luer connection to the larger diameter end of the repeater pump transfer set. Closed clamps on the unused lines of the 3000 mL Origen Bag. Staged the Baxa pump next to the BSC. Fed the transfer set tubing through the Baxa pump situated outside of the BSC. Set pump to "High" and "9". Opened all clamps from the Plasmalyte-A to the 3000 mL Origen Bag. Pumped all of the Plasmalyte-A into the 3000 mL Origen bag. Once all the Plasmalyte-A had been transferred, stopped the pump. If necessary, removed air from 3000 mL Origen bag by reversing the pump and manipulating the position of the bag. Closed all clamps.

Remove the 3000 mL bag from the repeater pump fluid transfer set via luer connection and placed a red cap (W3012845) on the line to the bag.

Added Human Albumin 25% to 3000 mL Bag. Opened vented mini spike. Without compromising sterility of spike, ensured blue cap is securely fastened. Spiked the septum of a Human Albumin 25% bottle with the vented mini spike. NOTE: Ensured to not compromise the sterility of the spike. Repeated two times for a total of three (3) spiked Human Albumin 25% bottles. Removed the blue cap from one vented mini spike and attach a 60 mL syringe to the Human Serum Albumin 25% bottle. Draw up 60 mL of Human Serum Albumin 25%. It may be necessary to use more than one bottle of Human Serum Albumin 25%. If necessary, disconnect the syringe from the vented mini spike and connect it to the next vented mini spike in a Human Serum Albumin 25% bottle. Once 60 mL has been obtained, remove the syringe from the vented mini spike. Attach syringe to needleless injection port on 3000 mL Origen bag filled with Plasmalyte-A. Dispensed all of the Human Albumin 25%. Repeated to obtain a final volume of 120.0 mL of Human Albumin 25%. Gently mixed the bag after all of the Human Albumin 25% had been added. Labeled as "LOVO-Wash Buffer" and assign a 24 hour expiry.

Prepared IL-2 Diluent. Using a 10 mL syringe, removed 5.0 mL of LOVO Wash Buffer using the needleless injection port on the LOVO Wash Buffer bag. Dispensed LOVO wash buffer into a 50 mL conical tube and label as "IL-2 Diluent".

CRF Blank Bag LOVO Wash Buffer Aliquoted. Using a 100 mL syringe, drew up 70.0 mL of LOVO Wash Buffer from the needleless injection port. NOTE: Wiped the needleless injection port with an alcohol pad before each use. Placed a red cap on the syringe and label as "blank cryo bag" and lot number. NOTE: Held the syringe at room temp until needed in Step 8.14.3

Completed Wash Buffer Prep. Closed all clamps on the LOVO Wash Buffer bag.

Thawed IL-2. Thawed one 1.1 mL of IL-2 ($6\times10^6$ IU/mL), until all ice has melted. Record IL-2 Lot number and Expiry. NOTE: Ensured IL-2 label is attached.

IL-2 Preparation. Added 504 IL-2 stock ($6\times10^6$ IU/mL) to the 50 mL conical tube labeled "IL-2 Diluent."

IL-2 Preparation. Relabeled conical as "IL-2 $6\times10^4$", the date, lot number, and 24 hour expiry. Cap and store at 2° C.-8° C.

Cryopreservation Prep. Placed 5 cryo-cassettes at 2° C.-8° C. to precondition them for final product cryopreservation.

Prepared Cell Count Dilutions. In the BSC, added 4.5 mL of AIM-V Media that has been labelled with lot number and "For Cell Count Dilutions" to 4 separate 15 mL conical tubes and labeled the tubes.

Prepared Cell Counts. Labeled 4 cryovials with vial number (1-4).

Day 22 TIL Harvest

Monitored the incubator. Incubator Parameters Temperature LED display: 37=2.0° C., CO2 Percentage: 5%±1.5%.

Removed G-Rex500MCS Flasks from Incubator. Checked flasks and confirmed incubation parameters were met before removing G-Rex500MCS from incubator (incubation time).

Prepared TIL collection bag Labeled a 3000 mL collection bag as "TIL Suspension", lot number, and initial/date.

Sealed off extra connections. Heat sealed off two luer connections on the collection bag near the end of each connection.

GatheRex Setup. Sterile welded (per Process Note 5.11) the red media removal line from the G-Rex500MCS to the 10 L labtainer bag prepared above. NOTE: Referenced Process Note 5.16 for use of multiple GatheRex devices. Sterile welded (per Process Note 5.11) the clear cell removal line from the G-Rex500MCS to the TIL Suspension collection bag prepared above. Placed the G-Rex500MCS flask on the left side of the GatheRex. Placed the supernatant Labtainer bag and pooled TIL suspension collection bag to the right side. Installed the red media removal line from the G-Rex500MCS to the top clamp (marked with a red line) and tubing guides on the GatheRex. Installed the clear harvest line from the G-Rex500MCS to the bottom clamp (marked with a blue line) and tubing guides on the GatheRex. Attached the gas line from the GatheRex to the sterile filter of the G-Rex500MCS. Before removing the supernatant from the G-Rex500MCS, ensured all clamps on the cell removal lines were closed.

Volume Reduction. Transferred ~4.5 L of supernatant from the G-Rex500MCS to the Supernatant bag. Visually inspected G-Rex500MCS to ensure flask is level and media had been reduced to the end of the aspirating dip tube. Repeat step if needed.

Prepared flask for TIL Harvest. After removal of the supernatant, closed all clamps to the red line.

Initiated collection of TIL. Recorded the start time of the TIL harvest. Vigorously tap flask and swirl media to release cells. Performed an inspection of the flask to ensure all cells have detached. Placed "TIL Suspension" 3000 mL collection bag on dry wipes on a flat surface. Tilted the flask to ensure hose is at the edge of the flask. NOTE: If the cell collection hose was not at the junction of the wall and bottom membrane, rapping the flask while tilted at a 45° angle is usually sufficient to properly position the hose.

TIL Harvest. Released all clamps leading to the TIL suspension collection bag. Using the GatheRex, transferred the TIL suspension into the 3000 mL collection bag. NOTE: Maintained the tilted edge until all cells and media were collected. Inspect membrane for adherent cells.

Rinsed flask membrane. Rinsed the bottom of the G-Rex500MCS. Covered ~¼ of gas exchange membrane with rinse media.

Closed clamps on G-Rex500MCS. Ensure all clamps are closed.

Heat sealed. Heat seal the collection bag containing the TIL as close to the weld as possible so that the overall tubing length remained approximately the same. Heat sealed the Supernatant bag.

Completed harvest of remaining G-Rex 500 MCS flasks. Repeat steps above, pooling all TIL into the same collection bag. It was necessary to replace the 10 L supernatant bag after every 2nd flask.

Prepared LOVO source bag. Obtained a new 3000 mL collection bag. Labeled as "LOVO Source Bag", lot number, and Initial/Date. Heat sealed the tubing on the "LOVO Source bag", removing the female luers, leaving enough line to weld.

Weighed LOVO Source Bag. Placed an appropriately sized plastic bin on the scale and tare. Place the LOVO Source Bag, including ports and lines, in the bin and record the dry weight.

Transferred cell suspension into LOVO source bag. Closed all clamps of a 170 µm gravity blood filter.

Transferred cell suspension into LOVO source bag. Sterile welded the long terminal end of the gravity blood filter to the LOVO source bag. Sterile welded one of the two source lines of the filter to "pooled TIL suspension" collection bag. Once weld was complete, heat sealed the unused line on the filter to remove it. Opened all necessary clamps and elevate the TIL suspension by hanging the collection bag on an IV pole to initiate gravity-flow transfer of TIL through the blood filter and into the LOVO source bag. Gently rotated or knead the TIL Suspension bag while draining in order to keep the TIL in even suspension.

Closed all clamps. Once all TIL were transferred to the LOVO source bag, closed all clamps.

Heat Sealed. Heat sealed (per Process Note 5.12) as close to weld as possible to remove gravity blood filter.

Removed Cell Counts Samples. In the BSC, using separate 3 mL syringes for each sample, removed 4×1.0 mL cell count samples from the LOVO source bag using the needless injection port. Placed samples in the cryovials prepared in Step 8.11.36.

Performed Cell Counts. Performed cell counts and calculations utilizing NC-200. Diluted cell count samples initially by adding 0.5 mL of cell suspension into 4.5 mL of AIM-V media prepared above. This gave a 1:10 dilution.

Recorded Cell Count and Sample Volumes. Calculated Total Viable TIL Cells. If Total Viable cells $\geq 1.5 \times 10^9$, proceeded. Calculate Total Nucleated Cells.

Prepared Mycoplasma Diluent. In the BSC, removed 10.0 mL from one supernatant bag via luer sample port and placed in a 15 mL conical. Label 15 mL conical "Mycoplasma Diluent".

LOVO

Turned on the LOVO and started the "TIL G-Rex Harvest" protocol and followed screen prompts. Buffer type was PlasmaLyte. Followed the LOVO touch screen prompts.

Determined the final product target volume. Using the total nucleated cells (TNC) value and the chart below, determined the final product target volume and recorded (mL).

TABLE 40

Calculate final product volume

| Cell Range | Final Product (Retentate) Volume to Target (mL) |
|---|---|
| 0 < Total (Viable + Dead) Cells ≤ $7.1 \times 10^{10}$ | 165 |
| $7.1 \times 10^{10}$ < Total (Viable + Dead) Cells ≤ $1.1 \times 10^{11}$ | 215 |
| $1.1 \times 10^{11}$ < Total (Viable + Dead) Cells ≤ $1.5 \times 10^{11}$ | 265 |

Followed the LOVO touch screen prompts.

Loaded disposable kit. Prior to loading the disposable kit, wipe pressure sensor port with an alcohol wipe followed by a lint-free wipe. Load the disposable kit. Follow screen directions on loading the disposable kit.

Removed filtrate bag. When the standard LOVO disposable kit had been loaded, touched the Next button. The Container Information and Location Screen displayed. Removed filtrate bag from scale Ensured Filtrate container was New and Off-Scale Entered Filtrate capacity. Sterile welded a LOVO Ancillary Bag onto the male luer line of the existing Filtrate Bag. Ensured all clamps are open and fluid path is clear. Touch the Filtrate Container Capacity entry field. A numeric keypad displays. Enter the total new Filtrate capacity (5,000 mL). Touch the button to accept the entry. NOTE: Estimated Filtrate Volume should not exceed 5000 mL.

Placed Filtrate container on benchtop. NOTE: If tubing was removed from the F clamp during welding, placed the tubing back into the clamp. Placed the new Filtrate container on the benchtop. DID NOT hang the Filtrate bag on weigh scale #3. Weigh scale #3 will be empty during the procedure.

Followed the LOVO touch screen prompts after changes to the filtrate container.

Ensured kit was loaded properly. The Disposable Kit Dry Checks overlay displays. Checked that the kit was loaded properly and all clamps were open. Checked all tubing for kinks or other obstructions and correct if possible. Ensured kit was properly installed and check all Robert's clamps. Pressed the Yes button. All LOVO mechanical clamps closed automatically and the Checking Disposable Kit Installation screen displays. The LOVO went through a series of pressurizing steps to check the kit.

Kit Check Results. If the Kit check passed, proceeded to the next step. *If No, a second Kit Check could be performed after checks have been complete. *If No, Checked all tubing for kinks or other obstructions and correct *If No, Ensured kit was properly installed and check all Robert's clamps. If the 2nd kit check failed: Contact area management and prepare to installation of new kit in Section 10.0. Repeat Step 8.13.23-Step 8.13.30 needed.

Attached PlasmaLyte. The Connect Solutions screen displayed. The wash value would always be 3000 mL. Entered this value on screen.

Sterile welded the 3000 mL bag of PlasmaLyte to the tubing passing through Clamp 1. Hung the PlasmaLyte bag on an IV pole placing both corner bag loops on the hook.

Verified that the PlasmaLyte was attached. Opened any plastic clamps. Verified that the Solution Volume entry was 3000 mL. Touched the "Next" button. The Disposable Kit Prime overlay displayed. Verified that the PlasmaLyte was attached and any welds and plastic clamps on the tubing leading to the PlasmaLyte bag were open, then touched the Yes button Observed that the PlasmaLyte is moving. Disposable kit prime starts and the Priming Disposable Kit Screen displays. Visually observed that PlasmaLyte moving through the tubing connected to the bag of PlasmaLyte. If no fluid was moving, pressed the Pause Button on the screen and determined if a clamp or weld was still closed. Once the problem had been solved, pressed the Resume button on the screen to resume the Disposable Kit Prime. Followed the LOVO touch screen prompts.

Attached Source container to tubing. Sterile weld the LOVO Source Bag prepared in Step 8.12.31 to the tubing passing through Clamp S per Process Note 5.11. It could be necessary to remove the tubing from the clamp. Note: Made sure to replace source tubing into the S clamp if removed.

Hung Source container. Hung the Source container on the IV pole placing both corner bag loops on the hook. DID NOT hang the Source on weigh scale #1. Opened all clamps to the source bag.

Verified Source container was attached. Touched the Next button. The Source Prime overlay displayed. Verified that the Source was attached to the disposable kit, and that any welds and plastic clamps on the tubing leading to the Source were open. Touched the Yes button.

Confirm PlasmaLyte was moving. Source prime started and the Priming Source Screen displayed. Visually observed that PlasmaLyte is moving through the tubing attached to the Source bag. If no fluid is moving, press the Pause Button on the screen and determine if a clamp or weld is still closed. Once the problem was solved, pressed the Resume button on the screen to resume the Source Prime.

Started Procedure Screen. When the Source prime finishes successfully, the Start Procedure Screen displays. Pressed Start, the "Pre-Wash Cycle 1" pause screen appears immediately after pressing start.

Inverted In Process Bag. Removed the In Process Bag from weigh scale #2 (can also remove tubing from the In Process top port tubing guide) and manually invert it to allow the wash buffer added during the disposable kit prime step to coat all interior surfaces of the bag. Re-hang the In Process Bag on weigh scale #2 (label on the bag was facing to the left). Replace the top port tubing in the tubing guide, if it was removed.

Inverted Source bag. Before pressing the Start button, mixed the Source bag without removing it from the IV pole by massaging the bag corners and gently agitating the cells to create a homogeneous cell suspension. Pressed the Resume button. The LOVO started processing fluid from the Source bag and the Wash Cycle 1 Screen displays.

Source Rinse Pause. The Rinse Source Pause screen displayed once the source container was drained and the LOVO had added wash buffer to the Source bag. Without removing the Source bag from IV pole, massaged the corners and mixed well. Pressed Resume.

Mixed In Process Bag Pause. To prepare cells for another pass through the spinner, the In Process Bag was diluted with wash buffer. After adding the wash buffer to the In Process Bag, the LOVO pauses automatically and displays the "Mix In Process Bag" Pause Screen. Without removing the bag from the weigh scale, mixed the product well by gently squeezing the bag. Press Resume.

Massaged In Process Corners Pause. When the In Process Bag was empty, wash buffer was added to the bottom port of the In Process Bag to rinse the bag. After adding the rinse fluid, the LOVO paused automatically and displayed the "Massage IP corners" Pause Screen. When the "Massage IP corners" Pause Screen displayed, DO NOT remove the bag from weigh scale #2. With the In Process Bag still hanging on weigh scale #2, massage the corners of the bag to bring any residual cells into suspension. Ensured the bag was not swinging on the weigh scale and pressed the Resume button.

Waited for Remove Products Screen. At the end of the LOVO procedure, the Remove Products Screen displayed. When this Screen displays, all bags on the LOVO kit could be manipulated. Note: Did not touch any bags until the Remove Products displayed.

Removed retentate bag. Placed a hemostat on the tubing very close to the port on the Retentate bag to keep the cell suspension from settling into the tubing. Heat sealed (per Process Note 5.12) below the hemostat, making sure to maintain enough line to weld in Step 8.13.48. Removed the retentate bag.

Prepared retentate bag for formulation. Welded the female luer lock end of a 4" Plasma Transfer Set to the retentate bag. Transferred the retentate bag.

Removed Products. Followed the instructions on the Remove Products Screen. Closed all clamps on the LOVO kit to prevent fluid movement.

Removed Products. Touched the Next button. All LOVO mechanical clamps opened and the Remove Kit Screen displayed.

Recorded Data. Followed the instructions on the Remove Kit screen. Touched the "Next" button. All LOVO mechanical clamps close and the Results Summary Screen displays. Recorded the data from the results summary screen. Closed all pumps and filter support. Removed the kit when prompted to do so by the LOVO. All Times recorded were recorded directly from the LOVO.

Final Formulation and Fill

Target volume/bag calculation. From table DDD below, selected the number of CS750 bags to be filled, target fill volume per bag, volume removed for retain per bag, and final target volume per bag that corresponded to the Volume of LOVO Retentate from above.

TABLE 41

Target volume/bag calculation

| Volume of LOVO product | Volume of CS10 to add to product | Final Predicted Volume of formulated product | Number of bags to be filled | Target Fill Volume per bag | Volume removed for retain per bag | Final Target Volume per bag |
|---|---|---|---|---|---|---|
| 165 mL | 165 mL | 330 mL | 3 | 107 mL | 7 mL | 100 mL |
| 215 mL | 215 mL | 430 mL | 4 | 105 mL | 5 mL | 100 mL |
| 265 mL | 265 mL | 530 mL | 4 | 130 mL | 5 mL | 125 mL |

Prepared CRF Blank. Calculated volume of CS-10 and LOVO wash buffer to formulate blank bag.

TABLE 42

Calculated volumes.

| Final Target Volume per Bag A | Blank LOVO Wash Buffer Volume B = A/2 | Blank CS-10 Volume (mL) C = B |
|---|---|---|
| mL | mL | mL |

Prepared CRF Blank. Outside of the BSC, using the syringe of LOVO Wash Buffer prepared in above, added volume calculated to an empty CS750 bag via luer connection. Note: Blank CS750 bag formulation does not need to be done aseptically. Using an appropriately sized syringe, added the volume of CS-10 calculated to the same CS750 bag prepared above. Placed a red cap on the CS750 bag. Removed as much air as possible from the CS-750 bag as possible. Heat sealed the CS750 bag as close to the bag as possible, removing the tubing. Label CS750 bag with "CRF Blank", lot number, and initial/date. Placed the CRF Blank on cold packs until it was placed in the CRF.

Calculated required volume of IL-2. Calculated the volume of IL-2 to add to the Final Product

TABLE 43

Calculated IL-2 volume

| Parameter | Formula | Result |
|---|---|---|
| Final Retentate Volume | Step 8.13.51 | A. mL |
| Final Formulated Volume | B = A × 2 | B. mL |
| Final IL-2 Concentration desired (IU/mL) | 300 IU/mL | C. 300 IU/mL |
| IU of IL-2 Required | D = B × C | D. IU |
| IL-2 Working Stock from Step 8.11.33 | $6 \times 10^4$ IU/mL | E. $6 \times 10^4$ IU/mL |
| Volume of IL-2 to Add to Final Product | F = D ÷ E | F. mL |

Assembled Connect apparatus. Sterile welded a 4S-4M60 to a CC2 Cell Connect replacing a single spike of the Cell Connect apparatus with the 4-spike end of the 4S-4M60 manifold.

Assembled Connected apparatus. Sterile welded the CS750 Cryobags to the harness prepared above, replacing one of the four male luer ends (E) with each bag. Welded (per Process Note 5.11) CS-10 bags to spikes of the 45-4M60. Kept CS-10 cold by placing the bags between two cold packs conditioned at 2-8° C.

Prepared TIL with IL-2. Using an appropriately sized syringe, removed amount of IL-2 determined above from the "IL-2 6×104" aliquot. Connect the syringe to the retentate bag prepared above via the Luer connection and inject IL-2. Clear the line by pushing air from the syringe through the line.

Labeled Formulated TIL Bag. Closed the clamp on the transfer set and label bag as "Formulated TIL" and passed the bag out of the BSC.

Added the Formulated TIL bag to the apparatus. Once IL-2 had been added, welded the "Formulated TIL" bag to the remaining spike on the apparatus.

Added CS10. Passed the assembled apparatus with attached Formulated TIL, CS-750 bags, and CS-10 into the BSC. NOTE: The CS-10 bag and all CS-750 bags were placed between two cold packs preconditioned at 2° C.-8° C. Did not place Formulated TIL bag on cold packs. Ensured all clamps were closed on the apparatus. Turn the stopcock so the syringe was closed.

Switched Syringes. Drew ~10 mL of air into a 100 mL syringe and replaced the 60 mL syringe on the apparatus.

Added CS10. Turned stopcock so that the line to the CS750 bags is closed. Open clamps to the CS-10 bags and pull volume calculated above into syringe. NOTE: Multiple syringes will be used to add appropriate volume of CS-10. Closed clamps to CS-10 and open clamps to the Formulated TIL bag and add the CS-10. Add first 10.0 mL of CS10 at approximately 10.0 mL/minute. Add remaining CS-10 at approximate rate of 1.0 mL/sec. Note: Multiple syringes were used to add appropriate volume of CS-10. Recorded time. NOTE: The target time from first addition of CS-10 to beginning of freeze is 30 minutes. Recorded the volume of each CS10 addition and the total volume added. Closed all clamps to the CS10 bags.

Prepared CS-750 bags. Turned the stopcock so that the syringe was open. Opened clamps to the Formulated TIL bag and drew up suspension stopping just before the suspension reaches the stopcock. Closed clamps to the formulated TIL bag. Turned stopcock so that it was open to the empty CS750 final product bags. Using a new syringe, removed as much air as possible from the CS750 final product bags by drawing the air out. While maintaining pressure on the syringe plunger, clamped the bags shut. Draw ~20 mL air into a new 100 mL syringe and connect to the apparatus. NOTE: Each CS-750 final product bag should be between two cold packs to keep formulated TIL suspension cold.

Dispensed cells. Turned the stopcock so the line to the final product bags was closed. Pulled the volume calculated above from the Formulated TIL bag into the syringe. NOTE: Multiple syringes could be used to obtain correct volume. Turned the stopcock so the line to the formulated TIL bag is closed. Working with one final product bag at a time, dispense cells into a final product bag. Recorded volume of cells added to each CS750 bag above. Cleared the line with air from the syringe so that the cells are even with the top of the spike port. Closed the clamp on the filled bag. Repeated steps for each final product bag, gently mixing formulated TIL bag between each. Recorded volume of TIL placed in each final product bag below.

Removed air from final product bags and take retain. Once the last final product bag was filled, closed all clamps. Drew 10 mL of air into a new 100 mL syringe and replace the syringe on the apparatus. Manipulating a single bag at a time, drew all of the air from each product bag plus the volume of product for retain determined above. NOTE: Upon removal of sample volume, inverted the syringe and used air to clear the line to the top port of the product bag. Clamped the line to the bag once the retain volume and air was removed.

Recorded volume of retain removed from each bag.

Dispensed Retain. Dispensed retain into a 50 mL conical tube and label tube as "Retain" and lot number. Repeat for each bag.

Prepared final product for cryopreservation. With a hemostat, clamped the lines close to the bags. Removed syringe and red cap luer connection on the apparatus that the syringe was on. Passed apparatus out of the BSC. Heat sealed (per Process Note 5.12) at F, removing the empty retentate bag and the CS-10 bags. NOTE: Retained luer connection for syringe on the apparatus. Disposed of empty retentate and CS-10 Bags.

Labeled final product bags. Attached sample final product label below.

Prepared final product for cryopreservation. Held the cryobags on cold pack or at 2-8° C. until cryopreservation.

Removed Cell Count Sample. Using an appropriately sized pipette, remove 2.0 mL of retain removed above and placed in a 15 mL conical tube to be used for cell counts.

Performed Cell Counts. Performed cell counts and calculations utilizing the NC-200. NOTE: Diluted only one sample to appropriate dilution to verify dilution is sufficient. Diluted additional samples to appropriate dilution factor and proceed with counts. Recorded Cell Count sample volumes. NOTE: If no dilution needed, "Sample [µL]"=200, "Dilution [µL]"=0. Determined the Average of Viable Cell Concentration and Viability of the cell counts performed.

Calculated Flow Cytometry Sample. Performed calculation to ensure sufficient cell concentration for flow cytometry sampling.

TABLE 44

Calculate flow cytometry cell concentration

| Viable Cell Concentration A | Target Volume Required for $6 \times 10^7$ TVC B = $6 \times 10^7$ cells/A | Is B ≤ 1.0 mL? (Yes/No**) |
|---|---|---|
| | mL | |

Calculated IFN-γ. Sample Performed calculation to ensure sufficient cell concentration for IFN-γ sampling.

Heat Sealed. Once sample volumes had been determined, heat sealed Final Product Bags as close to the bags as possible to remove from the apparatus.

TABLE 745

Labeling and collection of samples

| Sample | Number of Containers | Sample Volume to Add to Each | Container Type |
|---|---|---|---|
| *Mycoplasma | 1 | 1.0 mL | 15 mL Conical |
| Endotoxin | 2 | 1.0 mL | 2 mL Cryovial |
| Gram Stain | 1 | 1.0 mL | 2 mL Cryovial |
| IFN-g | 1 | 1.0 mL | 2 mL Cryovial |
| Flow Cytometry | 1 | 1.0 mL | 2 mL Cryovial |
| **Bac-T Sterility | 2 | 1.0 mL | Bac-T Bottle |
| QC Retain | 4 | 1.0 mL | 2 mL Cryovial |
| Satellite Vials | 10 | 0.5 mL | 2 mL Cryovial |

For the Mycoplasma sample, add formulated cell suspension volume to the 15 mL conical labelled "Mycoplasma Diluent" from above. Sterility & BacT. Testing Sampling. In the BSC, remove a 1.0 mL sample from the retained cell suspension collected in above using an appropriately sized syringe and inoculate the anaerobic bottle. Repeat the above for the aerobic bottle.

Labeled and stored samples. Labeled all samples with sample plan inventory labels and store appropriately until transfer. Proceeded to next steps for cryopreservation of final product and samples.

Final Product Cryopreservation

Prepared Controlled Rate Freezer. Verified the CRF had been set up prior to freeze. Record CRF Equipment. Cryopreservation is performed.

Set up CRF probes. Punctured the septum on the CRF blank bag. Inserted the 6 mL vial temperature probe.

Placed final product and samples in CRF. Placed blank bag into preconditioned cassette and transferred into the approximate middle of the CRF rack. Transferred final product cassettes into CRF rack and vials into CRF vial rack. Transferred product racks and vial racks into the CRF. Recorded the time that the product is transferred into the CRF and the chamber temperature.

Determined the time needed to reach 4° C.±1.5° C. and proceed with the CRF run. Once the chamber temperature reached 4° C.±1.5° C., started the run. Recorded time.

Completed and Stored. Stopped the CRF after the completion of the run. Remove cassettes and vials from CRF. Transferred cassettes and vials to vapor phase LN2 for storage.

Example 17: Generation of TIL Products Enriched for Tumor Antigen-Specific T Cells with Enhanced Therapeutic Activity Goal: To generate TIL products enriched for tumor antigen-specific T cells with enhanced therapeutic activity.

Background:

T cells associated with malignant lesions are typically dysfunctional and fail to control/prevent tumor growth (Schietinger et al. Immunity 2016). All references in this example are incorporated by reference in their entireties for all purposes.

Tumor-infiltrating lymphocytes (TILs) can be extracted, activated, and propagated ex vivo and induce an efficient anti-tumor response upon in vivo re-infusion (Rosenberg et al. Clin Cancer Res 2011). The adoptive cell transfer approach, first demonstrated in patients suffering from metastatic melanoma, is being tested in additional solid tumor histologies. Clinical activity of TIL therapy in melanoma, and head and neck and cervical cancer has been reported (SITC, 2017). Thus, tumor-specific TILs can be rescued from the inhibitory tumor microenvironment and re-conditioned and/or amplified to sufficient numbers to efficiently target the tumor.

Retrospective analyses of TIL clinical trials suggest that less differentiated tumor-reactive T cells with robust proliferative and survival capacities confer superior anti-tumor efficacy relative to effector and effector memory T cells and that next generations of TIL products should consistently comprise elevated levels of less differentiated T cells (Klebanoff et al. J Immunother 2012).

Stem memory T cells (TSCM) are early progenitors of antigen-experienced central memory T cells; they display the long-term survival, self-renewal, and multipotency abilities that define stem cells; and are thus considered most desirable for the generation of effective TIL products. TSCM have shown enhanced anti-tumor activity compared with other T cell subsets in mouse models of adoptive cell transfer (Gattinoni et al. Nat Med 2009, 2011; Gattinoni, Nature Rev. Cancer, 2012; Cieri et al. Blood 2013).

Strategies that bias the TIL composition toward a high proportion of TSCM are needed to insure optimal anti-tumor activity.

Rejuvenation of antigen-experienced T cells was achieved using reprogramming tools developed through induced pluripotent stem cell (iPSC) technology (Nishimura et al. Cell Stem Cell 2012; Vizcardo et al. Cell Stem Cell 2012). This approach requires further ex vivo differentiation of the iPSCs to T cell population(s) best suited to combat the tumor, making it a lengthy 2-step process prone to restricting the original T cell receptor (TCR) repertoire. See also, Stewart, et al. 538:183-192 (2016) regarding in vitro and in vivo delivery strategies for intracellular delivery of materials.

Signaling pathways including Wnt, NOTCH, and Myb have been shown to support the generation of TSCM-like cells directly from naïve and/or antigen-experienced T cells (Gattinoni et al. Nat Med 2009, Kondo et al. Nat Comm 2017, Gautam et al. SITC 2017).

Cell fate reprogramming requires transient exposure to the appropriate transcription factors (TFs). In the case of TILs, this exposure needs to target a large fraction of T cells to preserve the tumor-derived TCR repertoire.

The SQZ vector-free microfluidic platform represents an advanced intracellular delivery strategy; it has demonstrated the ability to deliver proteins, including transcription factors, to a variety of primary human cells, including T cells (Sharei et al. PNAS 2013, as well as Sharei et al. PLOS ONE 2015 and Greisbeck et al. The J of Immunology vol. 195, 2015). See also, International Patent Publications WO 2013/059343A1, WO 2017/008063A1, and WO 2017/123663A1, all of which are incorporated by reference herein in their entireties. Such methods as described in International Patent Publications WO 2013/059343A1, WO 2017/008063A1, and WO 2017/123663A1 can be employed with the present invention in order to expose a population of TILs to transcription factors (TFs) and/or other molecules capable of inducing transient protein expression, wherein the TFs and/or other molecules capable of inducing transient protein expression provide for increased expression of tumor antigens and/or an increase in the number of tumor antigen-specific T cells in the population of TILs, thus resulting in reprogramming of the TIL population and an increase in therapeutic efficacy of the reprogrammed TIL population as compared to a non-reprogrammed TIL population.

Strategy:

It is proposed to use SQZ intracellular TF protein delivery technology to compare the ability of various reprogramming strategies to generate TIL products enriched for tumor antigen-specific T cells with enhanced therapeutic activity.

Work plan to include the following points/questions:
1. Tumor type(s)
   Melanoma
2. Optimal delivery conditions
   SQZ human T cell optimized protocol+additional conditions
   Monitor delivery efficiency
3. Choice of TFs
   TCF-1
   NOTCH1/2 ICD
   MYB
   +/− prior iPSC cocktail for 'full' reprogramming?
4. Activation/expansion stage at which to target the TILs
   REP Day 0
   Others?
5. Kinetics of reprogramming
   Days 7, 11, 14, 18 . . .

6. TIL subset(s) to target
   Bulk initially
   Sorted individual subsets (TCM, TEM TEFF, TEMRA) to be compared later on.
7. Need for additional factors in culture medium
   IL7
   RSPO3/WNT3A
   Others?
8. Readouts
   Pre- and Post-REP TIL extended phenotyping with (modified?) panels 1, 2, and 3
   Post-REP TIL effector function assessments (cytokine and/or activation marker production assays)
   Post-REP TIL tumor reactivity assessments (autologous tumor cell co-culturing assays)
   TCR repertoire analyses (flow cytometry and/or RNA-seq)
   Live cell metabolic assay such as Seahorse
Additional Considerations
   1. Protein TF production
   2. Tumor procurement
   3. Logistics (cell shipments)

TABLE 46

Process
Tasks

Optimization of protein delivery conditions to TILs:
• Stored frozen melanoma pre-REP samples stored will be used to screen conditions
• Test reagent delivered will be . . .
• Conditions will include . . .
• Readout will be . . .
• Select conditions will be confirmed on 2-3 fresh pre-REPs
TF protein production:
• A vendor will be identified and contract established for the production of enough materials for 10 mini-REP scale experiments
• ~7 select TF proteins will be prepped at required purity level
Re-programming experiments:
• A minimum of 6 frozen and/or fresh pre-REP samples for which an autologous tumor line is available will be used
• The following TF combinations will be delivered, using SQZ's optimized protocol
 ○ iPSC cocktail
 ○ TCF-1
 ○ NOTCH1/2 ICD
 ○ MYB
• iPSCs will be confirmed and re-differentiation attempted using either published conditions and/or SQZ delivery of above TFs
• TIL reprogramming will be monitored over time, using flow cytometry
• Mini-REPs will be setup for each condition for 11 days, using potential adjuvants to the culture medium
Phenotypic assessments of post-REP TILs
Functional assessments of post-REP TILs

Example 18: Cryopreservation Process

This example describes the cryopreservation process method for TILs prepared with the abbreviated, closed procedure described in Example 16 using the CryoMed Controlled Rate Freezer, Model 7454 (Thermo Scientific).

The equipment used was as follows: aluminum cassette holder rack (compatible with CS750 freezer bags), cryostorage cassettes for 750 mL bags, low pressure (22 psi) liquid nitrogen tank, refrigerator, thermocouple sensor (ribbon type for bags), and CryoStore CS750 Freezing bags (OriGen Scientific).

The freezing process provides for a 0.5° C. rate from nucleation to −20° C. and 1° C. per minute cooling rate to −80° C. end temperature. The program parameters are as follows: Step 1—wait at 4° C.; Step 2: 1.0° C./min (sample temperature) to −4° C.; Step 3: 20.0° C./min (chamber temperature) to −45° C.; Step 4: 10.0° C./min (chamber temperature) to −10.0° C.; Step 5: 0.5° C./min (chamber temperature) to −20° C.; and Step 6: 1.0° C./min (sample temperature) to −80° C.

A depiction of the procedure of this example is provided in conjunction with the process of Example 16.

Example 19: Procedure for Generation of TIL Products Enriched for Tumor Antigen-Specific T Cells with Enhanced Therapeutic Activity Phase 1a: Procurement of One Validated sd-RNAfm for Efficient and Specific Silencing The initial phase will involved the procurement of one validated sd-RNAfm for the efficient and specific silencing of the 3 following genes: PD-1 (also known as PDCD1), TIM3, and CBLB.

Phase 1b: Identification of sequences for the Potent Silencing of LAG3 and CISH

Up to 20 sd-RNAs will be designed for new targets. Gene silencing will be assessed in HeLa cells on exogenous targets and in activated primary T cells on endogenous targets. One to two lead(s) will be selected per gene of interest that reduces expression levels by more than 80%, including PD-1 and LAG-3. Fully modified versions of the selected sd-RNA will be generated.

It is expected that one to two LAG3- and CISH-specific sd-RNAfm will be generated. Two targeting RNAs per target genes are preferred.

Phase 2: Validation of sd-RNA-Mediated Gene silencing in Pre-REP TILs.

Up to 6 frozen melanoma/other pre-REP lines will be used to validate the sd-RNA targets (including PD-1, TIM3, CBLB, LAG3, and CISH). Conditions will test sd-RNA concentrations, timing post-thaw, repeat/sequential deliveries, and culture conditions. Readout will be % of gene silencing, as assessed by flow and/or qPCR. The impact of RNA delivery on TIL growth and persistence of silencing over time will be evaluated by expanding TILs.

It is expected that 80% silencing 24 hours post REP harvest will be obtained with the lead(s). The total cell number will be within within 10% of untreated controls.

Phase 3: Implementation of sd-RNA-Mediated Gene Silencing to Process 2A.

Gene silencing will be optimized on 3-6 research-scale fresh TIL preps. Conditions will test sd-RNA concentrations, timing, repeat/sequential deliveries, and culture conditions. Readout will be % of gene silencing in post-REP TILs, as assessed by flow and/or qPCR. Impact of gene silencing on TIL phenotype and function will be evaluated using flow cytometry assays. Optional rescue experiments and/or gene expression analyses will be conducted to verify the specificity of the effects (e.g., extent and impact of potential off target silencing). At least 2 target/sd-RNA pairs will be selected for further work. TIL phenotypes will then the characterized. Non-specific and specific TIL activity equivalent or higher than that of control TILs will be evaluated to determine optimal target/sd-RNAs.

Phase 4: Implementation of Optimized Silencing Protocol(s) to Full Scale TIL Prep.

One full scale TIL preparation will be performed per target gene. TIL products with the new characteristics defined in Phase 3 will be developed in addition to those required for release.

Example 20: Exemplary sd-RNA Preparation and Use sd-RNA Design

Approximately 2 to 20 sd-RNA sequences will be generated to a given target. In some cases, sd-RNA sequences will be selected based on a selection algorithm (commercially available from Advirna LLC, Worcester, MA, USA), designed on the basis of a functional screen of over 500 sd-RNA sequences. Regression analysis will be used to establish a correlation between the frequency of occurrence of specific nucleotide and modification at any specific position in sd-RNA duplex and its functionality in gene suppression assay. Selected sequences will be synthesized commercially (for example, by TriLink Biotechnologies) in a 0.2-μmole scale and dissolved in sterile RNase-, DNase-free water for injection (commercially available from Cal-Biochem, 4.86505). Duplexes can be annealed by heating up at 95° C. for 5 min and gradually cooling down to room temperature.

sd-RNA Direct Delivery (Passive Uptake)

Oligonucleotides, including sd-RNA targeting genes described herein, can be diluted in serum-free medium and dispensed into 96-well culture plate in triplicates. Cells can be seeded in appropriate culture medium containing reduced FBS in the plate with pre-diluted compounds for indicated time. HeLa cells can be transfected in EMEM medium with 3% FBS at 10,000 cells/well. Primary human T cells (All-Cells, CA) can be cultured in complete AIM-V (Gibco) medium containing 500 IU/ml IL2 (ProSpec). Cells can be activated with anti-CD3/CD28 Dynabeads (Gibco, 11131) according to the manufacturer's instructions for at least 4 days prior to transfection. T cells can be transfected in 5% FBS at 100,000 cells/well without removing the Dynabeads, unless otherwise specified. Fluorescent images can be obtained from live cells transfected with Cy3-conjugated sd-RNA using Olympus BX-60 microscope in order to confirm transfection efficiency. Nuclear staining can be obtained by using Hoechst 33342 (Molecular Probes, H1398) added to transfected cells for 30 minutes and images processed.

Lead sd-RNA Compound Identification

Leads described in Example 18 can be identified using this protocol. Luciferase reporter plasmid can be constructed by inserting PDCD1 targeting regions into psiCheck2 plasmid (Promega, C8021) downstream Renilla luciferase sequence. For comparison, a previously validated MAP4K4 sd-RNA sequence can be inserted as a positive control.

For the screening, HeLa cells can be transfected with the cloned plasmid using Fugene HD (Promega, E2311) according to the manufacturer's instructions. Briefly, cellscan be seeded at $2.5 \times 10^6$ cells/10 cm$^2$ 390 dish in EMEM (ATCC, 30-2003) medium without antibiotics and transfected 6 hours later with the plasmid at 2.5:1 FuGENE:DNA ratio. Cells can be incubated for 16-18 hrs, washed 3 times with PBS, trypsinized and seeded into 96-well plate with prediluted sd-RNA compounds at final concentration 1 μM sd-RNA/10,000 cells/100 μl EMEM with 3% FBS. Cells can be treated with sd-RNA for 48 h to facilitate passive cellular uptake of compounds, lysed with Glo lysis buffer (Promega, E266A) and can be assayed for Renilla and Firefly luciferase expression. For that, 20 μl aliquots of each lysate were added into duplicate opaque 96-well plates and mixed with either Matthews (Renilla) assay buffer 59 397 or Firefly luciferase 398 assay buffer (25 mM glycylglycine, 15 mM MgSO4, 4 mM EGTA, 1 mM DTT, 2 mM ATP, 15 mM 399 K2PO4, pH 7.8 and 1 mM D-Luciferin). The substrates D-Luciferin (Promega, E1605) and h-Coelenterazine (NanoLight, 301) were added immediately prior to use. Luminescence can be measured on SpectraMax i3 (Molecular Devices), normalized (Renilla/Firefly) and expressed as a percent untreated control.

mRNA Quantification by qPCR

Total RNA can be isolated from transfected cells using the PureLink™ Pro96 purification Kit (Invitrogen, 12173-011A) according to the manufacturer's recommendations. Dilutions of non-transfected (NT) cells of 1:5 and 1:25 can be prepared for a standard curve generation. Gene expression was analyzed in a one-step multiplex qPCR 407 by mixing 20-40 ng purified RNA with Quanta qScript RT-qPCR ToughMix (VWR, 89236672) and Taqman probes—PDCD1-FAM (Taqman, Hs01550088_m1) and GAPDH-VIC (Applied Biosystems, 4326317E) in the same reaction. Samples can be amplified using Quanta's recommended settings in a StepOnePlus qPCR machine (Applied Biosystems). PDCD1 expression can be normalized to GAPDH, adjusted to the standard curve and expressed as a percent of non-targeting control (NTC)-transfected cells.

Cell Viability Assay

Expanded TILs according to the present invention can be transfected with sd-RNA oligonucleotides at various doses for 72 h. Cells were washed and incubated with 1:10 diluted CellTiter-Blue reagent (Promega, G808A) for 1 h at 37 C. Plates were brought to room temperature, and fluorescence recorded at 530 nm ex/590 nm em. Linear range can be confirmed by plating 4 series of 2-fold cells dilutions in the same conditions and plotting fluorescence readings.

Tumor Infiltrating Lymphocyte Isolation

Tumor infiltrating lymphocytes can be prepared as described herein, for example as outlined in FIG. 8, as well as FIG. 14.

TIL Expansion

TILs can be seeded in flasks as described herein and either a first and/or second expansion step performed. The sd-RNA can be added during the first expansion, for example Step b, after the first expansion, for example, during Step C, before or during the second expansion, for example before or during Step D, after Step D and before harvest in Step E, during or after harvest in Step F, before or during final formulation and/or transfer to infusion Bag in Step F, as well as before any optional cryopreservation step in Step F. Moreover, sd-RNA can be added after thawing from any cryopreservation step in Step F.

Thymidine Incorporation Assay

A TIL sample can be harvested during any of the expansion steps and seeded in triplicate on a 96 well plate (104 443 cells/well) in CellGro medium supplemented with 2% human AB serum. After 1 hour, 1 μCi/well of [methyl-3444 H] thymidine (PerkinElmer, Waltham, MA) can be added to each well and incubated for four hours. Cells can then be harvested and $^3$H-thymidine incorporation can be measured in a Trilux 1450 microBeta liquid scintillation counter (Wallac) to examine TIL growth.

IFN-γ Secretion of sd-RNA Treated Cells

IFN-γ production by stimulated T cells can be measured in the supernatant using the Human IFN-γ ELISA development kit (Mabtech) as per manufacturer's instructions. TILs can be prepared as provide herein and treated with, for example, 2 μM sd-RNA for a number of days, in some cases four days. After this period, the supernatant can be collected for ELISA analysis to determiner IFN-γ production levels.

TIL Treatment

TILs that have been treated with sd-RNA can be employed as described herein in methods for treating cancer patients.

Example 21: Exemplary Electroporation Methods

TILs were prepared according to any of the methods described herein. The following transfection methods will be tested: lipofectin and Lipofectamin Lipofection, electroporation using square wave BTX ECM 830 apparatus or Bio-Rad Gene Pulser II, exponential diminishing wave electroporation using Eppendorf Multiporator, and also Amaxa nucleofector. All methods will be initially based on the recommendations of the manufacturers with potential modifications as needed. The Amaxa nucleofection protocol may give the highest efficiency of transfection. The Amaxa procedure will be optimized using different combinations of one of three solutions (V, R, and T) and 8 programs of electroporation. See, also the methods described in U.S. Patent Application No. 2016/0230188 and U.S. Pat. No. 8,859,229, both of which are incorporated by reference herein in their entireties. Electroporation may also be carried out according to methods described by Menger et al., Cancer Res., 2016 Apr. 15; 76(8):2087-93, the disclosure of which is incorporated by reference herein, using an Agile Pulse BTX system (Harvard Apparatus). Electroporated cells may be expanded by pre-REP and REP methods described elsewhere herein. Electroporation methods known in the art, such as those described in U.S. Pat. Nos. 6,010,613 and 6,078,490, the disclosures of which are incorporated by reference herein, may also be used. Pulsed electroporation optimization may be performed using methods described using the following programs or modifications thereof:

sient expression of IL-2 or a membrane-bound form of IL-15 (mb-IL15). Strategy 2: NOTCH-mediated TIL reprogramming. In some embodiments, the NOTCH-mediated reprograming includes mRNA expression of the intracellular domain (ICD) of NOTCH1 or NOTCH2. In some embodiments, the NOTCH-mediated reprogramming includes mRNA expression of NOTCH ligand DLL1.

The tumor types studied will be melanoma, lung, sarcoma, as well as others.

TILs will be generated using the processes as described herein above, including for example, by the process described in Example 16.

RNA molecules will be delivered using the methods described in for example, Example 21 (see, also the methods described in U.S. Patent Application No. 2016/0230188 and U.S. Pat. No. 8,859,229, both of which are incorporated by reference herein in their entireties).

Delivery conditions will be determined, including for example, mRNA reagent validation, timing of transient transfection and reprogramming, compatibility of electroporation timing with TIL processes used, efficiency (including transfection efficiency), and scalability.

Readouts for the experiments will include TIL phenotype (flow cytometry), TIL effector functions (cytokine production assays), TIL tumor reactivity (autologous tumor cell co-culture assays), TCR repertoire analyses (flow cytometry and/or RNA-seq), and TIL metabolic state (live cell metabolic assay such as Seahorse) or any of the other parameters described herein above.

Expected Results:

Delivery conditions will be designed as needed to result in high expression of the protein of interest in post-REP TILs. Frozen melanoma pre-REP samples will be used to screen conditions. Reagent delivered for optimization

| | Group 1 | | | | Group 2 | | | | Group 3 | | |
|---|---|---|---|---|---|---|---|---|---|---|---|
| Program | Pulses | V | Duration (ms) | Interval (ms) | Pulses | V | Duration (ms) | Interval (ms) | Pulses | V | Duration (ms) | Interval (ms) |
| 1 | 1 | 600 | 0.1 | 0.2 | 1 | 600 | 0.1 | 100 | 4 | 130 | 0.2 | 2 |
| 2 | 1 | 900 | 0.1 | 0.2 | 1 | 900 | 0.1 | 100 | 4 | 130 | 0.2 | 2 |
| 3 | 1 | 1200 | 0.1 | 0.2 | 1 | 1200 | 0.1 | 100 | 4 | 130 | 0.2 | 2 |
| 4 | 1 | 1200 | 0.1 | 10 | 1 | 900 | 0.1 | 100 | 4 | 130 | 0.2 | 2 |
| 5 | 1 | 900 | 0.1 | 20 | 1 | 600 | 0,1 | 100 | 4 | 130 | 0.2 | 2 |

TILs may be electroporated in 0.4 cm gap cuvette (on the order of about $10^6$ cells/mL) with about 20 μg of plasmids encoding GFP and control plasmids pUC using the different electroporation programs or methods. About 24 hours post electroporation, GFP expression was analyzed in electroporated cells by flow cytometry to determine the efficiency of transfection. The minimal voltage required for plasmid electroporation in TILs has been previously reported in International Patent Application Publication No. WO 2014/184744 and U.S Patent Application Publication No. US 2013/0315884 A1, the disclosures of which are incorporated by reference herein.

Example 22: Transient Transfection Protocol for Preparation of TIL Products Enriched for Tumor Antigen-Specific T Cells with Enhanced Therapeutic Activity The experiments in this example will study the effects of two different TIL improvement strategies. Strategy 1: Tran-experiments will be GFP mRNA. Conditions will test several TIL activation methods and electroporation protocols. Readout will be cell viability and % of GFP-positive cells relative to non-electroporated controls, as assessed by flow cytometry. Select conditions will be confirmed on 2-3 fresh TIL preps of available histologies. In some embodiments, the efficiency of transfection (ET) can be determined approximately 3, 6, 9, 12, 15, and/or 18 hours after transfection by fluorescence activated cell sorting (FACS). In some experiments transfectants can be further analyzed every 12 hours to 24 hours until GFP can no longer be detected. In some embodiments, cell viability can be determined by trypan blue dye exclusion. It is expected that this protocol will result in >80% viability and >70 transfection efficiency.

Human IL-2 and mb-bound IL-15 mRNAs will be generated and tested functionally. The validated conditions will be used to transfect up to 6 TIL cultures from various histologies. Readouts will be transfection efficiency, TIL phenotype, and TIL effector functions. It is expected that this protocol will result in >80% viability, >70% transfection efficiency, TIL phenotypes comparable or improved relative to control, and significantly increased TIL effector functions.

Delivery conditions will be designed as needed to result in T cell reprogramming. Frozen melanoma pre-REP samples stored at lovance will be used to screen conditions. Reagent delivered will be NOTCH1 or 2 ICD mRNA. Conditions will test several TIL activation methods and timing of electroporation. Readouts will be cell viability, transfection efficiency, and % of stem memory T cells (TSCM) relative to non-electroporated controls, as assessed by flow cytometry. Select conditions will be confirmed on 2-3 fresh TIL preps of available histologies. It is expected that this protocol will result in >80% viability, >70% transfection efficiency, and a significant increase in TSCM frequency.

Re-programming experiments will be performed on up to 6 TIL preps from various histologies, using the above determined transfection conditions. Readouts will be transfection efficiency, TIL phenotype, TCR repertoire, and TIL effector functions. It is expected that this protocol will result in a significant increase in TSCM frequency, will allow for maintaining TCR repertoire of TSCM subset relative to whole TIL, and will allow for maintained effector functions relative to control.

Example 23: Procurement and Validation of sd-RXRNAs

The experiments in this example provide data regarding sd-rxRNA constructs for 5 targets of interest: PDCD1, TIM3, CBLB, LAG3, and CISH.

Phase 1: Procurement of sd-rxRNAs for the 5 targets of interest.

Phase 2: Validation of sd-rxRNA-mediated gene silencing in pre-REP TIL (8 weeks).

Up to 6 frozen melanoma/other pre-REP lines. Determination of experimental conditions.
Readouts:
  % silencing: ≥80% expected
  Persistence of silencing
  TIL growth: within 10% of control expected
  TIL function: increased cytokine production expected
Phase 3: Implementation of sd-rxRNA-mediated gene silencing to Gen 2 and/or 3 process (3 months)
  3-6 research-scale FRESH TIL preps
  Same readouts as above
  TIL phenotype
  TIL tumor reactivity
  At least 2 target/sd-rxRNA pairs will be selected for further work
Phase 4: Implementation of optimized silencing protocol(s) to full scale TIL prep (8 weeks).
  One full-scale prep per target gene.
Rationale:
  In the TME, TIL express several inhibitory molecules that negatively regulate their effector function.
  Functionality can be restored upon culturing of the TIL ex vivo, but immune suppression will be encountered again after re-infusion.
  Insuring that the T cell inhibitory pathways remain silent for at least a few days post-reinfusion may improve the potency of TIL for ACT.
  Self-delivering siRNAs (sd-rxRNAs) provide an efficient method to knock T cell genes down. See, for example, Ligtenberg, et al., *Mol. Therapy,* 26(6):1482-1493 (2018).

Figure 40:
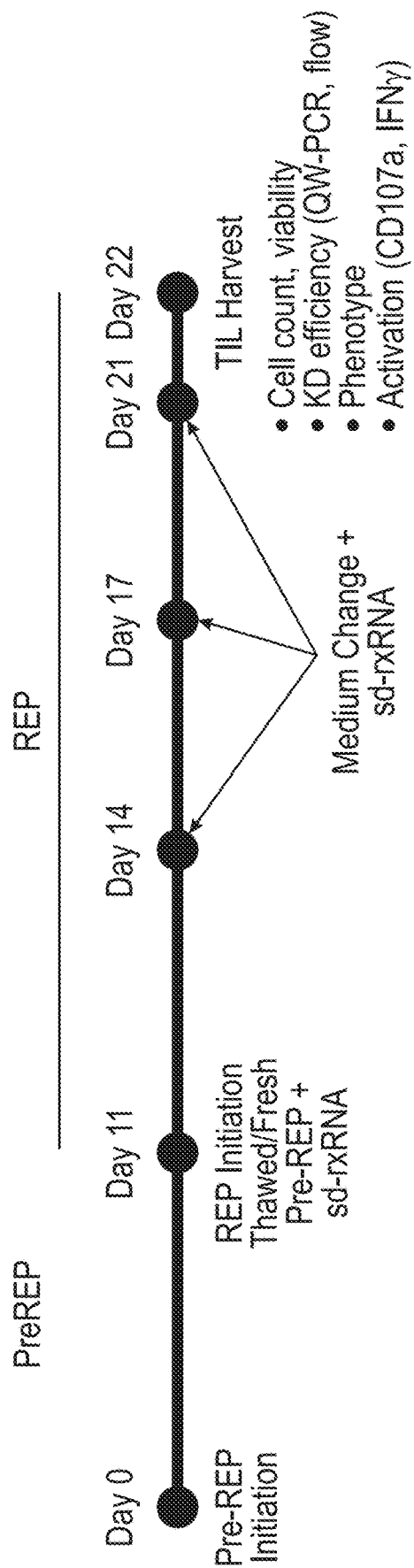
FIG. 40: Sd-rxRNA-mediated gene silencing in TIL; exemplary protocol. Exemplary tumors include melanoma (fresh or frozen; n=6), breast tumor (fresh or frozen; n=5), lung tumor (n=1), sarcoma (n=1), and/or ovarian (n=1).
Figure 41:
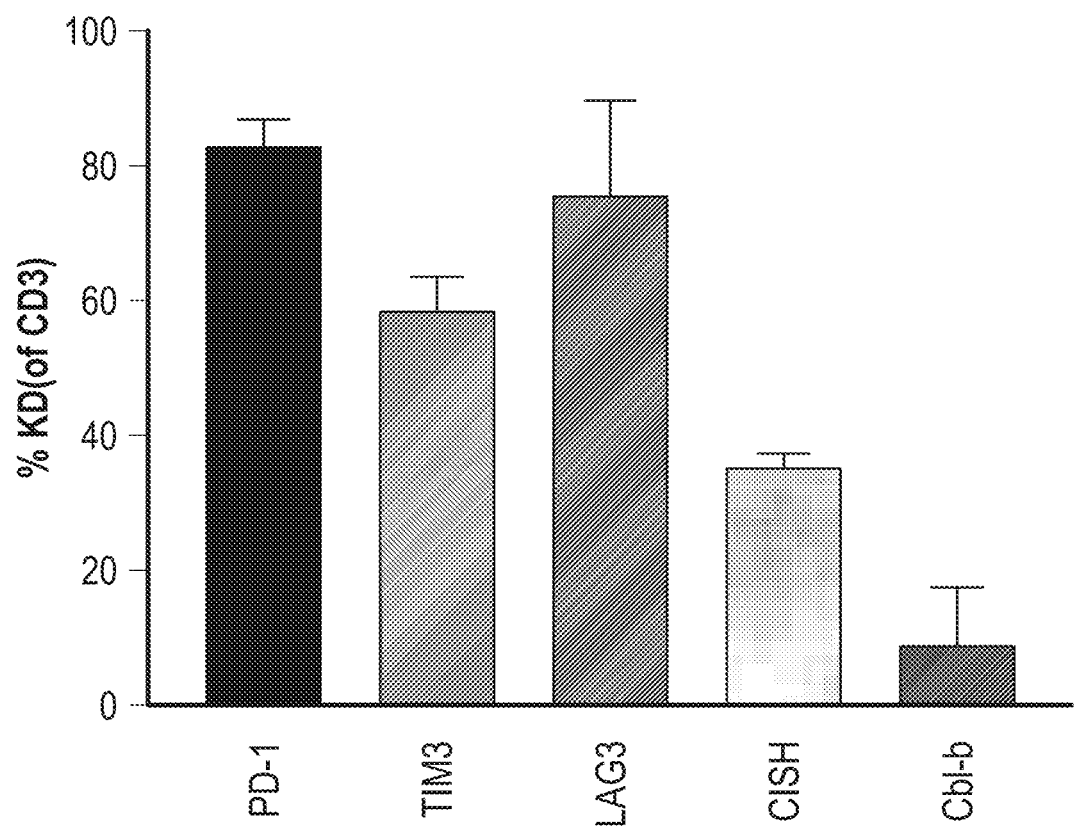
FIG. 41: Reduction of protein expression was detected in 4 out of the 5 targets. PD1: n=9, TIM3: n=8, LAG3/CISH: n=2, Cbl-b n=2. Preps from pre-REP melanoma and Fresh breast cancer TILs, 2 uM sd-rxRNA. % KD calculated as (100−(100*(gene of interest/NTC))).
Figure 42:
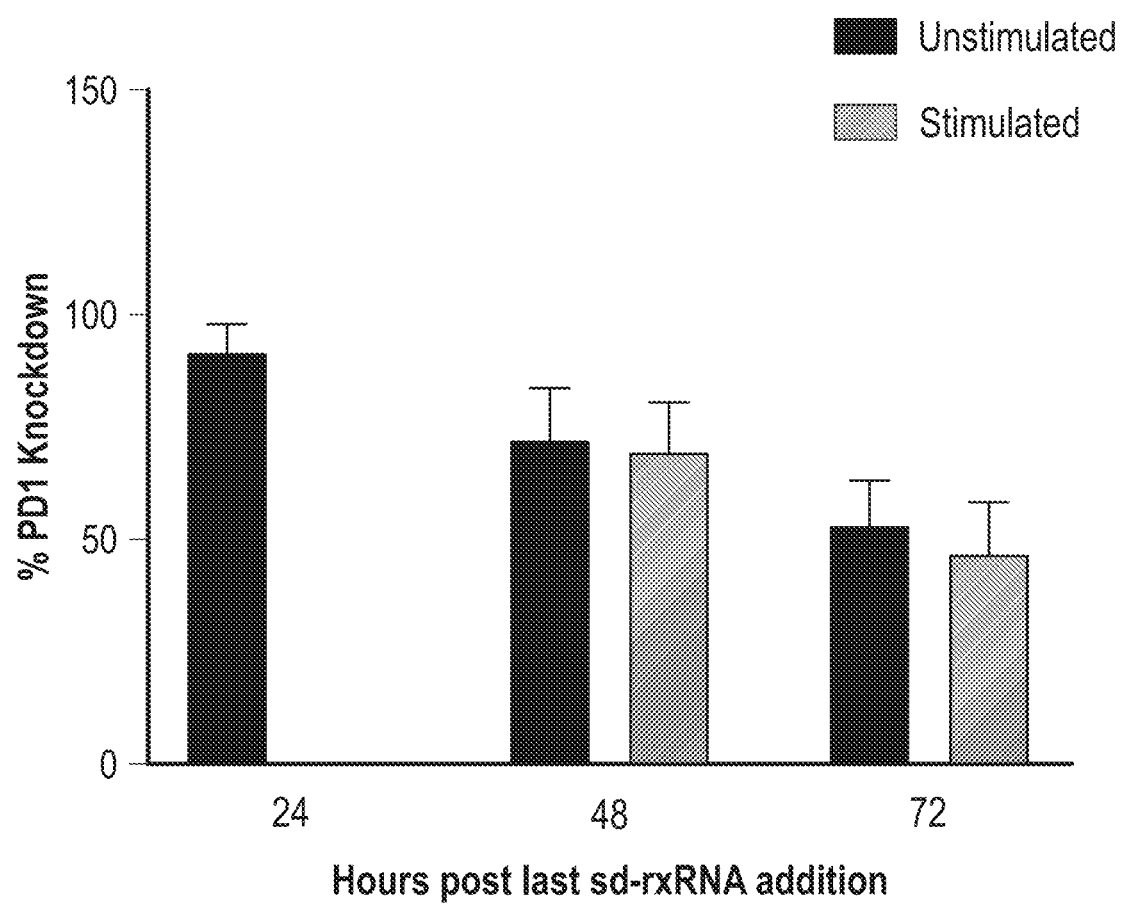
FIG. 42: Sd-rxRNA-induced KD descended with time and stimulation. n=3, preps from pre-REP melanoma TILs, 2 uM sd-rxRNA
Figure 43:
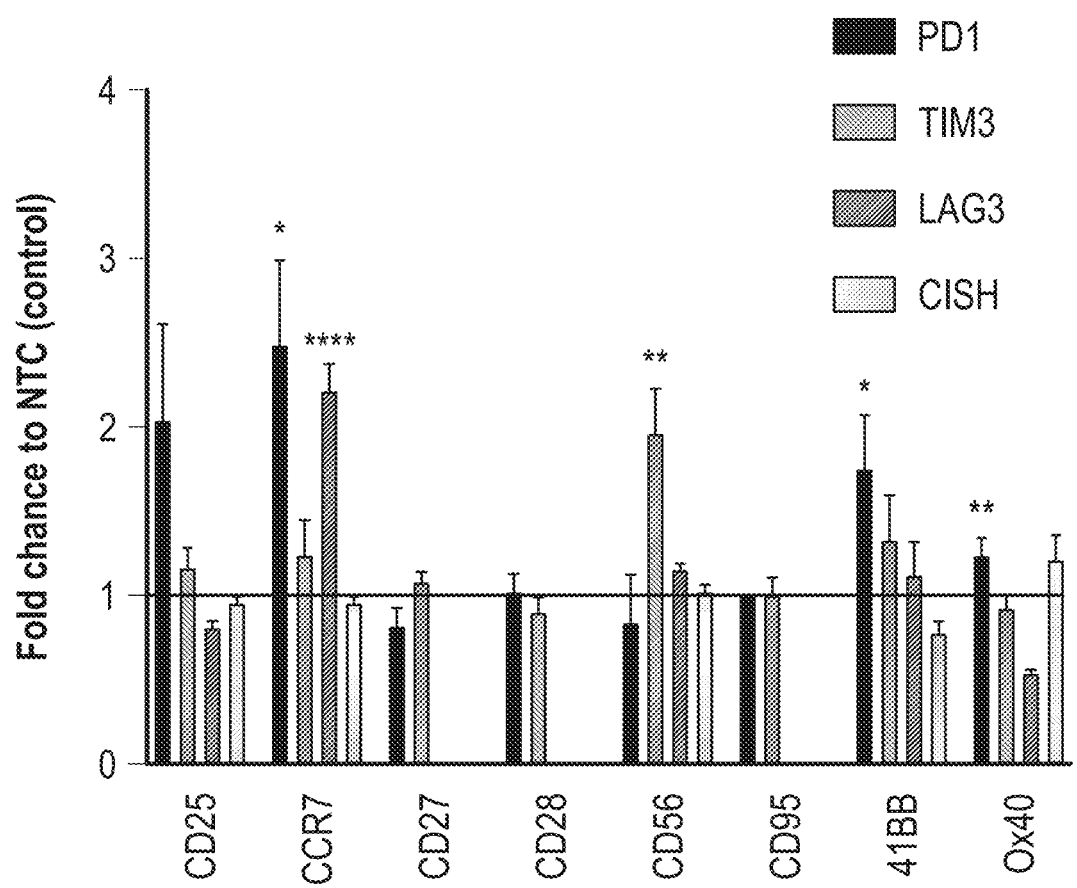
FIG. 43: TIL viability was slightly affected by PDCD1 sd-rxRNA. PD1, TIM3 n>6, preps from pre-REP melanoma/ Fresh breast cancer TILs. LAG3, CISH n=2, pre-REP melanoma and breast cancer TILs, 2 uM sd-rxRNA.
Figure 44:
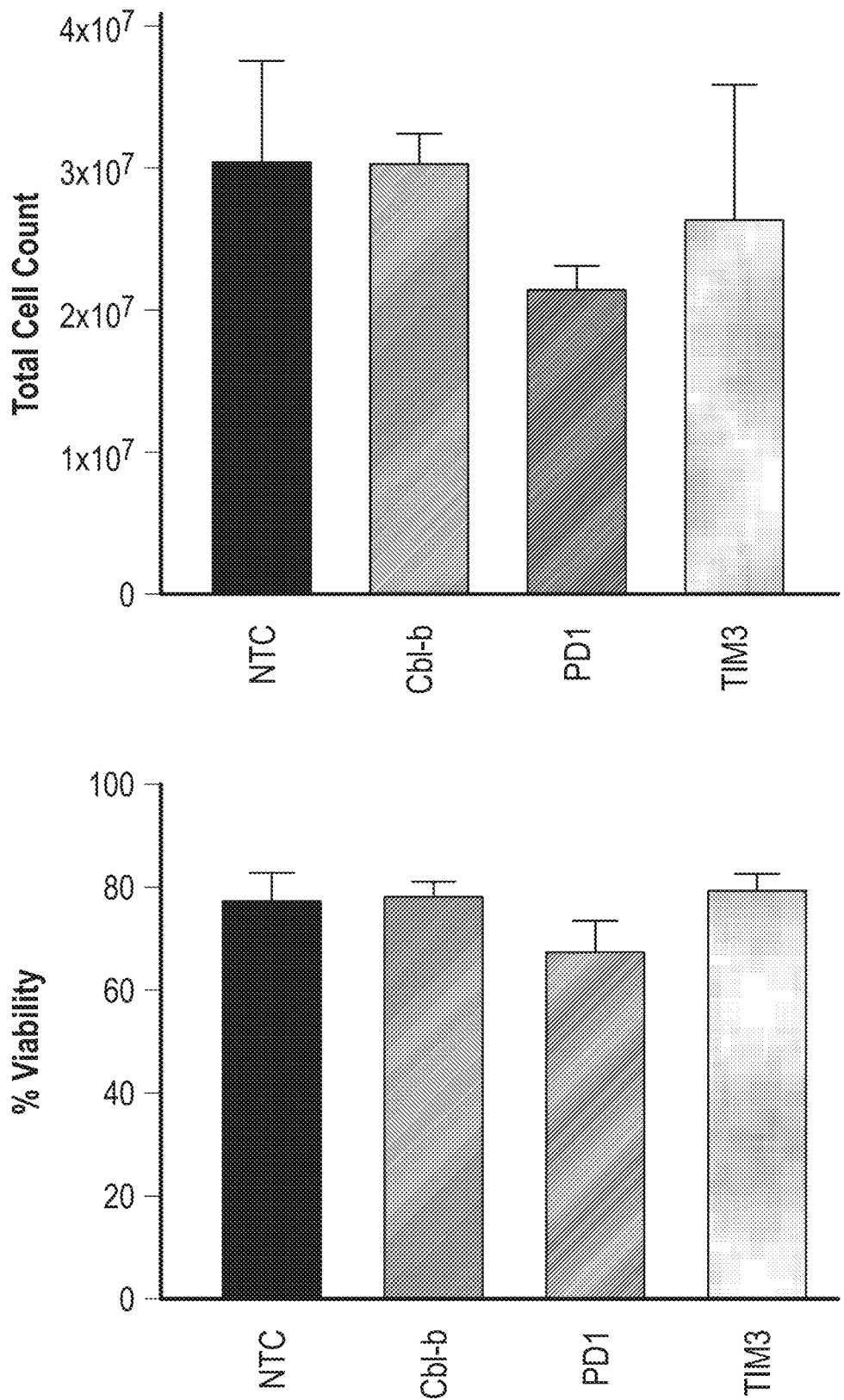
FIG. 44: Sd-rxRNA-mediated KD of PD1 and TIM3 were associated with phenotypic changes indicative of TIL activation. n=3, preps from pre-REP melanoma TILs, 2 uM sd-rxRNA.
Figure 45A:
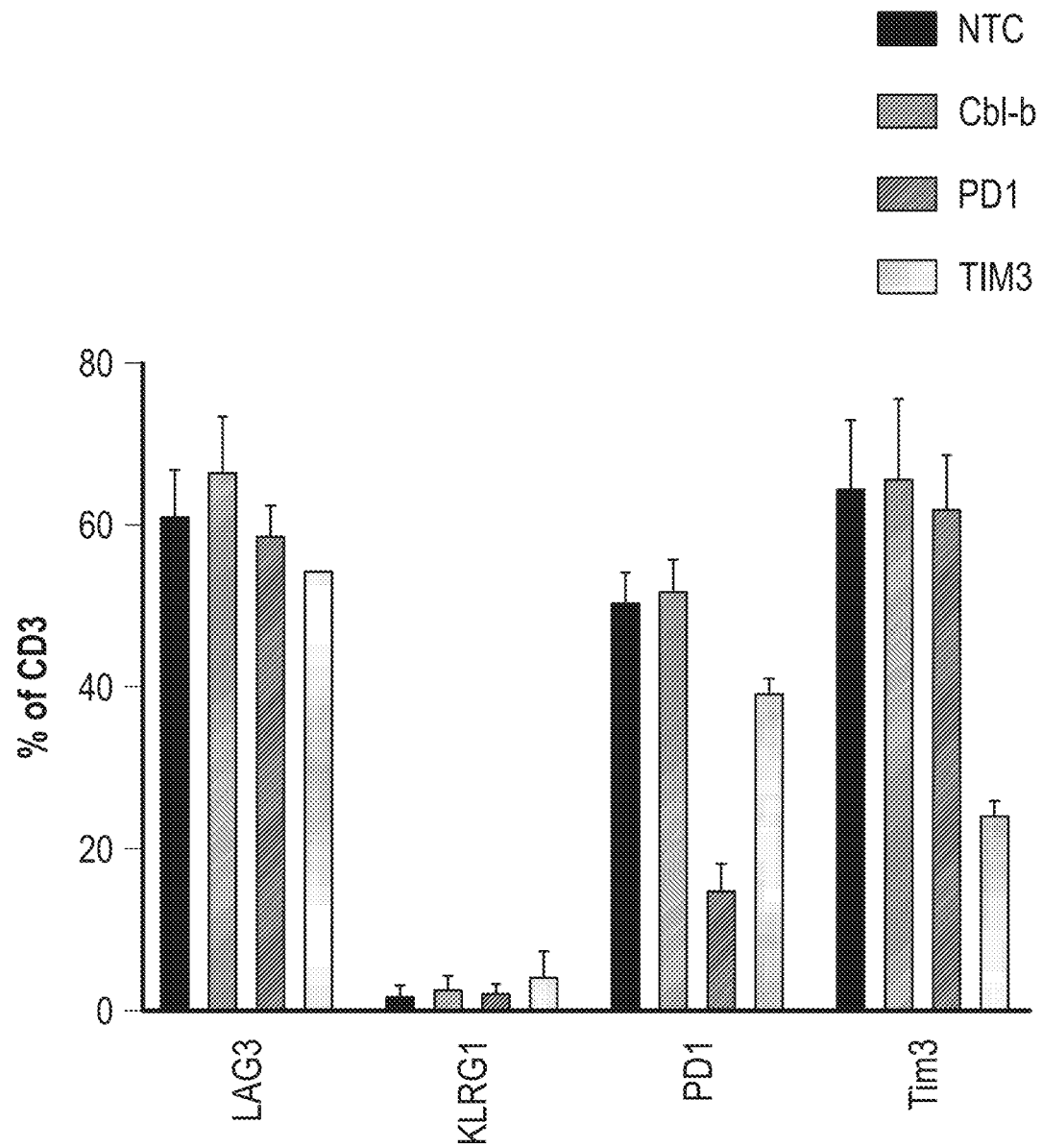
FIG. 45A and FIG. 45B: PD1 and TIM3 Knockdown by the sd-rxRNAs does not affect expression of other inhibitory/exhaustion markers. A) and B) n=3, TIM3: n=2, preps from pre-REP melanoma TILs, 2 uM sd-rxRNA.
Figure 45B:
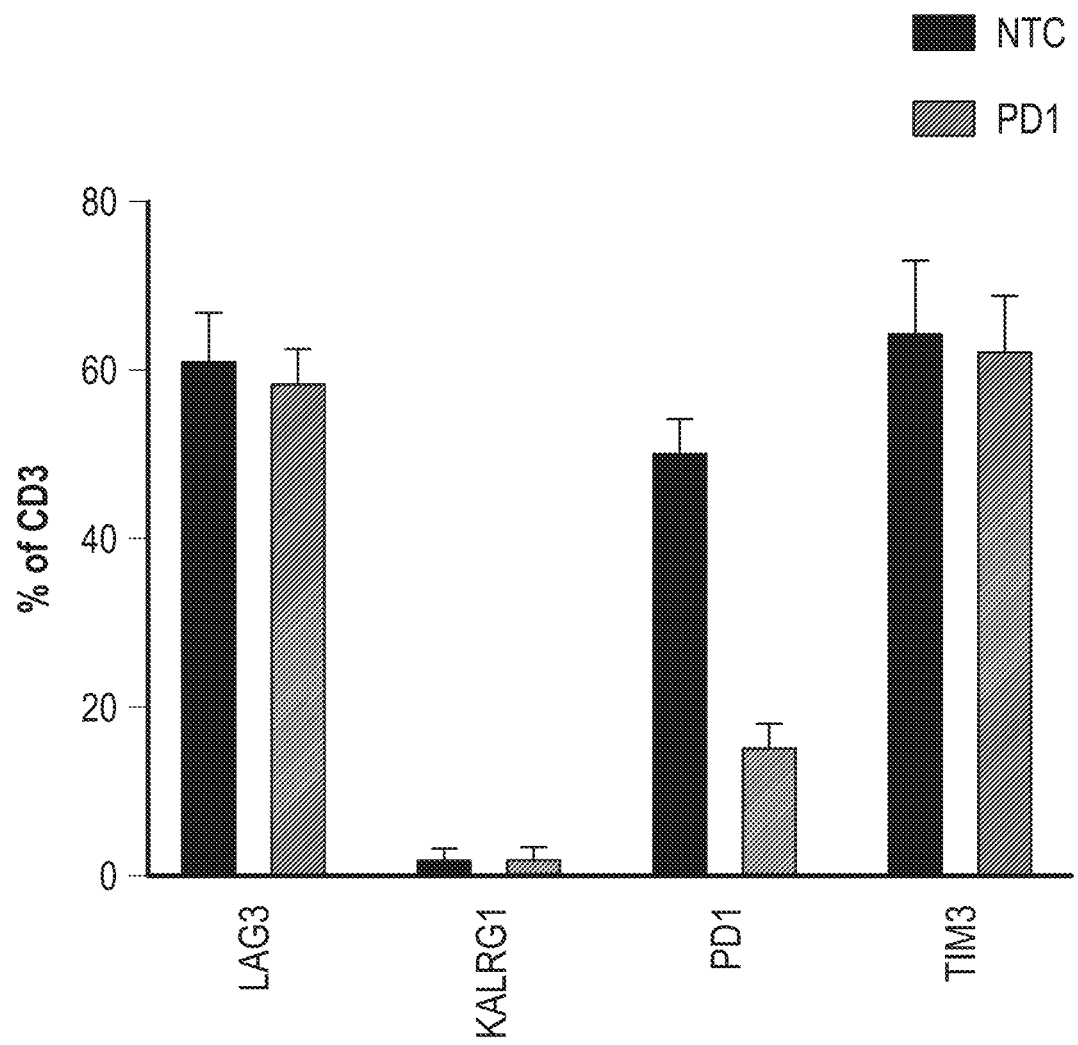
Figure 46:
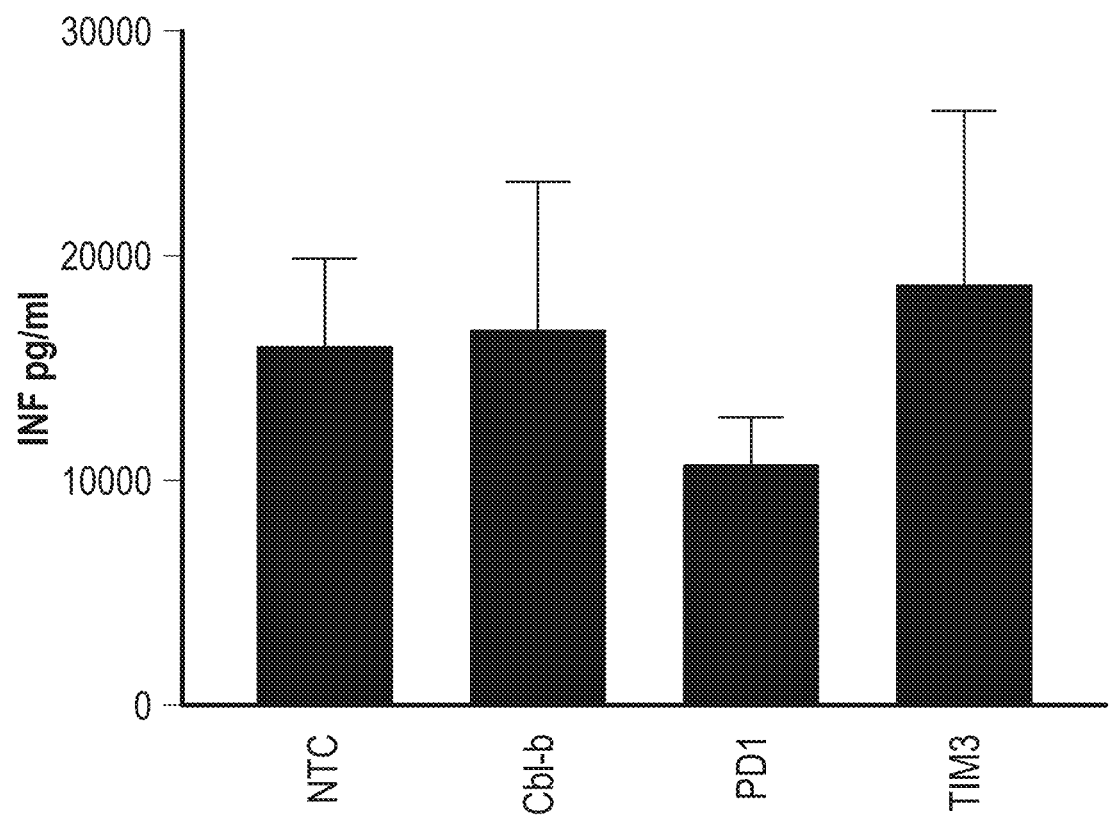
FIG. 46: PD1 and TIM3 KD did not improve IFNγ secretion significantly. n=3, preps from pre-REP melanoma TILs, 2 uM sd-rxRNA.
Figure 47A:
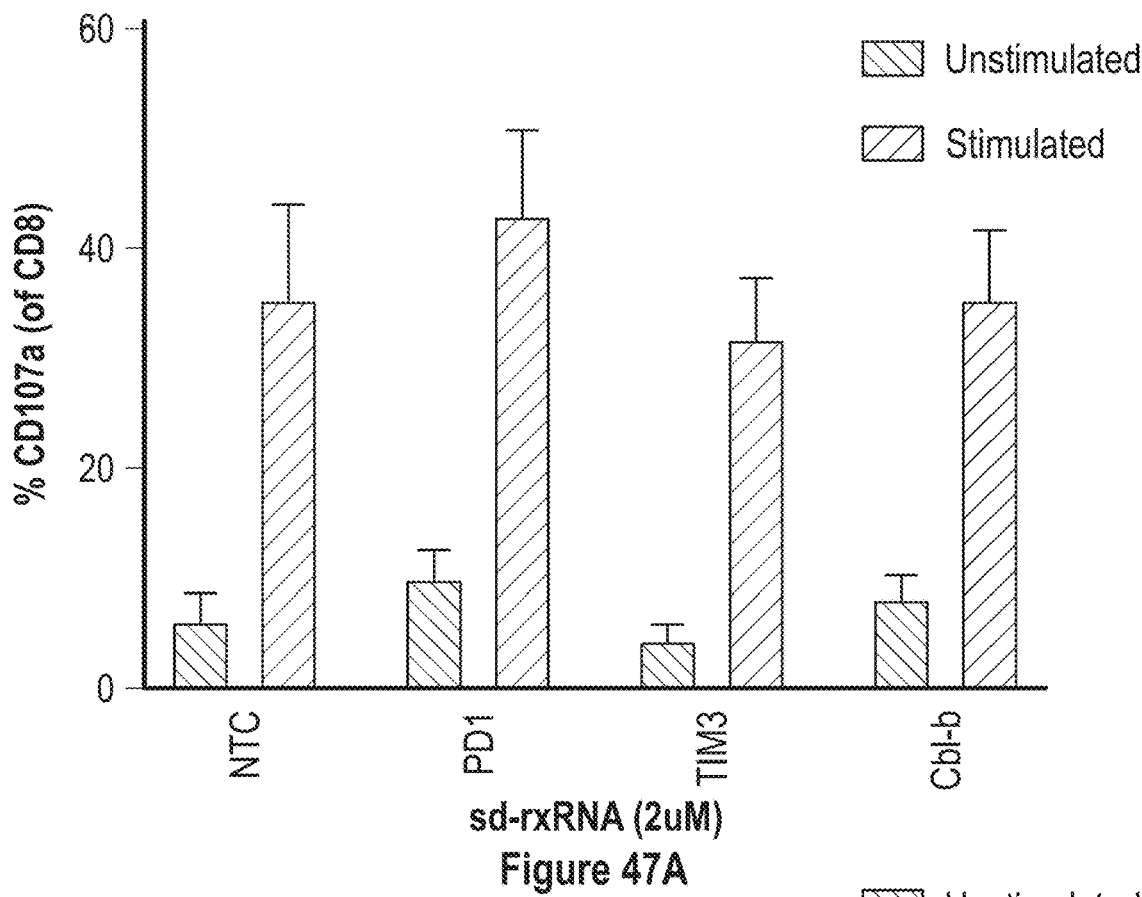
FIG. 47A-FIG. 47F: CD107a mobilization was unaffected by any of the sd-rxRNAs. A) n=6, preps from pre-REP melanoma TILs, 2 uM sd-rxRNA. B) n=2, preps from pre-REP melanoma and breast cancer TILs, 2 uM sd-rxRNA. C) n=3, Frozen Melanoma and fresh breast cancer TILs. D) n=3, Frozen Melanoma and fresh breast and lung cancer TILs. E) and F) n=3, fresh preps from breast cancer tumors.
Figure 47B:
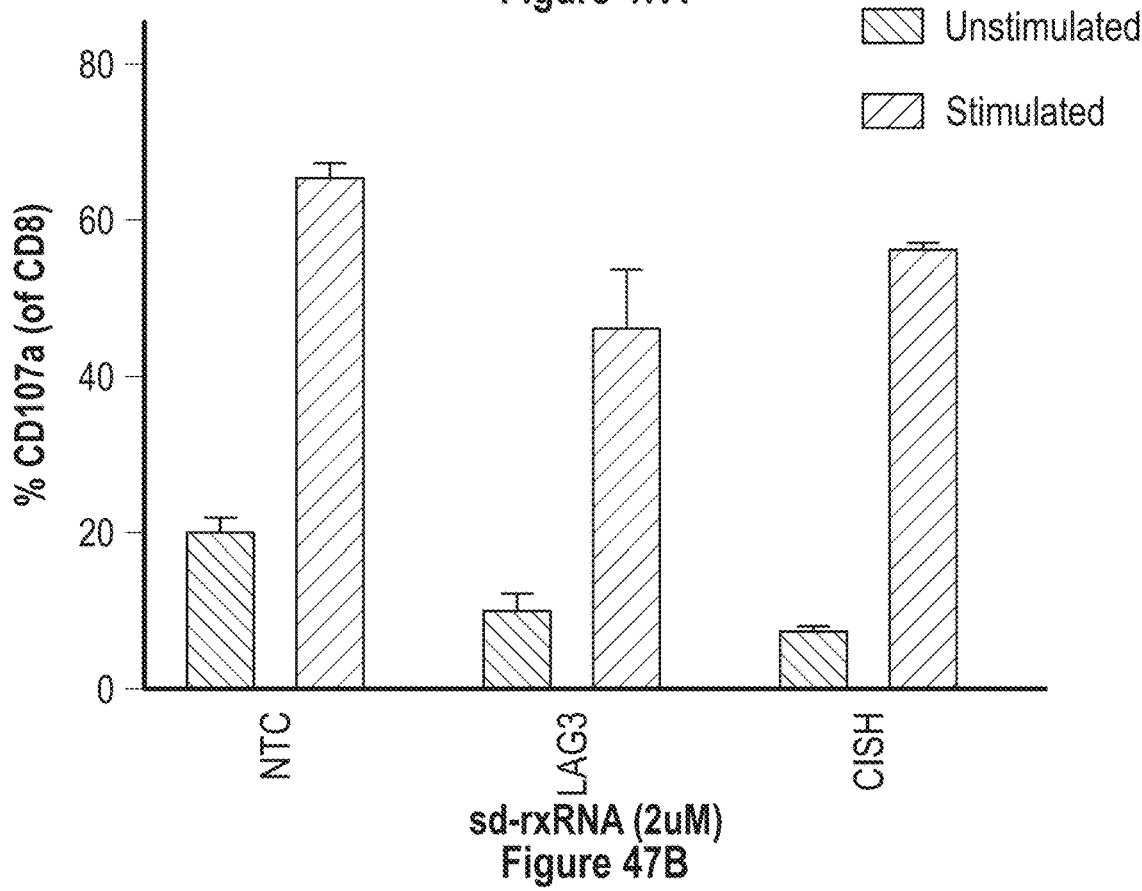
Figure 47C:
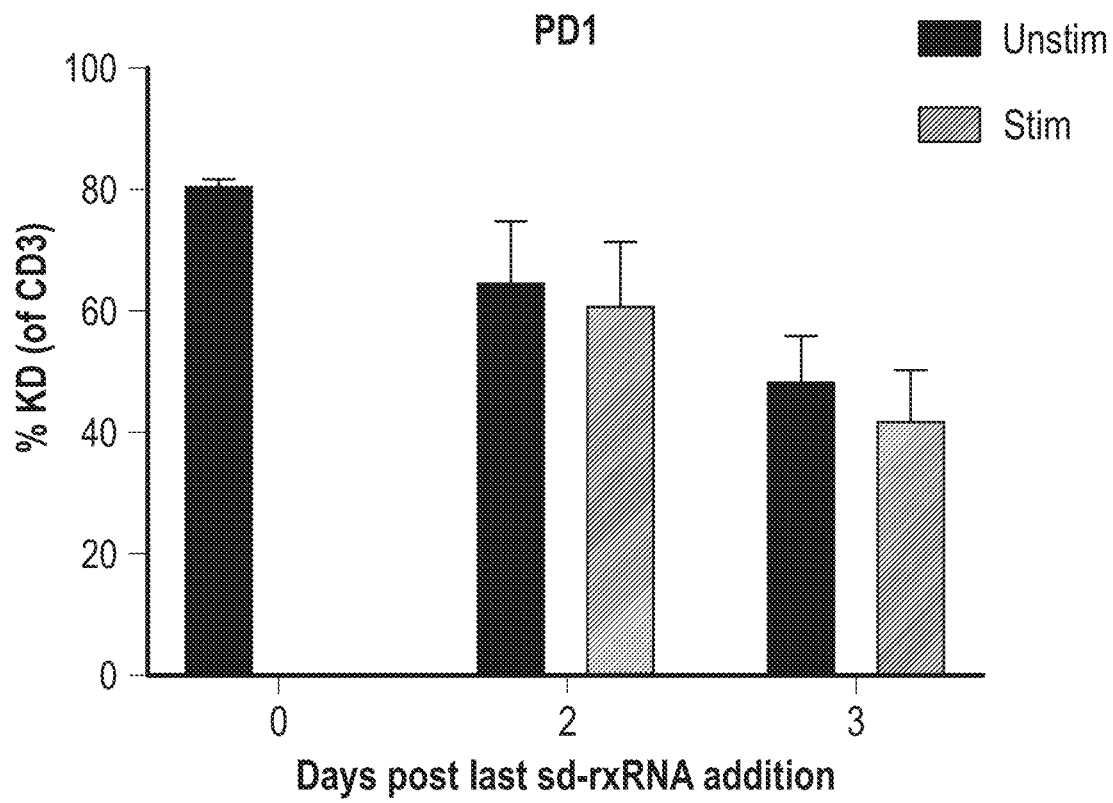
Figure 47D:
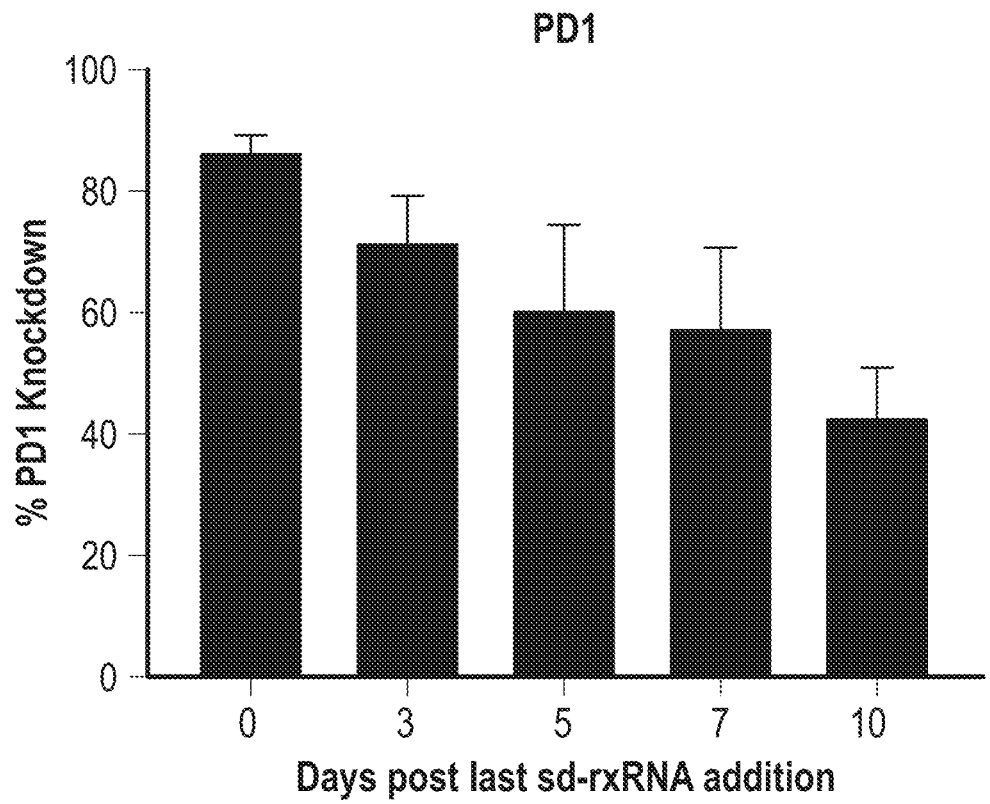
Figure 47E:
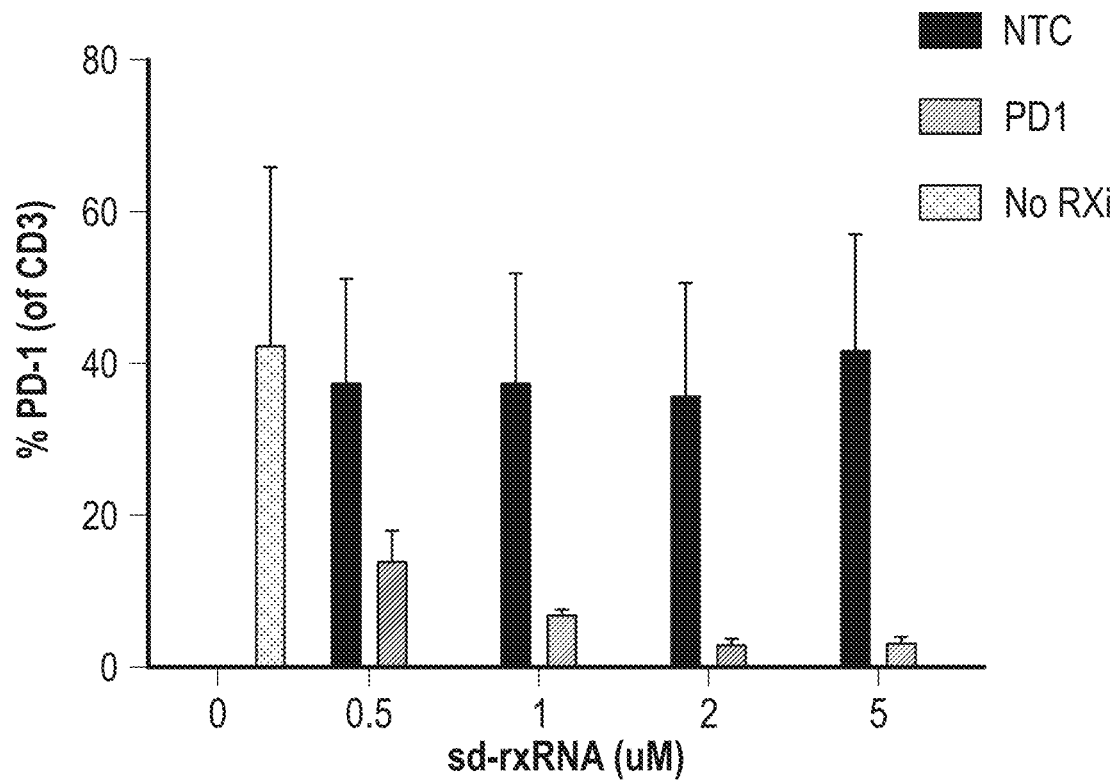
Figure 47F:
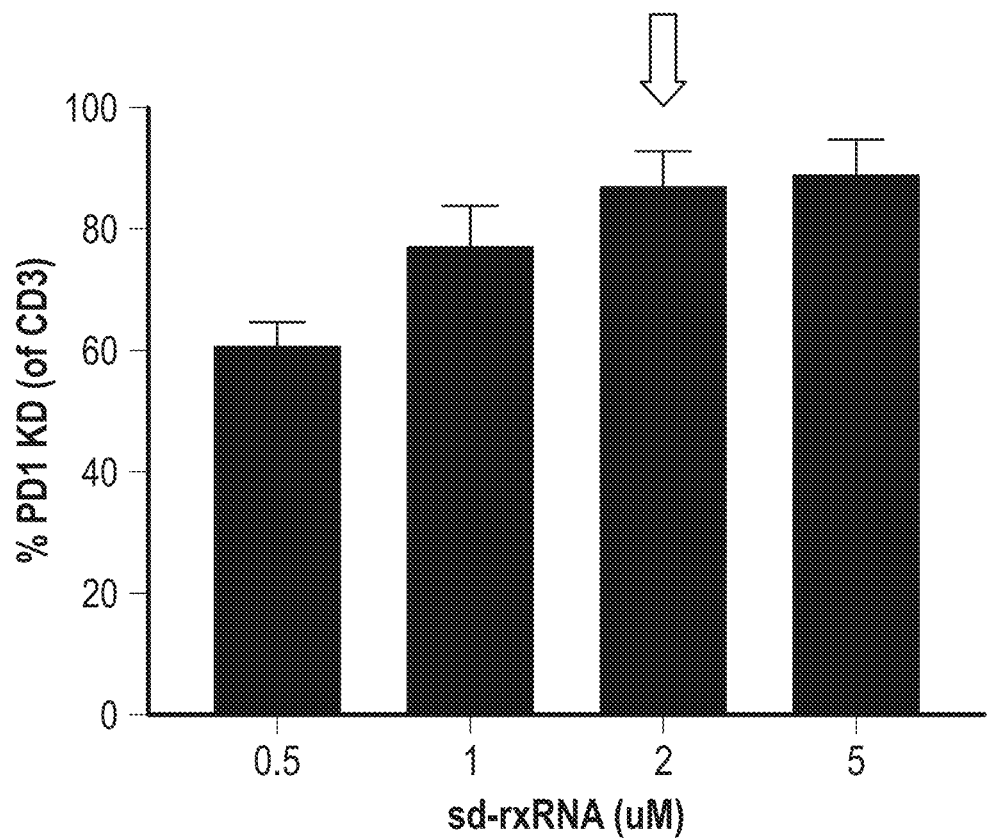
Figure 48:
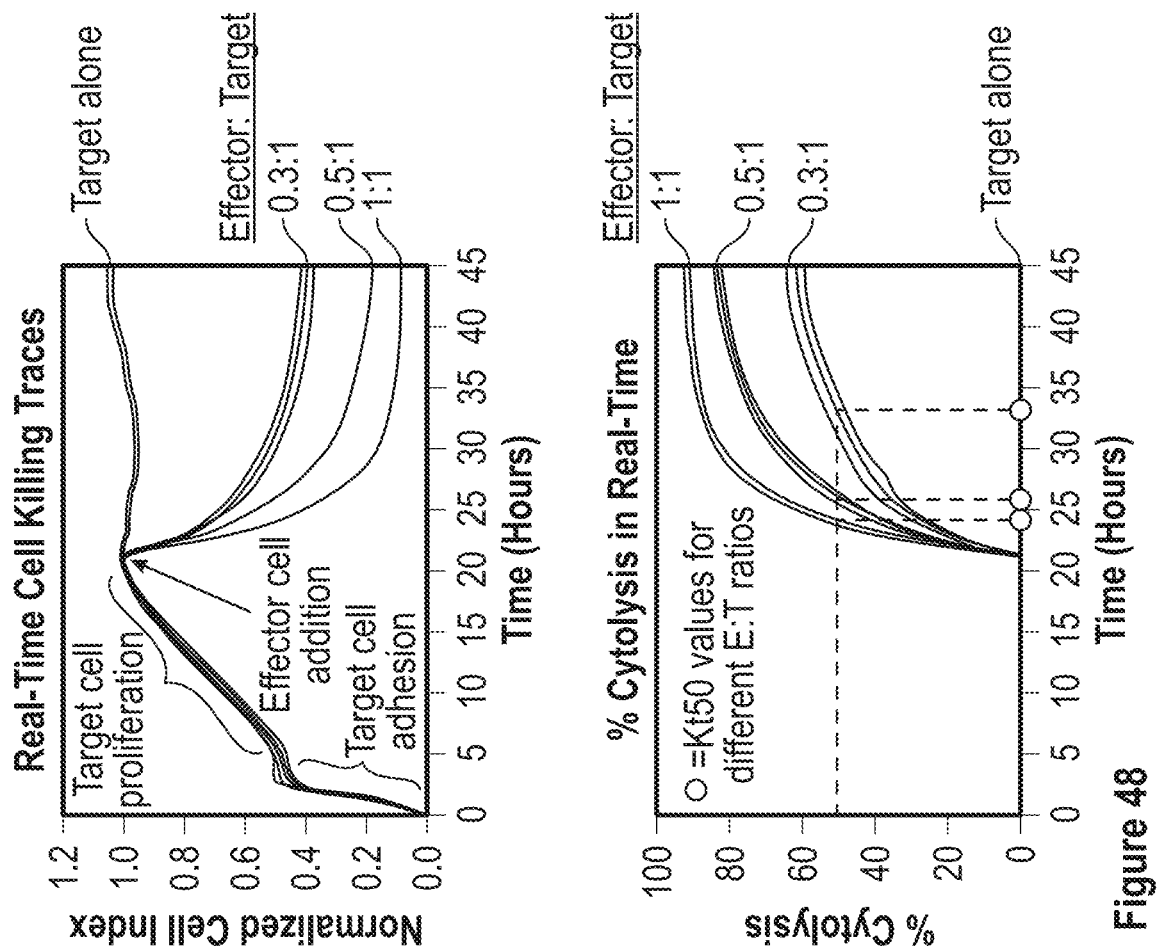
FIG. 48: The xCELLigence Real-Time Cell Analysis (RTCA).
Figure 49B:
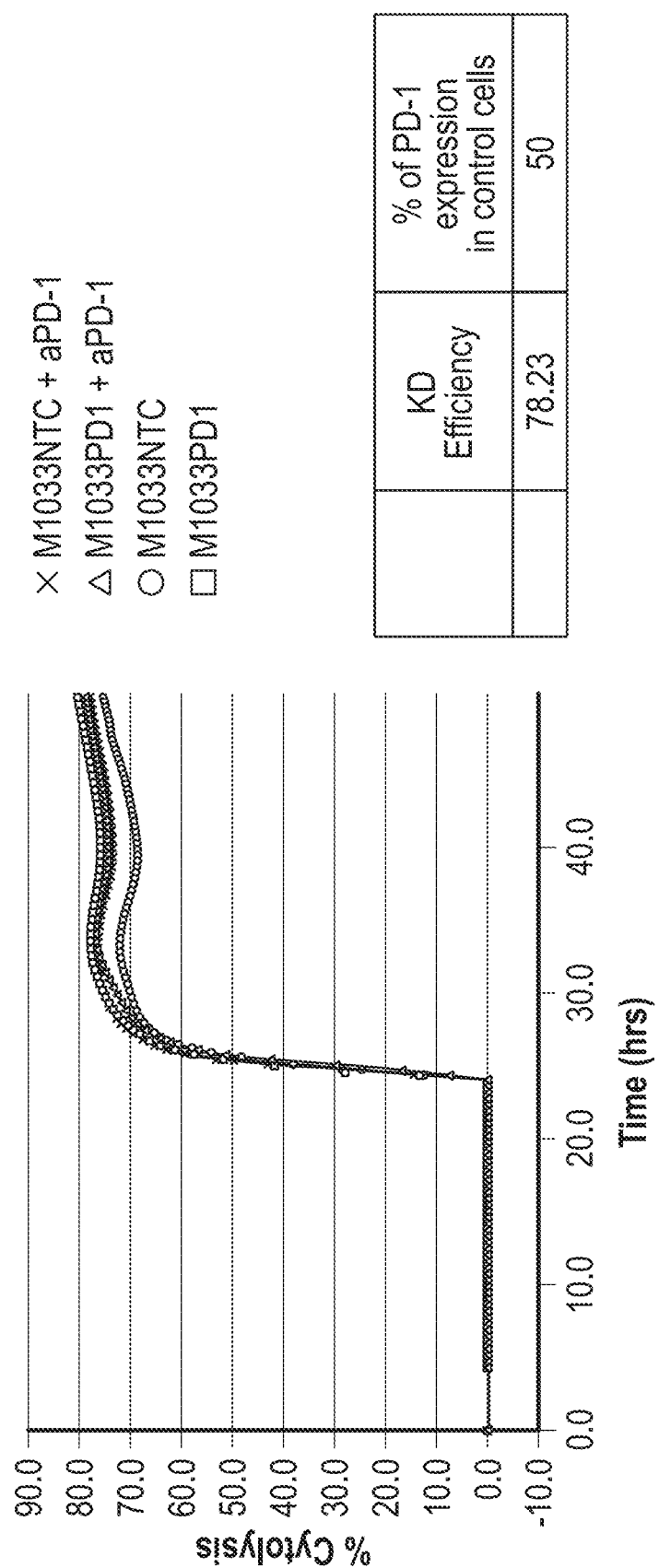
Figure 50A:
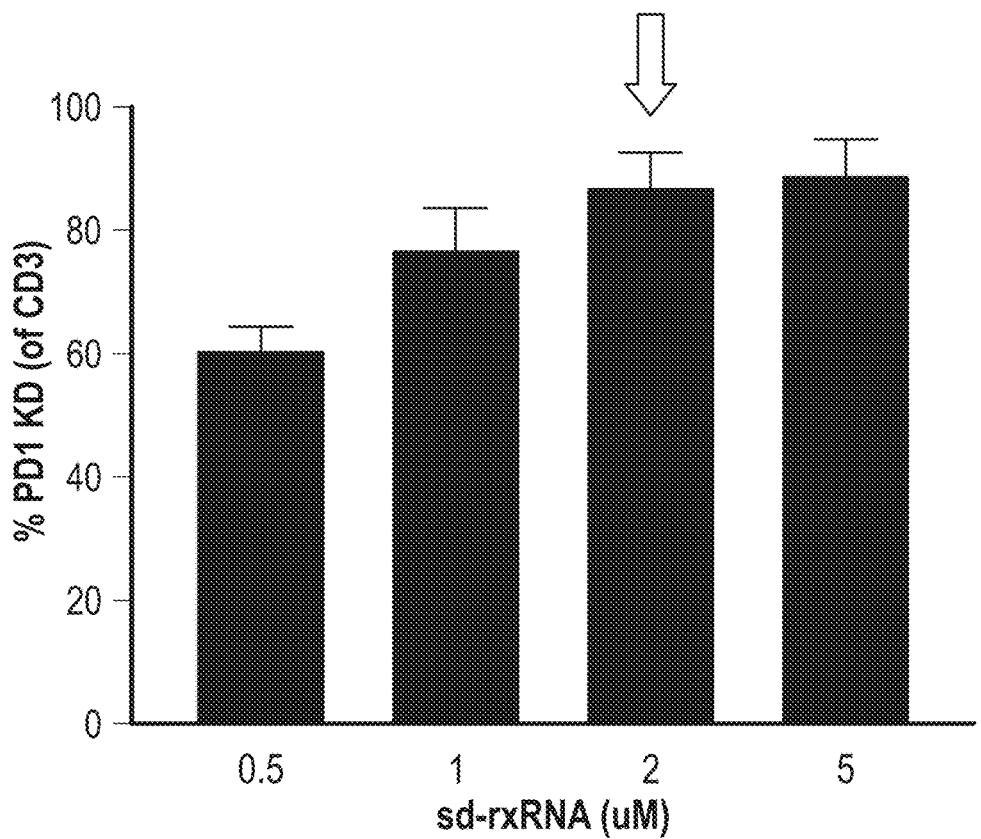
FIG. 50A and FIG. 50B: Sd-rxRNA dose-response experiments. A) n=3, fresh preps from breast cancer tumors. B) n=3, preps from pre-REP melanoma TILs.
Figure 50B:
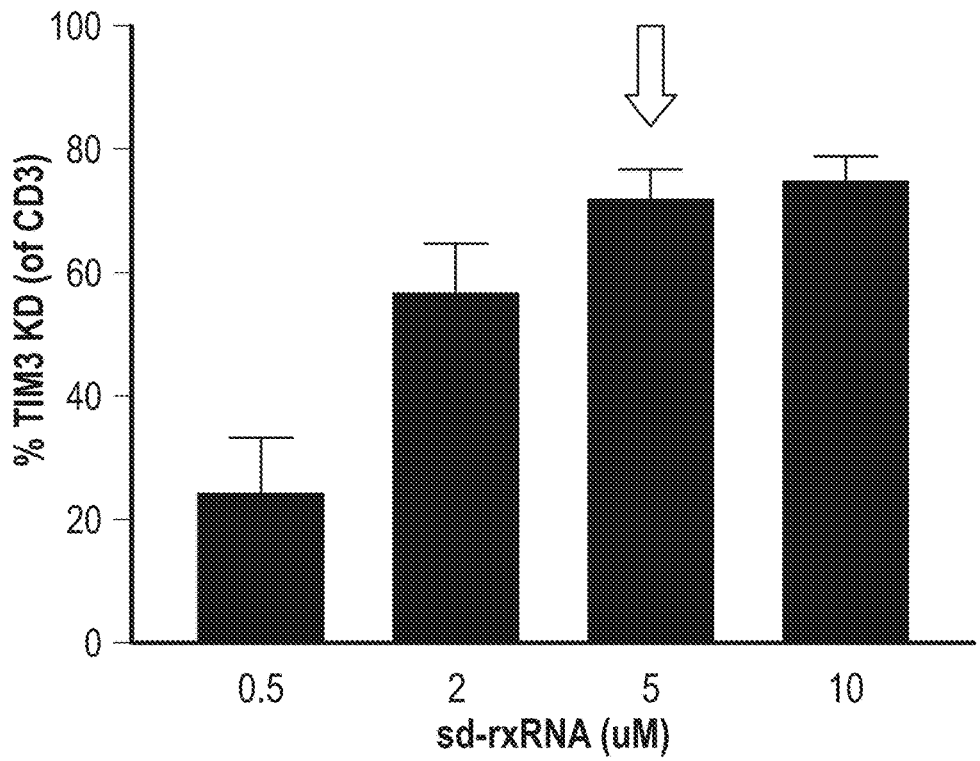
Figure 51A:
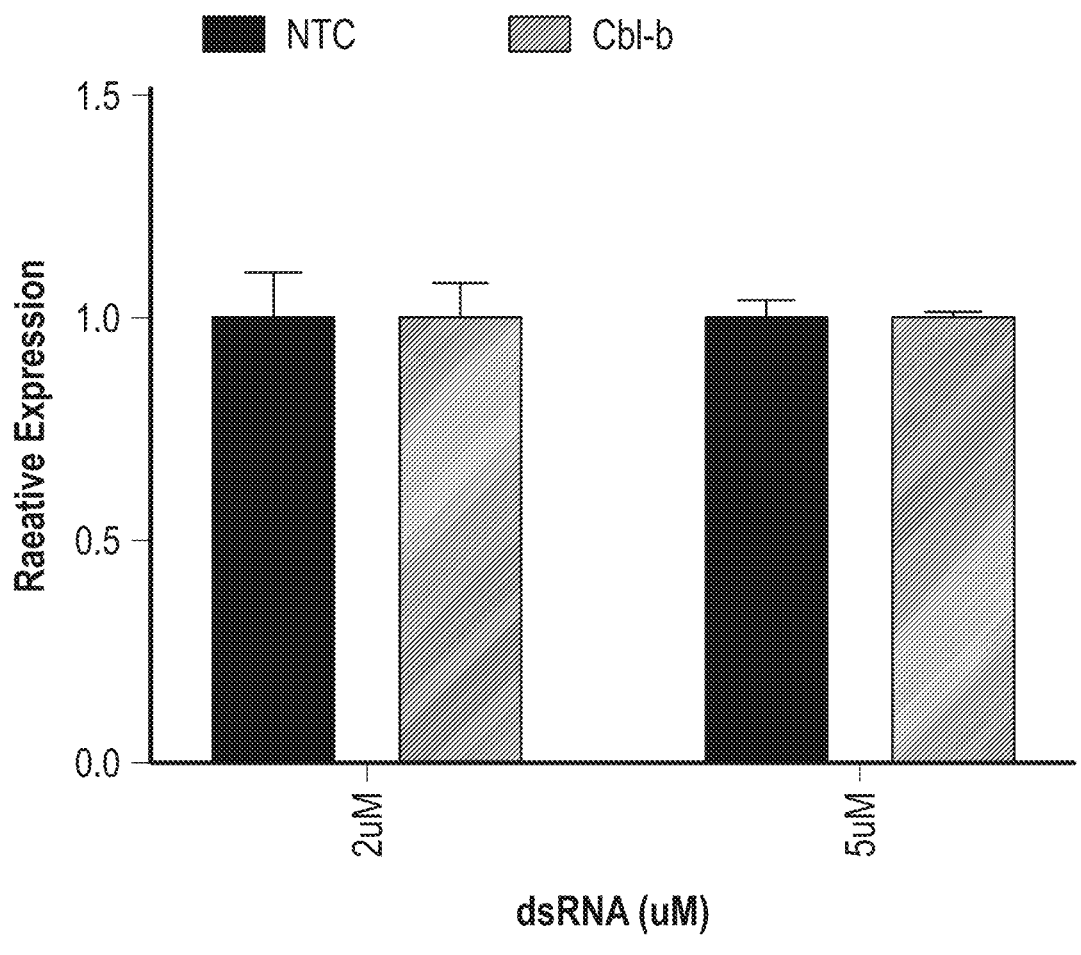
FIG. 51: Sd-rxRNA-mediated Knockdown of CBLB could not be detected. A) graph. B) Flow cytometry assay plots. n=2, preps from pre-REP melanoma and fresh breast cancer TILs. There was no change in mRNA levels of CBLB compare to NTC. There was no change in protein level of Cbl-b using Flow cytometry assay.
Figure 51B:
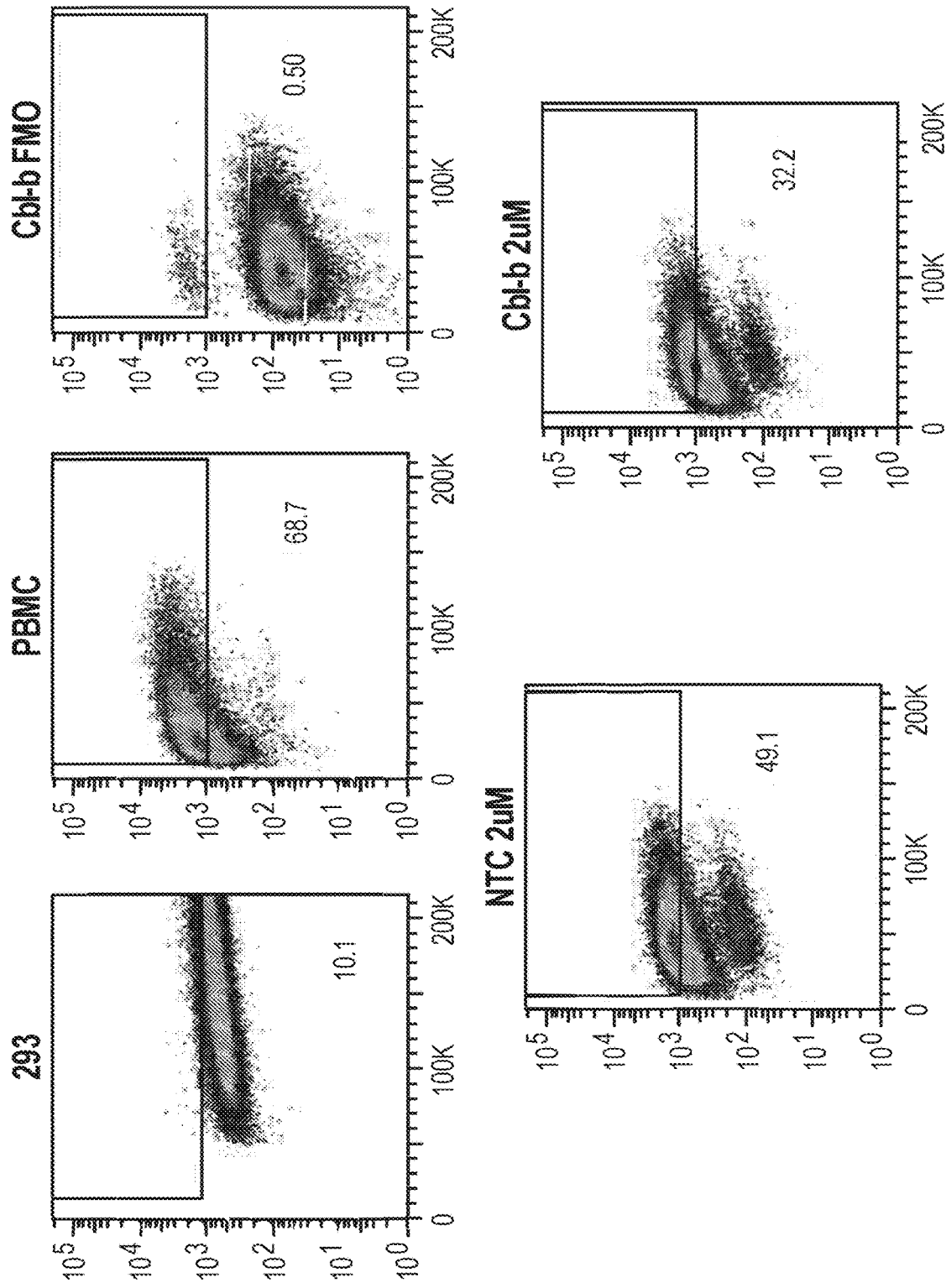
Figure 52A:
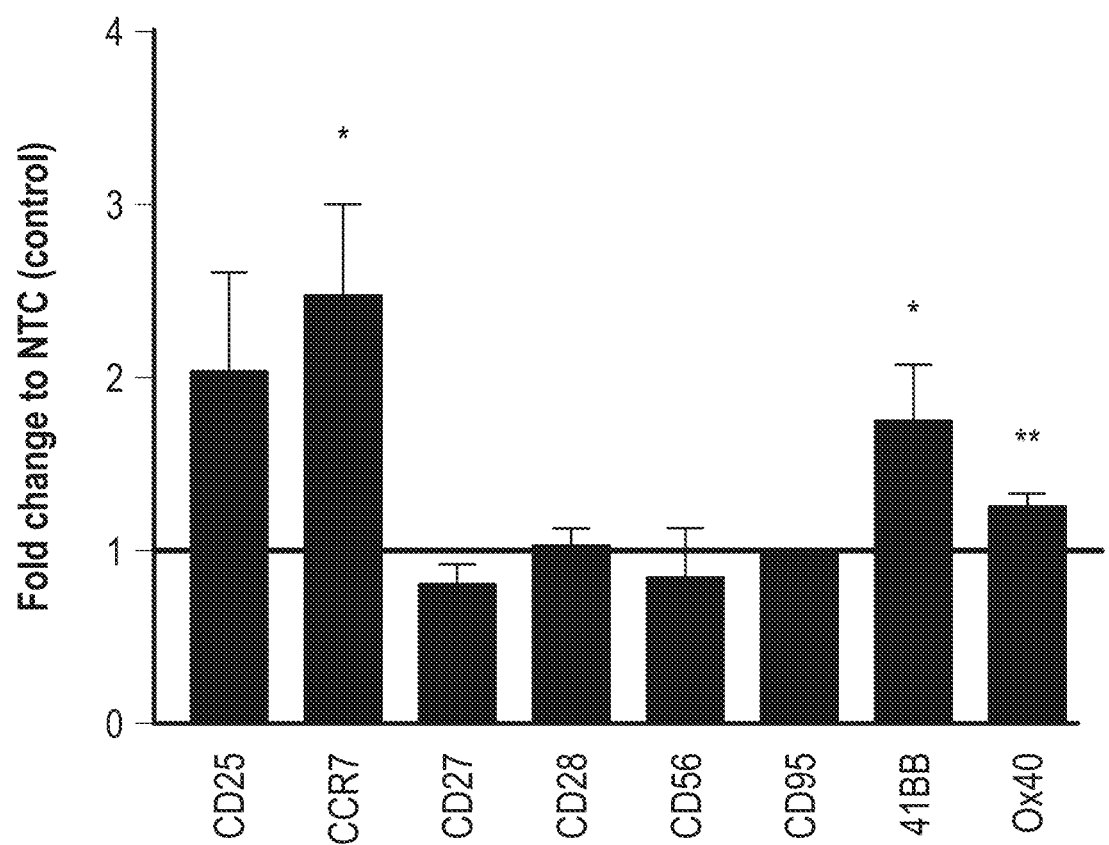
FIG. 52A and FIG. 52B: Shows testing of sd-rxRNA mediated gene silencing in Iovance's TIL manufacturing process, evaluating TIL phenotype. sd-rxRNA-mediated knock down of PD-1 was associated with phenotypic changes indicative of TIL activation. PD-1, n>6, preps from pre-REP melanoma/Fresh breast cancer TILs, 2 uM sd-rxRNA. A) CD25, CCR7, CD27, CD28, CD56, CD95, 4-1BB, and OX40. B) CD25, CD56, CCR7, 4-1BB, and OX40. N=12, Fresh and frozen TILS; breast, melanoma, ovarian, and lung.
Figure 52B:
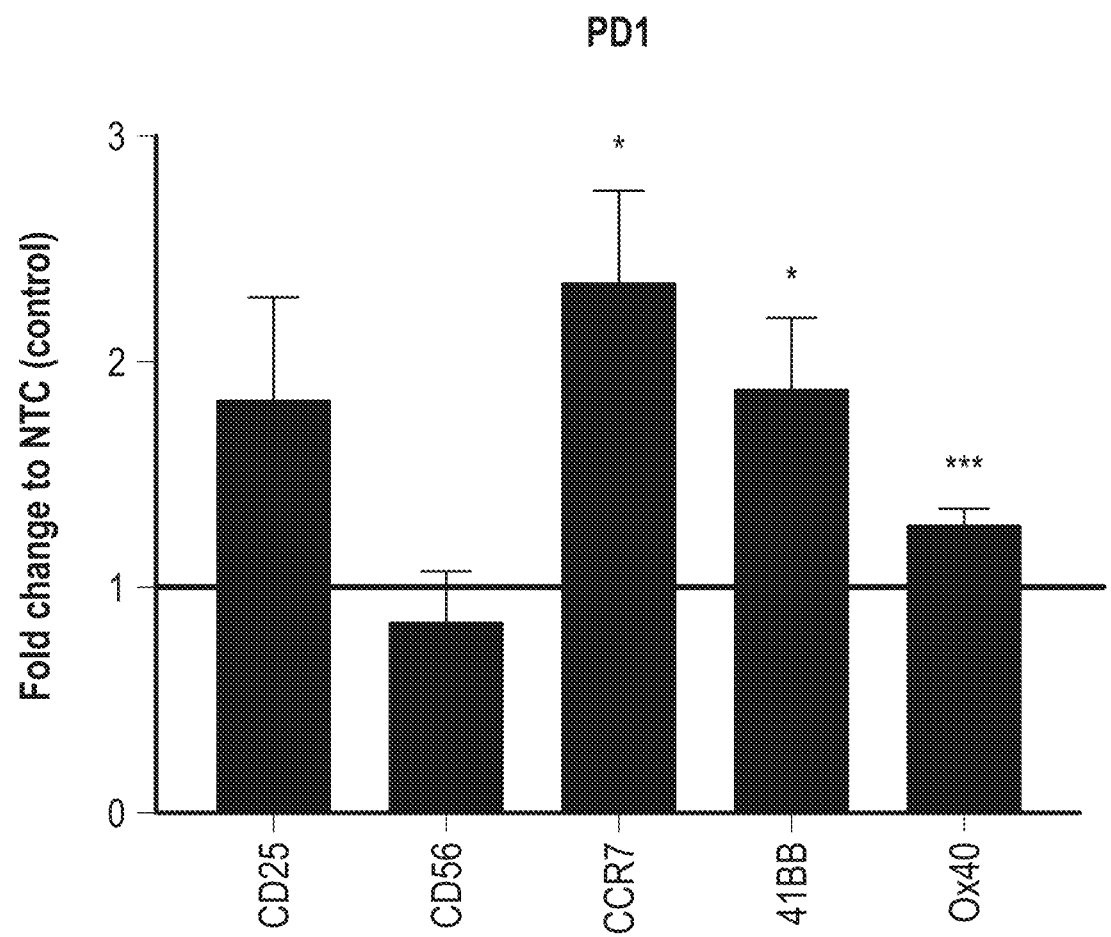
Figure 53A:
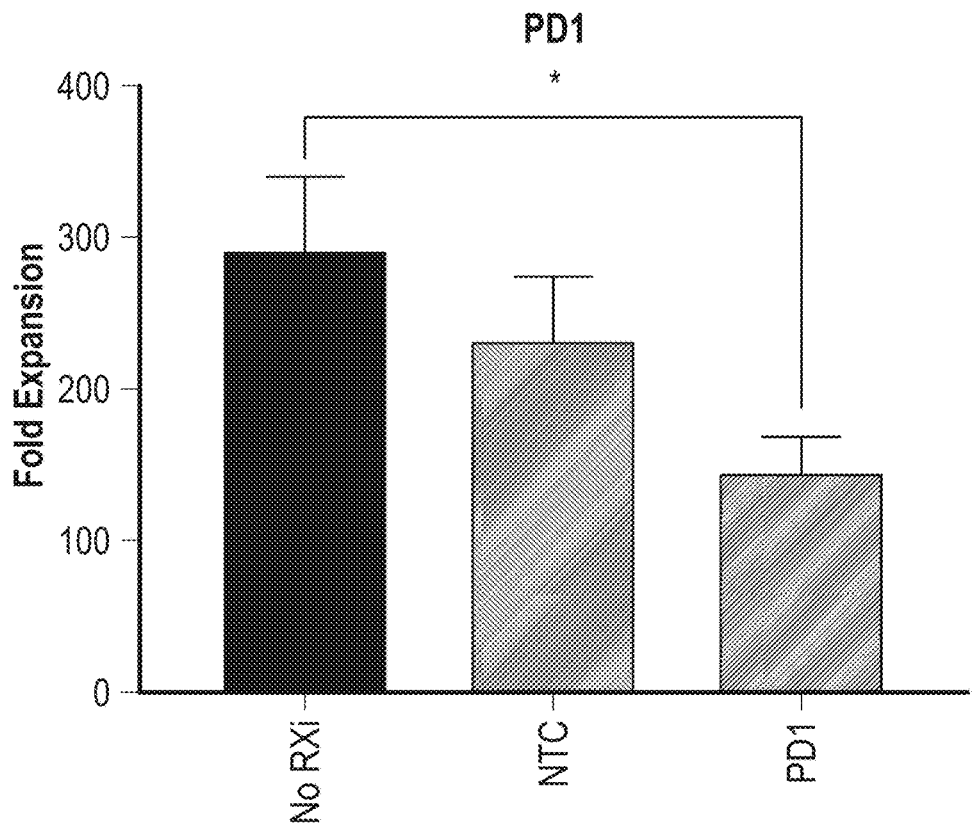
FIG. 53A and FIG. 53B: PD1 sd-rxRNA addition reduced significantly cell growth but not viability of TILs. A) Fold expansion. B) Cell viability. n=7, Breast, Sarcoma and Lung TILs.
Figure 53B:
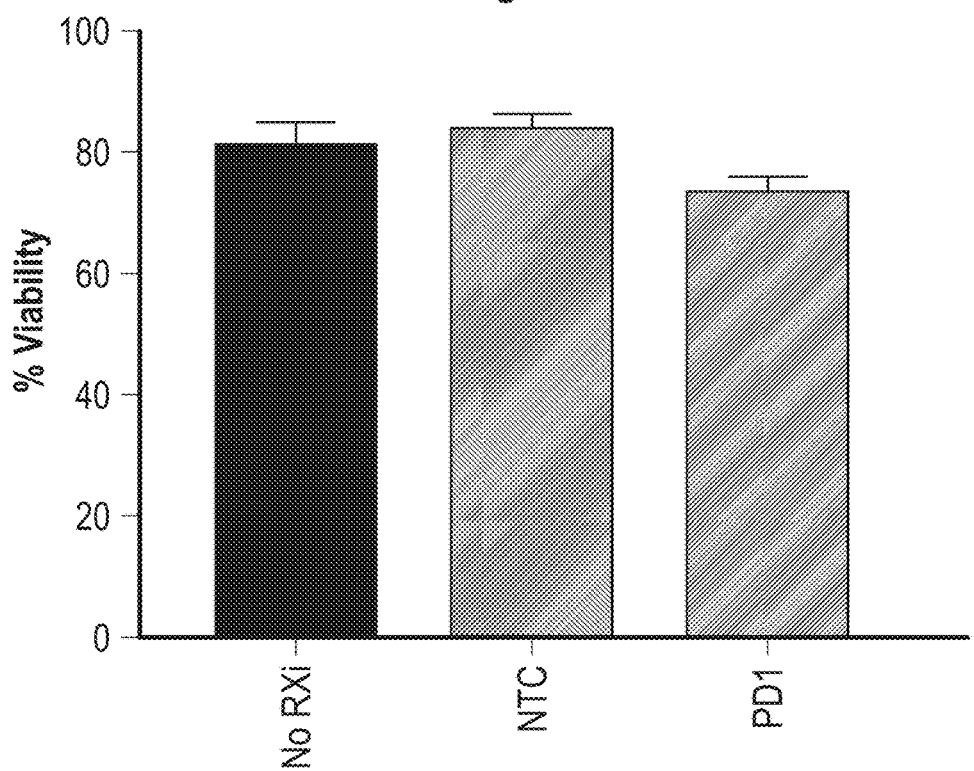
Figure 54A:
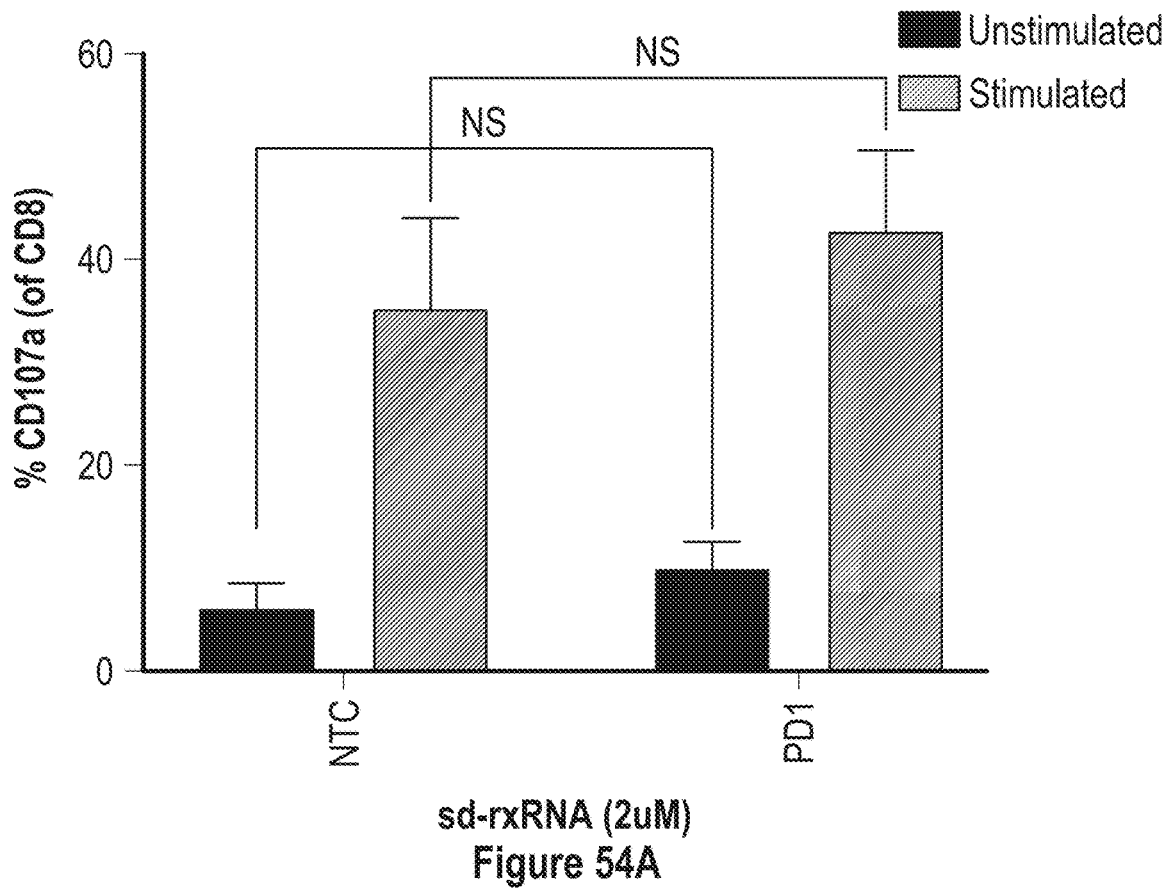
FIG. 54A and FIG. 54B: PD1 KD did not improve CD107a mobilization and IFNγ secretion in response to non-specific stimulation. A) Percentage of CD8 cells expressing CD107a before and after stimulation. B) IFNγ secretion before and after stimulation. n=6, melanoma TILs.
Figure 54B:
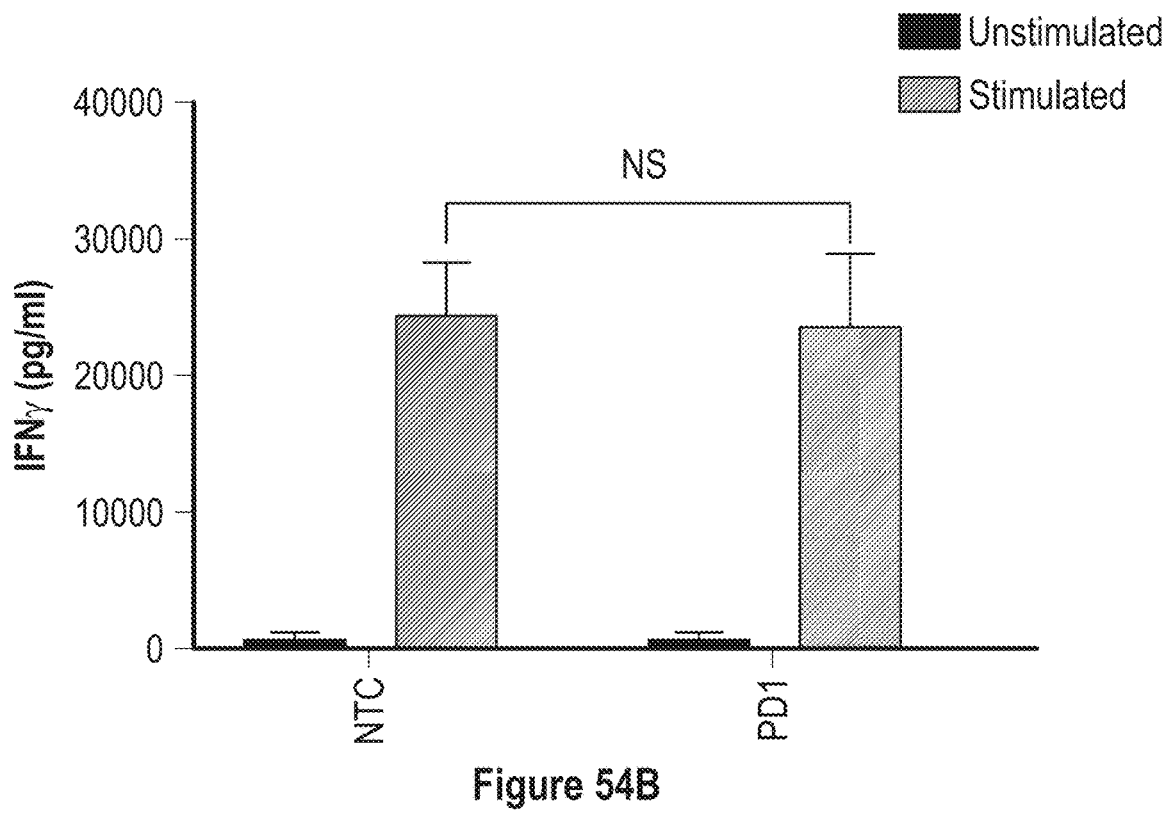

Goal:
  To re-establish TIL effector functions, by silencing inhibitory pathways.
Strategy:
  Transient knockdown of 1) PDCD1, 2) TIM3, 3) CBLB, 4) LAG3, and 5) CISH using sd-rxRNA during the rapid expansion protocol. Specific focus on transient knockdown of PD1 using sd-rxRNA during the rapid expansion protocol.
Procedure:
  Validation of sd-rxRNA-mediated gene silencing in REP'ed TIL (KD efficiency and persistence; T cell viability).
  Impact of gene silencing on TIL phenotype and function (tumor reactivity).
Results Summary
  Addition of targeted sd-rxRNAs during the REP resulted in successful gene KD for 3 out of 5 targets, including greater that 80% (>80%) PD1 knock-down.
    PD1: >80%
    TIM3: ~70%
    LAG3: ~70%
    CISH: ~40%
    CBLB: non detectable
  PD1 KD (knock-down) was associated with decreased viability. PD1 KD was associated with decreased TILs expansion.
  Significant phenotypic changes were associated with PD1 and TIM3 KD that suggest higher level of activation (enhanced CD25, CCR7, CD56, 4-1BB, and OX40 expression). In particular, significant phenotypic changes were associated with PD1 KD that suggest high level of activation (enhanced CD25, CCR7, 4-1BB, and OX40 expression, relative to NTC control).
  None of the sd-rxRNAs resulted in increased cytokine secretion in response to re-stimulation (INF g/IL-2/TNF-a) in these experiments. In particular, exposure of TIL to PDCD1 sd-rxRNA did not increase CD107a mobilization or cytokine secretion (INFγ/IL-2/TNF-α) in response to re-stimulation. See, for example, FIG. 54.
  PD1 KD (knock-down) increased in vitro killing capability of TILs (see, for example, FIG. 49).
Methods:
  Day 0: Pre-REP initiated. Medium plus IL-2 added.
  Day 11: REP initiated Thawed/Fresh pre-REP+sd-rxRNA (i.e., second expansion initiated) with medium comprising IL-2 plus PBMCs.
  Day 14: medium changed+sd-rxRNA, with IL-2, (optionally OKT3 and feeders (PBMCs)); however, performed with just IL-2 (for example, sd-rxRNA with IL-2 medium).
  Day 17: medium changed+sd-rxRNA (addition of additional sd-rxRNA) (for example, sd-rxRNA with IL-2 medium).
  Day 21: medium changed+sd-rxRNA (addition of additional of sd-rxRNA) (for example, sd-rxRNA with IL-2 medium).
  Day 22: TILs harvested as described above.
    Cells counted and determined viability.
    Determined KD (knock-down) efficiency (Q-PCR, flow)
    Performed phenotype assays to characterize TILs, as described above.
    Examined activation markers (CD107a, IFNγ) (see, for example, FIGS. 45, inhibitory/exhaustion markers, and FIG. 46, IFNγ).
This experiment was performed in five tumor types: melanoma, breast, lung, sarcoma, and ovarian, as provided in FIG. 40.

Example 24: Variant Embodiments of Example 23

According the methods discussed in Example 23, methods of expanding TILs in combination with transiently altering protein expression are described. This example provides further varied embodiments in line with the methods described in Example 23.

In some embodiments of the above described method, the method for expanding tumor infiltrating lymphocytes (TILs) into a therapeutic population of TILs can comprise:
(i) obtaining a first population of TILs from a tumor resected from a patient;
(ii) performing a first expansion by culturing the first population of TILs in a cell culture medium comprising IL-2, and optionally OKT-3, to produce a second population of TILs;
(iii) performing a second expansion by supplementing the cell culture medium of the second population of TILs with additional IL-2, OKT-3, and antigen presenting cells (APCs), to produce a third population of TILs, wherein the third population of TILs is at least 100-fold greater in number than the second population of TILs, and wherein the second expansion is performed for at least 14 days in order to obtain the third population of TILs, wherein the third population of TILs is a therapeutic population of TILs; and
(iv) exposing the second and/or third population of TILs to transcription factors (TFs) and/or other molecules capable of transiently altering protein expression between days 11 and 21, wherein the TFs and/or other molecules capable of transiently altering protein expression provide for altered expression of tumor antigens and/or an alteration in the number of tumor antigen-specific T cells in the therapeutic population of TILs; and
(v) harvesting the therapeutic population of TILs obtained from step (iv) at day 22 or after, wherein; and
(vi) optionally, transferring the harvested TIL population from step (v) to an infusion bag.

In some variant embodiments, the other molecules capable of transiently altering protein expression comprise sd-RNAs, including for example but not limited to, sd-rxRNAs. In some embodiments, the TILs are exposed to the sd-RNAs on Day 11, Day 14, Day 17, and/or Day 21. In some variant embodiments, the TILs are exposed to the sd-RNAs on at least two of Day 11, Day 14, Day 17, and/or Day 21. In some variant embodiments, the TILs are exposed to the sd-RNAs on at least three of Day 11, Day 14, Day 17, and/or Day 21. In some variant embodiments, the TILs are exposed to the sd-RNAs on all of Day 11, Day 14, Day 17, and Day 21. In some embodiments, the sd-RNA targets PD-1. In some embodiments, the sd-RNA sequences used in the invention exhibit a 70% reduction in expression of the target gene. In some embodiments, the sd-RNA sequences used in the invention exhibit a 75% reduction in expression of the target gene.

In some embodiments, the sd-RNA sequences used in the invention exhibit an 80% reduction in expression of the target gene. In some embodiments, the sd-RNA sequences used in the invention exhibit an 85% reduction in expression of the target gene. In some embodiments, the sd-RNA sequences used in the invention exhibit a 90% reduction in expression of the target gene. In some embodiments, the sd-RNA sequences used in the invention exhibit a 95% reduction in expression of the target gene. In some embodiments, the sd-RNA sequences used in the invention exhibit a 99% reduction in expression of the target gene. In some embodiments, the sd-RNA sequences used in the invention exhibit a reduction in expression of the target gene when delivered at a concentration of about 0.25 $\mu$M to about 10 $\mu$M, in some embodiments, about 0.25 $\mu$M to about 4 $\mu$M. In some embodiments, the sd-RNA sequences used in the invention exhibit a reduction in expression of the target gene when delivered at a concentration of about 0.25 $\mu$M. In some embodiments, the sd-RNA sequences used in the invention exhibit a reduction in expression of the target gene when delivered at a concentration of about 0.5 $\mu$M. In some embodiments, the sd-RNA sequences used in the invention exhibit a reduction in expression of the target gene when delivered at a concentration of about 0.75 $\mu$M. In some embodiments, the sd-RNA sequences used in the invention exhibit a reduction in expression of the target gene when delivered at a concentration of about 1.0 $\mu$M. In some embodiments, the sd-RNA sequences used in the invention exhibit a reduction in expression of the target gene when delivered at a concentration of about 1.25 $\mu$M. In some embodiments, the sd-RNA sequences used in the invention exhibit a reduction in expression of the target gene when delivered at a concentration of about 1.5 $\mu$M. In some embodiments, the sd-RNA sequences used in the invention exhibit a reduction in expression of the target gene when delivered at a concentration of about 1.75 $\mu$M. In some embodiments, the sd-RNA sequences used in the invention exhibit a reduction in expression of the target gene when delivered at a concentration of about 2.0 $\mu$M. In some embodiments, the sd-RNA sequences used in the invention exhibit a reduction in expression of the target gene when delivered at a concentration of about 2.25 $\mu$M. In some embodiments, the sd-RNA sequences used in the invention exhibit a reduction in expression of the target gene when delivered at a concentration of about 2.5 $\mu$M. In some embodiments, the sd-RNA sequences used in the invention exhibit a reduction in expression of the target gene when delivered at a concentration of about 2.75 $\mu$M. In some embodiments, the sd-RNA sequences used in the invention exhibit a reduction in expression of the target gene when delivered at a concentration of about 3.0 $\mu$M. In some embodiments, the sd-RNA sequences used in the invention exhibit a reduction in expression of the target gene when delivered at a concentration of about 3.25 $\mu$M. In some embodiments, the sd-RNA sequences used in the invention exhibit a reduction in expression of the target gene when delivered at a concentration of about 3.5 $\mu$M. In some embodiments, the sd-RNA sequences used in the invention exhibit a reduction in expression of the target gene when delivered at a concentration of about 3.75 $\mu$M. In some embodiments, the sd-RNA sequences used in the invention exhibit a reduction in expression of the target gene when delivered at a concentration of about 4.0 $\mu$M. In some embodiments, the sd-RNA sequences used in the invention exhibit a reduction in expression of the target gene when delivered at a concentration of about 5.0 $\mu$M. In some embodiments, the sd-RNA sequences used in the invention exhibit a reduction in expression of the target gene when delivered at a concentration of about 6.0 $\mu$M. In some embodiments, the sd-RNA sequences used in the invention exhibit a reduction in expression of the target gene when delivered at a concentration of about 7.0 $\mu$M. In some embodiments, the sd-RNA sequences used in the invention exhibit a reduction in expression of the target gene when delivered at a concentration of about 8.0 $\mu$M. In some embodiments, the sd-RNA sequences used in the invention exhibit a reduction in expression of the target gene when delivered at a concentration of about 9.0 $\mu$M. In some embodiments, the sd-RNA sequences used in the invention exhibit a reduction in expression of the target gene when delivered at a concentration of about 10.0 µM. In any of the foregoing embodiments, the concentrations specified may be determined with respect to TIL culture media before or after exchange of media.

In some embodiments, the sd-RNA sequences used in the invention exhibit a 70% reduction in expression of PD-1. In some embodiments, the sd-RNA sequences used in the invention exhibit a 75% reduction in expression of PD-1. In some embodiments, the sd-RNA sequences used in the invention exhibit an 80% reduction in expression of PD-1. In some embodiments, the sd-RNA sequences used in the invention exhibit an 85% reduction in expression of PD-1. In some embodiments, the sd-RNA sequences used in the invention exhibit a 90% reduction in expression of PD-1. In some embodiments, the sd-RNA sequences used in the invention exhibit a 95% reduction in expression of PD-1. In some embodiments, the sd-RNA sequences used in the invention exhibit a 99% reduction in expression PD-1. In some embodiments, the sd-RNA sequences used in the invention exhibit a reduction in expression of PD-1 when delivered at a concentration of about 0.25 µM to about 10 µM, in some embodiments, about 0.25 µM to about 4 µM. In some embodiments, the sd-RNA sequences used in the invention exhibit a reduction in expression of PD-1 when delivered at a concentration of about 0.25 µM. In some embodiments, the sd-RNA sequences used in the invention exhibit a reduction in expression of PD-1 when delivered at a concentration of about 0.5 µM. In some embodiments, the sd-RNA sequences used in the invention exhibit a reduction in expression of PD-1 when delivered at a concentration of about 0.75 µM. In some embodiments, the sd-RNA sequences used in the invention exhibit a reduction in expression of PD-1 when delivered at a concentration of about 1.0 µM. In some embodiments, the sd-RNA sequences used in the invention exhibit a reduction in expression of PD-1 when delivered at a concentration of about 1.25 µM. In some embodiments, the sd-RNA sequences used in the invention exhibit a reduction in expression of PD-1 when delivered at a concentration of about 1.5 µM. In some embodiments, the sd-RNA sequences used in the invention exhibit a reduction in expression of PD-1 when delivered at a concentration of about 1.75 µM. In some embodiments, the sd-RNA sequences used in the invention exhibit a reduction in expression of PD-1 when delivered at a concentration of about 2.0 µM. In some embodiments, the sd-RNA sequences used in the invention exhibit a reduction in expression of PD-1 when delivered at a concentration of about 2.25 µM. In some embodiments, the sd-RNA sequences used in the invention exhibit a reduction in expression of PD-1 when delivered at a concentration of about 2.5 µM. In some embodiments, the sd-RNA sequences used in the invention exhibit a reduction in expression of PD-1 when delivered at a concentration of about 2.75 µM. In some embodiments, the sd-RNA sequences used in the invention exhibit a reduction in expression of PD-1 when delivered at a concentration of about 3.0 µM. In some embodiments, the sd-RNA sequences used in the invention exhibit a reduction in expression of PD-1 when delivered at a concentration of about 3.25 µM. In some embodiments, the sd-RNA sequences used in the invention exhibit a reduction in expression of PD-1 when delivered at a concentration of about 3.5 µM. In some embodiments, the sd-RNA sequences used in the invention exhibit a reduction in expression of PD-1 when delivered at a concentration of about 3.75 µM. In some embodiments, the sd-RNA sequences used in the invention exhibit a reduction in expression of PD-1 when delivered at a concentration of about 4.0 µM. In some embodiments, the sd-RNA sequences used in the invention exhibit a reduction in expression of PD-1 when delivered at a concentration of about 5.0 µM. In some embodiments, the sd-RNA sequences used in the invention exhibit a reduction in expression of PD-1 when delivered at a concentration of about 6.0 µM. In some embodiments, the sd-RNA sequences used in the invention exhibit a reduction in expression of PD-1 when delivered at a concentration of about 7.0 µM. In some embodiments, the sd-RNA sequences used in the invention exhibit a reduction in expression of PD-1 when delivered at a concentration of about 8.0 µM. In some embodiments, the sd-RNA sequences used in the invention exhibit a reduction in expression of PD-1 when delivered at a concentration of about 9.0 µM. In some embodiments, the sd-RNA sequences used in the invention exhibit a reduction in expression of PD-1 when delivered at a concentration of about 10.0 µM. In any of the foregoing embodiments, the concentrations specified may be determined with respect to TIL culture media before or after exchange of media.

In some variant embodiments, the TILs are exposed to the sd-RNAs on at least two of Day 11, Day 14, Day 17, and/or Day 21 at an sd-RNA concentration of about 0.75 µM to about 3 µM. In some variant embodiments, the TILs are exposed to the sd-RNAs on at least three of Day 11, Day 14, Day 17, and/or Day 21 at an sd-RNA concentration of about 0.75 µM to about 3 µM. In some variant embodiments, the TILs are exposed to the sd-RNAs on all of Day 11, Day 14, Day 17, and Day 21 at an sd-RNA concentration of about 0.75 µM to about 3 µM. In some variant embodiments, the sd-RNA is added along with a media change at an sd-RNA concentration of about 0.75 µM to about 3 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.0 µM to about 2.5 µM. In some variant embodiments, the TILs are exposed to the sd-RNAs on at least three of Day 11, Day 14, Day 17, and/or Day 21 at an sd-RNA concentration of about 1.0 µM to about 2.5 µM. In some variant embodiments, the TILs are exposed to the sd-RNAs on all of Day 11, Day 14, Day 17, and Day 21 at an sd-RNA concentration of about 1.0 µM to about 2.5 µM. In some variant embodiments, the sd-RNA is added along with a media change at an sd-RNA concentration of about 1.0 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.5 µM to about 2.5 µM. In some variant embodiments, the TILs are exposed to the sd-RNAs on at least three of Day 11, Day 14, Day 17, and/or Day 21 at an sd-RNA concentration of about 1.5 µM to about 2.5 µM. In some variant embodiments, the TILs are exposed to the sd-RNAs on all of Day 11, Day 14, Day 17, and Day 21 at an sd-RNA concentration of about 1.5 µM to about 2.5 µM. In some variant embodiments, the sd-RNA is added along with a media change at an sd-RNA concentration of about 1.5 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of 2 µM. In some variant embodiments, the TILs are exposed to the sd-RNAs on at least three of Day 11, Day 14, Day 17, and/or Day 21 at an sd-RNA concentration of about 2 µM. In some variant embodiments, the TILs are exposed to the sd-RNAs on all of Day 11, Day 14, Day 17, and Day 21 at an sd-RNA concentration of about 2 µM. In some variant embodiments, the sd-RNA is added along with a media change at an sd-RNA concentration of about 2 µM. In some embodiments, the sd-RNA targets PD-1.

In some embodiments, the sd-RNA added at Day 11 is added in media comprising sd-RNA, IL-2, OKT3 and APCs (including, for example, PBMCs). In some embodiments, the sd-RNA added at Day 14 is added in media comprising sd-RNA and optionally includes one or more of IL-2, OKT3 and APCs (including, for example, PBMCs). In some embodiments, the sd-RNA added at Day 17 is added in media comprising sd-RNA and optionally includes one or more of IL-2, OKT3 and APCs (including, for example, PBMCs). In some embodiments, the sd-RNA added at Day 21 is added in media comprising sd-RNA and optionally includes one or more of IL-2, OKT3 and APCs (including, for example, PBMCs). In some embodiments, the sd-RNA added at Day 14 is added in media comprising sd-RNA and IL-2. In some embodiments, the sd-RNA added at Day 17 is added in media comprising sd-RNA and IL-2. In some embodiments, the sd-RNA added at Day 21 is added in media comprising sd-RNA and IL-2. In some embodiments, more sd-RNA is added at Day 14. In some embodiments, more sd-RNA added at Day 17. In some embodiments, more sd-RNA added at Day 21. In some embodiments, the sd-RNA is added at the same concentration at Day 11, Day 14, Day 17, and Day 21. In some embodiments, the sd-RNA is added at a different concentration at Day 11, Day 14, Day 17 and/or Day 21. In some embodiments, the sd-RNA targets PD-1.

Example 25: Variant Embodiments of Example 23

According the methods discussed in Example 23, methods of expanding TILs in combination with transiently altering protein expression are described. This example provides further varied embodiments in line with the methods described in Example 23.

In some embodiments of the above described method, the method for expanding tumor infiltrating lymphocytes (TILs) into a therapeutic population of TILs can comprise:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2, and optionally OKT-3, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
(d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;
(e) exposing the second and/or third population of TILs to transcription factors (TFs) and/or other molecules capable of transiently altering protein expression between days 11 and 21, wherein the TFs and/or other molecules capable of transiently altering protein expression provide for altered expression of tumor antigens and/or an alteration in the number of tumor antigen-specific T cells in the therapeutic population of TILs;
(f) harvesting the therapeutic population of TILs obtained from step (d) at day 22 or after, wherein the transition from step (d) to step (e) occurs without opening the system; and
(g) transferring the harvested TIL population from step (e) to an infusion bag, wherein the transfer from step (e) to (f) occurs without opening the system.

In some variant embodiments, the other molecules capable of transiently altering protein expression comprise sd-RNAs, including for example but not limited to, sd-rxRNAs. In some embodiments, the TILs are exposed to the sd-RNAs on Day 11, Day 14, Day 17, and/or Day 21. In some variant embodiments, the TILs are exposed to the sd-RNAs on at least two of Day 11, Day 14, Day 17, and/or Day 21. In some variant embodiments, the TILs are exposed to the sd-RNAs on at least three of Day 11, Day 14, and/or Day 21. In some variant embodiments, the TILs are exposed to the sd-RNAs on all of Day 11, Day 14, Day 17, and Day 21. In some embodiments, the sd-RNA targets PD-1.

In some embodiments, the sd-RNA sequences used in the invention exhibit a 70% reduction in expression of the target gene. In some embodiments, the sd-RNA sequences used in the invention exhibit a 75% reduction in expression of the target gene. In some embodiments, the sd-RNA sequences used in the invention exhibit an 80% reduction in expression of the target gene. In some embodiments, the sd-RNA sequences used in the invention exhibit an 85% reduction in expression of the target gene. In some embodiments, the sd-RNA sequences used in the invention exhibit a 90% reduction in expression of the target gene. In some embodiments, the sd-RNA sequences used in the invention exhibit a 95% reduction in expression of the target gene. In some embodiments, the sd-RNA sequences used in the invention exhibit a 99% reduction in expression of the target gene. In some embodiments, the sd-RNA sequences used in the invention exhibit a reduction in expression of the target gene when delivered at a concentration of about 0.25 µM to about 10 µM, in some embodiments, about 0.25 µM to about 4 µM. In some embodiments, the sd-RNA sequences used in the invention exhibit a reduction in expression of the target gene when delivered at a concentration of about 0.25 µM. In some embodiments, the sd-RNA sequences used in the invention exhibit a reduction in expression of the target gene when delivered at a concentration of about 0.5 µM. In some embodiments, the sd-RNA sequences used in the invention exhibit a reduction in expression of the target gene when delivered at a concentration of about 0.75 µM. In some embodiments, the sd-RNA sequences used in the invention exhibit a reduction in expression of the target gene when delivered at a concentration of about 1.0 µM. In some embodiments, the sd-RNA sequences used in the invention exhibit a reduction in expression of the target gene when delivered at a concentration of about 1.25 µM. In some embodiments, the sd-RNA sequences used in the invention exhibit a reduction in expression of the target gene when delivered at a concentration of about 1.5 µM. In some embodiments, the sd-RNA sequences used in the invention exhibit a reduction in expression of the target gene when delivered at a concentration of about 1.75 µM. In some embodiments, the sd-RNA sequences used in the invention exhibit a reduction in expression of the target gene when delivered at a concentration of about 2.0 µM. In some embodiments, the sd-RNA sequences used in the invention exhibit a reduction in expression of the target gene when delivered at a concentration of about 2.25 µM. In some embodiments, the sd-RNA sequences used in the invention exhibit a reduction in expression of the target gene when delivered at a concentration of about 2.5 µM. In some embodiments, the sd-RNA sequences used in the invention exhibit a reduction in expression of the target gene when delivered at a concentration of about 2.75 µM. In some embodiments, the sd-RNA sequences used in the invention exhibit a reduction in expression of the target gene when delivered at a concentration of about 3.0 µM. In some embodiments, the sd-RNA sequences used in the invention exhibit a reduction in expression of the target gene when delivered at a concentration of about 3.25 µM. In some embodiments, the sd-RNA sequences used in the invention exhibit a reduction in expression of the target gene when delivered at a concentration of about 3.5 µM. In some embodiments, the sd-RNA sequences used in the invention exhibit a reduction in expression of the target gene when delivered at a concentration of about 3.75 µM. In some embodiments, the sd-RNA sequences used in the invention exhibit a reduction in expression of the target gene when delivered at a concentration of about 4.0 µM. In some embodiments, the sd-RNA sequences used in the invention exhibit a reduction in expression of the target gene when delivered at a concentration of about 5.0 µM. In some embodiments, the sd-RNA sequences used in the invention exhibit a reduction in expression of the target gene when delivered at a concentration of about 6.0 µM. In some embodiments, the sd-RNA sequences used in the invention exhibit a reduction in expression of the target gene when delivered at a concentration of about 7.0 µM. In some embodiments, the sd-RNA sequences used in the invention exhibit a reduction in expression of the target gene when delivered at a concentration of about 8.0 µM. In some embodiments, the sd-RNA sequences used in the invention exhibit a reduction in expression of the target gene when delivered at a concentration of about 9.0 µM. In some embodiments, the sd-RNA sequences used in the invention exhibit a reduction in expression of the target gene when delivered at a concentration of about 10.0 µM. In any of the foregoing embodiments, the concentrations specified may be determined with respect to TIL culture media before or after exchange of media.

In some embodiments, the sd-RNA sequences used in the invention exhibit a 70% reduction in expression of PD-1. In some embodiments, the sd-RNA sequences used in the invention exhibit a 75% reduction in expression of PD-1. In some embodiments, the sd-RNA sequences used in the invention exhibit an 80% reduction in expression of PD-1. In some embodiments, the sd-RNA sequences used in the invention exhibit an 85% reduction in expression of PD-1. In some embodiments, the sd-RNA sequences used in the invention exhibit a 90% reduction in expression of PD-1. In some embodiments, the sd-RNA sequences used in the invention exhibit a 95% reduction in expression of PD-1. In some embodiments, the sd-RNA sequences used in the invention exhibit a 99% reduction in expression PD-1. In some embodiments, the sd-RNA sequences used in the invention exhibit a reduction in expression of PD-1 when delivered at a concentration of about 0.25 µM to about 10 µM, in some embodiments, about 0.25 µM to about 4 µM. In some embodiments, the sd-RNA sequences used in the invention exhibit a reduction in expression of PD-1 when delivered at a concentration of about 0.25 µM. In some embodiments, the sd-RNA sequences used in the invention exhibit a reduction in expression of PD-1 when delivered at a concentration of about 0.5 µM. In some embodiments, the sd-RNA sequences used in the invention exhibit a reduction in expression of PD-1 when delivered at a concentration of about 0.75 µM. In some embodiments, the sd-RNA sequences used in the invention exhibit a reduction in expression of PD-1 when delivered at a concentration of about 1.0 µM. In some embodiments, the sd-RNA sequences used in the invention exhibit a reduction in expression of PD-1 when delivered at a concentration of about 1.25 µM. In some embodiments, the sd-RNA sequences used in the invention exhibit a reduction in expression of PD-1 when delivered at a concentration of about 1.5 µM. In some embodiments, the sd-RNA sequences used in the invention exhibit a reduction in expression of PD-1 when delivered at a concentration of about 1.75 µM. In some embodiments, the sd-RNA sequences used in the invention exhibit a reduction in expression of PD-1 when delivered at a concentration of about 2.0 µM. In some embodiments, the sd-RNA sequences used in the invention exhibit a reduction in expression of PD-1 when delivered at a concentration of about 2.25 µM. In some embodiments, the sd-RNA sequences used in the invention exhibit a reduction in expression of PD-1 when delivered at a concentration of about 2.5 µM. In some embodiments, the sd-RNA sequences used in the invention exhibit a reduction in expression of PD-1 when delivered at a concentration of about 2.75 µM. In some embodiments, the sd-RNA sequences used in the invention exhibit a reduction in expression of PD-1 when delivered at a concentration of about 3.0 µM. In some embodiments, the sd-RNA sequences used in the invention exhibit a reduction in expression of PD-1 when delivered at a concentration of about 3.25 µM. In some embodiments, the sd-RNA sequences used in the invention exhibit a reduction in expression of PD-1 when delivered at a concentration of about 3.5 µM. In some embodiments, the sd-RNA sequences used in the invention exhibit a reduction in expression of PD-1 when delivered at a concentration of about 3.75 µM. In some embodiments, the sd-RNA sequences used in the invention exhibit a reduction in expression of PD-1 when delivered at a concentration of about 4.0 µM. In some embodiments, the sd-RNA sequences used in the invention exhibit a reduction in expression of PD-1 when delivered at a concentration of about 5.0 µM. In some embodiments, the sd-RNA sequences used in the invention exhibit a reduction in expression of PD-1 when delivered at a concentration of about 6.0 µM. In some embodiments, the sd-RNA sequences used in the invention exhibit a reduction in expression of PD-1 when delivered at a concentration of about 7.0 µM. In some embodiments, the sd-RNA sequences used in the invention exhibit a reduction in expression of PD-1 when delivered at a concentration of about 8.0 µM. In some embodiments, the sd-RNA sequences used in the invention exhibit a reduction in expression of PD-1 when delivered at a concentration of about 9.0 µM. In some embodiments, the sd-RNA sequences used in the invention exhibit a reduction in expression of PD-1 when delivered at a concentration of about 10.0 µM. In any of the foregoing embodiments, the concentrations specified may be determined with respect to TIL culture media before or after exchange of media.

In some variant embodiments, the TILs are exposed to the sd-RNAs on at least two of Day 11, Day 14, Day 17, and/or Day 21 at an sd-RNA concentration of about 0.75 µM to about 3 µM. In some variant embodiments, the TILs are exposed to the sd-RNAs on at least three of Day 11, Day 14, Day 17, and/or Day 21 at an sd-RNA concentration of about 0.75 µM to about 3 µM. In some variant embodiments, the TILs are exposed to the sd-RNAs on all of Day 11, Day 14, Day 17, and Day 21 at an sd-RNA concentration of about 0.75 µM to about 3 µM. In some variant embodiments, the sd-RNA is added along with a media change at an sd-RNA concentration of about 0.75 µM to about 3 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.0 µM to about 2.5 µM. In some variant embodiments, the TILs are exposed to the sd-RNAs on at least three of Day 11, Day 14, Day 17, and/or Day 21 at an sd-RNA concentration of about 1.0 µM to about 2.5 µM. In some variant embodiments, the TILs are exposed to the sd-RNAs on all of Day 11, Day 14, Day 17, and Day 21 at an sd-RNA concentration of about 1.0 µM to about 2.5 µM. In some variant embodiments, the sd-RNA is added along with a media change at an sd-RNA concentration of about 1.0 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.5 µM to about 2.5 µM. In some variant embodiments, the TILs are exposed to the sd-RNAs on at least three of Day 11, Day 14, Day 17, and/or Day 21 at an sd-RNA concentration of about 1.5 µM to about 2.5 µM. In some variant embodiments, the TILs are exposed to the sd-RNAs on all of Day 11, Day 14, Day 17, and Day 21 at an sd-RNA concentration of about 1.5 µM to about 2.5 µM. In some variant embodiments, the sd-RNA is added along with a media change at an sd-RNA concentration of about 1.5 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of 2 µM. In some variant embodiments, the TILs are exposed to the sd-RNAs on at least three of Day 11, Day 14, Day 17, and/or Day 21 at an sd-RNA concentration of about 2 µM. In some variant embodiments, the TILs are exposed to the sd-RNAs on all of Day 11, Day 14, Day 17, and Day 21 at an sd-RNA concentration of about 2 µM. In some variant embodiments, the sd-RNA is added along with a media change at an sd-RNA concentration of about 2 µM. In some embodiments, the sd-RNA targets PD-1.

In some embodiments, the sd-RNA added at Day 11 is added in media comprising sd-RNA, IL-2, OKT3 and APCs (including, for example, PBMCs). In some embodiments, the sd-RNA added at Day 14 is added in media comprising sd-RNA and optionally includes one or more of IL-2, OKT3 and APCs (including, for example, PBMCs). In some embodiments, the sd-RNA added at Day 17 is added in media comprising sd-RNA and optionally includes one or more of IL-2, OKT3 and APCs (including, for example, PBMCs). In some embodiments, the sd-RNA added at Day 21 is added in media comprising sd-RNA and optionally includes one or more of IL-2, OKT3 and APCs (including, for example, PBMCs). In some embodiments, the sd-RNA added at Day 14 is added in media comprising sd-RNA and IL-2. In some embodiments, the sd-RNA added at Day 17 is added in media comprising sd-RNA and IL-2. In some embodiments, the sd-RNA added at Day 21 is added in media comprising sd-RNA and IL-2. In some embodiments, more sd-RNA is added at Day 14. In some embodiments, more sd-RNA added at Day 17. In some embodiments, more sd-RNA added at Day 21. In some embodiments, the sd-RNA is added at the same concentration at Day 11, Day 14, Day 17, and Day 21. In some embodiments, the sd-RNA is added at a different concentration at Day 11, Day 14, Day 17 and/or Day 21. In some embodiments, the sd-RNA targets PD-1.

Example 26: Variant Embodiments of Example 23

According the methods discussed in Example 23, methods of expanding TILs in combination with transiently altering protein expression are described. This example provides further varied embodiments in line with the methods described in Example 23.

In some embodiments of the above described method, a method for treating a subject with cancer is provided and such a method comprises administering expanded tumor infiltrating lymphocytes (TILs) comprising:
(a) obtaining a first population of TILs from a tumor resected from a subject by processing a tumor sample obtained from the patient into multiple tumor fragments;
(b) adding the tumor fragments into a closed system;
(c) performing a first expansion by culturing the first population of TILs in a cell culture medium comprising IL-2, and optionally OKT-3, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
(d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;
(e) exposing the second and/or third population of TILs to transcription factors (TFs) and/or other molecules capable of transiently altering protein expression between days 11 and 21, wherein the TFs and/or other molecules capable of transiently altering protein expression provide for increased expression of tumor antigens and/or an increase in the number of tumor antigen-specific T cells in the therapeutic population of TILs;
(f) harvesting the therapeutic population of TILs obtained from step (d), wherein the transition from step (d) to step (e) occurs without opening the system; and (g) transferring the harvested TIL population from step (e) to an infusion bag, wherein the transfer from step (e) to (f) occurs without opening the system;

(h) optionally cryopreserving the infusion bag comprising the harvested TIL population from step (f) using a cryopreservation process; and (i) administering a therapeutically effective dosage of the third population of TILs from the infusion bag in step (g) to the patient.

In some variant embodiments, the other molecules capable of transiently altering protein expression comprise sd-RNAs, including for example but not limited to, sd-rxRNAs. In some embodiments, the TILs are exposed to the sd-RNAs on Day 11, Day 14, Day 17, and/or Day 21. In some variant embodiments, the TILs are exposed to the sd-RNAs on at least two of Day 11, Day 14, Day 17, and/or Day 21. In some variant embodiments, the TILs are exposed to the sd-RNAs on at least three of Day 11, Day 14, Day 17, and/or Day 21. In some variant embodiments, the TILs are exposed to the sd-RNAs on all of Day 11, Day 14, Day 17, and Day 21. In some embodiments, the sd-RNA targets PD-1.

In some embodiments, the sd-RNA sequences used in the invention exhibit a 70% reduction in expression of the target gene. In some embodiments, the sd-RNA sequences used in the invention exhibit a 75% reduction in expression of the target gene. In some embodiments, the sd-RNA sequences used in the invention exhibit an 80% reduction in expression of the target gene. In some embodiments, the sd-RNA sequences used in the invention exhibit an 85% reduction in expression of the target gene. In some embodiments, the sd-RNA sequences used in the invention exhibit a 90% reduction in expression of the target gene. In some embodiments, the sd-RNA sequences used in the invention exhibit a 95% reduction in expression of the target gene. In some embodiments, the sd-RNA sequences used in the invention exhibit a 99% reduction in expression of the target gene. In some embodiments, the sd-RNA sequences used in the invention exhibit a reduction in expression of the target gene when delivered at a concentration of about 0.25 µM to about 10 µM, in some embodiments, about 0.25 µM to about 4 µM. In some embodiments, the sd-RNA sequences used in the invention exhibit a reduction in expression of the target gene when delivered at a concentration of about 0.25 µM. In some embodiments, the sd-RNA sequences used in the invention exhibit a reduction in expression of the target gene when delivered at a concentration of about 0.5 µM. In some embodiments, the sd-RNA sequences used in the invention exhibit a reduction in expression of the target gene when delivered at a concentration of about 0.75 µM. In some embodiments, the sd-RNA sequences used in the invention exhibit a reduction in expression of the target gene when delivered at a concentration of about 1.0 µM. In some embodiments, the sd-RNA sequences used in the invention exhibit a reduction in expression of the target gene when delivered at a concentration of about 1.25 µM. In some embodiments, the sd-RNA sequences used in the invention exhibit a reduction in expression of the target gene when delivered at a concentration of about 1.5 µM. In some embodiments, the sd-RNA sequences used in the invention exhibit a reduction in expression of the target gene when delivered at a concentration of about 1.75 µM. In some embodiments, the sd-RNA sequences used in the invention exhibit a reduction in expression of the target gene when delivered at a concentration of about 2.0 µM. In some embodiments, the sd-RNA sequences used in the invention exhibit a reduction in expression of the target gene when delivered at a concentration of about 2.25 µM. In some embodiments, the sd-RNA sequences used in the invention exhibit a reduction in expression of the target gene when delivered at a concentration of about 2.5 µM. In some embodiments, the sd-RNA sequences used in the invention exhibit a reduction in expression of the target gene when delivered at a concentration of about 2.75 µM. In some embodiments, the sd-RNA sequences used in the invention exhibit a reduction in expression of the target gene when delivered at a concentration of about 3.0 µM. In some embodiments, the sd-RNA sequences used in the invention exhibit a reduction in expression of the target gene when delivered at a concentration of about 3.25 µM. In some embodiments, the sd-RNA sequences used in the invention exhibit a reduction in expression of the target gene when delivered at a concentration of about 3.5 µM. In some embodiments, the sd-RNA sequences used in the invention exhibit a reduction in expression of the target gene when delivered at a concentration of about 3.75 µM. In some embodiments, the sd-RNA sequences used in the invention exhibit a reduction in expression of the target gene when delivered at a concentration of about 4.0 µM. In some embodiments, the sd-RNA sequences used in the invention exhibit a reduction in expression of the target gene when delivered at a concentration of about 5.0 µM. In some embodiments, the sd-RNA sequences used in the invention exhibit a reduction in expression of the target gene when delivered at a concentration of about 6.0 µM. In some embodiments, the sd-RNA sequences used in the invention exhibit a reduction in expression of the target gene when delivered at a concentration of about 7.0 µM. In some embodiments, the sd-RNA sequences used in the invention exhibit a reduction in expression of the target gene when delivered at a concentration of about 8.0 µM. In some embodiments, the sd-RNA sequences used in the invention exhibit a reduction in expression of the target gene when delivered at a concentration of about 9.0 µM. In some embodiments, the sd-RNA sequences used in the invention exhibit a reduction in expression of the target gene when delivered at a concentration of about 10.0 µM. In any of the foregoing embodiments, the concentrations specified may be determined with respect to TIL culture media before or after exchange of media.

In some embodiments, the sd-RNA sequences used in the invention exhibit a 70% reduction in expression of PD-1. In some embodiments, the sd-RNA sequences used in the invention exhibit a 75% reduction in expression of PD-1. In some embodiments, the sd-RNA sequences used in the invention exhibit an 80% reduction in expression of PD-1. In some embodiments, the sd-RNA sequences used in the invention exhibit an 85% reduction in expression of PD-1. In some embodiments, the sd-RNA sequences used in the invention exhibit a 90% reduction in expression of PD-1. In some embodiments, the sd-RNA sequences used in the invention exhibit a 95% reduction in expression of PD-1. In some embodiments, the sd-RNA sequences used in the invention exhibit a 99% reduction in expression PD-1. In some embodiments, the sd-RNA sequences used in the invention exhibit a reduction in expression of PD-1 when delivered at a concentration of about 0.25 µM to about 10 µM, in some embodiments, about 0.25 µM to about 4 µM. In some embodiments, the sd-RNA sequences used in the invention exhibit a reduction in expression of PD-1 when delivered at a concentration of about 0.25 µM. In some embodiments, the sd-RNA sequences used in the invention exhibit a reduction in expression of PD-1 when delivered at a concentration of about 0.5 µM. In some embodiments, the sd-RNA sequences used in the invention exhibit a reduction in expression of PD-1 when delivered at a concentration of about 0.75 µM. In some embodiments, the sd-RNA sequences used in the invention exhibit a reduction in expression of PD-1 when delivered at a concentration of about 1.0 µM. In some embodiments, the sd-RNA sequences used in the invention exhibit a reduction in expression of PD-1 when delivered at a concentration of about 1.25 µM. In some embodiments, the sd-RNA sequences used in the invention exhibit a reduction in expression of PD-1 when delivered at a concentration of about 1.5 µM. In some embodiments, the sd-RNA sequences used in the invention exhibit a reduction in expression of PD-1 when delivered at a concentration of about 1.75 µM. In some embodiments, the sd-RNA sequences used in the invention exhibit a reduction in expression of PD-1 when delivered at a concentration of about 2.0 µM. In some embodiments, the sd-RNA sequences used in the invention exhibit a reduction in expression of PD-1 when delivered at a concentration of about 2.25 µM. In some embodiments, the sd-RNA sequences used in the invention exhibit a reduction in expression of PD-1 when delivered at a concentration of about 2.5 µM. In some embodiments, the sd-RNA sequences used in the invention exhibit a reduction in expression of PD-1 when delivered at a concentration of about 2.75 µM. In some embodiments, the sd-RNA sequences used in the invention exhibit a reduction in expression of PD-1 when delivered at a concentration of about 3.0 µM. In some embodiments, the sd-RNA sequences used in the invention exhibit a reduction in expression of PD-1 when delivered at a concentration of about 3.25 µM. In some embodiments, the sd-RNA sequences used in the invention exhibit a reduction in expression of PD-1 when delivered at a concentration of about 3.5 µM. In some embodiments, the sd-RNA sequences used in the invention exhibit a reduction in expression of PD-1 when delivered at a concentration of about 3.75 µM. In some embodiments, the sd-RNA sequences used in the invention exhibit a reduction in expression of PD-1 when delivered at a concentration of about 4.0 µM. In some embodiments, the sd-RNA sequences used in the invention exhibit a reduction in expression of PD-1 when delivered at a concentration of about 5.0 µM. In some embodiments, the sd-RNA sequences used in the invention exhibit a reduction in expression of PD-1 when delivered at a concentration of about 6.0 µM. In some embodiments, the sd-RNA sequences used in the invention exhibit a reduction in expression of PD-1 when delivered at a concentration of about 7.0 µM. In some embodiments, the sd-RNA sequences used in the invention exhibit a reduction in expression of PD-1 when delivered at a concentration of about 8.0 µM. In some embodiments, the sd-RNA sequences used in the invention exhibit a reduction in expression of PD-1 when delivered at a concentration of about 9.0 µM. In some embodiments, the sd-RNA sequences used in the invention exhibit a reduction in expression of PD-1 when delivered at a concentration of about 10.0 µM. In any of the foregoing embodiments, the concentrations specified may be determined with respect to TIL culture media before or after exchange of media.

In some variant embodiments, the TILs are exposed to the sd-RNAs on at least two of Day 11, Day 14, Day 17, and/or Day 21 at an sd-RNA concentration of about 0.75 µM to about 3 µM. In some variant embodiments, the TILs are exposed to the sd-RNAs on at least three of Day 11, Day 14, Day 17, and/or Day 21 at an sd-RNA concentration of about 0.75 µM to about 3 µM. In some variant embodiments, the TILs are exposed to the sd-RNAs on all of Day 11, Day 14, Day 17, and Day 21 at an sd-RNA concentration of about 0.75 µM to about 3 µM. In some variant embodiments, the sd-RNA is added along with a media change at an sd-RNA concentration of about 0.75 µM to about 3 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.0 µM to about 2.5 µM. In some variant embodiments, the TILs are exposed to the sd-RNAs on at least three of Day 11, Day 14, Day 17, and/or Day 21 at an sd-RNA concentration of about 1.0 µM to about 2.5 µM. In some variant embodiments, the TILs are exposed to the sd-RNAs on all of Day 11, Day 14, Day 17, and Day 21 at an sd-RNA concentration of about 1.0 µM to about 2.5 µM. In some variant embodiments, the sd-RNA is added along with a media change at an sd-RNA concentration of about 1.0 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.5 µM to about 2.5 µM. In some variant embodiments, the TILs are exposed to the sd-RNAs on at least three of Day 11, Day 14, Day 17, and/or Day 21 at an sd-RNA concentration of about 1.5 µM to about 2.5 µM. In some variant embodiments, the TILs are exposed to the sd-RNAs on all of Day 11, Day 14, Day 17, and Day 21 at an sd-RNA concentration of about 1.5 µM to about 2.5 µM. In some variant embodiments, the sd-RNA is added along with a media change at an sd-RNA concentration of about 1.5 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of 2 µM. In some variant embodiments, the TILs are exposed to the sd-RNAs on at least three of Day 11, Day 14, Day 17, and/or Day 21 at an sd-RNA concentration of about 2 µM. In some variant embodiments, the TILs are exposed to the sd-RNAs on all of Day 11, Day 14, Day 17, and Day 21 at an sd-RNA concentration of about 2 µM. In some variant embodiments, the sd-RNA is added along with a media change at an sd-RNA concentration of about 2 µM. In some embodiments, the sd-RNA targets PD-1.

In some embodiments, the sd-RNA added at Day 11 is added in media comprising sd-RNA, IL-2, OKT3 and APCs (including, for example, PBMCs). In some embodiments, the sd-RNA added at Day 14 is added in media comprising sd-RNA and optionally includes one or more of IL-2, OKT3 and APCs (including, for example, PBMCs). In some embodiments, the sd-RNA added at Day 17 is added in media comprising sd-RNA and optionally includes one or more of IL-2, OKT3 and APCs (including, for example, PBMCs). In some embodiments, the sd-RNA added at Day 21 is added in media comprising sd-RNA and optionally includes one or more of IL-2, OKT3 and APCs (including, for example, PBMCs). In some embodiments, the sd-RNA added at Day 14 is added in media comprising sd-RNA and IL-2. In some embodiments, the sd-RNA added at Day 17 is added in media comprising sd-RNA and IL-2. In some embodiments, the sd-RNA added at Day 21 is added in media comprising sd-RNA and IL-2. In some embodiments, more sd-RNA is added at Day 14. In some embodiments, more sd-RNA added at Day 17. In some embodiments, more sd-RNA added at Day 21. In some embodiments, the sd-RNA is added at the same concentration at Day 11, Day 14, Day 17, and Day 21. In some embodiments, the sd-RNA is added at a different concentration at Day 11, Day 14, Day 17 and/or Day 21. In some embodiments, the sd-RNA targets PD-1.

Example 27: Variant Embodiments of Example 23

According the methods discussed in Example 23, methods of expanding TILs in combination with transiently altering protein expression are described. This example provides further varied embodiments in line with the methods described in Example 23.

In some embodiments of the above described method, a population of expanded TILs for use in the treatment of a subject with cancer can be provided, wherein the population of expanded TILs is a third population of TILs obtainable by a method comprising:
  (a) obtaining a first population of TILs from a tumor resected from a subject by processing a tumor sample obtained from the patient into multiple tumor fragments;
  (b) adding the tumor fragments into a closed system;
  (c) performing a first expansion by culturing the first population of TILs in a cell culture medium comprising IL-2, and optionally OKT-3, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
  (d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;
  (e) exposing the second and/or third population of TILs to transcription factors (TFs) and/or other molecules capable of transiently altering protein expression between days 11 and 21, wherein the TFs and/or other molecules capable of transiently altering protein expression provide for increased expression of tumor antigens and/or an increase in the number of tumor antigen-specific T cells in the therapeutic population of TILs;
  (f) harvesting the therapeutic population of TILs obtained from step (d), wherein the transition from step (e) to step (f) occurs without opening the system; and
  (g) transferring the harvested TIL population from step (e) to an infusion bag, wherein the transfer from step (f) to (g) occurs without opening the system; and
  (h) optionally cryopreserving the infusion bag comprising the harvested TIL population from step (f) using a cryopreservation process.

In some variant embodiments, the other molecules capable of transiently altering protein expression comprise sd-RNAs, including for example but not limited to, sd-rxRNAs. In some embodiments, the TILs are exposed to the sd-RNAs on Day 11, Day 14, Day 17, and/or Day 21. In some variant embodiments, the TILs are exposed to the sd-RNAs on at least two of Day 11, Day 14, Day 17, and/or Day 21. In some variant embodiments, the TILs are exposed to the sd-RNAs on at least three of Day 11, Day 14, Day 17, and/or Day 21. In some variant embodiments, the TILs are exposed to the sd-RNAs on all of Day 11, Day 14, Day 17, and Day 21. In some embodiments, the sd-RNA targets PD-1.

In some embodiments, the sd-RNA sequences used in the invention exhibit a 70% reduction in expression of the target gene. In some embodiments, the sd-RNA sequences used in the invention exhibit a 75% reduction in expression of the target gene. In some embodiments, the sd-RNA sequences used in the invention exhibit an 80% reduction in expression of the target gene. In some embodiments, the sd-RNA sequences used in the invention exhibit an 85% reduction in expression of the target gene. In some embodiments, the sd-RNA sequences used in the invention exhibit a 90% reduction in expression of the target gene. In some embodiments, the sd-RNA sequences used in the invention exhibit a 95% reduction in expression of the target gene. In some embodiments, the sd-RNA sequences used in the invention exhibit a 99% reduction in expression of the target gene. In some embodiments, the sd-RNA sequences used in the invention exhibit a reduction in expression of the target gene when delivered at a concentration of about 0.25 µM to about 10 µM, in some embodiments, about 0.25 µM to about 4 µM. In some embodiments, the sd-RNA sequences used in the invention exhibit a reduction in expression of the target gene when delivered at a concentration of about 0.25 µM. In some embodiments, the sd-RNA sequences used in the invention exhibit a reduction in expression of the target gene when delivered at a concentration of about 0.5 µM. In some embodiments, the sd-RNA sequences used in the invention exhibit a reduction in expression of the target gene when delivered at a concentration of about 0.75 µM. In some embodiments, the sd-RNA sequences used in the invention exhibit a reduction in expression of the target gene when delivered at a concentration of about 1.0 µM. In some embodiments, the sd-RNA sequences used in the invention exhibit a reduction in expression of the target gene when delivered at a concentration of about 1.25 µM. In some embodiments, the sd-RNA sequences used in the invention exhibit a reduction in expression of the target gene when delivered at a concentration of about 1.5 µM. In some embodiments, the sd-RNA sequences used in the invention exhibit a reduction in expression of the target gene when delivered at a concentration of about 1.75 µM. In some embodiments, the sd-RNA sequences used in the invention exhibit a reduction in expression of the target gene when delivered at a concentration of about 2.0 µM. In some embodiments, the sd-RNA sequences used in the invention exhibit a reduction in expression of the target gene when delivered at a concentration of about 2.25 µM. In some embodiments, the sd-RNA sequences used in the invention exhibit a reduction in expression of the target gene when delivered at a concentration of about 2.5 µM. In some embodiments, the sd-RNA sequences used in the invention exhibit a reduction in expression of the target gene when delivered at a concentration of about 2.75 µM. In some embodiments, the sd-RNA sequences used in the invention exhibit a reduction in expression of the target gene when delivered at a concentration of about 3.0 µM. In some embodiments, the sd-RNA sequences used in the invention exhibit a reduction in expression of the target gene when delivered at a concentration of about 3.25 µM. In some embodiments, the sd-RNA sequences used in the invention exhibit a reduction in expression of the target gene when delivered at a concentration of about 3.5 µM. In some embodiments, the sd-RNA sequences used in the invention exhibit a reduction in expression of the target gene when delivered at a concentration of about 3.75 µM. In some embodiments, the sd-RNA sequences used in the invention exhibit a reduction in expression of the target gene when delivered at a concentration of about 4.0 µM. In some embodiments, the sd-RNA sequences used in the invention exhibit a reduction in expression of the target gene when delivered at a concentration of about 5.0 µM. In some embodiments, the sd-RNA sequences used in the invention exhibit a reduction in expression of the target gene when delivered at a concentration of about 6.0 µM. In some embodiments, the sd-RNA sequences used in the invention exhibit a reduction in expression of the target gene when delivered at a concentration of about 7.0 µM. In some embodiments, the sd-RNA sequences used in the invention exhibit a reduction in expression of the target gene when delivered at a concentration of about 8.0 µM. In some embodiments, the sd-RNA sequences used in the invention exhibit a reduction in expression of the target gene when delivered at a concentration of about 9.0 µM. In some embodiments, the sd-RNA sequences used in the invention exhibit a reduction in expression of the target gene when delivered at a concentration of about 10.0 µM. In any of the foregoing embodiments, the concentrations specified may be determined with respect to TIL culture media before or after exchange of media.

In some embodiments, the sd-RNA sequences used in the invention exhibit a 70% reduction in expression of PD-1. In some embodiments, the sd-RNA sequences used in the invention exhibit a 75% reduction in expression of PD-1. In some embodiments, the sd-RNA sequences used in the invention exhibit an 80% reduction in expression of PD-1. In some embodiments, the sd-RNA sequences used in the invention exhibit an 85% reduction in expression of PD-1. In some embodiments, the sd-RNA sequences used in the invention exhibit a 90% reduction in expression of PD-1. In some embodiments, the sd-RNA sequences used in the invention exhibit a 95% reduction in expression of PD-1. In some embodiments, the sd-RNA sequences used in the invention exhibit a 99% reduction in expression PD-1. In some embodiments, the sd-RNA sequences used in the invention exhibit a reduction in expression of PD-1 when delivered at a concentration of about 0.25 µM to about 10 µM, in some embodiments, about 0.25 µM to about 4 µM. In some embodiments, the sd-RNA sequences used in the invention exhibit a reduction in expression of PD-1 when delivered at a concentration of about 0.25 µM. In some embodiments, the sd-RNA sequences used in the invention exhibit a reduction in expression of PD-1 when delivered at a concentration of about 0.5 µM. In some embodiments, the sd-RNA sequences used in the invention exhibit a reduction in expression of PD-1 when delivered at a concentration of about 0.75 µM. In some embodiments, the sd-RNA sequences used in the invention exhibit a reduction in expression of PD-1 when delivered at a concentration of about 1.0 µM. In some embodiments, the sd-RNA sequences used in the invention exhibit a reduction in expression of PD-1 when delivered at a concentration of about 1.25 µM. In some embodiments, the sd-RNA sequences used in the invention exhibit a reduction in expression of PD-1 when delivered at a concentration of about 1.5 µM. In some embodiments, the sd-RNA sequences used in the invention exhibit a reduction in expression of PD-1 when delivered at a concentration of about 1.75 µM. In some embodiments, the sd-RNA sequences used in the invention exhibit a reduction in expression of PD-1 when delivered at a concentration of about 2.0 µM. In some embodiments, the sd-RNA sequences used in the invention exhibit a reduction in expression of PD-1 when delivered at a concentration of about 2.25 µM. In some embodiments, the sd-RNA sequences used in the invention exhibit a reduction in expression of PD-1 when delivered at a concentration of about 2.5 µM. In some embodiments, the sd-RNA sequences used in the invention exhibit a reduction in expression of PD-1 when delivered at a concentration of about 2.75 µM. In some embodiments, the sd-RNA sequences used in the invention exhibit a reduction in expression of PD-1 when delivered at a concentration of about 3.0 µM. In some embodiments, the sd-RNA sequences used in the invention exhibit a reduction in expression of PD-1 when delivered at a concentration of about 3.25 µM. In some embodiments, the sd-RNA sequences used in the invention exhibit a reduction in expression of PD-1 when delivered at a concentration of about 3.5 µM. In some embodiments, the sd-RNA sequences used in the invention exhibit a reduction in expression of PD-1 when delivered at a concentration of about 3.75 µM. In some embodiments, the sd-RNA sequences used in the invention exhibit a reduction in expression of PD-1 when delivered at a concentration of about 4.0 µM. In some embodiments, the sd-RNA sequences used in the invention exhibit a reduction in expression of PD-1 when delivered at a concentration of about 5.0 µM. In some embodiments, the sd-RNA sequences used in the invention exhibit a reduction in expression of PD-1 when delivered at a concentration of about 6.0 µM. In some embodiments, the sd-RNA sequences used in the invention exhibit a reduction in expression of PD-1 when delivered at a concentration of about 7.0 µM. In some embodiments, the sd-RNA sequences used in the invention exhibit a reduction in expression of PD-1 when delivered at a concentration of about 8.0 µM. In some embodiments, the sd-RNA sequences used in the invention exhibit a reduction in expression of PD-1 when delivered at a concentration of about 9.0 µM. In some embodiments, the sd-RNA sequences used in the invention exhibit a reduction in expression of PD-1 when delivered at a concentration of about 10.0 µM. In any of the foregoing embodiments, the concentrations specified may be determined with respect to TIL culture media before or after exchange of media.

In some variant embodiments, the TILs are exposed to the sd-RNAs on at least two of Day 11, Day 14, Day 17, and/or Day 21 at an sd-RNA concentration of about 0.75 µM to about 3 µM. In some variant embodiments, the TILs are exposed to the sd-RNAs on at least three of Day 11, Day 14, Day 17, and/or Day 21 at an sd-RNA concentration of about 0.75 µM to about 3 µM. In some variant embodiments, the TILs are exposed to the sd-RNAs on all of Day 11, Day 14, Day 17, and Day 21 at an sd-RNA concentration of about 0.75 µM to about 3 µM. In some variant embodiments, the sd-RNA is added along with a media change at an sd-RNA concentration of about 0.75 µM to about 3 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.0 µM to about 2.5 µM. In some variant embodiments, the TILs are exposed to the sd-RNAs on at least three of Day 11, Day 14, Day 17, and/or Day 21 at an sd-RNA concentration of about 1.0 µM to about 2.5 µM. In some variant embodiments, the TILs are exposed to the sd-RNAs on all of Day 11, Day 14, Day 17, and Day 21 at an sd-RNA concentration of about 1.0 µM to about 2.5 µM. In some variant embodiments, the sd-RNA is added along with a media change at an sd-RNA concentration of about 1.0 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.5 µM to about 2.5 µM. In some variant embodiments, the TILs are exposed to the sd-RNAs on at least three of Day 11, Day 14, Day 17, and/or Day 21 at an sd-RNA concentration of about 1.5 µM to about 2.5 µM. In some variant embodiments, the TILs are exposed to the sd-RNAs on all of Day 11, Day 14, Day 17, and Day 21 at an sd-RNA concentration of about 1.5 µM to about 2.5 µM. In some variant embodiments, the sd-RNA is added along with a media change at an sd-RNA concentration of about 1.5 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of 2 µM. In some variant embodiments, the TILs are exposed to the sd-RNAs on at least three of Day 11, Day 14, Day 17, and/or Day 21 at an sd-RNA concentration of about 2 µM. In some variant embodiments, the TILs are exposed to the sd-RNAs on all of Day 11, Day 14, Day 17, and Day 21 at an sd-RNA concentration of about 2 µM. In some variant embodiments, the sd-RNA is added along with a media change at an sd-RNA concentration of about 2 µM. In some embodiments, the sd-RNA targets PD-1.

In some embodiments, the sd-RNA added at Day 11 is added in media comprising sd-RNA, IL-2, OKT3 and APCs (including, for example, PBMCs). In some embodiments, the sd-RNA added at Day 14 is added in media comprising sd-RNA and optionally includes one or more of IL-2, OKT3 and APCs (including, for example, PBMCs). In some embodiments, the sd-RNA added at Day 17 is added in media comprising sd-RNA and optionally includes one or more of IL-2, OKT3 and APCs (including, for example, PBMCs). In some embodiments, the sd-RNA added at Day 21 is added in media comprising sd-RNA and optionally includes one or more of IL-2, OKT3 and APCs (including, for example, PBMCs). In some embodiments, the sd-RNA added at Day 14 is added in media comprising sd-RNA and IL-2. In some embodiments, the sd-RNA added at Day 17 is added in media comprising sd-RNA and IL-2. In some embodiments, the sd-RNA added at Day 21 is added in media comprising sd-RNA and IL-2. In some embodiments, more sd-RNA is added at Day 14. In some embodiments, more sd-RNA added at Day 17. In some embodiments, more sd-RNA added at Day 21. In some embodiments, the sd-RNA is added at the same concentration at Day 11, Day 14, Day 17, and Day 21. In some embodiments, the sd-RNA is added at a different concentration at Day 11, Day 14, Day 17 and/or Day 21. In some embodiments, the sd-RNA targets PD-1.

Example 28: Variant Embodiments of Example 23

According the methods discussed in Example 23, methods of expanding TILs in combination with transiently altering protein expression are described. This example provides further varied embodiments in line with the methods described in Example 23.

In some embodiments of the above described method, a method for expanding tumor infiltrating lymphocytes (TILs) into a therapeutic population of TILs is provided which comprises:

(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising a 4-1BB agonist antibody for about 2 to 5 days;
(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
(e) resting the second population of TILs for about 1 day;
(f) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transitions from step (c) to step (f) occur without opening the system;
(g) contacting the second population of TILs during any of steps (d), (e), and/or (f), including between days 11 and 21, with at least one sd-RNA, wherein the sd-RNA is added at a concentration of 0.1 µM sd-RNA, 0.5 µM sd-RNA, 0.75 µM sd-RNA, 1 µM sd-RNA, 1.25 µM sd-RNA, 1.5 µM sd-RNA, 2 µM sd-RNA, 5 µM sd-RNA, or 10 µM sd-RNA, and wherein the sd-RNA is for inhibiting the expression of a molecule selected from the group consisting of PD-1, LAG-3, TIM-3, CISH, and CBLB, and combinations thereof;
(h) optionally performing a sterile electroporation step on the second population of TILs, wherein the sterile electroporation step mediates the transfer of the at least one sd-RNA;
(i) harvesting the therapeutic population of TILs obtained from steps (g) or (h) to provide a harvested TIL population, wherein the transitions from step (g) to step (i) occur without opening the system, wherein the harvested population of TILs is a therapeutic population of TILs; and
(j) transferring the harvested TIL population from step (i) to an infusion bag, wherein the transfer from step (i) to (j) occurs without opening the system.

In some variant embodiments, the other molecules capable of transiently altering protein expression comprise sd-RNAs, including for example but not limited to, sd-rxRNAs. In some embodiments, the TILs are exposed to the sd-RNAs on Day 11, Day 14, Day 17, and/or Day 21. In some variant embodiments, the TILs are exposed to the sd-RNAs on at least two of Day 11, Day 14, Day 17, and/or Day 21. In some variant embodiments, the TILs are exposed to the sd-RNAs on at least three of Day 11, Day 14, Day 17, and/or Day 21. In some variant embodiments, the TILs are exposed to the sd-RNAs on all of Day 11, Day 14, Day 17, and Day 21. In some embodiments, the sd-RNA targets PD-1.

In some embodiments, the sd-RNA sequences used in the invention exhibit a 70% reduction in expression of the target gene. In some embodiments, the sd-RNA sequences used in the invention exhibit a 75% reduction in expression of the target gene. In some embodiments, the sd-RNA sequences used in the invention exhibit an 80% reduction in expression of the target gene. In some embodiments, the sd-RNA sequences used in the invention exhibit an 85% reduction in expression of the target gene. In some embodiments, the sd-RNA sequences used in the invention exhibit a 90% reduction in expression of the target gene. In some embodiments, the sd-RNA sequences used in the invention exhibit a 95% reduction in expression of the target gene. In some embodiments, the sd-RNA sequences used in the invention exhibit a 99% reduction in expression of the target gene. In some embodiments, the sd-RNA sequences used in the invention exhibit a reduction in expression of the target gene when delivered at a concentration of about 0.25 μM to about 10 μM, in some embodiments, about 0.25 μM to about 4 μM. In some embodiments, the sd-RNA sequences used in the invention exhibit a reduction in expression of the target gene when delivered at a concentration of about 0.25 μM. In some embodiments, the sd-RNA sequences used in the invention exhibit a reduction in expression of the target gene when delivered at a concentration of about 0.5 μM. In some embodiments, the sd-RNA sequences used in the invention exhibit a reduction in expression of the target gene when delivered at a concentration of about 0.75 μM. In some embodiments, the sd-RNA sequences used in the invention exhibit a reduction in expression of the target gene when delivered at a concentration of about 1.0 μM. In some embodiments, the sd-RNA sequences used in the invention exhibit a reduction in expression of the target gene when delivered at a concentration of about 1.25 μM. In some embodiments, the sd-RNA sequences used in the invention exhibit a reduction in expression of the target gene when delivered at a concentration of about 1.5 μM. In some embodiments, the sd-RNA sequences used in the invention exhibit a reduction in expression of the target gene when delivered at a concentration of about 1.75 μM. In some embodiments, the sd-RNA sequences used in the invention exhibit a reduction in expression of the target gene when delivered at a concentration of about 2.0 μM. In some embodiments, the sd-RNA sequences used in the invention exhibit a reduction in expression of the target gene when delivered at a concentration of about 2.25 μM. In some embodiments, the sd-RNA sequences used in the invention exhibit a reduction in expression of the target gene when delivered at a concentration of about 2.5 μM. In some embodiments, the sd-RNA sequences used in the invention exhibit a reduction in expression of the target gene when delivered at a concentration of about 2.75 μM. In some embodiments, the sd-RNA sequences used in the invention exhibit a reduction in expression of the target gene when delivered at a concentration of about 3.0 μM. In some embodiments, the sd-RNA sequences used in the invention exhibit a reduction in expression of the target gene when delivered at a concentration of about 3.25 μM. In some embodiments, the sd-RNA sequences used in the invention exhibit a reduction in expression of the target gene when delivered at a concentration of about 3.5 μM. In some embodiments, the sd-RNA sequences used in the invention exhibit a reduction in expression of the target gene when delivered at a concentration of about 3.75 μM. In some embodiments, the sd-RNA sequences used in the invention exhibit a reduction in expression of the target gene when delivered at a concentration of about 4.0 μM. In some embodiments, the sd-RNA sequences used in the invention exhibit a reduction in expression of the target gene when delivered at a concentration of about 5.0 μM. In some embodiments, the sd-RNA sequences used in the invention exhibit a reduction in expression of the target gene when delivered at a concentration of about 6.0 μM. In some embodiments, the sd-RNA sequences used in the invention exhibit a reduction in expression of the target gene when delivered at a concentration of about 7.0 μM. In some embodiments, the sd-RNA sequences used in the invention exhibit a reduction in expression of the target gene when delivered at a concentration of about 8.0 μM. In some embodiments, the sd-RNA sequences used in the invention exhibit a reduction in expression of the target gene when delivered at a concentration of about 9.0 μM. In some embodiments, the sd-RNA sequences used in the invention exhibit a reduction in expression of the target gene when delivered at a concentration of about 10.0 μM. In any of the foregoing embodiments, the concentrations specified may be determined with respect to TIL culture media before or after exchange of media.

In some embodiments, the sd-RNA sequences used in the invention exhibit a 70% reduction in expression of PD-1. In some embodiments, the sd-RNA sequences used in the invention exhibit a 75% reduction in expression of PD-1. In some embodiments, the sd-RNA sequences used in the invention exhibit an 80% reduction in expression of PD-1. In some embodiments, the sd-RNA sequences used in the invention exhibit an 85% reduction in expression of PD-1. In some embodiments, the sd-RNA sequences used in the invention exhibit a 90% reduction in expression of PD-1. In some embodiments, the sd-RNA sequences used in the invention exhibit a 95% reduction in expression of PD-1. In some embodiments, the sd-RNA sequences used in the invention exhibit a 99% reduction in expression PD-1. In some embodiments, the sd-RNA sequences used in the invention exhibit a reduction in expression of PD-1 when delivered at a concentration of about 0.25 μM to about 10 μM, in some embodiments, about 0.25 μM to about 4 μM. In some embodiments, the sd-RNA sequences used in the invention exhibit a reduction in expression of PD-1 when delivered at a concentration of about 0.25 μM. In some embodiments, the sd-RNA sequences used in the invention exhibit a reduction in expression of PD-1 when delivered at a concentration of about 0.5 μM. In some embodiments, the sd-RNA sequences used in the invention exhibit a reduction in expression of PD-1 when delivered at a concentration of about 0.75 μM. In some embodiments, the sd-RNA sequences used in the invention exhibit a reduction in expression of PD-1 when delivered at a concentration of about 1.0 μM. In some embodiments, the sd-RNA sequences used in the invention exhibit a reduction in expression of PD-1 when delivered at a concentration of about 1.25 μM. In some embodiments, the sd-RNA sequences used in the invention exhibit a reduction in expression of PD-1 when delivered at a concentration of about 1.5 μM. In some embodiments, the sd-RNA sequences used in the invention exhibit a reduction in expression of PD-1 when delivered at a concentration of about 1.75 μM. In some embodiments, the sd-RNA sequences used in the invention exhibit a reduction in expression of PD-1 when delivered at a concentration of about 2.0 μM. In some embodiments, the sd-RNA sequences used in the invention exhibit a reduction in expression of PD-1 when delivered at a concentration of about 2.25 μM. In some embodiments, the sd-RNA sequences used in the invention exhibit a reduction in expression of PD-1 when delivered at a concentration of about 2.5 μM. In some embodiments, the sd-RNA sequences used in the invention exhibit a reduction in expression of PD-1 when delivered at a concentration of about 2.75 µM. In some embodiments, the sd-RNA sequences used in the invention exhibit a reduction in expression of PD-1 when delivered at a concentration of about 3.0 µM. In some embodiments, the sd-RNA sequences used in the invention exhibit a reduction in expression of PD-1 when delivered at a concentration of about 3.25 µM. In some embodiments, the sd-RNA sequences used in the invention exhibit a reduction in expression of PD-1 when delivered at a concentration of about 3.5 µM. In some embodiments, the sd-RNA sequences used in the invention exhibit a reduction in expression of PD-1 when delivered at a concentration of about 3.75 µM. In some embodiments, the sd-RNA sequences used in the invention exhibit a reduction in expression of PD-1 when delivered at a concentration of about 4.0 µM. In some embodiments, the sd-RNA sequences used in the invention exhibit a reduction in expression of PD-1 when delivered at a concentration of about 5.0 µM. In some embodiments, the sd-RNA sequences used in the invention exhibit a reduction in expression of PD-1 when delivered at a concentration of about 6.0 µM. In some embodiments, the sd-RNA sequences used in the invention exhibit a reduction in expression of PD-1 when delivered at a concentration of about 7.0 µM. In some embodiments, the sd-RNA sequences used in the invention exhibit a reduction in expression of PD-1 when delivered at a concentration of about 8.0 µM. In some embodiments, the sd-RNA sequences used in the invention exhibit a reduction in expression of PD-1 when delivered at a concentration of about 9.0 µM. In some embodiments, the sd-RNA sequences used in the invention exhibit a reduction in expression of PD-1 when delivered at a concentration of about 10.0 µM. In any of the foregoing embodiments, the concentrations specified may be determined with respect to TIL culture media before or after exchange of media.

In some variant embodiments, the TILs are exposed to the sd-RNAs on at least two of Day 11, Day 14, Day 17, and/or Day 21 at an sd-RNA concentration of about 0.75 µM to about 3 µM. In some variant embodiments, the TILs are exposed to the sd-RNAs on at least three of Day 11, Day 14, Day 17, and/or Day 21 at an sd-RNA concentration of about 0.75 µM to about 3 µM. In some variant embodiments, the TILs are exposed to the sd-RNAs on all of Day 11, Day 14, Day 17, and Day 21 at an sd-RNA concentration of about 0.75 µM to about 3 µM. In some variant embodiments, the sd-RNA is added along with a media change at an sd-RNA concentration of about 0.75 µM to about 3 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.0 µM to about 2.5 µM. In some variant embodiments, the TILs are exposed to the sd-RNAs on at least three of Day 11, Day 14, Day 17, and/or Day 21 at an sd-RNA concentration of about 1.0 µM to about 2.5 µM. In some variant embodiments, the TILs are exposed to the sd-RNAs on all of Day 11, Day 14, Day 17, and Day 21 at an sd-RNA concentration of about 1.0 µM to about 2.5 µM. In some variant embodiments, the sd-RNA is added along with a media change at an sd-RNA concentration of about 1.0 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.5 µM to about 2.5 µM. In some variant embodiments, the TILs are exposed to the sd-RNAs on at least three of Day 11, Day 14, Day 17, and/or Day 21 at an sd-RNA concentration of about 1.5 µM to about 2.5 µM. In some variant embodiments, the TILs are exposed to the sd-RNAs on all of Day 11, Day 14, Day 17, and Day 21 at an sd-RNA concentration of about 1.5 µM to about 2.5 µM. In some variant embodiments, the sd-RNA is added along with a media change at an sd-RNA concentration of about 1.5 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of 2 µM. In some variant embodiments, the TILs are exposed to the sd-RNAs on at least three of Day 11, Day 14, Day 17, and/or Day 21 at an sd-RNA concentration of about 2 µM. In some variant embodiments, the TILs are exposed to the sd-RNAs on all of Day 11, Day 14, Day 17, and Day 21 at an sd-RNA concentration of about 2 µM. In some variant embodiments, the sd-RNA is added along with a media change at an sd-RNA concentration of about 2 µM. In some embodiments, the sd-RNA targets PD-1.

In some embodiments, the sd-RNA added at Day 11 is added in media comprising sd-RNA, IL-2, OKT3 and APCs (including, for example, PBMCs). In some embodiments, the sd-RNA added at Day 14 is added in media comprising sd-RNA and optionally includes one or more of IL-2, OKT3 and APCs (including, for example, PBMCs). In some embodiments, the sd-RNA added at Day 17 is added in media comprising sd-RNA and optionally includes one or more of IL-2, OKT3 and APCs (including, for example, PBMCs). In some embodiments, the sd-RNA added at Day 21 is added in media comprising sd-RNA and optionally includes one or more of IL-2, OKT3 and APCs (including, for example, PBMCs). In some embodiments, the sd-RNA added at Day 14 is added in media comprising sd-RNA and IL-2. In some embodiments, the sd-RNA added at Day 17 is added in media comprising sd-RNA and IL-2. In some embodiments, the sd-RNA added at Day 21 is added in media comprising sd-RNA and IL-2. In some embodiments, more sd-RNA is added at Day 14. In some embodiments, more sd-RNA added at Day 17. In some embodiments, more sd-RNA added at Day 21. In some embodiments, the sd-RNA is added at the same concentration at Day 11, Day 14, Day 17, and Day 21. In some embodiments, the sd-RNA is added at a different concentration at Day 11, Day 14, Day 17 and/or Day 21. In some embodiments, the sd-RNA targets PD-1.

Example 29: Variant Embodiments of Example 23

According the methods discussed in Example 23, methods of expanding TILs in combination with transiently altering protein expression are described. This example provides further varied embodiments in line with the methods described in Example 23.

In some embodiments of the above described method, a method for expanding tumor infiltrating lymphocytes (TILs) into a therapeutic population of TILs is provided which comprises:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising a 4-1BB agonist antibody for about 2 to 5 days;

(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;

(e) resting the second population of TILs for about 1 day;

(f) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transitions from step (c) to step (f) occur without opening the system;

(g) contacting the second population of TILs during any of steps (d), (e), and/or (f), including between days 11 and 21, with at least one sd-RNA, wherein the sd-RNA is added at a concentration of 2 µM sd-RNA and wherein the sd-RNA is for inhibiting the expression of a molecule selected from the group consisting of PD-1, LAG-3, TIM-3, CISH, and CBLB, and combinations thereof;

(h) optionally performing a sterile electroporation step on the second population of TILs, wherein the sterile electroporation step mediates the transfer of the at least one sd-RNA;

(i) harvesting the therapeutic population of TILs obtained from steps (g) or (h) to provide a harvested TIL population, wherein the transitions from step (g) to step (i) occur without opening the system, wherein the harvested population of TILs is a therapeutic population of TILs; and (j) transferring the harvested TIL population from step (i) to an infusion bag, wherein the transfer from step (i) to (j) occurs without opening the system.

In some variant embodiments, the other molecules capable of transiently altering protein expression comprise sd-RNAs, including for example but not limited to, sd-rxRNAs. In some embodiments, the TILs are exposed to the sd-RNAs on Day 11, Day 14, Day 17, and/or Day 21. In some variant embodiments, the TILs are exposed to the sd-RNAs on at least two of Day 11, Day 14, Day 17, and/or Day 21. In some variant embodiments, the TILs are exposed to the sd-RNAs on at least three of Day 11, Day 14, Day 17, and/or Day 21. In some variant embodiments, the TILs are exposed to the sd-RNAs on all of Day 11, Day 14, Day 17, and Day 21. In some embodiments, the sd-RNA targets PD-1.

In some embodiments, the sd-RNA sequences used in the invention exhibit a 70% reduction in expression of the target gene. In some embodiments, the sd-RNA sequences used in the invention exhibit a 75% reduction in expression of the target gene. In some embodiments, the sd-RNA sequences used in the invention exhibit an 80% reduction in expression of the target gene. In some embodiments, the sd-RNA sequences used in the invention exhibit an 85% reduction in expression of the target gene. In some embodiments, the sd-RNA sequences used in the invention exhibit a 90% reduction in expression of the target gene. In some embodiments, the sd-RNA sequences used in the invention exhibit a 95% reduction in expression of the target gene. In some embodiments, the sd-RNA sequences used in the invention exhibit a 99% reduction in expression of the target gene. In some embodiments, the sd-RNA sequences used in the invention exhibit a reduction in expression of the target gene when delivered at a concentration of about 2.0 µM. In any of the foregoing embodiments, the concentrations specified may be determined with respect to TIL culture media before or after exchange of media.

In some embodiments, the sd-RNA sequences used in the invention exhibit a 70% reduction in expression of PD-1. In some embodiments, the sd-RNA sequences used in the invention exhibit a 75% reduction in expression of PD-1. In some embodiments, the sd-RNA sequences used in the invention exhibit an 80% reduction in expression of PD-1. In some embodiments, the sd-RNA sequences used in the invention exhibit an 85% reduction in expression of PD-1. In some embodiments, the sd-RNA sequences used in the invention exhibit a 90% reduction in expression of PD-1. In some embodiments, the sd-RNA sequences used in the invention exhibit a 95% reduction in expression of PD-1. In some embodiments, the sd-RNA sequences used in the invention exhibit a 99% reduction in expression PD-1. In some embodiments, the sd-RNA sequences used in the invention exhibit a reduction in expression of PD-1 when delivered at a concentration of about 2.0 µM. In any of the foregoing embodiments, the concentrations specified may be determined with respect to TIL culture media before or after exchange of media.

In some variant embodiments, the TILs are exposed to the sd-RNAs on at least two of Day 11, Day 14, Day 17, and/or Day 21 at an sd-RNA concentration of about 0.75 µM to about 3 µM. In some variant embodiments, the TILs are exposed to the sd-RNAs on at least three of Day 11, Day 14, Day 17, and/or Day 21 at an sd-RNA concentration of about 0.75 µM to about 3 µM. In some variant embodiments, the TILs are exposed to the sd-RNAs on all of Day 11, Day 14, Day 17, and Day 21 at an sd-RNA concentration of about 2 µM. In some variant embodiments, the sd-RNA is added along with a media change at an sd-RNA concentration of about about 2 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.0 µM to about 2.5 µM. In some variant embodiments, the TILs are exposed to the sd-RNAs on at least three of Day 11, Day 14, Day 17, and/or Day 21 at an sd-RNA concentration of about 1.0 µM to about 2.5 µM. In some variant embodiments, the TILs are exposed to the sd-RNAs on all of Day 11, Day 14, Day 17, and Day 21 at an sd-RNA concentration of about 1.0 µM to about 2.5 µM. In some variant embodiments, the sd-RNA is added along with a media change at an sd-RNA concentration of about 2.0 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.5 µM to about 2.5 µM. In some variant embodiments, the TILs are exposed to the sd-RNAs on at least three of Day 11, Day 14, Day 17, and/or Day 21 at an sd-RNA concentration of about 1.5 µM to about 2.5 µM. In some variant embodiments, the TILs are exposed to the sd-RNAs on all of Day 11, Day 14, Day 17, and Day 21 at an sd-RNA concentration of about 1.5 µM to about 2.5 µM. In some variant embodiments, the sd-RNA is added along with a media change at an sd-RNA concentration of about 1.75 µM to about 2.25 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of 2 µM. In some variant embodiments, the TILs are exposed to the sd-RNAs on at least three of Day 11, Day 14, Day 17, and/or Day 21 at an sd-RNA concentration of about 2 µM. In some variant embodiments, the TILs are exposed to the sd-RNAs on all of Day 11, Day 14, Day 17, and Day 21 at an sd-RNA concentration of about 2 µM. In some variant embodiments, the sd-RNA is added along with a media change at an sd-RNA concentration of about 2 µM. In some embodiments, the sd-RNA targets PD-1.

In some embodiments, the sd-RNA added at Day 11 is added in media comprising sd-RNA, IL-2, OKT3 and APCs (including, for example, PBMCs). In some embodiments, the sd-RNA added at Day 14 is added in media comprising sd-RNA and optionally includes one or more of IL-2, OKT3 and APCs (including, for example, PBMCs). In some embodiments, the sd-RNA added at Day 17 is added in media comprising sd-RNA and optionally includes one or more of IL-2, OKT3 and APCs (including, for example, PBMCs). In some embodiments, the sd-RNA added at Day 21 is added in media comprising sd-RNA and optionally includes one or more of IL-2, OKT3 and APCs (including, for example, PBMCs). In some embodiments, the sd-RNA added at Day 14 is added in media comprising sd-RNA and IL-2. In some embodiments, the sd-RNA added at Day 17 is added in media comprising sd-RNA and IL-2. In some embodiments, the sd-RNA added at Day 21 is added in media comprising sd-RNA and IL-2. In some embodiments, more sd-RNA is added at Day 14. In some embodiments, more sd-RNA added at Day 17. In some embodiments, more sd-RNA added at Day 21. In some embodiments, the sd-RNA is added at the same concentration at Day 11, Day 14, Day 17, and Day 21. In some embodiments, the sd-RNA is added at a different concentration at Day 11, Day 14, Day 17 and/or Day 21, wherein the concentration of the sd-RNA is added at about 2 µM on at least one day. In some embodiments, the sd-RNA targets PD-1.

Example 30: Variant Embodiments of Example 23

According the methods discussed in Example 23, methods of expanding TILs in combination with transiently altering protein expression are described. This example provides further varied embodiments in line with the methods described in Example 23.

In some embodiments of the above described method, a method for expanding tumor infiltrating lymphocytes (TILs) into a therapeutic population of TILs is provided which comprises:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising a 4-1BB agonist antibody for about 2 to 5 days;
(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
(e) resting the second population of TILs for about 1 day;
(f) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transitions from step (c) to step (f) occur without opening the system;
(g) contacting the second population of TILs during any of steps (d), (e), and/or (f), including between days 11 and 21, with at least one sd-RNA, wherein the sd-RNA is added at a concentration of 0.1 µM sd-RNA, 0.5 µM sd-RNA, 0.75 µM sd-RNA, 1 µM sd-RNA, 1.25 µM sd-RNA, 1.5 µM sd-RNA, 2 µM sd-RNA, 5 µM sd-RNA, or 10 µM sd-RNA, and wherein the sd-RNA is for inhibiting the expression of a molecule selected from the group consisting of PD-1, LAG-3, TIM-3, CISH, and CBLB, and combinations thereof;
(h) optionally performing a sterile electroporation step on the second population of TILs, wherein the sterile electroporation step mediates the transfer of the at least one sd-RNA;
(i) harvesting the therapeutic population of TILs obtained from steps (g) or (h) to provide a harvested TIL population, wherein the transitions from step (g) to step (i) occur without opening the system, wherein the harvested population of TILs is a therapeutic population of TILs;
(j) transferring the harvested TIL population from step (i) to an infusion bag, wherein the transfer from step (i) to (j) occurs without opening the system; and
(k) cryopreserving the harvested TIL population using a dimethylsulfoxide-based cryopreservation medium.

In some variant embodiments, the other molecules capable of transiently altering protein expression comprise sd-RNAs, including for example but not limited to, sd-rxRNAs. In some embodiments, the TILs are exposed to the sd-RNAs on Day 11, Day 14, Day 17, and/or Day 21. In some variant embodiments, the TILs are exposed to the sd-RNAs on at least two of Day 11, Day 14, Day 17, and/or Day 21. In some variant embodiments, the TILs are exposed to the sd-RNAs on at least three of Day 11, Day 14, Day 17, and/or Day 21. In some variant embodiments, the TILs are exposed to the sd-RNAs on all of Day 11, Day 14, Day 17, and Day 21. In some embodiments, the sd-RNA targets PD-1.

In some embodiments, the sd-RNA sequences used in the invention exhibit a 70% reduction in expression of the target gene. In some embodiments, the sd-RNA sequences used in the invention exhibit a 75% reduction in expression of the target gene. In some embodiments, the sd-RNA sequences used in the invention exhibit an 80% reduction in expression of the target gene. In some embodiments, the sd-RNA sequences used in the invention exhibit an 85% reduction in expression of the target gene. In some embodiments, the sd-RNA sequences used in the invention exhibit a 90% reduction in expression of the target gene. In some embodiments, the sd-RNA sequences used in the invention exhibit a 95% reduction in expression of the target gene. In some embodiments, the sd-RNA sequences used in the invention exhibit a 99% reduction in expression of the target gene. In some embodiments, the sd-RNA sequences used in the invention exhibit a reduction in expression of the target gene when delivered at a concentration of about 0.25 μM to about 10 μM, in some embodiments, about 0.25 μM to about 4 μM. In some embodiments, the sd-RNA sequences used in the invention exhibit a reduction in expression of the target gene when delivered at a concentration of about 0.25 μM. In some embodiments, the sd-RNA sequences used in the invention exhibit a reduction in expression of the target gene when delivered at a concentration of about 0.5 μM. In some embodiments, the sd-RNA sequences used in the invention exhibit a reduction in expression of the target gene when delivered at a concentration of about 0.75 μM. In some embodiments, the sd-RNA sequences used in the invention exhibit a reduction in expression of the target gene when delivered at a concentration of about 1.0 μM. In some embodiments, the sd-RNA sequences used in the invention exhibit a reduction in expression of the target gene when delivered at a concentration of about 1.25 μM. In some embodiments, the sd-RNA sequences used in the invention exhibit a reduction in expression of the target gene when delivered at a concentration of about 1.5 μM. In some embodiments, the sd-RNA sequences used in the invention exhibit a reduction in expression of the target gene when delivered at a concentration of about 1.75 μM. In some embodiments, the sd-RNA sequences used in the invention exhibit a reduction in expression of the target gene when delivered at a concentration of about 2.0 μM. In some embodiments, the sd-RNA sequences used in the invention exhibit a reduction in expression of the target gene when delivered at a concentration of about 2.25 μM. In some embodiments, the sd-RNA sequences used in the invention exhibit a reduction in expression of the target gene when delivered at a concentration of about 2.5 μM. In some embodiments, the sd-RNA sequences used in the invention exhibit a reduction in expression of the target gene when delivered at a concentration of about 2.75 μM. In some embodiments, the sd-RNA sequences used in the invention exhibit a reduction in expression of the target gene when delivered at a concentration of about 3.0 μM. In some embodiments, the sd-RNA sequences used in the invention exhibit a reduction in expression of the target gene when delivered at a concentration of about 3.25 μM. In some embodiments, the sd-RNA sequences used in the invention exhibit a reduction in expression of the target gene when delivered at a concentration of about 3.5 μM. In some embodiments, the sd-RNA sequences used in the invention exhibit a reduction in expression of the target gene when delivered at a concentration of about 3.75 μM. In some embodiments, the sd-RNA sequences used in the invention exhibit a reduction in expression of the target gene when delivered at a concentration of about 4.0 μM. In some embodiments, the sd-RNA sequences used in the invention exhibit a reduction in expression of the target gene when delivered at a concentration of about 5.0 μM. In some embodiments, the sd-RNA sequences used in the invention exhibit a reduction in expression of the target gene when delivered at a concentration of about 6.0 μM. In some embodiments, the sd-RNA sequences used in the invention exhibit a reduction in expression of the target gene when delivered at a concentration of about 7.0 μM. In some embodiments, the sd-RNA sequences used in the invention exhibit a reduction in expression of the target gene when delivered at a concentration of about 8.0 μM. In some embodiments, the sd-RNA sequences used in the invention exhibit a reduction in expression of the target gene when delivered at a concentration of about 9.0 μM. In some embodiments, the sd-RNA sequences used in the invention exhibit a reduction in expression of the target gene when delivered at a concentration of about 10.0 μM. In any of the foregoing embodiments, the concentrations specified may be determined with respect to TIL culture media before or after exchange of media.

In some embodiments, the sd-RNA sequences used in the invention exhibit a 70% reduction in expression of PD-1. In some embodiments, the sd-RNA sequences used in the invention exhibit a 75% reduction in expression of PD-1. In some embodiments, the sd-RNA sequences used in the invention exhibit an 80% reduction in expression of PD-1. In some embodiments, the sd-RNA sequences used in the invention exhibit an 85% reduction in expression of PD-1. In some embodiments, the sd-RNA sequences used in the invention exhibit a 90% reduction in expression of PD-1. In some embodiments, the sd-RNA sequences used in the invention exhibit a 95% reduction in expression of PD-1. In some embodiments, the sd-RNA sequences used in the invention exhibit a 99% reduction in expression PD-1. In some embodiments, the sd-RNA sequences used in the invention exhibit a reduction in expression of PD-1 when delivered at a concentration of about 0.25 μM to about 10 μM, in some embodiments, about 0.25 μM to about 4 μM. In some embodiments, the sd-RNA sequences used in the invention exhibit a reduction in expression of PD-1 when delivered at a concentration of about 0.25 μM. In some embodiments, the sd-RNA sequences used in the invention exhibit a reduction in expression of PD-1 when delivered at a concentration of about 0.5 μM. In some embodiments, the sd-RNA sequences used in the invention exhibit a reduction in expression of PD-1 when delivered at a concentration of about 0.75 μM. In some embodiments, the sd-RNA sequences used in the invention exhibit a reduction in expression of PD-1 when delivered at a concentration of about 1.0 μM. In some embodiments, the sd-RNA sequences used in the invention exhibit a reduction in expression of PD-1 when delivered at a concentration of about 1.25 μM. In some embodiments, the sd-RNA sequences used in the invention exhibit a reduction in expression of PD-1 when delivered at a concentration of about 1.5 μM. In some embodiments, the sd-RNA sequences used in the invention exhibit a reduction in expression of PD-1 when delivered at a concentration of about 1.75 μM. In some embodiments, the sd-RNA sequences used in the invention exhibit a reduction in expression of PD-1 when delivered at a concentration of about 2.0 μM. In some embodiments, the sd-RNA sequences used in the invention exhibit a reduction in expression of PD-1 when delivered at a concentration of about 2.25 μM. In some embodiments, the sd-RNA sequences used in the invention exhibit a reduction in expression of PD-1 when delivered at a concentration of about 2.5 μM. In some embodiments, the sd-RNA sequences used in the invention exhibit a reduction in expression of PD-1 when delivered at a concentration of about 2.75 μM. In some embodiments, the sd-RNA sequences used in the invention exhibit a reduction in expression of PD-1 when delivered at a concentration of about 3.0 μM. In some embodiments, the sd-RNA sequences used in the invention exhibit a reduction in expression of PD-1 when delivered at a concentration of about 3.25 μM. In some embodiments, the sd-RNA sequences used in the invention exhibit a reduction in expression of PD-1 when delivered at a concentration of about 3.5 μM. In some embodiments, the sd-RNA sequences used in the invention exhibit a reduction in expression of PD-1 when delivered at a concentration of about 3.75 µM. In some embodiments, the sd-RNA sequences used in the invention exhibit a reduction in expression of PD-1 when delivered at a concentration of about 4.0 µM. In some embodiments, the sd-RNA sequences used in the invention exhibit a reduction in expression of PD-1 when delivered at a concentration of about 5.0 µM. In some embodiments, the sd-RNA sequences used in the invention exhibit a reduction in expression of PD-1 when delivered at a concentration of about 6.0 µM. In some embodiments, the sd-RNA sequences used in the invention exhibit a reduction in expression of PD-1 when delivered at a concentration of about 7.0 µM. In some embodiments, the sd-RNA sequences used in the invention exhibit a reduction in expression of PD-1 when delivered at a concentration of about 8.0 µM. In some embodiments, the sd-RNA sequences used in the invention exhibit a reduction in expression of PD-1 when delivered at a concentration of about 9.0 µM. In some embodiments, the sd-RNA sequences used in the invention exhibit a reduction in expression of PD-1 when delivered at a concentration of about 10.0 µM. In any of the foregoing embodiments, the concentrations specified may be determined with respect to TIL culture media before or after exchange of media.

In some variant embodiments, the TILs are exposed to the sd-RNAs on at least two of Day 11, Day 14, Day 17, and/or Day 21 at an sd-RNA concentration of about 0.75 µM to about 3 µM. In some variant embodiments, the TILs are exposed to the sd-RNAs on at least three of Day 11, Day 14, Day 17, and/or Day 21 at an sd-RNA concentration of about 0.75 µM to about 3 µM. In some variant embodiments, the TILs are exposed to the sd-RNAs on all of Day 11, Day 14, Day 17, and Day 21 at an sd-RNA concentration of about 0.75 µM to about 3 µM. In some variant embodiments, the sd-RNA is added along with a media change at an sd-RNA concentration of about 0.75 µM to about 3 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.0 µM to about 2.5 µM. In some variant embodiments, the TILs are exposed to the sd-RNAs on at least three of Day 11, Day 14, Day 17, and/or Day 21 at an sd-RNA concentration of about 1.0 µM to about 2.5 µM. In some variant embodiments, the TILs are exposed to the sd-RNAs on all of Day 11, Day 14, Day 17, and Day 21 at an sd-RNA concentration of about 1.0 µM to about 2.5 µM. In some variant embodiments, the sd-RNA is added along with a media change at an sd-RNA concentration of about 1.0 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.5 µM to about 2.5 µM. In some variant embodiments, the TILs are exposed to the sd-RNAs on at least three of Day 11, Day 14, Day 17, and/or Day 21 at an sd-RNA concentration of about 1.5 µM to about 2.5 µM. In some variant embodiments, the TILs are exposed to the sd-RNAs on all of Day 11, Day 14, Day 17, and Day 21 at an sd-RNA concentration of about 1.5 µM to about 2.5 µM. In some variant embodiments, the sd-RNA is added along with a media change at an sd-RNA concentration of about 1.5 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of 2 µM. In some variant embodiments, the TILs are exposed to the sd-RNAs on at least three of Day 11, Day 14, Day 17, and/or Day 21 at an sd-RNA concentration of about 2 µM. In some variant embodiments, the TILs are exposed to the sd-RNAs on all of Day 11, Day 14, Day 17, and Day 21 at an sd-RNA concentration of about 2 µM. In some variant embodiments, the sd-RNA is added along with a media change at an sd-RNA concentration of about 2 µM. In some embodiments, the sd-RNA targets PD-1.

In some embodiments, the sd-RNA added at Day 11 is added in media comprising sd-RNA, IL-2, OKT3 and APCs (including, for example, PBMCs). In some embodiments, the sd-RNA added at Day 14 is added in media comprising sd-RNA and optionally includes one or more of IL-2, OKT3 and APCs (including, for example, PBMCs). In some embodiments, the sd-RNA added at Day 17 is added in media comprising sd-RNA and optionally includes one or more of IL-2, OKT3 and APCs (including, for example, PBMCs). In some embodiments, the sd-RNA added at Day 21 is added in media comprising sd-RNA and optionally includes one or more of IL-2, OKT3 and APCs (including, for example, PBMCs). In some embodiments, the sd-RNA added at Day 14 is added in media comprising sd-RNA and IL-2. In some embodiments, the sd-RNA added at Day 17 is added in media comprising sd-RNA and IL-2. In some embodiments, the sd-RNA added at Day 21 is added in media comprising sd-RNA and IL-2. In some embodiments, more sd-RNA is added at Day 14. In some embodiments, more sd-RNA added at Day 17. In some embodiments, more sd-RNA added at Day 21. In some embodiments, the sd-RNA is added at the same concentration at Day 11, Day 14, Day 17, and Day 21. In some embodiments, the sd-RNA is added at a different concentration at Day 11, Day 14, Day 17 and/or Day 21. In some embodiments, the sd-RNA targets PD-1.

Example 31: Variant Embodiments of Example 23

According the methods discussed in Example 23, methods of expanding TILs in combination with transiently altering protein expression are described. This example provides further varied embodiments in line with the methods described in Example 23.

In some embodiments of the above described method, a method for expanding tumor infiltrating lymphocytes (TILs) into a therapeutic population of TILs is provided which comprises:
  (a) obtaining a first population of TILs from a tumor resected from a patient by processing a tumor sample obtained from the patient into multiple tumor fragments;
  (b) adding the tumor fragments into a closed system;
  (c) performing a first expansion by culturing the first population of TILs in a cell culture medium comprising IL-2 and optionally comprising a 4-1BB agonist antibody for about 2 to 5 days;
  (d) contacting the first population of TILs with at least one sd-RNA between days 11 and 21, wherein the sd-RNA is added at a concentration of 0.1 µM sd-RNA/10,000 TILs/100 µL media, 0.5 µM sd-RNA/10,000 TILs/100 µL media, 0.75 µM sd-RNA/10,000 TILs/100 µL media, 1 µM sd-RNA/10,000 TILs/100 µL media, 1.25 µM sd-RNA/10,000 TILs/100 µL media, 1.5 µM sd-RNA/10,000 TILs/100 µL media, 2 µM sd-RNA/10,000 TILs/100 µL media, 5 µM sd-RNA/10,000 TILs/100 µL media, or 10 µM sd-RNA/10,000 TILs/100 µL media, and wherein the sd-RNA is for inhibiting the expression of a molecule selected from the group consisting of PD-1, LAG-3, TIM-3, CISH, and CBLB, and combinations thereof;

(e) optionally performing a sterile electroporation step on the first population of TILs, wherein the sterile electroporation step mediates the transfer of the at least one sd-RNA;

(f) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transitions from step (c) to step (f) occur without opening the system;

(g) resting the second population of TILs for about 1 day;

(h) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transitions from step (c) to step (h) occur without opening the system;

(i) harvesting the therapeutic population of TILs obtained from step (h) to provide a harvested TIL population, wherein the transition from step (h) to step (i) occurs without opening the system, wherein the harvested population of TILs is a therapeutic population of TILs;

(j) transferring the harvested TIL population from step (i) to an infusion bag, wherein the transfer from step (i) to (j) occurs without opening the system; and (k) cryopreserving the harvested TIL population using a dimethylsulfoxide-based cryopreservation medium.

In some variant embodiments, the other molecules capable of transiently altering protein expression comprise sd-RNAs, including for example but not limited to, sd-rxRNAs. In some embodiments, the TILs are exposed to the sd-RNAs on Day 11, Day 14, Day 17, and/or Day 21. In some variant embodiments, the TILs are exposed to the sd-RNAs on at least two of Day 11, Day 14, Day 17, and/or Day 21. In some variant embodiments, the TILs are exposed to the sd-RNAs on at least three of Day 11, Day 14, Day 17, and/or Day 21. In some variant embodiments, the TILs are exposed to the sd-RNAs on all of Day 11, Day 14, Day 17, and Day 21. In some embodiments, the sd-RNA targets PD-1.

In some embodiments, the sd-RNA sequences used in the invention exhibit a 70% reduction in expression of the target gene. In some embodiments, the sd-RNA sequences used in the invention exhibit a 75% reduction in expression of the target gene. In some embodiments, the sd-RNA sequences used in the invention exhibit an 80% reduction in expression of the target gene. In some embodiments, the sd-RNA sequences used in the invention exhibit an 85% reduction in expression of the target gene. In some embodiments, the sd-RNA sequences used in the invention exhibit a 90% reduction in expression of the target gene. In some embodiments, the sd-RNA sequences used in the invention exhibit a 95% reduction in expression of the target gene. In some embodiments, the sd-RNA sequences used in the invention exhibit a 99% reduction in expression of the target gene. In some embodiments, the sd-RNA sequences used in the invention exhibit a reduction in expression of the target gene when delivered at a concentration of about 0.25 µM to about 10 µM, in some embodiments, about 0.25 µM to about 4 µM. In some embodiments, the sd-RNA sequences used in the invention exhibit a reduction in expression of the target gene when delivered at a concentration of about 0.25 µM. In some embodiments, the sd-RNA sequences used in the invention exhibit a reduction in expression of the target gene when delivered at a concentration of about 0.5 µM. In some embodiments, the sd-RNA sequences used in the invention exhibit a reduction in expression of the target gene when delivered at a concentration of about 0.75 µM. In some embodiments, the sd-RNA sequences used in the invention exhibit a reduction in expression of the target gene when delivered at a concentration of about 1.0 µM. In some embodiments, the sd-RNA sequences used in the invention exhibit a reduction in expression of the target gene when delivered at a concentration of about 1.25 µM. In some embodiments, the sd-RNA sequences used in the invention exhibit a reduction in expression of the target gene when delivered at a concentration of about 1.5 µM. In some embodiments, the sd-RNA sequences used in the invention exhibit a reduction in expression of the target gene when delivered at a concentration of about 1.75 µM. In some embodiments, the sd-RNA sequences used in the invention exhibit a reduction in expression of the target gene when delivered at a concentration of about 2.0 µM. In some embodiments, the sd-RNA sequences used in the invention exhibit a reduction in expression of the target gene when delivered at a concentration of about 2.25 µM. In some embodiments, the sd-RNA sequences used in the invention exhibit a reduction in expression of the target gene when delivered at a concentration of about 2.5 µM. In some embodiments, the sd-RNA sequences used in the invention exhibit a reduction in expression of the target gene when delivered at a concentration of about 2.75 µM. In some embodiments, the sd-RNA sequences used in the invention exhibit a reduction in expression of the target gene when delivered at a concentration of about 3.0 µM. In some embodiments, the sd-RNA sequences used in the invention exhibit a reduction in expression of the target gene when delivered at a concentration of about 3.25 µM. In some embodiments, the sd-RNA sequences used in the invention exhibit a reduction in expression of the target gene when delivered at a concentration of about 3.5 µM. In some embodiments, the sd-RNA sequences used in the invention exhibit a reduction in expression of the target gene when delivered at a concentration of about 3.75 µM. In some embodiments, the sd-RNA sequences used in the invention exhibit a reduction in expression of the target gene when delivered at a concentration of about 4.0 µM. In some embodiments, the sd-RNA sequences used in the invention exhibit a reduction in expression of the target gene when delivered at a concentration of about 5.0 µM. In some embodiments, the sd-RNA sequences used in the invention exhibit a reduction in expression of the target gene when delivered at a concentration of about 6.0 µM. In some embodiments, the sd-RNA sequences used in the invention exhibit a reduction in expression of the target gene when delivered at a concentration of about 7.0 µM. In some embodiments, the sd-RNA sequences used in the invention exhibit a reduction in expression of the target gene when delivered at a concentration of about 8.0 µM. In some embodiments, the sd-RNA sequences used in the invention exhibit a reduction in expression of the target gene when delivered at a concentration of about 9.0 µM. In some embodiments, the sd-RNA sequences used in the invention exhibit a reduction in expression of the target gene when delivered at a concentration of about 10.0 µM. In any of the foregoing embodiments, the concentrations specified may be determined with respect to TIL culture media before or after exchange of media.

In some embodiments, the sd-RNA sequences used in the invention exhibit a 70% reduction in expression of PD-1. In some embodiments, the sd-RNA sequences used in the invention exhibit a 75% reduction in expression of PD-1. In some embodiments, the sd-RNA sequences used in the invention exhibit an 80% reduction in expression of PD-1. In some embodiments, the sd-RNA sequences used in the invention exhibit an 85% reduction in expression of PD-1. In some embodiments, the sd-RNA sequences used in the invention exhibit a 90% reduction in expression of PD-1. In some embodiments, the sd-RNA sequences used in the invention exhibit a 95% reduction in expression of PD-1. In some embodiments, the sd-RNA sequences used in the invention exhibit a 99% reduction in expression PD-1. In some embodiments, the sd-RNA sequences used in the invention exhibit a reduction in expression of PD-1 when delivered at a concentration of about 0.25 µM to about 10 µM, in some embodiments, about 0.25 µM to about 4 µM. In some embodiments, the sd-RNA sequences used in the invention exhibit a reduction in expression of PD-1 when delivered at a concentration of about 0.25 µM. In some embodiments, the sd-RNA sequences used in the invention exhibit a reduction in expression of PD-1 when delivered at a concentration of about 0.5 µM. In some embodiments, the sd-RNA sequences used in the invention exhibit a reduction in expression of PD-1 when delivered at a concentration of about 0.75 µM. In some embodiments, the sd-RNA sequences used in the invention exhibit a reduction in expression of PD-1 when delivered at a concentration of about 1.0 µM. In some embodiments, the sd-RNA sequences used in the invention exhibit a reduction in expression of PD-1 when delivered at a concentration of about 1.25 µM. In some embodiments, the sd-RNA sequences used in the invention exhibit a reduction in expression of PD-1 when delivered at a concentration of about 1.5 µM. In some embodiments, the sd-RNA sequences used in the invention exhibit a reduction in expression of PD-1 when delivered at a concentration of about 1.75 µM. In some embodiments, the sd-RNA sequences used in the invention exhibit a reduction in expression of PD-1 when delivered at a concentration of about 2.0 µM. In some embodiments, the sd-RNA sequences used in the invention exhibit a reduction in expression of PD-1 when delivered at a concentration of about 2.25 µM. In some embodiments, the sd-RNA sequences used in the invention exhibit a reduction in expression of PD-1 when delivered at a concentration of about 2.5 µM. In some embodiments, the sd-RNA sequences used in the invention exhibit a reduction in expression of PD-1 when delivered at a concentration of about 2.75 µM. In some embodiments, the sd-RNA sequences used in the invention exhibit a reduction in expression of PD-1 when delivered at a concentration of about 3.0 µM. In some embodiments, the sd-RNA sequences used in the invention exhibit a reduction in expression of PD-1 when delivered at a concentration of about 3.25 µM. In some embodiments, the sd-RNA sequences used in the invention exhibit a reduction in expression of PD-1 when delivered at a concentration of about 3.5 µM. In some embodiments, the sd-RNA sequences used in the invention exhibit a reduction in expression of PD-1 when delivered at a concentration of about 3.75 µM. In some embodiments, the sd-RNA sequences used in the invention exhibit a reduction in expression of PD-1 when delivered at a concentration of about 4.0 µM. In some embodiments, the sd-RNA sequences used in the invention exhibit a reduction in expression of PD-1 when delivered at a concentration of about 5.0 µM. In some embodiments, the sd-RNA sequences used in the invention exhibit a reduction in expression of PD-1 when delivered at a concentration of about 6.0 µM. In some embodiments, the sd-RNA sequences used in the invention exhibit a reduction in expression of PD-1 when delivered at a concentration of about 7.0 µM. In some embodiments, the sd-RNA sequences used in the invention exhibit a reduction in expression of PD-1 when delivered at a concentration of about 8.0 µM. In some embodiments, the sd-RNA sequences used in the invention exhibit a reduction in expression of PD-1 when delivered at a concentration of about 9.0 µM. In some embodiments, the sd-RNA sequences used in the invention exhibit a reduction in expression of PD-1 when delivered at a concentration of about 10.0 µM. In any of the foregoing embodiments, the concentrations specified may be determined with respect to TIL culture media before or after exchange of media.

In some variant embodiments, the TILs are exposed to the sd-RNAs on at least two of Day 11, Day 14, Day 17, and/or Day 21 at an sd-RNA concentration of about 0.75 µM to about 3 µM. In some variant embodiments, the TILs are exposed to the sd-RNAs on at least three of Day 11, Day 14, Day 17, and/or Day 21 at an sd-RNA concentration of about 0.75 µM to about 3 µM. In some variant embodiments, the TILs are exposed to the sd-RNAs on all of Day 11, Day 14, Day 17, and Day 21 at an sd-RNA concentration of about 0.75 µM to about 3 µM. In some variant embodiments, the sd-RNA is added along with a media change at an sd-RNA concentration of about 0.75 µM to about 3 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.0 µM to about 2.5 µM. In some variant embodiments, the TILs are exposed to the sd-RNAs on at least three of Day 11, Day 14, Day 17, and/or Day 21 at an sd-RNA concentration of about 1.0 µM to about 2.5 µM. In some variant embodiments, the TILs are exposed to the sd-RNAs on all of Day 11, Day 14, Day 17, and Day 21 at an sd-RNA concentration of about 1.0 µM to about 2.5 µM. In some variant embodiments, the sd-RNA is added along with a media change at an sd-RNA concentration of about 1.0 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.5 µM to about 2.5 µM. In some variant embodiments, the TILs are exposed to the sd-RNAs on at least three of Day 11, Day 14, Day 17, and/or Day 21 at an sd-RNA concentration of about 1.5 µM to about 2.5 µM. In some variant embodiments, the TILs are exposed to the sd-RNAs on all of Day 11, Day 14, Day 17, and Day 21 at an sd-RNA concentration of about 1.5 µM to about 2.5 µM. In some variant embodiments, the sd-RNA is added along with a media change at an sd-RNA concentration of about 1.5 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of 2 µM. In some variant embodiments, the TILs are exposed to the sd-RNAs on at least three of Day 11, Day 14, Day 17, and/or Day 21 at an sd-RNA concentration of about 2 µM. In some variant embodiments, the TILs are exposed to the sd-RNAs on all of Day 11, Day 14, Day 17, and Day 21 at an sd-RNA concentration of about 2 µM. In some variant embodiments, the sd-RNA is added along with a media change at an sd-RNA concentration of about 2 µM. In some embodiments, the sd-RNA targets PD-1.

In some embodiments, the sd-RNA added at Day 11 is added in media comprising sd-RNA, IL-2, OKT3 and APCs (including, for example, PBMCs). In some embodiments, the sd-RNA added at Day 14 is added in media comprising sd-RNA and optionally includes one or more of IL-2, OKT3 and APCs (including, for example, PBMCs). In some embodiments, the sd-RNA added at Day 17 is added in media comprising sd-RNA and optionally includes one or more of IL-2, OKT3 and APCs (including, for example, PBMCs). In some embodiments, the sd-RNA added at Day 21 is added in media comprising sd-RNA and optionally includes one or more of IL-2, OKT3 and APCs (including, for example, PBMCs). In some embodiments, the sd-RNA added at Day 14 is added in media comprising sd-RNA and IL-2. In some embodiments, the sd-RNA added at Day 17 is added in media comprising sd-RNA and IL-2. In some embodiments, the sd-RNA added at Day 21 is added in media comprising sd-RNA and IL-2. In some embodiments, more sd-RNA is added at Day 14. In some embodiments, more sd-RNA added at Day 17. In some embodiments, more sd-RNA added at Day 21. In some embodiments, the sd-RNA is added at the same concentration at Day 11, Day 14, Day 17, and Day 21. In some embodiments, the sd-RNA is added at a different concentration at Day 11, Day 14, Day 17 and/or Day 21. In some embodiments, the sd-RNA targets PD-1.

Example 32: Variant Embodiments of Example 23

According the methods discussed in Example 23, methods of expanding TILs in combination with transiently altering protein expression are described. This example provides further varied embodiments in line with the methods described in Example 23.

In some embodiments of the above described method, a method for expanding tumor infiltrating lymphocytes (TILs) into a therapeutic population of TILs is provided which comprises:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising a 4-1BB agonist antibody for about 2 to 5 days;
(d) contacting the first population of TILs with at least one sd-RNA between days 11 and 21, wherein the sd-RNA is added at a concentration of 0.1 µM sd-RNA/10,000 TILs, 0.5 µM sd-RNA/10,000 TILs, 0.75 µM sd-RNA/10,000 TILS, 1 µM sd-RNA/10,000 TILs, 1.25 µM sd-RNA/10,000 TILs, 1.5 µM sd-RNA/10,000 TILs, 2 µM sd-RNA/10,000 TILs, 5 µM sd-RNA/10,000 TILs, or 10 µM sd-RNA/10,000 TILS, and wherein the sd-RNA is for inhibiting the expression of a molecule selected from the group consisting of PD-1, LAG-3, TIM-3, CISH, and CBLB, and combinations thereof;
(e) optionally performing a sterile electroporation step on the first population of TILs, wherein the sterile electroporation step mediates the transfer of the at least one sd-RNA;
(f) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transitions from step (c) to step (f) occur without opening the system;
(g) resting the second population of TILs for about 1 day;
(h) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (g) to step (h) occurs without opening the system;
(i) harvesting the therapeutic population of TILs obtained from step (h) to provide a harvested TIL population, wherein the transition from step (h) to step (i) occurs without opening the system, wherein the harvested population of TILs is a therapeutic population of TILs;
(j) transferring the harvested TIL population from step (i) to an infusion bag, wherein the transfer from step (i) to (j) occurs without opening the system; and
(k) cryopreserving the harvested TIL population using a dimethylsulfoxide-based cryopreservation medium.

In some variant embodiments, the other molecules capable of transiently altering protein expression comprise sd-RNAs, including for example but not limited to, sd-rxRNAs. In some embodiments, the TILs are exposed to the sd-RNAs on Day 11, Day 14, Day 17, and/or Day 21. In some variant embodiments, the TILs are exposed to the sd-RNAs on at least two of Day 11, Day 14, Day 17, and/or Day 21. In some variant embodiments, the TILs are exposed to the sd-RNAs on at least three of Day 11, Day 14, Day 17, and/or Day 21. In some variant embodiments, the TILs are exposed to the sd-RNAs on all of Day 11, Day 14, Day 17, and Day 21. In some embodiments, the sd-RNA targets PD-1.

In some embodiments, the sd-RNA sequences used in the invention exhibit a 70% reduction in expression of the target gene. In some embodiments, the sd-RNA sequences used in the invention exhibit a 75% reduction in expression of the target gene. In some embodiments, the sd-RNA sequences used in the invention exhibit an 80% reduction in expression of the target gene. In some embodiments, the sd-RNA sequences used in the invention exhibit an 85% reduction in expression of the target gene. In some embodiments, the sd-RNA sequences used in the invention exhibit a 90% reduction in expression of the target gene. In some embodiments, the sd-RNA sequences used in the invention exhibit a 95% reduction in expression of the target gene. In some embodiments, the sd-RNA sequences used in the invention exhibit a 99% reduction in expression of the target gene. In some embodiments, the sd-RNA sequences used in the invention exhibit a reduction in expression of the target gene when delivered at a concentration of about 0.25 µM to about 10 µM, in some embodiments, about 0.25 µM to about 4 µM. In some embodiments, the sd-RNA sequences used in the invention exhibit a reduction in expression of the target gene when delivered at a concentration of about 0.25 µM. In some embodiments, the sd-RNA sequences used in the invention exhibit a reduction in expression of the target gene when delivered at a concentration of about 0.5 µM. In some embodiments, the sd-RNA sequences used in the invention exhibit a reduction in expression of the target gene when delivered at a concentration of about 0.75 µM. In some embodiments, the sd-RNA sequences used in the invention exhibit a reduction in expression of the target gene when delivered at a concentration of about 1.0 µM. In some embodiments, the sd-RNA sequences used in the invention exhibit a reduction in expression of the target gene when delivered at a concentration of about 1.25 µM. In some embodiments, the sd-RNA sequences used in the invention exhibit a reduction in expression of the target gene when delivered at a concentration of about 1.5 µM. In some embodiments, the sd-RNA sequences used in the invention exhibit a reduction in expression of the target gene when delivered at a concentration of about 1.75 µM. In some embodiments, the sd-RNA sequences used in the invention exhibit a reduction in expression of the target gene when delivered at a concentration of about 2.0 µM. In some embodiments, the sd-RNA sequences used in the invention exhibit a reduction in expression of the target gene when delivered at a concentration of about 2.25 µM. In some embodiments, the sd-RNA sequences used in the invention exhibit a reduction in expression of the target gene when delivered at a concentration of about 2.5 µM. In some embodiments, the sd-RNA sequences used in the invention exhibit a reduction in expression of the target gene when delivered at a concentration of about 2.75 µM. In some embodiments, the sd-RNA sequences used in the invention exhibit a reduction in expression of the target gene when delivered at a concentration of about 3.0 µM. In some embodiments, the sd-RNA sequences used in the invention exhibit a reduction in expression of the target gene when delivered at a concentration of about 3.25 µM. In some embodiments, the sd-RNA sequences used in the invention exhibit a reduction in expression of the target gene when delivered at a concentration of about 3.5 µM. In some embodiments, the sd-RNA sequences used in the invention exhibit a reduction in expression of the target gene when delivered at a concentration of about 3.75 µM. In some embodiments, the sd-RNA sequences used in the invention exhibit a reduction in expression of the target gene when delivered at a concentration of about 4.0 µM. In some embodiments, the sd-RNA sequences used in the invention exhibit a reduction in expression of the target gene when delivered at a concentration of about 5.0 µM. In some embodiments, the sd-RNA sequences used in the invention exhibit a reduction in expression of the target gene when delivered at a concentration of about 6.0 µM. In some embodiments, the sd-RNA sequences used in the invention exhibit a reduction in expression of the target gene when delivered at a concentration of about 7.0 µM. In some embodiments, the sd-RNA sequences used in the invention exhibit a reduction in expression of the target gene when delivered at a concentration of about 8.0 µM. In some embodiments, the sd-RNA sequences used in the invention exhibit a reduction in expression of the target gene when delivered at a concentration of about 9.0 µM. In some embodiments, the sd-RNA sequences used in the invention exhibit a reduction in expression of the target gene when delivered at a concentration of about 10.0 µM. In any of the foregoing embodiments, the concentrations specified may be determined with respect to TIL culture media before or after exchange of media.

In some embodiments, the sd-RNA sequences used in the invention exhibit a 70% reduction in expression of PD-1. In some embodiments, the sd-RNA sequences used in the invention exhibit a 75% reduction in expression of PD-1. In some embodiments, the sd-RNA sequences used in the invention exhibit an 80% reduction in expression of PD-1. In some embodiments, the sd-RNA sequences used in the invention exhibit an 85% reduction in expression of PD-1. In some embodiments, the sd-RNA sequences used in the invention exhibit a 90% reduction in expression of PD-1. In some embodiments, the sd-RNA sequences used in the invention exhibit a 95% reduction in expression of PD-1. In some embodiments, the sd-RNA sequences used in the invention exhibit a 99% reduction in expression PD-1. In some embodiments, the sd-RNA sequences used in the invention exhibit a reduction in expression of PD-1 when delivered at a concentration of about 0.25 µM to about 10 µM, in some embodiments, about 0.25 µM to about 4 µM. In some embodiments, the sd-RNA sequences used in the invention exhibit a reduction in expression of PD-1 when delivered at a concentration of about 0.25 µM. In some embodiments, the sd-RNA sequences used in the invention exhibit a reduction in expression of PD-1 when delivered at a concentration of about 0.5 µM. In some embodiments, the sd-RNA sequences used in the invention exhibit a reduction in expression of PD-1 when delivered at a concentration of about 0.75 µM. In some embodiments, the sd-RNA sequences used in the invention exhibit a reduction in expression of PD-1 when delivered at a concentration of about 1.0 µM. In some embodiments, the sd-RNA sequences used in the invention exhibit a reduction in expression of PD-1 when delivered at a concentration of about 1.25 µM. In some embodiments, the sd-RNA sequences used in the invention exhibit a reduction in expression of PD-1 when delivered at a concentration of about 1.5 µM. In some embodiments, the sd-RNA sequences used in the invention exhibit a reduction in expression of PD-1 when delivered at a concentration of about 1.75 µM. In some embodiments, the sd-RNA sequences used in the invention exhibit a reduction in expression of PD-1 when delivered at a concentration of about 2.0 µM. In some embodiments, the sd-RNA sequences used in the invention exhibit a reduction in expression of PD-1 when delivered at a concentration of about 2.25 µM. In some embodiments, the sd-RNA sequences used in the invention exhibit a reduction in expression of PD-1 when delivered at a concentration of about 2.5 µM. In some embodiments, the sd-RNA sequences used in the invention exhibit a reduction in expression of PD-1 when delivered at a concentration of about 2.75 µM. In some embodiments, the sd-RNA sequences used in the invention exhibit a reduction in expression of PD-1 when delivered at a concentration of about 3.0 µM. In some embodiments, the sd-RNA sequences used in the invention exhibit a reduction in expression of PD-1 when delivered at a concentration of about 3.25 µM. In some embodiments, the sd-RNA sequences used in the invention exhibit a reduction in expression of PD-1 when delivered at a concentration of about 3.5 µM. In some embodiments, the sd-RNA sequences used in the invention exhibit a reduction in expression of PD-1 when delivered at a concentration of about 3.75 µM. In some embodiments, the sd-RNA sequences used in the invention exhibit a reduction in expression of PD-1 when delivered at a concentration of about 4.0 µM. In some embodiments, the sd-RNA sequences used in the invention exhibit a reduction in expression of PD-1 when delivered at a concentration of about 5.0 µM. In some embodiments, the sd-RNA sequences used in the invention exhibit a reduction in expression of PD-1 when delivered at a concentration of about 6.0 µM. In some embodiments, the sd-RNA sequences used in the invention exhibit a reduction in expression of PD-1 when delivered at a concentration of about 7.0 µM. In some embodiments, the sd-RNA sequences used in the invention exhibit a reduction in expression of PD-1 when delivered at a concentration of about 8.0 µM. In some embodiments, the sd-RNA sequences used in the invention exhibit a reduction in expression of PD-1 when delivered at a concentration of about 9.0 µM. In some embodiments, the sd-RNA sequences used in the invention exhibit a reduction in expression of PD-1 when delivered at a concentration of about 10.0 µM. In any of the foregoing embodiments, the concentrations specified may be determined with respect to TIL culture media before or after exchange of media.

In some variant embodiments, the TILs are exposed to the sd-RNAs on at least two of Day 11, Day 14, Day 17, and/or Day 21 at an sd-RNA concentration of about 0.75 µM to about 3 µM. In some variant embodiments, the TILs are exposed to the sd-RNAs on at least three of Day 11, Day 14, Day 17, and/or Day 21 at an sd-RNA concentration of about 0.75 µM to about 3 µM. In some variant embodiments, the TILs are exposed to the sd-RNAs on all of Day 11, Day 14, Day 17, and Day 21 at an sd-RNA concentration of about 0.75 µM to about 3 µM. In some variant embodiments, the sd-RNA is added along with a media change at an sd-RNA concentration of about 0.75 µM to about 3 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.0 µM to about 2.5 µM. In some variant embodiments, the TILs are exposed to the sd-RNAs on at least three of Day 11, Day 14, Day 17, and/or Day 21 at an sd-RNA concentration of about 1.0 µM to about 2.5 µM. In some variant embodiments, the TILs are exposed to the sd-RNAs on all of Day 11, Day 14, Day 17, and Day 21 at an sd-RNA concentration of about 1.0 µM to about 2.5 µM. In some variant embodiments, the sd-RNA is added along with a media change at an sd-RNA concentration of about 1.0 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.5 µM to about 2.5 µM. In some variant embodiments, the TILs are exposed to the sd-RNAs on at least three of Day 11, Day 14, Day 17, and/or Day 21 at an sd-RNA concentration of about 1.5 µM to about 2.5 µM. In some variant embodiments, the TILs are exposed to the sd-RNAs on all of Day 11, Day 14, Day 17, and Day 21 at an sd-RNA concentration of about 1.5 µM to about 2.5 µM. In some variant embodiments, the sd-RNA is added along with a media change at an sd-RNA concentration of about 1.5 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of 2 µM. In some variant embodiments, the TILs are exposed to the sd-RNAs on at least three of Day 11, Day 14, Day 17, and/or Day 21 at an sd-RNA concentration of about 2 µM. In some variant embodiments, the TILs are exposed to the sd-RNAs on all of Day 11, Day 14, Day 17, and Day 21 at an sd-RNA concentration of about 2 µM. In some variant embodiments, the sd-RNA is added along with a media change at an sd-RNA concentration of about 2 µM. In some embodiments, the sd-RNA targets PD-1.

In some embodiments, the sd-RNA added at Day 11 is added in media comprising sd-RNA, IL-2, OKT3 and APCs (including, for example, PBMCs). In some embodiments, the sd-RNA added at Day 14 is added in media comprising sd-RNA and optionally includes one or more of IL-2, OKT3 and APCs (including, for example, PBMCs). In some embodiments, the sd-RNA added at Day 17 is added in media comprising sd-RNA and optionally includes one or more of IL-2, OKT3 and APCs (including, for example, PBMCs). In some embodiments, the sd-RNA added at Day 21 is added in media comprising sd-RNA and optionally includes one or more of IL-2, OKT3 and APCs (including, for example, PBMCs). In some embodiments, the sd-RNA added at Day 14 is added in media comprising sd-RNA and IL-2. In some embodiments, the sd-RNA added at Day 17 is added in media comprising sd-RNA and IL-2. In some embodiments, the sd-RNA added at Day 21 is added in media comprising sd-RNA and IL-2. In some embodiments, more sd-RNA is added at Day 14. In some embodiments, more sd-RNA added at Day 17. In some embodiments, more sd-RNA added at Day 21. In some embodiments, the sd-RNA is added at the same concentration at Day 11, Day 14, Day 17, and Day 21. In some embodiments, the sd-RNA is added at a different concentration at Day 11, Day 14, Day 17 and/or Day 21. In some embodiments, the sd-RNA targets PD-1.

Example 33: Variant Embodiments of Example 23

According the methods discussed in Example 23, methods of expanding TILs in combination with transiently altering protein expression are described. This example provides further varied embodiments in line with the methods described in Example 23.

In some embodiments of the above described method, a method for expanding tumor infiltrating lymphocytes (TILs) into a therapeutic population of TILs is provided which comprises:

(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising a 4-1BB agonist antibody for about 2 to 5 days;
(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
(e) resting the second population of TILs for about 1 day;
(f) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transitions from step (c) to step (f) occur without opening the system;
(g) contacting the second population of TILs during any of steps (d), (e), and/or (f), including between days 11 and 21, with at least one sd-RNA, wherein the sd-RNA is added at a concentration of 0.1 μM sd-RNA/10,000 TILS/100 μL media, 0.5 μM sd-RNA/10,000 TILS/100 μL media, 0.75 μM sd-RNA/10,000 TILs/100 μL media, 1 μM sd-RNA/10,000 TILs/100 μL media, 1.25 μM sd-RNA/10,000 TILs/100 μL media, 1.5 μM sd-RNA/10,000 TILs/100 μL media, 2 μM sd-RNA/10,000 TILs/100 μL media, 5 μM sd-RNA/10,000 TILs/100 μL media, or 10 μM sd-RNA/10,000 TILS/100 μL media, and wherein the sd-RNA is for inhibiting the expression of a molecule selected from the group consisting of PD-1, LAG-3, TIM-3, CISH, and CBLB, and combinations thereof;

(h) optionally performing a sterile electroporation step on the second population of TILs, wherein the sterile electroporation step mediates the transfer of the at least one sd-RNA;

(i) harvesting the therapeutic population of TILs obtained from steps (g) or (h) to provide a harvested TIL population, wherein the transitions from step (g) to step (i) occur without opening the system, wherein the harvested population of TILs is a therapeutic population of TILs;

(j) transferring the harvested TIL population from step (i) to an infusion bag, wherein the transfer from step (i) to (j) occurs without opening the system; and (k) cryopreserving the harvested TIL population using a dimethylsulfoxide-based cryopreservation medium.

In some variant embodiments, the other molecules capable of transiently altering protein expression comprise sd-RNAs, including for example but not limited to, sd-rxRNAs. In some embodiments, the TILs are exposed to the sd-RNAs on Day 11, Day 14, Day 17, and/or Day 21. In some variant embodiments, the TILs are exposed to the sd-RNAs on at least two of Day 11, Day 14, Day 17, and/or Day 21. In some variant embodiments, the TILs are exposed to the sd-RNAs on at least three of Day 11, Day 14, Day 17, and/or Day 21. In some variant embodiments, the TILs are exposed to the sd-RNAs on all of Day 11, Day 14, Day 17, and Day 21. In some embodiments, the sd-RNA targets PD-1.

In some embodiments, the sd-RNA sequences used in the invention exhibit a 70% reduction in expression of the target gene. In some embodiments, the sd-RNA sequences used in the invention exhibit a 75% reduction in expression of the target gene. In some embodiments, the sd-RNA sequences used in the invention exhibit an 80% reduction in expression of the target gene. In some embodiments, the sd-RNA sequences used in the invention exhibit an 85% reduction in expression of the target gene. In some embodiments, the sd-RNA sequences used in the invention exhibit a 90% reduction in expression of the target gene. In some embodiments, the sd-RNA sequences used in the invention exhibit a 95% reduction in expression of the target gene. In some embodiments, the sd-RNA sequences used in the invention exhibit a 99% reduction in expression of the target gene. In some embodiments, the sd-RNA sequences used in the invention exhibit a reduction in expression of the target gene when delivered at a concentration of about 0.25 μM to about 10 μM, in some embodiments, about 0.25 μM to about 4 μM. In some embodiments, the sd-RNA sequences used in the invention exhibit a reduction in expression of the target gene when delivered at a concentration of about 0.25 μM. In some embodiments, the sd-RNA sequences used in the invention exhibit a reduction in expression of the target gene when delivered at a concentration of about 0.5 μM. In some embodiments, the sd-RNA sequences used in the invention exhibit a reduction in expression of the target gene when delivered at a concentration of about 0.75 μM. In some embodiments, the sd-RNA sequences used in the invention exhibit a reduction in expression of the target gene when delivered at a concentration of about 1.0 μM. In some embodiments, the sd-RNA sequences used in the invention exhibit a reduction in expression of the target gene when delivered at a concentration of about 1.25 μM. In some embodiments, the sd-RNA sequences used in the invention exhibit a reduction in expression of the target gene when delivered at a concentration of about 1.5 μM. In some embodiments, the sd-RNA sequences used in the invention exhibit a reduction in expression of the target gene when delivered at a concentration of about 1.75 μM. In some embodiments, the sd-RNA sequences used in the invention exhibit a reduction in expression of the target gene when delivered at a concentration of about 2.0 μM. In some embodiments, the sd-RNA sequences used in the invention exhibit a reduction in expression of the target gene when delivered at a concentration of about 2.25 μM. In some embodiments, the sd-RNA sequences used in the invention exhibit a reduction in expression of the target gene when delivered at a concentration of about 2.5 μM. In some embodiments, the sd-RNA sequences used in the invention exhibit a reduction in expression of the target gene when delivered at a concentration of about 2.75 μM. In some embodiments, the sd-RNA sequences used in the invention exhibit a reduction in expression of the target gene when delivered at a concentration of about 3.0 μM. In some embodiments, the sd-RNA sequences used in the invention exhibit a reduction in expression of the target gene when delivered at a concentration of about 3.25 μM. In some embodiments, the sd-RNA sequences used in the invention exhibit a reduction in expression of the target gene when delivered at a concentration of about 3.5 μM. In some embodiments, the sd-RNA sequences used in the invention exhibit a reduction in expression of the target gene when delivered at a concentration of about 3.75 μM. In some embodiments, the sd-RNA sequences used in the invention exhibit a reduction in expression of the target gene when delivered at a concentration of about 4.0 μM. In some embodiments, the sd-RNA sequences used in the invention exhibit a reduction in expression of the target gene when delivered at a concentration of about 5.0 μM. In some embodiments, the sd-RNA sequences used in the invention exhibit a reduction in expression of the target gene when delivered at a concentration of about 6.0 μM. In some embodiments, the sd-RNA sequences used in the invention exhibit a reduction in expression of the target gene when delivered at a concentration of about 7.0 μM. In some embodiments, the sd-RNA sequences used in the invention exhibit a reduction in expression of the target gene when delivered at a concentration of about 8.0 μM. In some embodiments, the sd-RNA sequences used in the invention exhibit a reduction in expression of the target gene when delivered at a concentration of about 9.0 μM. In some embodiments, the sd-RNA sequences used in the invention exhibit a reduction in expression of the target gene when delivered at a concentration of about 10.0 μM. In any of the foregoing embodiments, the concentrations specified may be determined with respect to TIL culture media before or after exchange of media.

In some embodiments, the sd-RNA sequences used in the invention exhibit a 70% reduction in expression of PD-1. In some embodiments, the sd-RNA sequences used in the invention exhibit a 75% reduction in expression of PD-1. In some embodiments, the sd-RNA sequences used in the invention exhibit an 80% reduction in expression of PD-1. In some embodiments, the sd-RNA sequences used in the invention exhibit an 85% reduction in expression of PD-1. In some embodiments, the sd-RNA sequences used in the invention exhibit a 90% reduction in expression of PD-1. In some embodiments, the sd-RNA sequences used in the invention exhibit a 95% reduction in expression of PD-1. In some embodiments, the sd-RNA sequences used in the invention exhibit a 99% reduction in expression PD-1. In some embodiments, the sd-RNA sequences used in the invention exhibit a reduction in expression of PD-1 when delivered at a concentration of about 0.25 µM to about 10 µM, in some embodiments, about 0.25 µM to about 4 µM. In some embodiments, the sd-RNA sequences used in the invention exhibit a reduction in expression of PD-1 when delivered at a concentration of about 0.25 µM. In some embodiments, the sd-RNA sequences used in the invention exhibit a reduction in expression of PD-1 when delivered at a concentration of about 0.5 µM. In some embodiments, the sd-RNA sequences used in the invention exhibit a reduction in expression of PD-1 when delivered at a concentration of about 0.75 µM. In some embodiments, the sd-RNA sequences used in the invention exhibit a reduction in expression of PD-1 when delivered at a concentration of about 1.0 µM. In some embodiments, the sd-RNA sequences used in the invention exhibit a reduction in expression of PD-1 when delivered at a concentration of about 1.25 µM. In some embodiments, the sd-RNA sequences used in the invention exhibit a reduction in expression of PD-1 when delivered at a concentration of about 1.5 µM. In some embodiments, the sd-RNA sequences used in the invention exhibit a reduction in expression of PD-1 when delivered at a concentration of about 1.75 µM. In some embodiments, the sd-RNA sequences used in the invention exhibit a reduction in expression of PD-1 when delivered at a concentration of about 2.0 µM. In some embodiments, the sd-RNA sequences used in the invention exhibit a reduction in expression of PD-1 when delivered at a concentration of about 2.25 µM. In some embodiments, the sd-RNA sequences used in the invention exhibit a reduction in expression of PD-1 when delivered at a concentration of about 2.5 µM. In some embodiments, the sd-RNA sequences used in the invention exhibit a reduction in expression of PD-1 when delivered at a concentration of about 2.75 µM. In some embodiments, the sd-RNA sequences used in the invention exhibit a reduction in expression of PD-1 when delivered at a concentration of about 3.0 µM. In some embodiments, the sd-RNA sequences used in the invention exhibit a reduction in expression of PD-1 when delivered at a concentration of about 3.25 µM. In some embodiments, the sd-RNA sequences used in the invention exhibit a reduction in expression of PD-1 when delivered at a concentration of about 3.5 µM. In some embodiments, the sd-RNA sequences used in the invention exhibit a reduction in expression of PD-1 when delivered at a concentration of about 3.75 µM. In some embodiments, the sd-RNA sequences used in the invention exhibit a reduction in expression of PD-1 when delivered at a concentration of about 4.0 µM. In some embodiments, the sd-RNA sequences used in the invention exhibit a reduction in expression of PD-1 when delivered at a concentration of about 5.0 µM. In some embodiments, the sd-RNA sequences used in the invention exhibit a reduction in expression of PD-1 when delivered at a concentration of about 6.0 µM. In some embodiments, the sd-RNA sequences used in the invention exhibit a reduction in expression of PD-1 when delivered at a concentration of about 7.0 µM. In some embodiments, the sd-RNA sequences used in the invention exhibit a reduction in expression of PD-1 when delivered at a concentration of about 8.0 µM. In some embodiments, the sd-RNA sequences used in the invention exhibit a reduction in expression of PD-1 when delivered at a concentration of about 9.0 µM. In some embodiments, the sd-RNA sequences used in the invention exhibit a reduction in expression of PD-1 when delivered at a concentration of about 10.0 µM. In any of the foregoing embodiments, the concentrations specified may be determined with respect to TIL culture media before or after exchange of media.

In some variant embodiments, the TILs are exposed to the sd-RNAs on at least two of Day 11, Day 14, Day 17, and/or Day 21 at an sd-RNA concentration of about 0.75 µM to about 3 µM. In some variant embodiments, the TILs are exposed to the sd-RNAs on at least three of Day 11, Day 14, Day 17, and/or Day 21 at an sd-RNA concentration of about 0.75 µM to about 3 µM. In some variant embodiments, the TILs are exposed to the sd-RNAs on all of Day 11, Day 14, Day 17, and Day 21 at an sd-RNA concentration of about 0.75 µM to about 3 µM. In some variant embodiments, the sd-RNA is added along with a media change at an sd-RNA concentration of about 0.75 µM to about 3 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.0 µM to about 2.5 µM. In some variant embodiments, the TILs are exposed to the sd-RNAs on at least three of Day 11, Day 14, Day 17, and/or Day 21 at an sd-RNA concentration of about 1.0 µM to about 2.5 µM. In some variant embodiments, the TILs are exposed to the sd-RNAs on all of Day 11, Day 14, Day 17, and Day 21 at an sd-RNA concentration of about 1.0 µM to about 2.5 µM. In some variant embodiments, the sd-RNA is added along with a media change at an sd-RNA concentration of about 1.0 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.5 µM to about 2.5 µM. In some variant embodiments, the TILs are exposed to the sd-RNAs on at least three of Day 11, Day 14, Day 17, and/or Day 21 at an sd-RNA concentration of about 1.5 µM to about 2.5 µM. In some variant embodiments, the TILs are exposed to the sd-RNAs on all of Day 11, Day 14, Day 17, and Day 21 at an sd-RNA concentration of about 1.5 µM to about 2.5 µM. In some variant embodiments, the sd-RNA is added along with a media change at an sd-RNA concentration of about 1.5 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of 2 µM. In some variant embodiments, the TILs are exposed to the sd-RNAs on at least three of Day 11, Day 14, Day 17, and/or Day 21 at an sd-RNA concentration of about 2 µM. In some variant embodiments, the TILs are exposed to the sd-RNAs on all of Day 11, Day 14, Day 17, and Day 21 at an sd-RNA concentration of about 2 µM. In some variant embodiments, the sd-RNA is added along with a media change at an sd-RNA concentration of about 2 µM. In some embodiments, the sd-RNA targets PD-1.

In some embodiments, the sd-RNA added at Day 11 is added in media comprising sd-RNA, IL-2, OKT3 and APCs (including, for example, PBMCs). In some embodiments, the sd-RNA added at Day 14 is added in media comprising sd-RNA and optionally includes one or more of IL-2, OKT3 and APCs (including, for example, PBMCs). In some embodiments, the sd-RNA added at Day 17 is added in media comprising sd-RNA and optionally includes one or more of IL-2, OKT3 and APCs (including, for example, PBMCs). In some embodiments, the sd-RNA added at Day 21 is added in media comprising sd-RNA and optionally includes one or more of IL-2, OKT3 and APCs (including, for example, PBMCs). In some embodiments, the sd-RNA added at Day 14 is added in media comprising sd-RNA and IL-2. In some embodiments, the sd-RNA added at Day 17 is added in media comprising sd-RNA and IL-2. In some embodiments, the sd-RNA added at Day 21 is added in media comprising sd-RNA and IL-2. In some embodiments, more sd-RNA is added at Day 14. In some embodiments, more sd-RNA added at Day 17. In some embodiments, more sd-RNA added at Day 21. In some embodiments, the sd-RNA is added at the same concentration at Day 11, Day 14, Day 17, and Day 21. In some embodiments, the sd-RNA is added at a different concentration at Day 11, Day 14, Day 17 and/or Day 21. In some embodiments, the sd-RNA targets PD-1.

Example 34: Variant Embodiments of Example 23

According the methods discussed in Example 23, methods of expanding TILs in combination with transiently altering protein expression are described. This example provides further varied embodiments in line with the methods described in Example 23.

In some embodiments of the above described method, a method for expanding tumor infiltrating lymphocytes (TILs) into a therapeutic population of TILs is provided which comprises:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising a 4-1BB agonist antibody for about 2 to 5 days;
(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
(e) resting the second population of TILs for about 1 day;
(f) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transitions from step (c) to step (f) occur without opening the system;
(g) contacting the second population of TILs during any of steps (d), (e), and/or (f), including between days 11 and 21, with at least one sd-RNA, wherein the sd-RNA is added at a concentration of 0.1 µM sd-RNA/10,000 TILs/100 µL media, 0.5 µM sd-RNA/10,000 TILs/100 µL media, 0.75 µM sd-RNA/10,000 TILs/100 µL media, 1 µM sd-RNA/10,000 TILs/100 µL media, 1.25 µM sd-RNA/10,000 TILs/100 µL media, 1.5 µM sd-RNA/10,000 TILs/100 µL media, 2 µM sd-RNA/10,000 TILs/100 µL media, 5 µM sd-RNA/10,000 TILs/100 µL media, or 10 µM sd-RNA/10,000 TILs/100 µL media, and wherein the sd-RNA is for inhibiting the expression of a molecule selected from the group consisting of PD-1, LAG-3, TIM-3, CISH, and CBLB, and combinations thereof;
(h) optionally performing a sterile electroporation step on the second population of TILs, wherein the sterile electroporation step mediates the transfer of the at least one sd-RNA;
(i) harvesting the therapeutic population of TILs obtained from steps (g) or (h) to provide a harvested TIL population, wherein the transitions from step (g) to step (i) occur without opening the system, wherein the harvested population of TILs is a therapeutic population of TILs;
(j) transferring the harvested TIL population from step (i) to an infusion bag, wherein the transfer from step (i) to (j) occurs without opening the system; and
(k) cryopreserving the harvested TIL population using a dimethylsulfoxide-based cryopreservation medium.

In some variant embodiments, the other molecules capable of transiently altering protein expression comprise sd-RNAs, including for example but not limited to, sd-rxRNAs. In some embodiments, the TILs are exposed to the sd-RNAs on Day 11, Day 14, Day 17, and/or Day 21. In some variant embodiments, the TILs are exposed to the sd-RNAs on at least two of Day 11, Day 14, Day 17, and/or Day 21. In some variant embodiments, the TILs are exposed to the sd-RNAs on at least three of Day 11, Day 14, Day 17, and/or Day 21. In some variant embodiments, the TILs are exposed to the sd-RNAs on all of Day 11, Day 14, Day 17, and Day 21. In some embodiments, the sd-RNA targets PD-1.

In some embodiments, the sd-RNA sequences used in the invention exhibit a 70% reduction in expression of the target gene. In some embodiments, the sd-RNA sequences used in the invention exhibit a 75% reduction in expression of the target gene. In some embodiments, the sd-RNA sequences used in the invention exhibit an 80% reduction in expression of the target gene. In some embodiments, the sd-RNA sequences used in the invention exhibit an 85% reduction in expression of the target gene. In some embodiments, the sd-RNA sequences used in the invention exhibit a 90% reduction in expression of the target gene. In some embodiments, the sd-RNA sequences used in the invention exhibit a 95% reduction in expression of the target gene. In some embodiments, the sd-RNA sequences used in the invention exhibit a 99% reduction in expression of the target gene. In some embodiments, the sd-RNA sequences used in the invention exhibit a reduction in expression of the target gene when delivered at a concentration of about 0.25 µM to about 10 µM, in some embodiments, about 0.25 µM to about 4 µM. In some embodiments, the sd-RNA sequences used in the invention exhibit a reduction in expression of the target gene when delivered at a concentration of about 0.25 µM. In some embodiments, the sd-RNA sequences used in the invention exhibit a reduction in expression of the target gene when delivered at a concentration of about 0.5 µM. In some embodiments, the sd-RNA sequences used in the invention exhibit a reduction in expression of the target gene when delivered at a concentration of about 0.75 µM. In some embodiments, the sd-RNA sequences used in the invention exhibit a reduction in expression of the target gene when delivered at a concentration of about 1.0 µM. In some embodiments, the sd-RNA sequences used in the invention exhibit a reduction in expression of the target gene when delivered at a concentration of about 1.25 µM. In some embodiments, the sd-RNA sequences used in the invention exhibit a reduction in expression of the target gene when delivered at a concentration of about 1.5 µM. In some embodiments, the sd-RNA sequences used in the invention exhibit a reduction in expression of the target gene when delivered at a concentration of about 1.75 µM. In some embodiments, the sd-RNA sequences used in the invention exhibit a reduction in expression of the target gene when delivered at a concentration of about 2.0 µM. In some embodiments, the sd-RNA sequences used in the invention exhibit a reduction in expression of the target gene when delivered at a concentration of about 2.25 µM. In some embodiments, the sd-RNA sequences used in the invention exhibit a reduction in expression of the target gene when delivered at a concentration of about 2.5 µM. In some embodiments, the sd-RNA sequences used in the invention exhibit a reduction in expression of the target gene when delivered at a concentration of about 2.75 µM. In some embodiments, the sd-RNA sequences used in the invention exhibit a reduction in expression of the target gene when delivered at a concentration of about 3.0 µM. In some embodiments, the sd-RNA sequences used in the invention exhibit a reduction in expression of the target gene when delivered at a concentration of about 3.25 µM. In some embodiments, the sd-RNA sequences used in the invention exhibit a reduction in expression of the target gene when delivered at a concentration of about 3.5 µM. In some embodiments, the sd-RNA sequences used in the invention exhibit a reduction in expression of the target gene when delivered at a concentration of about 3.75 µM. In some embodiments, the sd-RNA sequences used in the invention exhibit a reduction in expression of the target gene when delivered at a concentration of about 4.0 µM. In some embodiments, the sd-RNA sequences used in the invention exhibit a reduction in expression of the target gene when delivered at a concentration of about 5.0 µM. In some embodiments, the sd-RNA sequences used in the invention exhibit a reduction in expression of the target gene when delivered at a concentration of about 6.0 µM. In some embodiments, the sd-RNA sequences used in the invention exhibit a reduction in expression of the target gene when delivered at a concentration of about 7.0 µM. In some embodiments, the sd-RNA sequences used in the invention exhibit a reduction in expression of the target gene when delivered at a concentration of about 8.0 µM. In some embodiments, the sd-RNA sequences used in the invention exhibit a reduction in expression of the target gene when delivered at a concentration of about 9.0 µM. In some embodiments, the sd-RNA sequences used in the invention exhibit a reduction in expression of the target gene when delivered at a concentration of about 10.0 µM. In any of the foregoing embodiments, the concentrations specified may be determined with respect to TIL culture media before or after exchange of media.

In some embodiments, the sd-RNA sequences used in the invention exhibit a 70% reduction in expression of PD-1. In some embodiments, the sd-RNA sequences used in the invention exhibit a 75% reduction in expression of PD-1. In some embodiments, the sd-RNA sequences used in the invention exhibit an 80% reduction in expression of PD-1. In some embodiments, the sd-RNA sequences used in the invention exhibit an 85% reduction in expression of PD-1. In some embodiments, the sd-RNA sequences used in the invention exhibit a 90% reduction in expression of PD-1. In some embodiments, the sd-RNA sequences used in the invention exhibit a 95% reduction in expression of PD-1. In some embodiments, the sd-RNA sequences used in the invention exhibit a 99% reduction in expression PD-1. In some embodiments, the sd-RNA sequences used in the invention exhibit a reduction in expression of PD-1 when delivered at a concentration of about 0.25 µM to about 10 µM, in some embodiments, about 0.25 µM to about 4 µM. In some embodiments, the sd-RNA sequences used in the invention exhibit a reduction in expression of PD-1 when delivered at a concentration of about 0.25 µM. In some embodiments, the sd-RNA sequences used in the invention exhibit a reduction in expression of PD-1 when delivered at a concentration of about 0.5 µM. In some embodiments, the sd-RNA sequences used in the invention exhibit a reduction in expression of PD-1 when delivered at a concentration of about 0.75 µM. In some embodiments, the sd-RNA sequences used in the invention exhibit a reduction in expression of PD-1 when delivered at a concentration of about 1.0 µM. In some embodiments, the sd-RNA sequences used in the invention exhibit a reduction in expression of PD-1 when delivered at a concentration of about 1.25 µM. In some embodiments, the sd-RNA sequences used in the invention exhibit a reduction in expression of PD-1 when delivered at a concentration of about 1.5 µM. In some embodiments, the sd-RNA sequences used in the invention exhibit a reduction in expression of PD-1 when delivered at a concentration of about 1.75 µM. In some embodiments, the sd-RNA sequences used in the invention exhibit a reduction in expression of PD-1 when delivered at a concentration of about 2.0 µM. In some embodiments, the sd-RNA sequences used in the invention exhibit a reduction in expression of PD-1 when delivered at a concentration of about 2.25 µM. In some embodiments, the sd-RNA sequences used in the invention exhibit a reduction in expression of PD-1 when delivered at a concentration of about 2.5 µM. In some embodiments, the sd-RNA sequences used in the invention exhibit a reduction in expression of PD-1 when delivered at a concentration of about 2.75 µM. In some embodiments, the sd-RNA sequences used in the invention exhibit a reduction in expression of PD-1 when delivered at a concentration of about 3.0 µM. In some embodiments, the sd-RNA sequences used in the invention exhibit a reduction in expression of PD-1 when delivered at a concentration of about 3.25 µM. In some embodiments, the sd-RNA sequences used in the invention exhibit a reduction in expression of PD-1 when delivered at a concentration of about 3.5 µM. In some embodiments, the sd-RNA sequences used in the invention exhibit a reduction in expression of PD-1 when delivered at a concentration of about 3.75 µM. In some embodiments, the sd-RNA sequences used in the invention exhibit a reduction in expression of PD-1 when delivered at a concentration of about 4.0 µM. In some embodiments, the sd-RNA sequences used in the invention exhibit a reduction in expression of PD-1 when delivered at a concentration of about 5.0 µM. In some embodiments, the sd-RNA sequences used in the invention exhibit a reduction in expression of PD-1 when delivered at a concentration of about 6.0 µM. In some embodiments, the sd-RNA sequences used in the invention exhibit a reduction in expression of PD-1 when delivered at a concentration of about 7.0 µM. In some embodiments, the sd-RNA sequences used in the invention exhibit a reduction in expression of PD-1 when delivered at a concentration of about 8.0 µM. In some embodiments, the sd-RNA sequences used in the invention exhibit a reduction in expression of PD-1 when delivered at a concentration of about 9.0 µM. In some embodiments, the sd-RNA sequences used in the invention exhibit a reduction in expression of PD-1 when delivered at a concentration of about 10.0 µM. In any of the foregoing embodiments, the concentrations specified may be determined with respect to TIL culture media before or after exchange of media.

In some variant embodiments, the TILs are exposed to the sd-RNAs on at least two of Day 11, Day 14, Day 17, and/or Day 21 at an sd-RNA concentration of about 0.75 µM to about 3 µM. In some variant embodiments, the TILs are exposed to the sd-RNAs on at least three of Day 11, Day 14, Day 17, and/or Day 21 at an sd-RNA concentration of about 0.75 µM to about 3 µM. In some variant embodiments, the TILs are exposed to the sd-RNAs on all of Day 11, Day 14, Day 17, and Day 21 at an sd-RNA concentration of about 0.75 µM to about 3 µM. In some variant embodiments, the sd-RNA is added along with a media change at an sd-RNA concentration of about 0.75 µM to about 3 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.0 µM to about 2.5 µM. In some variant embodiments, the TILs are exposed to the sd-RNAs on at least three of Day 11, Day 14, Day 17, and/or Day 21 at an sd-RNA concentration of about 1.0 µM to about 2.5 µM. In some variant embodiments, the TILs are exposed to the sd-RNAs on all of Day 11, Day 14, Day 17, and Day 21 at an sd-RNA concentration of about 1.0 µM to about 2.5 µM. In some variant embodiments, the sd-RNA is added along with a media change at an sd-RNA concentration of about 1.0 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.5 µM to about 2.5 µM. In some variant embodiments, the TILs are exposed to the sd-RNAs on at least three of Day 11, Day 14, Day 17, and/or Day 21 at an sd-RNA concentration of about 1.5 µM to about 2.5 µM. In some variant embodiments, the TILs are exposed to the sd-RNAs on all of Day 11, Day 14, Day 17, and Day 21 at an sd-RNA concentration of about 1.5 µM to about 2.5 µM. In some variant embodiments, the sd-RNA is added along with a media change at an sd-RNA concentration of about 1.5 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of 2 µM. In some variant embodiments, the TILs are exposed to the sd-RNAs on at least three of Day 11, Day 14, Day 17, and/or Day 21 at an sd-RNA concentration of about 2 µM. In some variant embodiments, the TILs are exposed to the sd-RNAs on all of Day 11, Day 14, Day 17, and Day 21 at an sd-RNA concentration of about 2 µM. In some variant embodiments, the sd-RNA is added along with a media change at an sd-RNA concentration of about 2 µM. In some embodiments, the sd-RNA targets PD-1.

In some embodiments, the sd-RNA added at Day 11 is added in media comprising sd-RNA, IL-2, OKT3 and APCs (including, for example, PBMCs). In some embodiments, the sd-RNA added at Day 14 is added in media comprising sd-RNA and optionally includes one or more of IL-2, OKT3 and APCs (including, for example, PBMCs). In some embodiments, the sd-RNA added at Day 17 is added in media comprising sd-RNA and optionally includes one or more of IL-2, OKT3 and APCs (including, for example, PBMCs). In some embodiments, the sd-RNA added at Day 21 is added in media comprising sd-RNA and optionally includes one or more of IL-2, OKT3 and APCs (including, for example, PBMCs). In some embodiments, the sd-RNA added at Day 14 is added in media comprising sd-RNA and IL-2. In some embodiments, the sd-RNA added at Day 17 is added in media comprising sd-RNA and IL-2. In some embodiments, the sd-RNA added at Day 21 is added in media comprising sd-RNA and IL-2. In some embodiments, more sd-RNA is added at Day 14. In some embodiments, more sd-RNA added at Day 17. In some embodiments, more sd-RNA added at Day 21. In some embodiments, the sd-RNA is added at the same concentration at Day 11, Day 14, Day 17, and Day 21. In some embodiments, the sd-RNA is added at a different concentration at Day 11, Day 14, Day 17 and/or Day 21. In some embodiments, the sd-RNA targets PD-1.

Example 35: Variant Embodiments of Example 23

According the methods discussed in Example 23, methods of expanding TILs in combination with transiently altering protein expression are described. This example provides further varied embodiments in line with the methods described in Example 23.

In some embodiments of the above described method, a method for expanding tumor infiltrating lymphocytes (TILs) into a therapeutic population of TILs is provided which comprises:

(a) obtaining a first population of TILs from a tumor resected from a patient by processing a tumor sample obtained from the patient into multiple tumor fragments;

(b) adding the tumor fragments into a closed system;

(c) performing a first expansion by culturing the first population of TILs in a cell culture medium comprising IL-2 and optionally comprising a 4-1BB agonist antibody for about 2 to 5 days;

(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;

(e) resting the second population of TILs for about 1 day;

(f) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (e) to step (f) occurs without opening the system;

(g) contacting the second population of TILs during any of steps (d), (e), and/or (f), including between days 11 and 21, with at least one sd-RNA, wherein the sd-RNA is added at a concentration of 0.1 µM sd-RNA/10,000 TILs, 0.5 µM sd-RNA/10,000 TILs, 0.75 µM sd-RNA/10,000 TILs, 1 µM sd-RNA/10,000 TILs, 1.25 µM sd-RNA/10,000 TILs, 1.5 µM sd-RNA/10,000 TILs, 2 µM sd-RNA/10,000 TILs, 5 µM sd-RNA/10,000 TILs, or 10 μM sd-RNA/10,000 TILs, and wherein the sd-RNA is for inhibiting the expression of a molecule selected from the group consisting of PD-1, LAG-3, TIM-3, CISH, and CBLB, and combinations thereof;

(h) optionally performing a sterile electroporation step on the second population of TILs, wherein the sterile electroporation step mediates the transfer of the at least one sd-RNA;

(i) harvesting the therapeutic population of TILs obtained from steps (g) or (h) to provide a harvested TIL population, wherein the transitions from step (e) to step (h) occur without opening the system, wherein the harvested population of TILs is a therapeutic population of TILs;

(j) transferring the harvested TIL population from step (i) to an infusion bag, wherein the transfer from step (h) to (i) occurs without opening the system; and (k) cryopreserving the harvested TIL population using a dimethylsulfoxide-based cryopreservation medium.

In some variant embodiments, the other molecules capable of transiently altering protein expression comprise sd-RNAs, including for example but not limited to, sd-rxRNAs. In some embodiments, the TILs are exposed to the sd-RNAs on Day 11, Day 14, Day 17, and/or Day 21. In some variant embodiments, the TILs are exposed to the sd-RNAs on at least two of Day 11, Day 14, Day 17, and/or Day 21. In some variant embodiments, the TILs are exposed to the sd-RNAs on at least three of Day 11, Day 14, Day 17, and/or Day 21. In some variant embodiments, the TILs are exposed to the sd-RNAs on all of Day 11, Day 14, Day 17, and Day 21. In some embodiments, the sd-RNA targets PD-1.

In some embodiments, the sd-RNA sequences used in the invention exhibit a 70% reduction in expression of the target gene. In some embodiments, the sd-RNA sequences used in the invention exhibit a 75% reduction in expression of the target gene. In some embodiments, the sd-RNA sequences used in the invention exhibit an 80% reduction in expression of the target gene. In some embodiments, the sd-RNA sequences used in the invention exhibit an 85% reduction in expression of the target gene. In some embodiments, the sd-RNA sequences used in the invention exhibit a 90% reduction in expression of the target gene. In some embodiments, the sd-RNA sequences used in the invention exhibit a 95% reduction in expression of the target gene. In some embodiments, the sd-RNA sequences used in the invention exhibit a 99% reduction in expression of the target gene. In some embodiments, the sd-RNA sequences used in the invention exhibit a reduction in expression of the target gene when delivered at a concentration of about 0.25 μM to about 10 μM, in some embodiments, about 0.25 μM to about 4 μM. In some embodiments, the sd-RNA sequences used in the invention exhibit a reduction in expression of the target gene when delivered at a concentration of about 0.25 μM. In some embodiments, the sd-RNA sequences used in the invention exhibit a reduction in expression of the target gene when delivered at a concentration of about 0.5 μM. In some embodiments, the sd-RNA sequences used in the invention exhibit a reduction in expression of the target gene when delivered at a concentration of about 0.75 μM. In some embodiments, the sd-RNA sequences used in the invention exhibit a reduction in expression of the target gene when delivered at a concentration of about 1.0 μM. In some embodiments, the sd-RNA sequences used in the invention exhibit a reduction in expression of the target gene when delivered at a concentration of about 1.25 μM. In some embodiments, the sd-RNA sequences used in the invention exhibit a reduction in expression of the target gene when delivered at a concentration of about 1.5 μM. In some embodiments, the sd-RNA sequences used in the invention exhibit a reduction in expression of the target gene when delivered at a concentration of about 1.75 μM. In some embodiments, the sd-RNA sequences used in the invention exhibit a reduction in expression of the target gene when delivered at a concentration of about 2.0 μM. In some embodiments, the sd-RNA sequences used in the invention exhibit a reduction in expression of the target gene when delivered at a concentration of about 2.25 μM. In some embodiments, the sd-RNA sequences used in the invention exhibit a reduction in expression of the target gene when delivered at a concentration of about 2.5 μM. In some embodiments, the sd-RNA sequences used in the invention exhibit a reduction in expression of the target gene when delivered at a concentration of about 2.75 μM. In some embodiments, the sd-RNA sequences used in the invention exhibit a reduction in expression of the target gene when delivered at a concentration of about 3.0 μM. In some embodiments, the sd-RNA sequences used in the invention exhibit a reduction in expression of the target gene when delivered at a concentration of about 3.25 μM. In some embodiments, the sd-RNA sequences used in the invention exhibit a reduction in expression of the target gene when delivered at a concentration of about 3.5 μM. In some embodiments, the sd-RNA sequences used in the invention exhibit a reduction in expression of the target gene when delivered at a concentration of about 3.75 μM. In some embodiments, the sd-RNA sequences used in the invention exhibit a reduction in expression of the target gene when delivered at a concentration of about 4.0 μM. In some embodiments, the sd-RNA sequences used in the invention exhibit a reduction in expression of the target gene when delivered at a concentration of about 5.0 μM. In some embodiments, the sd-RNA sequences used in the invention exhibit a reduction in expression of the target gene when delivered at a concentration of about 6.0 μM. In some embodiments, the sd-RNA sequences used in the invention exhibit a reduction in expression of the target gene when delivered at a concentration of about 7.0 μM. In some embodiments, the sd-RNA sequences used in the invention exhibit a reduction in expression of the target gene when delivered at a concentration of about 8.0 μM. In some embodiments, the sd-RNA sequences used in the invention exhibit a reduction in expression of the target gene when delivered at a concentration of about 9.0 μM. In some embodiments, the sd-RNA sequences used in the invention exhibit a reduction in expression of the target gene when delivered at a concentration of about 10.0 μM. In any of the foregoing embodiments, the concentrations specified may be determined with respect to TIL culture media before or after exchange of media.

In some embodiments, the sd-RNA sequences used in the invention exhibit a 70% reduction in expression of PD-1. In some embodiments, the sd-RNA sequences used in the invention exhibit a 75% reduction in expression of PD-1. In some embodiments, the sd-RNA sequences used in the invention exhibit an 80% reduction in expression of PD-1. In some embodiments, the sd-RNA sequences used in the invention exhibit an 85% reduction in expression of PD-1. In some embodiments, the sd-RNA sequences used in the invention exhibit a 90% reduction in expression of PD-1. In some embodiments, the sd-RNA sequences used in the invention exhibit a 95% reduction in expression of PD-1. In some embodiments, the sd-RNA sequences used in the invention exhibit a 99% reduction in expression PD-1. In some embodiments, the sd-RNA sequences used in the invention exhibit a reduction in expression of PD-1 when delivered at a concentration of about 0.25 µM to about 10 µM, in some embodiments, about 0.25 µM to about 4 µM. In some embodiments, the sd-RNA sequences used in the invention exhibit a reduction in expression of PD-1 when delivered at a concentration of about 0.25 µM. In some embodiments, the sd-RNA sequences used in the invention exhibit a reduction in expression of PD-1 when delivered at a concentration of about 0.5 µM. In some embodiments, the sd-RNA sequences used in the invention exhibit a reduction in expression of PD-1 when delivered at a concentration of about 0.75 µM. In some embodiments, the sd-RNA sequences used in the invention exhibit a reduction in expression of PD-1 when delivered at a concentration of about 1.0 µM. In some embodiments, the sd-RNA sequences used in the invention exhibit a reduction in expression of PD-1 when delivered at a concentration of about 1.25 µM. In some embodiments, the sd-RNA sequences used in the invention exhibit a reduction in expression of PD-1 when delivered at a concentration of about 1.5 µM. In some embodiments, the sd-RNA sequences used in the invention exhibit a reduction in expression of PD-1 when delivered at a concentration of about 1.75 µM. In some embodiments, the sd-RNA sequences used in the invention exhibit a reduction in expression of PD-1 when delivered at a concentration of about 2.0 µM. In some embodiments, the sd-RNA sequences used in the invention exhibit a reduction in expression of PD-1 when delivered at a concentration of about 2.25 µM. In some embodiments, the sd-RNA sequences used in the invention exhibit a reduction in expression of PD-1 when delivered at a concentration of about 2.5 µM. In some embodiments, the sd-RNA sequences used in the invention exhibit a reduction in expression of PD-1 when delivered at a concentration of about 2.75 µM. In some embodiments, the sd-RNA sequences used in the invention exhibit a reduction in expression of PD-1 when delivered at a concentration of about 3.0 µM. In some embodiments, the sd-RNA sequences used in the invention exhibit a reduction in expression of PD-1 when delivered at a concentration of about 3.25 µM. In some embodiments, the sd-RNA sequences used in the invention exhibit a reduction in expression of PD-1 when delivered at a concentration of about 3.5 µM. In some embodiments, the sd-RNA sequences used in the invention exhibit a reduction in expression of PD-1 when delivered at a concentration of about 3.75 µM. In some embodiments, the sd-RNA sequences used in the invention exhibit a reduction in expression of PD-1 when delivered at a concentration of about 4.0 µM. In some embodiments, the sd-RNA sequences used in the invention exhibit a reduction in expression of PD-1 when delivered at a concentration of about 5.0 µM. In some embodiments, the sd-RNA sequences used in the invention exhibit a reduction in expression of PD-1 when delivered at a concentration of about 6.0 µM. In some embodiments, the sd-RNA sequences used in the invention exhibit a reduction in expression of PD-1 when delivered at a concentration of about 7.0 µM. In some embodiments, the sd-RNA sequences used in the invention exhibit a reduction in expression of PD-1 when delivered at a concentration of about 8.0 µM. In some embodiments, the sd-RNA sequences used in the invention exhibit a reduction in expression of PD-1 when delivered at a concentration of about 9.0 µM. In some embodiments, the sd-RNA sequences used in the invention exhibit a reduction in expression of PD-1 when delivered at a concentration of about 10.0 µM. In any of the foregoing embodiments, the concentrations specified may be determined with respect to TIL culture media before or after exchange of media.

In some variant embodiments, the TILs are exposed to the sd-RNAs on at least two of Day 11, Day 14, Day 17, and/or Day 21 at an sd-RNA concentration of about 0.75 µM to about 3 µM. In some variant embodiments, the TILs are exposed to the sd-RNAs on at least three of Day 11, Day 14, Day 17, and/or Day 21 at an sd-RNA concentration of about 0.75 µM to about 3 µM. In some variant embodiments, the TILs are exposed to the sd-RNAs on all of Day 11, Day 14, Day 17, and Day 21 at an sd-RNA concentration of about 0.75 µM to about 3 µM. In some variant embodiments, the sd-RNA is added along with a media change at an sd-RNA concentration of about 0.75 µM to about 3 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.0 µM to about 2.5 µM. In some variant embodiments, the TILs are exposed to the sd-RNAs on at least three of Day 11, Day 14, Day 17, and/or Day 21 at an sd-RNA concentration of about 1.0 µM to about 2.5 µM. In some variant embodiments, the TILs are exposed to the sd-RNAs on all of Day 11, Day 14, Day 17, and Day 21 at an sd-RNA concentration of about 1.0 µM to about 2.5 µM. In some variant embodiments, the sd-RNA is added along with a media change at an sd-RNA concentration of about 1.0 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of about 1.5 µM to about 2.5 µM. In some variant embodiments, the TILs are exposed to the sd-RNAs on at least three of Day 11, Day 14, Day 17, and/or Day 21 at an sd-RNA concentration of about 1.5 µM to about 2.5 µM. In some variant embodiments, the TILs are exposed to the sd-RNAs on all of Day 11, Day 14, Day 17, and Day 21 at an sd-RNA concentration of about 1.5 µM to about 2.5 µM. In some variant embodiments, the sd-RNA is added along with a media change at an sd-RNA concentration of about 1.5 µM to about 2.5 µM. In some embodiments, the sd-RNA targets PD-1.

In some variant embodiments, the TILs are exposed to the sd-RNAs on at least two of Day 11, Day 14, Day 17, and/or Day 21 at an sd-RNA concentration of 2 µM. In some variant embodiments, the TILs are exposed to the sd-RNAs on at least three of Day 11, Day 14, Day 17, and/or Day 21 at an sd-RNA concentration of about 2 µM. In some variant embodiments, the TILs are exposed to the sd-RNAs on all of Day 11, Day 14, Day 17, and Day 21 at an sd-RNA concentration of about 2 µM. In some variant embodiments, the sd-RNA is added along with a media change at an sd-RNA concentration of about 2 µM. In some embodiments, the sd-RNA targets PD-1.

In some embodiments, the sd-RNA added at Day 11 is added in media comprising sd-RNA, IL-2, OKT3 and APCs (including, for example, PBMCs). In some embodiments, the sd-RNA added at Day 14 is added in media comprising sd-RNA and optionally includes one or more of IL-2, OKT3 and APCs (including, for example, PBMCs). In some embodiments, the sd-RNA added at Day 17 is added in media comprising sd-RNA and optionally includes one or more of IL-2, OKT3 and APCs (including, for example, PBMCs). In some embodiments, the sd-RNA added at Day 21 is added in media comprising sd-RNA and optionally includes one or more of IL-2, OKT3 and APCs (including, for example, PBMCs). In some embodiments, the sd-RNA added at Day 14 is added in media comprising sd-RNA and IL-2. In some embodiments, the sd-RNA added at Day 17 is added in media comprising sd-RNA and IL-2. In some embodiments, the sd-RNA added at Day 21 is added in media comprising sd-RNA and IL-2. In some embodiments, more sd-RNA is added at Day 14. In some embodiments, more sd-RNA added at Day 17. In some embodiments, more sd-RNA added at Day 21. In some embodiments, the sd-RNA is added at the same concentration at Day 11, Day 14, Day 17, and Day 21. In some embodiments, the sd-RNA is added at a different concentration at Day 11, Day 14, Day 17 and/or Day 21. In some embodiments, the sd-RNA targets PD-1.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A method for expanding tumor infiltrating lymphocytes (TILs) into a therapeutic population of TILs comprising exposing TILs to transcription factors (TFs) and/or other molecules capable of transiently altering protein expression in order to generate a therapeutic population of TILs, wherein the TFs and/or other molecules capable of transiently altering protein expression provide for an increase in the number of tumor antigen-specific T cells in the therapeutic population of TILs, wherein the TFs are selected from TCF-1, NOTCH 1/2 ICD, and/or MYB and the other molecules capable of transiently altering protein expression are selected from one or more sd-RNAs, wherein the transient alteration of protein expression targets a gene selected from the group consisting of PD-1, CTLA-4, TIGIT, LAG-3, TIM-3, CISH, CBLB and combinations thereof, wherein the method comprises:
  a) performing a first expansion of a first population of TILs, which have been obtained from a tumor resected from a patient which has been processed into multiple tumor fragments, by culturing the first population of TILs in a cell culture medium comprising IL-2 to form a second population of TILs, wherein the first expansion proceeds for 3 to 12 days; and
  b) performing a second expansion by supplementing the cell culture medium of the second population of TILs with additional IL-2, OKT-3 and antigen-presenting cells (APCs) to produce a third population of TILs, wherein the third population of TILs is a therapeutic population of TILs, and wherein the second expansion proceeds for 7 to 12 days.

2. The method according to claim 1, wherein the first expansion proceeds for 3 days to 11 days.

3. The method according to claim 1, wherein the first expansion in step (a) and the second expansion in step (b) are each individually performed within a period of 10 days, 11 days, or 12 days.

4. The method according to claim 1, wherein the transient altering of protein expression results in induction of protein expression.

5. The method according to claim 1, wherein the transient altering of protein expression results in a reduction of protein expression.

6. The method according to claim 1, wherein first expansion is performed in a closed container and the second expansion is performed in a closed container, wherein the transition from step (a) to step (b) occurs in a closed system.

7. The method according to claim 1, wherein the first expansion is performed in a closed container providing a first gas-permeable surface area, wherein the second population of TILs is at least 50-fold greater in number than the first population of TILs, and wherein the second expansion is performed in a closed container providing a second gas-permeable surface area, and wherein the transition from step (a) to step (b) occurs in a closed system; and the method further comprises:
   c) exposing the second and/or third population of TILs to the TFs and/or other molecules capable of transiently altering protein expression between days 11 and 21 after initiation of step (a); and
   d) harvesting the therapeutic population of TILs obtained from step (c) at day 22 or after, wherein the transition from step (b) to step (c) occurs in the closed system; and
   e) transferring the harvested TIL population from step (d) to an infusion bag, wherein the transfer from step (d) to (e) occurs in the closed system.

8. The method according to claim 7, which further comprises a step of cryopreserving the infusion bag comprising the harvested TIL population in step e) using a cryopreservation process.

9. The method according to claim 8, wherein the cryopreservation process is performed using a 1:1 ratio of harvested TIL population to cryopreservation media, wherein the cryopreservation media comprises dimethylsulfoxide (DMSO) and comprises 7% to 10% dimethylsulfoxide (DMSO).

10. The method according to claim 1, wherein the antigen-presenting cells are peripheral blood mononuclear cells (PBMCs).

11. The method according to claim 1, wherein the antigen-presenting cells are artificial antigen-presenting cells.

12. The method according to claim 1, wherein the multiple fragments comprise about 4 to about 50 fragments, wherein each fragment has a volume of about 27 $mm^3$ or wherein the multiple fragments comprise about 30 to about 60 fragments with a total volume of about 1300 $mm^3$ to about 1500 $mm^3$ or wherein the multiple fragments comprise about 50 fragments with a total volume of about 1350 $mm^3$ or wherein the multiple fragments comprise about 50 fragments with a total mass of about 1 gram to about 1.5 grams.

13. The method according to claim 1, wherein the cell culture medium in step (b) further comprises IL-15 and/or IL-21, wherein the IL-2 concentration is about 10,000 IU/mL to about 5,000 IU/mL and wherein the IL-15 concentration is about 500 IU/mL to about 100 IU/mL and wherein the IL-21 concentration is about 20 IU/mL to about 0.5 IU/mL.

* * * * *

SEQUENCE LISTING

```
<160> NUMBER OF SEQ ID NOS: 126

<210> SEQ ID NO 1
<211> LENGTH: 450
<212> TYPE: PRT
<213> ORGANISM: Artificial Sequence
<220> FEATURE:
<223> OTHER INFORMATION: Muromonab heavy chain

<400> SEQUENCE: 1

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Leu Thr Val Ser Ser Ala Lys Thr Thr Ala Pro Ser Val Tyr
            115                 120                 125

Pro Leu Ala Pro Val Cys Gly Gly Thr Thr Gly Ser Ser Val Thr Leu
        130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
                180                 185                 190

Thr Trp Pro Ser Gln Ser Ile Thr Cys Asn Val Ala His Pro Ala Ser
            195                 200                 205
```

Ser Thr Lys Val Asp Lys Lys Ile Glu Pro Arg Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 2
<211> LENGTH: 213
<212> TYPE: PRT
<213> ORGANISM: Artificial Sequence
<220> FEATURE:
<223> OTHER INFORMATION: Muromonab light chain

<400> SEQUENCE: 2

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Ala Asp Thr Ala Pro
                100                 105                 110

```
Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 3
<211> LENGTH: 134
<212> TYPE: PRT
<213> ORGANISM: Artificial Sequence
<220> FEATURE:
<223> OTHER INFORMATION: recombinant human IL-2 (rhIL-2)

<400> SEQUENCE: 3

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130

<210> SEQ ID NO 4
<211> LENGTH: 132
<212> TYPE: PRT
<213> ORGANISM: Artificial Sequence
<220> FEATURE:
<223> OTHER INFORMATION: Aldesleukin

<400> SEQUENCE: 4

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60
```

```
Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Leu Glu Leu Lys
             85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 5
<211> LENGTH: 130
<212> TYPE: PRT
<213> ORGANISM: Artificial Sequence
<220> FEATURE:
<223> OTHER INFORMATION: recombinant human IL-4 (rhIL-4)

<400> SEQUENCE: 5

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Asn Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
        115                 120                 125

Ser Ser
    130

<210> SEQ ID NO 6
<211> LENGTH: 153
<212> TYPE: PRT
<213> ORGANISM: Artificial Sequence
<220> FEATURE:
<223> OTHER INFORMATION: recombinant human IL-7 (rhIL-7)

<400> SEQUENCE: 6

Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30

Ser Asn Cys Leu Asn Asn Glu Phe Asn Phe Phe Lys Arg His Ile Cys
        35                  40                  45

Asp Ala Asn Lys Glu Gly Met Phe Leu Phe Arg Ala Ala Arg Lys Leu
    50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
```

```
                85                  90                  95
Val Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
            115                 120                 125

Leu Cys Phe Leu Lys Arg Leu Leu Gln Glu Ile Lys Thr Cys Trp Asn
130                 135                 140

Lys Ile Leu Met Gly Thr Lys Glu His
145                 150

<210> SEQ ID NO 7
<211> LENGTH: 115
<212> TYPE: PRT
<213> ORGANISM: Artificial Sequence
<220> FEATURE:
<223> OTHER INFORMATION: recombinant human IL-15 (rhIL-15)

<400> SEQUENCE: 7

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 8
<211> LENGTH: 132
<212> TYPE: PRT
<213> ORGANISM: Artificial Sequence
<220> FEATURE:
<223> OTHER INFORMATION: recombinant human IL-21 (rhIL-21)

<400> SEQUENCE: 8

Met Gln Asp Arg His Met Ile Arg Met Arg Gln Leu Ile Asp Ile Val
1               5                   10                  15

Asp Gln Leu Lys Asn Tyr Val Asn Asp Leu Val Pro Glu Phe Leu Pro
            20                  25                  30

Ala Pro Glu Asp Val Glu Thr Asn Cys Glu Trp Ser Ala Phe Ser Cys
        35                  40                  45

Phe Gln Lys Ala Gln Leu Lys Ser Ala Asn Thr Gly Asn Asn Glu Arg
    50                  55                  60

Ile Ile Asn Val Ser Ile Lys Lys Leu Lys Arg Lys Pro Pro Ser Thr
65                  70                  75                  80

Asn Ala Gly Arg Arg Gln Lys His Arg Leu Thr Cys Pro Ser Cys Asp
                85                  90                  95

Ser Tyr Glu Lys Lys Pro Pro Lys Glu Phe Leu Glu Arg Phe Lys Ser
            100                 105                 110
```

```
Leu Leu Gln Lys Met Ile His Gln His Leu Ser Ser Arg Thr His Gly
            115                 120                 125

Ser Glu Asp Ser
        130

<210> SEQ ID NO 9
<211> LENGTH: 255
<212> TYPE: PRT
<213> ORGANISM: Artificial Sequence
<220> FEATURE:
<223> OTHER INFORMATION: human 4-1BB, Tumor necrosis factor receptor
      superfamily, member 9 (Homo sapiens)

<400> SEQUENCE: 9

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 10
<211> LENGTH: 256
<212> TYPE: PRT
<213> ORGANISM: Artificial Sequence
<220> FEATURE:
<223> OTHER INFORMATION: murine 4-1BB, Tumor necrosis factor receptor
      superfamily, member 9 (Mus musculus)

<400> SEQUENCE: 10

Met Gly Asn Asn Cys Tyr Asn Val Val Val Ile Val Leu Leu Leu Val
1               5                   10                  15
```

Gly Cys Glu Lys Val Gly Ala Val Gln Asn Ser Cys Asp Asn Cys Gln
                20                  25                  30

Pro Gly Thr Phe Cys Arg Lys Tyr Asn Pro Val Cys Lys Ser Cys Pro
            35                  40                  45

Pro Ser Thr Phe Ser Ser Ile Gly Gly Gln Pro Asn Cys Asn Ile Cys
50                  55                  60

Arg Val Cys Ala Gly Tyr Phe Arg Phe Lys Lys Phe Cys Ser Ser Thr
65                  70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
            100                 105                 110

Lys Gln Gly Cys Lys Thr Cys Ser Leu Gly Thr Phe Asn Asp Gln Asn
        115                 120                 125

Gly Thr Gly Val Cys Arg Pro Trp Thr Asn Cys Ser Leu Asp Gly Arg
    130                 135                 140

Ser Val Leu Lys Thr Gly Thr Thr Glu Lys Asp Val Val Cys Gly Pro
145                 150                 155                 160

Pro Val Val Ser Phe Ser Pro Ser Thr Thr Ile Ser Val Thr Pro Glu
                165                 170                 175

Gly Gly Pro Gly Gly His Ser Leu Gln Val Leu Thr Leu Phe Leu Ala
            180                 185                 190

Leu Thr Ser Ala Leu Leu Leu Ala Leu Ile Phe Ile Thr Leu Leu Phe
        195                 200                 205

Ser Val Leu Lys Trp Ile Arg Lys Lys Phe Pro His Ile Phe Lys Gln
210                 215                 220

Pro Phe Lys Lys Thr Thr Gly Ala Ala Gln Glu Glu Asp Ala Cys Ser
225                 230                 235                 240

Cys Arg Cys Pro Gln Glu Glu Glu Gly Gly Gly Gly Gly Tyr Glu Leu
                245                 250                 255

<210> SEQ ID NO 11
<211> LENGTH: 441
<212> TYPE: PRT
<213> ORGANISM: Artificial Sequence
<220> FEATURE:
<223> OTHER INFORMATION: heavy chain for utomilumab

<400> SEQUENCE: 11

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
                20                  25                  30

Trp Ile Ser Trp Val Arg Gln Met Pro Gly Lys Gly Leu Glu Trp Met
            35                  40                  45

Gly Lys Ile Tyr Pro Gly Asp Ser Tyr Thr Asn Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

```
Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
        435                 440

<210> SEQ ID NO 12
<211> LENGTH: 214
<212> TYPE: PRT
<213> ORGANISM: Artificial Sequence
<220> FEATURE:
<223> OTHER INFORMATION: light chain for utomilumab

<400> SEQUENCE: 12

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45
```

```
Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Ala Thr Tyr Thr Gly Phe Gly Ser Leu
                 85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
210

<210> SEQ ID NO 13
<211> LENGTH: 116
<212> TYPE: PRT
<213> ORGANISM: Artificial Sequence
<220> FEATURE:
<223> OTHER INFORMATION: heavy chain variable region for utomilumab

<400> SEQUENCE: 13

Glu Val Gln Leu Val Gln Ser Gly Ala Glu Val Lys Lys Pro Gly Glu
1               5                  10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Tyr Gly Ile Phe Asp Tyr Trp Gly Gln Gly Thr Leu Val
            100                 105                 110

Thr Val Ser Ser
        115

<210> SEQ ID NO 14
<211> LENGTH: 108
<212> TYPE: PRT
<213> ORGANISM: Artificial Sequence
<220> FEATURE:
<223> OTHER INFORMATION: light chain variable region for utomilumab

<400> SEQUENCE: 14

Ser Tyr Glu Leu Thr Gln Pro Pro Ser Val Ser Val Ser Pro Gly Gln
1               5                  10                  15
```

```
Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu
            100                 105

<210> SEQ ID NO 15
<211> LENGTH: 6
<212> TYPE: PRT
<213> ORGANISM: Artificial Sequence
<220> FEATURE:
<223> OTHER INFORMATION: heavy chain CDR1 for utomilumab

<400> SEQUENCE: 15

Ser Thr Tyr Trp Ile Ser
1               5

<210> SEQ ID NO 16
<211> LENGTH: 17
<212> TYPE: PRT
<213> ORGANISM: Artificial Sequence
<220> FEATURE:
<223> OTHER INFORMATION: heavy chain CDR2 for utomilumab

<400> SEQUENCE: 16

Lys Ile Tyr Pro Gly Asp Ser Tyr Thr Asn Tyr Ser Pro Ser Phe Gln
1               5                   10                  15

Gly

<210> SEQ ID NO 17
<211> LENGTH: 8
<212> TYPE: PRT
<213> ORGANISM: Artificial Sequence
<220> FEATURE:
<223> OTHER INFORMATION: heavy chain CDR3 for utomilumab

<400> SEQUENCE: 17

Arg Gly Tyr Gly Ile Phe Asp Tyr
1               5

<210> SEQ ID NO 18
<211> LENGTH: 11
<212> TYPE: PRT
<213> ORGANISM: Artificial Sequence
<220> FEATURE:
<223> OTHER INFORMATION: light chain CDR1 for utomilumab

<400> SEQUENCE: 18

Ser Gly Asp Asn Ile Gly Asp Gln Tyr Ala His
1               5                   10

<210> SEQ ID NO 19
<211> LENGTH: 7
<212> TYPE: PRT
<213> ORGANISM: Artificial Sequence
<220> FEATURE:
```

<223> OTHER INFORMATION: light chain CDR2 for utomilumab

<400> SEQUENCE: 19

Gln Asp Lys Asn Arg Pro Ser
1               5

<210> SEQ ID NO 20
<211> LENGTH: 11
<212> TYPE: PRT
<213> ORGANISM: Artificial Sequence
<220> FEATURE:
<223> OTHER INFORMATION: light chain CDR3 for utomilumab

<400> SEQUENCE: 20

Ala Thr Tyr Thr Gly Phe Gly Ser Leu Ala Val
1               5                   10

<210> SEQ ID NO 21
<211> LENGTH: 448
<212> TYPE: PRT
<213> ORGANISM: Artificial Sequence
<220> FEATURE:
<223> OTHER INFORMATION: heavy chain for urelumab

<400> SEQUENCE: 21

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro

```
                  260                 265                 270
Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 22
<211> LENGTH: 216
<212> TYPE: PRT
<213> ORGANISM: Artificial Sequence
<220> FEATURE:
<223> OTHER INFORMATION: light chain for urelumab

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Cys Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
```

```
                180             185             190
Val Tyr Ala Cys Glu Val Thr His Gln Gly Leu Ser Ser Pro Val Thr
            195                 200                 205

Lys Ser Phe Asn Arg Gly Glu Cys
            210                 215

<210> SEQ ID NO 23
<211> LENGTH: 120
<212> TYPE: PRT
<213> ORGANISM: Artificial Sequence
<220> FEATURE:
<223> OTHER INFORMATION: variable heavy chain for urelumab

<400> SEQUENCE: 23

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Ser Pro Glu Lys Gly Leu
    50                  55                  60

Glu Trp Ile Gly Glu Ile Asn His Gly Gly Tyr Val Thr Tyr Asn Pro
65                  70                  75                  80

Ser Leu Glu Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Tyr Gly Pro
        115                 120

<210> SEQ ID NO 24
<211> LENGTH: 110
<212> TYPE: PRT
<213> ORGANISM: Artificial Sequence
<220> FEATURE:
<223> OTHER INFORMATION: variable light chain for urelumab

<400> SEQUENCE: 24

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln
            100                 105                 110

<210> SEQ ID NO 25
<211> LENGTH: 5
<212> TYPE: PRT
<213> ORGANISM: Artificial Sequence
<220> FEATURE:
```

-continued

```
<223> OTHER INFORMATION: heavy chain CDR1 for urelumab

<400> SEQUENCE: 25

Gly Tyr Tyr Trp Ser
1               5

<210> SEQ ID NO 26
<211> LENGTH: 16
<212> TYPE: PRT
<213> ORGANISM: Artificial Sequence
<220> FEATURE:
<223> OTHER INFORMATION: heavy chain CDR2 for urelumab

<400> SEQUENCE: 26

Glu Ile Asn His Gly Gly Tyr Val Thr Tyr Asn Pro Ser Leu Glu Ser
1               5                   10                  15

<210> SEQ ID NO 27
<211> LENGTH: 13
<212> TYPE: PRT
<213> ORGANISM: Artificial Sequence
<220> FEATURE:
<223> OTHER INFORMATION: heavy chain CDR3 for urelumab

<400> SEQUENCE: 27

Asp Tyr Gly Pro Gly Asn Tyr Asp Trp Tyr Phe Asp Leu
1               5                   10

<210> SEQ ID NO 28
<211> LENGTH: 11
<212> TYPE: PRT
<213> ORGANISM: Artificial Sequence
<220> FEATURE:
<223> OTHER INFORMATION: light chain CDR1 for urelumab

<400> SEQUENCE: 28

Arg Ala Ser Gln Ser Val Ser Ser Tyr Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: light chain CDR2 for urelumab

<400> SEQUENCE: 29

Asp Ala Ser Asn Arg Ala Thr
1               5

<210> SEQ ID NO 30
<211> LENGTH: 11
<212> TYPE: PRT
<213> ORGANISM: Artificial Sequence
<220> FEATURE:
<223> OTHER INFORMATION: light chain CDR3 for urelumab

<400> SEQUENCE: 30

Gln Gln Arg Ser Asp Trp Pro Pro Ala Leu Thr
1               5                   10

<210> SEQ ID NO 31
<211> LENGTH: 230
<212> TYPE: PRT
<213> ORGANISM: Artificial Sequence
<220> FEATURE:
<223> OTHER INFORMATION: Fc domain
```

<400> SEQUENCE: 31

Lys Ser Cys Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225             230

<210> SEQ ID NO 32
<211> LENGTH: 22
<212> TYPE: PRT
<213> ORGANISM: Artificial Sequence
<220> FEATURE:
<223> OTHER INFORMATION: linker

<400> SEQUENCE: 32

Gly Gly Pro Gly Ser Ser Lys Ser Cys Asp Lys Thr His Thr Cys Pro
1               5                   10                  15

Pro Cys Pro Ala Pro Glu
            20

<210> SEQ ID NO 33
<211> LENGTH: 22
<212> TYPE: PRT
<213> ORGANISM: Artificial Sequence
<220> FEATURE:
<223> OTHER INFORMATION: linker

<400> SEQUENCE: 33

Gly Gly Ser Gly Ser Ser Lys Ser Cys Asp Lys Thr His Thr Cys Pro
1               5                   10                  15

Pro Cys Pro Ala Pro Glu
            20

<210> SEQ ID NO 34
<211> LENGTH: 27
<212> TYPE: PRT
<213> ORGANISM: Artificial Sequence
<220> FEATURE:
<223> OTHER INFORMATION: linker

<400> SEQUENCE: 34

Gly Gly Pro Gly Ser Ser Ser Ser Ser Ser Lys Ser Cys Asp Lys
1               5                   10                  15

Thr His Thr Cys Pro Pro Cys Pro Ala Pro Glu
            20                  25

<210> SEQ ID NO 35
<211> LENGTH: 27
<212> TYPE: PRT
<213> ORGANISM: Artificial Sequence
<220> FEATURE:
<223> OTHER INFORMATION: linker

<400> SEQUENCE: 35

Gly Gly Ser Gly Ser Ser Ser Ser Ser Ser Lys Ser Cys Asp Lys
1               5                   10                  15

Thr His Thr Cys Pro Pro Cys Pro Ala Pro Glu
            20                  25

<210> SEQ ID NO 36
<211> LENGTH: 29
<212> TYPE: PRT
<213> ORGANISM: Artificial Sequence
<220> FEATURE:
<223> OTHER INFORMATION: linker

<400> SEQUENCE: 36

Gly Gly Pro Gly Ser Ser Ser Ser Ser Ser Ser Ser Lys Ser Cys
1               5                   10                  15

Asp Lys Thr His Thr Cys Pro Pro Cys Pro Ala Pro Glu
            20                  25

<210> SEQ ID NO 37
<211> LENGTH: 29
<212> TYPE: PRT
<213> ORGANISM: Artificial Sequence
<220> FEATURE:
<223> OTHER INFORMATION: linker

<400> SEQUENCE: 37

Gly Gly Ser Gly Ser Ser Ser Ser Ser Ser Ser Ser Lys Ser Cys
1               5                   10                  15

Asp Lys Thr His Thr Cys Pro Pro Cys Pro Ala Pro Glu
            20                  25

<210> SEQ ID NO 38
<211> LENGTH: 24
<212> TYPE: PRT
<213> ORGANISM: Artificial Sequence
<220> FEATURE:
<223> OTHER INFORMATION: linker

<400> SEQUENCE: 38

Gly Gly Pro Gly Ser Ser Gly Ser Gly Ser Ser Asp Lys Thr His Thr
1               5                   10                  15

Cys Pro Pro Cys Pro Ala Pro Glu

20

<210> SEQ ID NO 39
<211> LENGTH: 23
<212> TYPE: PRT
<213> ORGANISM: Artificial Sequence
<220> FEATURE:
<223> OTHER INFORMATION: linker

<400> SEQUENCE: 39

Gly Gly Pro Gly Ser Ser Gly Ser Gly Ser Asp Lys Thr His Thr Cys
1               5                   10                  15

Pro Pro Cys Pro Ala Pro Glu
            20

<210> SEQ ID NO 40
<211> LENGTH: 21
<212> TYPE: PRT
<213> ORGANISM: Artificial Sequence
<220> FEATURE:
<223> OTHER INFORMATION: linker

<400> SEQUENCE: 40

Gly Gly Pro Ser Ser Gly Ser Asp Lys Thr His Thr Cys Pro Pro
1               5                   10                  15

Cys Pro Ala Pro Glu
            20

<210> SEQ ID NO 41
<211> LENGTH: 25
<212> TYPE: PRT
<213> ORGANISM: Artificial Sequence
<220> FEATURE:
<223> OTHER INFORMATION: linker

<400> SEQUENCE: 41

Gly Gly Ser Ser Ser Ser Ser Ser Gly Ser Asp Lys Thr His
1               5                   10                  15

Thr Cys Pro Pro Cys Pro Ala Pro Glu
            20                  25

<210> SEQ ID NO 42
<211> LENGTH: 246
<212> TYPE: PRT
<213> ORGANISM: Artificial Sequence
<220> FEATURE:
<223> OTHER INFORMATION: Fc domain

<400> SEQUENCE: 42

Met Glu Thr Asp Thr Leu Leu Leu Trp Val Leu Leu Leu Trp Val Pro
1               5                   10                  15

Ala Gly Asn Gly Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp

```
                    100                 105                 110
Trp Leu Asn Gly Lys Glu Tyr Lys Cys Lys Val Ser Asn Lys Ala Leu
            115                 120                 125

Pro Ala Pro Ile Glu Lys Thr Ile Ser Lys Ala Lys Gly Gln Pro Arg
130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly
                245

<210> SEQ ID NO 43
<211> LENGTH: 11
<212> TYPE: PRT
<213> ORGANISM: Artificial Sequence
<220> FEATURE:
<223> OTHER INFORMATION: linker

<400> SEQUENCE: 43

Ser Gly Ser Gly Ser Gly Ser Gly Ser Gly Ser
1               5                   10

<210> SEQ ID NO 44
<211> LENGTH: 12
<212> TYPE: PRT
<213> ORGANISM: Artificial Sequence
<220> FEATURE:
<223> OTHER INFORMATION: linker

<400> SEQUENCE: 44

Ser Ser Ser Ser Ser Gly Ser Gly Ser Gly Ser
1               5                   10

<210> SEQ ID NO 45
<211> LENGTH: 16
<212> TYPE: PRT
<213> ORGANISM: Artificial Sequence
<220> FEATURE:
<223> OTHER INFORMATION: linker

<400> SEQUENCE: 45

Ser Ser Ser Ser Ser Gly Ser Gly Ser Gly Ser Gly Ser Gly Ser
1               5                   10                  15

<210> SEQ ID NO 46
<211> LENGTH: 254
<212> TYPE: PRT
<213> ORGANISM: Artificial Sequence
<220> FEATURE:
<223> OTHER INFORMATION: 4-1BBL

<400> SEQUENCE: 46

Met Glu Tyr Ala Ser Asp Ala Ser Leu Asp Pro Glu Ala Pro Trp Pro
```

```
            1               5                   10                  15
        Pro Ala Pro Arg Ala Arg Ala Cys Arg Val Leu Pro Trp Ala Leu Val
                        20                  25                  30
        Ala Gly Leu Leu Leu Leu Leu Leu Ala Ala Cys Ala Val Phe
                    35                  40                  45
        Leu Ala Cys Pro Trp Ala Val Ser Gly Ala Arg Ala Ser Pro Gly Ser
                50                  55                  60
        Ala Ala Ser Pro Arg Leu Arg Glu Gly Pro Glu Leu Ser Pro Asp Asp
        65                  70                  75                  80
        Pro Ala Gly Leu Leu Asp Leu Arg Gln Gly Met Phe Ala Gln Leu Val
                        85                  90                  95
        Ala Gln Asn Val Leu Leu Ile Asp Gly Pro Leu Ser Trp Tyr Ser Asp
                    100                 105                 110
        Pro Gly Leu Ala Gly Val Ser Leu Thr Gly Gly Leu Ser Tyr Lys Glu
                    115                 120                 125
        Asp Thr Lys Glu Leu Val Val Ala Lys Ala Gly Val Tyr Tyr Val Phe
                130                 135                 140
        Phe Gln Leu Glu Leu Arg Arg Val Val Ala Gly Glu Gly Ser Gly Ser
        145                 150                 155                 160
        Val Ser Leu Ala Leu His Leu Gln Pro Leu Arg Ser Ala Ala Gly Ala
                        165                 170                 175
        Ala Ala Leu Ala Leu Thr Val Asp Leu Pro Pro Ala Ser Ser Glu Ala
                    180                 185                 190
        Arg Asn Ser Ala Phe Gly Phe Gln Gly Arg Leu Leu His Leu Ser Ala
                        195                 200                 205
        Gly Gln Arg Leu Gly Val His Leu His Thr Glu Ala Arg Ala Arg His
                    210                 215                 220
        Ala Trp Gln Leu Thr Gln Gly Ala Thr Val Leu Gly Leu Phe Arg Val
        225                 230                 235                 240
        Thr Pro Glu Ile Pro Ala Gly Leu Pro Ser Pro Arg Ser Glu
                        245                 250

<210> SEQ ID NO 47
<211> LENGTH: 168
<212> TYPE: PRT
<213> ORGANISM: Artificial Sequence
<220> FEATURE:
<223> OTHER INFORMATION: 4-1BBL soluble domain

<400> SEQUENCE: 47

Leu Arg Gln Gly Met Phe Ala Gln Leu Val Ala Gln Asn Val Leu Leu
        1               5                   10                  15
        Ile Asp Gly Pro Leu Ser Trp Tyr Ser Asp Pro Gly Leu Ala Gly Val
                        20                  25                  30
        Ser Leu Thr Gly Gly Leu Ser Tyr Lys Glu Asp Thr Lys Glu Leu Val
                    35                  40                  45
        Val Ala Lys Ala Gly Val Tyr Tyr Val Phe Phe Gln Leu Glu Leu Arg
                50                  55                  60
        Arg Val Val Ala Gly Glu Gly Ser Gly Ser Val Ser Leu Ala Leu His
        65                  70                  75                  80
        Leu Gln Pro Leu Arg Ser Ala Ala Gly Ala Ala Ala Leu Ala Leu Thr
                        85                  90                  95
        Val Asp Leu Pro Pro Ala Ser Ser Glu Ala Arg Asn Ser Ala Phe Gly
                    100                 105                 110
        Phe Gln Gly Arg Leu Leu His Leu Ser Ala Gly Gln Arg Leu Gly Val
```

```
                115                 120                 125
His Leu His Thr Glu Ala Arg Ala His Ala Trp Gln Leu Thr Gln
    130                 135                 140

Gly Ala Thr Val Leu Gly Leu Phe Arg Val Thr Pro Glu Ile Pro Ala
145                 150                 155                 160

Gly Leu Pro Ser Pro Arg Ser Glu
                165

<210> SEQ ID NO 48
<211> LENGTH: 118
<212> TYPE: PRT
<213> ORGANISM: Artificial Sequence
<220> FEATURE:
<223> OTHER INFORMATION: variable heavy chain for 4B4-1-1 version 1

<400> SEQUENCE: 48

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ser Ser Tyr
                20                  25                  30

Trp Met His Trp Val Lys Gln Arg Pro Gly Gln Val Leu Glu Trp Ile
            35                  40                  45

Gly Glu Ile Asn Pro Gly Asn Gly His Thr Asn Tyr Asn Glu Lys Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Phe Thr Thr Ala Arg Gly Phe Ala Tyr Trp Gly Gln Gly
                100                 105                 110

Thr Leu Val Thr Val Ser
        115

<210> SEQ ID NO 49
<211> LENGTH: 107
<212> TYPE: PRT
<213> ORGANISM: Artificial Sequence
<220> FEATURE:
<223> OTHER INFORMATION: variable light chain for 4B4-1-1 version 1

<400> SEQUENCE: 49

Asp Ile Val Met Thr Gln Ser Pro Ala Thr Gln Ser Val Thr Pro Gly
1               5                   10                  15

Asp Arg Val Ser Leu Ser Cys Arg Ala Ser Gln Thr Ile Ser Asp Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asp Gly His Ser Phe Pro Pro
                85                  90                  95

Thr Phe Gly Gly Gly Thr Lys Leu Glu Ile Lys
            100                 105

<210> SEQ ID NO 50
<211> LENGTH: 119
```

```
<212> TYPE: PRT
<213> ORGANISM: Artificial Sequence
<220> FEATURE:
<223> OTHER INFORMATION: variable heavy chain for 4B4-1-1 version 2

<400> SEQUENCE: 50

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Lys Gln Arg Pro Gly Gln Val Leu Glu Trp Ile
        35                  40                  45

Gly Glu Ile Asn Pro Gly Asn Gly His Thr Asn Tyr Asn Glu Lys Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Phe Thr Thr Ala Arg Gly Phe Ala Tyr Trp Gly Gln Gly
            100                 105                 110

Thr Leu Val Thr Val Ser Ala
            115

<210> SEQ ID NO 51
<211> LENGTH: 108
<212> TYPE: PRT
<213> ORGANISM: Artificial Sequence
<220> FEATURE:
<223> OTHER INFORMATION: variable light chain for 4B4-1-1 version 2

<400> SEQUENCE: 51

Asp Ile Val Met Thr Gln Ser Pro Ala Thr Gln Ser Val Thr Pro Gly
1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asp Gly His Ser Phe Pro Pro
                85                  90                  95

Thr Phe Gly Gly Gly Thr Lys Leu Glu Ile Lys Arg
            100                 105

<210> SEQ ID NO 52
<211> LENGTH: 120
<212> TYPE: PRT
<213> ORGANISM: Artificial Sequence
<220> FEATURE:
<223> OTHER INFORMATION: variable heavy chain for H39E3-2

<400> SEQUENCE: 52

Met Asp Trp Thr Trp Arg Ile Leu Phe Leu Val Ala Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
```

```
                35                  40                  45
Ser Asp Tyr Trp Met Ser Trp Val Arg Gln Ala Pro Gly Lys Gly Leu
 50                  55                  60

Glu Trp Val Ala Asp Ile Lys Asn Asp Gly Ser Tyr Thr Asn Tyr Ala
 65                  70                  75                  80

Pro Ser Leu Thr Asn Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Val
                100                 105                 110

Tyr Tyr Cys Ala Arg Glu Leu Thr
                115                 120

<210> SEQ ID NO 53
<211> LENGTH: 109
<212> TYPE: PRT
<213> ORGANISM: Artificial Sequence
<220> FEATURE:
<223> OTHER INFORMATION: variable light chain for H39E3-2

<400> SEQUENCE: 53

Met Glu Ala Pro Ala Gln Leu Leu Phe Leu Leu Leu Leu Trp Leu Pro
 1               5                  10                  15

Asp Thr Thr Gly Asp Ile Val Met Thr Gln Ser Pro Asp Ser Leu Ala
                 20                  25                  30

Val Ser Leu Gly Glu Arg Ala Thr Ile Asn Cys Lys Ser Ser Gln Ser
                 35                  40                  45

Leu Leu Ser Ser Gly Asn Gln Lys Asn Tyr Leu Trp Tyr Gln Gln Lys
 50                  55                  60

Pro Gly Gln Pro Pro Lys Leu Leu Ile Tyr Tyr Ala Ser Thr Arg Gln
 65                  70                  75                  80

Ser Gly Val Pro Asp Arg Phe Ser Gly Ser Gly Ser Gly Thr Asp Phe
                 85                  90                  95

Thr Leu Thr Ile Ser Ser Leu Gln Ala Glu Asp Val Ala
                100                 105

<210> SEQ ID NO 54
<211> LENGTH: 277
<212> TYPE: PRT
<213> ORGANISM: Artificial Sequence
<220> FEATURE:
<223> OTHER INFORMATION: human OX40 (Homo sapiens)

<400> SEQUENCE: 54

Met Cys Val Gly Ala Arg Arg Leu Gly Arg Gly Pro Cys Ala Ala Leu
 1               5                  10                  15

Leu Leu Leu Gly Leu Gly Leu Ser Thr Val Thr Gly Leu His Cys Val
                 20                  25                  30

Gly Asp Thr Tyr Pro Ser Asn Asp Arg Cys Cys His Glu Cys Arg Pro
                 35                  40                  45

Gly Asn Gly Met Val Ser Arg Cys Ser Arg Ser Gln Asn Thr Val Cys
 50                  55                  60

Arg Pro Cys Gly Pro Gly Phe Tyr Asn Asp Val Val Ser Ser Lys Pro
 65                  70                  75                  80

Cys Lys Pro Cys Thr Trp Cys Asn Leu Arg Ser Gly Ser Glu Arg Lys
                 85                  90                  95

Gln Leu Cys Thr Ala Thr Gln Asp Thr Val Cys Arg Cys Arg Ala Gly
                100                 105                 110
```

```
Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 55
<211> LENGTH: 272
<212> TYPE: PRT
<213> ORGANISM: Artificial Sequence
<220> FEATURE:
<223> OTHER INFORMATION: murine OX40 (Mus musculus)

<400> SEQUENCE: 55

Met Tyr Val Trp Val Gln Gln Pro Thr Ala Leu Leu Leu Leu Gly Leu
1               5                   10                  15

Thr Leu Gly Val Thr Ala Arg Arg Leu Asn Cys Val Lys His Thr Tyr
            20                  25                  30

Pro Ser Gly His Lys Cys Cys Arg Glu Cys Gln Pro Gly His Gly Met
        35                  40                  45

Val Ser Arg Cys Asp His Thr Arg Asp Thr Leu Cys His Pro Cys Glu
    50                  55                  60

Thr Gly Phe Tyr Asn Glu Ala Val Asn Tyr Asp Thr Cys Lys Gln Cys
65                  70                  75                  80

Thr Gln Cys Asn His Arg Ser Gly Ser Glu Leu Lys Gln Asn Cys Thr
                85                  90                  95

Pro Thr Gln Asp Thr Val Cys Arg Cys Arg Pro Gly Thr Gln Pro Arg
            100                 105                 110

Gln Asp Ser Gly Tyr Lys Leu Gly Val Asp Cys Val Pro Cys Pro Pro
        115                 120                 125

Gly His Phe Ser Pro Gly Asn Asn Gln Ala Cys Lys Pro Trp Thr Asn
    130                 135                 140

Cys Thr Leu Ser Gly Lys Gln Thr Arg His Pro Ala Ser Asp Ser Leu
145                 150                 155                 160

Asp Ala Val Cys Glu Asp Arg Ser Leu Leu Ala Thr Leu Leu Trp Glu
                165                 170                 175

Thr Gln Arg Pro Thr Phe Arg Pro Thr Thr Val Gln Ser Thr Thr Val
            180                 185                 190
```

```
Trp Pro Arg Thr Ser Glu Leu Pro Ser Pro Thr Leu Val Thr Pro
        195                 200                 205

Glu Gly Pro Ala Phe Ala Val Leu Leu Gly Leu Gly Leu Leu
    210                 215                 220

Ala Pro Leu Thr Val Leu Leu Ala Leu Tyr Leu Leu Arg Lys Ala Trp
225                 230                 235                 240

Arg Leu Pro Asn Thr Pro Lys Pro Cys Trp Gly Asn Ser Phe Arg Thr
                245                 250                 255

Pro Ile Gln Glu Glu His Thr Asp Ala His Phe Thr Leu Ala Lys Ile
            260                 265                 270

<210> SEQ ID NO 56
<211> LENGTH: 451
<212> TYPE: PRT
<213> ORGANISM: Artificial Sequence
<220> FEATURE:
<223> OTHER INFORMATION: heavy chain for tavolixizumab

<400> SEQUENCE: 56

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

```
His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
450

<210> SEQ ID NO 57
<211> LENGTH: 214
<212> TYPE: PRT
<213> ORGANISM: Artificial Sequence
<220> FEATURE:
<223> OTHER INFORMATION: light chain for tavolixizumab

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Lys Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 58
<211> LENGTH: 118
<212> TYPE: PRT
<213> ORGANISM: Artificial Sequence
<220> FEATURE:
<223> OTHER INFORMATION: heavy chain variable region for tavolixizumab

<400> SEQUENCE: 58

```
Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr
        115
```

<210> SEQ ID NO 59
<211> LENGTH: 108
<212> TYPE: PRT
<213> ORGANISM: Artificial Sequence
<220> FEATURE:
<223> OTHER INFORMATION: light chain variable region for tavolixizumab

<400> SEQUENCE: 59

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys Arg
            100                 105
```

<210> SEQ ID NO 60
<211> LENGTH: 9
<212> TYPE: PRT
<213> ORGANISM: Artificial Sequence
<220> FEATURE:
<223> OTHER INFORMATION: heavy chain CDR1 for tavolixizumab

```
<400> SEQUENCE: 60

Gly Ser Phe Ser Ser Gly Tyr Trp Asn
1               5

<210> SEQ ID NO 61
<211> LENGTH: 13
<212> TYPE: PRT
<213> ORGANISM: Artificial Sequence
<220> FEATURE:
<223> OTHER INFORMATION: heavy chain CDR2 for tavolixizumab

<400> SEQUENCE: 61

Tyr Ile Gly Tyr Ile Ser Tyr Asn Gly Ile Thr Tyr His
1               5                   10

<210> SEQ ID NO 62
<211> LENGTH: 14
<212> TYPE: PRT
<213> ORGANISM: Artificial Sequence
<220> FEATURE:
<223> OTHER INFORMATION: heavy chain CDR3 for tavolixizumab

<400> SEQUENCE: 62

Arg Tyr Lys Tyr Asp Tyr Asp Gly Gly His Ala Met Asp Tyr
1               5                   10

<210> SEQ ID NO 63
<211> LENGTH: 8
<212> TYPE: PRT
<213> ORGANISM: Artificial Sequence
<220> FEATURE:
<223> OTHER INFORMATION: light chain CDR1 for tavolixizumab

<400> SEQUENCE: 63

Gln Asp Ile Ser Asn Tyr Leu Asn
1               5

<210> SEQ ID NO 64
<211> LENGTH: 11
<212> TYPE: PRT
<213> ORGANISM: Artificial Sequence
<220> FEATURE:
<223> OTHER INFORMATION: light chain CDR2 for tavolixizumab

<400> SEQUENCE: 64

Leu Leu Ile Tyr Tyr Thr Ser Lys Leu His Ser
1               5                   10

<210> SEQ ID NO 65
<211> LENGTH: 8
<212> TYPE: PRT
<213> ORGANISM: Artificial Sequence
<220> FEATURE:
<223> OTHER INFORMATION: light chain CDR3 for tavolixizumab

<400> SEQUENCE: 65

Gln Gln Gly Ser Ala Leu Pro Trp
1               5

<210> SEQ ID NO 66
<211> LENGTH: 444
<212> TYPE: PRT
<213> ORGANISM: Artificial Sequence
<220> FEATURE:
<223> OTHER INFORMATION: heavy chain for 11D4

<400> SEQUENCE: 66
```

-continued

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Ser Gly Trp Tyr Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Asn Phe Gly Thr Gln Thr Tyr Thr Cys Asn Val Asp His Lys Pro Ser
    195                 200                 205

Asn Thr Lys Val Asp Lys Thr Val Glu Arg Lys Cys Cys Val Glu Cys
210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Gln Phe
        260                 265                 270

Asn Trp Tyr Val Asp Gly Val Glu Val His Asn Ala Lys Thr Lys Pro
    275                 280                 285

Arg Glu Glu Gln Phe Asn Ser Thr Phe Arg Val Val Ser Val Leu Thr
290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
            325                 330                 335

Lys Gly Gln Pro Arg Glu Pro Gln Val Tyr Thr Leu Pro Pro Ser Arg
        340                 345                 350

Glu Glu Met Thr Lys Asn Gln Val Ser Leu Thr Cys Leu Val Lys Gly
    355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
            405                 410                 415
```

```
Gly Asn Val Phe Ser Cys Ser Val Met His Glu Ala Leu His Asn His
                    420                 425                 430

Tyr Thr Gln Lys Ser Leu Ser Leu Ser Pro Gly Lys
            435                 440
```

<210> SEQ ID NO 67
<211> LENGTH: 214
<212> TYPE: PRT
<213> ORGANISM: Artificial Sequence
<220> FEATURE:
<223> OTHER INFORMATION: light chain for 11D4

<400> SEQUENCE: 67

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 68
<211> LENGTH: 118
<212> TYPE: PRT
<213> ORGANISM: Artificial Sequence
<220> FEATURE:
<223> OTHER INFORMATION: heavy chain variable region for 11D4

<400> SEQUENCE: 68

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Asp Tyr Ala Asp Ser Val
50                  55                  60
```

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Ser Gly Trp Tyr Leu Phe Asp Tyr Trp Gly Gln Gly Thr
            100                 105                 110

Leu Val Thr Val Ser Ser
        115

<210> SEQ ID NO 69
<211> LENGTH: 107
<212> TYPE: PRT
<213> ORGANISM: Artificial Sequence
<220> FEATURE:
<223> OTHER INFORMATION: light chain variable region for 11D4

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105

<210> SEQ ID NO 70
<211> LENGTH: 5
<212> TYPE: PRT
<213> ORGANISM: Artificial Sequence
<220> FEATURE:
<223> OTHER INFORMATION: heavy chain CDR1 for 11D4

<400> SEQUENCE: 70

Ser Tyr Ser Met Asn
1               5

<210> SEQ ID NO 71
<211> LENGTH: 17
<212> TYPE: PRT
<213> ORGANISM: Artificial Sequence
<220> FEATURE:
<223> OTHER INFORMATION: heavy chain CDR2 for 11D4

<400> SEQUENCE: 71

Tyr Ile Ser Ser Ser Ser Ser Thr Ile Asp Tyr Ala Asp Ser Val Lys
1               5                   10                  15

Gly

<210> SEQ ID NO 72
<211> LENGTH: 9
<212> TYPE: PRT
<213> ORGANISM: Artificial Sequence
<220> FEATURE:
<223> OTHER INFORMATION: heavy chain CDR3 for 11D4

<400> SEQUENCE: 72

Glu Ser Gly Trp Tyr Leu Phe Asp Tyr
1               5

<210> SEQ ID NO 73
<211> LENGTH: 11
<212> TYPE: PRT
<213> ORGANISM: Artificial Sequence
<220> FEATURE:
<223> OTHER INFORMATION: light chain CDR1 for 11D4

<400> SEQUENCE: 73

Arg Ala Ser Gln Gly Ile Ser Ser Trp Leu Ala
1               5                   10

<210> SEQ ID NO 74
<211> LENGTH: 7
<212> TYPE: PRT
<213> ORGANISM: Artificial Sequence
<220> FEATURE:
<223> OTHER INFORMATION: light chain CDR2 for 11D4

<400> SEQUENCE: 74

Ala Ala Ser Ser Leu Gln Ser
1               5

<210> SEQ ID NO 75
<211> LENGTH: 9
<212> TYPE: PRT
<213> ORGANISM: Artificial Sequence
<220> FEATURE:
<223> OTHER INFORMATION: light chain CDR3 for 11D4

<400> SEQUENCE: 75

Gln Gln Tyr Asn Ser Tyr Pro Pro Thr
1               5

<210> SEQ ID NO 76
<211> LENGTH: 450
<212> TYPE: PRT
<213> ORGANISM: Artificial Sequence
<220> FEATURE:
<223> OTHER INFORMATION: heavy chain for 18D8

<400> SEQUENCE: 76

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gln Ser Thr Ala Asp Tyr Tyr Phe Tyr Tyr Gly Met Asp
            100                 105                 110

Val Trp Gly Gln Gly Thr Thr Val Thr Val Ser Ser Ala Ser Thr Lys
        115                 120                 125

```
Gly Pro Ser Val Phe Pro Leu Ala Pro Cys Ser Arg Ser Thr Ser Glu
            130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
                195                 200                 205

Val Asp His Lys Pro Ser Asn Thr Lys Val Asp Lys Thr Val Glu Arg
210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Phe Arg
290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 77
<211> LENGTH: 213
<212> TYPE: PRT
<213> ORGANISM: Artificial Sequence
<220> FEATURE:
<223> OTHER INFORMATION: light chain for 18D8

<400> SEQUENCE: 77

Glu Ile Val Val Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

-continued

```
Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Thr
                 85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 78
<211> LENGTH: 124
<212> TYPE: PRT
<213> ORGANISM: Artificial Sequence
<220> FEATURE:
<223> OTHER INFORMATION: heavy chain variable region for 18D8

<400> SEQUENCE: 78

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Ile Ser Trp Asn Ser Gly Ser Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Gln Ser Thr Ala Asp Tyr Tyr Phe Tyr Tyr Gly Met Asp
                100                 105                 110

Val Trp Gly Gln Gly Thr Thr Val Thr Val Ser Ser
            115                 120

<210> SEQ ID NO 79
<211> LENGTH: 106
<212> TYPE: PRT
<213> ORGANISM: Artificial Sequence
<220> FEATURE:
<223> OTHER INFORMATION: light chain variable region for 18D

<400> SEQUENCE: 79
```

```
Glu Ile Val Val Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65              70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 80
<211> LENGTH: 5
<212> TYPE: PRT
<213> ORGANISM: Artificial Sequence
<220> FEATURE:
<223> OTHER INFORMATION: heavy chain CDR1 for 18D8

<400> SEQUENCE: 80

Asp Tyr Ala Met His
1               5

<210> SEQ ID NO 81
<211> LENGTH: 17
<212> TYPE: PRT
<213> ORGANISM: Artificial Sequence
<220> FEATURE:
<223> OTHER INFORMATION: heavy chain CDR2 for 18D8

<400> SEQUENCE: 81

Gly Ile Ser Trp Asn Ser Gly Ser Ile Gly Tyr Ala Asp Ser Val Lys
1               5                   10                  15

Gly

<210> SEQ ID NO 82
<211> LENGTH: 15
<212> TYPE: PRT
<213> ORGANISM: Artificial Sequence
<220> FEATURE:
<223> OTHER INFORMATION: heavy chain CDR3 for 18D8

<400> SEQUENCE: 82

Asp Gln Ser Thr Ala Asp Tyr Tyr Phe Tyr Tyr Gly Met Asp Val
1               5                   10                  15

<210> SEQ ID NO 83
<211> LENGTH: 11
<212> TYPE: PRT
<213> ORGANISM: Artificial Sequence
<220> FEATURE:
<223> OTHER INFORMATION: light chain CDR1 for 18D8

<400> SEQUENCE: 83

Arg Ala Ser Gln Ser Val Ser Ser Tyr Leu Ala
1               5                   10

<210> SEQ ID NO 84
<211> LENGTH: 7
```

```
<212> TYPE: PRT
<213> ORGANISM: Artificial Sequence
<220> FEATURE:
<223> OTHER INFORMATION: light chain CDR2 for 18D8

<400> SEQUENCE: 84

Asp Ala Ser Asn Arg Ala Thr
1               5

<210> SEQ ID NO 85
<211> LENGTH: 8
<212> TYPE: PRT
<213> ORGANISM: Artificial Sequence
<220> FEATURE:
<223> OTHER INFORMATION: light chain CDR3 for 18D8

<400> SEQUENCE: 85

Gln Gln Arg Ser Asn Trp Pro Thr
1               5

<210> SEQ ID NO 86
<211> LENGTH: 120
<212> TYPE: PRT
<213> ORGANISM: Artificial Sequence
<220> FEATURE:
<223> OTHER INFORMATION: heavy chain variable region for Hu119-122

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Glu Phe Pro Ser His
            20                  25                  30

Asp Met Ser Trp Val Arg Gln Ala Pro Gly Lys Gly Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Asp Asp Tyr Tyr Ala Trp Phe Ala Tyr Trp Gly Gln
            100                 105                 110

Gly Thr Met Val Thr Val Ser Ser
        115                 120

<210> SEQ ID NO 87
<211> LENGTH: 111
<212> TYPE: PRT
<213> ORGANISM: Artificial Sequence
<220> FEATURE:
<223> OTHER INFORMATION: light chain variable region for Hu119-122

<400> SEQUENCE: 87

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Val Pro Ala
    50                  55                  60
```

-continued

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Glu Leu Pro Leu Thr Phe Gly Gly Gly Thr Lys Val Glu Ile Lys
            100                 105                 110

<210> SEQ ID NO 88
<211> LENGTH: 5
<212> TYPE: PRT
<213> ORGANISM: Artificial Sequence
<220> FEATURE:
<223> OTHER INFORMATION: heavy chain CDR1 for Hu119-122

<400> SEQUENCE: 88

Ser His Asp Met Ser
1               5

<210> SEQ ID NO 89
<211> LENGTH: 17
<212> TYPE: PRT
<213> ORGANISM: Artificial Sequence
<220> FEATURE:
<223> OTHER INFORMATION: heavy chain CDR2 for Hu119-122

<400> SEQUENCE: 89

Ala Ile Asn Ser Asp Gly Gly Ser Thr Tyr Tyr Pro Asp Thr Met Glu
1               5                   10                  15

Arg

<210> SEQ ID NO 90
<211> LENGTH: 11
<212> TYPE: PRT
<213> ORGANISM: Artificial Sequence
<220> FEATURE:
<223> OTHER INFORMATION: heavy chain CDR3 for Hu119-122

<400> SEQUENCE: 90

His Tyr Asp Asp Tyr Tyr Ala Trp Phe Ala Tyr
1               5                   10

<210> SEQ ID NO 91
<211> LENGTH: 15
<212> TYPE: PRT
<213> ORGANISM: Artificial Sequence
<220> FEATURE:
<223> OTHER INFORMATION: light chain CDR1 for Hu119-122

<400> SEQUENCE: 91

Arg Ala Ser Lys Ser Val Ser Thr Ser Gly Tyr Ser Tyr Met His
1               5                   10                  15

<210> SEQ ID NO 92
<211> LENGTH: 7
<212> TYPE: PRT
<213> ORGANISM: Artificial Sequence
<220> FEATURE:
<223> OTHER INFORMATION: light chain CDR2 for Hu119-122

<400> SEQUENCE: 92

Leu Ala Ser Asn Leu Glu Ser
1               5

<210> SEQ ID NO 93
<211> LENGTH: 9

```
<212> TYPE: PRT
<213> ORGANISM: Artificial Sequence
<220> FEATURE:
<223> OTHER INFORMATION: light chain CDR3 for Hu119-122

<400> SEQUENCE: 93

Gln His Ser Arg Glu Leu Pro Leu Thr
1               5

<210> SEQ ID NO 94
<211> LENGTH: 122
<212> TYPE: PRT
<213> ORGANISM: Artificial Sequence
<220> FEATURE:
<223> OTHER INFORMATION: heavy chain variable region for Hu106-222

<400> SEQUENCE: 94

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Pro Tyr Tyr Asp Tyr Val Ser Tyr Tyr Ala Met Asp Tyr Trp
            100                 105                 110

Gly Gln Gly Thr Thr Val Thr Val Ser Ser
        115                 120

<210> SEQ ID NO 95
<211> LENGTH: 107
<212> TYPE: PRT
<213> ORGANISM: Artificial Sequence
<220> FEATURE:
<223> OTHER INFORMATION: light chain variable region for Hu106-222

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Leu Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Arg
                85                  90                  95

Thr Phe Gly Gln Gly Thr Lys Leu Glu Ile Lys
            100                 105

<210> SEQ ID NO 96
<211> LENGTH: 5
<212> TYPE: PRT
```

```
<213> ORGANISM: Artificial Sequence
<220> FEATURE:
<223> OTHER INFORMATION: heavy chain CDR1 for Hu106-222

<400> SEQUENCE: 96

Asp Tyr Ser Met His
1               5

<210> SEQ ID NO 97
<211> LENGTH: 17
<212> TYPE: PRT
<213> ORGANISM: Artificial Sequence
<220> FEATURE:
<223> OTHER INFORMATION: heavy chain CDR2 for Hu106-222

<400> SEQUENCE: 97

Trp Ile Asn Thr Glu Thr Gly Glu Pro Thr Tyr Ala Asp Asp Phe Lys
1               5                   10                  15
Gly

<210> SEQ ID NO 98
<211> LENGTH: 13
<212> TYPE: PRT
<213> ORGANISM: Artificial Sequence
<220> FEATURE:
<223> OTHER INFORMATION: heavy chain CDR3 for Hu106-222

<400> SEQUENCE: 98

Pro Tyr Tyr Asp Tyr Val Ser Tyr Tyr Ala Met Asp Tyr
1               5                   10

<210> SEQ ID NO 99
<211> LENGTH: 11
<212> TYPE: PRT
<213> ORGANISM: Artificial Sequence
<220> FEATURE:
<223> OTHER INFORMATION: light chain CDR1 for Hu106-222

<400> SEQUENCE: 99

Lys Ala Ser Gln Asp Val Ser Thr Ala Val Ala
1               5                   10

<210> SEQ ID NO 100
<211> LENGTH: 7
<212> TYPE: PRT
<213> ORGANISM: Artificial Sequence
<220> FEATURE:
<223> OTHER INFORMATION: light chain CDR2 for Hu106-222

<400> SEQUENCE: 100

Ser Ala Ser Tyr Leu Tyr Thr
1               5

<210> SEQ ID NO 101
<211> LENGTH: 9
<212> TYPE: PRT
<213> ORGANISM: Artificial Sequence
<220> FEATURE:
<223> OTHER INFORMATION: light chain CDR3 for Hu106-222

<400> SEQUENCE: 101

Gln Gln His Tyr Ser Thr Pro Arg Thr
1               5

<210> SEQ ID NO 102
<211> LENGTH: 183
```

```
<212> TYPE: PRT
<213> ORGANISM: Artificial Sequence
<220> FEATURE:
<223> OTHER INFORMATION: OX40L

<400> SEQUENCE: 102

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 103
<211> LENGTH: 131
<212> TYPE: PRT
<213> ORGANISM: Artificial Sequence
<220> FEATURE:
<223> OTHER INFORMATION: OX40L soluble domain

<400> SEQUENCE: 103

Ser His Arg Tyr Pro Arg Ile Gln Ser Ile Lys Val Gln Phe Thr Glu
1               5                   10                  15

Tyr Lys Lys Glu Lys Gly Phe Ile Leu Thr Ser Gln Lys Glu Asp Glu
            20                  25                  30

Ile Met Lys Val Gln Asn Asn Ser Val Ile Ile Asn Cys Asp Gly Phe
        35                  40                  45

Tyr Leu Ile Ser Leu Lys Gly Tyr Phe Ser Gln Glu Val Asn Ile Ser
    50                  55                  60

Leu His Tyr Gln Lys Asp Glu Glu Pro Leu Phe Gln Leu Lys Lys Val
65                  70                  75                  80

Arg Ser Val Asn Ser Leu Met Val Ala Ser Leu Thr Tyr Lys Asp Lys
                85                  90                  95

Val Tyr Leu Asn Val Thr Thr Asp Asn Thr Ser Leu Asp Phe His
            100                 105                 110

Val Asn Gly Gly Glu Leu Ile Leu Ile His Gln Asn Pro Gly Glu Phe
        115                 120                 125

Cys Val Leu
    130
```

<210> SEQ ID NO 104
<211> LENGTH: 128
<212> TYPE: PRT
<213> ORGANISM: Artificial Sequence
<220> FEATURE:
<223> OTHER INFORMATION: OX40L soluble domain (alternative)

<400> SEQUENCE: 104

Tyr Pro Arg Ile Gln Ser Ile Lys Val Gln Phe Thr Glu Tyr Lys Lys
1               5                   10                  15

Glu Lys Gly Phe Ile Leu Thr Ser Gln Lys Glu Asp Glu Ile Met Lys
            20                  25                  30

Val Gln Asn Asn Ser Val Ile Ile Asn Cys Asp Gly Phe Tyr Leu Ile
        35                  40                  45

Ser Leu Lys Gly Tyr Phe Ser Gln Glu Val Asn Ile Ser Leu His Tyr
    50                  55                  60

Gln Lys Asp Glu Glu Pro Leu Phe Gln Leu Lys Lys Val Arg Ser Val
65                  70                  75                  80

Asn Ser Leu Met Val Ala Ser Leu Thr Tyr Lys Asp Lys Val Tyr Leu
                85                  90                  95

Asn Val Thr Thr Asp Asn Thr Ser Leu Asp Asp Phe His Val Asn Gly
            100                 105                 110

Gly Glu Leu Ile Leu Ile His Gln Asn Pro Gly Glu Phe Cys Val Leu
        115                 120                 125

<210> SEQ ID NO 105
<211> LENGTH: 120
<212> TYPE: PRT
<213> ORGANISM: Artificial Sequence
<220> FEATURE:
<223> OTHER INFORMATION: variable heavy chain for 008

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Thr Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Ser Gln Val His Tyr Ala Leu Asp Tyr Trp Gly
            100                 105                 110

Gln Gly Thr Leu Val Thr Val Ser
        115                 120

<210> SEQ ID NO 106
<211> LENGTH: 108
<212> TYPE: PRT
<213> ORGANISM: Artificial Sequence
<220> FEATURE:
<223> OTHER INFORMATION: variable light chain for 008

<400> SEQUENCE: 106

```
Asp Ile Val Met Thr Gln Ser Pro Asp Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ala Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys
            100                 105
```

<210> SEQ ID NO 107
<211> LENGTH: 120
<212> TYPE: PRT
<213> ORGANISM: Artificial Sequence
<220> FEATURE:
<223> OTHER INFORMATION: variable heavy chain for 011

<400> SEQUENCE: 107

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Thr Met Asn Trp Val Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu Tyr Leu Gln
65                  70                  75                  80

Met Asn Asn Leu Arg Ala Glu Asp Thr Ala Val Tyr Tyr Cys Ala Arg
                85                  90                  95

Asp Arg Tyr Phe Arg Gln Gln Asn Ala Phe Asp Tyr Trp Gly Gln Gly
            100                 105                 110

Thr Leu Val Thr Val Ser Ser Ala
        115                 120
```

<210> SEQ ID NO 108
<211> LENGTH: 108
<212> TYPE: PRT
<213> ORGANISM: Artificial Sequence
<220> FEATURE:
<223> OTHER INFORMATION: variable light chain for 011

<400> SEQUENCE: 108

```
Asp Ile Val Met Thr Gln Ser Pro Asp Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ala Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Gln Gln Tyr
            85                  90                  95

Tyr Asn His Pro Thr Thr Phe Gly Gln Gly Thr Lys
            100                 105

<210> SEQ ID NO 109
<211> LENGTH: 120
<212> TYPE: PRT
<213> ORGANISM: Artificial Sequence
<220> FEATURE:
<223> OTHER INFORMATION: variable heavy chain for 021

<400> SEQUENCE: 109

Glu Val Gln Leu Val Glu Ser Gly Gly Gly Leu Val Gln Pro Arg Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Ile Thr Leu Pro Asn Ala Leu Asp Tyr Trp Gly
            100                 105                 110

Gln Gly Thr Leu Val Thr Val Ser
        115                 120

<210> SEQ ID NO 110
<211> LENGTH: 108
<212> TYPE: PRT
<213> ORGANISM: Artificial Sequence
<220> FEATURE:
<223> OTHER INFORMATION: variable light chain for 021

<400> SEQUENCE: 110

Asp Ile Gln Met Thr Gln Ser Pro Val Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Lys Ser Asn Pro Pro Thr Phe Gly Gln Gly Thr Lys
            100                 105

<210> SEQ ID NO 111
<211> LENGTH: 120
<212> TYPE: PRT
<213> ORGANISM: Artificial Sequence
<220> FEATURE:
<223> OTHER INFORMATION: variable heavy chain for 023

<400> SEQUENCE: 111

Glu Val Gln Leu Val Glu Ser Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Thr Tyr Tyr Ala Asp Ser Val Met
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Asp Asn Val Met Gly Leu Tyr Trp Phe Asp Tyr Trp Gly Gln
            100                 105                 110

Gly Thr Leu Val Thr Val Ser Ser
            115                 120

<210> SEQ ID NO 112
<211> LENGTH: 108
<212> TYPE: PRT
<213> ORGANISM: Artificial Sequence
<220> FEATURE:
<223> OTHER INFORMATION: variable light chain for 023

<400> SEQUENCE: 112

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Phe Gly Gly Gly Thr Lys Val Glu Ile Lys Arg
            100                 105

<210> SEQ ID NO 113
<211> LENGTH: 119
<212> TYPE: PRT
<213> ORGANISM: Artificial Sequence
<220> FEATURE:
<223> OTHER INFORMATION: heavy chain variable region

<400> SEQUENCE: 113

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

```
Lys Gly Lys Ala Thr Leu Thr Ser Asp Lys Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Asn Tyr Tyr Gly Ser Ser Leu Ser Met Asp Tyr Trp Gly Gln Gly
            100                 105                 110

Thr Ser Val Thr Val Ser Ser
        115
```

<210> SEQ ID NO 114
<211> LENGTH: 108
<212> TYPE: PRT
<213> ORGANISM: Artificial Sequence
<220> FEATURE:
<223> OTHER INFORMATION: light chain variable region

<400> SEQUENCE: 114

```
Asp Ile Gln Met Thr Gln Thr Thr Ser Ser Leu Ser Ala Ser Leu Gly
  1               5                  10                  15

Asp Arg Val Thr Ile Ser Cys Arg Ala Ser Gln Asp Ile Ser Asn Tyr
             20                  25                  30

Leu Asn Trp Tyr Gln Gln Lys Pro Asp Gly Thr Val Lys Leu Leu Ile
         35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Trp
                 85                  90                  95

Thr Phe Gly Gly Gly Thr Lys Leu Glu Ile Lys Arg
            100                 105
```

<210> SEQ ID NO 115
<211> LENGTH: 121
<212> TYPE: PRT
<213> ORGANISM: Artificial Sequence
<220> FEATURE:
<223> OTHER INFORMATION: heavy chain variable region

<400> SEQUENCE: 115

```
Glu Val Gln Leu Gln Gln Ser Gly Pro Glu Leu Val Lys Pro Gly Ala
  1               5                  10                  15

Ser Val Lys Ile Ser Cys Lys Thr Ser Gly Tyr Thr Phe Lys Asp Tyr
             20                  25                  30

Thr Met His Trp Val Lys Gln Ser His Gly Lys Ser Leu Glu Trp Ile
         35                  40                  45

Gly Gly Ile Tyr Pro Asn Asn Gly Gly Ser Thr Tyr Asn Gln Asn Phe
 50                  55                  60

Lys Asp Lys Ala Thr Leu Thr Val Asp Lys Ser Ser Thr Ala Tyr
 65                  70                  75                  80

Met Glu Phe Arg Ser Leu Thr Ser Glu Asp Ser Ala Val Tyr Tyr Cys
                 85                  90                  95

Ala Arg Met Gly Tyr His Gly Pro His Leu Asp Phe Asp Val Trp Gly
            100                 105                 110

Ala Gly Thr Thr Val Thr Val Ser Pro
        115                 120
```

```
<210> SEQ ID NO 116
<211> LENGTH: 108
<212> TYPE: PRT
<213> ORGANISM: Artificial Sequence
<220> FEATURE:
<223> OTHER INFORMATION: light chain variable region

<400> SEQUENCE: 116

Asp Ile Val Met Thr Gln Ser His Lys Phe Met Ser Thr Ser Leu Gly
1               5                   10                  15

Asp Arg Val Ser Ile Thr Cys Lys Ala Ser Gln Asp Val Gly Ala Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Gly Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ile Asn Tyr Pro Leu
                85                  90                  95

Thr Phe Gly Gly Gly Thr Lys Leu Glu Ile Lys Arg
            100                 105

<210> SEQ ID NO 117
<211> LENGTH: 122
<212> TYPE: PRT
<213> ORGANISM: Artificial Sequence
<220> FEATURE:
<223> OTHER INFORMATION: heavy chain variable region of humanized
      antibody

<400> SEQUENCE: 117

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Asn Pro Tyr Tyr Asp Tyr Val Ser Tyr Tyr Ala Met Asp Tyr Trp
            100                 105                 110

Gly His Gly Thr Ser Val Thr Val Ser Ser
        115                 120

<210> SEQ ID NO 118
<211> LENGTH: 122
<212> TYPE: PRT
<213> ORGANISM: Artificial Sequence
<220> FEATURE:
<223> OTHER INFORMATION: heavy chain variable region of humanized
      antibody

<400> SEQUENCE: 118

Gln Val Gln Leu Val Gln Ser Gly Ser Glu Leu Lys Lys Pro Gly Ala
1               5                   10                  15
```

```
Ser Val Lys Val Ser Cys Lys Ala Ser Gly Tyr Thr Phe Thr Asp Tyr
             20                  25                  30

Ser Met His Trp Val Arg Gln Ala Pro Gly Gln Gly Leu Lys Trp Met
             35                  40                  45

Gly Trp Ile Asn Thr Glu Thr Gly Glu Pro Thr Tyr Ala Asp Asp Phe
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Asn Pro Tyr Tyr Asp Tyr Val Ser Tyr Tyr Ala Met Asp Tyr Trp
                100                 105                 110

Gly Gln Gly Thr Thr Val Thr Val Ser Ser
                115                 120
```

```
<210> SEQ ID NO 119
<211> LENGTH: 107
<212> TYPE: PRT
<213> ORGANISM: Artificial Sequence
<220> FEATURE:
<223> OTHER INFORMATION: light chain variable region of humanized
      antibody

<400> SEQUENCE: 119

Asp Ile Val Met Thr Gln Ser His Lys Phe Met Ser Thr Ser Val Arg
1               5                   10                  15

Asp Arg Val Ser Ile Thr Cys Lys Ala Ser Gln Asp Val Ser Thr Ala
             20                  25                  30

Val Ala Trp Tyr Gln Gln Lys Pro Gly Gln Ser Pro Lys Leu Leu Ile
             35                  40                  45

Tyr Ser Ala Ser Tyr Leu Tyr Thr Gly Val Pro Asp Arg Phe Thr Gly
 50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro Arg
                 85                  90                  95

Thr Phe Gly Gly Gly Thr Lys Leu Glu Ile Lys
                100                 105
```

```
<210> SEQ ID NO 120
<211> LENGTH: 107
<212> TYPE: PRT
<213> ORGANISM: Artificial Sequence
<220> FEATURE:
<223> OTHER INFORMATION: light chain variable region of humanized
      antibody

<400> SEQUENCE: 120

Asp Ile Val Met Thr Gln Ser His Lys Phe Met Ser Thr Ser Val Arg
1               5                   10                  15

Asp Arg Val Ser Ile Thr Cys Lys Ala Ser Gln Asp Val Ser Thr Ala
             20                  25                  30

Val Ala Trp Tyr Gln Gln Lys Pro Gly Gln Ser Pro Lys Leu Leu Ile
             35                  40                  45

Tyr Ser Ala Ser Tyr Leu Tyr Thr Gly Val Pro Asp Arg Phe Thr Gly
 50                  55                  60

Ser Gly Ser Gly Thr Asp Phe Thr Phe Thr Ile Ser Ser Val Gln Ala
 65                  70                  75                  80
```

-continued

Glu Asp Leu Ala Val Tyr Tyr Cys Gln Gln His Tyr Ser Thr Pro Arg
                85                  90                  95

Thr Phe Gly Gly Gly Thr Lys Leu Glu Ile Lys
            100                 105

<210> SEQ ID NO 121
<211> LENGTH: 120
<212> TYPE: PRT
<213> ORGANISM: Artificial Sequence
<220> FEATURE:
<223> OTHER INFORMATION: heavy chain variable region of humanized
      antibody

<400> SEQUENCE: 121

Glu Val Gln Leu Val Glu Ser Gly Gly Gly Leu Val Gln Pro Gly Glu
1               5                   10                  15

Ser Leu Lys Leu Ser Cys Glu Ser Asn Glu Tyr Glu Phe Pro Ser His
            20                  25                  30

Asp Met Ser Trp Val Arg Lys Thr Pro Glu Lys Arg Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Ile Ile Ser Arg Asp Asn Thr Lys Lys Thr Leu Tyr
65                  70                  75                  80

Leu Gln Met Ser Ser Leu Arg Ser Glu Asp Thr Ala Leu Tyr Tyr Cys
                85                  90                  95

Ala Arg His Tyr Asp Asp Tyr Tyr Ala Trp Phe Ala Tyr Trp Gly Gln
            100                 105                 110

Gly Thr Leu Val Thr Val Ser Ala
        115                 120

<210> SEQ ID NO 122
<211> LENGTH: 120
<212> TYPE: PRT
<213> ORGANISM: Artificial Sequence
<220> FEATURE:
<223> OTHER INFORMATION: heavy chain variable region of humanized
      antibody

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Glu Phe Pro Ser His
            20                  25                  30

Asp Met Ser Trp Val Arg Gln Ala Pro Gly Lys Gly Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Asp Asp Tyr Tyr Ala Trp Phe Ala Tyr Trp Gly Gln
            100                 105                 110

Gly Thr Met Val Thr Val Ser Ser
        115                 120

<210> SEQ ID NO 123
<211> LENGTH: 111

```
<212> TYPE: PRT
<213> ORGANISM: Artificial Sequence
<220> FEATURE:
<223> OTHER INFORMATION: light chain variable region of humanized
      antibody

<400> SEQUENCE: 123

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Leu Thr Phe Gly Ala Gly Thr Lys Leu Glu Leu Lys
            100                 105                 110

<210> SEQ ID NO 124
<211> LENGTH: 111
<212> TYPE: PRT
<213> ORGANISM: Artificial Sequence
<220> FEATURE:
<223> OTHER INFORMATION: light chain variable region of humanized
      antibody

<400> SEQUENCE: 124

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Glu Leu Pro Leu Thr Phe Gly Gly Gly Thr Lys Val Glu Ile Lys
            100                 105                 110

<210> SEQ ID NO 125
<211> LENGTH: 138
<212> TYPE: PRT
<213> ORGANISM: Artificial Sequence
<220> FEATURE:
<223> OTHER INFORMATION: heavy chain variable region

<400> SEQUENCE: 125

Met Tyr Leu Gly Leu Asn Tyr Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45
```

```
Ser Asp Ala Trp Met Asp Trp Val Arg Gln Ser Pro Glu Lys Gly Leu
    50                  55                  60

Glu Trp Val Ala Glu Ile Arg Ser Lys Ala Asn Asn His Ala Thr Tyr
65                  70                  75                  80

Tyr Ala Glu Ser Val Asn Gly Arg Phe Thr Ile Ser Arg Asp Asp Ser
                85                  90                  95

Lys Ser Ser Val Tyr Leu Gln Met Asn Ser Leu Arg Ala Glu Asp Thr
            100                 105                 110

Gly Ile Tyr Tyr Cys Thr Trp Gly Glu Val Phe Tyr Phe Asp Tyr Trp
        115                 120                 125

Gly Gln Gly Thr Thr Leu Thr Val Ser Ser
    130                 135

<210> SEQ ID NO 126
<211> LENGTH: 126
<212> TYPE: PRT
<213> ORGANISM: Artificial Sequence
<220> FEATURE:
<223> OTHER INFORMATION: light chain variable region

<400> SEQUENCE: 126

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ser Ser Gln Asp
        35                  40                  45

Ile Asn Lys Tyr Ile Ala Trp Tyr Gln His Lys Pro Gly Lys Gly Pro
    50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Asn Leu Leu Thr Phe Gly Ala Gly Thr Lys Leu Glu Leu Lys
        115                 120                 125
```